US007132589B2

(12) United States Patent
Dunn-Coleman et al.

(10) Patent No.: US 7,132,589 B2
(45) Date of Patent: Nov. 7, 2006

(54) MANIPULATION OF THE PHENOLIC ACID CONTENT AND DIGESTIBILITY OF PLANT CELL WALLS BY TARGETED EXPRESSION OF GENES ENCODING CELL WALL DEGRADING ENZYMES

(75) Inventors: Nigel Dunn-Coleman, Los Gatos, CA (US); Timothy Langdon, Aberystwyth (GB); Phillip Morris, Aberystwyth (GB)

(73) Assignee: Genencor International, Inc., Palo Alto, CA (US)

( * ) Notice: Subject to any disclaimer, the term of this patent is extended or adjusted under 35 U.S.C. 154(b) by 98 days.

(21) Appl. No.: 09/991,209

(22) Filed: Nov. 16, 2001

(65) Prior Publication Data

US 2003/0024009 A1 Jan. 30, 2003

Related U.S. Application Data

(60) Provisional application No. 60/249,608, filed on Nov. 17, 2000.

(51) Int. Cl.
*C12N 15/52* (2006.01)
*C12N 15/63* (2006.01)
*C12N 15/82* (2006.01)

(52) U.S. Cl. ...................... 800/284; 800/287; 800/298; 800/320

(58) Field of Classification Search ................ 800/278, 800/287, 298, 284, 320

See application file for complete search history.

(56) References Cited

U.S. PATENT DOCUMENTS 5,723,764 A * 3/1998 Nichols et al. ............. 800/284
6,143,543 A * 11/2000 Michelsen et al. .......... 435/196

FOREIGN PATENT DOCUMENTS

GB 2 301 103 A 11/1996

OTHER PUBLICATIONS

Kroon P. et al. Biochemical Society Transactions, 1998; vol. 26; p. S167.* de Vries R. et al. Applied and Environmental Microbiology, Dec. 1997; vol. 63, No. 12; pp. 4638-4644.* de Vries R. et al. Biochem. J. ; 2002 vol. 363, pp. 377-386.*

Bartolome B. et al., Applied and Environmental Microbiology; Jan. 1997, pp. 208-212.*

De Vries, R. P. et al., "The faeA genes from *Aspergillus niger* and *Aspergillus tubingensis* encode ferulic acid esterases involved in degradation of complex cell wall polysaccharides," Applied and Environmental Microbiology, vol. 63, No. 12, Dec. 1997 pp. 4638-4644, XP002203731.

Garcia-Conesa, Maria-Teresa et al., "A cinnamoyl esterase from *Aspergillus niger* can break plant cell wall cross-links without release of free diferulic acids." European Journal Biochemistry, vol. 266, No. 2, Dec. 1999, pp. 644-652, XP002203732.

Copy of PCT International Search Report.

Darnowski, D. W. et al., <<A soybean lectin-GFP fusion labels the vacuoles in developing *Arabidopsis thaliana* embryos,>> Plant Cell Reports, vol. 20, No. 11, pp. 1033-1038, May 2002.

* cited by examiner

*Primary Examiner*—Russell P. Kallis
(74) *Attorney, Agent, or Firm*—Lynn Marcus-Wyner

(57) ABSTRACT

Described herein are methods to enhance the production of more highly fermentable carbohydrates in plants, especially forage grasses. The invention provides for transgenic plants transformed with expression vectors containing a DNA sequence encoding ferulic acid esterase I from *Aspergillus*, preferably *A. niger*. The expression vectors may optionally comprise a DNA sequence encoding xylanase from *Trichoderma*, preferably *T. reesei*. Expression of the enzyme(s) is targeted to specific cellular compartments, in specific tissues and under specific environmental conditions. Uses of this invention include, but are not limited to, forage with improved digestibility for livestock, and enhanced biomass conversion.

29 Claims, 154 Drawing Sheets
(3 of 154 Drawing Sheet(s) Filed in Color)

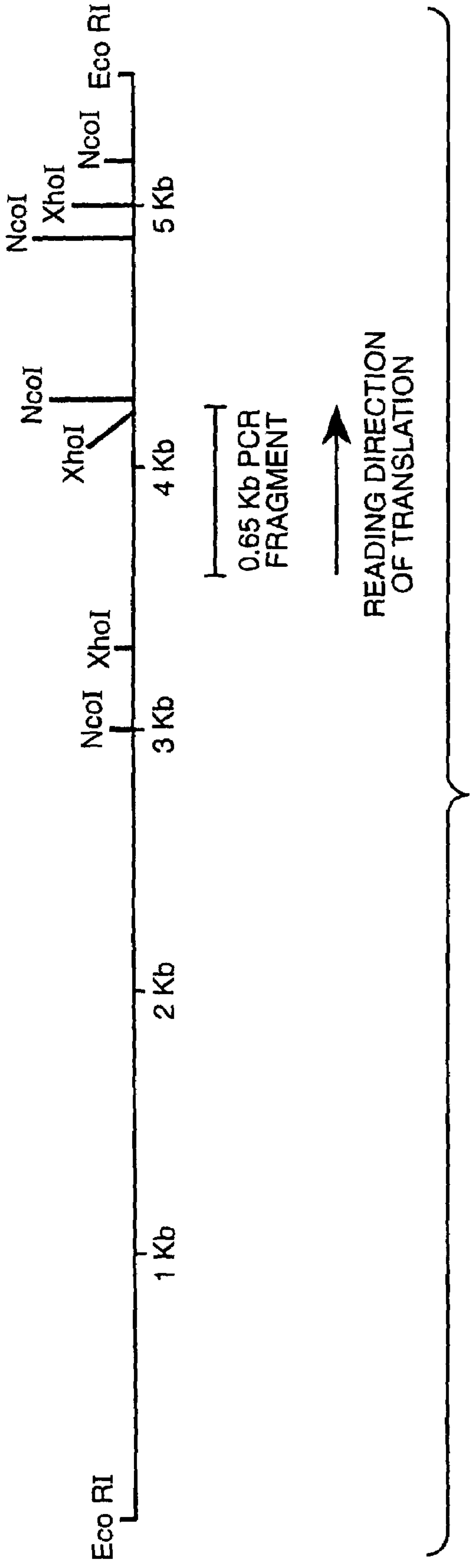
FIG._1

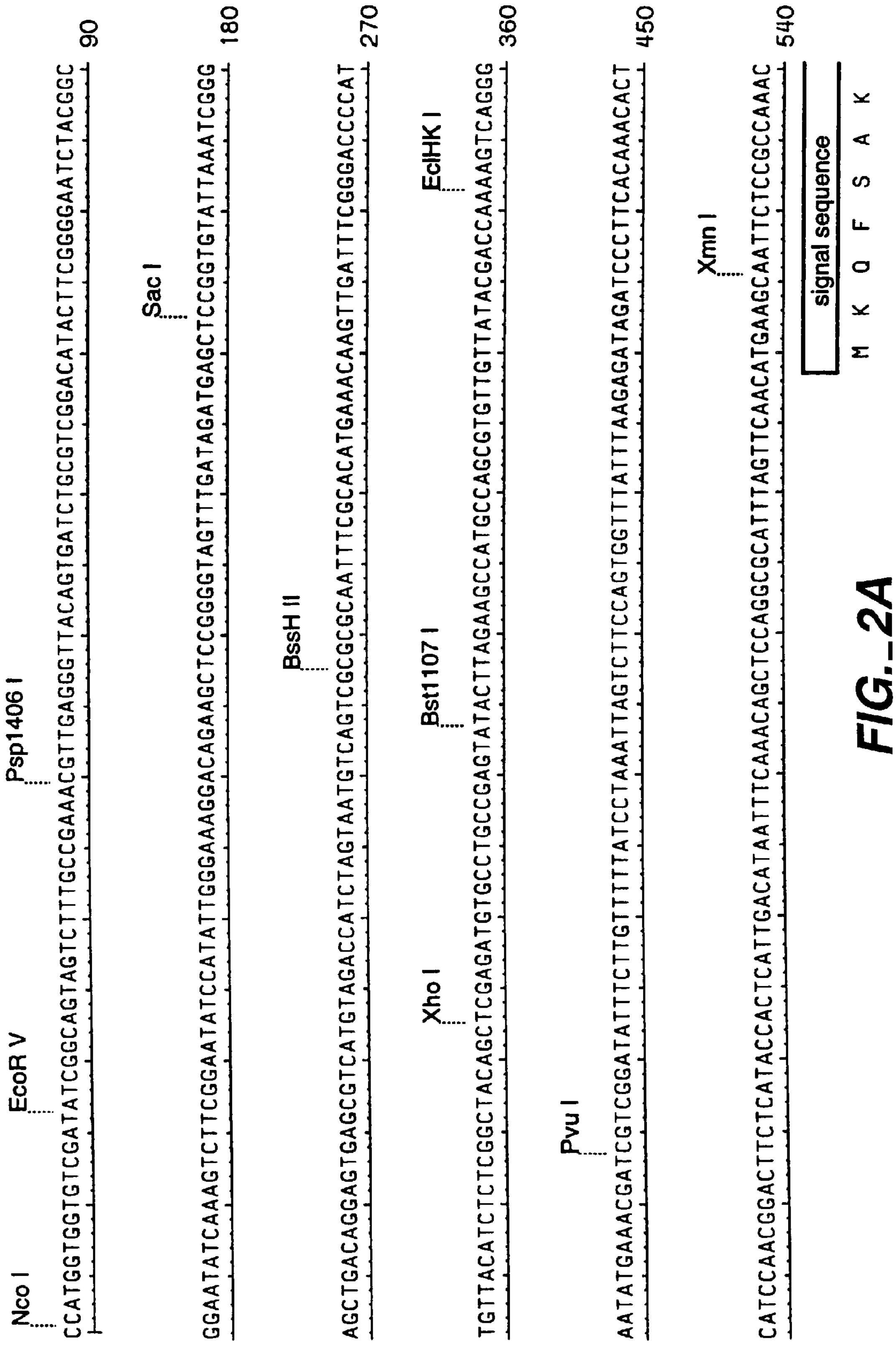

FIG._2A

```
Nco I        EcoR V                Psp1406 I
CCATGGTGGTCGTCGATATCGGCAGTAGTCTTTGCCGAAACGTTGAGGGTTACAGTGATCTCGCTGTCGGACATACTTCGGGAATCTACGGC    90

                                                            Sac I
GGAATATCAAAGTCTTCGGAAATATCCATATTGGGAAAGGACAGAAGCTCCGGGTAGTTTGATAGAGATGAGCTCCGGTGTATTAAATCGGG   180

                                        BssH II
AGCTGACAGGAGTGAGCGTCATGTAGACCATCTCTAGTAATGTCAGTCGCGCGCAATTTCGCACATGAAACAAGTTGATTTCGGGACCCCAT   270

        Xho I                Bst1107 I                            EclHK I
TGTTACATCTCTCGGCTACACAGCTCGAGATGTGCCTGCCGAGTATACTTAGAAGCCATGCCAGCGTGTTGTTATACGACCAAAGTCAGGG    360

    Pvu I
AATATGAAACGATCGTCGGATATTTCTTGTTTTTATCCTAAAATTAGTCTTCCAGTGGTTTATTTAAGAGATAGATCCCTTCACAAACACT   450

                                                        Xmn I
CATCCAACGGACTTCTCATTGACATAATTTCAAACAGCTCCAGGCGCATTAGTTCAACATGAAGCAATTCTCCGCCAAAC              540

                                                        ┌─────────────────┐
                                                        │ signal sequence │
                                                        └─────────────────┘
                                                         M K Q F S A K
```

FIG._2A

Pst I (at position 27) · Bpu10 I (at position 36)

ACGTCCTCGCAGTTGTGGTGACTGCAGGGCACGCCTTAGCAGCCTCTACGCAAGGCATCTCCGAAGACCTCTACAGCCGTTTAGTCGAAA 630 signal sequence

H V L A V V V T A G H A L A A S T Q G I S E D L Y S R L V E

Msc I (at position 3) · Sal I (at position 48)

TGGCCACTATCTCCCAAGCTGCCTACGCCGACCTGTGCAACATTCCGTCGACTATTATCAAGGGAGAGAAAATTTACAATTCTCAAACTG 720

M A T I S Q A A Y A D L C N I P S T I I K G E K I Y N S Q T

BamH I (at position 13) · BsaB I (at position 76)

ACATTAACGGATGGATCCTCCGCGACGACAGCAGCAAAGAAATAATCACCGTCTTCCGTGGCACTGGTAGTGATACGAATCTACAACTCG 810

D I N G W I L R D D S S K E I I T V F R G T G S D T N L Q L

Eco31 I (at position 90)

ATACTAACTACACCCTCACGCCTTTCGACACCCTACCACAATGCAACGGTTGTGAAGTACACGGTGGATATTATATTGGATGGGTCTCCG 900

Tth111 I BspM I Acc III

TCCAGGACCAAGTCGAGTCGCTTGTCAAACAGCAGGTTAGCCAGTATCCGGACTATGCGCTGACTGTGACGGGCCACAGGTATGCCCTCG 990 intron

V Q D Q V E S L V K Q Q V S Q Y P D Y A L T V T G H S

ApaB I Pvu II

TGATTTCTTTCAATTAAGTGTATAATACTCACTAACTCTACGATAGTCTCGGAGCGTCCCTGGCAGCACTCACTGCCGCCCAGCTGTCTG 1080 intron

L G A S L A A L T A A Q L S

BsrG I Stu I

CGACATACGACAACATCCGCCTGTACACCTTCGGCGAACCGCGCAGCGGCAATCAGGCCTTCGCGTCGTACATGAACGATGCCTTCCAAG 1170

A T Y D N I R L Y T F G E P R S G N Q A F A S Y M N D A F Q

Xho I BspM I Nco I

CCTCGAGCCCAGATACGACGCAGTATTTCCGGGTCACTCATGCCAACGACGGCATCCCAAACCTGCCCCCGGTGGAGCAGGGGTACGCCC 1260

A S S P D T T Q Y F R V T H A N D G I P N L P P V E Q G Y A

Sca I

ATGGCGGTGTAGAGTACTGGAGCGTTGATCCTTACAGCGCCCAGAACACATTTGTCTGCACTGGGGATGAAGTGCAGTGCTGTGAGGCCC 1350

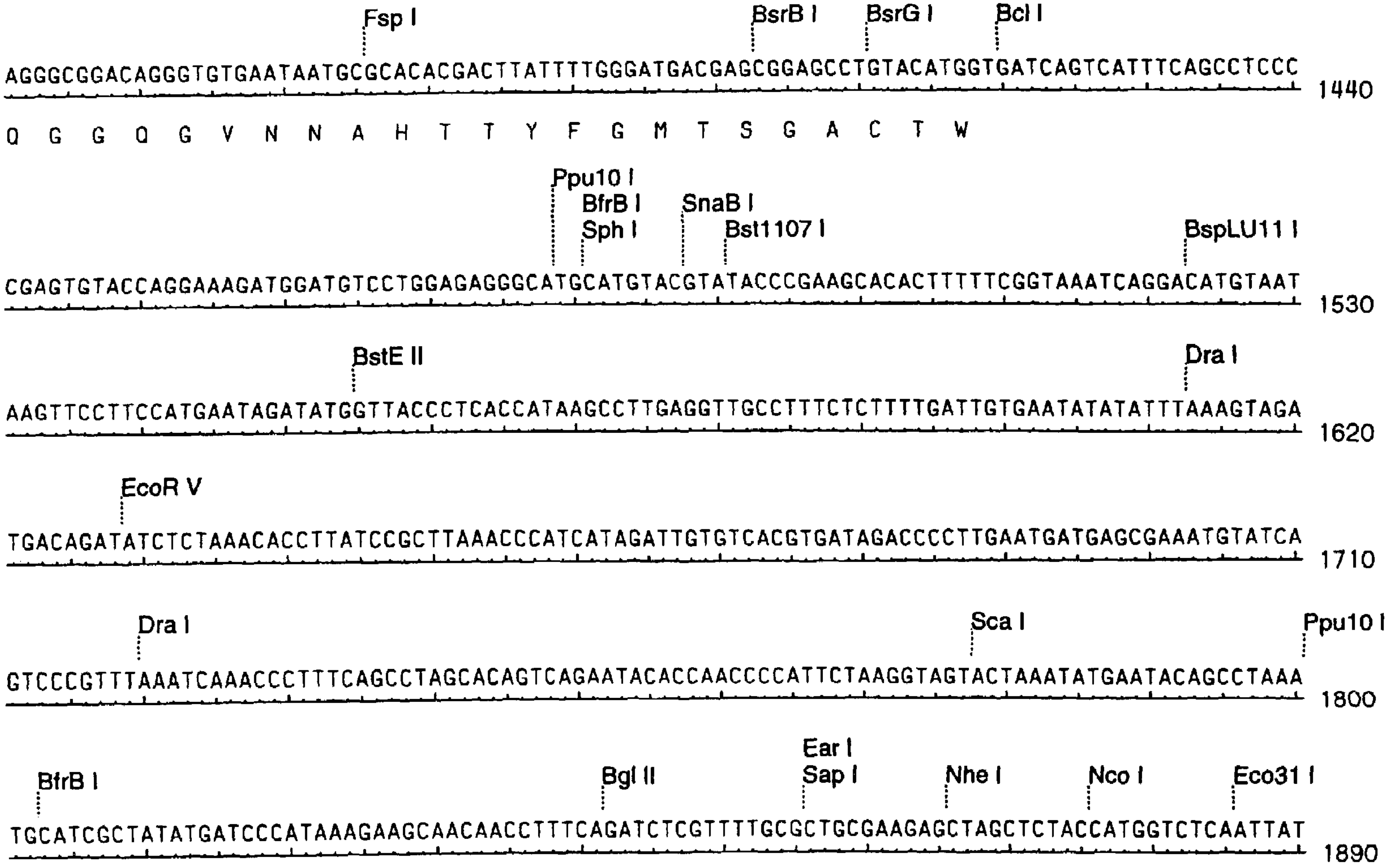

FIG._2D

```
                                  Fsp I                                    BsrB I        BsrG I       Bcl I
AGGGCGGGACAGGGTGTGAATAATGCGCACACGACTTATTTTGGGATGACGAGCGGAGCCTGTACATGGTGATCAGTCATTTCAGCCTCCC  1440
 Q  G  G  Q  G  V  N  N  A  H  T  T  Y  F  G  M  T  S  G  A  C  T  W

                            Ppu10 I
                             BfrB I    SnaB I                                                       BspLU11 I
                              Sph I      Bst1107 I
CGAGTGTACCAGGAGAAAGATGGATGTCCTGGAGAGGGCATGCATGTACGTATACCGAAGCACACTTTTTCGGTAAATCAGGACATGTAAT  1530

       BstE II                                                                              Dra I
AAGTTCCCTTCCATGAATAGATATGGTTACCCTCACCATAAGCCTTGAGGTTGCCTTTCTCTTTTGATTGTGAATATATATTTAAAGTAGA  1620

 EcoR V                                                                         Sca I        Ppu10 I
TGACAGATATCTCTAAACACCTTATCCGCTTAAACCCATCATAGATTGTGTCACGTGATAGACCCCTTGAATGATGAGCGAAATGTATCA  1710

       Dra I                                                                                            Ear I
                                                                                                        Sap I          Bgl II                         Nhe I            Nco I            Eco31 I
GTCCCGTTTAAATCAAACCCCTTTCAGCCTAGCACAGTCAGAATACACCAACCCCATTCTAAGGTAGTACTAAATATGAATACAGCCTAAA  1800

 BfrB I
TGCATCGCTATATGATCCCATAAAGAAGCAACAACCTTTCAGATCTCGTTTGCGCTGCGAAGAGCTAGCTCTACCATGGTCTCAATTAT  1890
```

FIG._2D

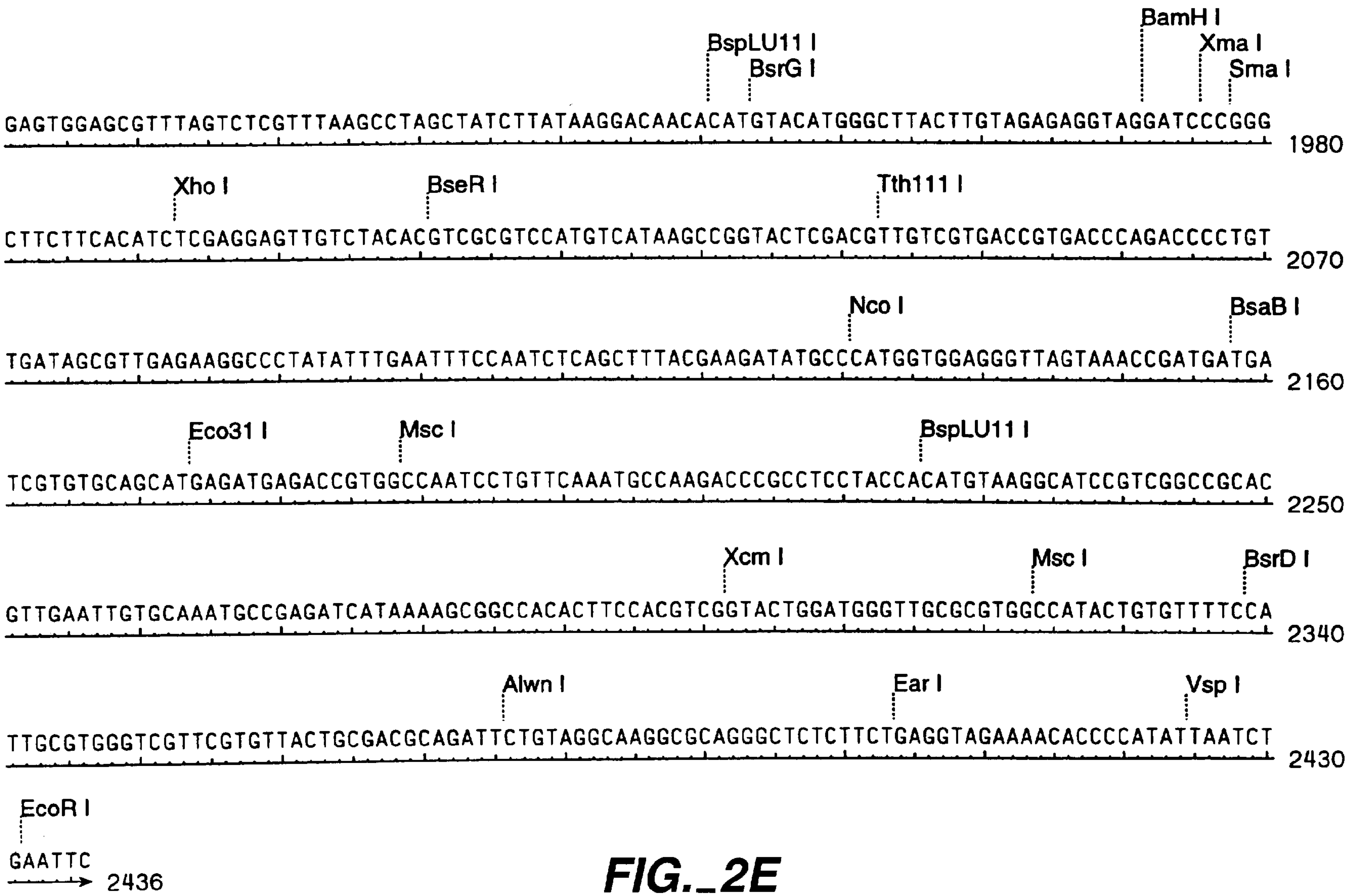

FIG._2E

```
                              BamH I
           BspLU11 I             Xma I
           BsrG I                Sma I
GAGTGGAGCGTTTAGTCTCGTTTAAGCCTAGCTATCTTATAAGGACAACACATGGGCTTACTTGTAGAGAGGTAGGATCCCGGG
                                                                               1980

   Xho I       BseR I                      Tth111 I
CTTCTTCACATCTCGAGGAGTTGTCTACACGTCGGTTCCATGTCATGTAAGCCGGTACTCGACGTTGTCGTGACCGTGACCCCTGT
                                                                               2070

                                         Nco I                            BsaB I
TGATAGCGTTGAGAAGGCCCTATATATTTGAATTTCCAATCTCAGCTTTACGAAGATATGCCCATGGTGGAGGGTTAGTAAACCGATGATGA
                                                                               2160

       Eco31 I      Msc I                               BspLU11 I
TCGTGTGCAGCATGAGATGAGACCGTGGCCAATCCTGTTCAAATGCCAAGAGACCCGCCTCCTACCACACATGTAAGGCATCCGTCGGCCCAC
                                                                               2250

                                     Xcm I                 Msc I           BsrD I
GTTGAATTGTGCAAATGCCGAGATCATAAAAGGCGGGCTACTGATGGGTTGCCGTGTGGCCATACTGTGTTTCCA
        Alwn I                        Ear I       Vsp I                        2340

TTGCGTGGGTCGTTCGTGTTACTGCGACGCAGATTCTGTAGGCAAGGGCCAGGGCTCTCTTCTTGAGGTAGAAAACACCCCATATTAATCT
                                                                               2430

  EcoR I
  GAATTC 2436
```

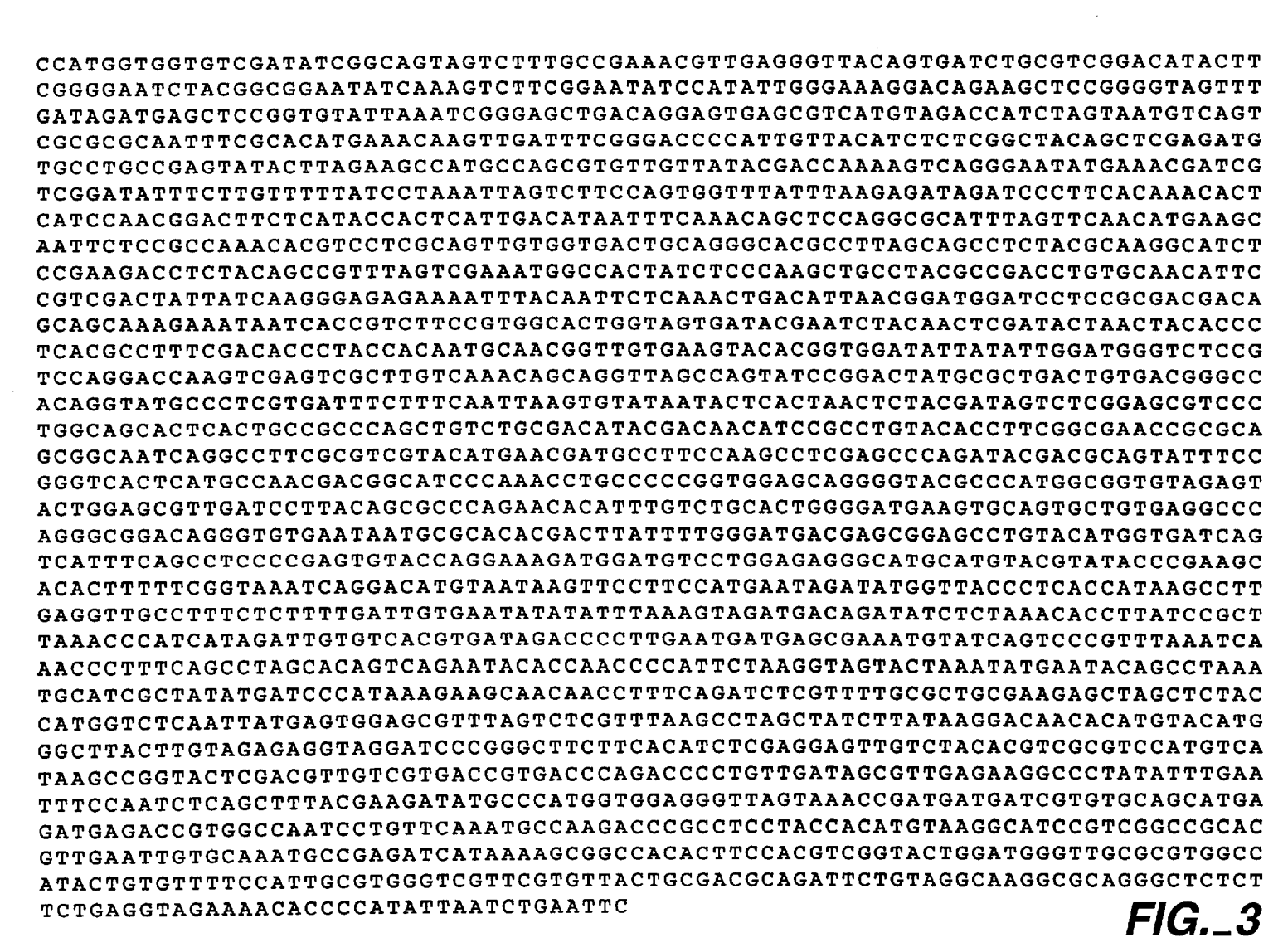

CCATGGTGGTGTCGATATCGGCAGTAGTCTTTGCCGAAACGTTGAGGGTTACAGTGATCTGCGTCGGACATACTT
CGGGGAATCTACGGCGGAATATCAAAGTCTTCGGAATATCCATATTGGGAAAGGACAGAAGCTCCGGGGTAGTTT
GATAGATGAGCTCCGGTGTATTAAATCGGGAGCTGACAGGAGTGAGCGTCATGTAGACCATCTAGTAATGTCAGT
CGCGCGCAATTTCGCACATGAAACAAGTTGATTTCGGGACCCCATTGTTACATCTCTCGGCTACAGCTCGAGATG
TGCCTGCCGAGTATACTTAGAAGCCATGCCAGCGTGTTGTTATACGACCAAAAGTCAGGGAATATGAAACGATCG
TCGGATATTTCTTGTTTTTATCCTAAATTAGTCTTCCAGTGGTTTATTTAAGAGATAGATCCCTTCACAAACACT
CATCCAACGGACTTCTCATACCACTCATTGACATAATTTCAAACAGCTCCAGGCGCATTTAGTTCAACATGAAGC
AATTCTCCGCCAAACACGTCCTCGCAGTTGTGGTGACTGCAGGGCACGCCTTAGCAGCCTCTACGCAAGGCATCT
CCGAAGACCTCTACAGCCGTTTAGTCGAAATGGCCACTATCTCCCAAGCTGCCTACGCCGACCTGTGCAACATTC
CGTCGACTATTATCAAGGGAGAGAAAATTTACAATTCTCAAACTGACATTAACGGATGGATCCTCCGCGACGACA
GCAGCAAAGAAATAATCACCGTCTTCCGTGGCACTGGTAGTGATACGAATCTACAACTCGATACTAACTACACCC
TCACGCCTTTCGACACCCTACCACAATGCAACGGTTGTGAAGTACACGGTGGATATTATATTGGATGGGTCTCCG
TCCAGGACCAAGTCGAGTCGCTTGTCAAACAGCAGGTTAGCCAGTATCCGGACTATGCGCTGACTGTGACGGGCC
ACAGGTATGCCCTCGTGATTTCTTTCAATTAAGTGTATAATACTCACTAACTCTACGATAGTCTCGGAGCGTCCC
TGGCAGCACTCACTGCCGCCCAGCTGTCTGCGACATACGACAACATCCGCCTGTACACCTTCGGCGAACCGCGCA
GCGGCAATCAGGCCTTCGCGTCGTACATGAACGATGCCTTCCAAGCCTCGAGCCCAGATACGACGCAGTATTTCC
GGGTCACTCATGCCAACGACGGCATCCCAAACCTGCCCCCGGTGGAGCAGGGGTACGCCCATGGCGGTGTAGAGT
ACTGGAGCGTTGATCCTTACAGCGCCCAGAACACATTTGTCTGCACTGGGGATGAAGTGCAGTGCTGTGAGGCCC
AGGGCGGACAGGGTGTGAATAATGCGCACACGACTTATTTTGGGATGACGAGCGGAGCCTGTACATGGTGATCAG
TCATTTCAGCCTCCCCGAGTGTACCAGGAAAGATGGATGTCCTGGAGAGGGCATGCATGTACGTATACCCGAAGC
ACACTTTTTCGGTAAATCAGGACATGTAATAAGTTCCTTCCATGAATAGATATGGTTACCCTCACCATAAGCCTT
GAGGTTGCCTTTCTCTTTTGATTGTGAATATATATTTAAAGTAGATGACAGATATCTCTAAACACCTTATCCGCT
TAAACCCATCATAGATTGTGTCACGTGATAGACCCCTTGAATGATGAGCGAAATGTATCAGTCCCGTTTAAATCA
AACCCTTTCAGCCTAGCACAGTCAGAATACACCAACCCCATTCTAAGGTAGTACTAAATATGAATACAGCCTAAA
TGCATCGCTATATGATCCCATAAAGAAGCAACAACCTTTCAGATCTCGTTTTGCGCTGCGAAGAGCTAGCTCTAC
CATGGTCTCAATTATGAGTGGAGCGTTTAGTCTCGTTTAAGCCTAGCTATCTTATAAGGACAACACATGTACATG
GGCTTACTTGTAGAGAGGTAGGATCCCGGGCTTCTTCACATCTCGAGGAGTTGTCTACACGTCGCGTCCATGTCA
TAAGCCGGTACTCGACGTTGTCGTGACCGTGACCCAGACCCCTGTTGATAGCGTTGAGAAGGCCCTATATTTGAA
TTTCCAATCTCAGCTTTACGAAGATATGCCCATGGTGGAGGGTTAGTAAACCGATGATGATCGTGTGCAGCATGA
GATGAGACCGTGGCCAATCCTGTTCAAATGCCAAGACCCGCCTCCTACCACATGTAAGGCATCCGTCGGCCGCAC
GTTGAATTGTGCAAATGCCGAGATCATAAAAGCGGCCACACTTCCACGTCGGTACTGGATGGGTTGCGCGTGGCC
ATACTGTGTTTTCCATTGCGTGGGTCGTTCGTGTTACTGCGACGCAGATTCTGTAGGCAAGGCGCAGGGCTCTCT
TCTGAGGTAGAAAACACCCCATATTAATCTGAATTC

FIG._3

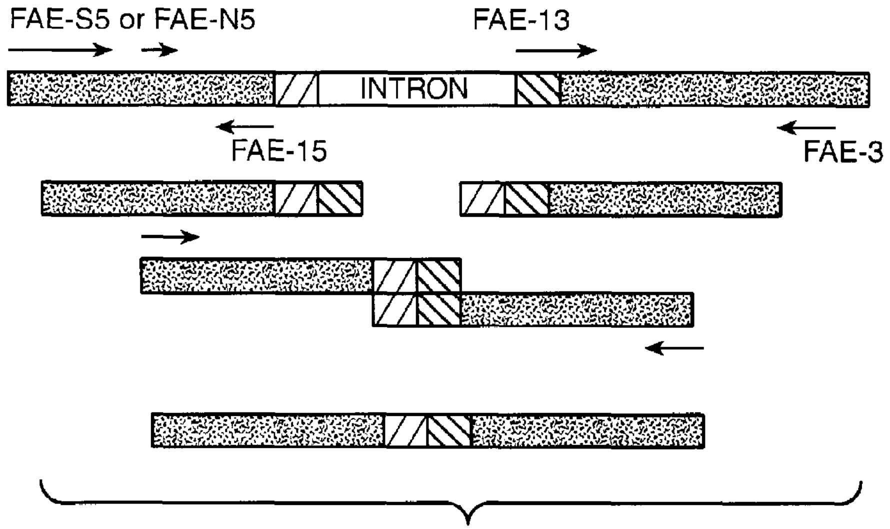
FIG._4
```
FAE-I3  CCGGCCACGCCCTCGGCGCCTCCCTGGCGGCACTC        35-mer
FAE-I5  GGCGCCGAGGGAGTGGCCGGTCACGGTCAGCGCGTAGTCC          40-mer

                             i                        intron position in original

   Y  A  L  T  V  T  G  H  S   L  G  A  S  L  A  A  L
GGACTACGCGCTGACCGTGACCGGCCACTCCCTCGGCGCC                    complement, FAE-I5
                     CCGGCCACGCCCTCGGCGCCTCCCTGGCGGCACTC          FAE-I3
   Y  A  L  T  V  T  G  H  A   L  G  A  S  L  A  A  L
```
FIG._5

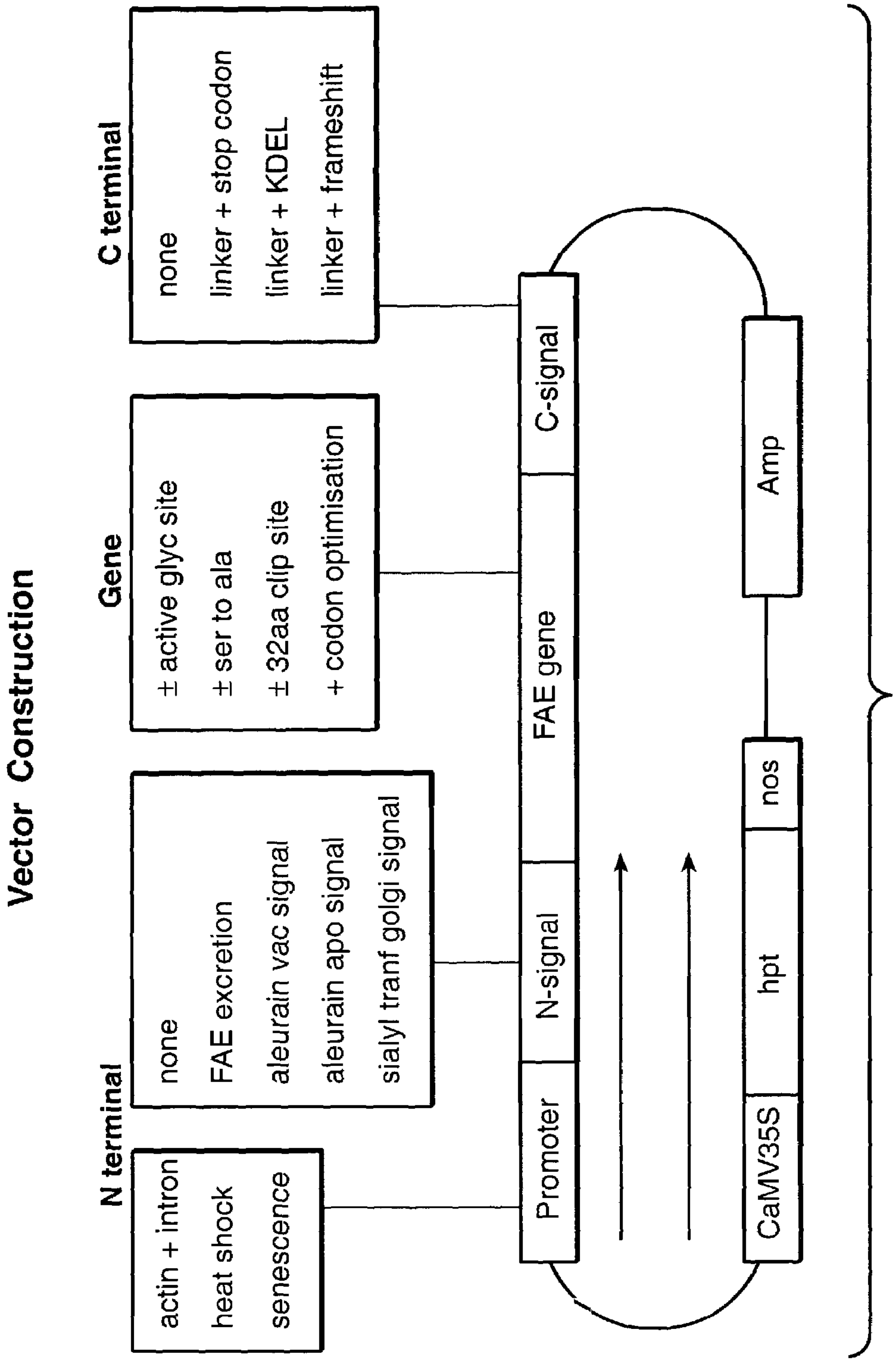
FIG._6

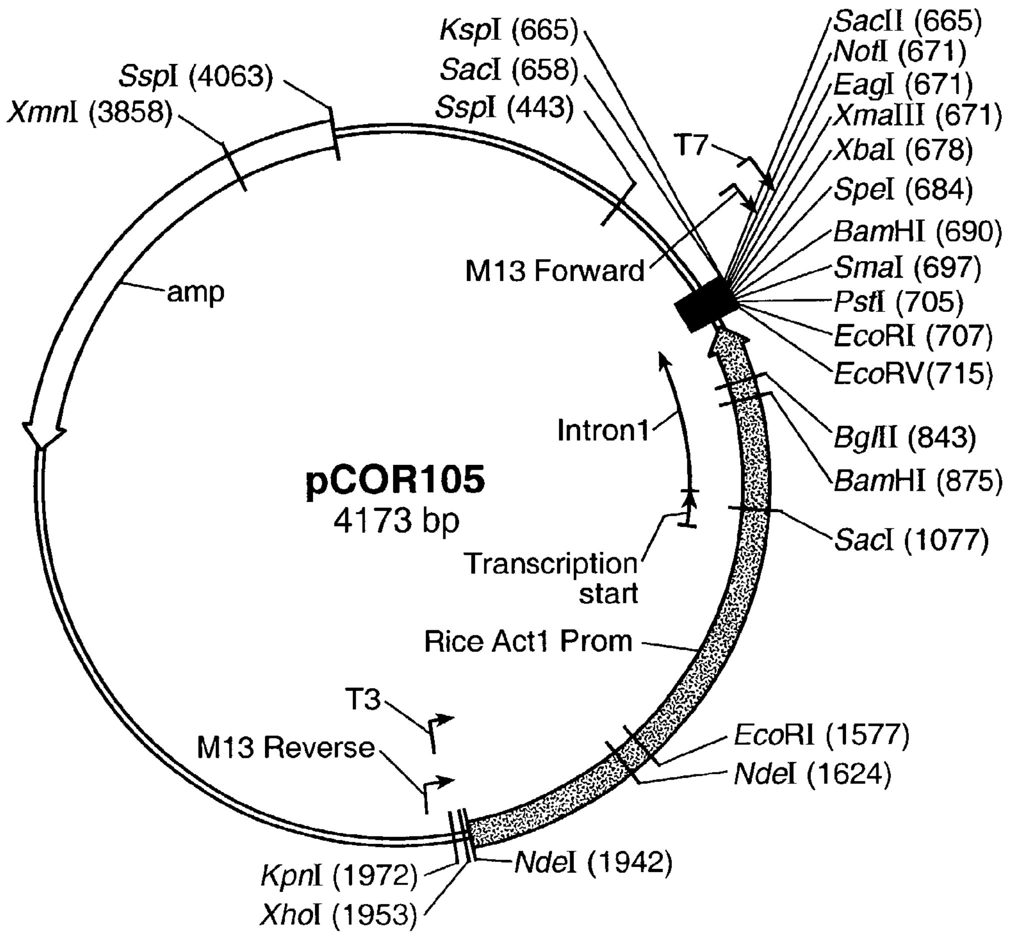
FIG._7

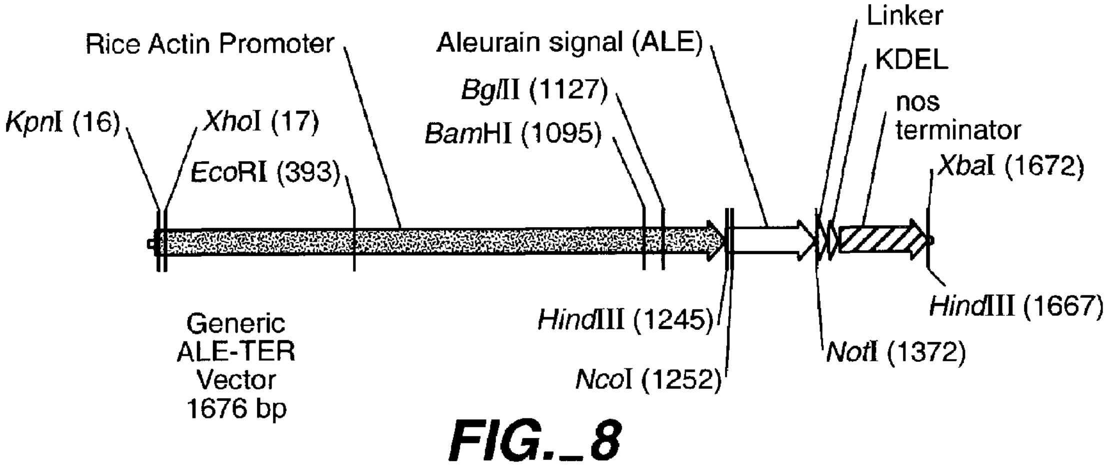
FIG._8
KDEL-COOH ER retention sequence
```
         NotI
       ~~~~~~~~
        A  A  A  K   P  L  K   D  E  L   *
1      GCGGCCGCGA AACCACTGAA GGATGAGCTG TAA
```
FIG._9
FAE-LINKER-FRAMESHIFT Structure and Sequence
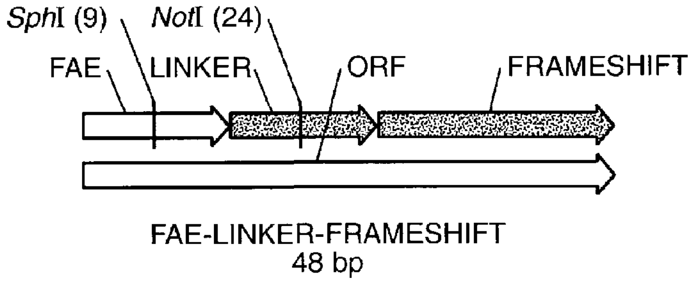
```
+1  G  A  C  T   W  P  V   A  A  A   E  T  T  E   G
      SphI                NotI
     ~~~~~~             ~~~~~~~~
1   GGCGCATGCA CCTGGCCGGT CGCGGCCGCG GAAACCACTG AAGGATGA
    CCGCGTACGT GGACCGGCCA GCGCCGGCGC CTTTGGTGAC TTCCTACT
```
FIG._10

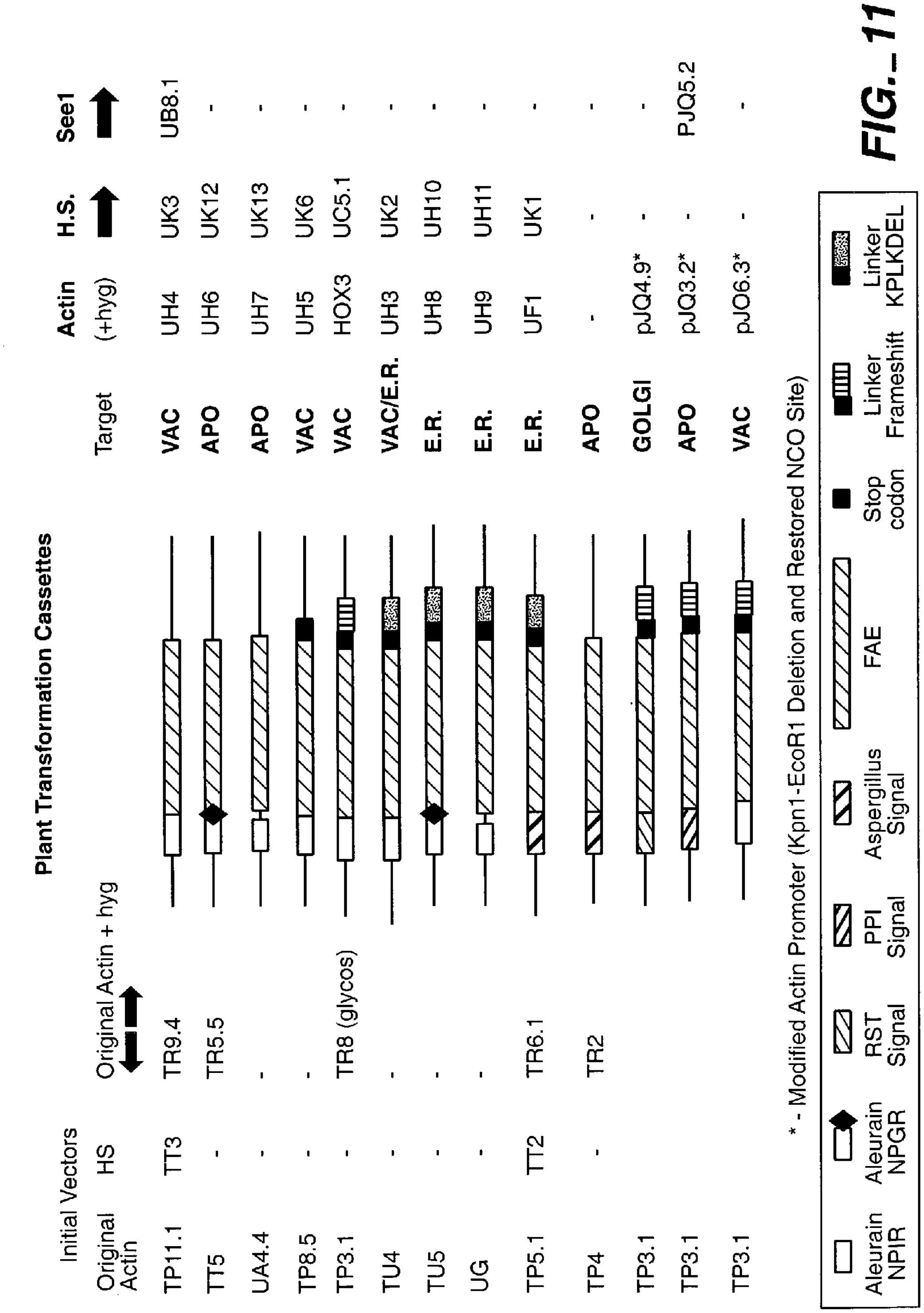
FIG._11

Vectors

Original Actin promoter in pCOR105

| | Target | Signal sequences | Vectors |
|---|---|---|---|
| (i) | APO | - aleurain-NPGR-FAE | pUH6, pTT5, TT5.5, pTT5.1 |
| | | - aleurain-delNPIR -FAE | pUH7, pUA4.4, |
| (ii) | ER | - aleurain-NPGR-FAE-linker-KDEL | pTU5, pUH8, |
| | | - aleurain-delNPIR-FAE-linker-KDEL | pUG4, pUH9, |
| (iii) | VAC | - aleurain-NPIR-FAE | pTP11.1, pTR9.4, pUH4, pUK3, |
| (iv) | ER/VAC | - aleurain-NPIR-FAE-linker-KDEL | pTU4, pUH3, |
| (v) | VAC | - aleurain-NPIR-FAE-linker-frameshift | pUA1K3, pTP3.1, pUC5.11 |
| (vi) | VAC | - aleurain-NPIR-FAE-linker-stop | pTP8.5, pUH5 |
| (vii) | ER | - Aspergillus signal -FAE-KDEL | pTP5.1, pTP6.1, pUF1, |

Modified actin promoter (Kpn1-EcoR1 deletion and restored NCO site)

| | | | |
|---|---|---|---|
| (i) | VAC | - aleurain-NPIR-FAE-linker-frameshift | pJO6.3 |
| (ii) | GOLGI | - RST-FAE-linker-frameshift | pJQ3.2 |
| (iii) | APO | - PPI-FAE-linker-frameshift | pJQ4.9 |

Heat-shock promoter

| | | | |
|---|---|---|---|
| (i) | APO | - aleurain-NPGR-FAE | pUH12 |
| | | - aleurain-delNPIR-FAE | pUH13 |
| | | - Aspergillus signal-FAE | pTP4a2, pTR2.22, |
| (ii) | ER | - aleurain-NPGR-FAE-linker-KDEL | pUH10 |
| | | - aleurain-delNPIR-FAE-linker-KDEL | pUH11 |
| (iii) | VAC | - aleurain-NPIR -FAE | pUK3,pTT3 |
| (iv) | ER/VAC | - aleurain-NPIR-FAE-linker-KDEL | pUK2 |
| (v) | VAC | - aleurain-NPIR-FAE-linker-frameshift | pUC5.11, pHOX3 |
| (vi) | VAC | - aleurain-NPIR-FAE-linker-stop | pUK6 |
| (vii) | ER | - Aspergillus signal -FAE-KDEL | pUK1, pTT2 |

Senescence promoter

| | | | |
|---|---|---|---|
| (i) | APO | - Sec1-PPI-FAE-linker-frameshift | pJQ5.2 |
| (ii) | VAC | - See1-aleurain-deleted NPIR-FAE | pUB8.1 |

FIG._12

**ALEURAIN-NPIR (Vacuolar) and NPGR (Apoplast)
Structure and Sequence**

NPIR Underline
NPGR Bold

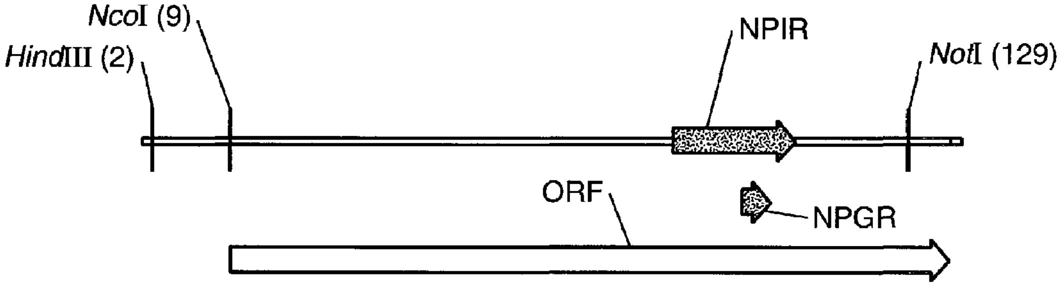

ALEURAIN-NPIR
134bp

```
+1          M   A   H   A   R   V   L   L   L   A   L   A   V   L   A   T   A   A   V   A
   HindIII NcoI
   ~~~~~~ ~~~~~~~

1  AAGCTTACCA TGGCCCACGC CCGCGTCCTC CTCCTGGCGC TCGCCGTGCT GGCCACGGCC GCCGTCGCCG
   TTCGAATGGT ACCGGGTGCG GGCGCAGGAG GAGGACCGCG AGCGGCACGA CCGGTGCCGG CGGCAGCGGC

+1 V   A   S   S   S   S   F   A   D   S   N   P   I   R   P   V   T   D   R   A   A
                                                                          NotI
                                                                        ~~~~~~~~

71 TCGCCTCCTC CTCCTCCTTC GCCGACTCCA ACCCGATCCG GCCCGTCACC GACCGCGCGG CCGC
   AGCGGAGGAG GAGGAGGAAG CGGCTGAGGT TGGGCTAGGC CGGGCAGTGG CTGGCGCGCC GGCG
```

FIG._13

RAT SIALYL TRANSFERASE Golgi signal sequence

```
        HindIII
        ~~~~~~
                   M  I H T  N L K  K K F S  L F I  L V F  L L F A
  1     AAGCTTACCA TGATCCACAC CAACCTCAAA AAGAAGTTCT CCCTCTTCAT CCTCGTCTTC CTCCTCTTCG

        · V I C  V W K  K G S D  Y E A  L T L  Q A K E  F Q M
 71     CCGTGATCTG CGTGTGGAAG AAGGGCTCCG ACTACGAGGC CCTCACCCTC CAAGCCAAGG AGTTCCAAAT

          NotI
         ~~~~~~~~
        · A  A
141     GGCGGCCGC
```

FIG._14

POTATO PROTEASE INHIBITOR II Apoplast signal sequence

```
        HindIII
        ~~~~~~
                   M  X V H  K E V  N F V A  Y L L  I V L  G L L L
  1     AAGCTTACMA TGGMCGTGCA CAAGGAGGTS AACTTCGTSG CCTACCTCCT GATCGTSCTC
        GGCCTCCTCT
                       NcoI
                      ~~~~~~
        · L V S  A M E  H V D A  K A C  T X E  C G N L
        G F G ·
 71     TGCTCGTSTC CGCCATGGAG CACGTGGACG CCAAGGCCTG CACCCKCGAG TGCGGCAACC
        TCGGCTTCGG
                    NotI
                  ~~~~~~~~
        · I C P  A A A
141     CATCTGCCCG GCGGCCGCC
```

FIG._15

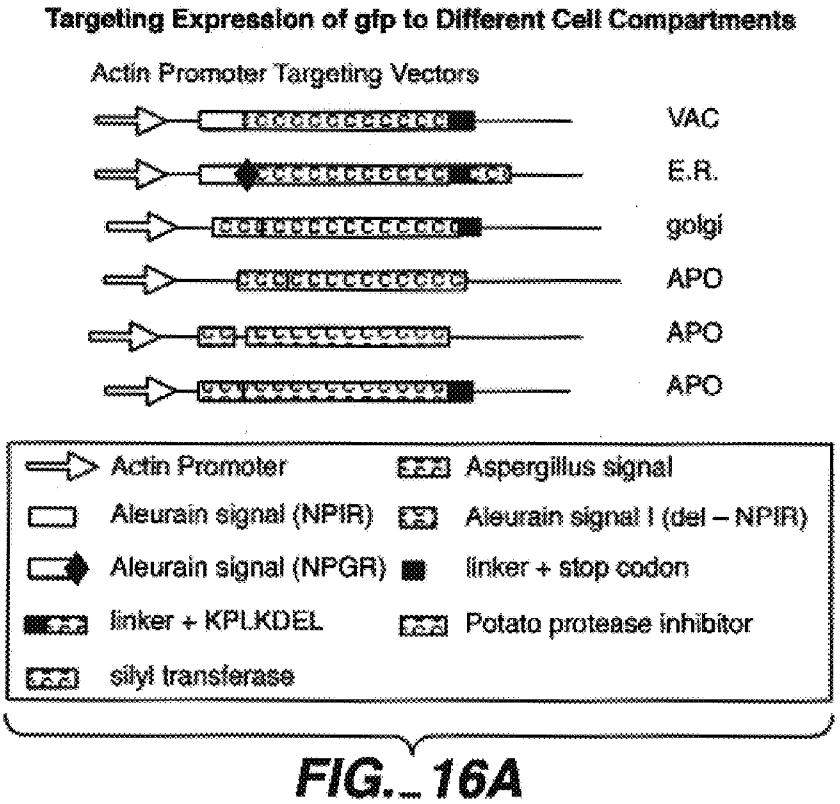
FIG._16A
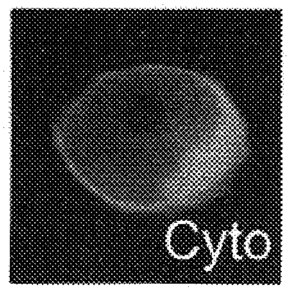
FIG._16B
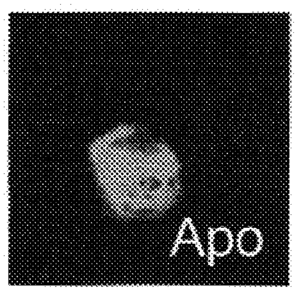
FIG._16C
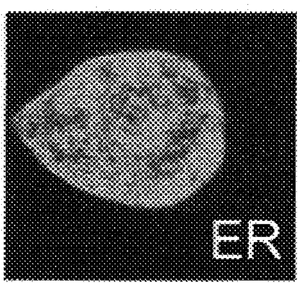
FIG._16D
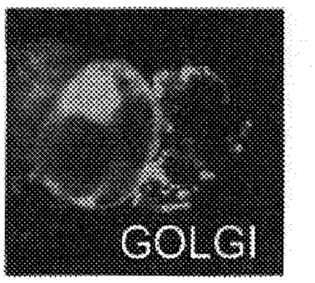
FIG._16E
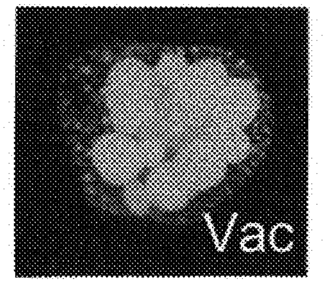
FIG._16F
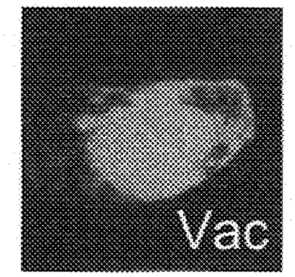
FIG._16G

**FAE Activity in Transgenic *Festuca arundinacea* Leaves of Different Ages Under ER and APO Targeting Sequence**
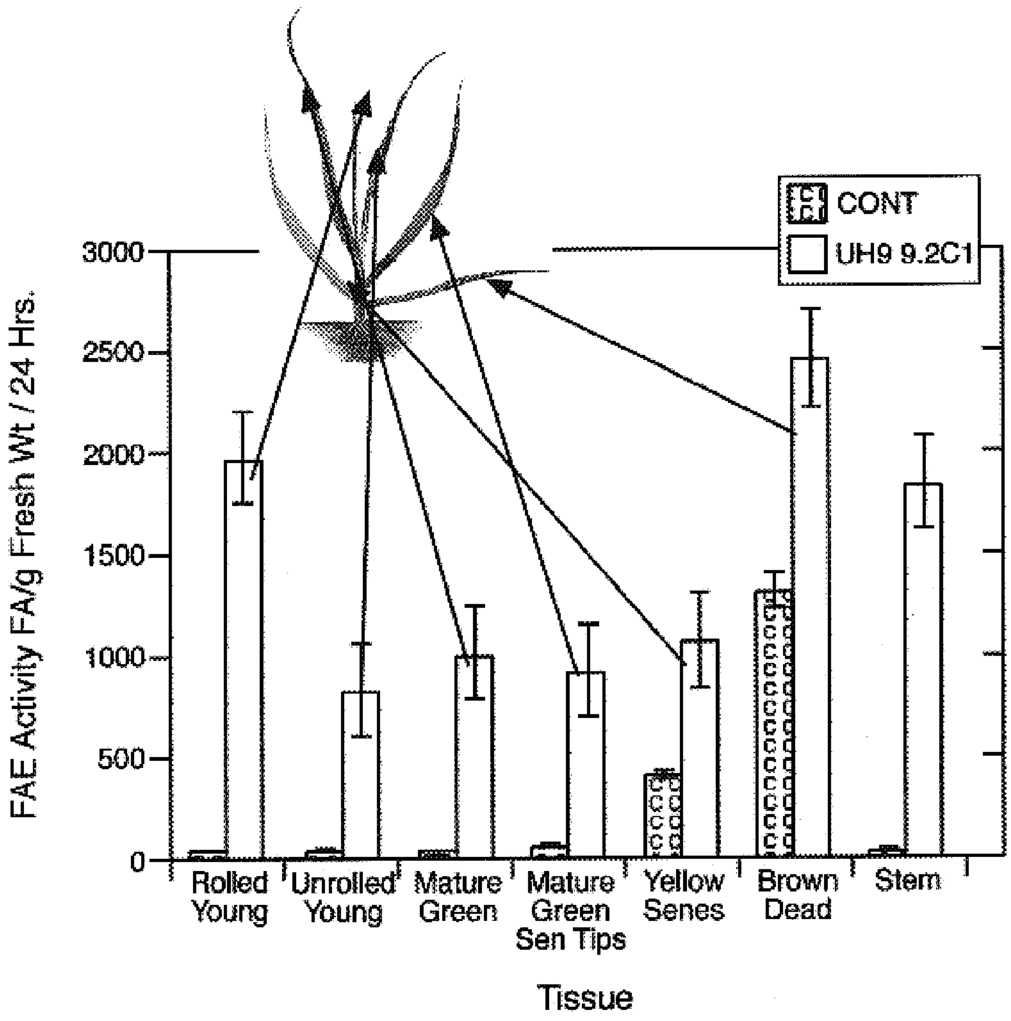
*FIG._17A*

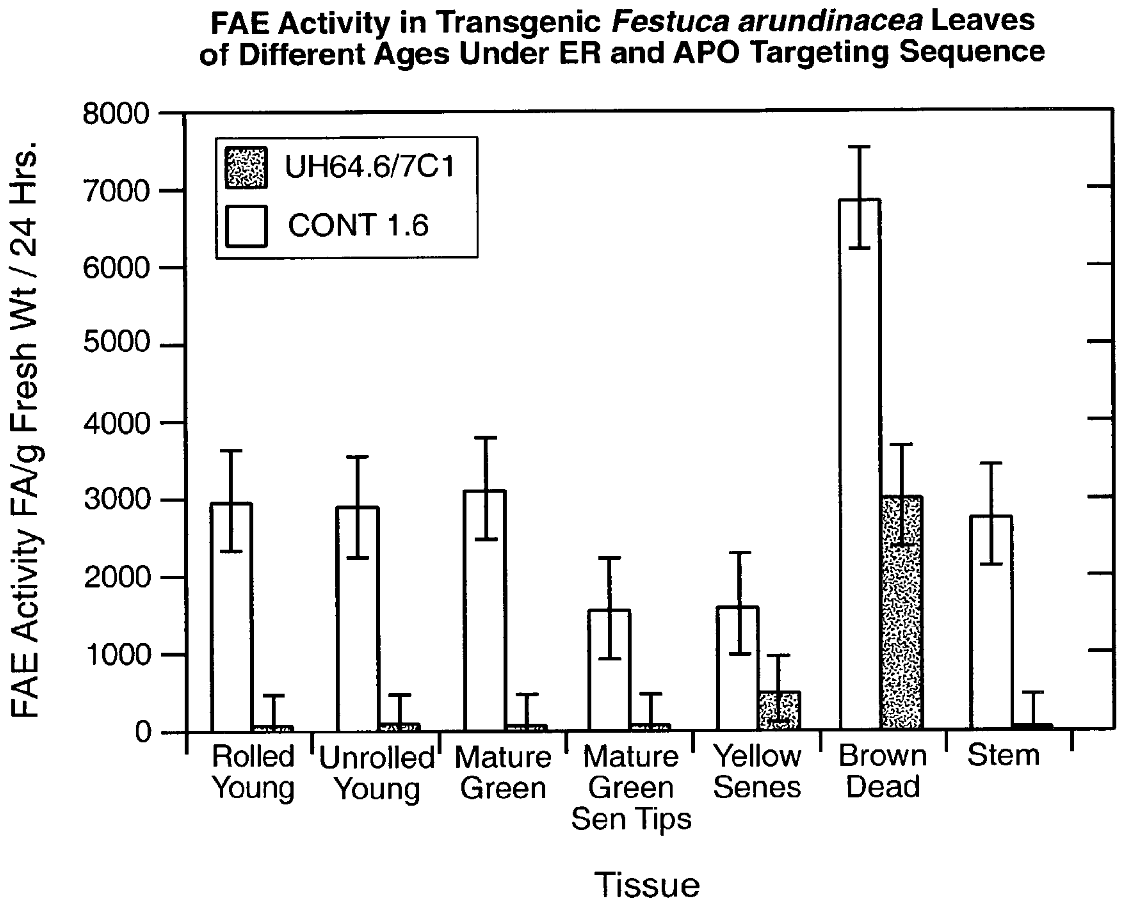
FIG._17B

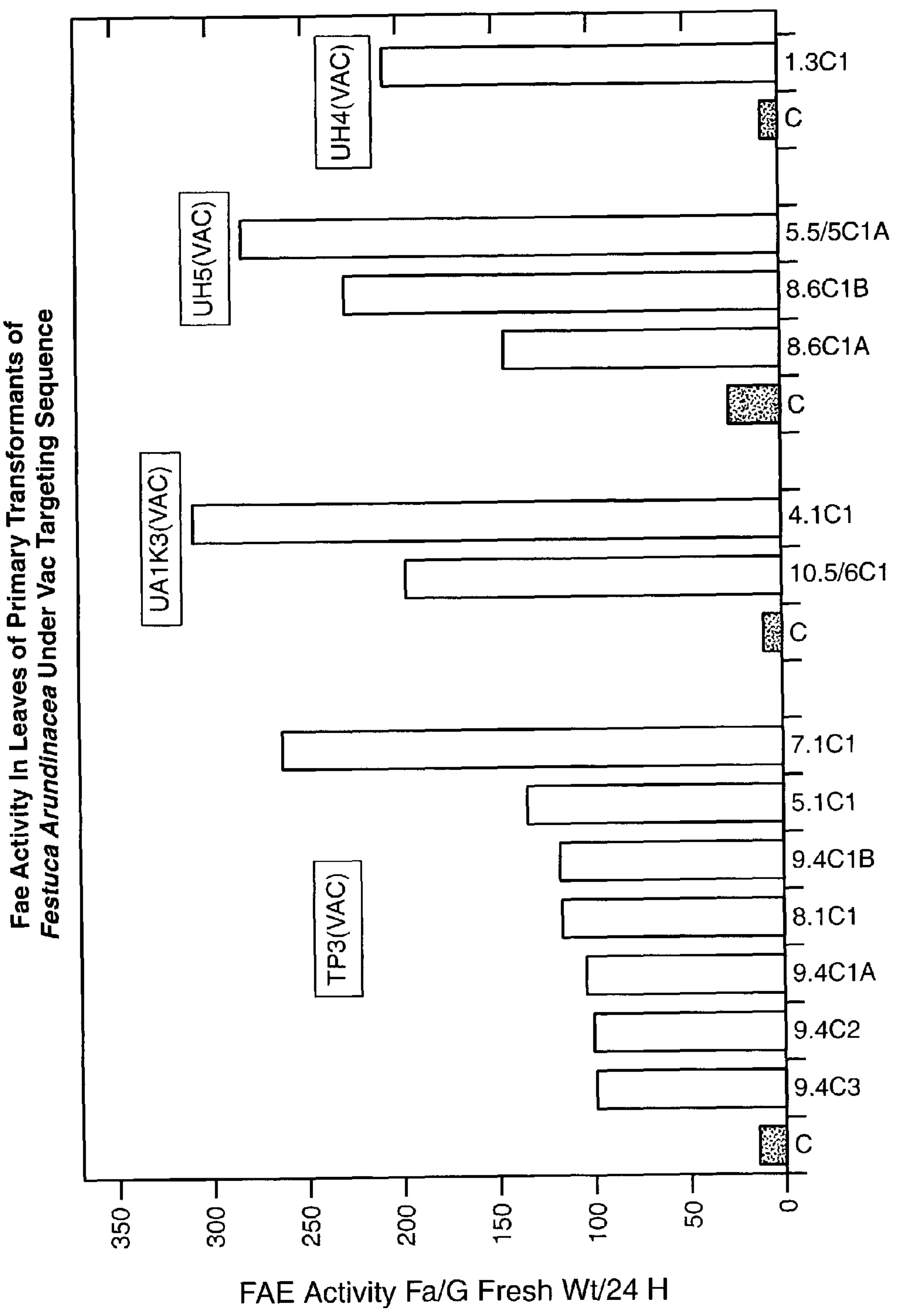
*FIG._18*

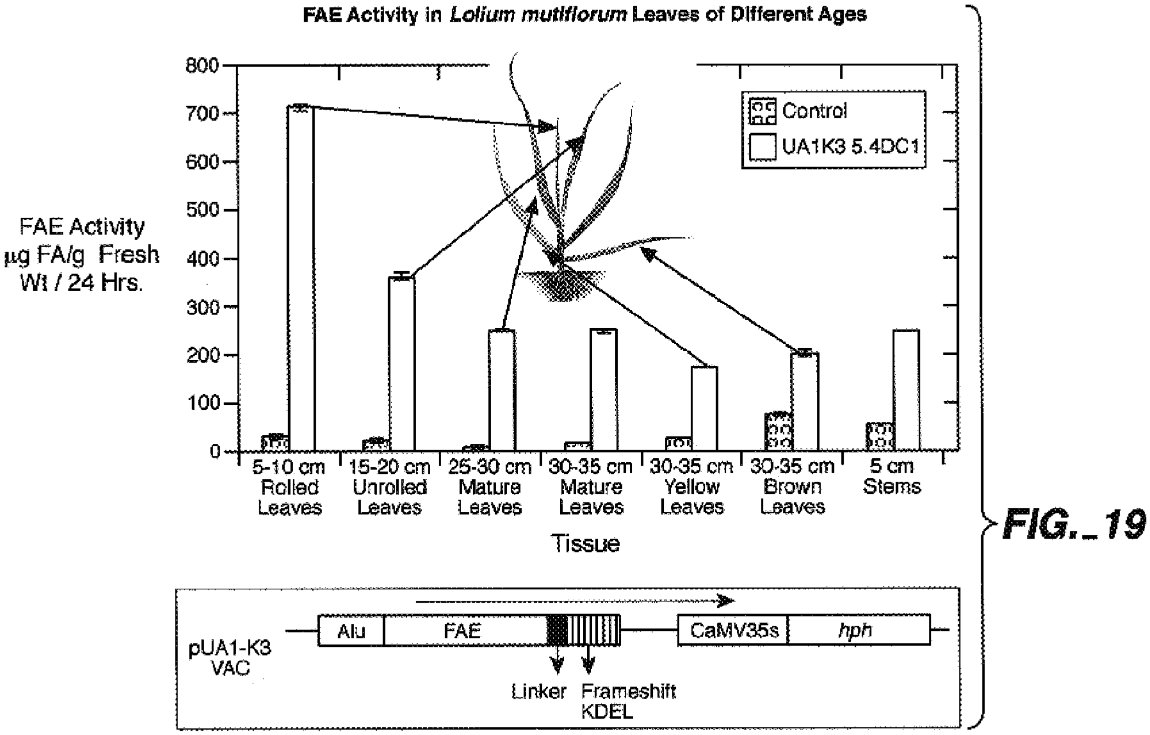
FIG._19

**FAE Activity in Leaves of Primary Transformants of *Lolium multiflorum* Under VAC APO and ER Targeting Sequence**
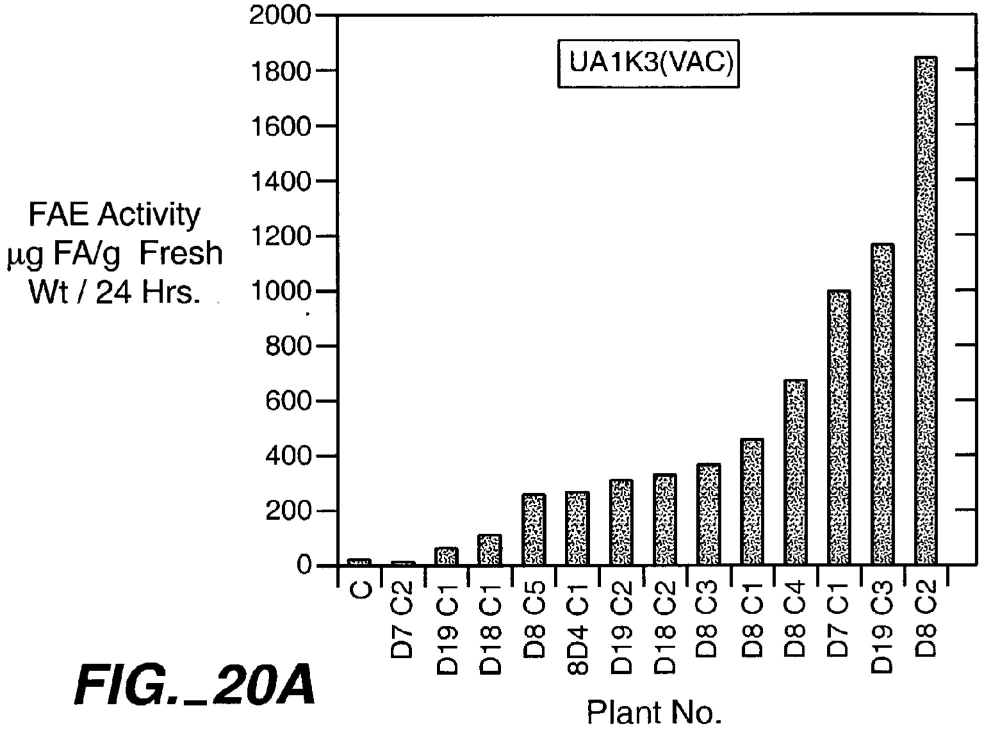
FIG._20A
**FAE Activity in Leaves of Primary Transformants of *Lolium multiflorum* Under VAC APO and ER Targeting Sequence**
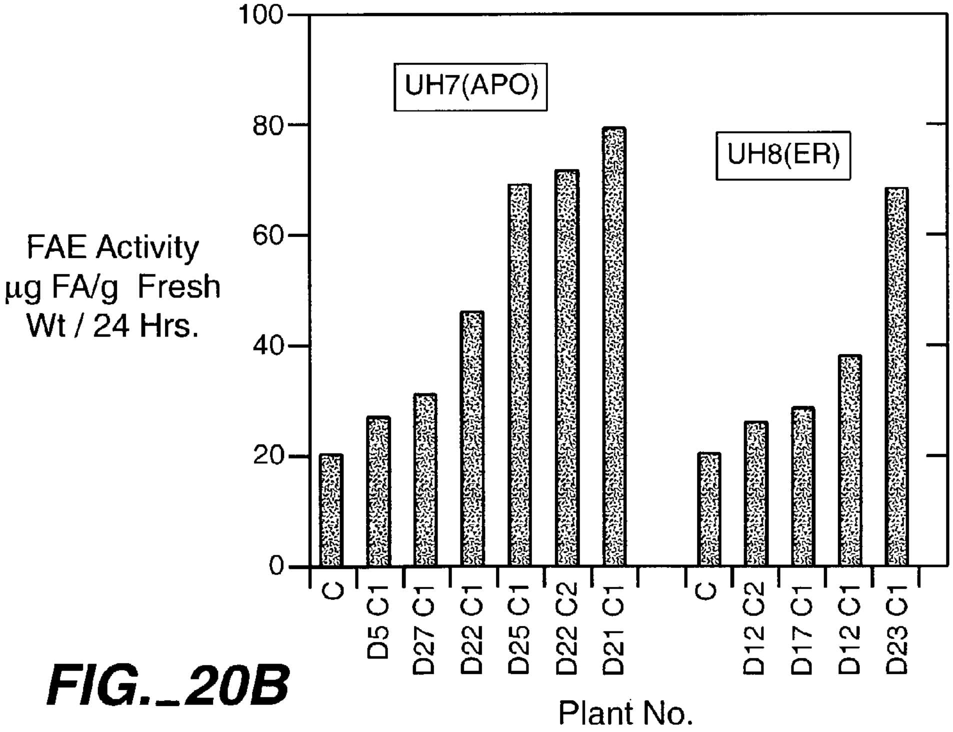
FIG._20B

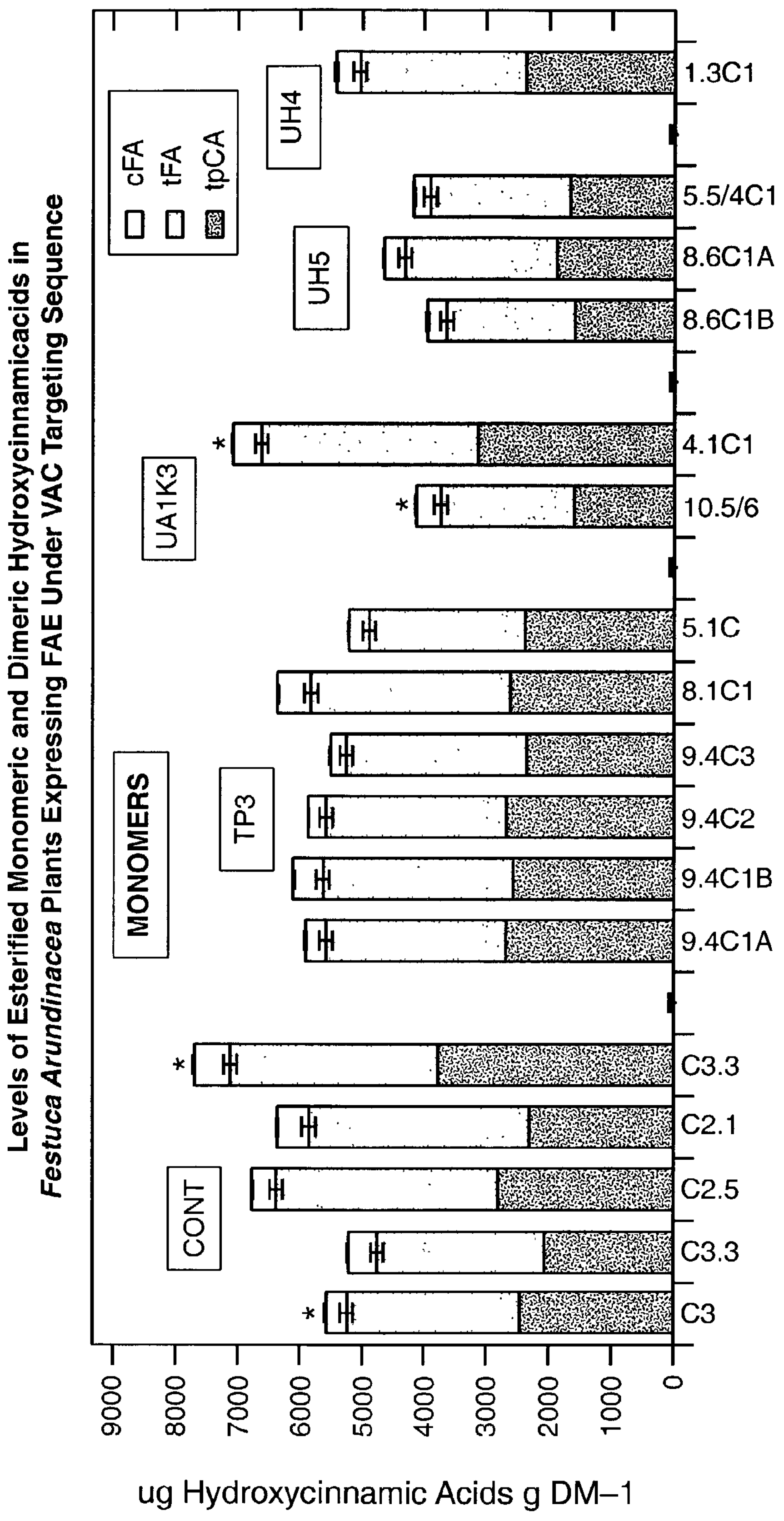
FIG._21A

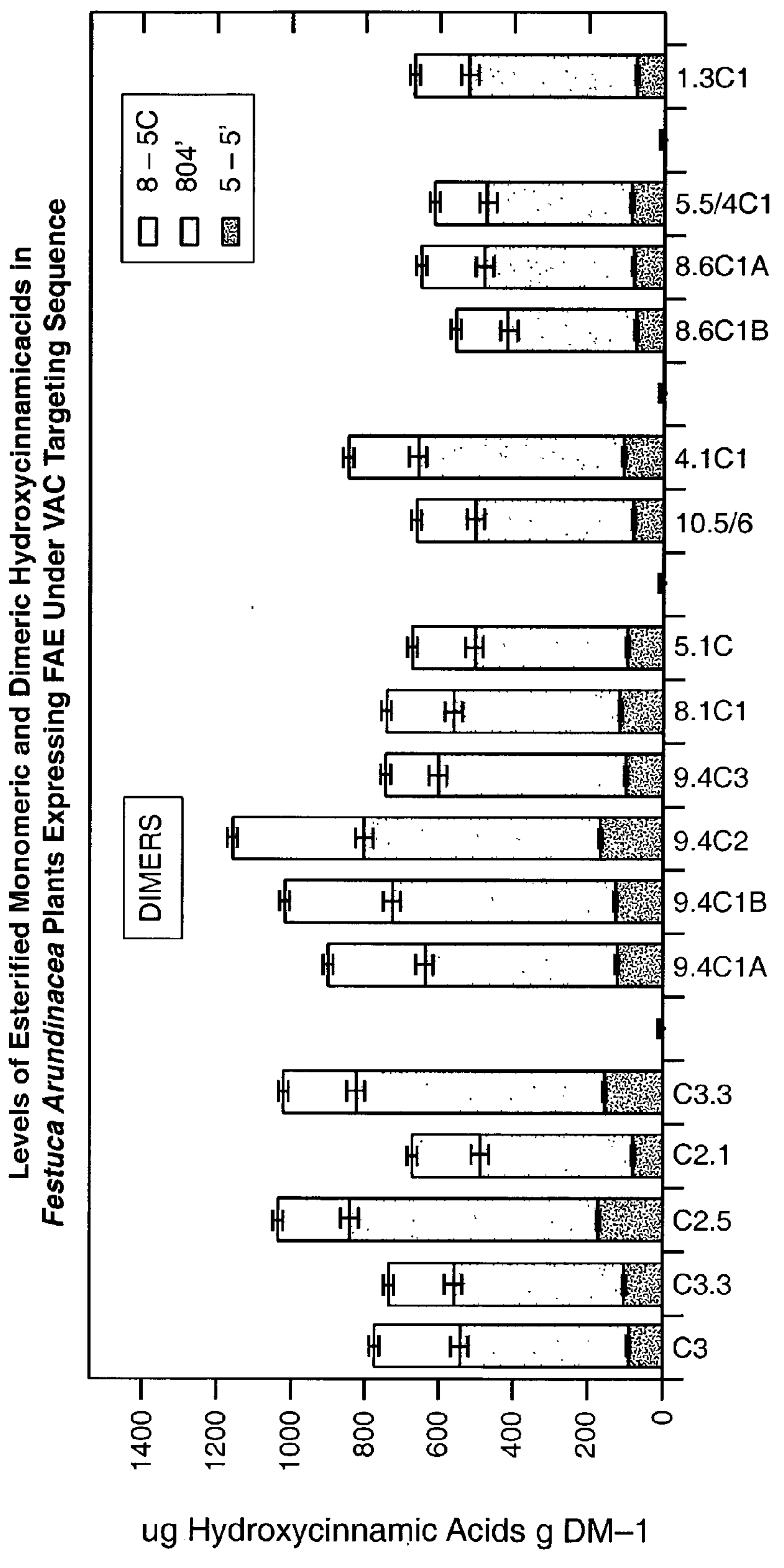
FIG._21B

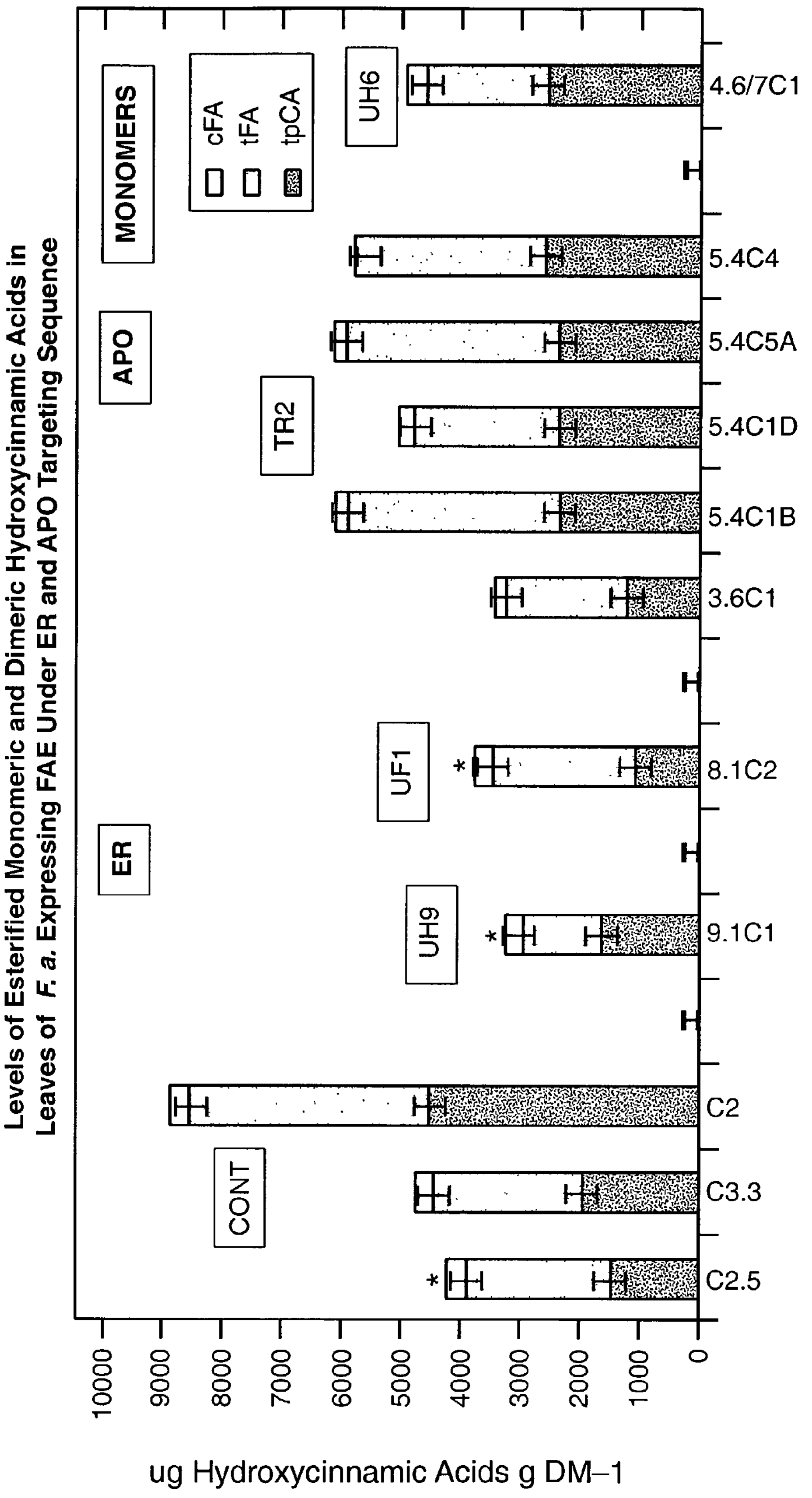
*FIG._22A*

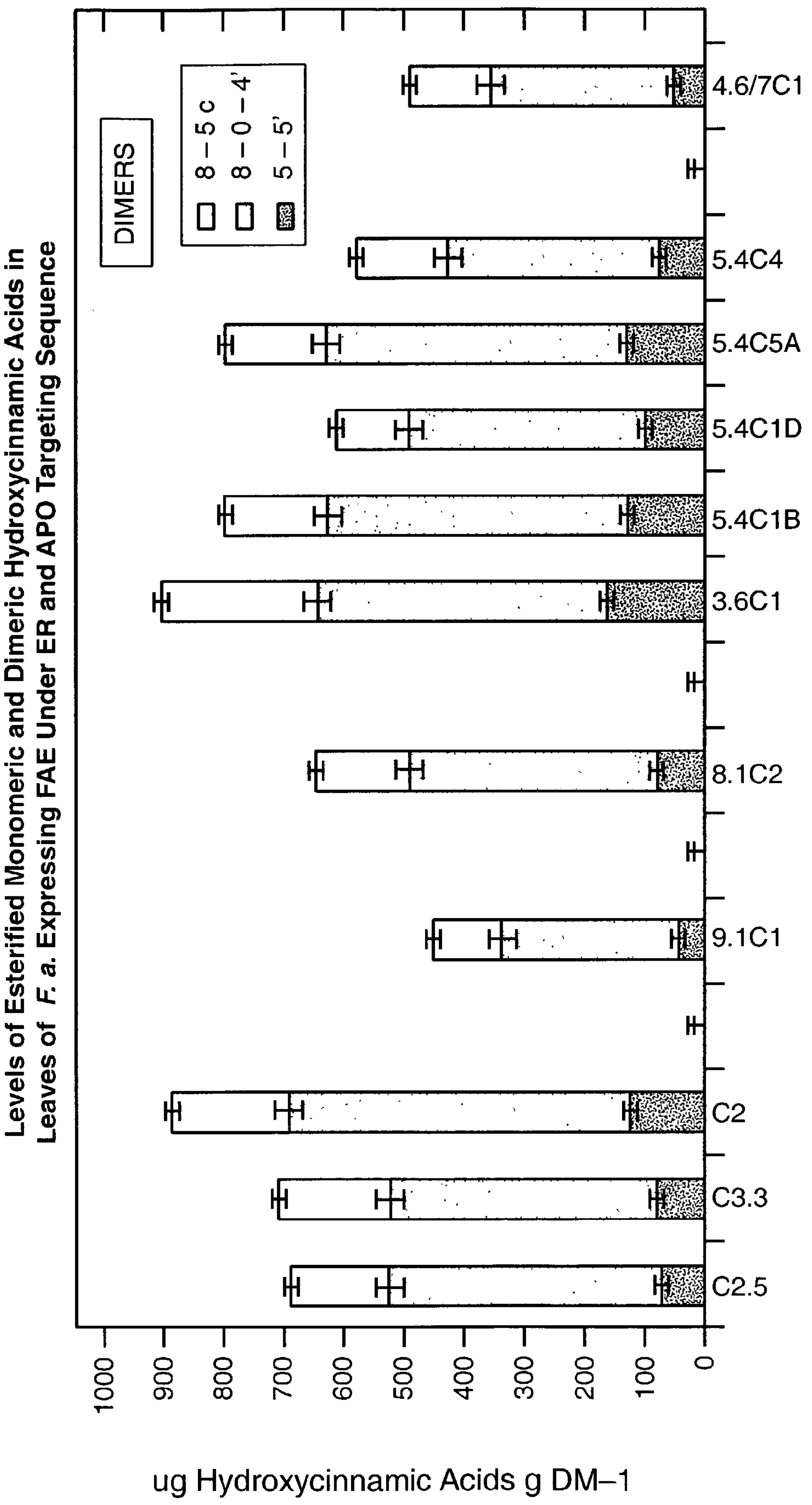
FIG._22B

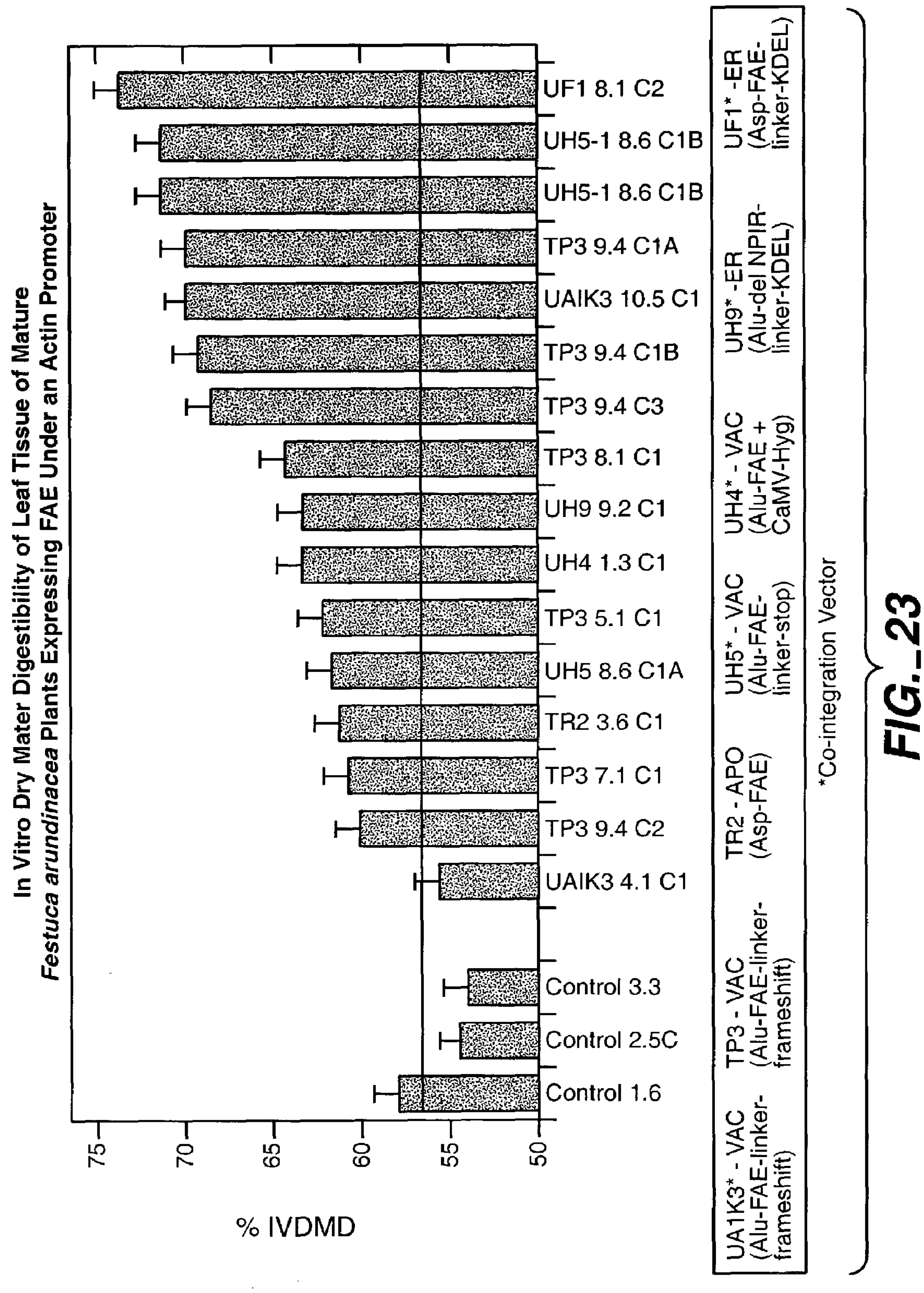
FIG._23

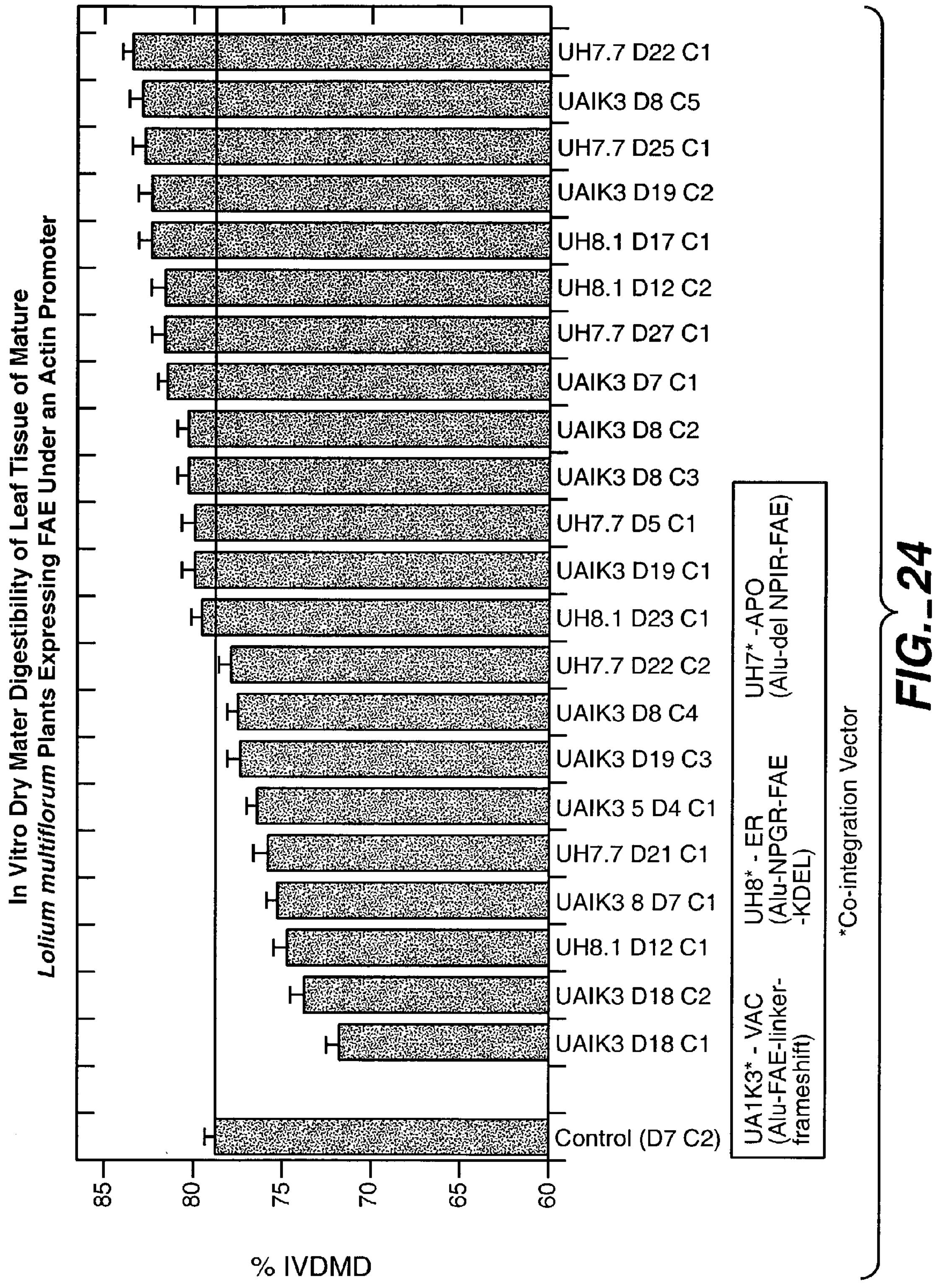
FIG._24

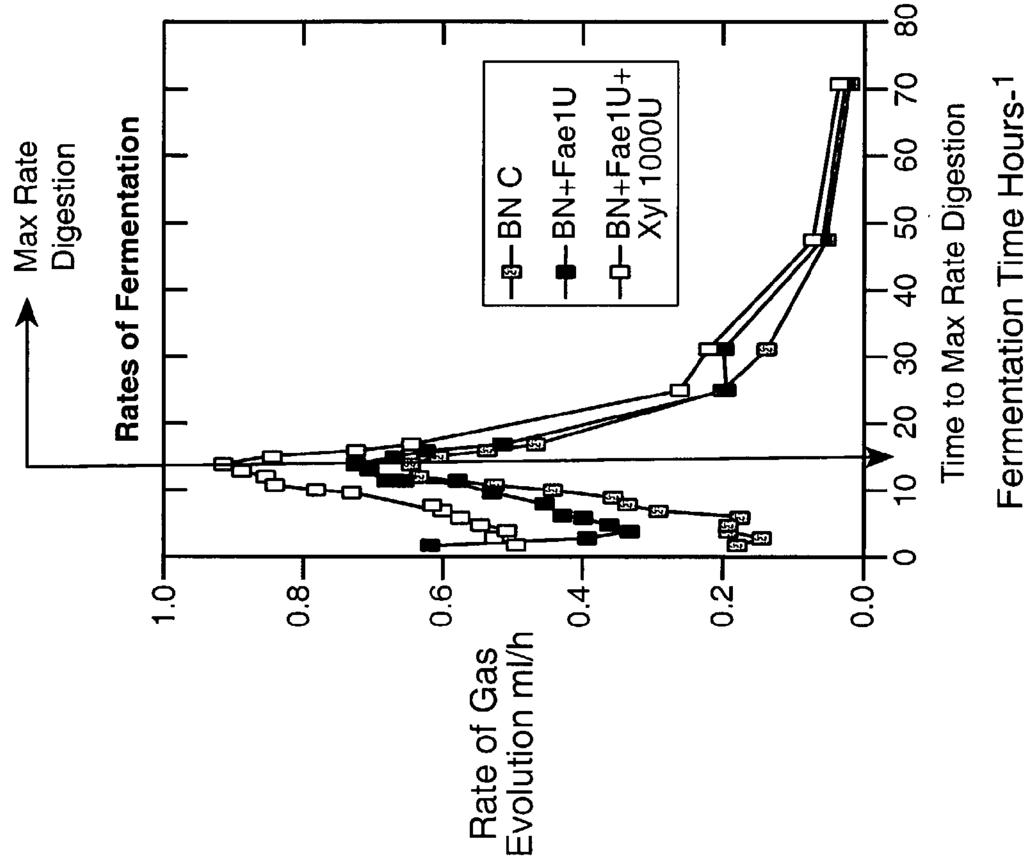
FIG._25B
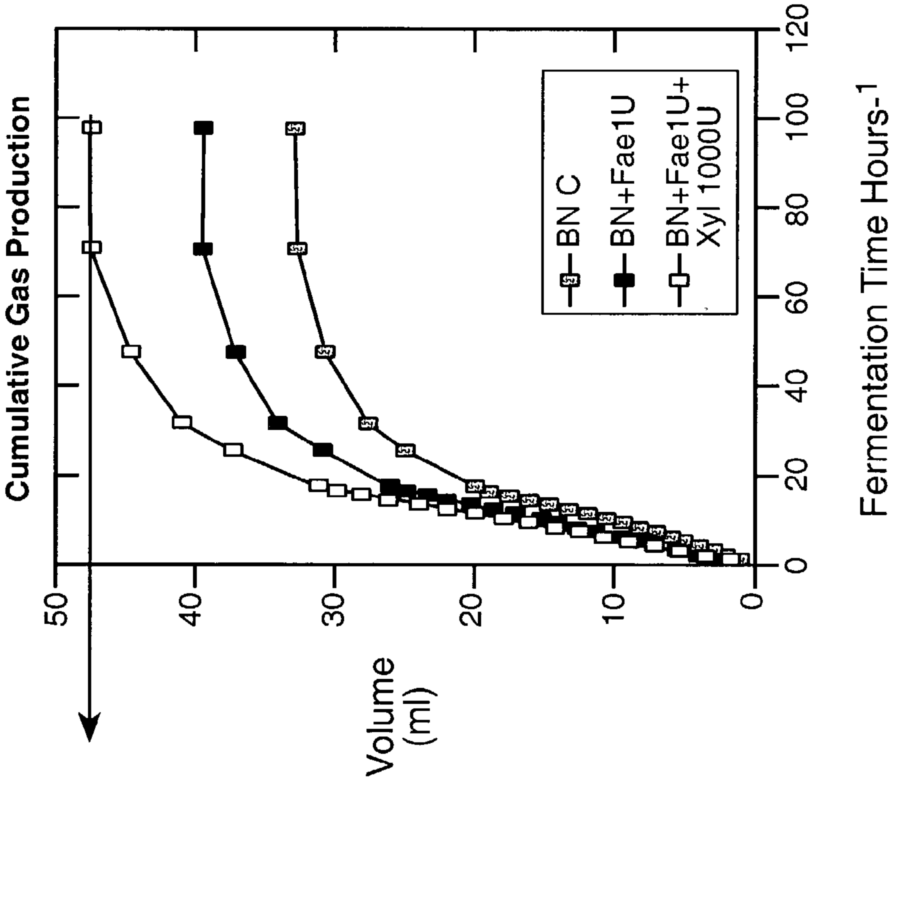
FIG._25A

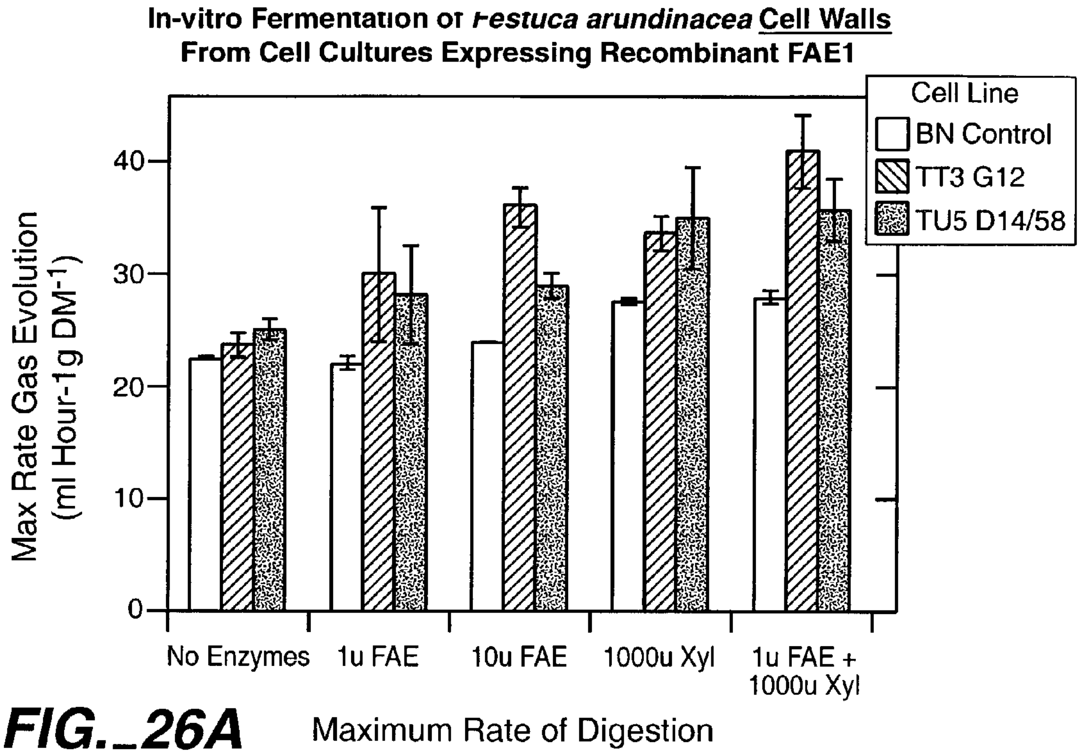
FIG._26A Maximum Rate of Digestion
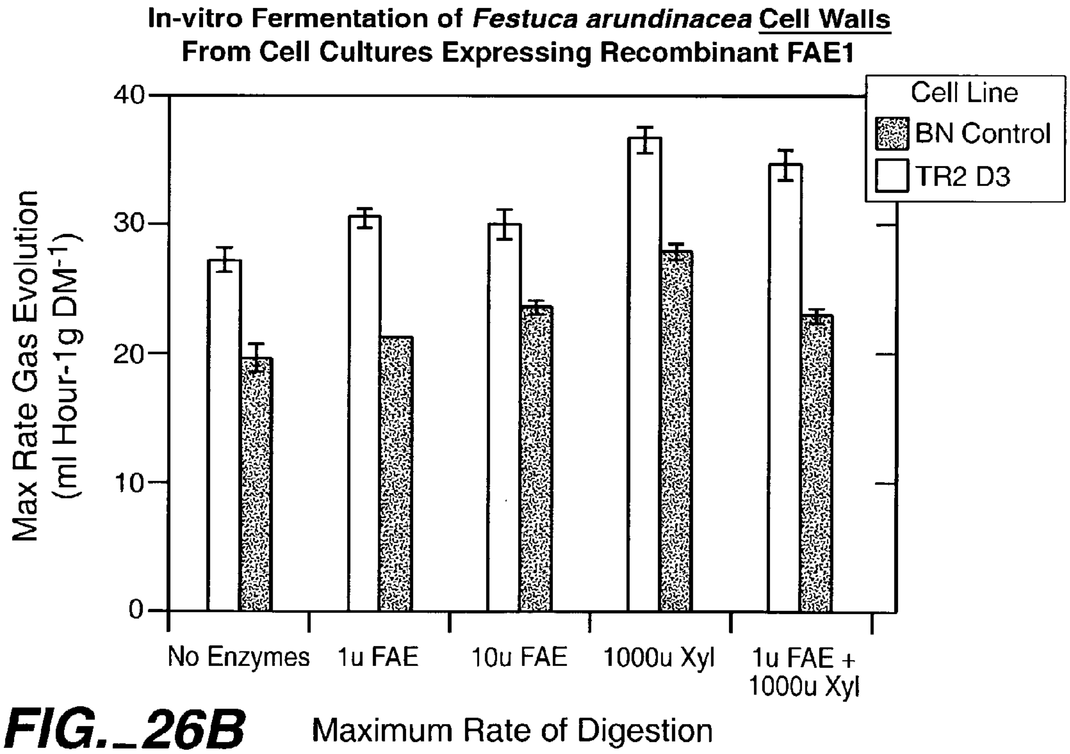
FIG._26B Maximum Rate of Digestion

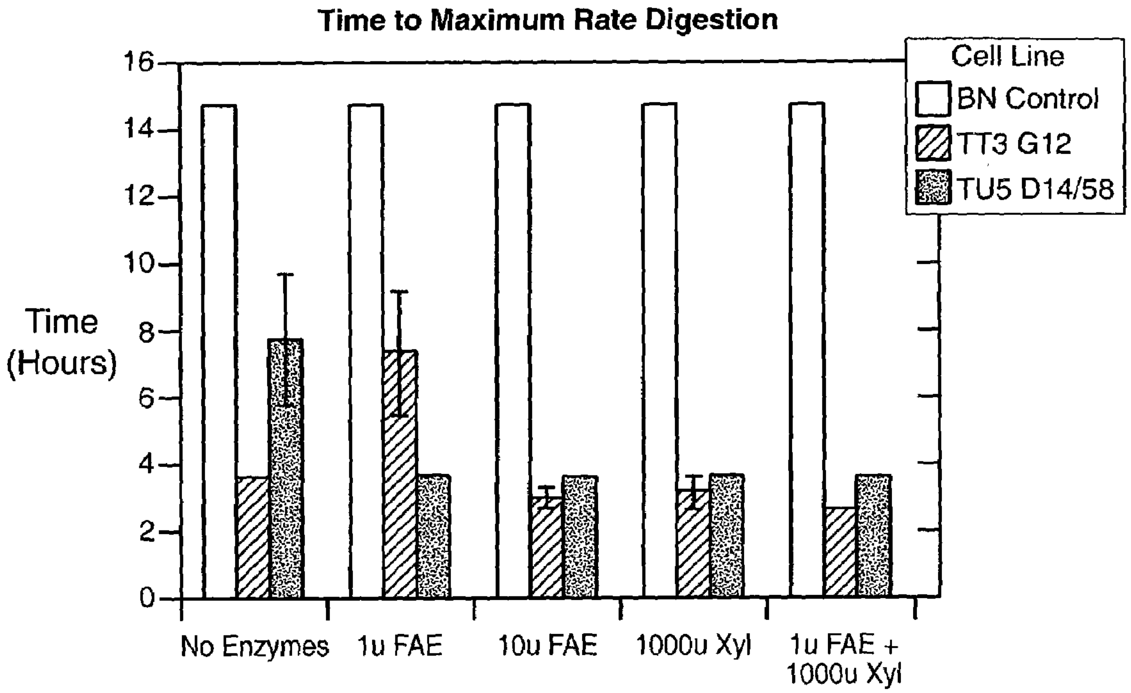
FIG._27A
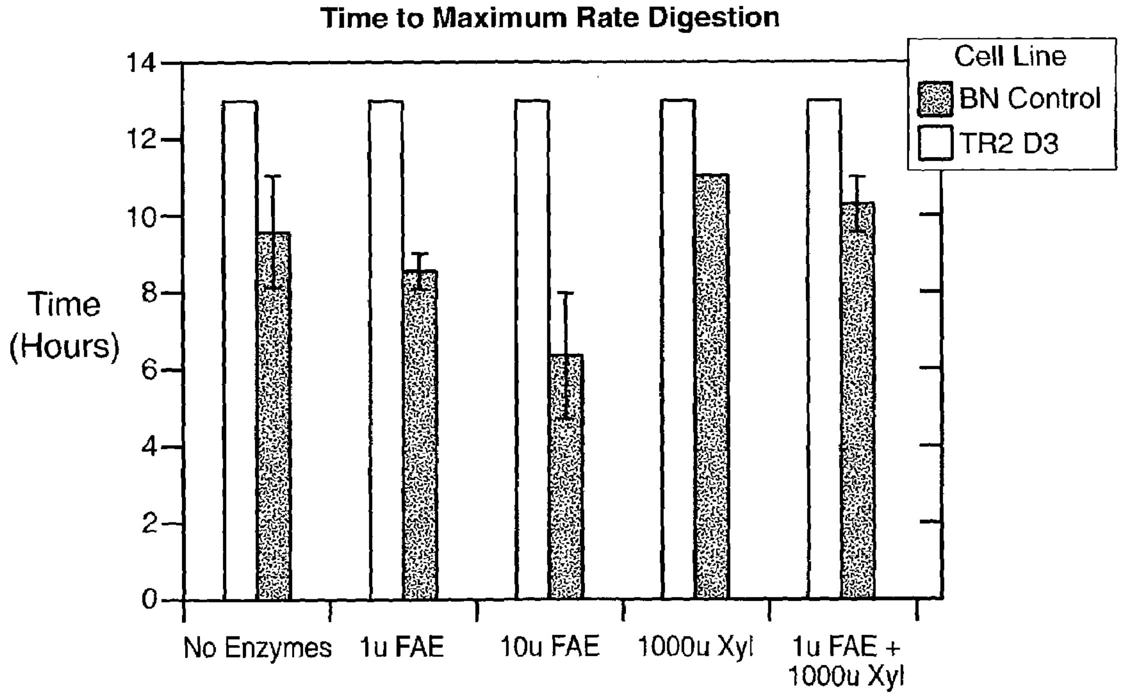
FIG._27B

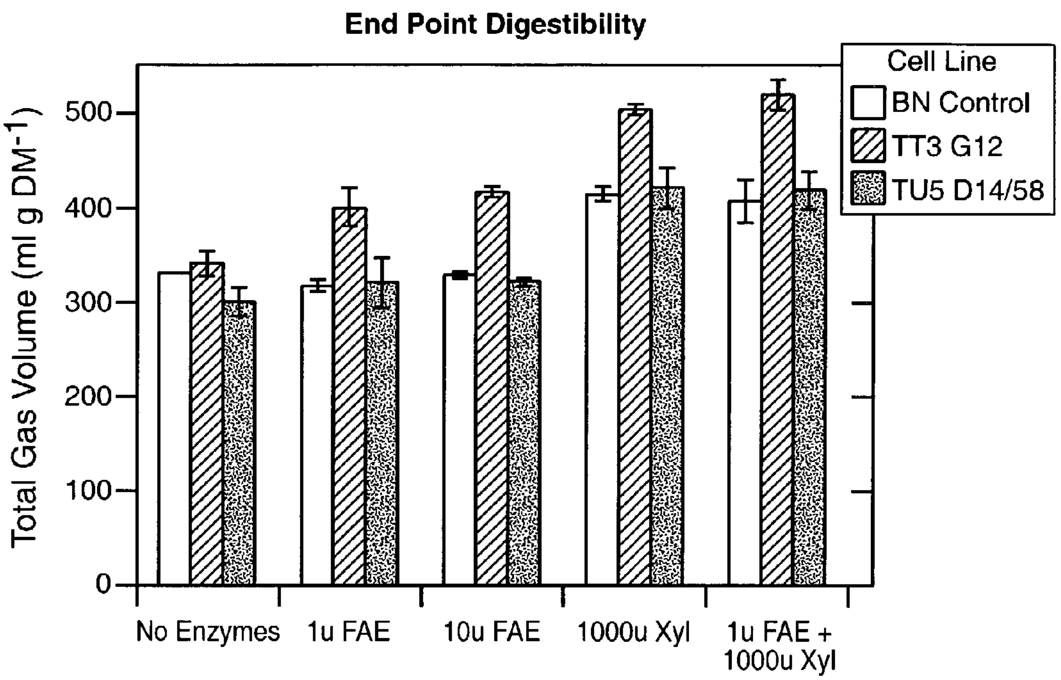
FIG._28A
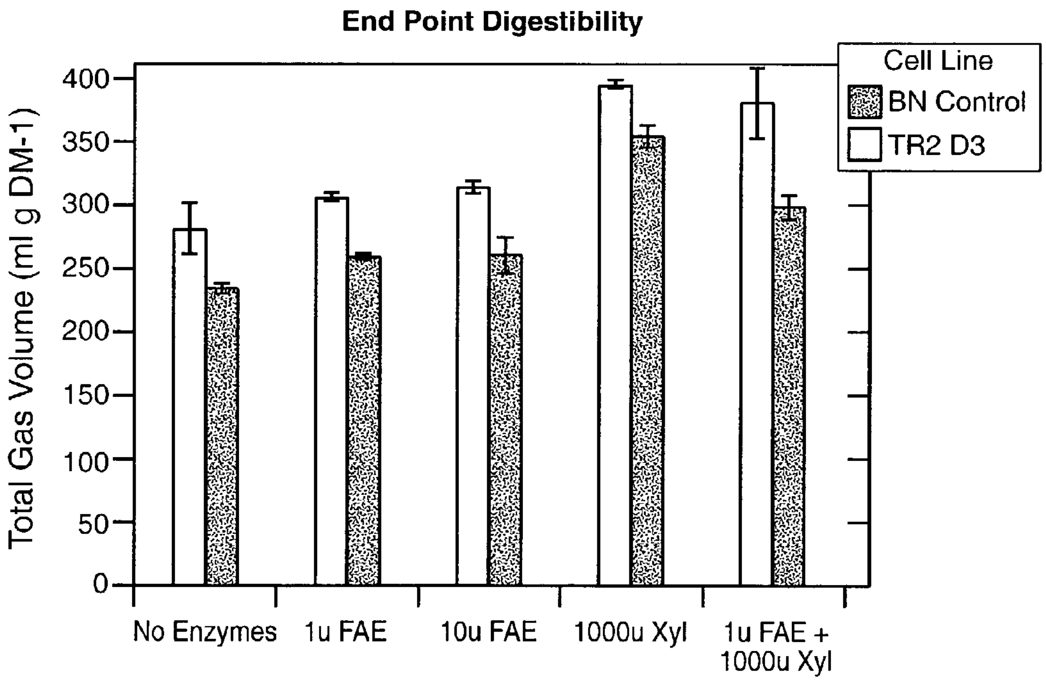
FIG._28B

**Kinetics of FAE Activity by Ferulic Acid Release from Cell Wall under Self Digestion in *Festuca arundinacea* and Stimulation by Xylanase**
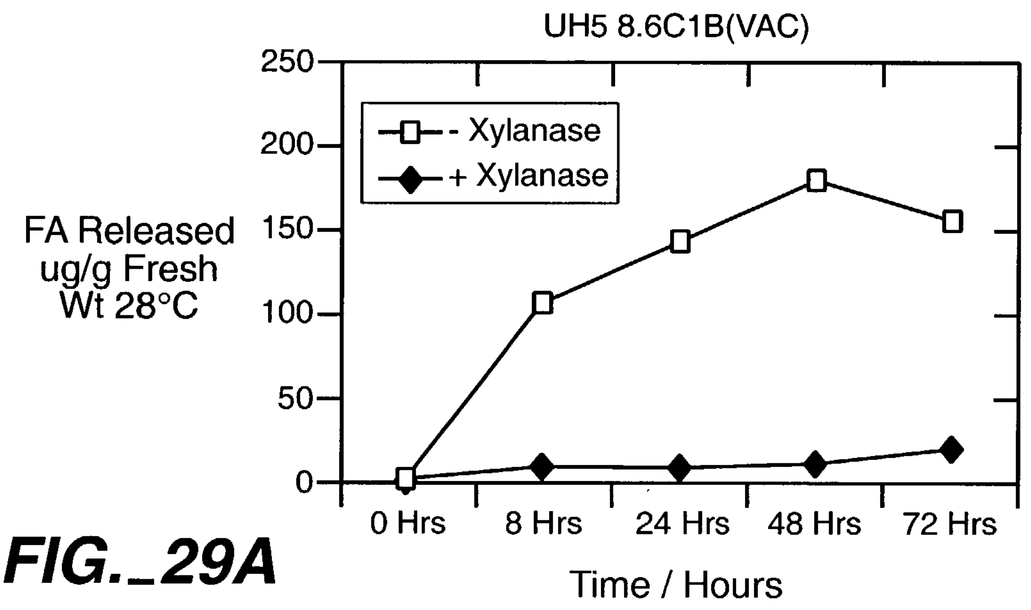
*FIG._29A*
**Kinetics of FAE Activity by Ferulic Acid Release from Cell Wall under Self Digestion in *Festuca arundinacea* and Stimulation by Xylanase.**
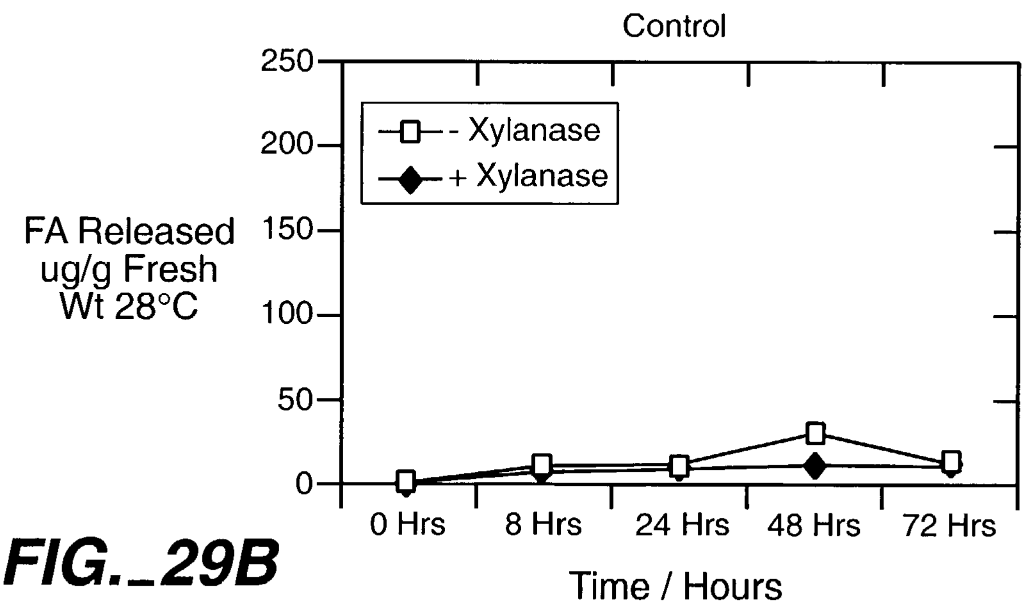
*FIG._29B*

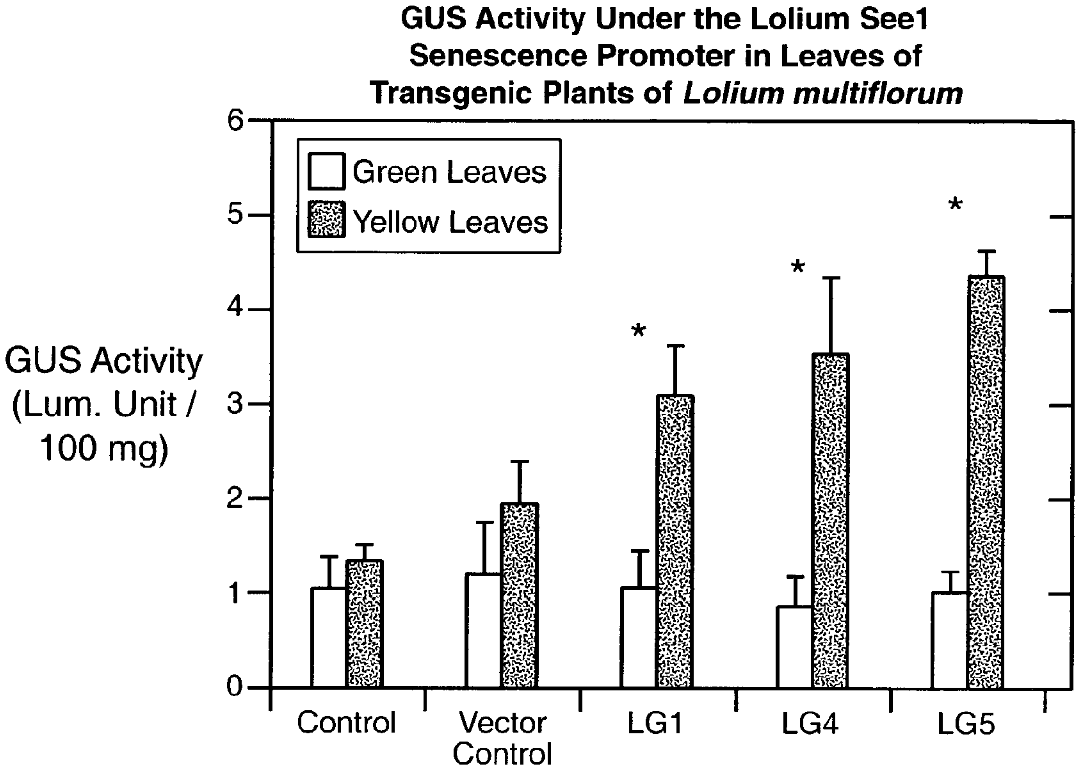
FIG._30

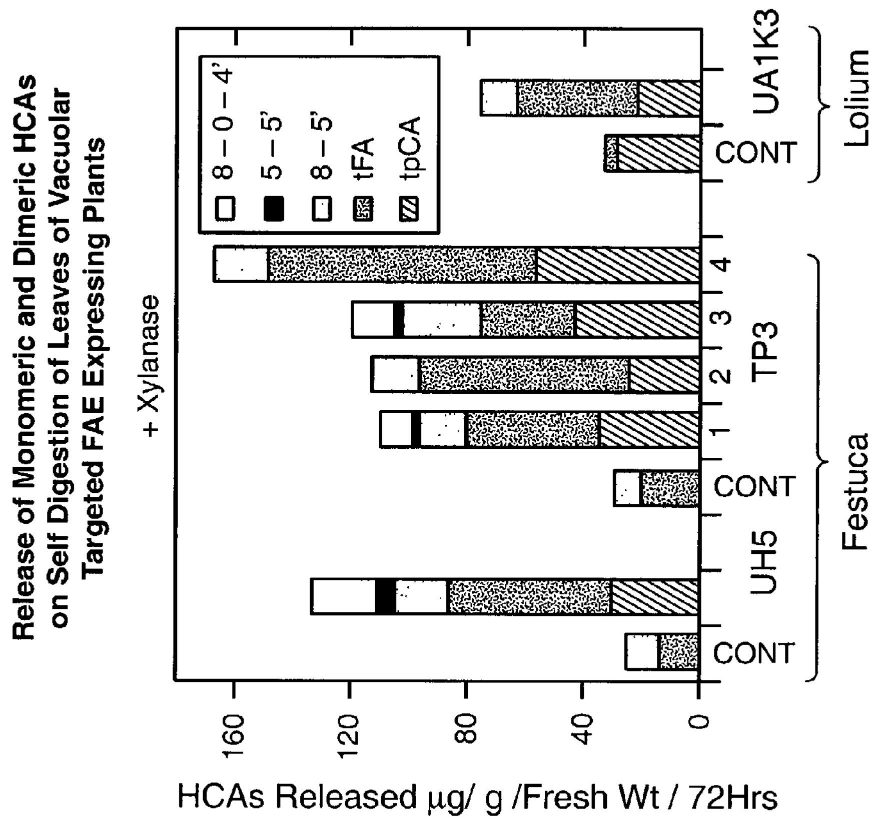
FIG._31B
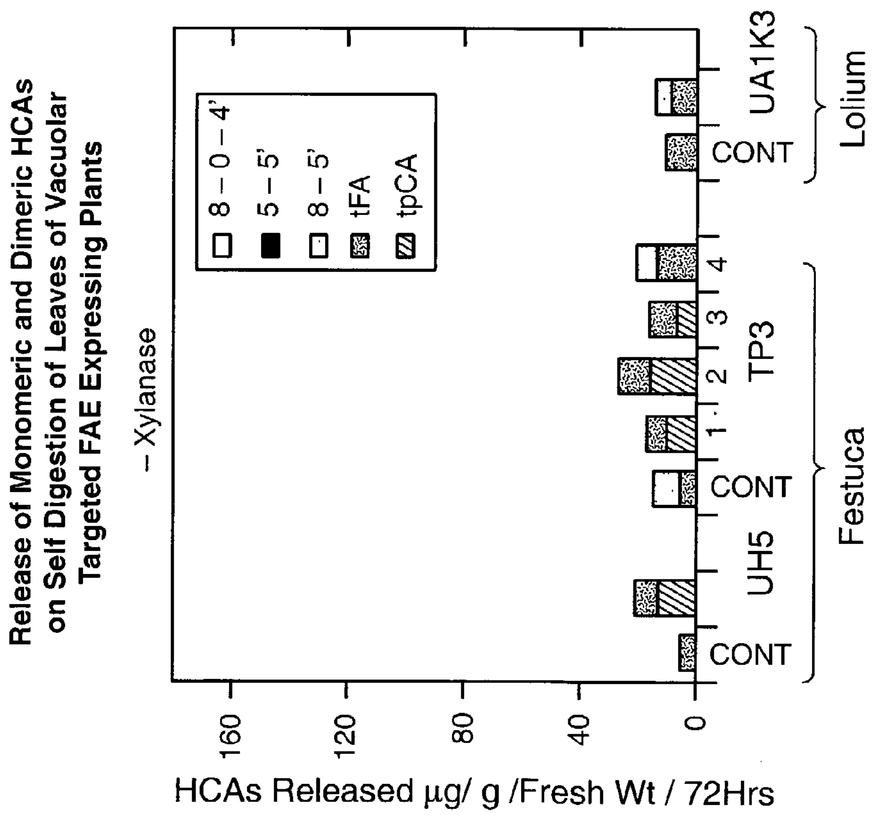
FIG._31A

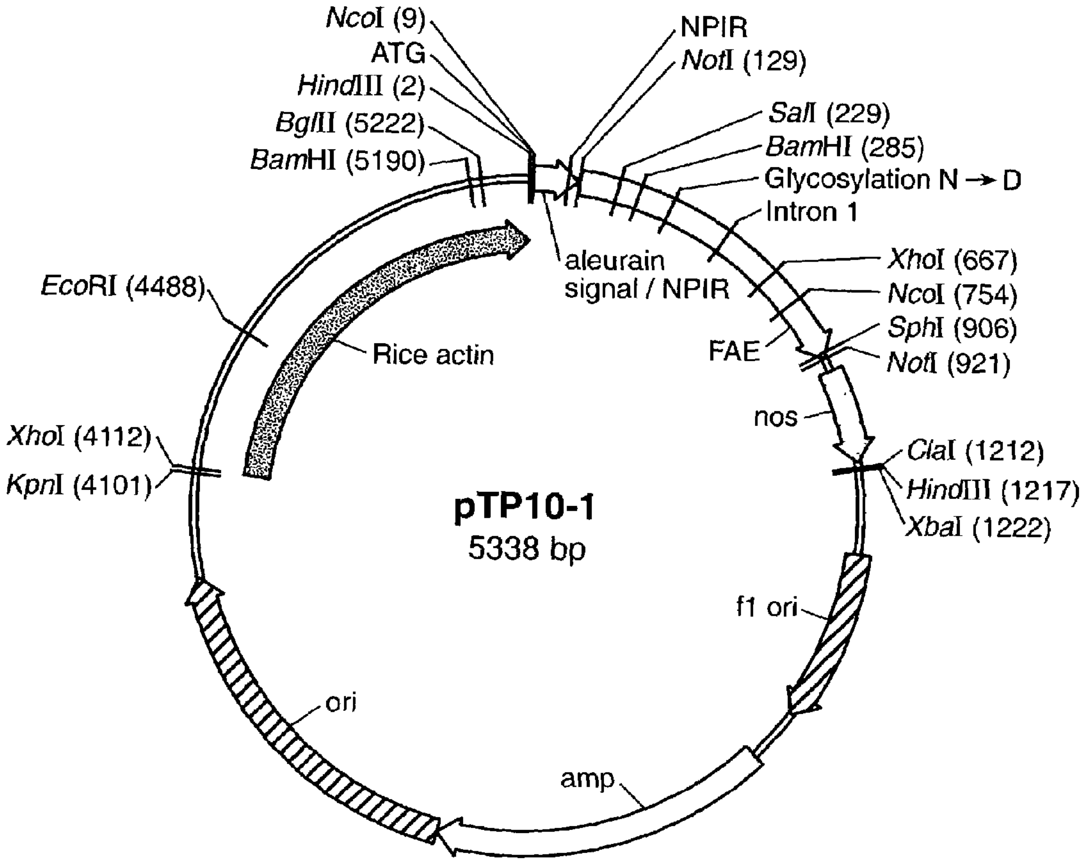
FIG._32A

```
                NcoI
               ~~~~~~~~
     HindIII
     ~~~~~~
                M  A  H  A   R  V  L   L  L  A  L   A  V  L   A  T  A   A  V  A  V
  1  AAGCTTACCA TGGCCCACGC CCGCGTCCTC CTCCTGGCGC TCGCCGTGCT GGCCACGGCC GCCGTCGCCG

                                            NPIR                      NotI
                                       ~~~~~~~~~~~~~~               ~~~~~~~~~
     · A  S  S   S  S  F   A  D  S  N   P  I  R   P  V  T   D  R  A  A   A  S  T ·
 71  TCGCCTCCTC CTCCTCCTTC GCCGACTCCA ACCCGATCCG GCCCGTCACC GACCGCGCGG CCGCCTCCAC
     ·Q  G  I   S  E  D  L   Y  S  R   L  V  E   M  A  T  I   S  Q  A   A  Y  A
141  GCAGGGCATC TCCGAAGACC TCTACAGCCG TTTAGTCGAA ATGGCCACTA TCTCCCAAGC TGCCTACGCC

                        SalI
                       ~~~~~~~~
      D  L  C  N   I  P  S   T  I  I   K  G  E  K   I  Y  N   S  Q  T   D  I  N  G
211  GACCTGTGCA ACATTCCGTC GACTATTATC AAGGGAGAGA AAATTTACAA TTCTCAAACT GACATTAACG

        BamHI
        ~~~~~~
     · W  I  L   R  D  D   S  S  K  E   I  I  T   V  F  R   G  T  G  S   D  T  N ·
281  GATGGATCCT CCGCGACGAC AGCAGCAAAG AAATAATCAC CGTCTTCCGT GGCACTGGTA GTGATACGAA

                       Glycosylation
                       ~~~~
     ·L  Q  L   D  T  D  Y   T  L  T   P  F  D   T  L  P  Q   C  N  G   C  E  V
351  TCTACAACTC GATACTGACT ACACCCTCAC GCCTTTCGAC ACCCTACCAC AATGCAACGG TTGTGAAGTA
      H  G  G  Y   Y  I  G   W  V  S   V  Q  D  Q   V  E  S   L  V  K   Q  Q  V  S
421  CACGGTGGAT ATTATATTGG ATGGGTCTCC GTCCAGGACC AAGTCGAGTC GCTTGTCAAA CAGCAGGTTA
     · Q  Y  P   D  Y  A   L  T  V  T   G  H  X   L  G  A   S  L  A  A   L  T  A ·
491  GCCAGTATCC GGACTACGCG CTGACCGTGA CCGGCCACKC CCTCGGCGCC TCCCTGGCGG CACTCACTGC
     ·A  Q  L   S  A  T  Y   D  N  I   R  L  Y   T  F  G  E   P  R  S   G  N  Q
561  CGCCCAGCTG TCTGCGACAT ACGACAACAT CCGCCTGTAC ACCTTCGGCG AACCGCGCAG CGGCAATCAG
```

FIG._32B

```
                                                  XhoI
                                                 ~~~~~~~
      A  F  A  S   Y  M  N   D  A  F   Q  A  S  S   P  D  T   T  Q  Y   F  R  V  T
631  GCCTTCGCGT CGTACATGAA CGATGCCTTC CAAGCCTCGA GCCCAGATAC GACGCAGTAT TTCCGGGTCA

                                                                 NcoI
                                                                ~~~~~~~
     · H  A  N   D  G  I   P  N  L  P   P  V  E   Q  G  Y   A  H  G  G   V  E  Y ·
701  CTCATGCCAA CGACGGCATC CCAAACCTGC CCCCGGTGGA GCAGGGGTAC GCCCATGGCG GTGTAGAGTA
     ·W  S  V   D  P  Y  S   A  Q  N   T  F  V   C  T  G  D   E  V  Q   C  C  E
771  CTGGAGCGTT GATCCTTACA GCGCCCAGAA CACATTTGTC TGCACTGGGG ATGAAGTGCA GTGCTGTGAG

                                                                        SphI
                                                                        ~~~~
      A  Q  G  G   Q  G  V   N  N  A   H  T  T  Y   F  G  M   T  S  G   A  C  T  W
841  GCCCAGGGCG GACAGGGTGT GAATAATGCG CACACGACTT ATTTTGGGAT GACGAGCGGC GCATGCACCT

             NotI                 KDEL
          ~~~~~~~~~~         ~~~~~~~~~~~~~~
     · P  V  A   A  A  E   T  T  E  G   *
911  GGCCGGTCGC GGCCGCGGAA ACCACTGAAG GATGAGCTGT AAAGAAGCAG ATCGTTCAAA CATTTGGCAA
981  TAAAGTTTCT TAAGATTGAA TCCTGTTGCC GGTCTTGCGA TGATTATCAT ATAATTTCTG TTGAATTACG
1051 TTAAGCATGT AATAATTAAC ATGTAATGCA TGACGTTATT TATGAGATGG GTTTTTATGA TTAGAGTCCC
1121 GCAATTATAC ATTTAATACG CGATAGAAAA CAAAATATAG CGCGCAAACT AGGATAAATT ATCGCGCGCG

                                HindIII
                                ~~~~~~~
                           ClaI       XbaI
                          ~~~~~~     ~~~~~~
1191 GTGTCATCTA TGTTACTAGA TCGATAAGCT TCTAGAGCGG CCGGTGGAGC TCCAATTCGC CCTATAGTGA
1261 GTCGTATTAC GCGCGCTCAC TGGCCGTCGT TTTACAACGT CGTGACTGGG AAAACCCTGG CGTTACCCAA
1331 CTTAATCGCC TTGCAGCACA TCCCCCTTTC GCCAGCTGGC GTAATAGCGA AGAGGCCCGC ACCGATCGCC
1401 CTTCCCAACA GTTGCGCAGC CTGAATGGCG AATGGGACGC GCCCTGTAGC GGCGCATTAA GCGCGGCGGG
```

FIG._32C

1471 TGTGGTGGTT ACGCGCAGCG TGACCGCTAC ACTTGCCAGC GCCCTAGCGC CCGCTCCTTT CGCTTTCTTC
1541 CCTTCCTTTC TCGCCACGTT CGCCGGCTTT CCCCGTCAAG CTCTAAATCG GGGGCTCCCT TTAGGGTTCC
1611 GATTTAGTGC TTTACGGCAC CTCGACCCCA AAAAACTTGA TTAGGGTGAT GGTTCACGTA GTGGGCCATC
1681 GCCCTGATAG ACGGTTTTTC GCCCTTTGAC GTTGGAGTCC ACGTTCTTTA ATAGTGGACT CTTGTTCCAA
1751 ACTGGAACAA CACTCAACCC TATCTCGGTC TATTCTTTTG ATTTATAAGG GATTTTGCCG ATTTCGGCCT
1821 ATTGGTTAAA AAATGAGCTG ATTTAACAAA AATTTAACGC GAATTTTAAC AAAATATTAA CGCTTACAAT
1891 TTAGGTGGCA CTTTTCGGGG AAATGTGCGC GGAACCCCTA TTTGTTTATT TTTCTAAATA CATTCAAATA
1961 TGTATCCGCT CATGAGACAA TAACCCTGAT AAATGCTTCA ATAATATTGA AAAAGGAAGA GTATGAGTAT
2031 TCAACATTTC CGTGTCGCCC TTATTCCCTT TTTTGCGGCA TTTTGCCTTC CTGTTTTTGC TCACCCAGAA
2101 ACGCTGGTGA AAGTAAAAGA TGCTGAAGAT CAGTTGGGTG CACGAGTGGG TTACATCGAA CTGGATCTCA
2171 ACAGCGGTAA GATCCTTGAG AGTTTTCGCC CCGAAGAACG TTTTCCAATG ATGAGCACTT TTAAAGTTCT
2241 GCTATGTGGC GCGGTATTAT CCCGTATTGA CGCCGGGCAA GAGCAACTCG GTCGCCGCAT ACACTATTCT
2311 CAGAATGACT TGGTTGAGTA CTCACCAGTC ACAGAAAAGC ATCTTACGGA TGGCATGACA GTAAGAGAAT
2381 TATGCAGTGC TGCCATAACC ATGAGTGATA ACACTGCGGC CAACTTACTT CTGACAACGA TCGGAGGACC
2451 GAAGGAGCTA ACCGCTTTTT TGCACAACAT GGGGGATCAT GTAACTCGCC TTGATCGTTG GGAACCGGAG
2521 CTGAATGAAG CCATACCAAA CGACGAGCGT GACACCACGA TGCCTGTAGC AATGGCAACA ACGTTGCGCA
2591 AACTATTAAC TGGCGAACTA CTTACTCTAG CTTCCCGGCA ACAATTAATA GACTGGATGG AGGCGGATAA
2661 AGTTGCAGGA CCACTTCTGC GCTCGGCCCT TCCGGCTGGC TGGTTTATTG CTGATAAATC TGGAGCCGGT
2731 GAGCGTGGGT CTCGCGGTAT CATTGCAGCA CTGGGGCCAG ATGGTAAGCC CTCCCGTATC GTAGTTATCT
2801 ACACGACGGG GAGTCAGGCA ACTATGGATG AACGAAATAG ACAGATCGCT GAGATAGGTG CCTCACTGAT
2871 TAAGCATTGG TAACTGTCAG ACCAAGTTTA CTCATATATA CTTTAGATTG ATTTAAAACT TCATTTTTAA
2941 TTTAAAAGGA TCTAGGTGAA GATCCTTTTT GATAATCTCA TGACCAAAAT CCCTTAACGT GAGTTTTCGT
3011 TCCACTGAGC GTCAGACCCC GTAGAAAAGA TCAAAGGATC TTCTTGAGAT CCTTTTTTTC TGCGCGTAAT
3081 CTGCTGCTTG CAAACAAAAA AACCACCGCT ACCAGCGGTG GTTTGTTTGC CGGATCAAGA GCTACCAACT
3151 CTTTTTCCGA AGGTAACTGG CTTCAGCAGA GCGCAGATAC CAAATACTGT CCTTCTAGTG TAGCCGTAGT
3221 TAGGCCACCA CTTCAAGAAC TCTGTAGCAC CGCCTACATA CCTCGCTCTG CTAATCCTGT TACCAGTGGC
3291 TGCTGCCAGT GGCGATAAGT CGTGTCTTAC CGGGTTGGAC TCAAGACGAT AGTTACCGGA TAAGGCGCAG
3361 CGGTCGGGCT GAACGGGGGG TTCGTGCACA CAGCCCAGCT TGGAGCGAAC GACCTACACC GAACTGAGAT
3431 ACCTACAGCG TGAGCTATGA GAAAGCGCCA CGCTTCCCGA AGGGAGAAAG GCGGACAGGT ATCCGGTAAG
3501 CGGCAGGGTC GGAACAGGAG AGCGCACGAG GGAGCTTCCA GGGGGAAACG CCTGGTATCT TTATAGTCCT
3571 GTCGGGTTTC GCCACCTCTG ACTTGAGCGT CGATTTTTGT GATGCTCGTC AGGGGGGCGG AGCCTATGGA
3641 AAAACGCCAG CAACGCGGCC TTTTTACGGT TCCTGGCCTT TTGCTGGCCT TTTGCTCACA TGTTCTTTCC
3711 TGCGTTATCC CCTGATTCTG TGGATAACCG TATTACCGCC TTTGAGTGAG CTGATACCGC TCGCCGCAGC
3781 CGAACGACCG AGCGCAGCGA GTCAGTGAGC GAGGAAGCGG AAGAGCGCCC AATACGCAAA CCGCCTCTCC
3851 CCGCGCGTTG GCCGATTCAT TAATGCAGCT GGCACGACAG GTTTCCCGAC TGGAAAGCGG GCAGTGAGCG

FIG._32D

```
3921  CAACGCAATT AATGTGAGTT AGCTCACTCA TTAGGCACCC CAGGCTTTAC ACTTTATGCT TCCGGCTCGT
3991  ATGTTGTGTG GAATTGTGAG CGGATAACAA TTTCACACAG GAAACAGCTA TGACCATGAT TACGCCAAGC
                                                   KpnI           XhoI
                                                 ~~~~~~~        ~~~~~~~
4061  GCGCAATTAA CCCTCACTAA AGGGAACAAA AGCTGGGTAC CGGGCCCCCC CTCGAGGTCA TTCATATGCT
4131  TGAGAAGAGA GTCGGGATAG TCCAAAATAA AACAAAGGTA AGATTACCTG GTCAAAAGTG AAAACATCAG
4201  TTAAAAGGTG GTATAAGTAA AATATCGGTA ATAAAAGGTG GCCCAAAGTG AAATTTACTC TTTTCTACTA
4271  TTATAAAAAT TGAGGATGTT TTGTCGGTAC TTTGATACGT CATTTTTGTA TGAATTGGTT TTTAAGTTTA
4341  TTCGCGATTT GGAAATGCAT ATCTGTATTT GAGTCGGTTT TTAAGTTCGT TGCTTTTGTA AATACAGAGG
4411  GATTTGTATA AGAAATATCT TTAAAAAACC CATATGCTAA TTTGACATAA TTTTTGAGAA AAATATATAT
           EcoRI
          ~~~~~~~
4481  TCAGGCGAAT TCCACAATGA ACAATAATAA GATTAAAATA GCTTGCCCCC GTTGCAGCGA TGGGTATTTT
4551  TTCTAGTAAA ATAAAAGATA AACTTAGACT CAAAACATTT ACAAAAACAA CCCCTAAAGT CCTAAAGCCC
4621  AAAGTGCTAT GCACGATCCA TAGCAAGCCC AGCCCAACCC AACCCAACCC AACCCACCCC AGTGCAGCCA
4691  ACTGGCAAAT AGTCTCCACC CCCGGCACTA TCACCGTGAG TTGTCCGCAC CACCGCACGT CTCGCAGCCA
4761  AAAAAAAAAA AAGAAAGAAA AAAAAGAAAA AGAAAAAACAG CAGGTGGGTC CGGGTCGTGG GGGCCGGAAA
4831  AGCGAGGAGG ATCGCGAGCA GCGACGAGGC CCGGCCCTCC CTCCGCTTCC AAAGAAACGC CCCCCATCGC
4901  CACTATATAC ATACCCCCCC CTCTCCTCCC ATCCCCCCAA CCCTACCACC ACCACCACCA CCACCTCCTC
4971  CCCCCTCGCT GCCGGACGAC GAGCTCCTCC CCCCTCCCCC TCCGCCGCCG CCGGTAACCA CCCCGCCCCT
5041  CTCCTCTTTC TTTCTCCGTT TTTTTTTTCG TCTCGGTCTC GATCTTTGGC CTTGGTAGTT TGGGTGGGCG
5111  AGAGCGGCTT CGTCGCCCAG ATCGGTGCGC GGGAGGGGCG GGATCTCGCG GCTGGCGTCT CCGGGCGTGA
            BamHI                             BglII
           ~~~~~~~                           ~~~~~~~
5181  GTCGGCCCGG ATCCTCGCGG GGAATGGGGC TCTCGGATGT AGATCTTCTT TCTTTCTTCT TTTTGTGGTA
5251  GAATTTGAAT CCCTCAGCAT TGTTCATCGG TAGTTTTTCT TTTCATGATT TGTGACAAAT GCAGCCTCGT
5321  GCGGAGCTTT TTTGTAGC
```

FIG._32E

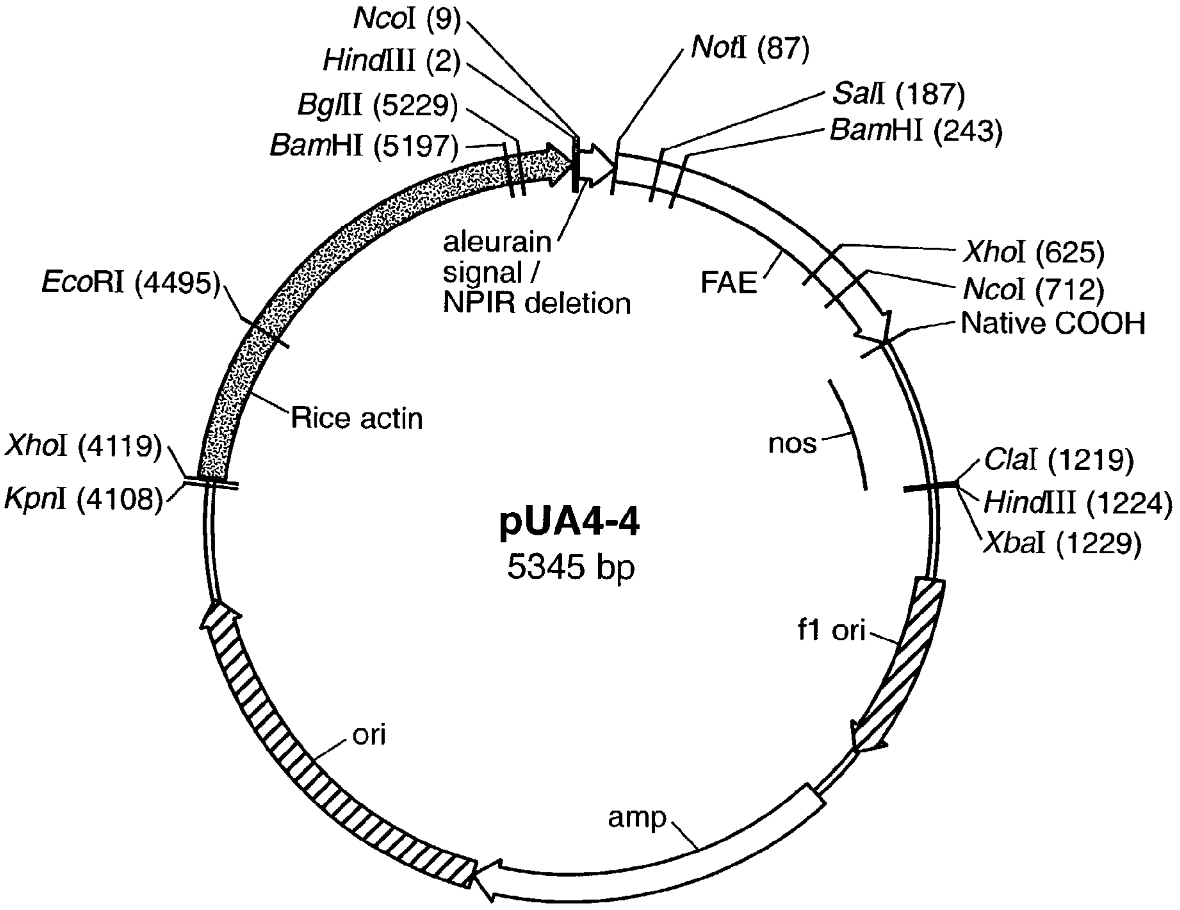
FIG._33A

```
              NcoI
             ~~~~~~~
     HindIII
     ~~~~~~
              M   A  H   A   R  V  L   L  L  A  L   A  V  L   A  T  A   A  V  A  V
  1  AAGCTTACCA TGGCCCACGC CCGCGTCCTC CTCCTGGCGC TCGCCGTGCT GGCCACGGCC GCCGTCGCCG
                   NotI
                 ~~~~~~~~~
     · A  S  S   R  A  A   A  S  T  Q   G  I  S   E  D  L   Y  S  R  L   V  E  M ·
 71  TCGCCTCCTC CCGCGCGGCC GCCTCCACGC AGGGCATCTC CGAAGACCTC TACAGCCGTT TAGTCGAAAT
                                                     SalI
                                                   ~~~~~~~
     ·A  T  I   S  Q  A  A   Y  A  D   L  C  N   I  P  S  T   I  I  K   G  E  K
141  GGCCACTATC TCCCAAGCTG CCTACGCCGA CCTGTGCAAC ATTCCGTCGA CTATTATCAA GGGAGAGAAA
                                  BamHI
                                 ~~~~~~~
      I  Y  N  S   Q  T  D   I  N  G   W  I  L  R   D  D  S   S  K  E   I  I  T  V
211  ATTTACAATT CTCAAACTGA CATTAACGGA TGGATCCTCC GCGACGACAG CAGCAAAGAA ATAATCACCG
     ·  F  R  G   T  G  S   D  T  N  L   Q  L  D   T  N  Y   T  L  T  P   F  D  T ·
281  TCTTCCGTGG CACTGGTAGT GATACGAATC TACAACTCGA TACTAACTAC ACCCTCACGC CTTTCGACAC
     ·L  P  Q   C  N  G  C   E  V  H   G  G  Y   Y  I  G  W   V  S  V   Q  D  Q
351  CCTACCACAA TGCAACGGTT GTGAAGTACA CGGTGGATAT TATATTGGAT GGGTCTCCGT CCAGGACCAA
      V  E  S  L   V  K  Q   Q  V  S   Q  Y  P  D   Y  A  L   T  V  T   G  H  X  L
421  GTCGAGTCGC TTGTCAAACA GCAGGTTAGC CAGTATCCGG ACTACGCGCT GACCGTGACC GGCCACKCCC
     ·  G  A  S   L  A  A   L  T  A  A   Q  L  S   A  T  Y   D  N  I  R   L  Y  T ·
491  TCGGCGCCTC CCTGGCGGCA CTCACTGCCG CCCAGCTGTC TGCGACATAC GACAACATCC GCCTGTACAC
                                                                         XhoI
                                                                           ~
     ·F  G  E   P  R  S  G   N  Q  A   F  A  S   Y  M  N  D   A  F  Q   A  S  S
561  CTTCGGCGAA CCGCGCAGCG GCAATCAGGC CTTCGCGTCG TACATGAACG ATGCCTTCCA AGCCTCGAGC
      P  D  T  T   Q  Y  F   R  V  T   H  A  N  D   G  I  P   N  L  P   P  V  E  Q
631  CCAGATACGA CGCAGTATTT CCGGGTCACT CATGCCAACG ACGGCATCCC AAACCTGCCC CCGGTGGAGC
                 NcoI
                ~~~~~~
     ·  G  Y  A   H  G  G   V  E  Y  W   S  V  D   P  Y  S   A  Q  N  T   F  V  C ·
```

FIG._33B

```
 701  AGGGGTACGC CCATGGCGGT GTAGAGTACT GGAGCGTTGA TCCTTACAGC GCCCAGAACA CATTTGTCTG
      ·T  G  D   E  V  Q  C   C  E  A   Q  G  G   Q  G  V  N   N  A  H   T  T  Y
 771  CACTGGGGAT GAAGTGCAGT GCTGTGAGGC CCAGGGCGGA CAGGGTGTGA ATAATGCGCA CACGACTTAT
       F  G  M  T   S  G  A   C  T  W   *
 841  TTTGGGATGA CGAGCGGAGC CTGTACATGG TGATCAGTCA TTTCAGCCTC CCCGAGTGTA CCAGGAAAGA
 911  TGGATGTCCT GGAGAGGGGG CCGCGTAACC ACTGAAGGAT GAGCTGTAAA GAAGCAGATC GTTCAAACAT
 981  TTGGCAATAA AGTTTCTTAA GATTGAATCC TGTTGCCGGT CTTGCGATGA TTATCATATA ATTTCTGTTG
1051  AATTACGTTA AGCATGTAAT AATTAACATG TAATGCATGA CGTTATTTAT GAGATGGGTT TTTATGATTA
1121  GAGTCCCGCA ATTATACATT TAATACGCGA TAGAAAACAA AATATAGCGC GCAAACTAGG ATAAATTATC
                                         HindIII
                                         ~~~~~~~
                                    ClaI        XbaI
                                   ~~~~~~~     ~~~~~~
1191  GCGCGCGGTG TCATCTATGT TACTAGATCG ATAAGCTTCT AGAGCGGCCG GTGGAGCTCC AATTCGCCCT
1261  ATAGTGAGTC GTATTACGCG CGCTCACTGG CCGTCGTTTT ACAACGTCGT GACTGGGAAA ACCCTGGCGT
1331  TACCCAACTT AATCGCCTTG CAGCACATCC CCCTTTCGCC AGCTGGCGTA ATAGCGAAGA GGCCCGCACC
1401  GATCGCCCTT CCCAACAGTT GCGCAGCCTG AATGGCGAAT GGGACGCGCC CTGTAGCGGC GCATTAAGCG
1471  CGGCGGGTGT GGTGGTTACG CGCAGCGTGA CCGCTACACT TGCCAGCGCC CTAGCGCCCG CTCCTTTCGC
1541  TTTCTTCCCT TCCTTTCTCG CCACGTTCGC CGGCTTTCCC CGTCAAGCTC TAAATCGGGG GCTCCCTTTA
1611  GGGTTCCGAT TTAGTGCTTT ACGGCACCTC GACCCCAAAA AACTTGATTA GGGTGATGGT TCACGTAGTG
1681  GGCCATCGCC CTGATAGACG GTTTTTCGCC CTTTGACGTT GGAGTCCACG TTCTTTAATA GTGGACTCTT
1751  GTTCCAAACT GGAACAACAC TCAACCCTAT CTCGGTCTAT TCTTTTGATT TATAAGGGAT TTTGCCGATT
1821  TCGGCCTATT GGTTAAAAAA TGAGCTGATT TAACAAAAAT TTAACGCGAA TTTTAACAAA ATATTAACGC
1891  TTACAATTTA GGTGGCACTT TTCGGGGAAA TGTGCGCGGA ACCCCTATTT GTTTATTTTT CTAAATACAT
1961  TCAAATATGT ATCCGCTCAT GAGACAATAA CCCTGATAAA TGCTTCAATA ATATTGAAAA AGGAAGAGTA
2031  TGAGTATTCA ACATTTCCGT GTCGCCCTTA TTCCCTTTTT TGCGGCATTT TGCCTTCCTG TTTTTGCTCA
2101  CCCAGAAACG CTGGTGAAAG TAAAAGATGC TGAAGATCAG TTGGGTGCAC GAGTGGGTTA CATCGAACTG
2171  GATCTCAACA GCGGTAAGAT CCTTGAGAGT TTTCGCCCCG AAGAACGTTT TCCAATGATG AGCACTTTTA
2241  AAGTTCTGCT ATGTGGCGCG GTATTATCCC GTATTGACGC CGGGCAAGAG CAACTCGGTC GCCGCATACA
2311  CTATTCTCAG AATGACTTGG TTGAGTACTC ACCAGTCACA GAAAAGCATC TTACGGATGG CATGACAGTA
2381  AGAGAATTAT GCAGTGCTGC CATAACCATG AGTGATAACA CTGCGGCCAA CTTACTTCTG ACAACGATCG
2451  GAGGACCGAA GGAGCTAACC GCTTTTTTGC ACAACATGGG GGATCATGTA ACTCGCCTTG ATCGTTGGGA
2521  ACCGGAGCTG AATGAAGCCA TACCAAACGA CGAGCGTGAC ACCACGATGC CTGTAGCAAT GGCAACAACG
2591  TTGCGCAAAC TATTAACTGG CGAACTACTT ACTCTAGCTT CCCGGCAACA ATTAATAGAC TGGATGGAGG
2661  CGGATAAAGT TGCAGGACCA CTTCTGCGCT CGGCCCTTCC GGCTGGCTGG TTTATTGCTG ATAAATCTGG
```

FIG._33C

```
2731  AGCCGGTGAG CGTGGGTCTC GCGGTATCAT TGCAGCACTG GGGCCAGATG GTAAGCCCTC CCGTATCGTA
2801  GTTATCTACA CGACGGGGAG TCAGGCAACT ATGGATGAAC GAAATAGACA GATCGCTGAG ATAGGTGCCT
2871  CACTGATTAA GCATTGGTAA CTGTCAGACC AAGTTTACTC ATATATACTT TAGATTGATT TAAAACTTCA
2941  TTTTTAATTT AAAAGGATCT AGGTGAAGAT CCTTTTTGAT AATCTCATGA CCAAAATCCC TTAACGTGAG
3011  TTTTCGTTCC ACTGAGCGTC AGACCCCGTA GAAAAGATCA AAGGATCTTC TTGAGATCCT TTTTTTCTGC
3081  GCGTAATCTG CTGCTTGCAA ACAAAAAAAC CACCGCTACC AGCGGTGGTT TGTTTGCCGG ATCAAGAGCT
3151  ACCAACTCTT TTTCCGAAGG TAACTGGCTT CAGCAGAGCG CAGATACCAA ATACTGTCCT TCTAGTGTAG
3221  CCGTAGTTAG GCCACCACTT CAAGAACTCT GTAGCACCGC CTACATACCT CGCTCTGCTA ATCCTGTTAC
3291  CAGTGGCTGC TGCCAGTGGC GATAAGTCGT GTCTTACCGG GTTGGACTCA AGACGATAGT TACCGGATAA
3361  GGCGCAGCGG TCGGGCTGAA CGGGGGGTTC GTGCACACAG CCCAGCTTGG AGCGAACGAC CTACACCGAA
3431  CTGAGATACC TACAGCGTGA GCTATGAGAA AGCGCCACGC TTCCCGAAGG GAGAAAGGCG GACAGGTATC
3501  CGGTAAGCGG CAGGGTCGGA ACAGGAGAGC GCACGAGGGA GCTTCCAGGG GGAAACGCCT GGTATCTTTA
3571  TAGTCCTGTC GGGTTTCGCC ACCTCTGACT TGAGCGTCGA TTTTTGTGAT GCTCGTCAGG GGGGCGGAGC
3641  CTATGGAAAA ACGCCAGCAA CGCGGCCTTT TTACGGTTCC TGGCCTTTTG CTGGCCTTTT GCTCACATGT
3711  TCTTTCCTGC GTTATCCCCT GATTCTGTGG ATAACCGTAT TACCGCCTTT GAGTGAGCTG ATACCGCTCG
3781  CCGCAGCCGA ACGACCGAGC GCAGCGAGTC AGTGAGCGAG GAAGCGGAAG AGCGCCCAAT ACGCAAACCG
3851  CCTCTCCCCG CGCGTTGGCC GATTCATTAA TGCAGCTGGC ACGACAGGTT TCCCGACTGG AAAGCGGGCA
3921  GTGAGCGCAA CGCAATTAAT GTGAGTTAGC TCACTCATTA GGCACCCCAG GCTTTACACT TTATGCTTCC
3991  GGCTCGTATG TTGTGTGGAA TTGTGAGCGG ATAACAATTT CACACAGGAA ACAGCTATGA CCATGATTAC
                                                    KpnI           XhoI
                                                  ~~~~~~~        ~~~~~~
4061  GCCAAGCGCG CAATTAACCC TCACTAAAGG GAACAAAAGC TGGGTACCGG GCCCCCCCTC GAGGTCATTC
4131  ATATGCTTGA GAAGAGAGTC GGGATAGTCC AAAATAAAAC AAAGGTAAGA TTACCTGGTC AAAAGTGAAA
4201  ACATCAGTTA AAAGGTGGTA TAAGTAAAAT ATCGGTAATA AAAGGTGGCC CAAAGTGAAA TTTACTCTTT
4271  TCTACTATTA TAAAAATTGA GGATGTTTTG TCGGTACTTT GATACGTCAT TTTTGTATGA ATTGGTTTTT
4341  AAGTTTATTC GCGATTTGGA AATGCATATC TGTATTTGAG TCGGTTTTTA AGTTCGTTGC TTTTGTAAAT
4411  ACAGAGGGAT TTGTATAAGA AATATCTTTA AAAAACCCAT ATGCTAATTT GACATAATTT TTGAGAAAAA
                 EcoRI
                ~~~~~~~
4481  TATATATTCA GGCGAATTCC ACAATGAACA ATAATAAGAT TAAAATAGCT TGCCCCCGTT GCAGCGATGG
4551  GTATTTTTTC TAGTAAAATA AAAGATAAAC TTAGACTCAA AACATTTACA AAAACAACCC CTAAAGTCCT
4621  AAAGCCCAAA GTGCTATGCA CGATCCATAG CAAGCCCAGC CCAACCCAAC CCAACCCAAC CCACCCCAGT
4691  GCAGCCAACT GGCAAATAGT CTCCACCCCC GGCACTATCA CCGTGAGTTG TCCGCACCAC CGCACGTCTC
4761  GCAGCCAAAA AAAAAAAAAG AAAGAAAAAA AAGAAAAAGA AAAACAGCAG GTGGGTCCGG GTCGTGGGGG
4831  CCGGAAAAGC GAGGAGGATC GCGAGCAGCG ACGAGGCCCG GCCCTCCCTC CGCTTCCAAA GAAACGCCCC
```

FIG._33D

```
4901  CCATCGCCAC TATATACATA CCCCCCCCTC TCCTCCCATC CCCCCAACCC TACCACCACC ACCACCACCA
4971  CCTCCTCCCC CCTCGCTGCC GGACGACGAG CTCCTCCCCC CTCCCCCTCC GCCGCCGCCG GTAACCACCC
5041  CGCCCCTCTC CTCTTTCTTT CTCCGTTTTT TTTTTCGTCT CGGTCTCGAT CTTTGGCCTT GGTAGTTTGG
5111  GTGGGCGAGA GCGGCTTCGT CGCCCAGATC GGTGCGCGGG AGGGGCGGGA TCTCGCGGCT GGCGTCTCCG
                         BamHI                                  BglII
                         ~~~~~~~                                ~~~~~~
5181  GGCGTGAGTC GGCCCGGATC CTCGCGGGGA ATGGGGCTCT CGGATGTAGA TCTTCTTTCT TTCTTCTTTT
5251  TGTGGTAGAA TTTGAATCCC TCAGCATTGT TCATCGGTAG TTTTTCTTTT CATGATTTGT GACAAATGCA
5321  GCCTCGTGCG GAGCTTTTTT GTAGC
```

FIG._33E

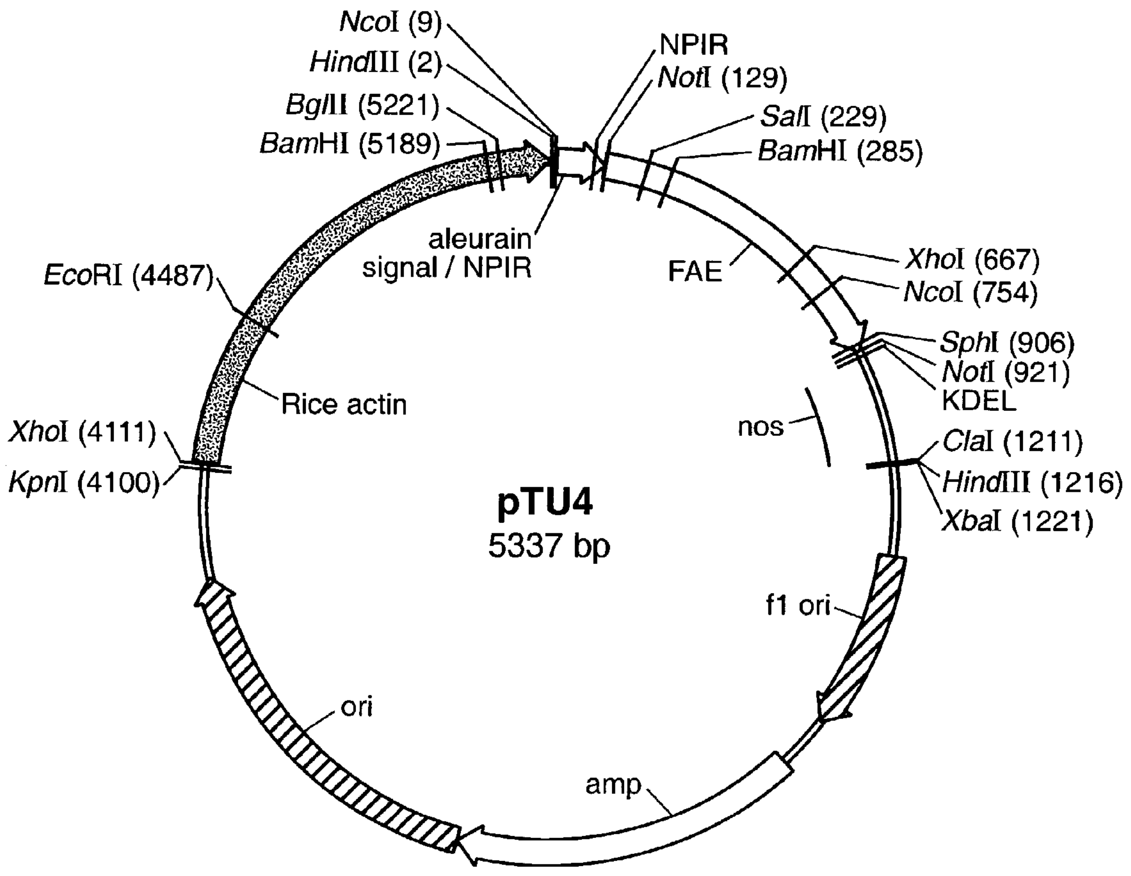
*FIG._34A*

```
           NcoI
          ~~~~~~~
     HindIII
     ~~~~~~
               M  A  H  A  R  V  L  L  L  A  L  A  V  L  A  T  A  A  V  A  V
  1  AAGCTTACCA TGGCCCACGC CCGCGTCCTC CTCCTGGCGC TCGCCGTGCT GGCCACGGCC GCCGTCGCCG
                                                                      NotI
                                                                    ~~~~~~~~
     · A  S  S  S  S  F  A  D  S  N  P  I  R  P  V  T  D  R  A  A  A  S  T ·
 71  TCGCCTCCTC CTCCTCCTTC GCCGACTCCA ACCCGATCCG GCCCGTCACC GACCGCGCGG CCGCCTCCAC
     ·Q  G  I  S  E  D  L  Y  S  R  L  V  E  M  A  T  I  S  Q  A  A  Y  A
141  GCAGGGCATC TCCGAAGACC TCTACAGCCG TTTAGTCGAA ATGGCCACTA TCTCCCAAGC TGCCTACGCC
                            SalI
                           ~~~~~~~
      D  L  C  N  I  P  S  T  I  I  K  G  E  K  I  Y  N  S  Q  T  D  I  N  G
211  GACCTGTGCA ACATTCCGTC GACTATTATC AAGGGAGAGA AAATTTACAA TTCTCAAACT GACATTAACG
       BamHI
       ~~~~~~
     · W  I  L  R  D  D  S  S  K  E  I  I  T  V  F  R  G  T  G  S  D  T  N ·
281  GATGGATCCT CCGCGACGAC AGCAGCAAAG AAATAATCAC CGTCTTCCGT GGCACTGGTA GTGATACGAA
     ·L  Q  L  D  T  N  Y  T  L  T  P  F  D  T  L  P  Q  C  N  G  C  E  V
351  TCTACAACTC GATACTAACT ACACCCTCAC GCCTTTCGAC ACCCTACCAC AATGCAACGG TTGTGAAGTA
      H  G  G  Y  Y  I  G  W  V  S  V  Q  D  Q  V  E  S  L  V  K  Q  Q  V  S
421  CACGGTGGAT ATTATATTGG ATGGGTCTCC GTCCAGGACC AAGTCGAGTC GCTTGTCAAA CAGCAGGTTA
     · Q  Y  P  D  Y  A  L  T  V  T  G  H  X  L  G  A  S  L  A  A  L  T  A ·
491  GCCAGTATCC GGACTACGCG CTGACCGTGA CCGGCCACKC CCTCGGCGCC TCCCTGGCGG CACTCACTGC
     ·A  Q  L  S  A  T  Y  D  N  I  R  L  Y  T  F  G  E  P  R  S  G  N  Q
561  CGCCCAGCTG TCTGCGACAT ACGACAACAT CCGCCTGTAC ACCTTCGGCG AACCGCGCAG CGGCAATCAG
                                              XhoI
                                             ~~~~~~~
      A  F  A  S  Y  M  N  D  A  F  Q  A  S  S  P  D  T  T  Q  Y  F  R  V  T
631  GCCTTCGCGT CGTACATGAA CGATGCCTTC CAAGCCTCGA GCCCAGATAC GACGCAGTAT TTCCGGGTCA
                                                                 NcoI
                                                                ~~~~~~~
     · H  A  N  D  G  I  P  N  L  P  P  V  E  Q  G  Y  A  H  G  G  V  E  Y ·
```

FIG._34B

```
 701 CTCATGCCAA CGACGGCATC CCAAACCTGC CCCCGGTGGA GCAGGGGTAC GCCCATGGCG GTGTAGAGTA
     ·W  S  V   D  P  Y  S   A  Q  N   T  F  V   C  T  G  D   E  V  Q   C  C  E
 771 CTGGAGCGTT GATCCTTACA GCGCCCAGAA CACATTTGTC TGCACTGGGG ATGAAGTGCA GTGCTGTGAG
                                                                        SphI
                                                                        ~~~~
      A  Q  G  G   Q  G  V   N  N  A   H  T  T  Y   F  G  M   T  S  G   A  C  T  W
 841 GCCCAGGGCG GACAGGGTGT GAATAATGCG CACACGACTT ATTTTGGGAT GACGAGCGGC GCATGCACCT
            NotI
          ~~~~~~~~~
     · P  V  A   A  A  E   P  L  K  D   E  L  *
 911 GGCCGGTCGC GGCCGCGGAA CCACTGAAGG ATGAGCTGTA AAGAAGCAGA TCGTTCAAAC ATTTGGCAAT
 981 AAAGTTTCTT AAGATTGAAT CCTGTTGCCG GTCTTGCGAT GATTATCATA TAATTTCTGT TGAATTACGT
1051 TAAGCATGTA ATAATTAACA TGTAATGCAT GACGTTATTT ATGAGATGGG TTTTTATGAT TAGAGTCCCG
1121 CAATTATACA TTTAATACGC GATAGAAAAC AAAATATAGC GCGCAAACTA GGATAAATTA TCGCGCGCGG
                                HindIII
                                ~~~~~~~
                          ClaI        XbaI
                         ~~~~~~~     ~~~~~~
1191 TGTCATCTAT GTTACTAGAT CGATAAGCTT CTAGAGCGGC CGGTGGAGCT CCAATTCGCC CTATAGTGAG
1261 TCGTATTACG CGCGCTCACT GGCCGTCGTT TTACAACGTC GTGACTGGGA AAACCCTGGC GTTACCCAAC
1331 TTAATCGCCT TGCAGCACAT CCCCCTTTCG CCAGCTGGCG TAATAGCGAA GAGGCCCGCA CCGATCGCCC
1401 TTCCCAACAG TTGCGCAGCC TGAATGGCGA ATGGGACGCG CCCTGTAGCG GCGCATTAAG CGCGGCGGGT
1471 GTGGTGGTTA CGCGCAGCGT GACCGCTACA CTTGCCAGCG CCCTAGCGCC CGCTCCTTTC GCTTTCTTCC
1541 CTTCCTTTCT CGCCACGTTC GCCGGCTTTC CCCGTCAAGC TCTAAATCGG GGGCTCCCTT TAGGGTTCCG
1611 ATTTAGTGCT TTACGGCACC TCGACCCCAA AAAACTTGAT TAGGGTGATG GTTCACGTAG TGGGCCATCG
1681 CCCTGATAGA CGGTTTTTCG CCCTTTGACG TTGGAGTCCA CGTTCTTTAA TAGTGGACTC TTGTTCCAAA
1751 CTGGAACAAC ACTCAACCCT ATCTCGGTCT ATTCTTTTGA TTTATAAGGG ATTTTGCCGA TTTCGGCCTA
1821 TTGGTTAAAA AATGAGCTGA TTTAACAAAA ATTTAACGCG AATTTTAACA AAATATTAAC GCTTACAATT
1891 TAGGTGGCAC TTTTCGGGGA AATGTGCGCG GAACCCCTAT TTGTTTATTT TTCTAAATAC ATTCAAATAT
1961 GTATCCGCTC ATGAGACAAT AACCCTGATA AATGCTTCAA TAATATTGAA AAAGGAAGAG TATGAGTATT
2031 CAACATTTCC GTGTCGCCCT TATTCCCTTT TTTGCGGCAT TTTGCCTTCC TGTTTTTGCT CACCCAGAAA
2101 CGCTGGTGAA AGTAAAAGAT GCTGAAGATC AGTTGGGTGC ACGAGTGGGT TACATCGAAC TGGATCTCAA
2171 CAGCGGTAAG ATCCTTGAGA GTTTTCGCCC CGAAGAACGT TTTCCAATGA TGAGCACTTT TAAAGTTCTG
2241 CTATGTGGCG CGGTATTATC CCGTATTGAC GCCGGGCAAG AGCAACTCGG TCGCCGCATA CACTATTCTC
2311 AGAATGACTT GGTTGAGTAC TCACCAGTCA CAGAAAAGCA TCTTACGGAT GGCATGACAG TAAGAGAATT
2381 ATGCAGTGCT GCCATAACCA TGAGTGATAA CACTGCGGCC AACTTACTTC TGACAACGAT CGGAGGACCG
```

FIG._34C

```
2451  AAGGAGCTAA CCGCTTTTTT GCACAACATG GGGGATCATG TAACTCGCCT TGATCGTTGG GAACCGGAGC
2521  TGAATGAAGC CATACCAAAC GACGAGCGTG ACACCACGAT GCCTGTAGCA ATGGCAACAA CGTTGCGCAA
2591  ACTATTAACT GGCGAACTAC TTACTCTAGC TTCCCGGCAA CAATTAATAG ACTGGATGGA GGCGGATAAA
2661  GTTGCAGGAC CACTTCTGCG CTCGGCCCTT CCGGCTGGCT GGTTTATTGC TGATAAATCT GGAGCCGGTG
2731  AGCGTGGGTC TCGCGGTATC ATTGCAGCAC TGGGGCCAGA TGGTAAGCCC TCCCGTATCG TAGTTATCTA
2801  CACGACGGGG AGTCAGGCAA CTATGGATGA ACGAAATAGA CAGATCGCTG AGATAGGTGC CTCACTGATT
2871  AAGCATTGGT AACTGTCAGA CCAAGTTTAC TCATATATAC TTTAGATTGA TTTAAAACTT CATTTTTAAT
2941  TTAAAAGGAT CTAGGTGAAG ATCCTTTTTG ATAATCTCAT GACCAAAATC CCTTAACGTG AGTTTTCGTT
3011  CCACTGAGCG TCAGACCCCG TAGAAAAGAT CAAAGGATCT TCTTGAGATC CTTTTTTTCT GCGCGTAATC
3081  TGCTGCTTGC AAACAAAAAA ACCACCGCTA CCAGCGGTGG TTTGTTTGCC GGATCAAGAG CTACCAACTC
3151  TTTTTCCGAA GGTAACTGGC TTCAGCAGAG CGCAGATACC AAATACTGTC CTTCTAGTGT AGCCGTAGTT
3221  AGGCCACCAC TTCAAGAACT CTGTAGCACC GCCTACATAC CTCGCTCTGC TAATCCTGTT ACCAGTGGCT
3291  GCTGCCAGTG GCGATAAGTC GTGTCTTACC GGGTTGGACT CAAGACGATA GTTACCGGAT AAGGCGCAGC
3361  GGTCGGGCTG AACGGGGGGT TCGTGCACAC AGCCCAGCTT GGAGCGAACG ACCTACACCG AACTGAGATA
3431  CCTACAGCGT GAGCTATGAG AAAGCGCCAC GCTTCCCGAA GGGAGAAAGG CGGACAGGTA TCCGGTAAGC
3501  GGCAGGGTCG GAACAGGAGA GCGCACGAGG GAGCTTCCAG GGGGAAACGC CTGGTATCTT TATAGTCCTG
3571  TCGGGTTTCG CCACCTCTGA CTTGAGCGTC GATTTTTGTG ATGCTCGTCA GGGGGGCGGA GCCTATGGAA
3641  AAACGCCAGC AACGCGGCCT TTTTACGGTT CCTGGCCTTT TGCTGGCCTT TTGCTCACAT GTTCTTTCCT
3711  GCGTTATCCC CTGATTCTGT GGATAACCGT ATTACCGCCT TTGAGTGAGC TGATACCGCT CGCCGCAGCC
3781  GAACGACCGA GCGCAGCGAG TCAGTGAGCG AGGAAGCGGA AGAGCGCCCA ATACGCAAAC CGCCTCTCCC
3851  CGCGCGTTGG CCGATTCATT AATGCAGCTG GCACGACAGG TTTCCCGACT GGAAAGCGGG CAGTGAGCGC
3921  AACGCAATTA ATGTGAGTTA GCTCACTCAT TAGGCACCCC AGGCTTTACA CTTTATGCTT CCGGCTCGTA
3991  TGTTGTGTGG AATTGTGAGC GGATAACAAT TTCACACAGG AAACAGCTAT GACCATGATT ACGCCAAGCG
                                                 KpnI            XhoI
                                               ~~~~~~~         ~~~~~~
4061  CGCAATTAAC CCTCACTAAA GGGAACAAAA GCTGGGTACC GGGCCCCCCC TCGAGGTCAT TCATATGCTT
4131  GAGAAGAGAG TCGGGATAGT CCAAAATAAA ACAAAGGTAA GATTACCTGG TCAAAAGTGA AAACATCAGT
4201  TAAAAGGTGG TATAAGTAAA ATATCGGTAA TAAAAGGTGG CCCAAAGTGA AATTTACTCT TTTCTACTAT
4271  TATAAAAATT GAGGATGTTT TGTCGGTACT TTGATACGTC ATTTTTGTAT GAATTGGTTT TTAAGTTTAT
4341  TCGCGATTTG GAAATGCATA TCTGTATTTG AGTCGGTTTT TAAGTTCGTT GCTTTTGTAA ATACAGAGGG
4411  ATTTGTATAA GAAATATCTT TAAAAAACCC ATATGCTAAT TTGACATAAT TTTTGAGAAA AATATATATT
          EcoRI
         ~~~~~~~
4481  CAGGCGAATT CCACAATGAA CAATAATAAG ATTAAAATAG CTTGCCCCCG TTGCAGCGAT GGGTATTTTT
4551  TCTAGTAAAA TAAAAGATAA ACTTAGACTC AAAACATTTA CAAAAACAAC CCCTAAAGTC CTAAAGCCCA
```

FIG._34D

```
4621  AAGTGCTATG CACGATCCAT AGCAAGCCCA GCCCAACCCA ACCCAACCCA ACCCACCCCA GTGCAGCCAA
4691  CTGGCAAATA GTCTCCACCC CCGGCACTAT CACCGTGAGT TGTCCGCACC ACCGCACGTC TCGCAGCCAA
4761  AAAAAAAAAA AGAAAGAAAA AAAAGAAAAA GAAAAACAGC AGGTGGGTCC GGGTCGTGGG GGCCGGAAAA
4831  GCGAGGAGGA TCGCGAGCAG CGACGAGGCC CGGCCCTCCC TCCGCTTCCA AAGAAACGCC CCCCATCGCC
4901  ACTATATACA TACCCCCCCC TCTCCTCCCA TCCCCCCAAC CCTACCACCA CCACCACCAC CACCTCCTCC
4971  CCCCTCGCTG CCGGACGACG AGCTCCTCCC CCCTCCCCCT CCGCCGCCGC CGGTAACCAC CCCGCCCCTC
5041  TCCTCTTTCT TTCTCCGTTT TTTTTTTCGT CTCGGTCTCG ATCTTTGGCC TTGGTAGTTT GGGTGGGCGA
5111  GAGCGGCTTC GTCGCCCAGA TCGGTGCGCG GGAGGGGCGG GATCTCGCGG CTGGCGTCTC CGGGCGTGAG
                 BamHI                           BglII
                 ~~~~~~~                         ~~~~~~
5181  TCGGCCCGGA TCCTCGCGGG GAATGGGGCT CTCGGATGTA GATCTTCTTT CTTTCTTCTT TTTGTGGTAG
5251  AATTTGAATC CCTCAGCATT GTTCATCGGT AGTTTTTCTT TTCATGATTT GTGACAAATG CAGCCTCGTG
5321  CGGAGCTTTT TTGTAGC
```

FIG._34E

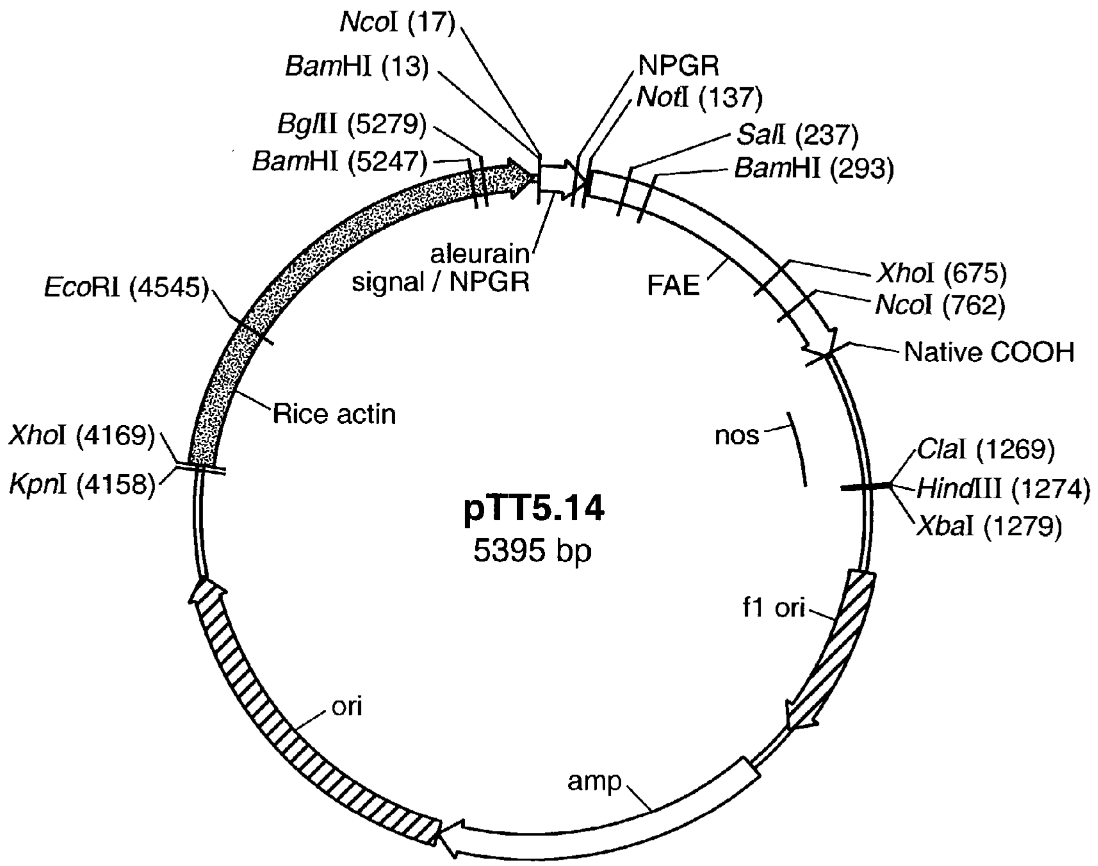
*FIG._35A*

```
                        NcoI
                      ~~~~~~~
                   BamHI
                   ~~~~~~
                        M  A  H  A  R  V  L  L  L  A  L  A  V  L  A  T  A  A ·
  1 CCTGACGCCG AGGATCCATG GCCCACGCCC GCGTCCTCCT CCTGGCGCTC GCCGTGCTGG CCACGGCCGC
                                                                          NotI
    ·V  A  V  A  S  S  S  S  F  A  D  S  N  P  G  R  P  V  T  D  R  A  A
 71 CGTCGCCGTC GCCTCCTCCT CCTCCTTCGC CGACTCCAAC CCGGGCCGGC CCGTCACCGA CCGCGCGGCC
    NotI
    ~~
     A  S  T  Q  G  I  S  E  D  L  Y  S  R  L  V  E  M  A  T  I  S  Q  A  A
141 GCCTCCACGC AGGGCATCTC CGAAGACCTC TACAGCCGTT TAGTCGAAAT GGCCACTATC TCCCAAGCTG
                                 SalI
                               ~~~~~~~
    · Y  A  D  L  C  N  I  P  S  T  I  I  K  G  E  K  I  Y  N  S  Q  T  D ·
211 CCTACGCCGA CCTGTGCAAC ATTCCGTCGA CTATTATCAA GGGAGAGAAA ATTTACAATT CTCAAACTGA
                   BamHI
                   ~~~~~~
    ·I  N  G  W  I  L  R  D  D  S  S  K  E  I  I  T  V  F  R  G  T  G  S
281 CATTAACGGA TGGATCCTCC GCGACGACAG CAGCAAAGAA ATAATCACCG TCTTCCGTGG CACTGGTAGT
     D  T  N  L  Q  L  D  T  N  Y  T  L  T  P  F  D  T  L  P  Q  C  N  G  C
351 GATACGAATC TACAACTCGA TACTAACTAC ACCCTCACGC CTTTCGACAC CCTACCACAA TGCAACGGTT
    · E  V  H  G  G  Y  Y  I  G  W  V  S  V  Q  D  Q  V  E  S  L  V  K  Q ·
421 GTGAAGTACA CGGTGGATAT TATATTGGAT GGGTCTCCGT CCAGGACCAA GTCGAGTCGC TTGTCAAACA
    ·Q  V  S  Q  Y  P  D  Y  A  L  T  V  T  G  H  X  L  G  A  S  L  A  A
491 GCAGGTTAGC CAGTATCCGG ACTACGCGCT GACCGTGACC GGCCACKCCC TCGGCGCCTC CCTGGCGGCA
     L  T  A  A  Q  L  S  A  T  Y  D  N  I  R  L  Y  T  F  G  E  P  R  S  G
561 CTCACTGCCG CCCAGCTGTC TGCGACATAC GACAACATCC GCCTGTACAC CTTCGGCGAA CCGCGCAGCG
                                                 XhoI
                                               ~~~~~~~
    · N  Q  A  F  A  S  Y  M  N  D  A  F  Q  A  S  S  P  D  T  T  Q  Y  F ·
631 GCAATCAGGC CTTCGCGTCG TACATGAACG ATGCCTTCCA AGCCTCGAGC CCAGATACGA CGCAGTATTT
                                                                       NcoI
                                                                      ~~~~
    ·R  V  T  H  A  N  D  G  I  P  N  L  P  P  V  E  Q  G  Y  A  H  G  G
```

FIG._35B

```
 701 CCGGGTCACT CATGCCAACG ACGGCATCCC AAACCTGCCC CCGGTGGAGC AGGGGTACGC CCATGGCGGT
      V  E  Y  W   S  V  D   P  Y  S   A  Q  N  T   F  V  C   T  G  D   E  V  Q  C
 771 GTAGAGTACT GGAGCGTTGA TCCTTACAGC GCCCAGAACA CATTTGTCTG CACTGGGGAT GAAGTGCAGT
     · C  E  A   Q  G  G   Q  G  V  N   N  A  H   T  T  Y   F  G  M  T   S  G  A ·
 841 GCTGTGAGGC CCAGGGCGGA CAGGGTGTGA ATAATGCGCA CACGACTTAT TTTGGGATGA CGAGCGGAGC
     ·C  T  W   *
 911 CTGTACATGG TGATCAGTCA TTTCAGCCTC CCCGAGTGTA CCAGGAAAGA TGGATGTCCT GGAGAGGGGG
 981 CCGCGTAACC ACTGAAGGAT GAGCTGTAAA GAAGCAGATC GTTCAAACAT TTGGCAATAA AGTTTCTTAA
1051 GATTGAATCC TGTTGCCGGT CTTGCGATGA TTATCATATA ATTTCTGTTG AATTACGTTA AGCATGTAAT
1121 AATTAACATG TAATGCATGA CGTTATTTAT GAGATGGGTT TTTATGATTA GAGTCCCGCA ATTATACATT
1191 TAATACGCGA TAGAAAACAA AATATAGCGC GCAAACTAGG ATAAATTATC GCGCGCGGTG TCATCTATGT
                  HindIII
                  ~~~~~~
              ClaI        XbaI
             ~~~~~~~     ~~~~~~~
1261 TACTAGATCG ATAAGCTTCT AGAGCGGCCG GTGGAGCTCC AATTCGCCCT ATAGTGAGTC GTATTACGCG
1331 CGCTCACTGG CCGTCGTTTT ACAACGTCGT GACTGGGAAA ACCCTGGCGT TACCCAACTT AATCGCCTTG
1401 CAGCACATCC CCCTTTCGCC AGCTGGCGTA ATAGCGAAGA GGCCCGCACC GATCGCCCTT CCCAACAGTT
1471 GCGCAGCCTG AATGGCGAAT GGGACGCGCC CTGTAGCGGC GCATTAAGCG CGGCGGGTGT GGTGGTTACG
1541 CGCAGCGTGA CCGCTACACT TGCCAGCGCC CTAGCGCCCG CTCCTTTCGC TTTCTTCCCT TCCTTTCTCG
1611 CCACGTTCGC CGGCTTTCCC CGTCAAGCTC TAAATCGGGG GCTCCCTTTA GGGTTCCGAT TTAGTGCTTT
1681 ACGGCACCTC GACCCCAAAA AACTTGATTA GGGTGATGGT TCACGTAGTG GGCCATCGCC CTGATAGACG
1751 GTTTTTCGCC CTTTGACGTT GGAGTCCACG TTCTTTAATA GTGGACTCTT GTTCCAAACT GGAACAACAC
1821 TCAACCCTAT CTCGGTCTAT TCTTTTGATT TATAAGGGAT TTTGCCGATT TCGGCCTATT GGTTAAAAAA
1891 TGAGCTGATT TAACAAAAAT TTAACGCGAA TTTTAACAAA ATATTAACGC TTACAATTTA GGTGGCACTT
1961 TTCGGGGAAA TGTGCGCGGA ACCCCTATTT GTTTATTTTT CTAAATACAT TCAAATATGT ATCCGCTCAT
2031 GAGACAATAA CCCTGATAAA TGCTTCAATA ATATTGAAAA AGGAAGAGTA TGAGTATTCA ACATTTCCGT
2101 GTCGCCCTTA TTCCCTTTTT TGCGGCATTT TGCCTTCCTG TTTTTGCTCA CCCAGAAACG CTGGTGAAAG
2171 TAAAAGATGC TGAAGATCAG TTGGGTGCAC GAGTGGGTTA CATCGAACTG GATCTCAACA GCGGTAAGAT
2241 CCTTGAGAGT TTTCGCCCCG AAGAACGTTT TCCAATGATG AGCACTTTTA AAGTTCTGCT ATGTGGCGCG
2311 GTATTATCCC GTATTGACGC CGGGCAAGAG CAACTCGGTC GCCGCATACA CTATTCTCAG AATGACTTGG
2381 TTGAGTACTC ACCAGTCACA GAAAAGCATC TTACGGATGG CATGACAGTA AGAGAATTAT GCAGTGCTGC
2451 CATAACCATG AGTGATAACA CTGCGGCCAA CTTACTTCTG ACAACGATCG GAGGACCGAA GGAGCTAACC
2521 GCTTTTTTGC ACAACATGGG GGATCATGTA ACTCGCCTTG ATCGTTGGGA ACCGGAGCTG AATGAAGCCA
2591 TACCAAACGA CGAGCGTGAC ACCACGATGC CTGTAGCAAT GGCAACAACG TTGCGCAAAC TATTAACTGG
2661 CGAACTACTT ACTCTAGCTT CCCGGCAACA ATTAATAGAC TGGATGGAGG CGGATAAAGT TGCAGGACCA
```

FIG._35C

```
2731  CTTCTGCGCT CGGCCCTTCC GGCTGGCTGG TTTATTGCTG ATAAATCTGG AGCCGGTGAG CGTGGGTCTC
2801  GCGGTATCAT TGCAGCACTG GGGCCAGATG GTAAGCCCTC CCGTATCGTA GTTATCTACA CGACGGGGAG
2871  TCAGGCAACT ATGGATGAAC GAAATAGACA GATCGCTGAG ATAGGTGCCT CACTGATTAA GCATTGGTAA
2941  CTGTCAGACC AAGTTTACTC ATATATACTT TAGATTGATT TAAAACTTCA TTTTTAATTT AAAAGGATCT
3011  AGGTGAAGAT CCTTTTTGAT AATCTCATGA CCAAAATCCC TTAACGTGAG TTTTCGTTCC ACTGAGCGTC
3081  AGACCCCGTA GAAAAGATCA AAGGATCTTC TTGAGATCCT TTTTTTCTGC GCGTAATCTG CTGCTTGCAA
3151  ACAAAAAAAC CACCGCTACC AGCGGTGGTT TGTTTGCCGG ATCAAGAGCT ACCAACTCTT TTTCCGAAGG
3221  TAACTGGCTT CAGCAGAGCG CAGATACCAA ATACTGTCCT TCTAGTGTAG CCGTAGTTAG GCCACCACTT
3291  CAAGAACTCT GTAGCACCGC CTACATACCT CGCTCTGCTA ATCCTGTTAC CAGTGGCTGC TGCCAGTGGC
3361  GATAAGTCGT GTCTTACCGG GTTGGACTCA AGACGATAGT TACCGGATAA GGCGCAGCGG TCGGGCTGAA
3431  CGGGGGGTTC GTGCACACAG CCCAGCTTGG AGCGAACGAC CTACACCGAA CTGAGATACC TACAGCGTGA
3501  GCTATGAGAA AGCGCCACGC TTCCCGAAGG GAGAAAGGCG GACAGGTATC CGGTAAGCGG CAGGGTCGGA
3571  ACAGGAGAGC GCACGAGGGA GCTTCCAGGG GGAAACGCCT GGTATCTTTA TAGTCCTGTC GGGTTTCGCC
3641  ACCTCTGACT TGAGCGTCGA TTTTTGTGAT GCTCGTCAGG GGGGCGGAGC CTATGGAAAA ACGCCAGCAA
3711  CGCGGCCTTT TTACGGTTCC TGGCCTTTTG CTGGCCTTTT GCTCACATGT TCTTTCCTGC GTTATCCCCT
3781  GATTCTGTGG ATAACCGTAT TACCGCCTTT GAGTGAGCTG ATACCGCTCG CCGCAGCCGA ACGACCGAGC
3851  GCAGCGAGTC AGTGAGCGAG GAAGCGGAAG AGCGCCCAAT ACGCAAACCG CCTCTCCCCG CGCGTTGGCC
3921  GATTCATTAA TGCAGCTGGC ACGACAGGTT TCCCGACTGG AAAGCGGGCA GTGAGCGCAA CGCAATTAAT
3991  GTGAGTTAGC TCACTCATTA GGCACCCCAG GCTTTACACT TTATGCTTCC GGCTCGTATG TTGTGTGGAA
4061  TTGTGAGCGG ATAACAATTT CACACAGGAA ACAGCTATGA CCATGATTAC GCCAAGCGCG CAATTAACCC
                               KpnI          XhoI
                              ~~~~~~~       ~~~~~~
4131  TCACTAAAGG GAACAAAAGC TGGGTACCGG GCCCCCCCTC GAGGTCATTC ATATGCTTGA GAAGAGAGTC
4201  GGGATAGTCC AAAATAAAAC AAAGGTAAGA TTACCTGGTC AAAAGTGAAA ACATCAGTTA AAAGGTGGTA
4271  TAAGTAAAAT ATCGGTAATA AAAGGTGGCC CAAAGTGAAA TTTACTCTTT TCTACTATTA TAAAAATTGA
4341  GGATGTTTTG TCGGTACTTT GATACGTCAT TTTTGTATGA ATTGGTTTTT AAGTTTATTC GCGATTTGGA
4411  AATGCATATC TGTATTTGAG TCGGTTTTTA AGTTCGTTGC TTTTGTAAAT ACAGAGGGAT TTGTATAAGA
                                                                      EcoRI
                                                                      ~
4481  AATATCTTTA AAAAACCCAT ATGCTAATTT GACATAATTT TTGAGAAAAA TATATATTCA GGCGAATTCC
4551  ACAATGAACA ATAATAAGAT TAAAATAGCT TGCCCCCGTT GCAGCGATGG GTATTTTTTC TAGTAAAATA
4621  AAAGATAAAC TTAGACTCAA AACATTTACA AAAACAACCC CTAAAGTCCT AAAGCCCAAA GTGCTATGCA
4691  CGATCCATAG CAAGCCCAGC CCAACCCAAC CCAACCCAAC CCACCCCAGT GCAGCCAACT GGCAAATAGT
4761  CTCCACCCCC GGCACTATCA CCGTGAGTTG TCCGCACCAC CGCACGTCTC GCAGCCAAAA AAAAAAAAAG
4831  AAAGAAAAAA AAGAAAAAGA AAAACAGCAG GTGGGTCCGG GTCGTGGGGG CCGGAAAAGC GAGGAGGATC
```

FIG._35D

```
4901  GCGAGCAGCG ACGAGGCCCG GCCCTCCCTC CGCTTCCAAA GAAACGCCCC CCATCGCCAC TATATACATA
4971  CCCCCCCCTC TCCTCCCATC CCCCCAACCC TACCACCACC ACCACCACCA CCTCCTCCCC CCTCGCTGCC
5041  GGACGACGAG CTCCTCCCCC CTCCCCCTCC GCCGCCGCCG GTAACCACCC CGCCCCTCTC CTCTTTCTTT
5111  CTCCGTTTTT TTTTTCGTCT CGGTCTCGAT CTTTGGCCTT GGTAGTTTGG GTGGGCGAGA GCGGCTTCGT
                                                                            BamHI
5181  CGCCCAGATC GGTGCGCGGG AGGGGCGGGA TCTCGCGGCT GGCGTCTCCG GGCGTGAGTC GGCCCGGATC
      BamHI                         BglII
      ~                             ~~~~~~~~
5251  CTCGCGGGGA ATGGGGCTCT CGGATGTAGA TCTTCTTTCT TTCTTCTTTT TGTGGTAGAA TTTGAATCCC
5321  TCAGCATTGT TCATCGGTAG TTTTTCTTTT CATGATTTGT GACAAATGCA GCCTCGTGCG GAGCTTTTTT
5391  GTAGC
```

FIG._35E

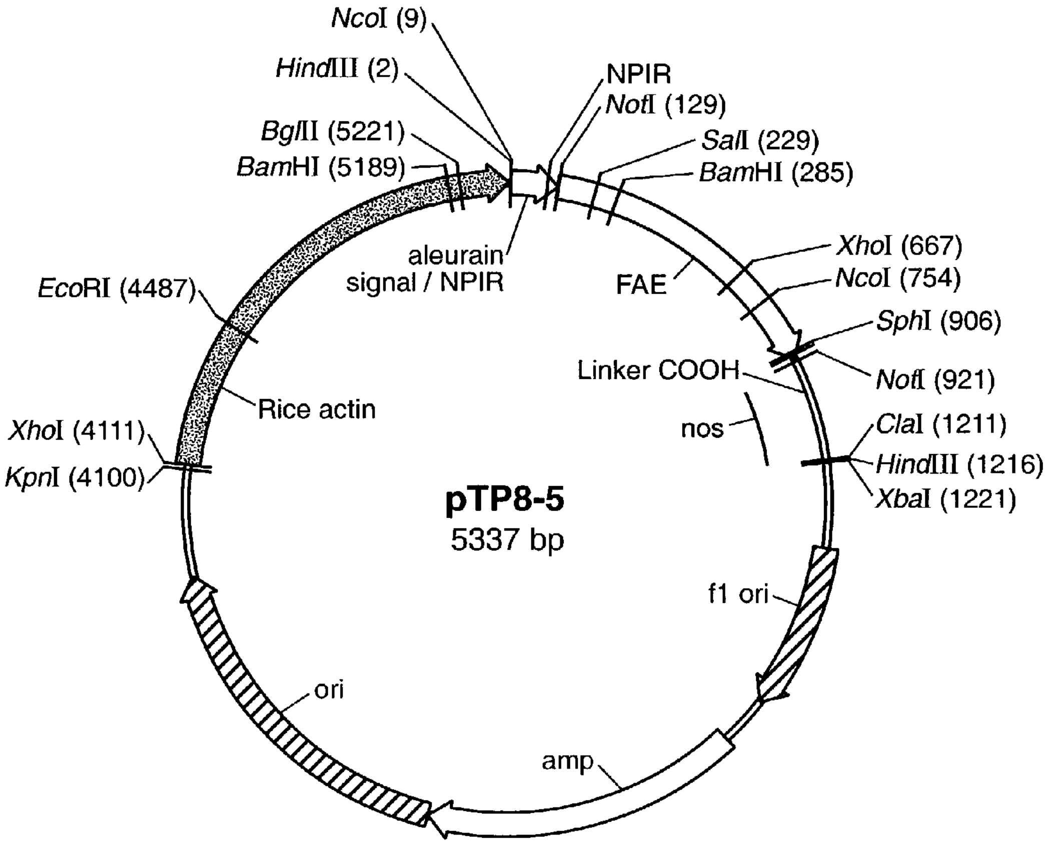
FIG._36A

```
                   NcoI
                 ~~~~~~~
           HindIII
           ~~~~~~
                  M   A  H  A   R  V  L   L  L  A  L   A  V  L   A  T  A   A  V  A  V
   1   AAGCTTACCA TGGCCCACGC CCGCGTCCTC CTCCTGGCGC TCGCCGTGCT GGCCACGGCC GCCGTCGCCG
                                                                   NotI
                                                                 ~~~~~~~~
       · A  S  S   S  S  F   A  D  S  N   P  I  R   P  V  T   D  R  A  A   A  S  T ·
  71   TCGCCTCCTC CTCCTCCTTC GCCGACTCCA ACCCGATCCG GCCCGTCACC GACCGCGCGG CCGCCTCCAC
       ·Q  G  I   S  E  D  L   Y  S  R   L  V  E   M  A  T  I   S  Q  A   A  Y  A
 141   GCAGGGCATC TCCGAAGACC TCTACAGCCG TTTAGTCGAA ATGGCCACTA TCTCCCAAGC TGCCTACGCC
                           SalI
                          ~~~~~~~
        D  L  C  N   I  P  S   T  I  I   K  G  E  K   I  Y  N   S  Q  T   D  I  N  G
 211   GACCTGTGCA ACATTCCGTC GACTATTATC AAGGGAGAGA AAATTTACAA TTCTCAAACT GACATTAACG
          BamHI
          ~~~~~~
       · W  I  L   R  D  D   S  S  K  E   I  I  T   V  F  R   G  T  G  S   D  T  N ·
 281   GATGGATCCT CCGCGACGAC AGCAGCAAAG AAATAATCAC CGTCTTCCGT GGCACTGGTA GTGATACGAA
       ·L  Q  L   D  T  N  Y   T  L  T   P  F  D   T  L  P  Q   C  N  G   C  E  V
 351   TCTACAACTC GATACTAACT ACACCCTCAC GCCTTTCGAC ACCCTACCAC AATGCAACGG TTGTGAAGTA
        H  G  G  Y   Y  I  G   W  V  S   V  Q  D  Q   V  E  S   L  V  K   Q  Q  V  S
 421   CACGGTGGAT ATTATATTGG ATGGGTCTCC GTCCAGGACC AAGTCGAGTC GCTTGTCAAA CAGCAGGTTA
       · Q  Y  P   D  Y  A   L  T  V  T   G  H  X   L  G  A   S  L  A  A   L  T  A ·
 491   GCCAGTATCC GGACTACGCG CTGACCGTGA CCGGCCACKC CCTCGGCGCC TCCCTGGCGG CACTCACTGC
       ·A  Q  L   S  A  T  Y   D  N  I   R  L  Y   T  F  G  E   P  R  S   G  N  Q
 561   CGCCCAGCTG TCTGCGACAT ACGACAACAT CCGCCTGTAC ACCTTCGGCG AACCGCGCAG CGGCAATCAG
                                             XhoI
                                            ~~~~~~~
        A  F  A  S   Y  M  N   D  A  F   Q  A  S  S   P  D  T   T  Q  Y   F  R  V  T
 631   GCCTTCGCGT CGTACATGAA CGATGCCTTC CAAGCCTCGA GCCCAGATAC GACGCAGTAT TTCCGGGTCA
                                                              NcoI
                                                             ~~~~~~~
       · H  A  N   D  G  I   P  N  L  P   P  V  E   Q  G  Y   A  H  G  G   V  E  Y ·
```

FIG._36B

```
 701 CTCATGCCAA CGACGGCATC CCAAACCTGC CCCCGGTGGA GCAGGGGTAC GCCCATGGCG GTGTAGAGTA
      ·W  S  V   D  P  Y  S   A  Q  N   T  F  V   C  T  G  D   E  V  Q   C  C  E
 771 CTGGAGCGTT GATCCTTACA GCGCCCAGAA CACATTTGTC TGCACTGGGG ATGAAGTGCA GTGCTGTGAG
                                                                       SphI
                                                                       ~~~~
      A  Q  G  G   Q  G  V   N  N  A   H  T  T  Y   F  G  M   T  S  G   A  C  T  W
 841 GCCCAGGGCG GACAGGGTGT GAATAATGCG CACACGACTT ATTTTGGGAT GACGAGCGGC GCATGCACCT
                 NotI
              ~~~~~~~~~~
     ·  P  V  A   A  A  *
 911 GGCCGGTCGC GGCCGCGTAA CCACTGAAGG ATGAGCTGTA AAGAAGCAGA TCGTTCAAAC ATTTGGCAAT
 981 AAAGTTTCTT AAGATTGAAT CCTGTTGCCG GTCTTGCGAT GATTATCATA TAATTTCTGT TGAATTACGT
1051 TAAGCATGTA ATAATTAACA TGTAATGCAT GACGTTATTT ATGAGATGGG TTTTTATGAT TAGAGTCCCG
1121 CAATTATACA TTTAATACGC GATAGAAAAC AAAATATAGC GCGCAAACTA GGATAAATTA TCGCGCGCGG
                                  HindIII
                                  ~~~~~~~~
                           ClaI        XbaI
                         ~~~~~~~~    ~~~~~~
1191 TGTCATCTAT GTTACTAGAT CGATAAGCTT CTAGAGCGGC CGGTGGAGCT CCAATTCGCC CTATAGTGAG
1261 TCGTATTACG CGCGCTCACT GGCCGTCGTT TTACAACGTC GTGACTGGGA AAACCCTGGC GTTACCCAAC
1331 TTAATCGCCT TGCAGCACAT CCCCCTTTCG CCAGCTGGCG TAATAGCGAA GAGGCCCGCA CCGATCGCCC
1401 TTCCCAACAG TTGCGCAGCC TGAATGGCGA ATGGGACGCG CCCTGTAGCG GCGCATTAAG CGCGGCGGGT
1471 GTGGTGGTTA CGCGCAGCGT GACCGCTACA CTTGCCAGCG CCCTAGCGCC CGCTCCTTTC GCTTTCTTCC
1541 CTTCCTTTCT CGCCACGTTC GCCGGCTTTC CCCGTCAAGC TCTAAATCGG GGGCTCCCTT TAGGGTTCCG
1611 ATTTAGTGCT TTACGGCACC TCGACCCCAA AAAACTTGAT TAGGGTGATG GTTCACGTAG TGGGCCATCG
1681 CCCTGATAGA CGGTTTTTCG CCCTTTGACG TTGGAGTCCA CGTTCTTTAA TAGTGGACTC TTGTTCCAAA
1751 CTGGAACAAC ACTCAACCCT ATCTCGGTCT ATTCTTTTGA TTTATAAGGG ATTTTGCCGA TTTCGGCCTA
1821 TTGGTTAAAA AATGAGCTGA TTTAACAAAA ATTTAACGCG AATTTTAACA AAATATTAAC GCTTACAATT
1891 TAGGTGGCAC TTTTCGGGGA AATGTGCGCG GAACCCCTAT TTGTTTATTT TTCTAAATAC ATTCAAATAT
1961 GTATCCGCTC ATGAGACAAT AACCCTGATA AATGCTTCAA TAATATTGAA AAAGGAAGAG TATGAGTATT
2031 CAACATTTCC GTGTCGCCCT TATTCCCTTT TTTGCGGCAT TTTGCCTTCC TGTTTTTGCT CACCCAGAAA
2101 CGCTGGTGAA AGTAAAAGAT GCTGAAGATC AGTTGGGTGC ACGAGTGGGT TACATCGAAC TGGATCTCAA
2171 CAGCGGTAAG ATCCTTGAGA GTTTTCGCCC CGAAGAACGT TTTCCAATGA TGAGCACTTT TAAAGTTCTG
2241 CTATGTGGCG CGGTATTATC CCGTATTGAC GCCGGGCAAG AGCAACTCGG TCGCCGCATA CACTATTCTC
2311 AGAATGACTT GGTTGAGTAC TCACCAGTCA CAGAAAAGCA TCTTACGGAT GGCATGACAG TAAGAGAATT
```

FIG._36C

```
2381  ATGCAGTGCT GCCATAACCA TGAGTGATAA CACTGCGGCC AACTTACTTC TGACAACGAT CGGAGGACCG
2451  AAGGAGCTAA CCGCTTTTTT GCACAACATG GGGGATCATG TAACTCGCCT TGATCGTTGG GAACCGGAGC
2521  TGAATGAAGC CATACCAAAC GACGAGCGTG ACACCACGAT GCCTGTAGCA ATGGCAACAA CGTTGCGCAA
2591  ACTATTAACT GGCGAACTAC TTACTCTAGC TTCCCGGCAA CAATTAATAG ACTGGATGGA GGCGGATAAA
2661  GTTGCAGGAC CACTTCTGCG CTCGGCCCTT CCGGCTGGCT GGTTTATTGC TGATAAATCT GGAGCCGGTG
2731  AGCGTGGGTC TCGCGGTATC ATTGCAGCAC TGGGGCCAGA TGGTAAGCCC TCCCGTATCG TAGTTATCTA
2801  CACGACGGGG AGTCAGGCAA CTATGGATGA ACGAAATAGA CAGATCGCTG AGATAGGTGC CTCACTGATT
2871  AAGCATTGGT AACTGTCAGA CCAAGTTTAC TCATATATAC TTTAGATTGA TTTAAAACTT CATTTTTAAT
2941  TTAAAAGGAT CTAGGTGAAG ATCCTTTTTG ATAATCTCAT GACCAAAATC CCTTAACGTG AGTTTTCGTT
3011  CCACTGAGCG TCAGACCCCG TAGAAAAGAT CAAAGGATCT TCTTGAGATC CTTTTTTTCT GCGCGTAATC
3081  TGCTGCTTGC AAACAAAAAA ACCACCGCTA CCAGCGGTGG TTTGTTTGCC GGATCAAGAG CTACCAACTC
3151  TTTTTCCGAA GGTAACTGGC TTCAGCAGAG CGCAGATACC AAATACTGTC CTTCTAGTGT AGCCGTAGTT
3221  AGGCCACCAC TTCAAGAACT CTGTAGCACC GCCTACATAC CTCGCTCTGC TAATCCTGTT ACCAGTGGCT
3291  GCTGCCAGTG GCGATAAGTC GTGTCTTACC GGGTTGGACT CAAGACGATA GTTACCGGAT AAGGCGCAGC
3361  GGTCGGGCTG AACGGGGGGT TCGTGCACAC AGCCCAGCTT GGAGCGAACG ACCTACACCG AACTGAGATA
3431  CCTACAGCGT GAGCTATGAG AAAGCGCCAC GCTTCCCGAA GGGAGAAAGG CGGACAGGTA TCCGGTAAGC
3501  GGCAGGGTCG GAACAGGAGA GCGCACGAGG GAGCTTCCAG GGGGAAACGC CTGGTATCTT TATAGTCCTG
3571  TCGGGTTTCG CCACCTCTGA CTTGAGCGTC GATTTTTGTG ATGCTCGTCA GGGGGGCGGA GCCTATGGAA
3641  AAACGCCAGC AACGCGGCCT TTTTACGGTT CCTGGCCTTT TGCTGGCCTT TTGCTCACAT GTTCTTTCCT
3711  GCGTTATCCC CTGATTCTGT GGATAACCGT ATTACCGCCT TTGAGTGAGC TGATACCGCT CGCCGCAGCC
3781  GAACGACCGA GCGCAGCGAG TCAGTGAGCG AGGAAGCGGA AGAGCGCCCA ATACGCAAAC CGCCTCTCCC
3851  CGCGCGTTGG CCGATTCATT AATGCAGCTG GCACGACAGG TTTCCCGACT GGAAAGCGGG CAGTGAGCGC
3921  AACGCAATTA ATGTGAGTTA GCTCACTCAT TAGGCACCCC AGGCTTTACA CTTTATGCTT CCGGCTCGTA
3991  TGTTGTGTGG AATTGTGAGC GGATAACAAT TTCACACAGG AAACAGCTAT GACCATGATT ACGCCAAGCG
                                          KpnI           XhoI
                                        ~~~~~~~        ~~~~~~
4061  CGCAATTAAC CCTCACTAAA GGGAACAAAA GCTGGGTACC GGGCCCCCCC TCGAGGTCAT TCATATGCTT
4131  GAGAAGAGAG TCGGGATAGT CCAAAATAAA ACAAAGGTAA GATTACCTGG TCAAAAGTGA AAACATCAGT
4201  TAAAAGGTGG TATAAGTAAA ATATCGGTAA TAAAAGGTGG CCCAAAGTGA AATTTACTCT TTTCTACTAT
4271  TATAAAAATT GAGGATGTTT TGTCGGTACT TTGATACGTC ATTTTTGTAT GAATTGGTTT TTAAGTTTAT
4341  TCGCGATTTG GAAATGCATA TCTGTATTTG AGTCGGTTTT TAAGTTCGTT GCTTTTGTAA ATACAGAGGG
4411  ATTTGTATAA GAAATATCTT TAAAAAACCC ATATGCTAAT TTGACATAAT TTTTGAGAAA AATATATATT
         EcoRI
        ~~~~~~~
4481  CAGGCGAATT CCACAATGAA CAATAATAAG ATTAAAATAG CTTGCCCCCG TTGCAGCGAT GGGTATTTTT
```

FIG._36D

```
4551  TCTAGTAAAA TAAAAGATAA ACTTAGACTC AAAACATTTA CAAAAACAAC CCCTAAAGTC CTAAAGCCCA
4621  AAGTGCTATG CACGATCCAT AGCAAGCCCA GCCCAACCCA ACCCAACCCA ACCCACCCCA GTGCAGCCAA
4691  CTGGCAAATA GTCTCCACCC CCGGCACTAT CACCGTGAGT TGTCCGCACC ACCGCACGTC TCGCAGCCAA
4761  AAAAAAAAAA AGAAAGAAAA AAAAGAAAAA GAAAAACAGC AGGTGGGTCC GGGTCGTGGG GGCCGGAAAA
4831  GCGAGGAGGA TCGCGAGCAG CGACGAGGCC CGGCCCTCCC TCCGCTTCCA AAGAAACGCC CCCCATCGCC
4901  ACTATATACA TACCCCCCCC TCTCCTCCCA TCCCCCCAAC CCTACCACCA CCACCACCAC CACCTCCTCC
4971  CCCCTCGCTG CCGGACGACG AGCTCCTCCC CCCTCCCCCT CCGCCGCCGC CGGTAACCAC CCCGCCCCTC
5041  TCCTCTTTCT TTCTCCGTTT TTTTTTTCGT CTCGGTCTCG ATCTTTGGCC TTGGTAGTTT GGGTGGGCGA
5111  GAGCGGCTTC GTCGCCCAGA TCGGTGCGCG GGAGGGGCGG GATCTCGCGG CTGGCGTCTC CGGGCGTGAG
                  BamHI                                     BglII
                  ~~~~~~~                                   ~~~~~~
5181  TCGGCCCGGA TCCTCGCGGG GAATGGGGCT CTCGGATGTA GATCTTCTTT CTTTCTTCTT TTTGTGGTAG
5251  AATTTGAATC CCTCAGCATT GTTCATCGGT AGTTTTTCTT TTCATGATTT GTGACAAATG CAGCCTCGTG
5321  CGGAGCTTTT TTGTAGC
```

FIG._36E

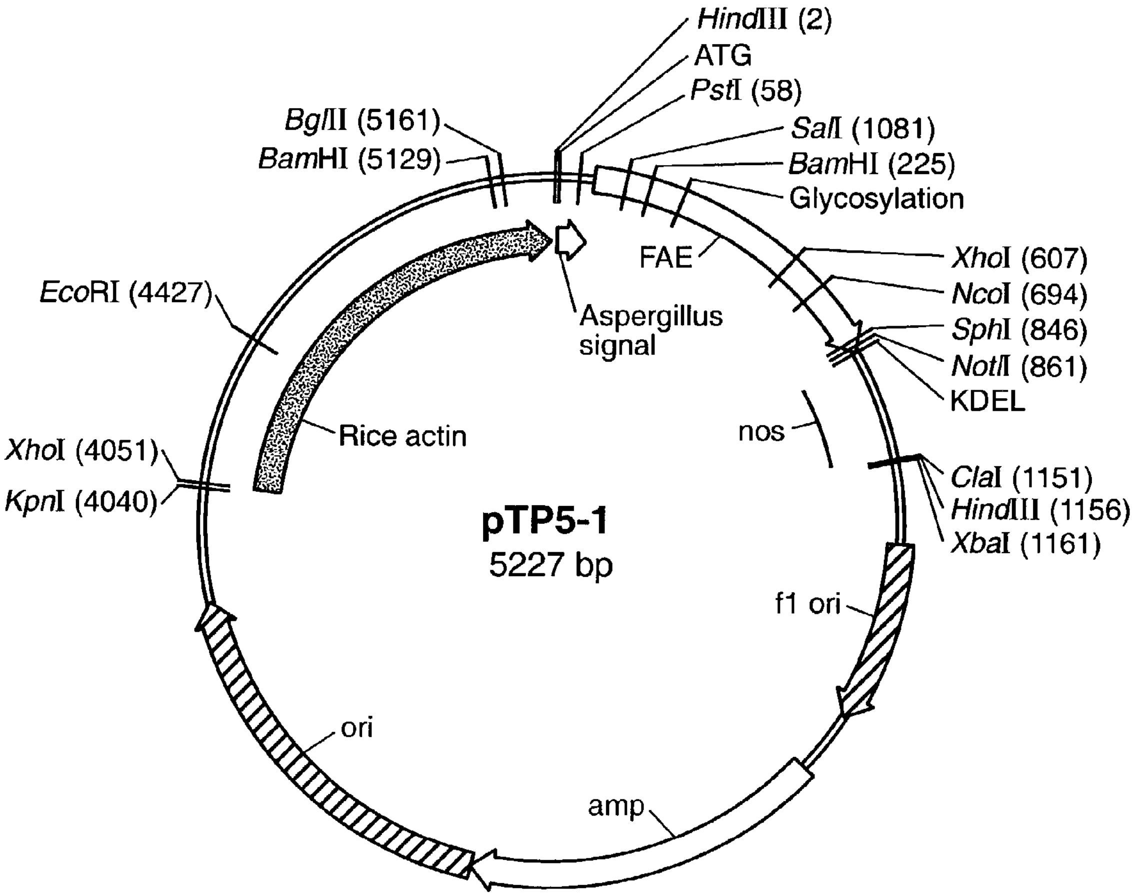
FIG._37A

```
     HindIII                                                      PstI
     ~~~~~~                                                       ~~~~~~~
               M  K  Q  F   S  A  K   H  V  L  A   V  V  V   T  A  G   H  A  L  A
  1  AAGCTTAACA TGAAGCAGTT CTCCGCCAAA CACGTCCTCG CAGTTGTGGT GACTGCAGGG CACGCCTTAG
     · A  S  T   Q  G  I   S  E  D  L   Y  S  R   L  V  E   M  A  T  I   S  Q  A ·
 71  CAGCCTCTAC GCAAGGCATC TCCGAAGACC TCTACAGCCG TTTAGTCGAA ATGGCCACTA TCTCCCAAGC
                                  SalI
                                 ~~~~~~~
     ·A  Y  A   D  L  C  N   I  P  S   T  I  I   K  G  E  K   I  Y  N   S  Q  T
141  TGCCTACGCC GACCTGTGCA ACATTCCGTC GACTATTATC AAGGGAGAGA AAATTTACAA TTCTCAAACT
                 BamHI
                ~~~~~~~
      D  I  N  G   W  I  L   R  D  D   S  S  K  E   I  I  T   V  F  R   G  T  G  S
211  GACATTAACG GATGGATCCT CCGCGACGAC AGCAGCAAAG AAATAATCAC CGTCTTCCGT GGCACTGGTA
     · D  T  N   L  Q  L   D  T  N  Y   T  L  T   P  F  D   T  L  P  Q   C  N  G ·
281  GTGATACGAA TCTACAACTC GATACTAACT ACACCCTCAC GCCTTTCGAC ACCCTACCAC AATGCAACGG
     ·C  E  V   H  G  G  Y   Y  I  G   W  V  S   V  Q  D  Q   V  E  S   L  V  K
351  TTGTGAAGTA CACGGTGGAT ATTATATTGG ATGGGTCTCC GTCCAGGACC AAGTCGAGTC GCTTGTCAAA
      Q  Q  V  S   Q  Y  P   D  Y  A   L  T  V  T   G  H  X   L  G  A   S  L  A  A
421  CAGCAGGTTA GCCAGTATCC GGACTACGCG CTGACCGTGA CCGGCCACKC CCTCGGCGCC TCCCTGGCGG
     · L  T  A   A  Q  L   S  A  T  Y   D  N  I   R  L  Y   T  F  G  E   P  R  S ·
491  CACTCACTGC CGCCCAGCTG TCTGCGACAT ACGACAACAT CCGCCTGTAC ACCTTCGGCG AACCGCGCAG
                                                        XhoI
                                                       ~~~~~~~
     ·G  N  Q   A  F  A  S   Y  M  N   D  A  F   Q  A  S  S   P  D  T   T  Q  Y
561  CGGCAATCAG GCCTTCGCGT CGTACATGAA CGATGCCTTC CAAGCCTCGA GCCCAGATAC GACGCAGTAT
                                                                       NcoI
                                                                       ~~
      F  R  V  T   H  A  N   D  G  I   P  N  L  P   P  V  E   Q  G  Y   A  H  G  G
631  TTCCGGGTCA CTCATGCCAA CGACGGCATC CCAAACCTGC CCCCGGTGGA GCAGGGGTAC GCCCATGGCG
     · V  E  Y   W  S  V   D  P  Y  S   A  Q  N   T  F  V   C  T  G  D   E  V  Q ·
701  GTGTAGAGTA CTGGAGCGTT GATCCTTACA GCGCCCAGAA CACATTTGTC TGCACTGGGG ATGAAGTGCA
     ·C  C  E   A  Q  G  G   Q  G  V   N  N  A   H  T  T  Y   F  G  M   T  S  G
771  GTGCTGTGAG GCCCAGGGCG GACAGGGTGT GAATAATGCG CACACGACTT ATTTTGGGAT GACGAGCGGC
```

FIG._37B

```
      SphI              NotI
      ~~~~~~          ~~~~~~~~~~
       A  C  T  W  P  V  A  A  A  E  P  L  K  D  E  L  *
 841  GCATGCACCT GGCCGGTCGC GGCCGCGGAA CCACTGAAGG ATGAGCTGTA AAGAAGCAGA TCGTTCAAAC
 911  ATTTGGCAAT AAAGTTTCTT AAGATTGAAT CCTGTTGCCG GTCTTGCGAT GATTATCATA TAATTTCTGT
 981  TGAATTACGT TAAGCATGTA ATAATTAACA TGTAATGCAT GACGTTATTT ATGAGATGGG TTTTTATGAT
1051  TAGAGTCCCG CAATTATACA TTTAATACGC GATAGAAAAC AAAATATAGC GCGCAAACTA GGATAAATTA
                                          HindIII
                                          ~~~~~~~
                                    ClaI        XbaI
                                   ~~~~~~      ~~~~~~
1121  TCGCGCGCGG TGTCATCTAT GTTACTAGAT CGATAAGCTT CTAGAGCGGC CGGTGGAGCT CCAATTCGCC
1191  CTATAGTGAG TCGTATTACG CGCGCTCACT GGCCGTCGTT TTACAACGTC GTGACTGGGA AAACCCTGGC
1261  GTTACCCAAC TTAATCGCCT TGCAGCACAT CCCCCTTTCG CCAGCTGGCG TAATAGCGAA GAGGCCCGCA
1331  CCGATCGCCC TTCCCAACAG TTGCGCAGCC TGAATGGCGA ATGGGACGCG CCCTGTAGCG GCGCATTAAG
1401  CGCGGCGGGT GTGGTGGTTA CGCGCAGCGT GACCGCTACA CTTGCCAGCG CCCTAGCGCC CGCTCCTTTC
1471  GCTTTCTTCC CTTCCTTTCT CGCCACGTTC GCCGGCTTTC CCCGTCAAGC TCTAAATCGG GGGCTCCCTT
1541  TAGGGTTCCG ATTTAGTGCT TTACGGCACC TCGACCCCAA AAAACTTGAT TAGGGTGATG GTTCACGTAG
1611  TGGGCCATCG CCCTGATAGA CGGTTTTTCG CCCTTTGACG TTGGAGTCCA CGTTCTTTAA TAGTGGACTC
1681  TTGTTCCAAA CTGGAACAAC ACTCAACCCT ATCTCGGTCT ATTCTTTTGA TTTATAAGGG ATTTTGCCGA
1751  TTTCGGCCTA TTGGTTAAAA AATGAGCTGA TTTAACAAAA ATTTAACGCG AATTTTAACA AAATATTAAC
1821  GCTTACAATT TAGGTGGCAC TTTTCGGGGA AATGTGCGCG GAACCCCTAT TTGTTTATTT TTCTAAATAC
1891  ATTCAAATAT GTATCCGCTC ATGAGACAAT AACCCTGATA AATGCTTCAA TAATATTGAA AAAGGAAGAG
1961  TATGAGTATT CAACATTTCC GTGTCGCCCT TATTCCCTTT TTTGCGGCAT TTTGCCTTCC TGTTTTTGCT
2031  CACCCAGAAA CGCTGGTGAA AGTAAAAGAT GCTGAAGATC AGTTGGGTGC ACGAGTGGGT TACATCGAAC
2101  TGGATCTCAA CAGCGGTAAG ATCCTTGAGA GTTTTCGCCC CGAAGAACGT TTTCCAATGA TGAGCACTTT
2171  TAAAGTTCTG CTATGTGGCG CGGTATTATC CCGTATTGAC GCCGGGCAAG AGCAACTCGG TCGCCGCATA
2241  CACTATTCTC AGAATGACTT GGTTGAGTAC TCACCAGTCA CAGAAAAGCA TCTTACGGAT GGCATGACAG
2311  TAAGAGAATT ATGCAGTGCT GCCATAACCA TGAGTGATAA CACTGCGGCC AACTTACTTC TGACAACGAT
2381  CGGAGGACCG AAGGAGCTAA CCGCTTTTTT GCACAACATG GGGGATCATG TAACTCGCCT TGATCGTTGG
2451  GAACCGGAGC TGAATGAAGC CATACCAAAC GACGAGCGTG ACACCACGAT GCCTGTAGCA ATGGCAACAA
2521  CGTTGCGCAA ACTATTAACT GGCGAACTAC TTACTCTAGC TTCCCGGCAA CAATTAATAG ACTGGATGGA
2591  GGCGGATAAA GTTGCAGGAC CACTTCTGCG CTCGGCCCTT CCGGCTGGCT GGTTTATTGC TGATAAATCT
2661  GGAGCCGGTG AGCGTGGGTC TCGCGGTATC ATTGCAGCAC TGGGGCCAGA TGGTAAGCCC TCCCGTATCG
```

FIG._37C

```
2731 TAGTTATCTA CACGACGGGG AGTCAGGCAA CTATGGATGA ACGAAATAGA CAGATCGCTG AGATAGGTGC
2801 CTCACTGATT AAGCATTGGT AACTGTCAGA CCAAGTTTAC TCATATATAC TTTAGATTGA TTTAAAACTT
2871 CATTTTTAAT TTAAAAGGAT CTAGGTGAAG ATCCTTTTTG ATAATCTCAT GACCAAAATC CCTTAACGTG
2941 AGTTTTCGTT CCACTGAGCG TCAGACCCCG TAGAAAAGAT CAAAGGATCT TCTTGAGATC CTTTTTTTCT
3011 GCGCGTAATC TGCTGCTTGC AAACAAAAAA ACCACCGCTA CCAGCGGTGG TTTGTTTGCC GGATCAAGAG
3081 CTACCAACTC TTTTTCCGAA GGTAACTGGC TTCAGCAGAG CGCAGATACC AAATACTGTC CTTCTAGTGT
3151 AGCCGTAGTT AGGCCACCAC TTCAAGAACT CTGTAGCACC GCCTACATAC CTCGCTCTGC TAATCCTGTT
3221 ACCAGTGGCT GCTGCCAGTG GCGATAAGTC GTGTCTTACC GGGTTGGACT CAAGACGATA GTTACCGGAT
3291 AAGGCGCAGC GGTCGGGCTG AACGGGGGGT TCGTGCACAC AGCCCAGCTT GGAGCGAACG ACCTACACCG
3361 AACTGAGATA CCTACAGCGT GAGCTATGAG AAAGCGCCAC GCTTCCCGAA GGGAGAAAGG CGGACAGGTA
3431 TCCGGTAAGC GGCAGGGTCG GAACAGGAGA GCGCACGAGG GAGCTTCCAG GGGGAAACGC CTGGTATCTT
3501 TATAGTCCTG TCGGGTTTCG CCACCTCTGA CTTGAGCGTC GATTTTTGTG ATGCTCGTCA GGGGGGCGGA
3571 GCCTATGGAA AAACGCCAGC AACGCGGCCT TTTTACGGTT CCTGGCCTTT TGCTGGCCTT TTGCTCACAT
3641 GTTCTTTCCT GCGTTATCCC CTGATTCTGT GGATAACCGT ATTACCGCCT TTGAGTGAGC TGATACCGCT
3711 CGCCGCAGCC GAACGACCGA GCGCAGCGAG TCAGTGAGCG AGGAAGCGGA AGAGCGCCCA ATACGCAAAC
3781 CGCCTCTCCC CGCGCGTTGG CCGATTCATT AATGCAGCTG GCACGACAGG TTTCCCGACT GGAAAGCGGG
3851 CAGTGAGCGC AACGCAATTA ATGTGAGTTA GCTCACTCAT TAGGCACCCC AGGCTTTACA CTTTATGCTT
3921 CCGGCTCGTA TGTTGTGTGG AATTGTGAGC GGATAACAAT TTCACACAGG AAACAGCTAT GACCATGATT
                                                        KpnI            XhoI
                                                      ~~~~~~~         ~~~~~~
3991 ACGCCAAGCG CGCAATTAAC CCTCACTAAA GGGAACAAAA GCTGGGTACC GGGCCCCCCC TCGAGGTCAT
4061 TCATATGCTT GAGAAGAGAG TCGGGATAGT CCAAAATAAA ACAAAGGTAA GATTACCTGG TCAAAAGTGA
4131 AAACATCAGT TAAAAGGTGG TATAAGTAAA ATATCGGTAA TAAAAGGTGG CCCAAAGTGA AATTTACTCT
4201 TTTCTACTAT TATAAAAATT GAGGATGTTT TGTCGGTACT TTGATACGTC ATTTTTGTAT GAATTGGTTT
4271 TTAAGTTTAT TCGCGATTTG GAAATGCATA TCTGTATTTG AGTCGGTTTT TAAGTTCGTT GCTTTTGTAA
4341 ATACAGAGGG ATTTGTATAA GAAATATCTT TAAAAAACCC ATATGCTAAT TTGACATAAT TTTTGAGAAA
                     EcoRI
                    ~~~~~~~
4411 AATATATATT CAGGCGAATT CCACAATGAA CAATAATAAG ATTAAAATAG CTTGCCCCCG TTGCAGCGAT
4481 GGGTATTTTT TCTAGTAAAA TAAAAGATAA ACTTAGACTC AAAACATTTA CAAAAACAAC CCCTAAAGTC
4551 CTAAAGCCCA AAGTGCTATG CACGATCCAT AGCAAGCCCA GCCCAACCCA ACCCAACCCA ACCCACCCCA
4621 GTGCAGCCAA CTGGCAAATA GTCTCCACCC CCGGCACTAT CACCGTGAGT TGTCCGCACC ACCGCACGTC
4691 TCGCAGCCAA AAAAAAAAAA AGAAAGAAAA AAAAGAAAAA GAAAAACAGC AGGTGGGTCC GGGTCGTGGG
```

FIG._37D

```
4761  GGCCGGAAAA GCGAGGAGGA TCGCGAGCAG CGACGAGGCC CGGCCCTCCC TCCGCTTCCA AAGAAACGCC
4831  CCCCATCGCC ACTATATACA TACCCCCCCC TCTCCTCCCA TCCCCCCAAC CCTACCACCA CCACCACCAC
4901  CACCTCCTCC CCCCTCGCTG CCGGACGACG AGCTCCTCCC CCCTCCCCCT CCGCCGCCGC CGGTAACCAC
4971  CCCGCCCCTC TCCTCTTTCT TTCTCCGTTT TTTTTTTCGT CTCGGTCTCG ATCTTTGGCC TTGGTAGTTT
5041  GGGTGGGCGA GAGCGGCTTC GTCGCCCAGA TCGGTGCGCG GGAGGGGCGG GATCTCGCGG CTGGCGTCTC
                            BamHI                                  BglII
                           ~~~~~~~                                ~~~~~~
5111  CGGGCGTGAG TCGGCCCGGA TCCTCGCGGG GAATGGGGCT CTCGGATGTA GATCTTCTTT CTTTCTTCTT
5181  TTTGTGGTAG AATTTGAATC CCTCAGCATT GTTCATCGGT AGTTTTTCTT TTCATGATTT GTGACAAATG
5251  CAGCCTCGTG CGGAGCTTTT TTGTAGC
```

FIG._37E

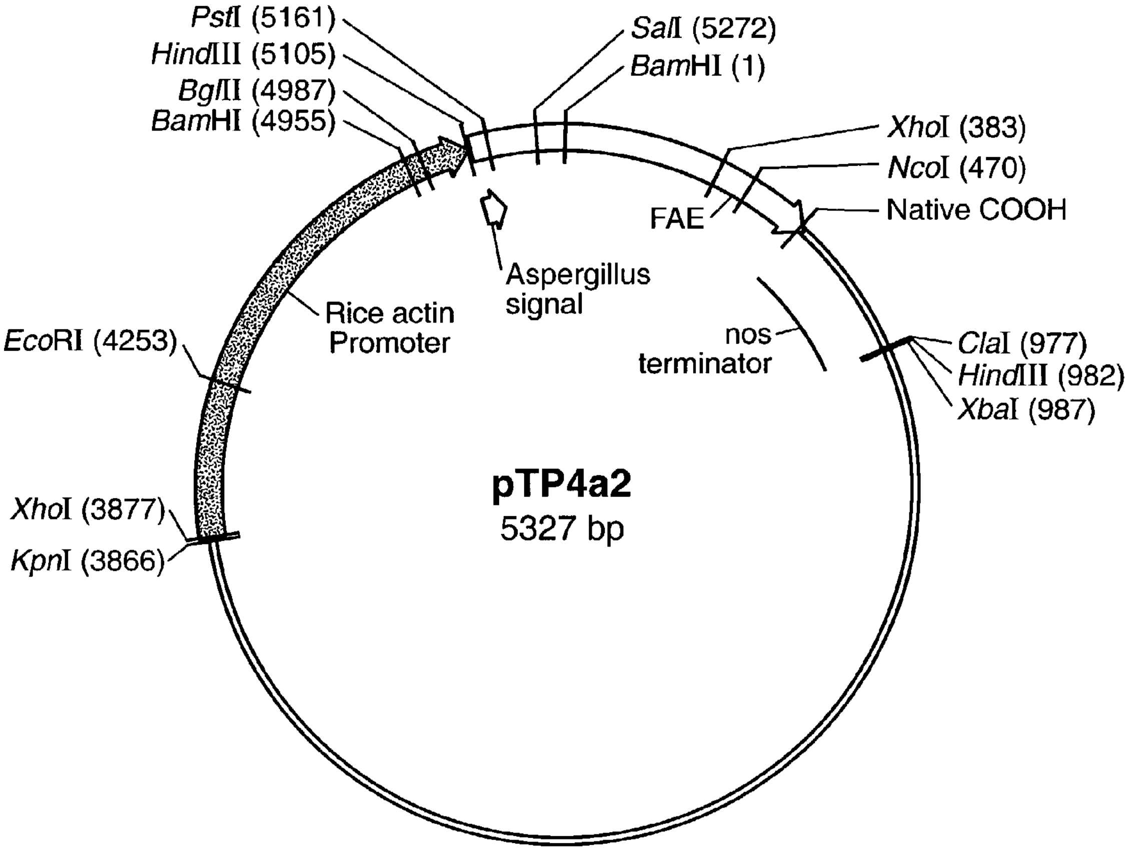
FIG._38A

```
                                     BamHI
                                     ~~~~~
     ·I  L  R   D  D  S  S   K  E  I   I  T  V   F  R  G  T   G  S  D   T  N  L
  1  GATCCTCCGC GACGACAGCA GCAAAGAAAT AATCACCGTC TTCCGTGGCA CTGGTAGTGA TACGAATCTA
      Q  L  D  T   N  Y  T   L  T  P   F  D  T  L   P  Q  C   N  G  C   E  V  H  G
 71  CAACTCGATA CTAACTACAC CCTCACGCCT TTCGACACCC TACCACAATG CAACGGTTGT GAAGTACACG
     · G  Y  Y   I  G  W   V  S  V  Q   D  Q  V   E  S  L   V  K  Q  Q   V  S  Q ·
141  GTGGATATTA TATTGGATGG GTCTCCGTCC AGGACCAAGT CGAGTCGCTT GTCAAACAGC AGGTTAGCCA
     ·Y  P  D   Y  A  L  T   V  T  G   H  X  L   G  A  S  L   A  A  L   T  A  A
211  GTATCCGGAC TACGCGCTGA CCGTGACCGG CCACKCCCTC GGCGCCTCCC TGGCGGCACT CACTGCCGCC
      Q  L  S  A   T  Y  D   N  I  R   L  Y  T  F   G  E  P   R  S  G   N  Q  A  F
281  CAGCTGTCTG CGACATACGA CAACATCCGC CTGTACACCT TCGGCGAACC GCGCAGCGGC AATCAGGCCT
                                                             XhoI
                                                           ~~~~~~~
     · A  S  Y   M  N  D   A  F  Q  A   S  S  P   D  T  T   Q  Y  F  R   V  T  H ·
351  TCGCGTCGTA CATGAACGAT GCCTTCCAAG CCTCGAGCCC AGATACGACG CAGTATTTCC GGGTCACTCA
                                                                 NcoI
                                                                ~~~~~~
     ·A  N  D   G  I  P  N   L  P  P   V  E  Q   G  Y  A  H   G  G  V   E  Y  W
421  TGCCAACGAC GGCATCCCAA ACCTGCCCCC GGTGGAGCAG GGGTACGCCC ATGGCGGTGT AGAGTACTGG
      S  V  D  P   Y  S  A   Q  N  T   F  V  C  T   G  D  E   V  Q  C   C  E  A  Q
491  AGCGTTGATC CTTACAGCGC CCAGAACACA TTTGTCTGCA CTGGGGATGA AGTGCAGTGC TGTGAGGCCC
     · G  G  Q   G  V  N   N  A  H  T   T  Y  F   G  M  T   S  G  A  C   T  W  * ·
561  AGGGCGGACA GGGTGTGAAT AATGCGCACA CGACTTATTT TGGGATGACG AGCGGAGCCT GTACATGGTG
     · *
631  ATCAGTCATT TCAGCCTCCC CGAGTGTACC AGGAAAGATG GATGTCCTGG AGAGGGGGCC GCGTAACCAC
701  TGAAGGATGA GCTGTAAAGA AGCAGATCGT TCAAACATTT GGCAATAAAG TTTCTTAAGA TTGAATCCTG
771  TTGCCGGTCT TGCGATGATT ATCATATAAT TTCTGTTGAA TTACGTTAAG CATGTAATAA TTAACATGTA
841  ATGCATGACG TTATTTATGA GATGGGTTTT TATGATTAGA GTCCCGCAAT TATACATTTA ATACGCGATA
                                                                           ClaI
911  GAAAACAAAA TATAGCGCGC AAACTAGGAT AAATTATCGC GCGCGGTGTC ATCTATGTTA CTAGATCGAT
                                     XbaI
                                   ~~~~~~~
                                 HindIII
                                 ~~~~~~
```

FIG._38B

```
 981 AAGCTTCTAG AGCGGCCGGT GGAGCTCCAA TTCGCCCTAT AGTGAGTCGT ATTACGCGCG CTCACTGGCC
1051 GTCGTTTTAC AACGTCGTGA CTGGGAAAAC CCTGGCGTTA CCCAACTTAA TCGCCTTGCA GCACATCCCC
1121 CTTTCGCCAG CTGGCGTAAT AGCGAAGAGG CCCGCACCGA TCGCCCTTCC CAACAGTTGC GCAGCCTGAA
1191 TGGCGAATGG GACGCGCCCT GTAGCGGCGC ATTAAGCGCG GCGGGTGTGG TGGTTACGCG CAGCGTGACC
1261 GCTACACTTG CCAGCGCCCT AGCGCCCGCT CCTTTCGCTT TCTTCCCTTC CTTTCTCGCC ACGTTCGCCG
1331 GCTTTCCCCG TCAAGCTCTA AATCGGGGGC TCCCTTTAGG GTTCCGATTT AGTGCTTTAC GGCACCTCGA
1401 CCCCAAAAAA CTTGATTAGG GTGATGGTTC ACGTAGTGGG CCATCGCCCT GATAGACGGT TTTTCGCCCT
1471 TTGACGTTGG AGTCCACGTT CTTTAATAGT GGACTCTTGT TCCAAACTGG AACAACACTC AACCCTATCT
1541 CGGTCTATTC TTTTGATTTA TAAGGGATTT TGCCGATTTC GGCCTATTGG TTAAAAAATG AGCTGATTTA
1611 ACAAAAATTT AACGCGAATT TTAACAAAAT ATTAACGCTT ACAATTTAGG TGGCACTTTT CGGGGAAATG
1681 TGCGCGGAAC CCCTATTTGT TTATTTTTCT AAATACATTC AAATATGTAT CCGCTCATGA GACAATAACC
1751 CTGATAAATG CTTCAATAAT ATTGAAAAAG GAAGAGTATG AGTATTCAAC ATTTCCGTGT CGCCCTTATT
1821 CCCTTTTTTG CGGCATTTTG CCTTCCTGTT TTTGCTCACC CAGAAACGCT GGTGAAAGTA AAAGATGCTG
1891 AAGATCAGTT GGGTGCACGA GTGGGTTACA TCGAACTGGA TCTCAACAGC GGTAAGATCC TTGAGAGTTT
1961 TCGCCCCGAA GAACGTTTTC CAATGATGAG CACTTTTAAA GTTCTGCTAT GTGGCGCGGT ATTATCCCGT
2031 ATTGACGCCG GGCAAGAGCA ACTCGGTCGC CGCATACACT ATTCTCAGAA TGACTTGGTT GAGTACTCAC
2101 CAGTCACAGA AAAGCATCTT ACGGATGGCA TGACAGTAAG AGAATTATGC AGTGCTGCCA TAACCATGAG
2171 TGATAACACT GCGGCCAACT TACTTCTGAC AACGATCGGA GGACCGAAGG AGCTAACCGC TTTTTTGCAC
2241 AACATGGGGG ATCATGTAAC TCGCCTTGAT CGTTGGGAAC CGGAGCTGAA TGAAGCCATA CCAAACGACG
2311 AGCGTGACAC CACGATGCCT GTAGCAATGG CAACAACGTT GCGCAAACTA TTAACTGGCG AACTACTTAC
2381 TCTAGCTTCC CGGCAACAAT TAATAGACTG GATGGAGGCG GATAAAGTTG CAGGACCACT TCTGCGCTCG
2451 GCCCTTCCGG CTGGCTGGTT TATTGCTGAT AAATCTGGAG CCGGTGAGCG TGGGTCTCGC GGTATCATTG
2521 CAGCACTGGG GCCAGATGGT AAGCCCTCCC GTATCGTAGT TATCTACACG ACGGGGAGTC AGGCAACTAT
2591 GGATGAACGA AATAGACAGA TCGCTGAGAT AGGTGCCTCA CTGATTAAGC ATTGGTAACT GTCAGACCAA
2661 GTTTACTCAT ATATACTTTA GATTGATTTA AAACTTCATT TTTAATTTAA AAGGATCTAG GTGAAGATCC
2731 TTTTTGATAA TCTCATGACC AAAATCCCTT AACGTGAGTT TTCGTTCCAC TGAGCGTCAG ACCCCGTAGA
2801 AAAGATCAAA GGATCTTCTT GAGATCCTTT TTTTCTGCGC GTAATCTGCT GCTTGCAAAC AAAAAAACCA
2871 CCGCTACCAG CGGTGGTTTG TTTGCCGGAT CAAGAGCTAC CAACTCTTTT TCCGAAGGTA ACTGGCTTCA
2941 GCAGAGCGCA GATACCAAAT ACTGTCCTTC TAGTGTAGCC GTAGTTAGGC CACCACTTCA AGAACTCTGT
3011 AGCACCGCCT ACATACCTCG CTCTGCTAAT CCTGTTACCA GTGGCTGCTG CCAGTGGCGA TAAGTCGTGT
3081 CTTACCGGGT TGGACTCAAG ACGATAGTTA CCGGATAAGG CGCAGCGGTC GGGCTGAACG GGGGGTTCGT
3151 GCACACAGCC CAGCTTGGAG CGAACGACCT ACACCGAACT GAGATACCTA CAGCGTGAGC TATGAGAAAG
3221 CGCCACGCTT CCCGAAGGGA GAAAGGCGGA CAGGTATCCG GTAAGCGGCA GGGTCGGAAC AGGAGAGCGC
3291 ACGAGGGAGC TTCCAGGGGG AAACGCCTGG TATCTTTATA GTCCTGTCGG GTTTCGCCAC CTCTGACTTG
3361 AGCGTCGATT TTTGTGATGC TCGTCAGGGG GGCGGAGCCT ATGGAAAAAC GCCAGCAACG CGGCCTTTTT
```

FIG._38C

```
3431  ACGGTTCCTG GCCTTTTGCT GGCCTTTTGC TCACATGTTC TTTCCTGCGT TATCCCCTGA TTCTGTGGAT
3501  AACCGTATTA CCGCCTTTGA GTGAGCTGAT ACCGCTCGCC GCAGCCGAAC GACCGAGCGC AGCGAGTCAG
3571  TGAGCGAGGA AGCGGAAGAG CGCCCAATAC GCAAACCGCC TCTCCCCGCG CGTTGGCCGA TTCATTAATG
3641  CAGCTGGCAC GACAGGTTTC CCGACTGGAA AGCGGGCAGT GAGCGCAACG CAATTAATGT GAGTTAGCTC
3711  ACTCATTAGG CACCCCAGGC TTTACACTTT ATGCTTCCGG CTCGTATGTT GTGTGGAATT GTGAGCGGAT
3781  AACAATTTCA CACAGGAAAC AGCTATGACC ATGATTACGC CAAGCGCGCA ATTAACCCTC ACTAAAGGGA
                                 KpnI            XhoI
                                ~~~~~~          ~~~~~~~~
3851  ACAAAAGCTG GGTACCGGGC CCCCCCTCGA GGTCATTCAT ATGCTTGAGA AGAGAGTCGG GATAGTCCAA
3921  AATAAAACAA AGGTAAGATT ACCTGGTCAA AAGTGAAAAC ATCAGTTAAA AGGTGGTATA AGTAAAATAT
3991  CGGTAATAAA AGGTGGCCCA AAGTGAAATT TACTCTTTTC TACTATTATA AAAATTGAGG ATGTTTTGTC
4061  GGTACTTTGA TACGTCATTT TTGTATGAAT TGGTTTTTAA GTTTATTCGC GATTTGGAAA TGCATATCTG
4131  TATTTGAGTC GGTTTTTAAG TTCGTTGCTT TTGTAAATAC AGAGGGATTT GTATAAGAAA TATCTTTAAA
                                                                       EcoRI
                                                                      ~~~~~~~~
4201  AAACCCATAT GCTAATTTGA CATAATTTTT GAGAAAAATA TATATTCAGG CGAATTCCAC AATGAACAAT
4271  AATAAGATTA AAATAGCTTG CCCCCGTTGC AGCGATGGGT ATTTTTTCTA GTAAAATAAA AGATAAACTT
4341  AGACTCAAAA CATTTACAAA AACAACCCCT AAAGTCCTAA AGCCCAAAGT GCTATGCACG ATCCATAGCA
4411  AGCCCAGCCC AACCCAACCC AACCCAACCC ACCCCAGTGC AGCCAACTGG CAAATAGTCT CCACCCCCGG
4481  CACTATCACC GTGAGTTGTC CGCACCACCG CACGTCTCGC AGCCAAAAAA AAAAAAAGAA AGAAAAAAAA
4551  GAAAAAGAAA AACAGCAGGT GGGTCCGGGT CGTGGGGGCC GGAAAAGCGA GGAGGATCGC GAGCAGCGAC
4621  GAGGCCCGGC CCTCCCTCCG CTTCCAAAGA AACGCCCCCC ATCGCCACTA TATACATACC CCCCCCTCTC
4691  CTCCCATCCC CCCAACCCTA CCACCACCAC CACCACCACC TCCTCCCCCC TCGCTGCCGG ACGACGAGCT
4761  CCTCCCCCCT CCCCCTCCGC CGCCGCCGGT AACCACCCCG CCCCTCTCCT CTTTCTTTCT CCGTTTTTTT
4831  TTTCGTCTCG GTCTCGATCT TTGGCCTTGG TAGTTTGGGT GGGCGAGAGC GGCTTCGTCG CCCAGATCGG
                                                                      BamHI
                                                                     ~~~~~~~~
4901  TGCGCGGGAG GGGCGGGATC TCGCGGCTGG CGTCTCCGGG CGTGAGTCGG CCCGGATCCT CGCGGGGAAT
                                                   BglII
                                                  ~~~~~~~~
4971  GGGGCTCTCG GATGTAGATC TTCTTTCTTT CTTCTTTTTG TGGTAGAATT TGAATCCCTC AGCATTGTTC
                                                                        HindIII
                                                                           ~
5041  ATCGGTAGTT TTTCTTTTCA TGATTTGTGA CAAATGCAGC CTCGTGCGGA GCTTTTTTGT AGCAAGCTTA
```

FIG._38D

```
                                                                    PstI
                                                                  ~~~~~~~~
        M  K  Q   F  S  A   K  H  V  L   A  V  V   V  T  A   G  H  A  L   A  A  S ·
5111  ACATGAAGCA GTTCTCCGCC AAACACGTCC TCGCAGTTGT GGTGACTGCA GGGCACGCCT TAGCAGCCTC
       · T  Q  G   I  S  E  D   L  Y  S   R  L  V   E  M  A  T   I  S  Q   A  A  Y
5181  TACGCAAGGC ATCTCCGAAG ACCTCTACAG CCGTTTAGTC GAAATGGCCA CTATCTCCCA AGCTGCCTAC
                                                    SalI
                                                   ~~~~~~
       A  D  L  C   N  I  P   S  T  I   I  K  G  E   K  I  Y   N  S  Q   T  D  I  N
5251  GCCGACCTGT GCAACATTCC GTCGACTATT ATCAAGGGAG AGAAAATTTA CAATTCTCAA ACTGACATTA
          B
          ~
       · G  W
5321  ACGGATG
```

FIG._38E

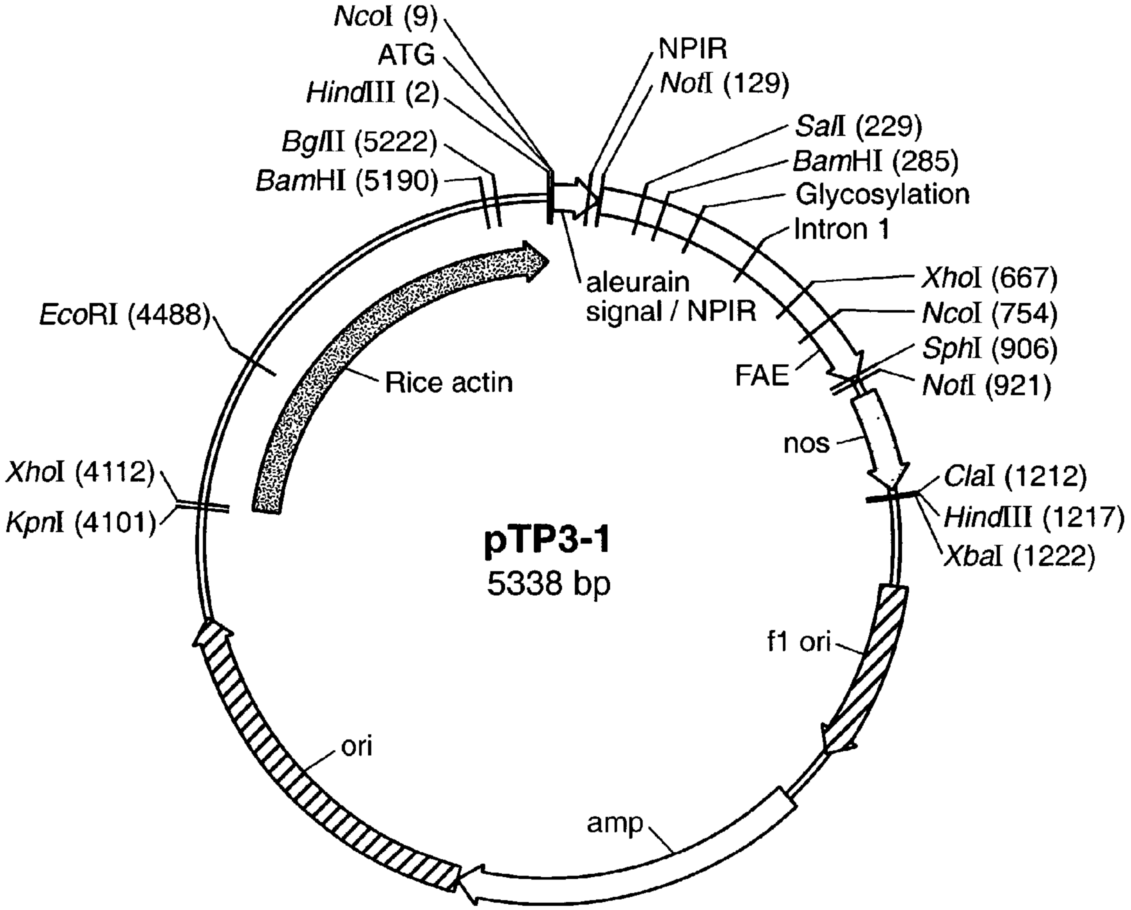
FIG._39A

```
                 NcoI
               ~~~~~~~~
     HindIII
     ~~~~~~
               M  A  H  A  R  V  L  L  L  A  L  A  V  L  A  T  A  A  V  A  V
  1  AAGCTTACCA TGGCCCACGC CCGCGTCCTC CTCCTGGCGC TCGCCGTGCT GGCCACGGCC GCCGTCGCCG

                                     NPIR                  NotI
                                 ~~~~~~~~~~~~~~         ~~~~~~~~
     · A  S  S  S  S  F  A  D  S  N  P  I  R  P  V  T  D  R  A  A  A  S  T ·
 71  TCGCCTCCTC CTCCTCCTTC GCCGACTCCA ACCCGATCCG GCCCGTCACC GACCGCGCGG CCGCCTCCAC
     ·Q  G  I  S  E  D  L  Y  S  R  L  V  E  M  A  T  I  S  Q  A  A  Y  A
141  GCAGGGCATC TCCGAAGACC TCTACAGCCG TTTAGTCGAA ATGGCCACTA TCTCCCAAGC TGCCTACGCC

                      SalI
                    ~~~~~~~~
      D  L  C  N  I  P  S  T  I  I  K  G  E  K  I  Y  N  S  Q  T  D  I  N  G
211  GACCTGTGCA ACATTCCGTC GACTATTATC AAGGGAGAGA AAATTTACAA TTCTCAAACT GACATTAACG

        BamHI
        ~~~~~~
     · W  I  L  R  D  D  S  S  K  E  I  I  T  V  F  R  G  T  G  S  D  T  N ·
281  GATGGATCCT CCGCGACGAC AGCAGCAAAG AAATAATCAC CGTCTTCCGT GGCACTGGTA GTGATACGAA

                  Glycosylation
                    ~~~~
     ·L  Q  L  D  T  N  Y  T  L  T  P  F  D  T  L  P  Q  C  N  G  C  E  V
351  TCTACAACTC GATACTAACT ACACCCTCAC GCCTTTCGAC ACCCTACCAC AATGCAACGG TTGTGAAGTA
      H  G  G  Y  Y  I  G  W  V  S  V  Q  D  Q  V  E  S  L  V  K  Q  Q  V  S
421  CACGGTGGAT ATTATATTGG ATGGGTCTCC GTCCAGGACC AAGTCGAGTC GCTTGTCAAA CAGCAGGTTA
     · Q  Y  P  D  Y  A  L  T  V  T  G  H  X  L  G  A  S  L  A  A  L  T  A ·
491  GCCAGTATCC GGACTACGCG CTGACCGTGA CCGGCCACKC CCTCGGCGCC TCCCTGGCGG CACTCACTGC
     ·A  Q  L  S  A  T  Y  D  N  I  R  L  Y  T  F  G  E  P  R  S  G  N  Q
561  CGCCCAGCTG TCTGCGACAT ACGACAACAT CCGCCTGTAC ACCTTCGGCG AACCGCGCAG CGGCAATCAG
```

FIG._39B

```
                                                    XhoI
                                                  ~~~~~~~
       A  F  A  S   Y  M  N   D  A  F   Q  A  S  S   P  D  T   T  Q  Y   F  R  V  T
 631  GCCTTCGCGT CGTACATGAA CGATGCCTTC CAAGCCTCGA GCCCAGATAC GACGCAGTAT TTCCGGGTCA

                                                                    NcoI
                                                                  ~~~~~~~
      · H  A  N   D  G  I   P  N  L  P   P  V  E   Q  G  Y   A  H  G  G   V  E  Y ·
 701  CTCATGCCAA CGACGGCATC CCAAACCTGC CCCCGGTGGA GCAGGGGTAC GCCCATGGCG GTGTAGAGTA
      ·W  S  V   D  P  Y  S   A  Q  N   T  F  V   C  T  G  D   E  V  Q   C  C  E
 771  CTGGAGCGTT GATCCTTACA GCGCCCAGAA CACATTTGTC TGCACTGGGG ATGAAGTGCA GTGCTGTGAG

                                                                             SphI
                                                                             ~~~~
       A  Q  G  G   Q  G  V   N  N  A   H  T  T  Y   F  G  M   T  S  G   A  C  T  W
 841  GCCCAGGGCG GACAGGGTGT GAATAATGCG CACACGACTT ATTTTGGGAT GACGAGCGGC GCATGCACCT


                NotI                 KDEL
              ~~~~~~~~~         ~~~~~~~~~~~~~~
      · P  V  A   A  A  E   T  T  E  G   *
 911  GGCCGGTCGC GGCCGCGGAA ACCACTGAAG GATGAGCTGT AAAGAAGCAG ATCGTTCAAA CATTTGGCAA
 981  TAAAGTTTCT TAAGATTGAA TCCTGTTGCC GGTCTTGCGA TGATTATCAT ATAATTTCTG TTGAATTACG
1051  TTAAGCATGT AATAATTAAC ATGTAATGCA TGACGTTATT TATGAGATGG GTTTTTATGA TTAGAGTCCC
1121  GCAATTATAC ATTTAATACG CGATAGAAAA CAAAATATAG CGCGCAAACT AGGATAAATT ATCGCGCGCG

                                   HindIII
                                   ~~~~~~~
                             ClaI        XbaI
                            ~~~~~~      ~~~~~~
1191  GTGTCATCTA TGTTACTAGA TCGATAAGCT TCTAGAGCGG CCGGTGGAGC TCCAATTCGC CCTATAGTGA
1261  GTCGTATTAC GCGCGCTCAC TGGCCGTCGT TTTACAACGT CGTGACTGGG AAAACCCTGG CGTTACCCAA
1331  CTTAATCGCC TTGCAGCACA TCCCCCTTTC GCCAGCTGGC GTAATAGCGA AGAGGCCCGC ACCGATCGCC
1401  CTTCCCAACA GTTGCGCAGC CTGAATGGCG AATGGGACGC GCCCTGTAGC GGCGCATTAA GCGCGGCGGG
```

FIG._39C

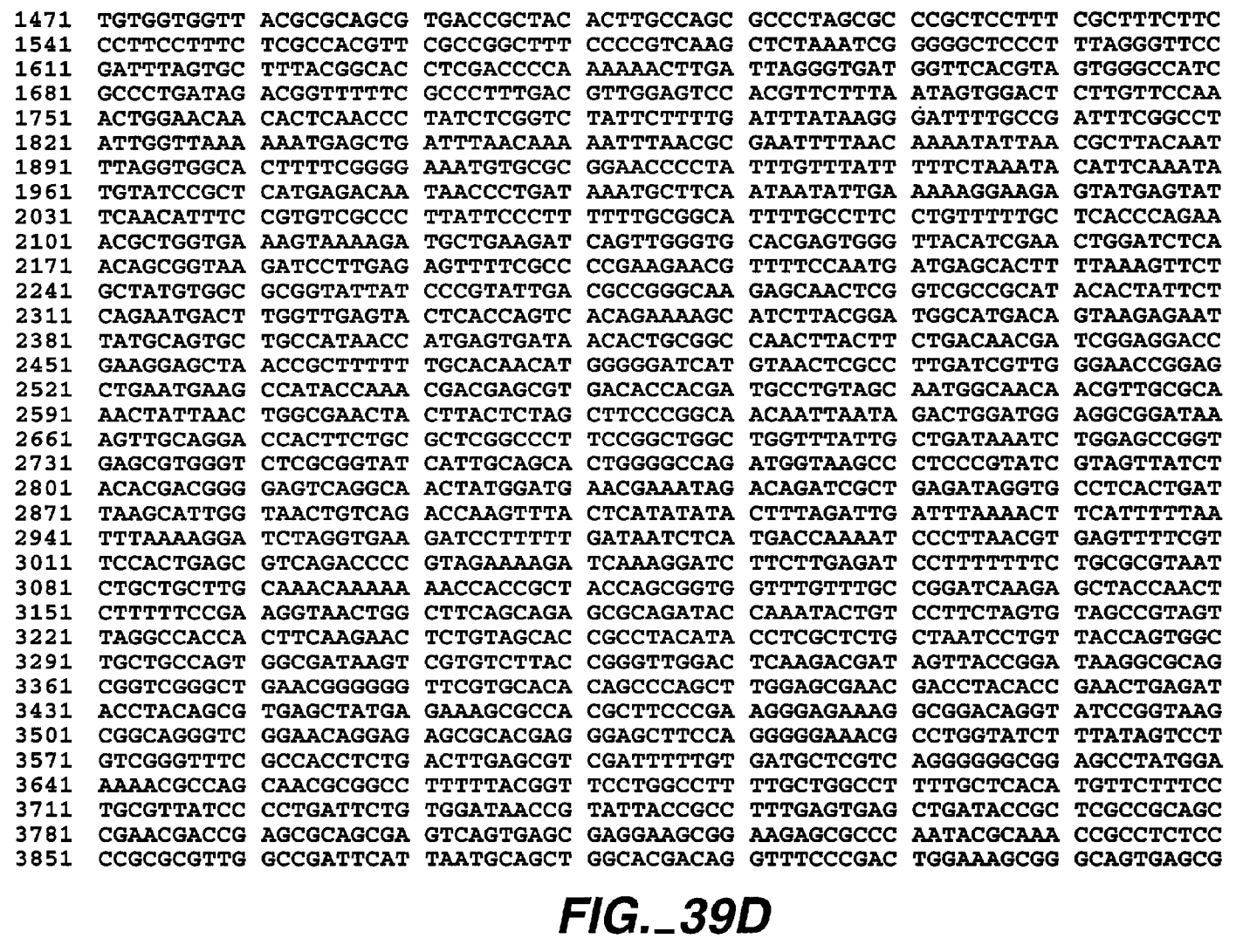

```
1471 TGTGGTGGTT ACGCGCAGCG TGACCGCTAC ACTTGCCAGC GCCCTAGCGC CCGCTCCTTT CGCTTTCTTC
1541 CCTTCCTTTC TCGCCACGTT CGCCGGCTTT CCCCGTCAAG CTCTAAATCG GGGGCTCCCT TTAGGGTTCC
1611 GATTTAGTGC TTTACGGCAC CTCGACCCCA AAAAACTTGA TTAGGGTGAT GGTTCACGTA GTGGGCCATC
1681 GCCCTGATAG ACGGTTTTTC GCCCTTTGAC GTTGGAGTCC ACGTTCTTTA ATAGTGGACT CTTGTTCCAA
1751 ACTGGAACAA CACTCAACCC TATCTCGGTC TATTCTTTTG ATTTATAAGG GATTTTGCCG ATTTCGGCCT
1821 ATTGGTTAAA AAATGAGCTG ATTTAACAAA AATTTAACGC GAATTTTAAC AAAATATTAA CGCTTACAAT
1891 TTAGGTGGCA CTTTTCGGGG AAATGTGCGC GGAACCCCTA TTTGTTTATT TTTCTAAATA CATTCAAATA
1961 TGTATCCGCT CATGAGACAA TAACCCTGAT AAATGCTTCA ATAATATTGA AAAAGGAAGA GTATGAGTAT
2031 TCAACATTTC CGTGTCGCCC TTATTCCCTT TTTTGCGGCA TTTTGCCTTC CTGTTTTTGC TCACCCAGAA
2101 ACGCTGGTGA AAGTAAAAGA TGCTGAAGAT CAGTTGGGTG CACGAGTGGG TTACATCGAA CTGGATCTCA
2171 ACAGCGGTAA GATCCTTGAG AGTTTTCGCC CCGAAGAACG TTTTCCAATG ATGAGCACTT TTAAAGTTCT
2241 GCTATGTGGC GCGGTATTAT CCCGTATTGA CGCCGGGCAA GAGCAACTCG GTCGCCGCAT ACACTATTCT
2311 CAGAATGACT TGGTTGAGTA CTCACCAGTC ACAGAAAAGC ATCTTACGGA TGGCATGACA GTAAGAGAAT
2381 TATGCAGTGC TGCCATAACC ATGAGTGATA ACACTGCGGC CAACTTACTT CTGACAACGA TCGGAGGACC
2451 GAAGGAGCTA ACCGCTTTTT TGCACAACAT GGGGGATCAT GTAACTCGCC TTGATCGTTG GGAACCGGAG
2521 CTGAATGAAG CCATACCAAA CGACGAGCGT GACACCACGA TGCCTGTAGC AATGGCAACA ACGTTGCGCA
2591 AACTATTAAC TGGCGAACTA CTTACTCTAG CTTCCCGGCA ACAATTAATA GACTGGATGG AGGCGGATAA
2661 AGTTGCAGGA CCACTTCTGC GCTCGGCCCT TCCGGCTGGC TGGTTTATTG CTGATAAATC TGGAGCCGGT
2731 GAGCGTGGGT CTCGCGGTAT CATTGCAGCA CTGGGGCCAG ATGGTAAGCC CTCCCGTATC GTAGTTATCT
2801 ACACGACGGG GAGTCAGGCA ACTATGGATG AACGAAATAG ACAGATCGCT GAGATAGGTG CCTCACTGAT
2871 TAAGCATTGG TAACTGTCAG ACCAAGTTTA CTCATATATA CTTTAGATTG ATTTAAAACT TCATTTTTAA
2941 TTTAAAAGGA TCTAGGTGAA GATCCTTTTT GATAATCTCA TGACCAAAAT CCCTTAACGT GAGTTTTCGT
3011 TCCACTGAGC GTCAGACCCC GTAGAAAAGA TCAAAGGATC TTCTTGAGAT CCTTTTTTTC TGCGCGTAAT
3081 CTGCTGCTTG CAAACAAAAA AACCACCGCT ACCAGCGGTG GTTTGTTTGC CGGATCAAGA GCTACCAACT
3151 CTTTTTCCGA AGGTAACTGG CTTCAGCAGA GCGCAGATAC CAAATACTGT CCTTCTAGTG TAGCCGTAGT
3221 TAGGCCACCA CTTCAAGAAC TCTGTAGCAC CGCCTACATA CCTCGCTCTG CTAATCCTGT TACCAGTGGC
3291 TGCTGCCAGT GGCGATAAGT CGTGTCTTAC CGGGTTGGAC TCAAGACGAT AGTTACCGGA TAAGGCGCAG
3361 CGGTCGGGCT GAACGGGGGG TTCGTGCACA CAGCCCAGCT TGGAGCGAAC GACCTACACC GAACTGAGAT
3431 ACCTACAGCG TGAGCTATGA GAAAGCGCCA CGCTTCCCGA AGGGAGAAAG GCGGACAGGT ATCCGGTAAG
3501 CGGCAGGGTC GGAACAGGAG AGCGCACGAG GGAGCTTCCA GGGGGAAACG CCTGGTATCT TTATAGTCCT
3571 GTCGGGTTTC GCCACCTCTG ACTTGAGCGT CGATTTTTGT GATGCTCGTC AGGGGGGCGG AGCCTATGGA
3641 AAAACGCCAG CAACGCGGCC TTTTTACGGT TCCTGGCCTT TTGCTGGCCT TTTGCTCACA TGTTCTTTCC
3711 TGCGTTATCC CCTGATTCTG TGGATAACCG TATTACCGCC TTTGAGTGAG CTGATACCGC TCGCCGCAGC
3781 CGAACGACCG AGCGCAGCGA GTCAGTGAGC GAGGAAGCGG AAGAGCGCCC AATACGCAAA CCGCCTCTCC
3851 CCGCGCGTTG GCCGATTCAT TAATGCAGCT GGCACGACAG GTTTCCCGAC TGGAAAGCGG GCAGTGAGCG
```

FIG._39D

```
3921  CAACGCAATT AATGTGAGTT AGCTCACTCA TTAGGCACCC CAGGCTTTAC ACTTTATGCT TCCGGCTCGT
3991  ATGTTGTGTG GAATTGTGAG CGGATAACAA TTTCACACAG GAAACAGCTA TGACCATGAT TACGCCAAGC
                                                  KpnI         XhoI
                                                ~~~~~~~      ~~~~~~~
4061  GCGCAATTAA CCCTCACTAA AGGGAACAAA AGCTGGGTAC CGGGCCCCCC CTCGAGGTCA TTCATATGCT
4131  TGAGAAGAGA GTCGGGATAG TCCAAAATAA AACAAAGGTA AGATTACCTG GTCAAAAGTG AAAACATCAG
4201  TTAAAAGGTG GTATAAGTAA AATATCGGTA ATAAAAGGTG GCCCAAAGTG AAATTTACTC TTTTCTACTA
4271  TTATAAAAAT TGAGGATGTT TTGTCGGTAC TTTGATACGT CATTTTTGTA TGAATTGGTT TTTAAGTTTA
4341  TTCGCGATTT GGAAATGCAT ATCTGTATTT GAGTCGGTTT TTAAGTTCGT TGCTTTTGTA AATACAGAGG
4411  GATTTGTATA AGAAATATCT TTAAAAAACC CATATGCTAA TTTGACATAA TTTTTGAGAA AAATATATAT
             EcoRI
            ~~~~~~~
4481  TCAGGCGAAT TCCACAATGA ACAATAATAA GATTAAAATA GCTTGCCCCC GTTGCAGCGA TGGGTATTTT
4551  TTCTAGTAAA ATAAAAGATA AACTTAGACT CAAAACATTT ACAAAAACAA CCCCTAAAGT CCTAAAGCCC
4621  AAAGTGCTAT GCACGATCCA TAGCAAGCCC AGCCCAACCC AACCCAACCC AACCCACCCC AGTGCAGCCA
4691  ACTGGCAAAT AGTCTCCACC CCCGGCACTA TCACCGTGAG TTGTCCGCAC CACCGCACGT CTCGCAGCCA
4761  AAAAAAAAAA AAGAAAGAAA AAAAAGAAAA AGAAAAAACAG CAGGTGGGTC CGGGTCGTGG GGGCCGGAAA
4831  AGCGAGGAGG ATCGCGAGCA GCGACGAGGC CCGGCCCTCC CTCCGCTTCC AAAGAAACGC CCCCCATCGC
4901  CACTATATAC ATACCCCCCC CTCTCCTCCC ATCCCCCCAA CCCTACCACC ACCACCACCA CCACCTCCTC
4971  CCCCCTCGCT GCCGGACGAC GAGCTCCTCC CCCCTCCCCC TCCGCCGCCG CCGGTAACCA CCCCGCCCCT
5041  CTCCTCTTTC TTTCTCCGTT TTTTTTTTCG TCTCGGTCTC GATCTTTGGC CTTGGTAGTT TGGGTGGGCG
5111  AGAGCGGCTT CGTCGCCCAG ATCGGTGCGC GGGAGGGGCG GGATCTCGCG GCTGGCGTCT CCGGGCGTGA
               BamHI                              BglII
              ~~~~~~~                            ~~~~~~~
5181  GTCGGCCCGG ATCCTCGCGG GGAATGGGGC TCTCGGATGT AGATCTTCTT TCTTTCTTCT TTTTGTGGTA
5251  GAATTTGAAT CCCTCAGCAT TGTTCATCGG TAGTTTTTCT TTTCATGATT TGTGACAAAT GCAGCCTCGT
5321  GCGGAGCTTT TTTGTAGC
```

FIG._39E

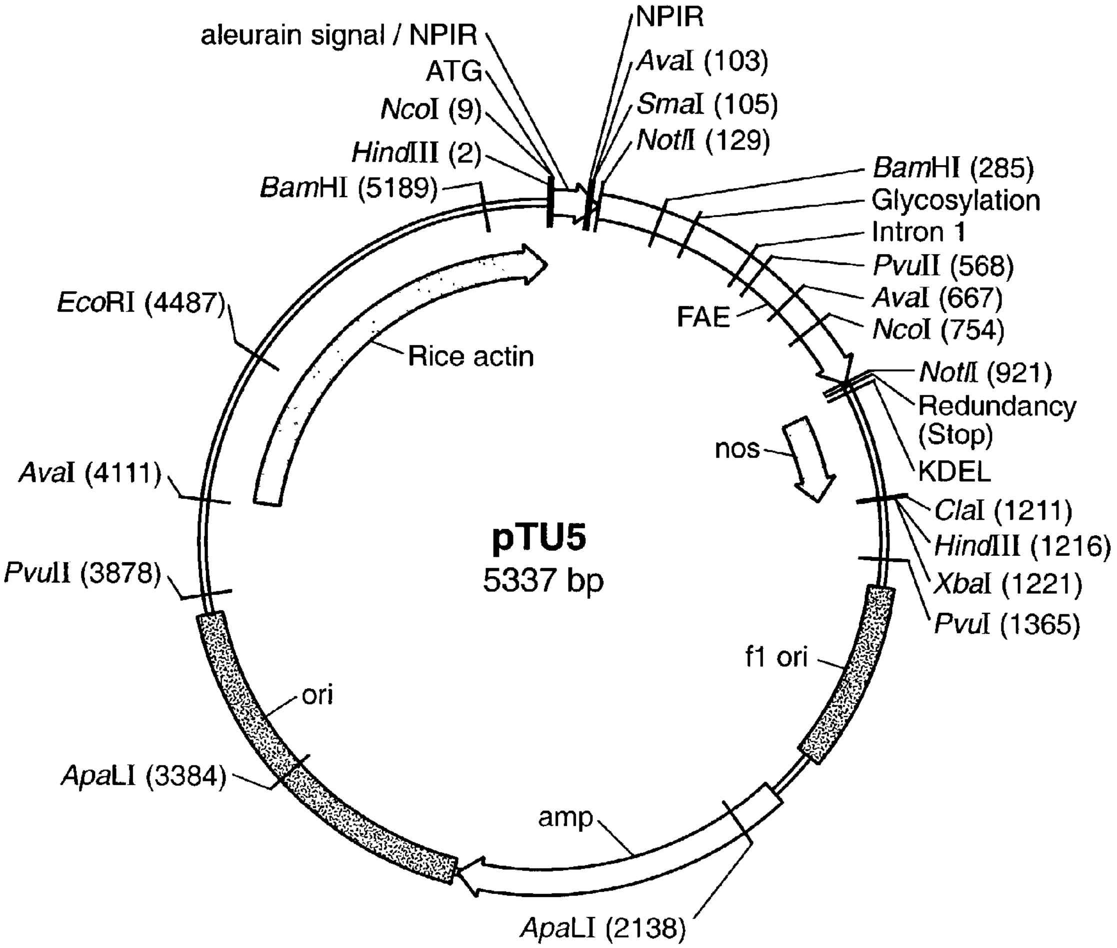
FIG._40A

```
          HindIII NcoI
          ~~~~~~ ~~~~~~~~
   1      AAGCTTACCA TGGCCCACGC CCGCGTCCTC CTCCTGGCGC TCGCCGTGCT
          TTCGAATGGT ACCGGGTGCG GGCGCAGGAG GAGGACCGCG AGCGGCACGA

  51      GGCCACGGCC GCCGTCGCCG TCGCCTCCTC CTCCTCCTTC GCCGACTCCA
          CCGGTGCCGG CGGCAGCGGC AGCGGAGGAG GAGGAGGAAG CGGCTGAGGT

            SmaI
           ~~~~~~
            AvaI                         NotI
           ~~~~~~                      ~~~~~~~~~
 101      ACCCGGGCCG GCCCGTCACC GACCGCGCGG CCGCCTCCAC GCAGGGCATC
          TGGGCCCGGC CGGGCAGTGG CTGGCGCGCC GGCGGAGGTG CGTCCCGTAG

 151      TCCGAAGACC TCTACAGCCG TTTAGTCGAA ATGGCCACTA TCTCCCAAGC
          AGGCTTCTGG AGATGTCGGC AAATCAGCTT TACCGGTGAT AGAGGGTTCG

 201      TGCCTACGCC GACCTGTGCA ACATTCCGTC GACTATTATC AAGGGAGAGA
          ACGGATGCGG CTGGACACGT TGTAAGGCAG CTGATAATAG TTCCCTCTCT

                                               BamHI
                                              ~~~~~~
 251      AAATTTACAA TTCTCAAACT GACATTAACG GATGGATCCT CCGCGACGAC
          TTTAAATGTT AAGAGTTTGA CTGTAATTGC CTACCTAGGA GGCGCTGCTG

 301      AGCAGCAAAG AAATAATCAC CGTCTTCCGT GGCACTGGTA GTGATACGAA
          TCGTCGTTTC TTTATTAGTG GCAGAAGGCA CCGTGACCAT CACTATGCTT

 351      TCTACAACTC GATACTAACT ACACCCTCAC GCCTTTCGAC ACCCTACCAC
          AGATGTTGAG CTATGATTGA TGTGGGAGTG CGGAAAGCTG TGGGATGGTG

 401      AATGCAACGG TTGTGAAGTA CACGGTGGAT ATTATATTGG ATGGGTCTCC
          TTACGTTGCC AACACTTCAT GTGCCACCTA TAATATAACC TACCCAGAGG

 451      GTCCAGGACC AAGTCGAGTC GCTTGTCAAA CAGCAGGTTA GCCAGTATCC
          CAGGTCCTGG TTCAGCTCAG CGAACAGTTT GTCGTCCAAT CGGTCATAGG

 501      GGACTACGCG CTGACCGTGA CCGGCCACKC CCTCGGCGCC TCCCTGGCGG
          CCTGATGCGC GACTGGCACT GGCCGGTGMG GGAGCCGCGG AGGGACCGCC

                         PvuII
                        ~~~~~~
 551      CACTCACTGC CGCCCAGCTG TCTGCGACAT ACGACAACAT CCGCCTGTAC
          GTGAGTGACG GCGGGTCGAC AGACGCTGTA TGCTGTTGTA GGCGGACATG

 601      ACCTTCGGCG AACCGCGCAG CGGCAATCAG GCCTTCGCGT CGTACATGAA
          TGGAAGCCGC TTGGCGCGTC GCCGTTAGTC CGGAAGCGCA GCATGTACTT

                          AvaI
                        ~~~~~~~
 651      CGATGCCTTC CAAGCCTCGA GCCCAGATAC GACGCAGTAT TTCCGGGTCA
          GCTACGGAAG GTTCGGAGCT CGGGTCTATG CTGCGTCATA AAGGCCCAGT
```

FIG._40B

```
 701  CTCATGCCAA CGACGGCATC CCAAACCTGC CCCCGGTGGA GCAGGGGTAC
      GAGTACGGTT GCTGCCGTAG GGTTTGGACG GGGGCCACCT CGTCCCCATG

         NcoI
        ~~~~~~
 751  GCCCATGGCG GTGTAGAGTA CTGGAGCGTT GATCCTTACA GCGCCCAGAA
      CGGGTACCGC CACATCTCAT GACCTCGCAA CTAGGAATGT CGCGGGTCTT

 801  CACATTTGTC TGCACTGGGG ATGAAGTGCA GTGCTGTGAG GCCCAGGGCG
      GTGTAAACAG ACGTGACCCC TACTTCACGT CACGACACTC CGGGTCCCGC

 851  GACAGGGTGT GAATAATGCG CACACGACTT ATTTTGGGAT GACGAGCGGC
      CTGTCCCACA CTTATTACGC GTGTGCTGAA TAAAACCCTA CTGCTCGCCG

                                NotI
                             ~~~~~~~~~
 901  GCATGCACCT GGCCGGTCGC GGCCGCGGAA CCACTGAAGG ATGAGCTGTA
      CGTACGTGGA CCGGCCAGCG CCGGCGCCTT GGTGACTTCC TACTCGACAT

 951  AAGAAGCAGA TCGTTCAAAC ATTTGGCAAT AAAGTTTCTT AAGATTGAAT
      TTCTTCGTCT AGCAAGTTTG TAAACCGTTA TTTCAAAGAA TTCTAACTTA

1001  CCTGTTGCCG GTCTTGCGAT GATTATCATA TAATTTCTGT TGAATTACGT
      GGACAACGGC CAGAACGCTA CTAATAGTAT ATTAAAGACA ACTTAATGCA

1051  TAAGCATGTA ATAATTAACA TGTAATGCAT GACGTTATTT ATGAGATGGG
      ATTCGTACAT TATTAATTGT ACATTACGTA CTGCAATAAA TACTCTACCC

1101  TTTTTATGAT TAGAGTCCCG CAATTATACA TTTAATACGC GATAGAAAAC
      AAAAATACTA ATCTCAGGGC GTTAATATGT AAATTATGCG CTATCTTTTG

1151  AAAATATAGC GCGCAAACTA GGATAAATTA TCGCGCGCGG TGTCATCTAT
      TTTTATATCG CGCGTTTGAT CCTATTTAAT AGCGCGCGCC ACAGTAGATA

                                XbaI
                               ~~~~~~~
                ClaI  HindIII
               ~~~~~~~~~~~~~~
1201  GTTACTAGAT CGATAAGCTT CTAGAGCGGC CGGTGGAGCT CCAATTCGCC
      CAATGATCTA GCTATTCGAA GATCTCGCCG GCCACCTCGA GGTTAAGCGG

1251  CTATAGTGAG TCGTATTACG CGCGCTCACT GGCCGTCGTT TTACAACGTC
      GATATCACTC AGCATAATGC GCGCGAGTGA CCGGCAGCAA AATGTTGCAG

1301  GTGACTGGGA AAACCCTGGC GTTACCCAAC TTAATCGCCT TGCAGCACAT
      CACTGACCCT TTTGGGACCG CAATGGGTTG AATTAGCGGA ACGTCGTGTA

                  PvuII
                 ~~~~~~
1351  CCCCCTTTCG CCAGCTGGCG TAATAGCGAA GAGGCCCGCA CCGATCGCCC
      GGGGGAAAGC GGTCGACCGC ATTATCGCTT CTCCGGGCGT GGCTAGCGGG

1401  TTCCCAACAG TTGCGCAGCC TGAATGGCGA ATGGGACGCG CCCTGTAGCG
      AAGGGTTGTC AACGCGTCGG ACTTACCGCT TACCCTGCGC GGGACATCGC
```

FIG._40C

```
1451  GCGCATTAAG CGCGGCGGGT GTGGTGGTTA CGCGCAGCGT GACCGCTACA
      CGCGTAATTC GCGCCGCCCA CACCACCAAT GCGCGTCGCA CTGGCGATGT

1501  CTTGCCAGCG CCCTAGCGCC CGCTCCTTTC GCTTTCTTCC CTTCCTTTCT
      GAACGGTCGC GGGATCGCGG GCGAGGAAAG CGAAAGAAGG GAAGGAAAGA

1551  CGCCACGTTC GCCGGCTTTC CCCGTCAAGC TCTAAATCGG GGGCTCCCTT
      GCGGTGCAAG CGGCCGAAAG GGGCAGTTCG AGATTTAGCC CCCGAGGGAA

1601  TAGGGTTCCG ATTTAGTGCT TTACGGCACC TCGACCCCAA AAAACTTGAT
      ATCCCAAGGC TAAATCACGA AATGCCGTGG AGCTGGGGTT TTTTGAACTA

1651  TAGGGTGATG GTTCACGTAG TGGGCCATCG CCCTGATAGA CGGTTTTTCG
      ATCCCACTAC CAAGTGCATC ACCCGGTAGC GGGACTATCT GCCAAAAAGC

1701  CCCTTTGACG TTGGAGTCCA CGTTCTTTAA TAGTGGACTC TTGTTCCAAA
      GGGAAACTGC AACCTCAGGT GCAAGAAATT ATCACCTGAG AACAAGGTTT

1751  CTGGAACAAC ACTCAACCCT ATCTCGGTCT ATTCTTTTGA TTTATAAGGG
      GACCTTGTTG TGAGTTGGGA TAGAGCCAGA TAAGAAAACT AAATATTCCC

1801  ATTTTGCCGA TTTCGGCCTA TTGGTTAAAA AATGAGCTGA TTTAACAAAA
      TAAAACGGCT AAAGCCGGAT AACCAATTTT TTACTCGACT AAATTGTTTT

1851  ATTTAACGCG AATTTTAACA AAATATTAAC GCTTACAATT TAGGTGGCAC
      TAAATTGCGC TTAAAATTGT TTTATAATTG CGAATGTTAA ATCCACCGTG

1901  TTTTCGGGGA AATGTGCGCG GAACCCCTAT TTGTTTATTT TTCTAAATAC
      AAAAGCCCCT TTACACGCGC CTTGGGGATA AACAAATAAA AAGATTTATG

1951  ATTCAAATAT GTATCCGCTC ATGAGACAAT AACCCTGATA AATGCTTCAA
      TAAGTTTATA CATAGGCGAG TACTCTGTTA TTGGGACTAT TTACGAAGTT

2001  TAATATTGAA AAAGGAAGAG TATGAGTATT CAACATTTCC GTGTCGCCCT
      ATTATAACTT TTTCCTTCTC ATACTCATAA GTTGTAAAGG CACAGCGGGA

2051  TATTCCCTTT TTTGCGGCAT TTTGCCTTCC TGTTTTTGCT CACCCAGAAA
      ATAAGGGAAA AAACGCCGTA AAACGGAAGG ACAAAAACGA GTGGGTCTTT

                                              ApaLI
                                             ~~~~~~~
2101  CGCTGGTGAA AGTAAAAGAT GCTGAAGATC AGTTGGGTGC ACGAGTGGGT
      GCGACCACTT TCATTTTCTA CGACTTCTAG TCAACCCACG TGCTCACCCA

2151  TACATCGAAC TGGATCTCAA CAGCGGTAAG ATCCTTGAGA GTTTTCGCCC
      ATGTAGCTTG ACCTAGAGTT GTCGCCATTC TAGGAACTCT CAAAAGCGGG

2201  CGAAGAACGT TTTCCAATGA TGAGCACTTT TAAAGTTCTG CTATGTGGCG
      GCTTCTTGCA AAAGGTTACT ACTCGTGAAA ATTTCAAGAC GATACACCGC

2251  CGGTATTATC CCGTATTGAC GCCGGGCAAG AGCAACTCGG TCGCCGCATA
      GCCATAATAG GGCATAACTG CGGCCCGTTC TCGTTGAGCC AGCGGCGTAT

2301  CACTATTCTC AGAATGACTT GGTTGAGTAC TCACCAGTCA CAGAAAAGCA
      GTGATAAGAG TCTTACTGAA CCAACTCATG AGTGGTCAGT GTCTTTTCGT
```

FIG._40D

```
2351  TCTTACGGAT GGCATGACAG TAAGAGAATT ATGCAGTGCT GCCATAACCA
      AGAATGCCTA CCGTACTGTC ATTCTCTTAA TACGTCACGA CGGTATTGGT

2401  TGAGTGATAA CACTGCGGCC AACTTACTTC TGACAACGAT CGGAGGACCG
      ACTCACTATT GTGACGCCGG TTGAATGAAG ACTGTTGCTA GCCTCCTGGC

2451  AAGGAGCTAA CCGCTTTTTT GCACAACATG GGGGATCATG TAACTCGCCT
      TTCCTCGATT GGCGAAAAAA CGTGTTGTAC CCCCTAGTAC ATTGAGCGGA

2501  TGATCGTTGG GAACCGGAGC TGAATGAAGC CATACCAAAC GACGAGCGTG
      ACTAGCAACC CTTGGCCTCG ACTTACTTCG GTATGGTTTG CTGCTCGCAC

2551  ACACCACGAT GCCTGTAGCA ATGGCAACAA CGTTGCGCAA ACTATTAACT
      TGTGGTGCTA CGGACATCGT TACCGTTGTT GCAACGCGTT TGATAATTGA

2601  GGCGAACTAC TTACTCTAGC TTCCCGGCAA CAATTAATAG ACTGGATGGA
      CCGCTTGATG AATGAGATCG AAGGGCCGTT GTTAATTATC TGACCTACCT

2651  GGCGGATAAA GTTGCAGGAC CACTTCTGCG CTCGGCCCTT CCGGCTGGCT
      CCGCCTATTT CAACGTCCTG GTGAAGACGC GAGCCGGGAA GGCCGACCGA

2701  GGTTTATTGC TGATAAATCT GGAGCCGGTG AGCGTGGGTC TCGCGGTATC
      CCAAATAACG ACTATTTAGA CCTCGGCCAC TCGCACCCAG AGCGCCATAG

2751  ATTGCAGCAC TGGGGCCAGA TGGTAAGCCC TCCCGTATCG TAGTTATCTA
      TAACGTCGTG ACCCCGGTCT ACCATTCGGG AGGGCATAGC ATCAATAGAT

2801  CACGACGGGG AGTCAGGCAA CTATGGATGA ACGAAATAGA CAGATCGCTG
      GTGCTGCCCC TCAGTCCGTT GATACCTACT TGCTTTATCT GTCTAGCGAC

2851  AGATAGGTGC CTCACTGATT AAGCATTGGT AACTGTCAGA CCAAGTTTAC
      TCTATCCACG GAGTGACTAA TTCGTAACCA TTGACAGTCT GGTTCAAATG

2901  TCATATATAC TTTAGATTGA TTTAAAACTT CATTTTTAAT TTAAAAGGAT
      AGTATATATG AAATCTAACT AAATTTTGAA GTAAAAATTA AATTTTCCTA

2951  CTAGGTGAAG ATCCTTTTTG ATAATCTCAT GACCAAAATC CCTTAACGTG
      GATCCACTTC TAGGAAAAAC TATTAGAGTA CTGGTTTTAG GGAATTGCAC

3001  AGTTTTCGTT CCACTGAGCG TCAGACCCCG TAGAAAAGAT CAAAGGATCT
      TCAAAAGCAA GGTGACTCGC AGTCTGGGGC ATCTTTTCTA GTTTCCTAGA

3051  TCTTGAGATC CTTTTTTTCT GCGCGTAATC TGCTGCTTGC AAACAAAAAA
      AGAACTCTAG GAAAAAAAGA CGCGCATTAG ACGACGAACG TTTGTTTTTT

3101  ACCACCGCTA CCAGCGGTGG TTTGTTTGCC GGATCAAGAG CTACCAACTC
      TGGTGGCGAT GGTCGCCACC AAACAAACGG CCTAGTTCTC GATGGTTGAG

3151  TTTTTCCGAA GGTAACTGGC TTCAGCAGAG CGCAGATACC AAATACTGTC
      AAAAAGGCTT CCATTGACCG AAGTCGTCTC GCGTCTATGG TTTATGACAG

3201  CTTCTAGTGT AGCCGTAGTT AGGCCACCAC TTCAAGAACT CTGTAGCACC
      GAAGATCACA TCGGCATCAA TCCGGTGGTG AAGTTCTTGA GACATCGTGG

3251  GCCTACATAC CTCGCTCTGC TAATCCTGTT ACCAGTGGCT GCTGCCAGTG
      CGGATGTATG GAGCGAGACG ATTAGGACAA TGGTCACCGA CGACGGTCAC
```

FIG._40E

```
3301  GCGATAAGTC GTGTCTTACC GGGTTGGACT CAAGACGATA GTTACCGGAT
      CGCTATTCAG CACAGAATGG CCCAACCTGA GTTCTGCTAT CAATGGCCTA

                                           ApaLI
                                          ~~~~~~
3351  AAGGCGCAGC GGTCGGGCTG AACGGGGGGT TCGTGCACAC AGCCCAGCTT
      TTCCGCGTCG CCAGCCCGAC TTGCCCCCCA AGCACGTGTG TCGGGTCGAA

3401  GGAGCGAACG ACCTACACCG AACTGAGATA CCTACAGCGT GAGCTATGAG
      CCTCGCTTGC TGGATGTGGC TTGACTCTAT GGATGTCGCA CTCGATACTC

3451  AAAGCGCCAC GCTTCCCGAA GGGAGAAAGG CGGACAGGTA TCCGGTAAGC
      TTTCGCGGTG CGAAGGGCTT CCCTCTTTCC GCCTGTCCAT AGGCCATTCG

3501  GGCAGGGTCG GAACAGGAGA GCGCACGAGG GAGCTTCCAG GGGGAAACGC
      CCGTCCCAGC CTTGTCCTCT CGCGTGCTCC CTCGAAGGTC CCCCTTTGCG

3551  CTGGTATCTT TATAGTCCTG TCGGGTTTCG CCACCTCTGA CTTGAGCGTC
      GACCATAGAA ATATCAGGAC AGCCCAAAGC GGTGGAGACT GAACTCGCAG

3601  GATTTTTGTG ATGCTCGTCA GGGGGGCGGA GCCTATGGAA AAACGCCAGC
      CTAAAAACAC TACGAGCAGT CCCCCCGCCT CGGATACCTT TTTGCGGTCG

3651  AACGCGGCCT TTTTACGGTT CCTGGCCTTT TGCTGGCCTT TTGCTCACAT
      TTGCGCCGGA AAAATGCCAA GGACCGGAAA ACGACCGGAA AACGAGTGTA

3701  GTTCTTTCCT GCGTTATCCC CTGATTCTGT GGATAACCGT ATTACCGCCT
      CAAGAAAGGA CGCAATAGGG GACTAAGACA CCTATTGGCA TAATGGCGGA

3751  TTGAGTGAGC TGATACCGCT CGCCGCAGCC GAACGACCGA GCGCAGCGAG
      AACTCACTCG ACTATGGCGA GCGGCGTCGG CTTGCTGGCT CGCGTCGCTC

3801  TCAGTGAGCG AGGAAGCGGA AGAGCGCCCA ATACGCAAAC CGCCTCTCCC
      AGTCACTCGC TCCTTCGCCT TCTCGCGGGT TATGCGTTTG GCGGAGAGGG

                                 PvuII
                                ~~~~~~
3851  CGCGCGTTGG CCGATTCATT AATGCAGCTG GCACGACAGG TTTCCCGACT
      GCGCGCAACC GGCTAAGTAA TTACGTCGAC CGTGCTGTCC AAAGGGCTGA

3901  GGAAAGCGGG CAGTGAGCGC AACGCAATTA ATGTGAGTTA GCTCACTCAT
      CCTTTCGCCC GTCACTCGCG TTGCGTTAAT TACACTCAAT CGAGTGAGTA

3951  TAGGCACCCC AGGCTTTACA CTTTATGCTT CCGGCTCGTA TGTTGTGTGG
      ATCCGTGGGG TCCGAAATGT GAAATACGAA GGCCGAGCAT ACAACACACC

4001  AATTGTGAGC GGATAACAAT TTCACACAGG AAACAGCTAT GACCATGATT
      TTAACACTCG CCTATTGTTA AAGTGTGTCC TTTGTCGATA CTGGTACTAA

4051  ACGCCAAGCG CGCAATTAAC CCTCACTAAA GGGAACAAAA GCTGGGTACC
      TGCGGTTCGC GCGTTAATTG GGAGTGATTT CCCTTGTTTT CGACCCATGG

                  AvaI
                ~~~~~~~
4101  GGGCCCCCCC TCGAGGTCAT TCATATGCTT GAGAAGAGAG TCGGGATAGT
      CCCGGGGGGG AGCTCCAGTA AGTATACGAA CTCTTCTCTC AGCCCTATCA
```

FIG._40F

```
4151  CCAAAATAAA ACAAAGGTAA GATTACCTGG TCAAAAGTGA AAACATCAGT
      GGTTTTATTT TGTTTCCATT CTAATGGACC AGTTTTCACT TTTGTAGTCA

4201  TAAAAGGTGG TATAAGTAAA ATATCGGTAA TAAAAGGTGG CCCAAAGTGA
      ATTTTCCACC ATATTCATTT TATAGCCATT ATTTTCCACC GGGTTTCACT

4251  AATTTACTCT TTTCTACTAT TATAAAAATT GAGGATGTTT TGTCGGTACT
      TTAAATGAGA AAAGATGATA ATATTTTTAA CTCCTACAAA ACAGCCATGA

4301  TTGATACGTC ATTTTTGTAT GAATTGGTTT TTAAGTTTAT TCGCGATTTG
      AACTATGCAG TAAAAACATA CTTAACCAAA AATTCAAATA AGCGCTAAAC

4351  GAAATGCATA TCTGTATTTG AGTCGGTTTT TAAGTTCGTT GCTTTTGTAA
      CTTTACGTAT AGACATAAAC TCAGCCAAAA ATTCAAGCAA CGAAAACATT

4401  ATACAGAGGG ATTTGTATAA GAAATATCTT TAAAAAACCC ATATGCTAAT
      TATGTCTCCC TAAACATATT CTTTATAGAA ATTTTTTGGG TATACGATTA

                                          EcoRI
                                         ~~~~~~~
4451  TTGACATAAT TTTTGAGAAA AATATATATT CAGGCGAATT CCACAATGAA
      AACTGTATTA AAAACTCTTT TTATATATAA GTCCGCTTAA GGTGTTACTT

4501  CAATAATAAG ATTAAAATAG CTTGCCCCCG TTGCAGCGAT GGGTATTTTT
      GTTATTATTC TAATTTTATC GAACGGGGGC AACGTCGCTA CCCATAAAAA

4551  TCTAGTAAAA TAAAAGATAA ACTTAGACTC AAAACATTTA CAAAAACAAC
      AGATCATTTT ATTTTCTATT TGAATCTGAG TTTTGTAAAT GTTTTTGTTG

4601  CCCTAAAGTC CTAAAGCCCA AAGTGCTATG CACGATCCAT AGCAAGCCCA
      GGGATTTCAG GATTTCGGGT TTCACGATAC GTGCTAGGTA TCGTTCGGGT

4651  GCCCAACCCA ACCCAACCCA ACCCACCCCA GTGCAGCCAA CTGGCAAATA
      CGGGTTGGGT TGGGTTGGGT TGGGTGGGGT CACGTCGGTT GACCGTTTAT

4701  GTCTCCACCC CCGGCACTAT CACCGTGAGT TGTCCGCACC ACCGCACGTC
      CAGAGGTGGG GGCCGTGATA GTGGCACTCA ACAGGCGTGG TGGCGTGCAG

4751  TCGCAGCCAA AAAAAAAAAA AGAAAGAAAA AAAAGAAAAA GAAAAACAGC
      AGCGTCGGTT TTTTTTTTTT TCTTTCTTTT TTTTCTTTTT CTTTTTGTCG

4801  AGGTGGGTCC GGGTCGTGGG GGCCGGAAAA GCGAGGAGGA TCGCGAGCAG
      TCCACCCAGG CCCAGCACCC CCGGCCTTTT CGCTCCTCCT AGCGCTCGTC

4851  CGACGAGGCC CGGCCCTCCC TCCGCTTCCA AAGAAACGCC CCCCATCGCC
      GCTGCTCCGG GCCGGGAGGG AGGCGAAGGT TTCTTTGCGG GGGGTAGCGG

4901  ACTATATACA TACCCCCCCC TCTCCTCCCA TCCCCCCAAC CCTACCACCA
      TGATATATGT ATGGGGGGGG AGAGGAGGGT AGGGGGGTTG GGATGGTGGT

4951  CCACCACCAC CACCTCCTCC CCCCTCGCTG CCGGACGACG AGCTCCTCCC
      GGTGGTGGTG GTGGAGGAGG GGGGAGCGAC GGCCTGCTGC TCGAGGAGGG

5001  CCCTCCCCCT CCGCCGCCGC CGGTAACCAC CCCGCCCCTC TCCTCTTTCT
      GGGAGGGGGA GGCGGCGGCG GCCATTGGTG GGGCGGGGAG AGGAGAAAGA
```

FIG._40G

```
5051  TTCTCCGTTT TTTTTTTCGT CTCGGTCTCG ATCTTTGGCC TTGGTAGTTT
      AAGAGGCAAA AAAAAAAGCA GAGCCAGAGC TAGAAACCGG AACCATCAAA

5101  GGGTGGGCGA GAGCGGCTTC GTCGCCCAGA TCGGTGCGCG GGAGGGGCGG
      CCCACCCGCT CTCGCCGAAG CAGCGGGTCT AGCCACGCGC CCTCCCCGCC

                                            BamHI
                                           ~~~~~~~
5151  GATCTCGCGG CTGGCGTCTC CGGGCGTGAG TCGGCCCGGA TCCTCGCGGG
      CTAGAGCGCC GACCGCAGAG GCCCGCACTC AGCCGGGCCT AGGAGCGCCC

5201  GAATGGGGCT CTCGGATGTA GATCTTCTTT CTTTCTTCTT TTTGTGGTAG
      CTTACCCCGA GAGCCTACAT CTAGAAGAAA GAAAGAAGAA AAACACCATC

5251  AATTTGAATC CCTCAGCATT GTTCATCGGT AGTTTTTCTT TTCATGATTT
      TTAAACTTAG GGAGTCGTAA CAAGTAGCCA TCAAAAAGAA AAGTACTAAA

5301  GTGACAAATG CAGCCTCGTG CGGAGCTTTT TTGTAGC
      CACTGTTTAC GTCGGAGCAC GCCTCGAAAA AACATCG
```

FIG._40H

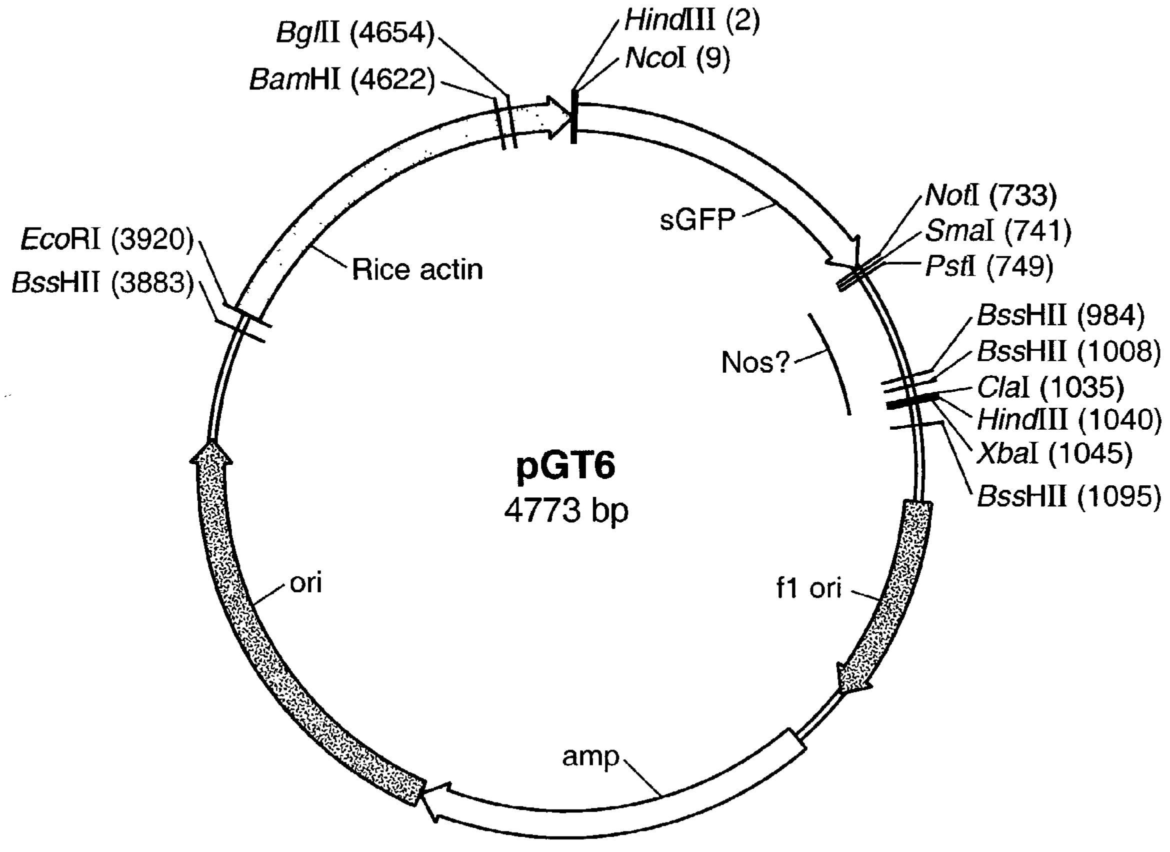
*FIG._41A*

```
    HindIII NcoI
    ~~~~~~ ~~~~~~~
  1 AAGCTTACCA TGGTGAGCAA GGGCGAGGAG CTGTTCACCG GGGTGGTGCC CATCCTGGTC GAGCTGGACG
    TTCGAATGGT ACCACTCGTT CCCGCTCCTC GACAAGTGGC CCCACCACGG GTAGGACCAG CTCGACCTGC

 71 GCGACGTGAA CGGCCACAAG TTCAGCGTGT CCGGCGAGGG CGAGGGCGAT GCCACCTACG GCAAGCTGAC
    CGCTGCACTT GCCGGTGTTC AAGTCGCACA GGCCGCTCCC GCTCCCGCTA CGGTGGATGC CGTTCGACTG

141 CCTGAAGTTC ATCTGCACCA CCGGCAAGCT GCCCGTGCCC TGGCCCACCC TCGTGACCAC CTTCACCTAC
    GGACTTCAAG TAGACGTGGT GGCCGTTCGA CGGGCACGGG ACCGGGTGGG AGCACTGGTG GAAGTGGATG

211 GGCGTGCAGT GCTTCAGCCG CTACCCCGAC CACATGAAGC AGCACGACTT CTTCAAGTCC GCCATGCCCG
    CCGCACGTCA CGAAGTCGGC GATGGGGCTG GTGTACTTCG TCGTGCTGAA GAAGTTCAGG CGGTACGGGC

281 AAGGCTACGT CCAGGAGCGC ACCATCTTCT TCAAGGACGA CGGCAACTAC AAGACCCGCG CCGAGGTGAA
    TTCCGATGCA GGTCCTCGCG TGGTAGAAGA AGTTCCTGCT GCCGTTGATG TTCTGGGCGC GGCTCCACTT

351 GTTCGAGGGC GACACCCTGG TGAACCGCAT CGAGCTGAAG GGCATCGACT TCAAGGAGGA CGGCAACATC
    CAAGCTCCCG CTGTGGGACC ACTTGGCGTA GCTCGACTTC CCGTAGCTGA AGTTCCTCCT GCCGTTGTAG

421 CTGGGGCACA AGCTGGAGTA CAACTACAAC AGCCACAACG TCTATATCAT GGCCGACAAG CAGAAGAACG
    GACCCCGTGT TCGACCTCAT GTTGATGTTG TCGGTGTTGC AGATATAGTA CCGGCTGTTC GTCTTCTTGC

491 GCATCAAGGT GAACTTCAAG ATCCGCCACA ACATCGAGGA CGGCAGCGTG CAGCTCGCCG ACCACTACCA
    CGTAGTTCCA CTTGAAGTTC TAGGCGGTGT TGTAGCTCCT GCCGTCGCAC GTCGAGCGGC TGGTGATGGT

561 GCAGAACACC CCCATCGGCG ACGGCCCCGT GCTGCTGCCC GACAACCACT ACCTGAGCAC CCAGTCCGCC
    CGTCTTGTGG GGGTAGCCGC TGCCGGGGCA CGACGACGGG CTGTTGGTGA TGGACTCGTG GGTCAGGCGG

631 CTGAGCAAAG ACCCCAACGA GAAGCGCGAT CACATGGTCC TGCTGGAGTT CGTGACCGCC GCCGGGATCA
    GACTCGTTTC TGGGGTTGCT CTTCGCGCTA GTGTACCAGG ACGACCTCAA GCACTGGCGG CGGCCCTAGT
```

FIG._41B

```
                                                        SmaI
                                                       ~~~~~~~~
                                                  NotI        PstI
                                                ~~~~~~~~~    ~~~~~~
701   CTCACGGCAT GGACGAGCTG TACAAGTAAA GCGGCCGCCC GGGCTGCAGG GAAACCACTG AAGGATGAGC
      GAGTGCCGTA CCTGCTCGAC ATGTTCATTT CGCCGGCGGG CCCGACGTCC CTTTGGTGAC TTCCTACTCG

771   TGTAAAGAAG CAGATCGTTC AAACATTTGG CAATAAAGTT TCTTAAGATT GAATCCTGTT GCCGGTCTTG
      ACATTTCTTC GTCTAGCAAG TTTGTAAACC GTTATTTCAA AGAATTCTAA CTTAGGACAA CGGCCAGAAC

841   CGATGATTAT CATATAATTT CTGTTGAATT ACGTTAAGCA TGTAATAATT AACATGTAAT GCATGACGTT
      GCTACTAATA GTATATTAAA GACAACTTAA TGCAATTCGT ACATTATTAA TTGTACATTA CGTACTGCAA

911   ATTTATGAGA TGGGTTTTTA TGATTAGAGT CCCGCAATTA TACATTTAAT ACGCGATAGA AAACAAAATA
      TAAATACTCT ACCCAAAAAT ACTAATCTCA GGGCGTTAAT ATGTAAATTA TGCGCTATCT TTTGTTTTAT

                                                                          XbaI
                                                                         ~~~~~~
        BssHII                 BssHII                           ClaI HindIII
        ~~~~~~                ~~~~~~~                          ~~~~~~~~~~~~~~
981   TAGCGCGCAA ACTAGGATAA ATTATCGCGC GCGGTGTCAT CTATGTTACT AGATCGATAA GCTTCTAGAG
      ATCGCGCGTT TGATCCTATT TAATAGCGCG CGCCACAGTA GATACAATGA TCTAGCTATT CGAAGATCTC

                                                   BssHII
                                                   ~~~~~~
1051  CGGCCGGTGG AGCTCCAATT CGCCCTATAG TGAGTCGTAT TACGCGCGCT CACTGGCCGT CGTTTTACAA
      GCCGGCCACC TCGAGGTTAA GCGGGATATC ACTCAGCATA ATGCGCGCGA GTGACCGGCA GCAAAATGTT

1121  CGTCGTGACT GGGAAAACCC TGGCGTTACC CAACTTAATC GCCTTGCAGC ACATCCCCCT TTCGCCAGCT
      GCAGCACTGA CCCTTTTGGG ACCGCAATGG GTTGAATTAG CGGAACGTCG TGTAGGGGGA AAGCGGTCGA

1191  GGCGTAATAG CGAAGAGGCC CGCACCGATC GCCCTTCCCA ACAGTTGCGC AGCCTGAATG GCGAATGGGA
      CCGCATTATC GCTTCTCCGG GCGTGGCTAG CGGGAAGGGT TGTCAACGCG TCGGACTTAC CGCTTACCCT

1261  CGCGCCCTGT AGCGGCGCAT TAAGCGCGGC GGGTGTGGTG GTTACGCGCA GCGTGACCGC TACACTTGCC
      GCGCGGGACA TCGCCGCGTA ATTCGCGCCG CCCACACCAC CAATGCGCGT CGCACTGGCG ATGTGAACGG
```

FIG._41C

```
1331  AGCGCCCTAG CGCCCGCTCC TTTCGCTTTC TTCCCTTCCT TTCTCGCCAC GTTCGCCGGC TTTCCCCGTC
      TCGCGGGATC GCGGGCGAGG AAAGCGAAAG AAGGGAAGGA AAGAGCGGTG CAAGCGGCCG AAAGGGGCAG

1401  AAGCTCTAAA TCGGGGGCTC CCTTTAGGGT TCCGATTTAG TGCTTTACGG CACCTCGACC CCAAAAAACT
      TTCGAGATTT AGCCCCCGAG GGAAATCCCA AGGCTAAATC ACGAAATGCC GTGGAGCTGG GGTTTTTTGA

1471  TGATTAGGGT GATGGTTCAC GTAGTGGGCC ATCGCCCTGA TAGACGGTTT TTCGCCCTTT GACGTTGGAG
      ACTAATCCCA CTACCAAGTG CATCACCCGG TAGCGGGACT ATCTGCCAAA AAGCGGGAAA CTGCAACCTC

1541  TCCACGTTCT TTAATAGTGG ACTCTTGTTC CAAACTGGAA CAACACTCAA CCCTATCTCG GTCTATTCTT
      AGGTGCAAGA AATTATCACC TGAGAACAAG GTTTGACCTT GTTGTGAGTT GGGATAGAGC CAGATAAGAA

1611  TTGATTTATA AGGGATTTTG CCGATTTCGG CCTATTGGTT AAAAAATGAG CTGATTTAAC AAAAATTTAA
      AACTAAATAT TCCCTAAAAC GGCTAAAGCC GGATAACCAA TTTTTTACTC GACTAAATTG TTTTTAAATT

1681  CGCGAATTTT AACAAAATAT TAACGCTTAC AATTTAGGTG GCACTTTTCG GGGAAATGTG CGCGGAACCC
      GCGCTTAAAA TTGTTTTATA ATTGCGAATG TTAAATCCAC CGTGAAAAGC CCCTTTACAC GCGCCTTGGG

1751  CTATTTGTTT ATTTTTCTAA ATACATTCAA ATATGTATCC GCTCATGAGA CAATAACCCT GATAAATGCT
      GATAAACAAA TAAAAAGATT TATGTAAGTT TATACATAGG CGAGTACTCT GTTATTGGGA CTATTTACGA

1821  TCAATAATAT TGAAAAAGGA AGAGTATGAG TATTCAACAT TTCCGTGTCG CCCTTATTCC CTTTTTTGCG
      AGTTATTATA ACTTTTTCCT TCTCATACTC ATAAGTTGTA AAGGCACAGC GGGAATAAGG GAAAAAACGC

1891  GCATTTTGCC TTCCTGTTTT TGCTCACCCA GAAACGCTGG TGAAAGTAAA AGATGCTGAA GATCAGTTGG
      CGTAAAACGG AAGGACAAAA ACGAGTGGGT CTTTGCGACC ACTTTCATTT TCTACGACTT CTAGTCAACC

1961  GTGCACGAGT GGGTTACATC GAACTGGATC TCAACAGCGG TAAGATCCTT GAGAGTTTTC GCCCCGAAGA
      CACGTGCTCA CCCAATGTAG CTTGACCTAG AGTTGTCGCC ATTCTAGGAA CTCTCAAAAG CGGGGCTTCT

2031  ACGTTTTCCA ATGATGAGCA CTTTTAAAGT TCTGCTATGT GGCGCGGTAT TATCCCGTAT TGACGCCGGG
      TGCAAAAGGT TACTACTCGT GAAAATTTCA AGACGATACA CCGCGCCATA ATAGGGCATA ACTGCGGCCC

2101  CAAGAGCAAC TCGGTCGCCG CATACACTAT TCTCAGAATG ACTTGGTTGA GTACTCACCA GTCACAGAAA
      GTTCTCGTTG AGCCAGCGGC GTATGTGATA AGAGTCTTAC TGAACCAACT CATGAGTGGT CAGTGTCTTT
```

FIG._41D

```
2171  AGCATCTTAC GGATGGCATG ACAGTAAGAG AATTATGCAG TGCTGCCATA ACCATGAGTG ATAACACTGC
      TCGTAGAATG CCTACCGTAC TGTCATTCTC TTAATACGTC ACGACGGTAT TGGTACTCAC TATTGTGACG

2241  GGCCAACTTA CTTCTGACAA CGATCGGAGG ACCGAAGGAG CTAACCGCTT TTTTGCACAA CATGGGGGAT
      CCGGTTGAAT GAAGACTGTT GCTAGCCTCC TGGCTTCCTC GATTGGCGAA AAAACGTGTT GTACCCCCTA

2311  CATGTAACTC GCCTTGATCG TTGGGAACCG GAGCTGAATG AAGCCATACC AAACGACGAG CGTGACACCA
      GTACATTGAG CGGAACTAGC AACCCTTGGC CTCGACTTAC TTCGGTATGG TTTGCTGCTC GCACTGTGGT

2381  CGATGCCTGT AGCAATGGCA ACAACGTTGC GCAAACTATT AACTGGCGAA CTACTTACTC TAGCTTCCCG
      GCTACGGACA TCGTTACCGT TGTTGCAACG CGTTTGATAA TTGACCGCTT GATGAATGAG ATCGAAGGGC

2451  GCAACAATTA ATAGACTGGA TGGAGGCGGA TAAAGTTGCA GGACCACTTC TGCGCTCGGC CCTTCCGGCT
      CGTTGTTAAT TATCTGACCT ACCTCCGCCT ATTTCAACGT CCTGGTGAAG ACGCGAGCCG GGAAGGCCGA

2521  GGCTGGTTTA TTGCTGATAA ATCTGGAGCC GGTGAGCGTG GGTCTCGCGG TATCATTGCA GCACTGGGGC
      CCGACCAAAT AACGACTATT TAGACCTCGG CCACTCGCAC CCAGAGCGCC ATAGTAACGT CGTGACCCCG

2591  CAGATGGTAA GCCCTCCCGT ATCGTAGTTA TCTACACGAC GGGGAGTCAG GCAACTATGG ATGAACGAAA
      GTCTACCATT CGGGAGGGCA TAGCATCAAT AGATGTGCTG CCCCTCAGTC CGTTGATACC TACTTGCTTT

2661  TAGACAGATC GCTGAGATAG GTGCCTCACT GATTAAGCAT TGGTAACTGT CAGACCAAGT TTACTCATAT
      ATCTGTCTAG CGACTCTATC CACGGAGTGA CTAATTCGTA ACCATTGACA GTCTGGTTCA AATGAGTATA

2731  ATACTTTAGA TTGATTTAAA ACTTCATTTT TAATTTAAAA GGATCTAGGT GAAGATCCTT TTTGATAATC
      TATGAAATCT AACTAAATTT TGAAGTAAAA ATTAAATTTT CCTAGATCCA CTTCTAGGAA AAACTATTAG

2801  TCATGACCAA AATCCCTTAA CGTGAGTTTT CGTTCCACTG AGCGTCAGAC CCCGTAGAAA AGATCAAAGG
      AGTACTGGTT TTAGGGAATT GCACTCAAAA GCAAGGTGAC TCGCAGTCTG GGGCATCTTT TCTAGTTTCC

2871  ATCTTCTTGA GATCCTTTTT TTCTGCGCGT AATCTGCTGC TTGCAAACAA AAAAACCACC GCTACCAGCG
      TAGAAGAACT CTAGGAAAAA AAGACGCGCA TTAGACGACG AACGTTTGTT TTTTTGGTGG CGATGGTCGC

2941  GTGGTTTGTT TGCCGGATCA AGAGCTACCA ACTCTTTTTC CGAAGGTAAC TGGCTTCAGC AGAGCGCAGA
      CACCAAACAA ACGGCCTAGT TCTCGATGGT TGAGAAAAAG GCTTCCATTG ACCGAAGTCG TCTCGCGTCT
```

FIG._41E

```
3011  TACCAAATAC TGTCCTTCTA GTGTAGCCGT AGTTAGGCCA CCACTTCAAG AACTCTGTAG CACCGCCTAC
      ATGGTTTATG ACAGGAAGAT CACATCGGCA TCAATCCGGT GGTGAAGTTC TTGAGACATC GTGGCGGATG

3081  ATACCTCGCT CTGCTAATCC TGTTACCAGT GGCTGCTGCC AGTGGCGATA AGTCGTGTCT TACCGGGTTG
      TATGGAGCGA GACGATTAGG ACAATGGTCA CCGACGACGG TCACCGCTAT TCAGCACAGA ATGGCCCAAC

3151  GACTCAAGAC GATAGTTACC GGATAAGGCG CAGCGGTCGG GCTGAACGGG GGGTTCGTGC ACACAGCCCA
      CTGAGTTCTG CTATCAATGG CCTATTCCGC GTCGCCAGCC CGACTTGCCC CCCAAGCACG TGTGTCGGGT

3221  GCTTGGAGCG AACGACCTAC ACCGAACTGA GATACCTACA GCGTGAGCTA TGAGAAAGCG CCACGCTTCC
      CGAACCTCGC TTGCTGGATG TGGCTTGACT CTATGGATGT CGCACTCGAT ACTCTTTCGC GGTGCGAAGG

3291  CGAAGGGAGA AAGGCGGACA GGTATCCGGT AAGCGGCAGG GTCGGAACAG GAGAGCGCAC GAGGGAGCTT
      GCTTCCCTCT TTCCGCCTGT CCATAGGCCA TTCGCCGTCC CAGCCTTGTC CTCTCGCGTG CTCCCTCGAA

3361  CCAGGGGGAA ACGCCTGGTA TCTTTATAGT CCTGTCGGGT TTCGCCACCT CTGACTTGAG CGTCGATTTT
      GGTCCCCCTT TGCGGACCAT AGAAATATCA GGACAGCCCA AAGCGGTGGA GACTGAACTC GCAGCTAAAA

3431  TGTGATGCTC GTCAGGGGGG CGGAGCCTAT GGAAAAACGC CAGCAACGCG GCCTTTTTAC GGTTCCTGGC
      ACACTACGAG CAGTCCCCCC GCCTCGGATA CCTTTTTGCG GTCGTTGCGC CGGAAAAATG CCAAGGACCG

3501  CTTTTGCTGG CCTTTTGCTC ACATGTTCTT TCCTGCGTTA TCCCCTGATT CTGTGGATAA CCGTATTACC
      GAAAACGACC GGAAAACGAG TGTACAAGAA AGGACGCAAT AGGGGACTAA GACACCTATT GGCATAATGG

3571  GCCTTTGAGT GAGCTGATAC CGCTCGCCGC AGCCGAACGA CCGAGCGCAG CGAGTCAGTG AGCGAGGAAG
      CGGAAACTCA CTCGACTATG GCGAGCGGCG TCGGCTTGCT GGCTCGCGTC GCTCAGTCAC TCGCTCCTTC

3641  CGGAAGAGCG CCCAATACGC AAACCGCCTC TCCCCGCGCG TTGGCCGATT CATTAATGCA GCTGGCACGA
      GCCTTCTCGC GGGTTATGCG TTTGGCGGAG AGGGGCGCGC AACCGGCTAA GTAATTACGT CGACCGTGCT

3711  CAGGTTTCCC GACTGGAAAG CGGGCAGTGA GCGCAACGCA ATTAATGTGA GTTAGCTCAC TCATTAGGCA
      GTCCAAAGGG CTGACCTTTC GCCCGTCACT CGCGTTGCGT TAATTACACT CAATCGAGTG AGTAATCCGT

3781  CCCCAGGCTT TACACTTTAT GCTTCCGGCT CGTATGTTGT GTGGAATTGT GAGCGGATAA CAATTTCACA
      GGGGTCCGAA ATGTGAAATA CGAAGGCCGA GCATACAACA CACCTTAACA CTCGCCTATT GTTAAAGTGT
```

FIG._41F

```
                                              BssHII                                  EcoRI
                                              ~~~~~~                                     ~~
3851  CAGGAAACAG CTATGACCAT GATTACGCCA AGCGCGCAAT TAACCCTCAC TAAAGGGAAC AAAAGCTGGA
      GTCCTTTGTC GATACTGGTA CTAATGCGGT TCGCGCGTTA ATTGGGAGTG ATTTCCCTTG TTTTCGACCT

      EcoRI
      ~~~~
3921  ATTCCACAAT GAACAATAAT AAGATTAAAA TAGCTTGCCC CCGTTGCAGC GATGGGTATT TTTTCTAGTA
      TAAGGTGTTA CTTGTTATTA TTCTAATTTT ATCGAACGGG GGCAACGTCG CTACCCATAA AAAAGATCAT

3991  AAATAAAAGA TAAACTTAGA CTCAAAACAT TTACAAAAAC AACCCCTAAA GTCCTAAAGC CCAAAGTGCT
      TTTATTTTCT ATTTGAATCT GAGTTTTGTA AATGTTTTTG TTGGGGATTT CAGGATTTCG GGTTTCACGA

4061  ATGCACGATC CATAGCAAGC CCAGCCCAAC CCAACCCAAC CCAACCCACC CCAGTGCAGC CAACTGGCAA
      TACGTGCTAG GTATCGTTCG GGTCGGGTTG GGTTGGGTTG GGTTGGGTGG GGTCACGTCG GTTGACCGTT

4131  ATAGTCTCCA CCCCCGGCAC TATCACCGTG AGTTGTCCGC ACCACCGCAC GTCTCGCAGC CAAAAAAAAA
      TATCAGAGGT GGGGGCCGTG ATAGTGGCAC TCAACAGGCG TGGTGGCGTG CAGAGCGTCG GTTTTTTTTT

4201  AAAAGAAAGA AAAAAAAGAA AAAGAAAAAC AGCAGGTGGG TCCGGGTCGT GGGGGCCGGA AAAGCGAGGA
      TTTTCTTTCT TTTTTTTCTT TTTCTTTTTG TCGTCCACCC AGGCCCAGCA CCCCCGGCCT TTTCGCTCCT

4271  GGATCGCGAG CAGCGACGAG GCCCGGCCCT CCCTCCGCTT CCAAAGAAAC GCCCCCCATC GCCACTATAT
      CCTAGCGCTC GTCGCTGCTC CGGGCCGGGA GGGAGGCGAA GGTTTCTTTG CGGGGGGTAG CGGTGATATA

4341  ACATACCCCC CCCTCTCCTC CCATCCCCCC AACCCTACCA CCACCACCAC CACCACCTCC TCCCCCCTCG
      TGTATGGGGG GGGAGAGGAG GGTAGGGGGG TTGGGATGGT GGTGGTGGTG GTGGTGGAGG AGGGGGGAGC

4411  CTGCCGGACG ACGAGCTCCT CCCCCCTCCC CCTCCGCCGC CGCCGGTAAC CACCCCGCCC CTCTCCTCTT
      GACGGCCTGC TGCTCGAGGA GGGGGGAGGG GGAGGCGGCG GCGGCCATTG GTGGGGCGGG GAGAGGAGAA

4481  TCTTTCTCCG TTTTTTTTTT CGTCTCGGTC TCGATCTTTG GCCTTGGTAG TTTGGGTGGG CGAGAGCGGC
      AGAAAGAGGC AAAAAAAAAA GCAGAGCCAG AGCTAGAAAC CGGAACCATC AAACCCACCC GCTCTCGCCG

4551  TTCGTCGCCC AGATCGGTGC GCGGGAGGGG CGGGATCTCG CGGCTGGCGT CTCCGGGCGT GAGTCGGCCC
      AAGCAGCGGG TCTAGCCACG CGCCCTCCCC GCCCTAGAGC GCCGACCGCA GAGGCCCGCA CTCAGCCGGG
```

FIG._41G

```
         BamHI                                            BglII
         ~~~~~~                                           ~~~~~~
4621     GGATCCTCGC GGGGAATGGG GCTCTCGGAT GTAGATCTTC TTTCTTTCTT CTTTTTGTGG TAGAATTTGA
         CCTAGGAGCG CCCCTTACCC CGAGAGCCTA CATCTAGAAG AAAGAAAGAA GAAAAACACC ATCTTAAACT

4691     ATCCCTCAGC ATTGTTCATC GGTAGTTTTT CTTTTCATGA TTTGTGACAA ATGCAGCCTC GTGCGGAGCT
         TAGGGAGTCG TAACAAGTAG CCATCAAAAA GAAAAGTACT AAACACTGTT TACGTCGGAG CACGCCTCGA

4761     TTTTTGTAGG TAG
         AAAAACATCC ATC
```

FIG._41H

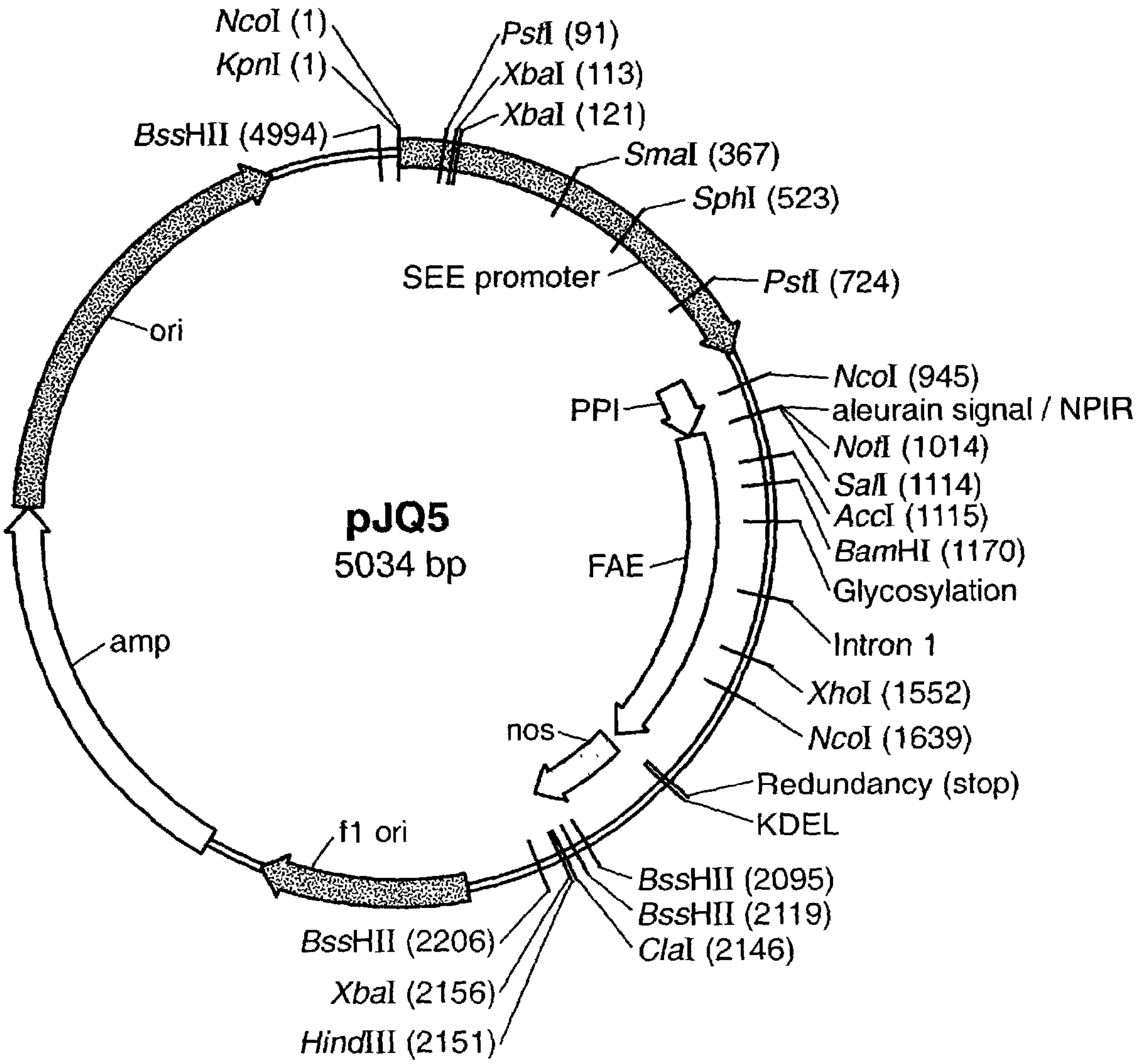
FIG._42A

```
     NcoI
     ~~~~~
     KpnI
     ~
  1  CATGGGCCAG GTATAATTAT GGGATATCTC AAGCAAATAA TCGAAATATC ACCATTGGCT ACAATATCTG
     GTACCCGGTC CATATTAATA CCCTATAGAG TTCGTTTATT AGCTTTATAG TGGTAACCGA TGTTATAGAC

                   PstI                                XbaI     XbaI
                  ~~~~~~~~                            ~~~~~~  ~~~~~~~~
 71  AGCTCCGAGT TCTGACTGCA GTCTGGATGA CGCGTGTTGT ATCTAGAACT CTAGATAGCA CAGCCACAGC
     TCGAGGCTCA AGACTGACGT CAGACCTACT GCGCACAACA TAGATCTTGA GATCTATCGT GTCGGTGTCG

141  ACCTACAGGA GTGCGACACT TGTGGACTGT AGTAGTGTTG GAGACGGAGC TCTTTCCTAC CTCCTGACGT
     TGGATGTCCT CACGCTGTGA ACACCTGACA TCATCACAAC CTCTGCCTCG AGAAAGGATG GAGGACTGCA

211  TGCCGCCGTT GTCCATTCCA ACGGCATCAC TCTCAACCAA TCACGCGCTC CCAACAAAAT ATCGTCCCCC
     ACGGCGGCAA CAGGTAAGGT TGCCGTAGTG AGAGTTGGTT AGTGCGCGAG GGTTGTTTTA TAGCAGGGGG

281  ATGTCTTGGC GGAGAGAGAG TACATACATG CTGTCGCGCC GTTTTTGTCT GAATCTCGCT TCCACTGGCC
     TACAGAACCG CCTCTCTCTC ATGTATGTAC GACAGCGCGG CAAAAACAGA CTTAGAGCGA AGGTGACCGG

                 SmaI
                ~~~~~~
351  AATCAGCTCA GCTCCCGGGA GCTCACTCAT TCAAGATCCC ATCGTCGTCG TCACCCCTGG CGTCATGGGA
     TTAGTCGAGT CGAGGGCCCT CGAGTGAGTA AGTTCTAGGG TAGCAGCAGC AGTGGGGACC GCAGTACCCT

421  TGGAAAAGAA CCTCCGTTGC TCGGATGAGT CAGCCATATC CCCGAACAGA GTACTGCAAG ATAACCCAAT
     ACCTTTTCTT GGAGGCAACG AGCCTACTCA GTCGGTATAG GGGCTTGTCT CATGACGTTC TATTGGGTTA

                                  SphI
                                 ~~~~~~~~
491  TCAGATTCCC CCAATAGAGA AAGTATAGCA TGCTTTCGGG TTTTGTTTGG CTTAATTGAC TTTATTTTTG
     AGTCTAAGGG GGTTATCTCT TTCATATCGT ACGAAAGCCC AAAACAAACC GAATTAACTG AAATAAAAAC

561  TTGGAGTTGA ATGCTGATTT GTTGTGTAAA ATGCCCAACC ATCTGAATAT CGAGACGGAT AATAGGCTGG
     AACCTCAACT TACGACTAAA CAACACATTT TACGGGTTGG TAGACTTATA GCTCTGCCTA TTATCCGACC
```

FIG._42B

```
                                 PstI
                                ~~~~~~~~
 631  CTAATTAATT TATAGCAAGA TTCTGTAGTG CACATCGCAA ATATCTTTCT GGGCATTACA GCTGGAGGCT
      GATTAATTAA ATATCGTTCT AAGACATCAC GTGTAGCGTT TATAGAAAGA CCCGTAATGT CGACCTCCGA

 701  TCATCAGCCT GAAACACTCT GCAGAGCCTG AAGCAAGTGG TGAAGCGTGG CGATGAGATG GGTATAAAAC
      AGTAGTCGGA CTTTGTGAGA CGTCTCGGAC TTCGTTCACC ACTTCGCACC GCTACTCTAC CCATATTTTG

 771  CCCCGGCACC GGGACGCGAG CTCCCGCCTA CCAGTACCAT CTCGCCTCGC TCCCCCTGCC GGACGACCCA
      GGGGCCGTGG CCCTGCGCTC GAGGGCGGAT GGTCATGGTA GAGCGGAGCG AGGGGGACGG CCTGCTGGGT

 841  GTAAAATACT GTTGCCCACT CGCCGGCGAG ATGGMCGTGC ACAAGGAGGT SAACTTCGTS GCCTACCTCC
      CATTTTATGA CAACGGGTGA GCGGCCGCTC TACCKGCACG TGTTCCTCCA STTGAAGCAS CGGATGGAGG

                                           NcoI
                                          ~~~~~~
 911  TGATCGTSCT CGGCCTCCTC TTGCTCGTST CCGCCATGGA GCACGTGGAC GCCAAGGCCT GCACCCKCGA
      ACTAGCASGA GCCGGAGGAG AACGAGCASA GGCGGTACCT CGTGCACCTG CGGTTCCGGA CGTGGGMGCT

                                         NotI
                                       ~~~~~~~~
 981  GTGCGGCAAC CTCGGCTTCG GCATCTGCCC GGCGGCCGCC TCCACGCAGG GCATCTCCGA AGACCTCTAC
      CACGCCGTTG GAGCCGAAGC CGTAGACGGG CCGCCGGCGG AGGTGCGTCC CGTAGAGGCT TCTGGAGATG

                                                                         SalI
                                                                        ~~~~~~
                                                                         AccI
                                                                        ~~~~~~
1051  AGCCGTTTAG TCGAAATGGC CACTATCTCC CAAGCTGCCT ACGCCGACCT GTGCAACATT CCGTCGACTA
      TCGGCAAATC AGCTTTACCG GTGATAGAGG GTTCGACGGA TGCGGCTGGA CACGTTGTAA GGCAGCTGAT

                                                       BamHI
                                                      ~~~~~~~
1121  TTATCAAGGG AGAGAAAATT TACAATTCTC AAACTGACAT TAACGGATGG ATCCTCCGCG ACGACAGCAG
      AATAGTTCCC TCTCTTTTAA ATGTTAAGAG TTTGACTGTA ATTGCCTACC TAGGAGGCGC TGCTGTCGTC
```

FIG._42C

```
1191  CAAAGAAATA ATCACCGTCT TCCGTGGCAC TGGTAGTGAT ACGAATCTAC AACTCGATAC TAACTACACC
      GTTTCTTTAT TAGTGGCAGA AGGCACCGTG ACCATCACTA TGCTTAGATG TTGAGCTATG ATTGATGTGG

1261  CTCACGCCTT TCGACACCCT ACCACAATGC AACGGTTGTG AAGTACACGG TGGATATTAT ATTGGATGGG
      GAGTGCGGAA AGCTGTGGGA TGGTGTTACG TTGCCAACAC TTCATGTGCC ACCTATAATA TAACCTACCC

1331  TCTCCGTCCA GGACCAAGTC GAGTCGCTTG TCAAACAGCA GGTTAGCCAG TATCCGGACT ACGCGCTGAC
      AGAGGCAGGT CCTGGTTCAG CTCAGCGAAC AGTTTGTCGT CCAATCGGTC ATAGGCCTGA TGCGCGACTG

1401  CGTGACCGGC CACKCCCTCG GCGCCTCCCT GGCGGCACTC ACTGCCGCCC AGCTGTCTGC GACATACGAC
      GCACTGGCCG GTGMGGGAGC CGCGGAGGGA CCGCCGTGAG TGACGGCGGG TCGACAGACG CTGTATGCTG

1471  AACATCCGCC TGTACACCTT CGGCGAACCG CGCAGCGGCA ATCAGGCCTT CGCGTCGTAC ATGAACGATG
      TTGTAGGCGG ACATGTGGAA GCCGCTTGGC GCGTCGCCGT TAGTCCGGAA GCGCAGCATG TACTTGCTAC

                  XhoI
                 ~~~~~~
1541  CCTTCCAAGC CTCGAGCCCA GATACGACGC AGTATTTCCG GGTCACTCAT GCCAACGACG GCATCCCAAA
      GGAAGGTTCG GAGCTCGGGT CTATGCTGCG TCATAAAGGC CCAGTGAGTA CGGTTGCTGC CGTAGGGTTT

                             NcoI
                           ~~~~~~~~
1611  CCTGCCCCCG GTGGAGCAGG GGTACGCCCA TGGCGGTGTA GAGTACTGGA GCGTTGATCC TTACAGCGCC
      GGACGGGGGC CACCTCGTCC CCATGCGGGT ACCGCCACAT CTCATGACCT CGCAACTAGG AATGTCGCGG

1681  CAGAACACAT TTGTCTGCAC TGGGGATGAA GTGCAGTGCT GTGAGGCCCA GGGCGGACAG GGTGTGAATA
      GTCTTGTGTA AACAGACGTG ACCCCTACTT CACGTCACGA CACTCCGGGT CCCGCCTGTC CCACACTTAT

1751  ATGCGCACAC GACTTATTTT GGGATGACGA GCGGAGCCTG TACATGGTGA TCAGTCATTT CAGCCTCCCC
      TACGCGTGTG CTGAATAAAA CCCTACTGCT CGCCTCGGAC ATGTACCACT AGTCAGTAAA GTCGGAGGGG

1821  GAGTGTACCA GGAAAGATGG ATGTCCTGGA GAGGGGGCCG CGTAACCACT GAAGGATGAG CTGTAAAGAA
      CTCACATGGT CCTTTCTACC TACAGGACCT CTCCCCCGGC GCATTGGTGA CTTCCTACTC GACATTTCTT
```

FIG._42D

```
                                                                                  BssHII
                                                                                  ~~~~~~
2031  ATGGGTTTTT ATGATTAGAG TCCCGCAATT ATACATTTAA TACGCGATAG AAAACAAAAT ATAGCGCGCA
      TACCCAAAAA TACTAATCTC AGGGCGTTAA TATGTAAATT ATGCGCTATC TTTTGTTTTA TATCGCGCGT
```

```
1891  GCAGATCGTT CAAACATTTG GCAATAAAGT TTCTTAAGAT TGAATCCTGT TGCCGGTCTT GCGATGATTA
      CGTCTAGCAA GTTTGTAAAC CGTTATTTCA AAGAATTCTA ACTTAGGACA ACGGCCAGAA CGCTACTAAT

1961  TCATATAATT TCTGTTGAAT TACGTTAAGC ATGTAATAAT TAACATGTAA TGCATGACGT TATTTATGAG
      AGTATATTAA AGACAACTTA ATGCAATTCG TACATTATTA ATTGTACATT ACGTACTGCA ATAAATACTC

                                                                                  BssHII
                                                                                  ~~~~~~
2031  ATGGGTTTTT ATGATTAGAG TCCCGCAATT ATACATTTAA TACGCGATAG AAAACAAAAT ATAGCGCGCA
      TACCCAAAAA TACTAATCTC AGGGCGTTAA TATGTAAATT ATGCGCTATC TTTTGTTTTA TATCGCGCGT

                                                                         XbaI
                                                                        ~~~~~~
                      BssHII                           ClaI HindIII
                     ~~~~~~~                          ~~~~~~~~~~~~~
2101  AACTAGGATA AATTATCGCG CGCGGTGTCA TCTATGTTAC TAGATCGATA AGCTTCTAGA GCGGCCGGTG
      TTGATCCTAT TTAATAGCGC GCGCCACAGT AGATACAATG ATCTAGCTAT TCGAAGATCT CGCCGGCCAC

                                         BssHII
                                         ~~~~~~
2171  GAGCTCCAAT TCGCCCTATA GTGAGTCGTA TTACGCGCGC TCACTGGCCG TCGTTTTACA ACGTCGTGAC
      CTCGAGGTTA AGCGGGATAT CACTCAGCAT AATGCGCGCG AGTGACCGGC AGCAAAATGT TGCAGCACTG

2241  TGGGAAAACC CTGGCGTTAC CCAACTTAAT CGCCTTGCAG CACATCCCCC TTTCGCCAGC TGGCGTAATA
      ACCCTTTTGG GACCGCAATG GGTTGAATTA GCGGAACGTC GTGTAGGGGG AAAGCGGTCG ACCGCATTAT

2311  GCGAAGAGGC CCGCACCGAT CGCCCTTCCC AACAGTTGCG CAGCCTGAAT GGCGAATGGG ACGCGCCCTG
      CGCTTCTCCG GGCGTGGCTA GCGGGAAGGG TTGTCAACGC GTCGGACTTA CCGCTTACCC TGCGCGGGAC

2381  TAGCGGCGCA TTAAGCGCGG CGGGTGTGGT GGTTACGCGC AGCGTGACCG CTACACTTGC CAGCGCCCTA
      ATCGCCGCGT AATTCGCGCC GCCCACACCA CCAATGCGCG TCGCACTGGC GATGTGAACG GTCGCGGGAT

2451  GCGCCCGCTC CTTTCGCTTT CTTCCCTTCC TTTCTCGCCA CGTTCGCCGG CTTTCCCCGT CAAGCTCTAA
      CGCGGGCGAG GAAAGCGAAA GAAGGGAAGG AAAGAGCGGT GCAAGCGGCC GAAAGGGGCA GTTCGAGATT
```

FIG._42E

```
2521 ATCGGGGGCT CCCTTTAGGG TTCCGATTTA GTGCTTTACG GCACCTCGAC CCCAAAAAAC TTGATTAGGG
     TAGCCCCCGA GGGAAATCCC AAGGCTAAAT CACGAAATGC CGTGGAGCTG GGGTTTTTTG AACTAATCCC

2591 TGATGGTTCA CGTAGTGGGC CATCGCCCTG ATAGACGGTT TTTCGCCCTT TGACGTTGGA GTCCACGTTC
     ACTACCAAGT GCATCACCCG GTAGCGGGAC TATCTGCCAA AAAGCGGGAA ACTGCAACCT CAGGTGCAAG

2661 TTTAATAGTG GACTCTTGTT CCAAACTGGA ACAACACTCA ACCCTATCTC GGTCTATTCT TTTGATTTAT
     AAATTATCAC CTGAGAACAA GGTTTGACCT TGTTGTGAGT TGGGATAGAG CCAGATAAGA AAACTAAATA

2731 AAGGGATTTT GCCGATTTCG GCCTATTGGT TAAAAAATGA GCTGATTTAA CAAAAATTTA ACGCGAATTT
     TTCCCTAAAA CGGCTAAAGC CGGATAACCA ATTTTTTACT CGACTAAATT GTTTTTAAAT TGCGCTTAAA

2801 TAACAAAATA TTAACGCTTA CAATTTAGGT GGCACTTTTC GGGGAAATGT GCGCGGAACC CCTATTTGTT
     ATTGTTTTAT AATTGCGAAT GTTAAATCCA CCGTGAAAAG CCCCTTTACA CGCGCCTTGG GGATAAACAA

2871 TATTTTTCTA AATACATTCA AATATGTATC CGCTCATGAG ACAATAACCC TGATAAATGC TTCAATAATA
     ATAAAAAGAT TTATGTAAGT TTATACATAG GCGAGTACTC TGTTATTGGG ACTATTTACG AAGTTATTAT

2941 TTGAAAAAGG AAGAGTATGA GTATTCAACA TTTCCGTGTC GCCCTTATTC CCTTTTTTGC GGCATTTTGC
     AACTTTTTCC TTCTCATACT CATAAGTTGT AAAGGCACAG CGGGAATAAG GGAAAAAACG CCGTAAAACG

3011 CTTCCTGTTT TTGCTCACCC AGAAACGCTG GTGAAAGTAA AAGATGCTGA AGATCAGTTG GGTGCACGAG
     GAAGGACAAA AACGAGTGGG TCTTTGCGAC CACTTTCATT TTCTACGACT TCTAGTCAAC CCACGTGCTC

3081 TGGGTTACAT CGAACTGGAT CTCAACAGCG GTAAGATCCT TGAGAGTTTT CGCCCCGAAG AACGTTTTCC
     ACCCAATGTA GCTTGACCTA GAGTTGTCGC CATTCTAGGA ACTCTCAAAA GCGGGGCTTC TTGCAAAAGG

3151 AATGATGAGC ACTTTTAAAG TTCTGCTATG TGGCGCGGTA TTATCCCGTA TTGACGCCGG GCAAGAGCAA
     TTACTACTCG TGAAAATTTC AAGACGATAC ACCGCGCCAT AATAGGGCAT AACTGCGGCC CGTTCTCGTT

3221 CTCGGTCGCC GCATACACTA TTCTCAGAAT GACTTGGTTG AGTACTCACC AGTCACAGAA AAGCATCTTA
     GAGCCAGCGG CGTATGTGAT AAGAGTCTTA CTGAACCAAC TCATGAGTGG TCAGTGTCTT TTCGTAGAAT

3291 CGGATGGCAT GACAGTAAGA GAATTATGCA GTGCTGCCAT AACCATGAGT GATAACACTG CGGCCAACTT
     GCCTACCGTA CTGTCATTCT CTTAATACGT CACGACGGTA TTGGTACTCA CTATTGTGAC GCCGGTTGAA
```

FIG._42F

```
3361  ACTTCTGACA ACGATCGGAG GACCGAAGGA GCTAACCGCT TTTTTGCACA ACATGGGGGA TCATGTAACT
      TGAAGACTGT TGCTAGCCTC CTGGCTTCCT CGATTGGCGA AAAAACGTGT TGTACCCCCT AGTACATTGA

3431  CGCCTTGATC GTTGGGAACC GGAGCTGAAT GAAGCCATAC CAAACGACGA GCGTGACACC ACGATGCCTG
      GCGGAACTAG CAACCCTTGG CCTCGACTTA CTTCGGTATG GTTTGCTGCT CGCACTGTGG TGCTACGGAC

3501  TAGCAATGGC AACAACGTTG CGCAAACTAT TAACTGGCGA ACTACTTACT CTAGCTTCCC GGCAACAATT
      ATCGTTACCG TTGTTGCAAC GCGTTTGATA ATTGACCGCT TGATGAATGA GATCGAAGGG CCGTTGTTAA

3571  AATAGACTGG ATGGAGGCGG ATAAAGTTGC AGGACCACTT CTGCGCTCGG CCCTTCCGGC TGGCTGGTTT
      TTATCTGACC TACCTCCGCC TATTTCAACG TCCTGGTGAA GACGCGAGCC GGGAAGGCCG ACCGACCAAA

3641  ATTGCTGATA AATCTGGAGC CGGTGAGCGT GGGTCTCGCG GTATCATTGC AGCACTGGGG CCAGATGGTA
      TAACGACTAT TTAGACCTCG GCCACTCGCA CCCAGAGCGC CATAGTAACG TCGTGACCCC GGTCTACCAT

3711  AGCCCTCCCG TATCGTAGTT ATCTACACGA CGGGGAGTCA GGCAACTATG GATGAACGAA ATAGACAGAT
      TCGGGAGGGC ATAGCATCAA TAGATGTGCT GCCCCTCAGT CCGTTGATAC CTACTTGCTT TATCTGTCTA

3781  CGCTGAGATA GGTGCCTCAC TGATTAAGCA TTGGTAACTG TCAGACCAAG TTTACTCATA TATACTTTAG
      GCGACTCTAT CCACGGAGTG ACTAATTCGT AACCATTGAC AGTCTGGTTC AAATGAGTAT ATATGAAATC

3851  ATTGATTTAA AACTTCATTT TTAATTTAAA AGGATCTAGG TGAAGATCCT TTTTGATAAT CTCATGACCA
      TAACTAAATT TTGAAGTAAA AATTAAATTT TCCTAGATCC ACTTCTAGGA AAAACTATTA GAGTACTGGT

3921  AAATCCCTTA ACGTGAGTTT TCGTTCCACT GAGCGTCAGA CCCCGTAGAA AAGATCAAAG GATCTTCTTG
      TTTAGGGAAT TGCACTCAAA AGCAAGGTGA CTCGCAGTCT GGGGCATCTT TTCTAGTTTC CTAGAAGAAC

3991  AGATCCTTTT TTTCTGCGCG TAATCTGCTG CTTGCAAACA AAAAAACCAC CGCTACCAGC GGTGGTTTGT
      TCTAGGAAAA AAAGACGCGC ATTAGACGAC GAACGTTTGT TTTTTTGGTG GCGATGGTCG CCACCAAACA

4061  TTGCCGGATC AAGAGCTACC AACTCTTTTT CCGAAGGTAA CTGGCTTCAG CAGAGCGCAG ATACCAAATA
      AACGGCCTAG TTCTCGATGG TTGAGAAAAA GGCTTCCATT GACCGAAGTC GTCTCGCGTC TATGGTTTAT

4131  CTGTCCTTCT AGTGTAGCCG TAGTTAGGCC ACCACTTCAA GAACTCTGTA GCACCGCCTA CATACCTCGC
      GACAGGAAGA TCACATCGGC ATCAATCCGG TGGTGAAGTT CTTGAGACAT CGTGGCGGAT GTATGGAGCG
```

FIG._42G

```
4201  TCTGCTAATC CTGTTACCAG TGGCTGCTGC CAGTGGCGAT AAGTCGTGTC TTACCGGGTT GGACTCAAGA
      AGACGATTAG GACAATGGTC ACCGACGACG GTCACCGCTA TTCAGCACAG AATGGCCCAA CCTGAGTTCT

4271  CGATAGTTAC CGGATAAGGC GCAGCGGTCG GGCTGAACGG GGGGTTCGTG CACACAGCCC AGCTTGGAGC
      GCTATCAATG GCCTATTCCG CGTCGCCAGC CCGACTTGCC CCCCAAGCAC GTGTGTCGGG TCGAACCTCG

4341  GAACGACCTA CACCGAACTG AGATACCTAC AGCGTGAGCT ATGAGAAAGC GCCACGCTTC CCGAAGGGAG
      CTTGCTGGAT GTGGCTTGAC TCTATGGATG TCGCACTCGA TACTCTTTCG CGGTGCGAAG GGCTTCCCTC

4411  AAAGGCGGAC AGGTATCCGG TAAGCGGCAG GGTCGGAACA GGAGAGCGCA CGAGGGAGCT TCCAGGGGGA
      TTTCCGCCTG TCCATAGGCC ATTCGCCGTC CCAGCCTTGT CCTCTCGCGT GCTCCCTCGA AGGTCCCCCT

4481  AACGCCTGGT ATCTTTATAG TCCTGTCGGG TTTCGCCACC TCTGACTTGA GCGTCGATTT TTGTGATGCT
      TTGCGGACCA TAGAAATATC AGGACAGCCC AAAGCGGTGG AGACTGAACT CGCAGCTAAA AACACTACGA

4551  CGTCAGGGGG GCGGAGCCTA TGGAAAAACG CCAGCAACGC GGCCTTTTTA CGGTTCCTGG CCTTTTGCTG
      GCAGTCCCCC CGCCTCGGAT ACCTTTTTGC GGTCGTTGCG CCGGAAAAAT GCCAAGGACC GGAAAACGAC

4621  GCCTTTTGCT CACATGTTCT TTCCTGCGTT ATCCCCTGAT TCTGTGGATA ACCGTATTAC CGCCTTTGAG
      CGGAAAACGA GTGTACAAGA AAGGACGCAA TAGGGGACTA AGACACCTAT TGGCATAATG GCGGAAACTC

4691  TGAGCTGATA CCGCTCGCCG CAGCCGAACG ACCGAGCGCA GCGAGTCAGT GAGCGAGGAA GCGGAAGAGC
      ACTCGACTAT GGCGAGCGGC GTCGGCTTGC TGGCTCGCGT CGCTCAGTCA CTCGCTCCTT CGCCTTCTCG

4761  GCCCAATACG CAAACCGCCT CTCCCCGCGC GTTGGCCGAT TCATTAATGC AGCTGGCACG ACAGGTTTCC
      CGGGTTATGC GTTTGGCGGA GAGGGGCGCG CAACCGGCTA AGTAATTACG TCGACCGTGC TGTCCAAAGG

4831  CGACTGGAAA GCGGGCAGTG AGCGCAACGC AATTAATGTG AGTTAGCTCA CTCATTAGGC ACCCCAGGCT
      GCTGACCTTT CGCCCGTCAC TCGCGTTGCG TTAATTACAC TCAATCGAGT GAGTAATCCG TGGGGTCCGA

4901  TTACACTTTA TGCTTCCGGC TCGTATGTTG TGTGGAATTG TGAGCGGATA ACAATTTCAC ACAGGAAACA
      AATGTGAAAT ACGAAGGCCG AGCATACAAC ACACCTTAAC ACTCGCCTAT TGTTAAAGTG TGTCCTTTGT
```

FIG._42H

```
                                                                                 NcoI
                         BssHII                                                  KpnI
                         ~~~~~~                                                 ~~~~~
4971  GCTATGACCA TGATTACGCC AAGCGCGCAA TTAACCCTCA CTAAAGGGAA CAAAAGCTGG GTAC
      CGATACTGGT ACTAATGCGG TTCGCGCGTT AATTGGGAGT GATTTCCCTT GTTTTCGACC CATG
```

FIG._42I

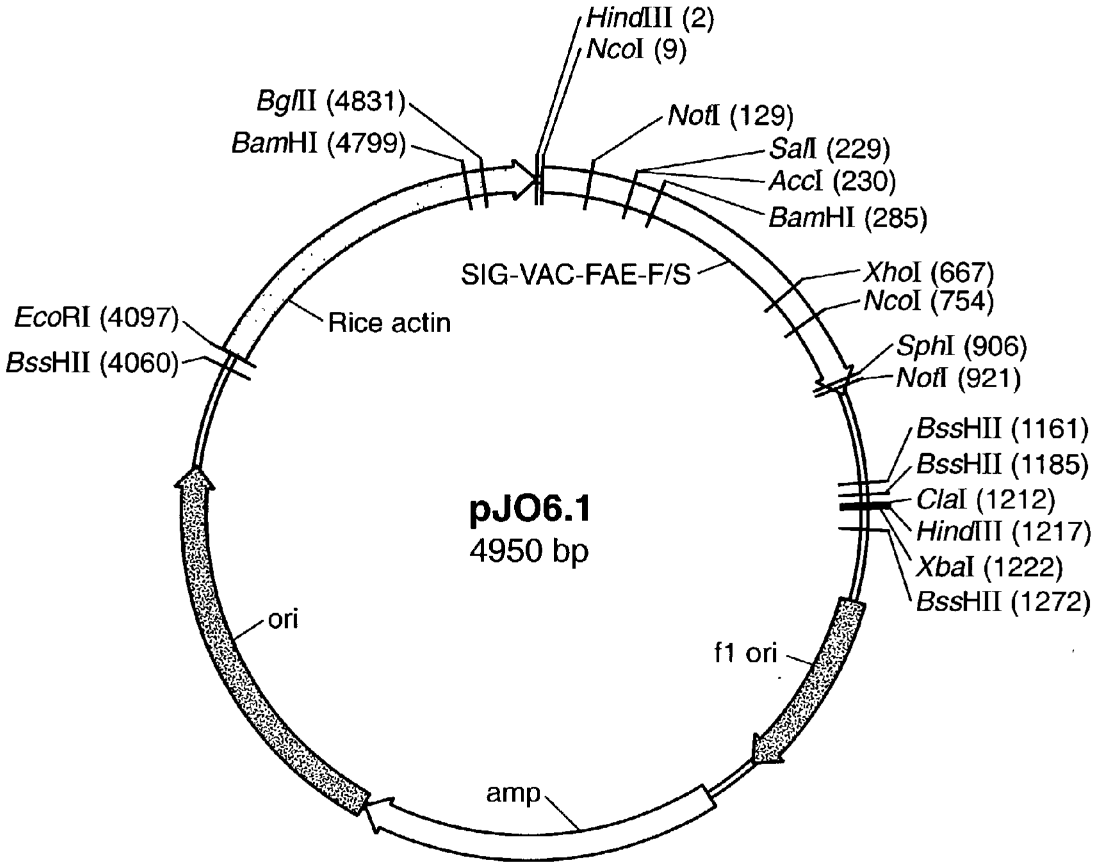
FIG._43A

```
     HindIII NcoI
     ~~~~~~~ ~~~~~~~~
  1  AAGCTTACCA TGGCCCACGC CCGCGTCCTC CTCCTGGCGC TCGCCGTGCT GGCCACGGCC GCCGTCGCCG
     TTCGAATGGT ACCGGGTGCG GGCGCAGGAG GAGGACCGCG AGCGGCACGA CCGGTGCCGG CGGCAGCGGC

                                                                 NotI
                                                               ~~~~~~~~~~
 71  TCGCCTCCTC CTCCTCCTTC GCCGACTCCA ACCCGATCCG GCCCGTCACC GACCGCGCGG CCGCCTCCAC
     AGCGGAGGAG GAGGAGGAAG CGGCTGAGGT TGGGCTAGGC CGGGCAGTGG CTGGCGCGCC GGCGGAGGTG

141  GCAGGGCATC TCCGAAGACC TCTACAGCCG TTTAGTCGAA ATGGCCACTA TCTCCCAAGC TGCCTACGCC
     CGTCCCGTAG AGGCTTCTGG AGATGTCGGC AAATCAGCTT TACCGGTGAT AGAGGGTTCG ACGGATGCGG

                           SalI
                         ~~~~~~~~
                           AccI
                         ~~~~~~~~
211  GACCTGTGCA ACATTCCGTC GACTATTATC AAGGGAGAGA AAATTTACAA TTCTCAAACT GACATTAACG
     CTGGACACGT TGTAAGGCAG CTGATAATAG TTCCCTCTCT TTTAAATGTT AAGAGTTTGA CTGTAATTGC

        BamHI
       ~~~~~~~
281  GATGGATCCT CCGCGACGAC AGCAGCAAAG AAATAATCAC CGTCTTCCGT GGCACTGGTA GTGATACGAA
     CTACCTAGGA GGCGCTGCTG TCGTCGTTTC TTTATTAGTG GCAGAAGGCA CCGTGACCAT CACTATGCTT

351  TCTACAACTC GATACTAACT ACACCCTCAC GCCTTTCGAC ACCCTACCAC AATGCAACGG TTGTGAAGTA
     AGATGTTGAG CTATGATTGA TGTGGGAGTG CGGAAAGCTG TGGGATGGTG TTACGTTGCC AACACTTCAT

421  CACGGTGGAT ATTATATTGG ATGGGTCTCC GTCCAGGACC AAGTCGAGTC GCTTGTCAAA CAGCAGGTTA
     GTGCCACCTA TAATATAACC TACCCAGAGG CAGGTCCTGG TTCAGCTCAG CGAACAGTTT GTCGTCCAAT

491  GCCAGTATCC GGACTACGCG CTGACCGTGA CCGGCCACKC CCTCGGCGCC TCCCTGGCGG CACTCACTGC
     CGGTCATAGG CCTGATGCGC GACTGGCACT GGCCGGTGMG GGAGCCGCGG AGGGACCGCC GTGAGTGACG

561  CGCCCAGCTG TCTGCGACAT ACGACAACAT CCGCCTGTAC ACCTTCGGCG AACCGCGCAG CGGCAATCAG
     GCGGGTCGAC AGACGCTGTA TGCTGTTGTA GGCGGACATG TGGAAGCCGC TTGGCGCGTC GCCGTTAGTC
```

FIG._43B

```
                                               XhoI
                                             ~~~~~~~~
631   GCCTTCGCGT CGTACATGAA CGATGCCTTC CAAGCCTCGA GCCCAGATAC GACGCAGTAT TTCCGGGTCA
      CGGAAGCGCA GCATGTACTT GCTACGGAAG GTTCGGAGCT CGGGTCTATG CTGCGTCATA AAGGCCCAGT

                                                                 NcoI
                                                                ~~~~~~
701   CTCATGCCAA CGACGGCATC CCAAACCTGC CCCCGGTGGA GCAGGGGTAC GCCCATGGCG GTGTAGAGTA
      GAGTACGGTT GCTGCCGTAG GGTTTGGACG GGGGCCACCT CGTCCCCATG CGGGTACCGC CACATCTCAT

771   CTGGAGCGTT GATCCTTACA GCGCCCAGAA CACATTTGTC TGCACTGGGG ATGAAGTGCA GTGCTGTGAG
      GACCTCGCAA CTAGGAATGT CGCGGGTCTT GTGTAAACAG ACGTGACCCC TACTTCACGT CACGACACTC

                                                                            SphI
                                                                           ~~~~~~
841   GCCCAGGGCG GACAGGGTGT GAATAATGCG CACACGACTT ATTTTGGGAT GACGAGCGGC GCATGCACCT
      CGGGTCCCGC CTGTCCCACA CTTATTACGC GTGTGCTGAA TAAAACCCTA CTGCTCGCCG CGTACGTGGA

                 NotI
             ~~~~~~~~~~
911   GGCCGGTCGC GGCCGCGGAA ACCACTGAAG GATGAGCTGT AAAGAAGCAG ATCGTTCAAA CATTTGGCAA
      CCGGCCAGCG CCGGCGCCTT TGGTGACTTC CTACTCGACA TTTCTTCGTC TAGCAAGTTT GTAAACCGTT

981   TAAAGTTTCT TAAGATTGAA TCCTGTTGCC GGTCTTGCGA TGATTATCAT ATAATTTCTG TTGAATTACG
      ATTTCAAAGA ATTCTAACTT AGGACAACGG CCAGAACGCT ACTAATAGTA TATTAAAGAC AACTTAATGC

1051  TTAAGCATGT AATAATTAAC ATGTAATGCA TGACGTTATT TATGAGATGG GTTTTTATGA TTAGAGTCCC
      AATTCGTACA TTATTAATTG TACATTACGT ACTGCAATAA ATACTCTACC CAAAAATACT AATCTCAGGG

                                                  BssHII                     BssHII
                                                 ~~~~~~~~                    ~~~~~~
1121  GCAATTATAC ATTTAATACG CGATAGAAAA CAAAATATAG CGCGCAAACT AGGATAAATT ATCGCGCGCG
      CGTTAATATG TAAATTATGC GCTATCTTTT GTTTTATATC GCGCGTTTGA TCCTATTTAA TAGCGCGCGC
```

FIG._43C

```
                                  XbaI
                                 ~~~~~~
                         ClaI HindIII
                       ~~~~~~~~~~~~~~~
1191  GTGTCATCTA TGTTACTAGA TCGATAAGCT TCTAGAGCGG CCGGTGGAGC TCCAATTCGC CCTATAGTGA
      CACAGTAGAT ACAATGATCT AGCTATTCGA AGATCTCGCC GGCCACCTCG AGGTTAAGCG GGATATCACT

                 BssHII
                 ~~~~~~
1261  GTCGTATTAC GCGCGCTCAC TGGCCGTCGT TTTACAACGT CGTGACTGGG AAAACCCTGG CGTTACCCAA
      CAGCATAATG CGCGCGAGTG ACCGGCAGCA AAATGTTGCA GCACTGACCC TTTTGGGACC GCAATGGGTT

1331  CTTAATCGCC TTGCAGCACA TCCCCCTTTC GCCAGCTGGC GTAATAGCGA AGAGGCCCGC ACCGATCGCC
      GAATTAGCGG AACGTCGTGT AGGGGGAAAG CGGTCGACCG CATTATCGCT TCTCCGGGCG TGGCTAGCGG

1401  CTTCCCAACA GTTGCGCAGC CTGAATGGCG AATGGGACGC GCCCTGTAGC GGCGCATTAA GCGCGGCGGG
      GAAGGGTTGT CAACGCGTCG GACTTACCGC TTACCCTGCG CGGGACATCG CCGCGTAATT CGCGCCGCCC

1471  TGTGGTGGTT ACGCGCAGCG TGACCGCTAC ACTTGCCAGC GCCCTAGCGC CCGCTCCTTT CGCTTTCTTC
      ACACCACCAA TGCGCGTCGC ACTGGCGATG TGAACGGTCG CGGGATCGCG GGCGAGGAAA GCGAAAGAAG

1541  CCTTCCTTTC TCGCCACGTT CGCCGGCTTT CCCCGTCAAG CTCTAAATCG GGGGCTCCCT TTAGGGTTCC
      GGAAGGAAAG AGCGGTGCAA GCGGCCGAAA GGGGCAGTTC GAGATTTAGC CCCCGAGGGA AATCCCAAGG

1611  GATTTAGTGC TTTACGGCAC CTCGACCCCA AAAAACTTGA TTAGGGTGAT GGTTCACGTA GTGGGCCATC
      CTAAATCACG AAATGCCGTG GAGCTGGGGT TTTTTGAACT AATCCCACTA CCAAGTGCAT CACCCGGTAG

1681  GCCCTGATAG ACGGTTTTTC GCCCTTTGAC GTTGGAGTCC ACGTTCTTTA ATAGTGGACT CTTGTTCCAA
      CGGGACTATC TGCCAAAAAG CGGGAAACTG CAACCTCAGG TGCAAGAAAT TATCACCTGA GAACAAGGTT

1751  ACTGGAACAA CACTCAACCC TATCTCGGTC TATTCTTTTG ATTTATAAGG GATTTTGCCG ATTTCGGCCT
      TGACCTTGTT GTGAGTTGGG ATAGAGCCAG ATAAGAAAAC TAAATATTCC CTAAAACGGC TAAAGCCGGA

1821  ATTGGTTAAA AAATGAGCTG ATTTAACAAA AATTTAACGC GAATTTTAAC AAAATATTAA CGCTTACAAT
      TAACCAATTT TTTACTCGAC TAAATTGTTT TTAAATTGCG CTTAAAATTG TTTTATAATT GCGAATGTTA
```

FIG._43D

```
1891  TTAGGTGGCA CTTTTCGGGG AAATGTGCGC GGAACCCCTA TTTGTTTATT TTTCTAAATA CATTCAAATA
      AATCCACCGT GAAAAGCCCC TTTACACGCG CCTTGGGGAT AAACAAATAA AAAGATTTAT GTAAGTTTAT

1961  TGTATCCGCT CATGAGACAA TAACCCTGAT AAATGCTTCA ATAATATTGA AAAAGGAAGA GTATGAGTAT
      ACATAGGCGA GTACTCTGTT ATTGGGACTA TTTACGAAGT TATTATAACT TTTTCCTTCT CATACTCATA

2031  TCAACATTTC CGTGTCGCCC TTATTCCCTT TTTTGCGGCA TTTTGCCTTC CTGTTTTTGC TCACCCAGAA
      AGTTGTAAAG GCACAGCGGG AATAAGGGAA AAAACGCCGT AAAACGGAAG GACAAAAACG AGTGGGTCTT

2101  ACGCTGGTGA AAGTAAAAGA TGCTGAAGAT CAGTTGGGTG CACGAGTGGG TTACATCGAA CTGGATCTCA
      TGCGACCACT TTCATTTTCT ACGACTTCTA GTCAACCCAC GTGCTCACCC AATGTAGCTT GACCTAGAGT

2171  ACAGCGGTAA GATCCTTGAG AGTTTTCGCC CCGAAGAACG TTTTCCAATG ATGAGCACTT TTAAAGTTCT
      TGTCGCCATT CTAGGAACTC TCAAAAGCGG GGCTTCTTGC AAAAGGTTAC TACTCGTGAA AATTTCAAGA

2241  GCTATGTGGC GCGGTATTAT CCCGTATTGA CGCCGGGCAA GAGCAACTCG GTCGCCGCAT ACACTATTCT
      CGATACACCG CGCCATAATA GGGCATAACT GCGGCCCGTT CTCGTTGAGC CAGCGGCGTA TGTGATAAGA

2311  CAGAATGACT TGGTTGAGTA CTCACCAGTC ACAGAAAAGC ATCTTACGGA TGGCATGACA GTAAGAGAAT
      GTCTTACTGA ACCAACTCAT GAGTGGTCAG TGTCTTTTCG TAGAATGCCT ACCGTACTGT CATTCTCTTA

2381  TATGCAGTGC TGCCATAACC ATGAGTGATA ACACTGCGGC CAACTTACTT CTGACAACGA TCGGAGGACC
      ATACGTCACG ACGGTATTGG TACTCACTAT TGTGACGCCG GTTGAATGAA GACTGTTGCT AGCCTCCTGG

2451  GAAGGAGCTA ACCGCTTTTT TGCACAACAT GGGGGATCAT GTAACTCGCC TTGATCGTTG GGAACCGGAG
      CTTCCTCGAT TGGCGAAAAA ACGTGTTGTA CCCCCTAGTA CATTGAGCGG AACTAGCAAC CCTTGGCCTC

2521  CTGAATGAAG CCATACCAAA CGACGAGCGT GACACCACGA TGCCTGTAGC AATGGCAACA ACGTTGCGCA
      GACTTACTTC GGTATGGTTT GCTGCTCGCA CTGTGGTGCT ACGGACATCG TTACCGTTGT TGCAACGCGT

2591  AACTATTAAC TGGCGAACTA CTTACTCTAG CTTCCCGGCA ACAATTAATA GACTGGATGG AGGCGGATAA
      TTGATAATTG ACCGCTTGAT GAATGAGATC GAAGGGCCGT TGTTAATTAT CTGACCTACC TCCGCCTATT

2661  AGTTGCAGGA CCACTTCTGC GCTCGGCCCT TCCGGCTGGC TGGTTTATTG CTGATAAATC TGGAGCCGGT
      TCAACGTCCT GGTGAAGACG CGAGCCGGGA AGGCCGACCG ACCAAATAAC GACTATTTAG ACCTCGGCCA
```

FIG._43E

```
2731  GAGCGTGGGT CTCGCGGTAT CATTGCAGCA CTGGGGCCAG ATGGTAAGCC CTCCCGTATC GTAGTTATCT
      CTCGCACCCA GAGCGCCATA GTAACGTCGT GACCCCGGTC TACCATTCGG GAGGGCATAG CATCAATAGA

2801  ACACGACGGG GAGTCAGGCA ACTATGGATG AACGAAATAG ACAGATCGCT GAGATAGGTG CCTCACTGAT
      TGTGCTGCCC CTCAGTCCGT TGATACCTAC TTGCTTTATC TGTCTAGCGA CTCTATCCAC GGAGTGACTA

2871  TAAGCATTGG TAACTGTCAG ACCAAGTTTA CTCATATATA CTTTAGATTG ATTTAAAACT TCATTTTTAA
      ATTCGTAACC ATTGACAGTC TGGTTCAAAT GAGTATATAT GAAATCTAAC TAAATTTTGA AGTAAAAATT

2941  TTTAAAAGGA TCTAGGTGAA GATCCTTTTT GATAATCTCA TGACCAAAAT CCCTTAACGT GAGTTTTCGT
      AAATTTTCCT AGATCCACTT CTAGGAAAAA CTATTAGAGT ACTGGTTTTA GGGAATTGCA CTCAAAAGCA

3011  TCCACTGAGC GTCAGACCCC GTAGAAAAGA TCAAAGGATC TTCTTGAGAT CCTTTTTTTC TGCGCGTAAT
      AGGTGACTCG CAGTCTGGGG CATCTTTTCT AGTTTCCTAG AAGAACTCTA GGAAAAAAAG ACGCGCATTA

3081  CTGCTGCTTG CAAACAAAAA AACCACCGCT ACCAGCGGTG GTTTGTTTGC CGGATCAAGA GCTACCAACT
      GACGACGAAC GTTTGTTTTT TTGGTGGCGA TGGTCGCCAC CAAACAAACG GCCTAGTTCT CGATGGTTGA

3151  CTTTTTCCGA AGGTAACTGG CTTCAGCAGA GCGCAGATAC CAAATACTGT CCTTCTAGTG TAGCCGTAGT
      GAAAAAGGCT TCCATTGACC GAAGTCGTCT CGCGTCTATG GTTTATGACA GGAAGATCAC ATCGGCATCA

3221  TAGGCCACCA CTTCAAGAAC TCTGTAGCAC CGCCTACATA CCTCGCTCTG CTAATCCTGT TACCAGTGGC
      ATCCGGTGGT GAAGTTCTTG AGACATCGTG GCGGATGTAT GGAGCGAGAC GATTAGGACA ATGGTCACCG

3291  TGCTGCCAGT GGCGATAAGT CGTGTCTTAC CGGGTTGGAC TCAAGACGAT AGTTACCGGA TAAGGCGCAG
      ACGACGGTCA CCGCTATTCA GCACAGAATG GCCCAACCTG AGTTCTGCTA TCAATGGCCT ATTCCGCGTC

3361  CGGTCGGGCT GAACGGGGGG TTCGTGCACA CAGCCCAGCT TGGAGCGAAC GACCTACACC GAACTGAGAT
      GCCAGCCCGA CTTGCCCCCC AAGCACGTGT GTCGGGTCGA ACCTCGCTTG CTGGATGTGG CTTGACTCTA

3431  ACCTACAGCG TGAGCTATGA GAAAGCGCCA CGCTTCCCGA AGGGAGAAAG GCGGACAGGT ATCCGGTAAG
      TGGATGTCGC ACTCGATACT CTTTCGCGGT GCGAAGGGCT TCCCTCTTTC CGCCTGTCCA TAGGCCATTC

3501  CGGCAGGGTC GGAACAGGAG AGCGCACGAG GGAGCTTCCA GGGGGAAACG CCTGGTATCT TTATAGTCCT
      GCCGTCCCAG CCTTGTCCTC TCGCGTGCTC CCTCGAAGGT CCCCCTTTGC GGACCATAGA AATATCAGGA
```

FIG._43F

```
3571  GTCGGGTTTC GCCACCTCTG ACTTGAGCGT CGATTTTTGT GATGCTCGTC AGGGGGGCGG AGCCTATGGA
      CAGCCCAAAG CGGTGGAGAC TGAACTCGCA GCTAAAAACA CTACGAGCAG TCCCCCCGCC TCGGATACCT

3641  AAAACGCCAG CAACGCGGCC TTTTTACGGT TCCTGGCCTT TTGCTGGCCT TTTGCTCACA TGTTCTTTCC
      TTTTGCGGTC GTTGCGCCGG AAAAATGCCA AGGACCGGAA AACGACCGGA AAACGAGTGT ACAAGAAAGG

3711  TGCGTTATCC CCTGATTCTG TGGATAACCG TATTACCGCC TTTGAGTGAG CTGATACCGC TCGCCGCAGC
      ACGCAATAGG GGACTAAGAC ACCTATTGGC ATAATGGCGG AAACTCACTC GACTATGGCG AGCGGCGTCG

3781  CGAACGACCG AGCGCAGCGA GTCAGTGAGC GAGGAAGCGG AAGAGCGCCC AATACGCAAA CCGCCTCTCC
      GCTTGCTGGC TCGCGTCGCT CAGTCACTCG CTCCTTCGCC TTCTCGCGGG TTATGCGTTT GGCGGAGAGG

3851  CCGCGCGTTG GCCGATTCAT TAATGCAGCT GGCACGACAG GTTTCCCGAC TGGAAAGCGG GCAGTGAGCG
      GGCGCGCAAC CGGCTAAGTA ATTACGTCGA CCGTGCTGTC CAAAGGGCTG ACCTTTCGCC CGTCACTCGC

3921  CAACGCAATT AATGTGAGTT AGCTCACTCA TTAGGCACCC CAGGCTTTAC ACTTTATGCT TCCGGCTCGT
      GTTGCGTTAA TTACACTCAA TCGAGTGAGT AATCCGTGGG GTCCGAAATG TGAAATACGA AGGCCGAGCA

                                                                         BssHII
                                                                             ~~
3991  ATGTTGTGTG GAATTGTGAG CGGATAACAA TTTCACACAG GAAACAGCTA TGACCATGAT TACGCCAAGC
      TACAACACAC CTTAACACTC GCCTATTGTT AAAGTGTGTC CTTTGTCGAT ACTGGTACTA ATGCGGTTCG

      BssHII                                EcoRI
      ~~~~                                ~~~~~~~
4061  GCGCAATTAA CCCTCACTAA AGGGAACAAA AGCTGGAATT CCACAATGAA CAATAATAAG ATTAAAATAG
      CGCGTTAATT GGGAGTGATT TCCCTTGTTT TCGACCTTAA GGTGTTACTT GTTATTATTC TAATTTTATC

4131  CTTGCCCCCG TTGCAGCGAT GGGTATTTTT TCTAGTAAAA TAAAAGATAA ACTTAGACTC AAAACATTTA
      GAACGGGGGC AACGTCGCTA CCCATAAAAA AGATCATTTT ATTTTCTATT TGAATCTGAG TTTTGTAAAT

4201  CAAAAACAAC CCCTAAAGTC CTAAAGCCCA AAGTGCTATG CACGATCCAT AGCAAGCCCA GCCCAACCCA
      GTTTTTGTTG GGGATTTCAG GATTTCGGGT TTCACGATAC GTGCTAGGTA TCGTTCGGGT CGGGTTGGGT
```

FIG._43G

```
4271  ACCCAACCCA ACCCACCCCA GTGCAGCCAA CTGGCAAATA GTCTCCACCC CCGGCACTAT CACCGTGAGT
      TGGGTTGGGT TGGGTGGGGT CACGTCGGTT GACCGTTTAT CAGAGGTGGG GGCCGTGATA GTGGCACTCA

4341  TGTCCGCACC ACCGCACGTC TCGCAGCCAA AAAAAAAAAA AGAAAGAAAA AAAAGAAAAA GAAAAACAGC
      ACAGGCGTGG TGGCGTGCAG AGCGTCGGTT TTTTTTTTTT TCTTTCTTTT TTTTCTTTTT CTTTTTGTCG

4411  AGGTGGGTCC GGGTCGTGGG GGCCGGAAAA GCGAGGAGGA TCGCGAGCAG CGACGAGGCC CGGCCCTCCC
      TCCACCCAGG CCCAGCACCC CCGGCCTTTT CGCTCCTCCT AGCGCTCGTC GCTGCTCCGG GCCGGGAGGG

4481  TCCGCTTCCA AAGAAACGCC CCCCATCGCC ACTATATACA TACCCCCCCC TCTCCTCCCA TCCCCCCAAC
      AGGCGAAGGT TTCTTTGCGG GGGGTAGCGG TGATATATGT ATGGGGGGGG AGAGGAGGGT AGGGGGGTTG

4551  CCTACCACCA CCACCACCAC CACCTCCTCC CCCCTCGCTG CCGGACGACG AGCTCCTCCC CCCTCCCCCT
      GGATGGTGGT GGTGGTGGTG GTGGAGGAGG GGGGAGCGAC GGCCTGCTGC TCGAGGAGGG GGGAGGGGGA

4621  CCGCCGCCGC CGGTAACCAC CCCGCCCCTC TCCTCTTTCT TTCTCCGTTT TTTTTTTCGT CTCGGTCTCG
      GGCGGCGGCG GCCATTGGTG GGGCGGGGAG AGGAGAAAGA AAGAGGCAAA AAAAAAAGCA GAGCCAGAGC

4691  ATCTTTGGCC TTGGTAGTTT GGGTGGGCGA GAGCGGCTTC GTCGCCCAGA TCGGTGCGCG GGAGGGGCGG
      TAGAAACCGG AACCATCAAA CCCACCCGCT CTCGCCGAAG CAGCGGGTCT AGCCACGCGC CCTCCCCGCC

                                                 BamHI                      BglII
                                               ~~~~~~~~                        ~
4761  GATCTCGCGG CTGGCGTCTC CGGGCGTGAG TCGGCCCGGA TCCTCGCGGG GAATGGGGCT CTCGGATGTA
      CTAGAGCGCC GACCGCAGAG GCCCGCACTC AGCCGGGCCT AGGAGCGCCC CTTACCCCGA GAGCCTACAT

      BglII
      ~~~~~
4831  GATCTTCTTT CTTTCTTCTT TTTGTGGTAG AATTTGAATC CCTCAGCATT GTTCATCGGT AGTTTTTCTT
      CTAGAAGAAA GAAAGAAGAA AAACACCATC TTAAACTTAG GGAGTCGTAA CAAGTAGCCA TCAAAAAGAA

4901  TTCATGATTT GTGACAAATG CAGCCTCGTG CGGAGCTTTT TTGTAGGTAG
      AAGTACTAAA CACTGTTTAC GTCGGAGCAC GCCTCGAAAA AACATCCATC
```

FIG._43H

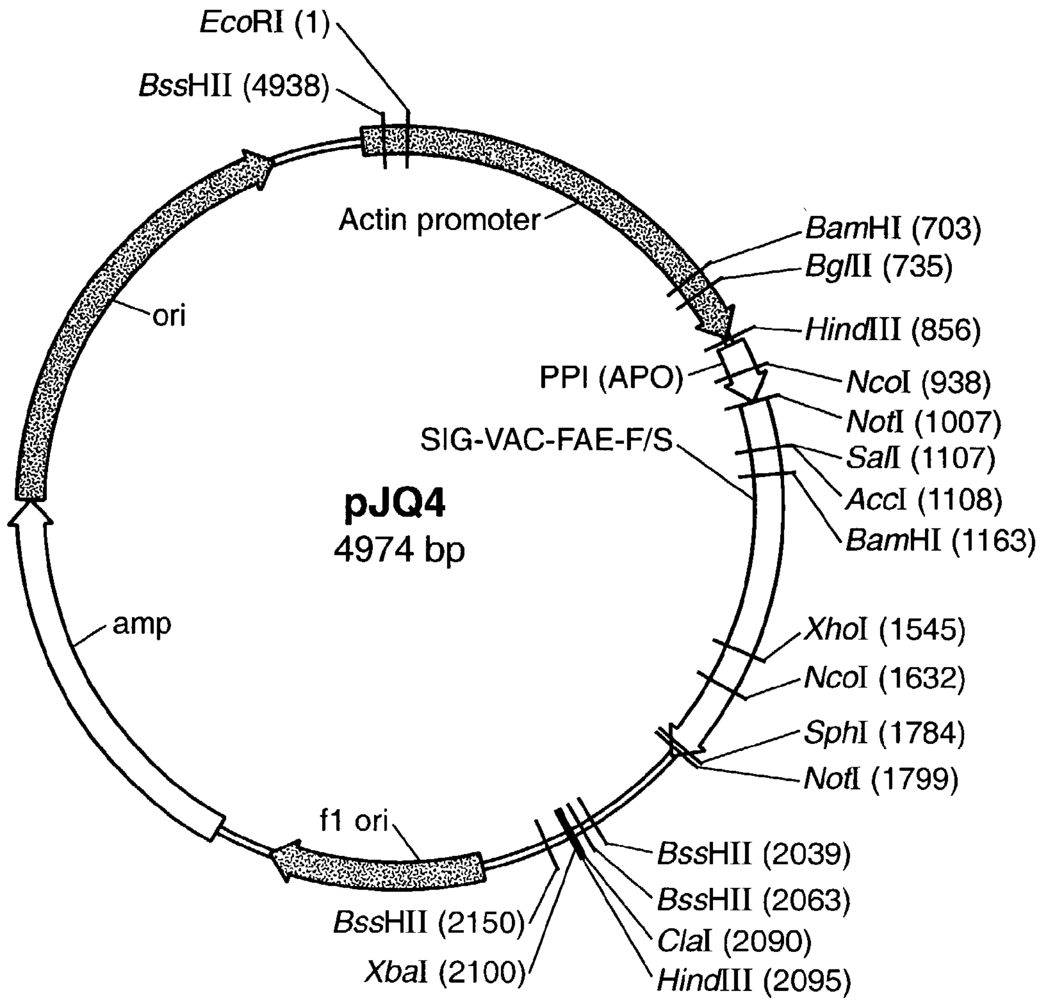
FIG._44A

```
      EcoRI
      ~~~~~
  1   AATTCCACAA TGAACAATAA TAAGATTAAA ATAGCTTGCC CCCGTTGCAG CGATGGGTAT TTTTTCTAGT
      TTAAGGTGTT ACTTGTTATT ATTCTAATTT TATCGAACGG GGGCAACGTC GCTACCCATA AAAAAGATCA

 71   AAAATAAAAG ATAAACTTAG ACTCAAAACA TTTACAAAAA CAACCCCTAA AGTCCTAAAG CCCAAAGTGC
      TTTTATTTTC TATTTGAATC TGAGTTTTGT AAATGTTTTT GTTGGGGATT TCAGGATTTC GGGTTTCACG

141   TATGCACGAT CCATAGCAAG CCCAGCCCAA CCCAACCCAA CCCAACCCAC CCCAGTGCAG CCAACTGGCA
      ATACGTGCTA GGTATCGTTC GGGTCGGGTT GGGTTGGGTT GGGTTGGGTG GGGTCACGTC GGTTGACCGT

211   AATAGTCTCC ACCCCCGGCA CTATCACCGT GAGTTGTCCG CACCACCGCA CGTCTCGCAG CCAAAAAAAA
      TTATCAGAGG TGGGGGCCGT GATAGTGGCA CTCAACAGGC GTGGTGGCGT GCAGAGCGTC GGTTTTTTTT

281   AAAAAGAAAG AAAAAAAAGA AAAAGAAAAA CAGCAGGTGG GTCCGGGTCG TGGGGGCCGG AAAAGCGAGG
      TTTTTCTTTC TTTTTTTTCT TTTTCTTTTT GTCGTCCACC CAGGCCCAGC ACCCCCGGCC TTTTCGCTCC

351   AGGATCGCGA GCAGCGACGA GGCCCGGCCC TCCCTCCGCT TCCAAAGAAA CGCCCCCCAT CGCCACTATA
      TCCTAGCGCT CGTCGCTGCT CCGGGCCGGG AGGGAGGCGA AGGTTTCTTT GCGGGGGGTA GCGGTGATAT

421   TACATACCCC CCCCTCTCCT CCCATCCCCC CAACCCTACC ACCACCACCA CCACCACCTC CTCCCCCCTC
      ATGTATGGGG GGGGAGAGGA GGGTAGGGGG GTTGGGATGG TGGTGGTGGT GGTGGTGGAG GAGGGGGGAG

491   GCTGCCGGAC GACGAGCTCC TCCCCCCTCC CCCTCCGCCG CCGCCGGTAA CCACCCCGCC CCTCTCCTCT
      CGACGGCCTG CTGCTCGAGG AGGGGGGAGG GGGAGGCGGC GGCGGCCATT GGTGGGGCGG GGAGAGGAGA

561   TTCTTTCTCC GTTTTTTTTT TCGTCTCGGT CTCGATCTTT GGCCTTGGTA GTTTGGGTGG GCGAGAGCGG
      AAGAAAGAGG CAAAAAAAAA AGCAGAGCCA GAGCTAGAAA CCGGAACCAT CAAACCCACC CGCTCTCGCC

631   CTTCGTCGCC CAGATCGGTG CGCGGGAGGG GCGGGATCTC GCGGCTGGCG TCTCCGGGCG TGAGTCGGCC
      GAAGCAGCGG GTCTAGCCAC GCGCCCTCCC CGCCCTAGAG CGCCGACCGC AGAGGCCCGC ACTCAGCCGG

        BamHI                            BglII
       ~~~~~~                           ~~~~~~
701   CGGATCCTCG CGGGGAATGG GGCTCTCGGA TGTAGATCTT CTTTCTTTCT TCTTTTTGTG GTAGAATTTG
      GCCTAGGAGC GCCCCTTACC CCGAGAGCCT ACATCTAGAA GAAAGAAAGA AGAAAAACAC CATCTTAAAC
```

FIG._44B

```
 771  AATCCCTCAG CATTGTTTCAT CGGTAGTTTT TCTTTTCATG ATTTGTGACA AATGCAGCCT CGTGCGGAGC
      TTAGGGAGTC GTAACAAGTA GCCATCAAAA AGAAAAGTAC TAAACACTGT TTACGTCGGA GCACGCCTCG
                                          HindIII
                                          ~~~~~~~

 841  TTTTTTGTAG GTAGAAGCTT ACMATGGMCG TGCACAAGGA GGTSAACTTC GTSGCCTACC TCCTGATCGT
      AAAAAACATC CATCTTCGAA TGKTACCCKGC ACGTGTTCCT CCASTTGAAG CASCGGATGG AGGACTAGCA
                                NcoI
                                ~~~~

 911  SCTCGGCCTC CTCTTGCTCG TSTCCGCCAT GGAGCACGTG GACGCCAAGG CCTGCACCCK CGAGTGCGGC
      SGAGCCGGAG GAGAACGAGC ASAGGCGGTA CCTCGTGCAC CTGCGGTTCC GGACGTGGGM GCTCACGCCG
                                                                    NotI
                                                                    ~~~~

 981  AACCTCGGCT TCGGCATCTG CCCGGCGGCC GCCTCCACGC AGGGCATCTC CGAAGACCTC TACAGCCGTT
      TTGGAGCCGA AGCCGTAGAC GGGCCGCCGG CGGAGGTGCG TCCCGTAGAG GCTTCTGGAG ATGTCGGCAA
                                                                           SalI
                                                                           ~~~~
                                                                            AccI
                                                                            ~~~~

1051  TAGTCGAAAT GGCCACTATC TCCCAAGCTG CCTACGCCGA CCTGTGCAAC ATTCCGTCGA CTATTATCAA
      ATCAGCTTTA CCGGTGATAG AGGGTTCGAC GGATGCGGCT GGACACGTTG TAAGGCAGCT GATAATAGTT
                                                BamHI
                                                ~~~~~

1121  GGGAGAGAAA ATTTACAATT CTCAAACTGA CATTAACGGA TGGATCCTCC GCGACGACAG CAGCAAAGAA
      CCCTCTCTTT TAAATGTTAA GAGTTTGACT GTAATTGCCT ACCTAGGAGG CGCTGCTGTC GTCGTTTCTT

1191  ATAATCACCG TCTTCCGTGG CACTGGTAGT GATACGAATC TACAACTCGA ACCCTCACGC
      TATTAGTGGC AGAAGGCACC GTGACCATCA CTATGCTTAG ATGTTGAGCT TGGGAGTGCG

1261  CTTTCGACAC CCTACCACAA TGCAACGGTT GTGAAGTACA CGGTGGATAT TATATTGGAT GGGTCTCCGT
      GAAAGCTGTG GGATGGTGTT ACGTTGCCAA CACTTCATGT GCCACCTATA ATATAACCTA CCCAGAGGCA
```

*FIG._44C*

```
1331  CCAGGACCAA GTCGAGTCGC TTGTCAAACA GCAGGTTAGC CAGTATCCGG ACTACGCGCT GACCGTGACC
      GGTCCTGGTT CAGCTCAGCG AACAGTTTGT CGTCCAATCG GTCATAGGCC TGATGCGCGA CTGGCACTGG

1401  GGCCACKCCC TCGGCGCCTC CCTGGCGGCA CTCACTGCCG CCCAGCTGTC TGCGACATAC GACAACATCC
      CCGGTGMGGG AGCCGCGGAG GGACCGCCGT GAGTGACGGC GGGTCGACAG ACGCTGTATG CTGTTGTAGG

1471  GCCTGTACAC CTTCGGCGAA CCGCGCAGCG GCAATCAGGC CTTCGCGTCG TACATGAACG ATGCCTTCCA
      CGGACATGTG GAAGCCGCTT GGCGCGTCGC CGTTAGTCCG GAAGCGCAGC ATGTACTTGC TACGGAAGGT

         XhoI
        ~~~~~~
1541  AGCCTCGAGC CCAGATACGA CGCAGTATTT CCGGGTCACT CATGCCAACG ACGGCATCCC AAACCTGCCC
      TCGGAGCTCG GGTCTATGCT GCGTCATAAA GGCCCAGTGA GTACGGTTGC TGCCGTAGGG TTTGGACGGG

                                NcoI
                               ~~~~~~
1611  CCGGTGGAGC AGGGGTACGC CCATGGCGGT GTAGAGTACT GGAGCGTTGA TCCTTACAGC GCCCAGAACA
      GGCCACCTCG TCCCCATGCG GGTACCGCCA CATCTCATGA CCTCGCAACT AGGAATGTCG CGGGTCTTGT

1681  CATTTGTCTG CACTGGGGAT GAAGTGCAGT GCTGTGAGGC CCAGGGCGGA CAGGGTGTGA ATAATGCGCA
      GTAAACAGAC GTGACCCCTA CTTCACGTCA CGACACTCCG GGTCCCGCCT GTCCCACACT TATTACGCGT

                                         SphI                 NotI
                                        ~~~~~~~~            ~~~~~~~~~~
1751  CACGACTTAT TTTGGGATGA CGAGCGGCGC ATGCACCTGG CCGGTCGCGG CCGCGGAAAC CACTGAAGGA
      GTGCTGAATA AAACCCTACT GCTCGCCGCG TACGTGGACC GGCCAGCGCC GGCGCCTTTG GTGACTTCCT

1821  TGAGCTGTAA AGAAGCAGAT CGTTCAAACA TTTGGCAATA AAGTTTCTTA AGATTGAATC CTGTTGCCGG
      ACTCGACATT TCTTCGTCTA GCAAGTTTGT AAACCGTTAT TTCAAAGAAT TCTAACTTAG GACAACGGCC

1891  TCTTGCGATG ATTATCATAT AATTTCTGTT GAATTACGTT AAGCATGTAA TAATTAACAT GTAATGCATG
      AGAACGCTAC TAATAGTATA TTAAAGACAA CTTAATGCAA TTCGTACATT ATTAATTGTA CATTACGTAC

1961  ACGTTATTTA TGAGATGGGT TTTTATGATT AGAGTCCCGC AATTATACAT TTAATACGCG ATAGAAAACA
      TGCAATAAAT ACTCTACCCA AAAATACTAA TCTCAGGGCG TTAATATGTA AATTATGCGC TATCTTTTGT
```

FIG._44D

```
                                                                          XbaI
                                                                            ~~
           BssHII                   BssHII                      ClaI  HindIII
            ~~~~~~~                  ~~~~~~                    ~~~~~~~~~~~~~~
2031 AAATATAGCG CGCAAACTAG GATAAATTAT CGCGCGCGGT GTCATCTATG TTACTAGATC GATAAGCTTC
     TTTATATCGC GCGTTTGATC CTATTTAATA GCGCGCGCCA CAGTAGATAC AATGATCTAG CTATTCGAAG

     XbaI                                                BssHII
     ~~~~                                                 ~~~~~~~
2101 TAGAGCGGCC GGTGGAGCTC CAATTCGCCC TATAGTGAGT CGTATTACGC GCGCTCACTG GCCGTCGTTT
     ATCTCGCCGG CCACCTCGAG GTTAAGCGGG ATATCACTCA GCATAATGCG CGCGAGTGAC CGGCAGCAAA

2171 TACAACGTCG TGACTGGGAA AACCCTGGCG TTACCCAACT TAATCGCCTT GCAGCACATC CCCCTTTCGC
     ATGTTGCAGC ACTGACCCTT TTGGGACCGC AATGGGTTGA ATTAGCGGAA CGTCGTGTAG GGGGAAAGCG

2241 CAGCTGGCGT AATAGCGAAG AGGCCCGCAC CGATCGCCCT TCCCAACAGT TGCGCAGCCT GAATGGCGAA
     GTCGACCGCA TTATCGCTTC TCCGGGCGTG GCTAGCGGGA AGGGTTGTCA ACGCGTCGGA CTTACCGCTT

2311 TGGGACGCGC CCTGTAGCGG CGCATTAAGC GCGGCGGGTG TGGTGGTTAC GCGCAGCGTG ACCGCTACAC
     ACCCTGCGCG GGACATCGCC GCGTAATTCG CGCCGCCCAC ACCACCAATG CGCGTCGCAC TGGCGATGTG

2381 TTGCCAGCGC CCTAGCGCCC GCTCCTTTCG CTTTCTTCCC TTCCTTTCTC GCCACGTTCG CCGGCTTTCC
     AACGGTCGCG GGATCGCGGG CGAGGAAAGC GAAAGAAGGG AAGGAAAGAG CGGTGCAAGC GGCCGAAAGG

2451 CCGTCAAGCT CTAAATCGGG GGCTCCCTTT AGGGTTCCGA TTTAGTGCTT TACGGCACCT CGACCCCAAA
     GGCAGTTCGA GATTTAGCCC CCGAGGGAAA TCCCAAGGCT AAATCACGAA ATGCCGTGGA GCTGGGGTTT

2521 AAACTTGATT AGGGTGATGG TTCACGTAGT GGGCCATCGC CCTGATAGAC GGTTTTTCGC CCTTTGACGT
     TTTGAACTAA TCCCACTACC AAGTGCATCA CCCGGTAGCG GGACTATCTG CCAAAAAGCG GGAAACTGCA

2591 TGGAGTCCAC GTTCTTTAAT AGTGGACTCT TGTTCCAAAC TGGAACAACA CTCAACCCTA TCTCGGTCTA
     ACCTCAGGTG CAAGAAATTA TCACCTGAGA ACAAGGTTTG ACCTTGTTGT GAGTTGGGAT AGAGCCAGAT

2661 TTCTTTTGAT TTATAAGGGA TTTTGCCGAT TTCGGCCTAT TGGTTAAAAA ATGAGCTGAT TTAACAAAAA
     AAGAAAACTA AATATTCCCT AAAACGGCTA AAGCCGGATA ACCAATTTTT TACTCGACTA AATTGTTTTT
```

FIG._44E

```
2731 TTTAACGCGA ATTTTAACAA AATATTAACG CTTACAATTT AGGTGGCACT TTTCGGGGAA ATGTGCGCGG
     AAATTGCGCT TAAAATTGTT TTATAATTGC GAATGTTAAA TCCACCGTGA AAAGCCCCTT TACACGCGCC

2801 AACCCCTATT TGTTTATTTT TCTAAATACA TTCAAATATG TATCCGCTCA TGAGACAATA ACCCTGATAA
     TTGGGGATAA ACAAATAAAA AGATTTATGT AAGTTTATAC ATAGGCGAGT ACTCTGTTAT TGGGACTATT

2871 ATGCTTCAAT AATATTGAAA AAGGAAGAGT ATGAGTATTC AACATTTCCG TGTCGCCCTT ATTCCCTTTT
     TACGAAGTTA TTATAACTTT TTCCTTCTCA TACTCATAAG TTGTAAAGGC ACAGCGGGAA TAAGGGAAAA

2941 TTGCGGCATT TTGCCTTCCT GTTTTTGCTC ACCCAGAAAC GCTGGTGAAA GTAAAAGATG CTGAAGATCA
     AACGCCGTAA AACGGAAGGA CAAAAACGAG TGGGTCTTTG CGACCACTTT CATTTTCTAC GACTTCTAGT

3011 GTTGGGTGCA CGAGTGGGTT ACATCGAACT GGATCTCAAC AGCGGTAAGA TCCTTGAGAG TTTTCGCCCC
     CAACCCACGT GCTCACCCAA TGTAGCTTGA CCTAGAGTTG TCGCCATTCT AGGAACTCTC AAAAGCGGGG

3081 GAAGAACGTT TTCCAATGAT GAGCACTTTT AAAGTTCTGC TATGTGGCGC GGTATTATCC CGTATTGACG
     CTTCTTGCAA AAGGTTACTA CTCGTGAAAA TTTCAAGACG ATACACCGCG CCATAATAGG GCATAACTGC

3151 CCGGGCAAGA GCAACTCGGT CGCCGCATAC ACTATTCTCA GAATGACTTG GTTGAGTACT CACCAGTCAC
     GGCCCGTTCT CGTTGAGCCA GCGGCGTATG TGATAAGAGT CTTACTGAAC CAACTCATGA GTGGTCAGTG

3221 AGAAAAGCAT CTTACGGATG GCATGACAGT AAGAGAATTA TGCAGTGCTG CCATAACCAT GAGTGATAAC
     TCTTTTCGTA GAATGCCTAC CGTACTGTCA TTCTCTTAAT ACGTCACGAC GGTATTGGTA CTCACTATTG

3291 ACTGCGGCCA ACTTACTTCT GACAACGATC GGAGGACCGA AGGAGCTAAC CGCTTTTTTG CACAACATGG
     TGACGCCGGT TGAATGAAGA CTGTTGCTAG CCTCCTGGCT TCCTCGATTG GCGAAAAAAC GTGTTGTACC

3361 GGGATCATGT AACTCGCCTT GATCGTTGGG AACCGGAGCT GAATGAAGCC ATACCAAACG ACGAGCGTGA
     CCCTAGTACA TTGAGCGGAA CTAGCAACCC TTGGCCTCGA CTTACTTCGG TATGGTTTGC TGCTCGCACT

3431 CACCACGATG CCTGTAGCAA TGGCAACAAC GTTGCGCAAA CTATTAACTG GCGAACTACT TACTCTAGCT
     GTGGTGCTAC GGACATCGTT ACCGTTGTTG CAACGCGTTT GATAATTGAC CGCTTGATGA ATGAGATCGA

3501 TCCCGGCAAC AATTAATAGA CTGGATGGAG GCGGATAAAG TTGCAGGACC ACTTCTGCGC TCGGCCCTTC
     AGGGCCGTTG TTAATTATCT GACCTACCTC CGCCTATTTC AACGTCCTGG TGAAGACGCG AGCCGGGAAG
```

FIG._44F

```
3571  CGGCTGGCTG GTTTATTGCT GATAAATCTG GAGCCGGTGA GCGTGGGTCT CGCGGTATCA TTGCAGCACT
      GCCGACCGAC CAAATAACGA CTATTTAGAC CTCGGCCACT CGCACCCAGA GCGCCATAGT AACGTCGTGA

3641  GGGGCCAGAT GGTAAGCCCT CCCGTATCGT AGTTATCTAC ACGACGGGGA GTCAGGCAAC TATGGATGAA
      CCCCGGTCTA CCATTCGGGA GGGCATAGCA TCAATAGATG TGCTGCCCCT CAGTCCGTTG ATACCTACTT

3711  CGAAATAGAC AGATCGCTGA GATAGGTGCC TCACTGATTA AGCATTGGTA ACTGTCAGAC CAAGTTTACT
      GCTTTATCTG TCTAGCGACT CTATCCACGG AGTGACTAAT TCGTAACCAT TGACAGTCTG GTTCAAATGA

3781  CATATATACT TTAGATTGAT TTAAAACTTC ATTTTTAATT TAAAAGGATC TAGGTGAAGA TCCTTTTTGA
      GTATATATGA AATCTAACTA AATTTTGAAG TAAAAATTAA ATTTTCCTAG ATCCACTTCT AGGAAAAACT

3851  TAATCTCATG ACCAAAATCC CTTAACGTGA GTTTTCGTTC CACTGAGCGT CAGACCCCGT AGAAAAGATC
      ATTAGAGTAC TGGTTTTAGG GAATTGCACT CAAAAGCAAG GTGACTCGCA GTCTGGGGCA TCTTTTCTAG

3921  AAAGGATCTT CTTGAGATCC TTTTTTTCTG CGCGTAATCT GCTGCTTGCA AACAAAAAAA CCACCGCTAC
      TTTCCTAGAA GAACTCTAGG AAAAAAAGAC GCGCATTAGA CGACGAACGT TTGTTTTTTT GGTGGCGATG

3991  CAGCGGTGGT TTGTTTGCCG GATCAAGAGC TACCAACTCT TTTTCCGAAG GTAACTGGCT TCAGCAGAGC
      GTCGCCACCA AACAAACGGC CTAGTTCTCG ATGGTTGAGA AAAAGGCTTC CATTGACCGA AGTCGTCTCG

4061  GCAGATACCA AATACTGTCC TTCTAGTGTA GCCGTAGTTA GGCCACCACT TCAAGAACTC TGTAGCACCG
      CGTCTATGGT TTATGACAGG AAGATCACAT CGGCATCAAT CCGGTGGTGA AGTTCTTGAG ACATCGTGGC

4131  CCTACATACC TCGCTCTGCT AATCCTGTTA CCAGTGGCTG CTGCCAGTGG CGATAAGTCG TGTCTTACCG
      GGATGTATGG AGCGAGACGA TTAGGACAAT GGTCACCGAC GACGGTCACC GCTATTCAGC ACAGAATGGC

4201  GGTTGGACTC AAGACGATAG TTACCGGATA AGGCGCAGCG GTCGGGCTGA ACGGGGGGTT CGTGCACACA
      CCAACCTGAG TTCTGCTATC AATGGCCTAT TCCGCGTCGC CAGCCCGACT TGCCCCCCAA GCACGTGTGT

4271  GCCCAGCTTG GAGCGAACGA CCTACACCGA ACTGAGATAC CTACAGCGTG AGCTATGAGA AAGCGCCACG
      CGGGTCGAAC CTCGCTTGCT GGATGTGGCT TGACTCTATG GATGTCGCAC TCGATACTCT TTCGCGGTGC

4341  CTTCCCGAAG GGAGAAAGGC GGACAGGTAT CCGGTAAGCG GCAGGGTCGG AACAGGAGAG CGCACGAGGG
      GAAGGGCTTC CCTCTTTCCG CCTGTCCATA GGCCATTCGC CGTCCCAGCC TTGTCCTCTC GCGTGCTCCC
```

FIG._44G

```
4411  AGCTTCCAGG GGGAAACGCC TGGTATCTTT ATAGTCCTGT CGGGTTTCGC CACCTCTGAC TTGAGCGTCG
      TCGAAGGTCC CCCTTTGCGG ACCATAGAAA TATCAGGACA GCCCAAAGCG GTGGAGACTG AACTCGCAGC

4481  ATTTTTGTGA TGCTCGTCAG GGGGGCGGAG CCTATGGAAA AACGCCAGCA ACGCGGCCTT TTTACGGTTC
      TAAAAACACT ACGAGCAGTC CCCCCGCCTC GGATACCTTT TTGCGGTCGT TGCGCCGGAA AAATGCCAAG

4551  CTGGCCTTTT GCTGGCCTTT TGCTCACATG TTCTTTCCTG CGTTATCCCC TGATTCTGTG GATAACCGTA
      GACCGGAAAA CGACCGGAAA ACGAGTGTAC AAGAAAGGAC GCAATAGGGG ACTAAGACAC CTATTGGCAT

4621  TTACCGCCTT TGAGTGAGCT GATACCGCTC GCCGCAGCCG AACGACCGAG CGCAGCGAGT CAGTGAGCGA
      AATGGCGGAA ACTCACTCGA CTATGGCGAG CGGCGTCGGC TTGCTGGCTC GCGTCGCTCA GTCACTCGCT

4691  GGAAGCGGAA GAGCGCCCAA TACGCAAACC GCCTCTCCCC GCGCGTTGGC CGATTCATTA ATGCAGCTGG
      CCTTCGCCTT CTCGCGGGTT ATGCGTTTGG CGGAGAGGGG CGCGCAACCG GCTAAGTAAT TACGTCGACC

4761  CACGACAGGT TTCCCGACTG GAAAGCGGGC AGTGAGCGCA ACGCAATTAA TGTGAGTTAG CTCACTCATT
      GTGCTGTCCA AAGGGCTGAC CTTTCGCCCG TCACTCGCGT TGCGTTAATT ACACTCAATC GAGTGAGTAA

4831  AGGCACCCCA GGCTTTACAC TTTATGCTTC CGGCTCGTAT GTTGTGTGGA ATTGTGAGCG GATAACAATT
      TCCGTGGGGT CCGAAATGTG AAATACGAAG GCCGAGCATA CAACACACCT TAACACTCGC CTATTGTTAA

                                         BssHII
                                         ~~~~~~~~
4901  TCACACAGGA AACAGCTATG ACCATGATTA CGCCAAGCGC GCAATTAACC CTCACTAAAG GGAACAAAAG
      AGTGTGTCCT TTGTCGATAC TGGTACTAAT GCGGTTCGCG CGTTAATTGG GAGTGATTTC CCTTGTTTTC

      EcoR

4971  CTGG
      GACC
```

FIG._44H

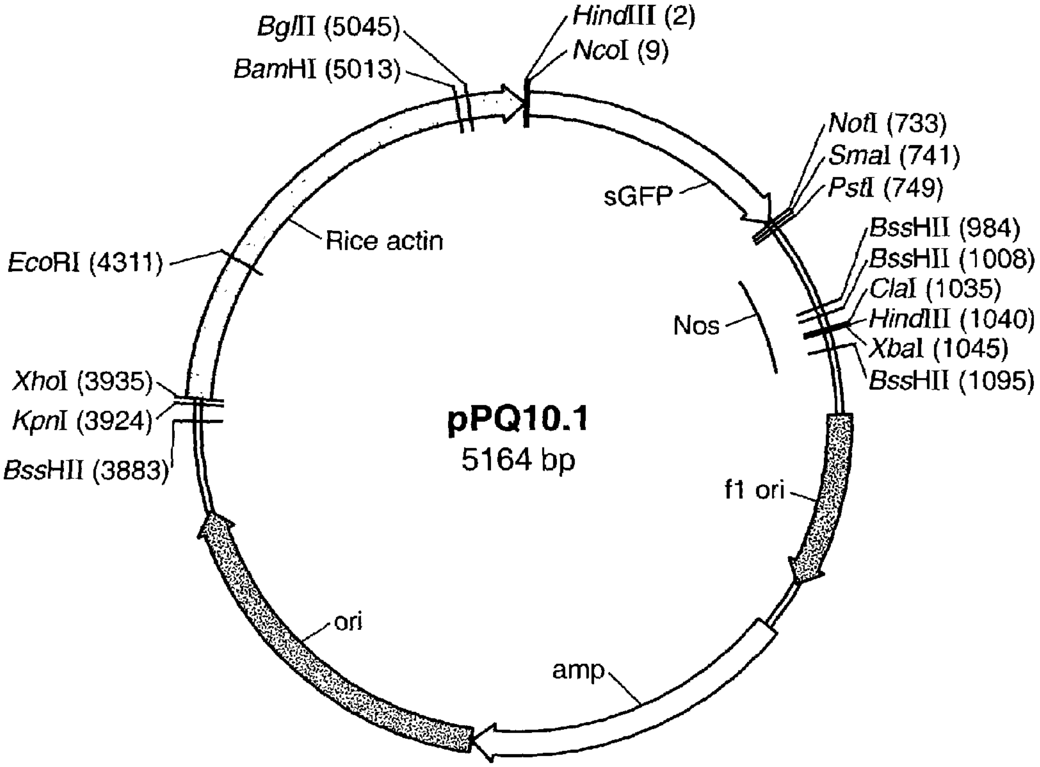
FIG._45A

```
     HindIII NcoI
     ~~~~~~ ~~~~~~~
  1  AAGCTTACCA TGGTGAGCAA GGGCGAGGAG CTGTTCACCG GGGTGGTGCC CATCCTGGTC GAGCTGGACG
     TTCGAATGGT ACCACTCGTT CCCGCTCCTC GACAAGTGGC CCCACCACGG GTAGGACCAG CTCGACCTGC

 71  GCGACGTGAA CGGCCACAAG TTCAGCGTGT CCGGCGAGGG CGAGGGCGAT GCCACCTACG GCAAGCTGAC
     CGCTGCACTT GCCGGTGTTC AAGTCGCACA GGCCGCTCCC GCTCCCGCTA CGGTGGATGC CGTTCGACTG

141  CCTGAAGTTC ATCTGCACCA CCGGCAAGCT GCCCGTGCCC TGGCCCACCC TCGTGACCAC CTTCACCTAC
     GGACTTCAAG TAGACGTGGT GGCCGTTCGA CGGGCACGGG ACCGGGTGGG AGCACTGGTG GAAGTGGATG

211  GGCGTGCAGT GCTTCAGCCG CTACCCCGAC CACATGAAGC AGCACGACTT CTTCAAGTCC GCCATGCCCG
     CCGCACGTCA CGAAGTCGGC GATGGGGCTG GTGTACTTCG TCGTGCTGAA GAAGTTCAGG CGGTACGGGC

281  AAGGCTACGT CCAGGAGCGC ACCATCTTCT TCAAGGACGA CGGCAACTAC AAGACCCGCG CCGAGGTGAA
     TTCCGATGCA GGTCCTCGCG TGGTAGAAGA AGTTCCTGCT GCCGTTGATG TTCTGGGCGC GGCTCCACTT

351  GTTCGAGGGC GACACCCTGG TGAACCGCAT CGAGCTGAAG GGCATCGACT TCAAGGAGGA CGGCAACATC
     CAAGCTCCCG CTGTGGGACC ACTTGGCGTA GCTCGACTTC CCGTAGCTGA AGTTCCTCCT GCCGTTGTAG

421  CTGGGGCACA AGCTGGAGTA CAACTACAAC AGCCACAACG TCTATATCAT GGCCGACAAG CAGAAGAACG
     GACCCCGTGT TCGACCTCAT GTTGATGTTG TCGGTGTTGC AGATATAGTA CCGGCTGTTC GTCTTCTTGC

491  GCATCAAGGT GAACTTCAAG ATCCGCCACA ACATCGAGGA CGGCAGCGTG CAGCTCGCCG ACCACTACCA
     CGTAGTTCCA CTTGAAGTTC TAGGCGGTGT TGTAGCTCCT GCCGTCGCAC GTCGAGCGGC TGGTGATGGT

561  GCAGAACACC CCCATCGGCG ACGGCCCCGT GCTGCTGCCC GACAACCACT ACCTGAGCAC CCAGTCCGCC
     CGTCTTGTGG GGGTAGCCGC TGCCGGGGCA CGACGACGGG CTGTTGGTGA TGGACTCGTG GGTCAGGCGG

631  CTGAGCAAAG ACCCCAACGA GAAGCGCGAT CACATGGTCC TGCTGGAGTT CGTGACCGCC GCCGGGATCA
     GACTCGTTTC TGGGGTTGCT CTTCGCGCTA GTGTACCAGG ACGACCTCAA GCACTGGCGG CGGCCCTAGT
```

FIG._45B

```
                                                      SmaI
                                                    ~~~~~~~~
                                               NotI         PstI
                                             ~~~~~~~~~    ~~~~~~~
701   CTCACGGCAT GGACGAGCTG TACAAGTAAA GCGGCCGCCC GGGCTGCAGG GAAACCACTG AAGGATGAGC
      GAGTGCCGTA CCTGCTCGAC ATGTTCATTT CGCCGGCGGG CCCGACGTCC CTTTGGTGAC TTCCTACTCG

771   TGTAAAGAAG CAGATCGTTC AAACATTTGG CAATAAAGTT TCTTAAGATT GAATCCTGTT GCCGGTCTTG
      ACATTTCTTC GTCTAGCAAG TTTGTAAACC GTTATTTCAA AGAATTCTAA CTTAGGACAA CGGCCAGAAC

841   CGATGATTAT CATATAATTT CTGTTGAATT ACGTTAAGCA TGTAATAATT AACATGTAAT GCATGACGTT
      GCTACTAATA GTATATTAAA GACAACTTAA TGCAATTCGT ACATTATTAA TTGTACATTA CGTACTGCAA

911   ATTTATGAGA TGGGTTTTTA TGATTAGAGT CCCGCAATTA TACATTTAAT ACGCGATAGA AAACAAAATA
      TAAATACTCT ACCCAAAAAT ACTAATCTCA GGGCGTTAAT ATGTAAATTA TGCGCTATCT TTTGTTTTAT

                                                                             XbaI
                                                                            ~~~~~~
        BssHII                   BssHII                         ClaI HindIII
        ~~~~~~                   ~~~~~~~                      ~~~~~~~~~~~~~~
981   TAGCGCGCAA ACTAGGATAA ATTATCGCGC GCGGTGTCAT CTATGTTACT AGATCGATAA GCTTCTAGAG
      ATCGCGCGTT TGATCCTATT TAATAGCGCG CGCCACAGTA GATACAATGA TCTAGCTATT CGAAGATCTC

                                                  BssHII
                                                  ~~~~~~
1051  CGGCCGGTGG AGCTCCAATT CGCCCTATAG TGAGTCGTAT TACGCGCGCT CACTGGCCGT CGTTTTACAA
      GCCGGCCACC TCGAGGTTAA GCGGGATATC ACTCAGCATA ATGCGCGCGA GTGACCGGCA GCAAAATGTT

1121  CGTCGTGACT GGGAAAACCC TGGCGTTACC CAACTTAATC GCCTTGCAGC ACATCCCCCT TTCGCCAGCT
      GCAGCACTGA CCCTTTTGGG ACCGCAATGG GTTGAATTAG CGGAACGTCG TGTAGGGGGA AAGCGGTCGA

1191  GGCGTAATAG CGAAGAGGCC CGCACCGATC GCCCTTCCCA ACAGTTGCGC AGCCTGAATG GCGAATGGGA
      CCGCATTATC GCTTCTCCGG GCGTGGCTAG CGGGAAGGGT TGTCAACGCG TCGGACTTAC CGCTTACCCT
```

FIG._45C

```
1261 CGCGCCCTGT AGCGGCGCAT TAAGCGCGGC GGGTGTGGTG GTTACGCGCA GCGTGACCGC TACACTTGCC
     GCGCGGGACA TCGCCGCGTA ATTCGCGCCG CCCACACCAC CAATGCGCGT CGCACTGGCG ATGTGAACGG

1331 AGCGCCCTAG CGCCCGCTCC TTTCGCTTTC TTCCCTTCCT TTCTCGCCAC GTTCGCCGGC TTTCCCCGTC
     TCGCGGGATC GCGGGCGAGG AAAGCGAAAG AAGGGAAGGA AAGAGCGGTG CAAGCGGCCG AAAGGGGCAG

1401 AAGCTCTAAA TCGGGGGCTC CCTTTAGGGT TCCGATTTAG TGCTTTACGG CACCTCGACC CCAAAAAACT
     TTCGAGATTT AGCCCCCGAG GGAAATCCCA AGGCTAAATC ACGAAATGCC GTGGAGCTGG GGTTTTTTGA

1471 TGATTAGGGT GATGGTTCAC GTAGTGGGCC ATCGCCCTGA TAGACGGTTT TTCGCCCTTT GACGTTGGAG
     ACTAATCCCA CTACCAAGTG CATCACCCGG TAGCGGGACT ATCTGCCAAA AAGCGGGAAA CTGCAACCTC

1541 TCCACGTTCT TTAATAGTGG ACTCTTGTTC CAAACTGGAA CAACACTCAA CCCTATCTCG GTCTATTCTT
     AGGTGCAAGA AATTATCACC TGAGAACAAG GTTTGACCTT GTTGTGAGTT GGGATAGAGC CAGATAAGAA

1611 TTGATTTATA AGGGATTTTG CCGATTTCGG CCTATTGGTT AAAAAATGAG CTGATTTAAC AAAAATTTAA
     AACTAAATAT TCCCTAAAAC GGCTAAAGCC GGATAACCAA TTTTTTACTC GACTAAATTG TTTTTAAATT

1681 CGCGAATTTT AACAAAATAT TAACGCTTAC AATTTAGGTG GCACTTTTCG GGGAAATGTG CGCGGAACCC
     GCGCTTAAAA TTGTTTTATA ATTGCGAATG TTAAATCCAC CGTGAAAAGC CCCTTTACAC GCGCCTTGGG

1751 CTATTTGTTT ATTTTTCTAA ATACATTCAA ATATGTATCC GCTCATGAGA CAATAACCCT GATAAATGCT
     GATAAACAAA TAAAAAGATT TATGTAAGTT TATACATAGG CGAGTACTCT GTTATTGGGA CTATTTACGA

1821 TCAATAATAT TGAAAAAGGA AGAGTATGAG TATTCAACAT TTCCGTGTCG CCCTTATTCC CTTTTTTGCG
     AGTTATTATA ACTTTTTCCT TCTCATACTC ATAAGTTGTA AAGGCACAGC GGGAATAAGG GAAAAAACGC

1891 GCATTTTGCC TTCCTGTTTT TGCTCACCCA GAAACGCTGG TGAAAGTAAA AGATGCTGAA GATCAGTTGG
     CGTAAAACGG AAGGACAAAA ACGAGTGGGT CTTTGCGACC ACTTTCATTT TCTACGACTT CTAGTCAACC

1961 GTGCACGAGT GGGTTACATC GAACTGGATC TCAACAGCGG TAAGATCCTT GAGAGTTTTC GCCCCGAAGA
     CACGTGCTCA CCCAATGTAG CTTGACCTAG AGTTGTCGCC ATTCTAGGAA CTCTCAAAAG CGGGGCTTCT

2031 ACGTTTTCCA ATGATGAGCA CTTTTAAAGT TCTGCTATGT GGCGCGGTAT TATCCCGTAT TGACGCCGGG
     TGCAAAAGGT TACTACTCGT GAAAATTTCA AGACGATACA CCGCGCCATA ATAGGGCATA ACTGCGGCCC
```

FIG._45D

```
2101  CAAGAGCAAC TCGGTCGCCG CATACACTAT TCTCAGAATG ACTTGGTTGA GTACTCACCA GTCACAGAAA
      GTTCTCGTTG AGCCAGCGGC GTATGTGATA AGAGTCTTAC TGAACCAACT CATGAGTGGT CAGTGTCTTT

2171  AGCATCTTAC GGATGGCATG ACAGTAAGAG AATTATGCAG TGCTGCCATA ACCATGAGTG ATAACACTGC
      TCGTAGAATG CCTACCGTAC TGTCATTCTC TTAATACGTC ACGACGGTAT TGGTACTCAC TATTGTGACG

2241  GGCCAACTTA CTTCTGACAA CGATCGGAGG ACCGAAGGAG CTAACCGCTT TTTTGCACAA CATGGGGGAT
      CCGGTTGAAT GAAGACTGTT GCTAGCCTCC TGGCTTCCTC GATTGGCGAA AAAACGTGTT GTACCCCCTA

2311  CATGTAACTC GCCTTGATCG TTGGGAACCG GAGCTGAATG AAGCCATACC AAACGACGAG CGTGACACCA
      GTACATTGAG CGGAACTAGC AACCCTTGGC CTCGACTTAC TTCGGTATGG TTTGCTGCTC GCACTGTGGT

2381  CGATGCCTGT AGCAATGGCA ACAACGTTGC GCAAACTATT AACTGGCGAA CTACTTACTC TAGCTTCCCG
      GCTACGGACA TCGTTACCGT TGTTGCAACG CGTTTGATAA TTGACCGCTT GATGAATGAG ATCGAAGGGC

2451  GCAACAATTA ATAGACTGGA TGGAGGCGGA TAAAGTTGCA GGACCACTTC TGCGCTCGGC CCTTCCGGCT
      CGTTGTTAAT TATCTGACCT ACCTCCGCCT ATTTCAACGT CCTGGTGAAG ACGCGAGCCG GGAAGGCCGA

2521  GGCTGGTTTA TTGCTGATAA ATCTGGAGCC GGTGAGCGTG GGTCTCGCGG TATCATTGCA GCACTGGGGC
      CCGACCAAAT AACGACTATT TAGACCTCGG CCACTCGCAC CCAGAGCGCC ATAGTAACGT CGTGACCCCG

2591  CAGATGGTAA GCCCTCCCGT ATCGTAGTTA TCTACACGAC GGGGAGTCAG GCAACTATGG ATGAACGAAA
      GTCTACCATT CGGGAGGGCA TAGCATCAAT AGATGTGCTG CCCCTCAGTC CGTTGATACC TACTTGCTTT

2661  TAGACAGATC GCTGAGATAG GTGCCTCACT GATTAAGCAT TGGTAACTGT CAGACCAAGT TTACTCATAT
      ATCTGTCTAG CGACTCTATC CACGGAGTGA CTAATTCGTA ACCATTGACA GTCTGGTTCA AATGAGTATA

2731  ATACTTTAGA TTGATTTAAA ACTTCATTTT TAATTTAAAA GGATCTAGGT GAAGATCCTT TTTGATAATC
      TATGAAATCT AACTAAATTT TGAAGTAAAA ATTAAATTTT CCTAGATCCA CTTCTAGGAA AAACTATTAG

2801  TCATGACCAA AATCCCTTAA CGTGAGTTTT CGTTCCACTG AGCGTCAGAC CCCGTAGAAA AGATCAAAGG
      AGTACTGGTT TTAGGGAATT GCACTCAAAA GCAAGGTGAC TCGCAGTCTG GGGCATCTTT TCTAGTTTCC

2871  ATCTTCTTGA GATCCTTTTT TTCTGCGCGT AATCTGCTGC TTGCAAACAA AAAAACCACC GCTACCAGCG
      TAGAAGAACT CTAGGAAAAA AAGACGCGCA TTAGACGACG AACGTTTGTT TTTTTGGTGG CGATGGTCGC
```

FIG._45E

```
2941  GTGGTTTGTT TGCCGGATCA AGAGCTACCA ACTCTTTTTC CGAAGGTAAC TGGCTTCAGC AGAGCGCAGA
      CACCAAACAA ACGGCCTAGT TCTCGATGGT TGAGAAAAAG GCTTCCATTG ACCGAAGTCG TCTCGCGTCT

3011  TACCAAATAC TGTCCTTCTA GTGTAGCCGT AGTTAGGCCA CCACTTCAAG AACTCTGTAG CACCGCCTAC
      ATGGTTTATG ACAGGAAGAT CACATCGGCA TCAATCCGGT GGTGAAGTTC TTGAGACATC GTGGCGGATG

3081  ATACCTCGCT CTGCTAATCC TGTTACCAGT GGCTGCTGCC AGTGGCGATA AGTCGTGTCT TACCGGGTTG
      TATGGAGCGA GACGATTAGG ACAATGGTCA CCGACGACGG TCACCGCTAT TCAGCACAGA ATGGCCCAAC

3151  GACTCAAGAC GATAGTTACC GGATAAGGCG CAGCGGTCGG GCTGAACGGG GGGTTCGTGC ACACAGCCCA
      CTGAGTTCTG CTATCAATGG CCTATTCCGC GTCGCCAGCC CGACTTGCCC CCCAAGCACG TGTGTCGGGT

3221  GCTTGGAGCG AACGACCTAC ACCGAACTGA GATACCTACA GCGTGAGCTA TGAGAAAGCG CCACGCTTCC
      CGAACCTCGC TTGCTGGATG TGGCTTGACT CTATGGATGT CGCACTCGAT ACTCTTTCGC GGTGCGAAGG

3291  CGAAGGGAGA AAGGCGGACA GGTATCCGGT AAGCGGCAGG GTCGGAACAG GAGAGCGCAC GAGGGAGCTT
      GCTTCCCTCT TTCCGCCTGT CCATAGGCCA TTCGCCGTCC CAGCCTTGTC CTCTCGCGTG CTCCCTCGAA

3361  CCAGGGGGAA ACGCCTGGTA TCTTTATAGT CCTGTCGGGT TTCGCCACCT CTGACTTGAG CGTCGATTTT
      GGTCCCCCTT TGCGGACCAT AGAAATATCA GGACAGCCCA AAGCGGTGGA GACTGAACTC GCAGCTAAAA

3431  TGTGATGCTC GTCAGGGGGG CGGAGCCTAT GGAAAAACGC CAGCAACGCG GCCTTTTTAC GGTTCCTGGC
      ACACTACGAG CAGTCCCCCC GCCTCGGATA CCTTTTTGCG GTCGTTGCGC CGGAAAAATG CCAAGGACCG

3501  CTTTTGCTGG CCTTTTGCTC ACATGTTCTT TCCTGCGTTA TCCCCTGATT CTGTGGATAA CCGTATTACC
      GAAAACGACC GGAAAACGAG TGTACAAGAA AGGACGCAAT AGGGGACTAA GACACCTATT GGCATAATGG

3571  GCCTTTGAGT GAGCTGATAC CGCTCGCCGC AGCCGAACGA CCGAGCGCAG CGAGTCAGTG AGCGAGGAAG
      CGGAAACTCA CTCGACTATG GCGAGCGGCG TCGGCTTGCT GGCTCGCGTC GCTCAGTCAC TCGCTCCTTC

3641  CGGAAGAGCG CCCAATACGC AAACCGCCTC TCCCCGCGCG TTGGCCGATT CATTAATGCA GCTGGCACGA
      GCCTTCTCGC GGGTTATGCG TTTGGCGGAG AGGGGCGCGC AACCGGCTAA GTAATTACGT CGACCGTGCT

3711  CAGGTTTCCC GACTGGAAAG CGGGCAGTGA GCGCAACGCA ATTAATGTGA GTTAGCTCAC TCATTAGGCA
      GTCCAAAGGG CTGACCTTTC GCCCGTCACT CGCGTTGCGT TAATTACACT CAATCGAGTG AGTAATCCGT
```

FIG._45F

```
                                                    BssHII                              KpnI
                                                    ~~~~~~                                ~~
3781  CCCCAGGCTT TACACTTTAT GCTTCCGGCT CGTATGTTGT GTGGAATTGT GAGCGGATAA CAATTTCACA
      GGGGTCCGAA ATGTGAAATA CGAAGGCCGA GCATACAACA CACCTTAACA CTCGCCTATT GTTAAAGTGT

3851  CAGGAAACAG CTATGACCAT GATTACGCCA AGCGCGCAAT TAACCCTCAC TAAAGGGAAC AAAAGCTGGG
      GTCCTTTGTC GATACTGGTA CTAATGCGGT TCGCGCGTTA ATTGGGAGTG ATTTCCCTTG TTTTCGACCC

      KpnI          XhoI
      ~~~~        ~~~~~~~
3921  TACCGGGCCC CCCCTCGAGG TCATTCATAT GCTTGAGAAG AGAGTCGGGA TAGTCCAAAA TAAAACAAAG
      ATGGCCCGGG GGGGAGCTCC AGTAAGTATA CGAACTCTTC TCTCAGCCCT ATCAGGTTTT ATTTTGTTTC

3991  GTAAGATTAC CTGGTCAAAA GTGAAAACAT CAGTTAAAAG GTGGTATAAG TAAAATATCG GTAATAAAAG
      CATTCTAATG GACCAGTTTT CACTTTTGTA GTCAATTTTC CACCATATTC ATTTTATAGC CATTATTTTC

4061  GTGGCCCAAA GTGAAATTTA CTCTTTTCTA CTATTATAAA AATTGAGGAT GTTTTGTCGG TACTTTGATA
      CACCGGGTTT CACTTTAAAT GAGAAAAGAT GATAATATTT TTAACTCCTA CAAAACAGCC ATGAAACTAT

4131  CGTCATTTTT GTATGAATTG GTTTTTAAGT TTATTCGCGA TTTGGAAATG CATATCTGTA TTTGAGTCGG
      GCAGTAAAAA CATACTTAAC CAAAAATTCA AATAAGCGCT AAACCTTTAC GTATAGACAT AAACTCAGCC

4201  TTTTTAAGTT CGTTGCTTTT GTAAATACAG AGGGATTTGT ATAAGAAATA TCTTTAAAAA ACCCATATGC
      AAAAATTCAA GCAACGAAAA CATTTATGTC TCCCTAAACA TATTCTTTAT AGAAATTTTT TGGGTATACG

                                                       EcoRI
                                                     ~~~~~~~
4271  TAATTTGACA TAATTTTTGA GAAAAATATA TATTCAGGCG AATTCCACAA TGAACAATAA TAAGATTAAA
      ATTAAACTGT ATTAAAAACT CTTTTTATAT ATAAGTCCGC TTAAGGTGTT ACTTGTTATT ATTCTAATTT

4341  ATAGCTTGCC CCCGTTGCAG CGATGGGTAT TTTTTCTAGT AAAATAAAAG ATAAACTTAG ACTCAAAACA
      TATCGAACGG GGGCAACGTC GCTACCCATA AAAAAGATCA TTTTATTTTC TATTTGAATC TGAGTTTTGT

4411  TTTACAAAAA CAACCCCTAA AGTCCTAAAG CCCAAAGTGC TATGCACGAT CCATAGCAAG CCCAGCCCAA
      AAATGTTTTT GTTGGGGATT TCAGGATTTC GGGTTTCACG ATACGTGCTA GGTATCGTTC GGGTCGGGTT
```

FIG._45G

```
4481  CCCAACCCAA CCCAACCCAC CCCAGTGCAG CCAACTGGCA AATAGTCTCC ACCCCCGGCA CTATCACCGT
      GGGTTGGGTT GGGTTGGGTG GGGTCACGTC GGTTGACCGT TTATCAGAGG TGGGGGCCGT GATAGTGGCA

4551  GAGTTGTCCG CACCACCGCA CGTCTCGCAG CCAAAAAAAA AAAAAGAAAG AAAAAAAAGA AAAAGAAAAA
      CTCAACAGGC GTGGTGGCGT GCAGAGCGTC GGTTTTTTTT TTTTTCTTTC TTTTTTTTCT TTTTCTTTTT

4621  CAGCAGGTGG GTCCGGGTCG TGGGGGCCGG AAAAGCGAGG AGGATCGCGA GCAGCGACGA GGCCCGGCCC
      GTCGTCCACC CAGGCCCAGC ACCCCCGGCC TTTTCGCTCC TCCTAGCGCT CGTCGCTGCT CCGGGCCGGG

4691  TCCCTCCGCT TCCAAAGAAA CGCCCCCCAT CGCCACTATA TACATACCCC CCCCTCTCCT CCCATCCCCC
      AGGGAGGCGA AGGTTTCTTT GCGGGGGGTA GCGGTGATAT ATGTATGGGG GGGGAGAGGA GGGTAGGGGG

4761  CAACCCTACC ACCACCACCA CCACCACCTC CTCCCCCCTC GCTGCCGGAC GACGAGCTCC TCCCCCCTCC
      GTTGGGATGG TGGTGGTGGT GGTGGTGGAG GAGGGGGGAG CGACGGCCTG CTGCTCGAGG AGGGGGGAGG

4831  CCCTCCGCCG CCGCCGGTAA CCACCCCGCC CCTCTCCTCT TTCTTTCTCC GTTTTTTTTT TCGTCTCGGT
      GGGAGGCGGC GGCGGCCATT GGTGGGGCGG GGAGAGGAGA AAGAAAGAGG CAAAAAAAAA AGCAGAGCCA

4901  CTCGATCTTT GGCCTTGGTA GTTTGGGTGG GCGAGAGCGG CTTCGTCGCC CAGATCGGTG CGCGGGAGGG
      GAGCTAGAAA CCGGAACCAT CAAACCCACC CGCTCTCGCC GAAGCAGCGG GTCTAGCCAC GCGCCCTCCC

                                                BamHI
                                               ~~~~~~
4971  GCGGGATCTC GCGGCTGGCG TCTCCGGGCG TGAGTCGGCC CGGATCCTCG CGGGGAATGG GGCTCTCGGA
      CGCCCTAGAG CGCCGACCGC AGAGGCCCGC ACTCAGCCGG GCCTAGGAGC GCCCCTTACC CCGAGAGCCT

         BglII
        ~~~~~~
5041  TGTAGATCTT CTTTCTTTCT TCTTTTTGTG GTAGAATTTG AATCCCTCAG CATTGTTCAT CGGTAGTTTT
      ACATCTAGAA GAAAGAAAGA AGAAAAACAC CATCTTAAAC TTAGGGAGTC GTAACAAGTA GCCATCAAAA

5111  TCTTTTCATG ATTTGTGACA AATGCAGCCT CGTGCGGAGC TTTTTTGTAG GTAG
      AGAAAAGTAC TAAACACTGT TTACGTCGGA GCACGCCTCG AAAAAACATC CATC
```

FIG._45H

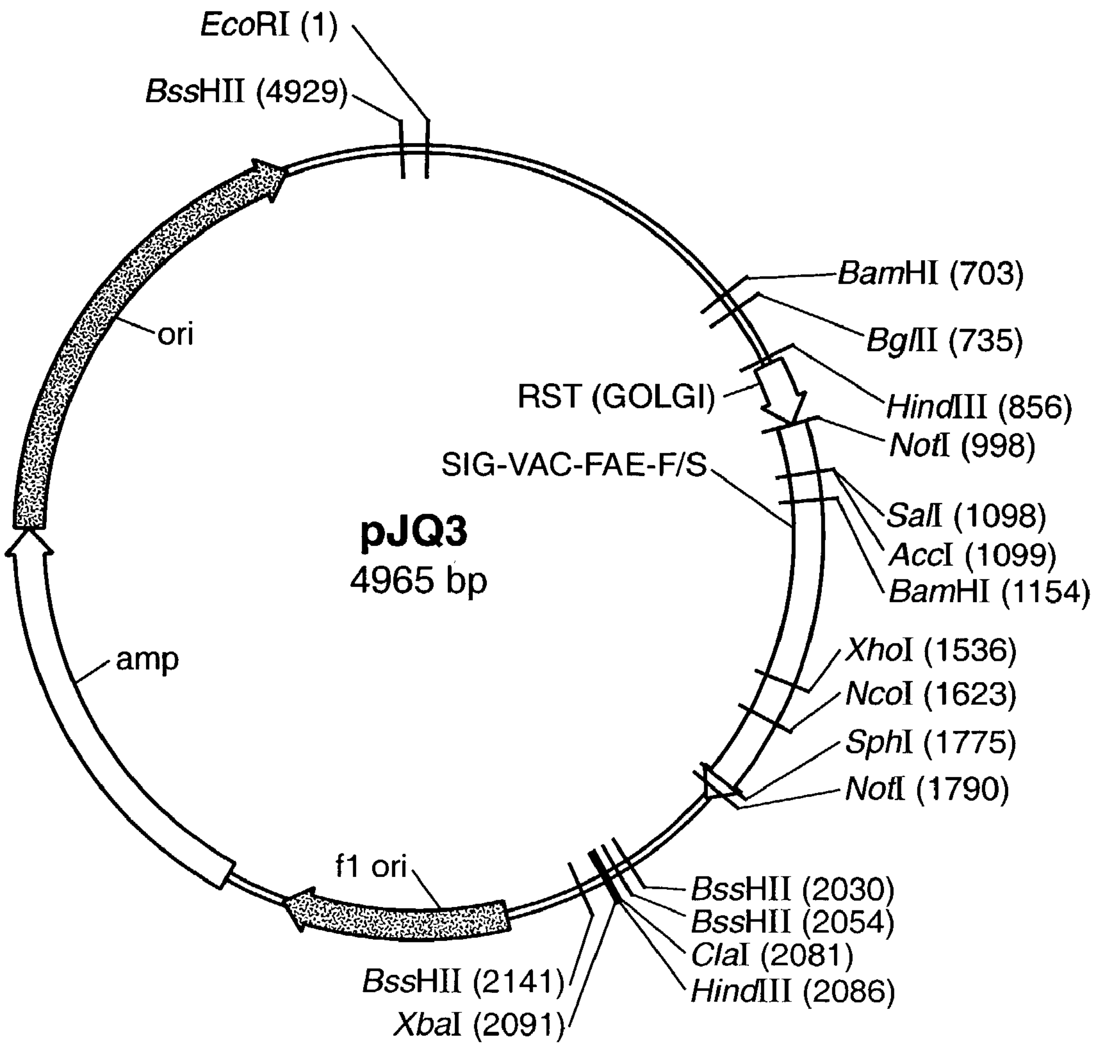
FIG._46A

```
       EcoRI
       ~~~~~
  1    AATTCCACAA TGAACAATAA TAAGATTAAA ATAGCTTGCC CCCGTTGCAG CGATGGGTAT TTTTTCTAGT
       TTAAGGTGTT ACTTGTTATT ATTCTAATTT TATCGAACGG GGGCAACGTC GCTACCCATA AAAAAGATCA

 71    AAAATAAAAG ATAAACTTAG ACTCAAAACA TTTACAAAAA CAACCCCTAA AGTCCTAAAG CCCAAAGTGC
       TTTTATTTTC TATTTGAATC TGAGTTTTGT AAATGTTTTT GTTGGGGATT TCAGGATTTC GGGTTTCACG

141    TATGCACGAT CCATAGCAAG CCCAGCCCAA CCCAACCCAA CCCAACCCAC CCCAGTGCAG CCAACTGGCA
       ATACGTGCTA GGTATCGTTC GGGTCGGGTT GGGTTGGGTT GGGTTGGGTG GGGTCACGTC GGTTGACCGT

211    AATAGTCTCC ACCCCCGGCA CTATCACCGT GAGTTGTCCG CACCACCGCA CGTCTCGCAG CCAAAAAAAA
       TTATCAGAGG TGGGGGCCGT GATAGTGGCA CTCAACAGGC GTGGTGGCGT GCAGAGCGTC GGTTTTTTTT

281    AAAAAGAAAG AAAAAAAAGA AAAAGAAAAA CAGCAGGTGG GTCCGGGTCG TGGGGGCCGG AAAAGCGAGG
       TTTTTCTTTC TTTTTTTTCT TTTTCTTTTT GTCGTCCACC CAGGCCCAGC ACCCCCGGCC TTTTCGCTCC

351    AGGATCGCGA GCAGCGACGA GGCCCGGCCC TCCCTCCGCT TCCAAAGAAA CGCCCCCCAT CGCCACTATA
       TCCTAGCGCT CGTCGCTGCT CCGGGCCGGG AGGGAGGCGA AGGTTTCTTT GCGGGGGGTA GCGGTGATAT

421    TACATACCCC CCCCTCTCCT CCCATCCCCC CAACCCTACC ACCACCACCA CCACCACCTC CTCCCCCCTC
       ATGTATGGGG GGGGAGAGGA GGGTAGGGGG GTTGGGATGG TGGTGGTGGT GGTGGTGGAG GAGGGGGGAG

491    GCTGCCGGAC GACGAGCTCC TCCCCCCTCC CCCTCCGCCG CCGCCGGTAA CCACCCCGCC CCTCTCCTCT
       CGACGGCCTG CTGCTCGAGG AGGGGGGAGG GGGAGGCGGC GGCGGCCATT GGTGGGGCGG GGAGAGGAGA

561    TTCTTTCTCC GTTTTTTTTT TCGTCTCGGT CTCGATCTTT GGCCTTGGTA GTTTGGGTGG GCGAGAGCGG
       AAGAAAGAGG CAAAAAAAAA AGCAGAGCCA GAGCTAGAAA CCGGAACCAT CAAACCCACC CGCTCTCGCC

631    CTTCGTCGCC CAGATCGGTG CGCGGGAGGG GCGGGATCTC GCGGCTGGCG TCTCCGGGCG TGAGTCGGCC
       GAAGCAGCGG GTCTAGCCAC GCGCCCTCCC CGCCCTAGAG CGCCGACCGC AGAGGCCCGC ACTCAGCCGG

          BamHI                              BglII
         ~~~~~~                             ~~~~~~
701    CGGATCCTCG CGGGGAATGG GGCTCTCGGA TGTAGATCTT CTTTCTTTCT TCTTTTTGTG GTAGAATTTG
       GCCTAGGAGC GCCCCTTACC CCGAGAGCCT ACATCTAGAA GAAAGAAAGA AGAAAAACAC CATCTTAAAC
```

FIG._46B

```
 771  AATCCCTCAG CATTGTTCAT CGGTAGTTTT TCTTTTCATG ATTTGTGACA AATGCAGCCT CGTGCGGAGC
      TTAGGGAGTC GTAACAAGTA GCCATCAAAA AGAAAAGTAC TAAACACTGT TTACGTCGGA GCACGCCTCG

                     HindIII
                     ~~~~~~
 841  TTTTTTGTAG GTAGAAGCTT ACCATGATCC ACACCAACCT CAAAAAGAAG TTCTCCCTCT TCATCCTCGT
      AAAAAACATC CATCTTCGAA TGGTACTAGG TGTGGTTGGA GTTTTTCTTC AAGAGGGAGA AGTAGGAGCA

 911  CTTCCTCCTC TTCGCCGTGA TCTGCGTGTG GAAGAAGGGC TCCGACTACG AGGCCCTCAC CCTCCAAGCC
      GAAGGAGGAG AAGCGGCACT AGACGCACAC CTTCTTCCCG AGGCTGATGC TCCGGGAGTG GGAGGTTCGG

                       NotI
                     ~~~~~~~~
 981  AAGGAGTTCC AAATGGCGGC CGCCTCCACG CAGGGCATCT CCGAAGACCT CTACAGCCGT TTAGTCGAAA
      TTCCTCAAGG TTTACCGCCG GCGGAGGTGC GTCCCGTAGA GGCTTCTGGA GATGTCGGCA AATCAGCTTT

                                                  SalI
                                                 ~~~~~~
                                                  AccI
                                                 ~~~~~~
1051  TGGCCACTAT CTCCCAAGCT GCCTACGCCG ACCTGTGCAA CATTCCGTCG ACTATTATCA AGGGAGAGAA
      ACCGGTGATA GAGGGTTCGA CGGATGCGGC TGGACACGTT GTAAGGCAGC TGATAATAGT TCCCTCTCTT

                                  BamHI
                                 ~~~~~~
1121  AATTTACAAT TCTCAAACTG ACATTAACGG ATGGATCCTC CGCGACGACA GCAGCAAAGA AATAATCACC
      TTAAATGTTA AGAGTTTGAC TGTAATTGCC TACCTAGGAG GCGCTGCTGT CGTCGTTTCT TTATTAGTGG

1191  GTCTTCCGTG GCACTGGTAG TGATACGAAT CTACAACTCG ATACTAACTA CACCCTCACG CCTTTCGACA
      CAGAAGGCAC CGTGACCATC ACTATGCTTA GATGTTGAGC TATGATTGAT GTGGGAGTGC GGAAAGCTGT

1261  CCCTACCACA ATGCAACGGT TGTGAAGTAC ACGGTGGATA TTATATTGGA TGGGTCTCCG TCCAGGACCA
      GGGATGGTGT TACGTTGCCA ACACTTCATG TGCCACCTAT AATATAACCT ACCCAGAGGC AGGTCCTGGT
```

FIG._46C

```
1331  AGTCGAGTCG CTTGTCAAAC AGCAGGTTAG CCAGTATCCG GACTACGCGC TGACCGTGAC CGGCCACKCC
      TCAGCTCAGC GAACAGTTTG TCGTCCAATC GGTCATAGGC CTGATGCGCG ACTGGCACTG GCCGGTGMGG

1401  CTCGGCGCCT CCCTGGCGGC ACTCACTGCC GCCCAGCTGT CTGCGACATA CGACAACATC CGCCTGTACA
      GAGCCGCGGA GGGACCGCCG TGAGTGACGG CGGGTCGACA GACGCTGTAT GCTGTTGTAG GCGGACATGT

                                                                           XhoI
                                                                          ~~~~~~
1471  CCTTCGGCGA ACCGCGCAGC GGCAATCAGG CCTTCGCGTC GTACATGAAC GATGCCTTCC AAGCCTCGAG
      GGAAGCCGCT TGGCGCGTCG CCGTTAGTCC GGAAGCGCAG CATGTACTTG CTACGGAAGG TTCGGAGCTC

1541  CCCAGATACG ACGCAGTATT TCCGGGTCAC TCATGCCAAC GACGGCATCC CAAACCTGCC CCCGGTGGAG
      GGGTCTATGC TGCGTCATAA AGGCCCAGTG AGTACGGTTG CTGCCGTAGG GTTTGGACGG GGGCCACCTC

                 NcoI
                ~~~~~~
1611  CAGGGGTACG CCCATGGCGG TGTAGAGTAC TGGAGCGTTG ATCCTTACAG CGCCCAGAAC ACATTTGTCT
      GTCCCCATGC GGGTACCGCC ACATCTCATG ACCTCGCAAC TAGGAATGTC GCGGGTCTTG TGTAAACAGA

1681  GCACTGGGGA TGAAGTGCAG TGCTGTGAGG CCCAGGGCGG ACAGGGTGTG AATAATGCGC ACACGACTTA
      CGTGACCCCT ACTTCACGTC ACGACACTCC GGGTCCCGCC TGTCCCACAC TTATTACGCG TGTGCTGAAT

                            SphI                NotI
                          ~~~~~~~~           ~~~~~~~~~~
1751  TTTTGGGATG ACGAGCGGCG CATGCACCTG GCCGGTCGCG GCCGCGGAAA CCACTGAAGG ATGAGCTGTA
      AAAACCCTAC TGCTCGCCGC GTACGTGGAC CGGCCAGCGC CGGCGCCTTT GGTGACTTCC TACTCGACAT

1821  AAGAAGCAGA TCGTTCAAAC ATTTGGCAAT AAAGTTTCTT AAGATTGAAT CCTGTTGCCG GTCTTGCGAT
      TTCTTCGTCT AGCAAGTTTG TAAACCGTTA TTTCAAAGAA TTCTAACTTA GGACAACGGC CAGAACGCTA

1891  GATTATCATA TAATTTCTGT TGAATTACGT TAAGCATGTA ATAATTAACA TGTAATGCAT GACGTTATTT
      CTAATAGTAT ATTAAAGACA ACTTAATGCA ATTCGTACAT TATTAATTGT ACATTACGTA CTGCAATAAA
```

FIG._46D

```
                                                                                BssHII
                                                                                    ~~
1961  ATGAGATGGG TTTTTATGAT TAGAGTCCCG CAATTATACA TTTAATACGC GATAGAAAAC AAAATATAGC
      TACTCTACCC AAAAATACTA ATCTCAGGGC GTTAATATGT AAATTATGCG CTATCTTTTG TTTTATATCG

                                                                            XbaI
                                                                          ~~~~~~~
      BssHII                BssHII                      ClaI  HindIII
      ~~~~                  ~~~~~~                     ~~~~~~~~~~~~~
2031  GCGCAAACTA GGATAAATTA TCGCGCGCGG TGTCATCTAT GTTACTAGAT CGATAAGCTT CTAGAGCGGC
      CGCGTTTGAT CCTATTTAAT AGCGCGCGCC ACAGTAGATA CAATGATCTA GCTATTCGAA GATCTCGCCG

                                                BssHII
                                                ~~~~~~~
2101  CGGTGGAGCT CCAATTCGCC CTATAGTGAG TCGTATTACG CGCGCTCACT GGCCGTCGTT TTACAACGTC
      GCCACCTCGA GGTTAAGCGG GATATCACTC AGCATAATGC GCGCGAGTGA CCGGCAGCAA AATGTTGCAG

2171  GTGACTGGGA AAACCCTGGC GTTACCCAAC TTAATCGCCT TGCAGCACAT CCCCCTTTCG CCAGCTGGCG
      CACTGACCCT TTTGGGACCG CAATGGGTTG AATTAGCGGA ACGTCGTGTA GGGGGAAAGC GGTCGACCGC

2241  TAATAGCGAA GAGGCCCGCA CCGATCGCCC TTCCCAACAG TTGCGCAGCC TGAATGGCGA ATGGGACGCG
      ATTATCGCTT CTCCGGGCGT GGCTAGCGGG AAGGGTTGTC AACGCGTCGG ACTTACCGCT TACCCTGCGC

2311  CCCTGTAGCG GCGCATTAAG CGCGGCGGGT GTGGTGGTTA CGCGCAGCGT GACCGCTACA CTTGCCAGCG
      GGGACATCGC CGCGTAATTC GCGCCGCCCA CACCACCAAT GCGCGTCGCA CTGGCGATGT GAACGGTCGC

2381  CCCTAGCGCC CGCTCCTTTC GCTTTCTTCC CTTCCTTTCT CGCCACGTTC GCCGGCTTTC CCCGTCAAGC
      GGGATCGCGG GCGAGGAAAG CGAAAGAAGG GAAGGAAAGA GCGGTGCAAG CGGCCGAAAG GGGCAGTTCG

2451  TCTAAATCGG GGGCTCCCTT TAGGGTTCCG ATTTAGTGCT TTACGGCACC TCGACCCCAA AAAACTTGAT
      AGATTTAGCC CCCGAGGGAA ATCCCAAGGC TAAATCACGA AATGCCGTGG AGCTGGGGTT TTTTGAACTA

2521  TAGGGTGATG GTTCACGTAG TGGGCCATCG CCCTGATAGA CGGTTTTTCG CCCTTTGACG TTGGAGTCCA
      ATCCCACTAC CAAGTGCATC ACCCGGTAGC GGGACTATCT GCCAAAAAGC GGGAAACTGC AACCTCAGGT
```

FIG._46E

```
2591  CGTTCTTTAA TAGTGGACTC TTGTTCCAAA CTGGAACAAC ACTCAACCCT ATCTCGGTCT ATTCTTTTGA
      GCAAGAAATT ATCACCTGAG AACAAGGTTT GACCTTGTTG TGAGTTGGGA TAGAGCCAGA TAAGAAAACT

2661  TTTATAAGGG ATTTTGCCGA TTTCGGCCTA TTGGTTAAAA AATGAGCTGA TTTAACAAAA ATTTAACGCG
      AAATATTCCC TAAAACGGCT AAAGCCGGAT AACCAATTTT TTACTCGACT AAATTGTTTT TAAATTGCGC

2731  AATTTTAACA AAATATTAAC GCTTACAATT TAGGTGGCAC TTTTCGGGGA AATGTGCGCG GAACCCCTAT
      TTAAAATTGT TTTATAATTG CGAATGTTAA ATCCACCGTG AAAAGCCCCT TTACACGCGC CTTGGGGATA

2801  TTGTTTATTT TTCTAAATAC ATTCAAATAT GTATCCGCTC ATGAGACAAT AACCCTGATA AATGCTTCAA
      AACAAATAAA AAGATTTATG TAAGTTTATA CATAGGCGAG TACTCTGTTA TTGGGACTAT TTACGAAGTT

2871  TAATATTGAA AAAGGAAGAG TATGAGTATT CAACATTTCC GTGTCGCCCT TATTCCCTTT TTTGCGGCAT
      ATTATAACTT TTTCCTTCTC ATACTCATAA GTTGTAAAGG CACAGCGGGA ATAAGGGAAA AAACGCCGTA

2941  TTTGCCTTCC TGTTTTTGCT CACCCAGAAA CGCTGGTGAA AGTAAAAGAT GCTGAAGATC AGTTGGGTGC
      AAACGGAAGG ACAAAAACGA GTGGGTCTTT GCGACCACTT TCATTTTCTA CGACTTCTAG TCAACCCACG

3011  ACGAGTGGGT TACATCGAAC TGGATCTCAA CAGCGGTAAG ATCCTTGAGA GTTTTCGCCC CGAAGAACGT
      TGCTCACCCA ATGTAGCTTG ACCTAGAGTT GTCGCCATTC TAGGAACTCT CAAAAGCGGG GCTTCTTGCA

3081  TTTCCAATGA TGAGCACTTT TAAAGTTCTG CTATGTGGCG CGGTATTATC CCGTATTGAC GCCGGGCAAG
      AAAGGTTACT ACTCGTGAAA ATTTCAAGAC GATACACCGC GCCATAATAG GGCATAACTG CGGCCCGTTC

3151  AGCAACTCGG TCGCCGCATA CACTATTCTC AGAATGACTT GGTTGAGTAC TCACCAGTCA CAGAAAAGCA
      TCGTTGAGCC AGCGGCGTAT GTGATAAGAG TCTTACTGAA CCAACTCATG AGTGGTCAGT GTCTTTTCGT

3221  TCTTACGGAT GGCATGACAG TAAGAGAATT ATGCAGTGCT GCCATAACCA TGAGTGATAA CACTGCGGCC
      AGAATGCCTA CCGTACTGTC ATTCTCTTAA TACGTCACGA CGGTATTGGT ACTCACTATT GTGACGCCGG

3291  AACTTACTTC TGACAACGAT CGGAGGACCG AAGGAGCTAA CCGCTTTTTT GCACAACATG GGGGATCATG
      TTGAATGAAG ACTGTTGCTA GCCTCCTGGC TTCCTCGATT GGCGAAAAAA CGTGTTGTAC CCCCTAGTAC

3361  TAACTCGCCT TGATCGTTGG GAACCGGAGC TGAATGAAGC CATACCAAAC GACGAGCGTG ACACCACGAT
      ATTGAGCGGA ACTAGCAACC CTTGGCCTCG ACTTACTTCG GTATGGTTTG CTGCTCGCAC TGTGGTGCTA
```

FIG._46F

```
3431  GCCTGTAGCA ATGGCAACAA CGTTGCGCAA ACTATTAACT GGCGAACTAC TTACTCTAGC TTCCCGGCAA
      CGGACATCGT TACCGTTGTT GCAACGCGTT TGATAATTGA CCGCTTGATG AATGAGATCG AAGGGCCGTT

3501  CAATTAATAG ACTGGATGGA GGCGGATAAA GTTGCAGGAC CACTTCTGCG CTCGGCCCTT CCGGCTGGCT
      GTTAATTATC TGACCTACCT CCGCCTATTT CAACGTCCTG GTGAAGACGC GAGCCGGGAA GGCCGACCGA

3571  GGTTTATTGC TGATAAATCT GGAGCCGGTG AGCGTGGGTC TCGCGGTATC ATTGCAGCAC TGGGGCCAGA
      CCAAATAACG ACTATTTAGA CCTCGGCCAC TCGCACCCAG AGCGCCATAG TAACGTCGTG ACCCCGGTCT

3641  TGGTAAGCCC TCCCGTATCG TAGTTATCTA CACGACGGGG AGTCAGGCAA CTATGGATGA ACGAAATAGA
      ACCATTCGGG AGGGCATAGC ATCAATAGAT GTGCTGCCCC TCAGTCCGTT GATACCTACT TGCTTTATCT

3711  CAGATCGCTG AGATAGGTGC CTCACTGATT AAGCATTGGT AACTGTCAGA CCAAGTTTAC TCATATATAC
      GTCTAGCGAC TCTATCCACG GAGTGACTAA TTCGTAACCA TTGACAGTCT GGTTCAAATG AGTATATATG

3781  TTTAGATTGA TTTAAAACTT CATTTTTAAT TTAAAAGGAT CTAGGTGAAG ATCCTTTTTG ATAATCTCAT
      AAATCTAACT AAATTTTGAA GTAAAAATTA AATTTTCCTA GATCCACTTC TAGGAAAAAC TATTAGAGTA

3851  GACCAAAATC CCTTAACGTG AGTTTTCGTT CCACTGAGCG TCAGACCCCG TAGAAAAGAT CAAAGGATCT
      CTGGTTTTAG GGAATTGCAC TCAAAAGCAA GGTGACTCGC AGTCTGGGGC ATCTTTTCTA GTTTCCTAGA

3921  TCTTGAGATC CTTTTTTTCT GCGCGTAATC TGCTGCTTGC AAACAAAAAA ACCACCGCTA CCAGCGGTGG
      AGAACTCTAG GAAAAAAAGA CGCGCATTAG ACGACGAACG TTTGTTTTTT TGGTGGCGAT GGTCGCCACC

3991  TTTGTTTGCC GGATCAAGAG CTACCAACTC TTTTTCCGAA GGTAACTGGC TTCAGCAGAG CGCAGATACC
      AAACAAACGG CCTAGTTCTC GATGGTTGAG AAAAAGGCTT CCATTGACCG AAGTCGTCTC GCGTCTATGG

4061  AAATACTGTC CTTCTAGTGT AGCCGTAGTT AGGCCACCAC TTCAAGAACT CTGTAGCACC GCCTACATAC
      TTTATGACAG GAAGATCACA TCGGCATCAA TCCGGTGGTG AAGTTCTTGA GACATCGTGG CGGATGTATG

4131  CTCGCTCTGC TAATCCTGTT ACCAGTGGCT GCTGCCAGTG GCGATAAGTC GTGTCTTACC GGGTTGGACT
      GAGCGAGACG ATTAGGACAA TGGTCACCGA CGACGGTCAC CGCTATTCAG CACAGAATGG CCCAACCTGA

4201  CAAGACGATA GTTACCGGAT AAGGCGCAGC GGTCGGGCTG AACGGGGGGT TCGTGCACAC AGCCCAGCTT
      GTTCTGCTAT CAATGGCCTA TTCCGCGTCG CCAGCCCGAC TTGCCCCCCA AGCACGTGTG TCGGGTCGAA
```

FIG._46G

```
4271  GGAGCGAACG ACCTACACCG AACTGAGATA CCTACAGCGT GAGCTATGAG AAAGCGCCAC GCTTCCCGAA
      CCTCGCTTGC TGGATGTGGC TTGACTCTAT GGATGTCGCA CTCGATACTC TTTCGCGGTG CGAAGGGCTT

4341  GGGAGAAAGG CGGACAGGTA TCCGGTAAGC GGCAGGGTCG GAACAGGAGA GCGCACGAGG GAGCTTCCAG
      CCCTCTTTCC GCCTGTCCAT AGGCCATTCG CCGTCCCAGC CTTGTCCTCT CGCGTGCTCC CTCGAAGGTC

4411  GGGGAAACGC CTGGTATCTT TATAGTCCTG TCGGGTTTCG CCACCTCTGA CTTGAGCGTC GATTTTTGTG
      CCCCTTTGCG GACCATAGAA ATATCAGGAC AGCCCAAAGC GGTGGAGACT GAACTCGCAG CTAAAAACAC

4481  ATGCTCGTCA GGGGGGCGGA GCCTATGGAA AAACGCCAGC AACGCGGCCT TTTTACGGTT CCTGGCCTTT
      TACGAGCAGT CCCCCCGCCT CGGATACCTT TTTGCGGTCG TTGCGCCGGA AAAATGCCAA GGACCGGAAA

4551  TGCTGGCCTT TTGCTCACAT GTTCTTTCCT GCGTTATCCC CTGATTCTGT GGATAACCGT ATTACCGCCT
      ACGACCGGAA AACGAGTGTA CAAGAAAGGA CGCAATAGGG GACTAAGACA CCTATTGGCA TAATGGCGGA

4621  TTGAGTGAGC TGATACCGCT CGCCGCAGCC GAACGACCGA GCGCAGCGAG TCAGTGAGCG AGGAAGCGGA
      AACTCACTCG ACTATGGCGA GCGGCGTCGG CTTGCTGGCT CGCGTCGCTC AGTCACTCGC TCCTTCGCCT

4691  AGAGCGCCCA ATACGCAAAC CGCCTCTCCC CGCGCGTTGG CCGATTCATT AATGCAGCTG GCACGACAGG
      TCTCGCGGGT TATGCGTTTG GCGGAGAGGG GCGCGCAACC GGCTAAGTAA TTACGTCGAC CGTGCTGTCC

4761  TTTCCCGACT GGAAAGCGGG CAGTGAGCGC AACGCAATTA ATGTGAGTTA GCTCACTCAT TAGGCACCCC
      AAAGGGCTGA CCTTTCGCCC GTCACTCGCG TTGCGTTAAT TACACTCAAT CGAGTGAGTA ATCCGTGGGG

4831  AGGCTTTACA CTTTATGCTT CCGGCTCGTA TGTTGTGTGG AATTGTGAGC GGATAACAAT TTCACACAGG
      TCCGAAATGT GAAATACGAA GGCCGAGCAT ACAACACACC TTAACACTCG CCTATTGTTA AAGTGTGTCC

                             BssHII                              EcoRI
                            ~~~~~~~~
4901  AAACAGCTAT GACCATGATT ACGCCAAGCG CGCAATTAAC CCTCACTAAA GGGAACAAAA GCTGG
      TTTGTCGATA CTGGTACTAA TGCGGTTCGC GCGTTAATTG GGAGTGATTT CCCTTGTTTT CGACC
```

FIG._46H

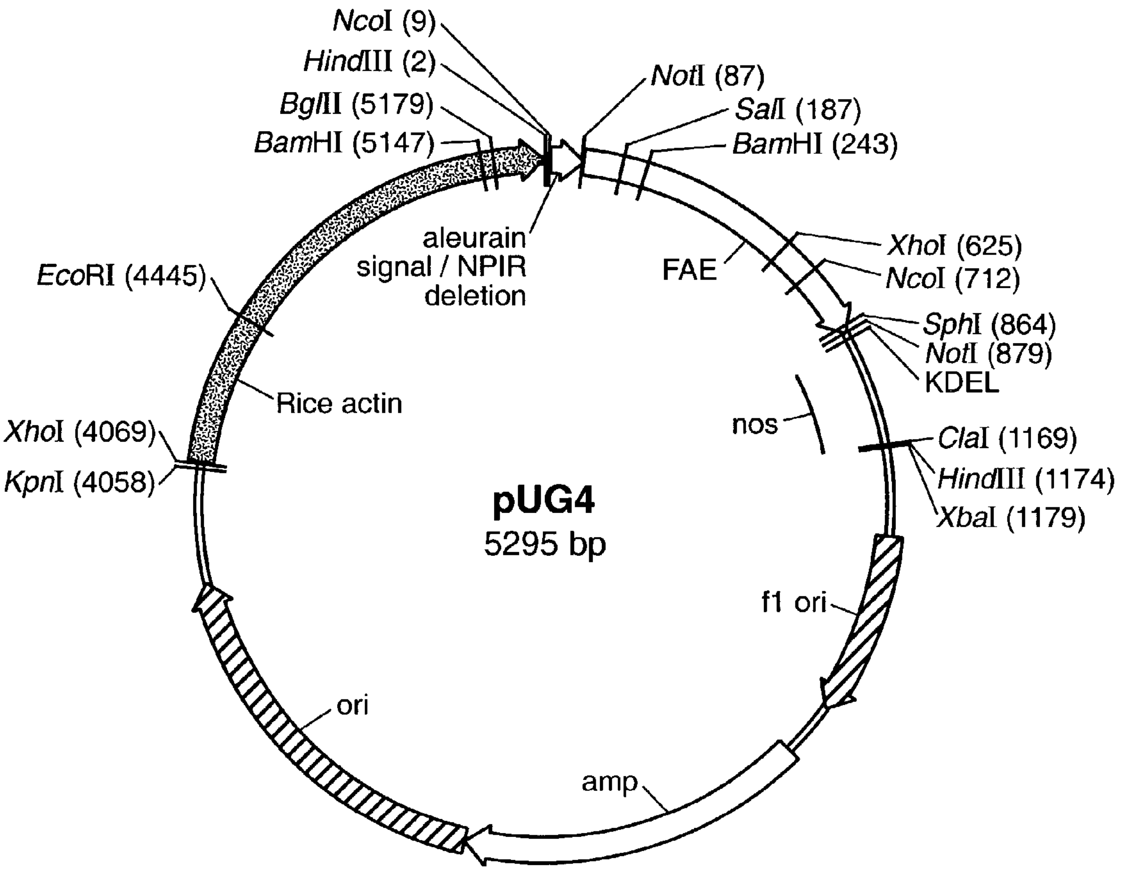
FIG._47A

```
              NcoI
             ~~~~~~~~
         HindIII
         ~~~~~~
                    M  A  H  A  R  V  L  L  L  A  L  A  V  L  A  T  A  A  V  A  V
  1  AAGCTTACCA TGGCCCACGC CCGCGTCCTC CTCCTGGCGC TCGCCGTGCT GGCCACGGCC GCCGTCGCCG
                    NotI
                  ~~~~~~~~~~
     · A  S  S  R  A  A  A  S  T  Q  G  I  S  E  D  L  Y  S  R  L  V  E  M ·
 71  TCGCCTCCTC CCGCGCGGCC GCCTCCACGC AGGGCATCTC CGAAGACCTC TACAGCCGTT TAGTCGAAAT
                                                    SalI
                                                   ~~~~~~~~
     · A  T  I  S  Q  A  A  Y  A  D  L  C  N  I  P  S  T  I  I  K  G  E  K
141  GGCCACTATC TCCCAAGCTG CCTACGCCGA CCTGTGCAAC ATTCCGTCGA CTATTATCAA GGGAGAGAAA
                                     BamHI
                                     ~~~~~~~
      I  Y  N  S  Q  T  D  I  N  G  W  I  L  R  D  D  S  S  K  E  I  I  T  V
211  ATTTACAATT CTCAAACTGA CATTAACGGA TGGATCCTCC GCGACGACAG CAGCAAAGAA ATAATCACCG
     · F  R  G  T  G  S  D  T  N  L  Q  L  D  T  N  Y  T  L  T  P  F  D  T ·
281  TCTTCCGTGG CACTGGTAGT GATACGAATC TACAACTCGA TACTAACTAC ACCCTCACGC CTTTCGACAC
     · L  P  Q  C  N  G  C  E  V  H  G  G  Y  Y  I  G  W  V  S  V  Q  D  Q
351  CCTACCACAA TGCAACGGTT GTGAAGTACA CGGTGGATAT TATATTGGAT GGGTCTCCGT CCAGGACCAA
      V  E  S  L  V  K  Q  Q  V  S  Q  Y  P  D  Y  A  L  T  V  T  G  H  X  L
421  GTCGAGTCGC TTGTCAAACA GCAGGTTAGC CAGTATCCGG ACTACGCGCT GACCGTGACC GGCCACKCCC
     · G  A  S  L  A  A  L  T  A  A  Q  L  S  A  T  Y  D  N  I  R  L  Y  T ·
491  TCGGCGCCTC CCTGGCGGCA CTCACTGCCG CCCAGCTGTC TGCGACATAC GACAACATCC GCCTGTACAC
                                                                      XhoI
                                                                       ~
     · F  G  E  P  R  S  G  N  Q  A  F  A  S  Y  M  N  D  A  F  Q  A  S  S
561  CTTCGGCGAA CCGCGCAGCG GCAATCAGGC CTTCGCGTCG TACATGAACG ATGCCTTCCA AGCCTCGAGC
      P  D  T  T  Q  Y  F  R  V  T  H  A  N  D  G  I  P  N  L  P  P  V  E  Q
631  CCAGATACGA CGCAGTATTT CCGGGTCACT CATGCCAACG ACGGCATCCC AAACCTGCCC CCGGTGGAGC
               NcoI
              ~~~~~~
```

FIG._47B

```
      · G  Y  A   H  G  G   V  E  Y  W   S  V  D   P  Y  S   A  Q  N  T   F  V  C ·
 701  AGGGGTACGC CCATGGCGGT GTAGAGTACT GGAGCGTTGA TCCTTACAGC GCCCAGAACA CATTTGTCTG
      ·T  G  D   E  V  Q  C   C  E  A   Q  G  G   Q  G  V  N   N  A  H   T  T  Y
 771  CACTGGGGAT GAAGTGCAGT GCTGTGAGGC CCAGGGCGGA CAGGGTGTGA ATAATGCGCA CACGACTTAT
                               SphI                NotI
                             ~~~~~~~~           ~~~~~~~~~~
       F  G  M  T   S  G  A   C  T  W   P  V  A  A   A  E  P   L  K  D   E  L  *
 841  TTTGGGATGA CGAGCGGCGC ATGCACCTGG CCGGTCGCGG CCGCGGAACC ACTGAAGGAT GAGCTGTAAA
 911  GAAGCAGATC GTTCAAACAT TTGGCAATAA AGTTTCTTAA GATTGAATCC TGTTGCCGGT CTTGCGATGA
 981  TTATCATATA ATTTCTGTTG AATTACGTTA AGCATGTAAT AATTAACATG TAATGCATGA CGTTATTTAT
1051  GAGATGGGTT TTTATGATTA GAGTCCCGCA ATTATACATT TAATACGCGA TAGAAAACAA AATATAGCGC
                                                             HindIII
                                                            ~~~~~~~~
                                                       ClaI        XbaI
                                                      ~~~~~~      ~~~~~~
1121  GCAAACTAGG ATAAATTATC GCGCGCGGTG TCATCTATGT TACTAGATCG ATAAGCTTCT AGAGCGGCCG
1191  GTGGAGCTCC AATTCGCCCT ATAGTGAGTC GTATTACGCG CGCTCACTGG CCGTCGTTTT ACAACGTCGT
1261  GACTGGGAAA ACCCTGGCGT TACCCAACTT AATCGCCTTG CAGCACATCC CCCTTTCGCC AGCTGGCGTA
1331  ATAGCGAAGA GGCCCGCACC GATCGCCCTT CCCAACAGTT GCGCAGCCTG AATGGCGAAT GGGACGCGCC
1401  CTGTAGCGGC GCATTAAGCG CGGCGGGTGT GGTGGTTACG CGCAGCGTGA CCGCTACACT TGCCAGCGCC
1471  CTAGCGCCCG CTCCTTTCGC TTTCTTCCCT TCCTTTCTCG CCACGTTCGC CGGCTTTCCC CGTCAAGCTC
1541  TAAATCGGGG GCTCCCTTTA GGGTTCCGAT TTAGTGCTTT ACGGCACCTC GACCCCAAAA AACTTGATTA
1611  GGGTGATGGT TCACGTAGTG GGCCATCGCC CTGATAGACG GTTTTTCGCC CTTTGACGTT GGAGTCCACG
1681  TTCTTTAATA GTGGACTCTT GTTCCAAACT GGAACAACAC TCAACCCTAT CTCGGTCTAT TCTTTTGATT
1751  TATAAGGGAT TTTGCCGATT TCGGCCTATT GGTTAAAAAA TGAGCTGATT TAACAAAAAT TTAACGCGAA
1821  TTTTAACAAA ATATTAACGC TTACAATTTA GGTGGCACTT TTCGGGGAAA TGTGCGCGGA ACCCCTATTT
1891  GTTTATTTTT CTAAATACAT TCAAATATGT ATCCGCTCAT GAGACAATAA CCCTGATAAA TGCTTCAATA
1961  ATATTGAAAA AGGAAGAGTA TGAGTATTCA ACATTTCCGT GTCGCCCTTA TTCCCTTTTT TGCGGCATTT
2031  TGCCTTCCTG TTTTTGCTCA CCCAGAAACG CTGGTGAAAG TAAAAGATGC TGAAGATCAG TTGGGTGCAC
2101  GAGTGGGTTA CATCGAACTG GATCTCAACA GCGGTAAGAT CCTTGAGAGT TTTCGCCCCG AAGAACGTTT
2171  TCCAATGATG AGCACTTTTA AAGTTCTGCT ATGTGGCGCG GTATTATCCC GTATTGACGC CGGGCAAGAG
2241  CAACTCGGTC GCCGCATACA CTATTCTCAG AATGACTTGG TTGAGTACTC ACCAGTCACA GAAAAGCATC
2311  TTACGGATGG CATGACAGTA AGAGAATTAT GCAGTGCTGC CATAACCATG AGTGATAACA CTGCGGCCAA
2381  CTTACTTCTG ACAACGATCG GAGGACCGAA GGAGCTAACC GCTTTTTTGC ACAACATGGG GGATCATGTA
2451  ACTCGCCTTG ATCGTTGGGA ACCGGAGCTG AATGAAGCCA TACCAAACGA CGAGCGTGAC ACCACGATGC
2521  CTGTAGCAAT GGCAACAACG TTGCGCAAAC TATTAACTGG CGAACTACTT ACTCTAGCTT CCCGGCAACA
```

FIG._47C

```
2591  ATTAATAGAC TGGATGGAGG CGGATAAAGT TGCAGGACCA CTTCTGCGCT CGGCCCTTCC GGCTGGCTGG
2661  TTTATTGCTG ATAAATCTGG AGCCGGTGAG CGTGGGTCTC GCGGTATCAT TGCAGCACTG GGGCCAGATG
2731  GTAAGCCCTC CCGTATCGTA GTTATCTACA CGACGGGGAG TCAGGCAACT ATGGATGAAC GAAATAGACA
2801  GATCGCTGAG ATAGGTGCCT CACTGATTAA GCATTGGTAA CTGTCAGACC AAGTTTACTC ATATATACTT
2871  TAGATTGATT TAAAACTTCA TTTTTAATTT AAAAGGATCT AGGTGAAGAT CCTTTTTGAT AATCTCATGA
2941  CCAAAATCCC TTAACGTGAG TTTTCGTTCC ACTGAGCGTC AGACCCCGTA GAAAAGATCA AAGGATCTTC
3011  TTGAGATCCT TTTTTTCTGC GCGTAATCTG CTGCTTGCAA ACAAAAAAAC CACCGCTACC AGCGGTGGTT
3081  TGTTTGCCGG ATCAAGAGCT ACCAACTCTT TTTCCGAAGG TAACTGGCTT CAGCAGAGCG CAGATACCAA
3151  ATACTGTCCT TCTAGTGTAG CCGTAGTTAG GCCACCACTT CAAGAACTCT GTAGCACCGC CTACATACCT
3221  CGCTCTGCTA ATCCTGTTAC CAGTGGCTGC TGCCAGTGGC GATAAGTCGT GTCTTACCGG GTTGGACTCA
3291  AGACGATAGT TACCGGATAA GGCGCAGCGG TCGGGCTGAA CGGGGGGTTC GTGCACACAG CCCAGCTTGG
3361  AGCGAACGAC CTACACCGAA CTGAGATACC TACAGCGTGA GCTATGAGAA AGCGCCACGC TTCCCGAAGG
3431  GAGAAAGGCG GACAGGTATC CGGTAAGCGG CAGGGTCGGA ACAGGAGAGC GCACGAGGGA GCTTCCAGGG
3501  GGAAACGCCT GGTATCTTTA TAGTCCTGTC GGGTTTCGCC ACCTCTGACT TGAGCGTCGA TTTTTGTGAT
3571  GCTCGTCAGG GGGGCGGAGC CTATGGAAAA ACGCCAGCAA CGCGGCCTTT TTACGGTTCC TGGCCTTTTG
3641  CTGGCCTTTT GCTCACATGT TCTTTCCTGC GTTATCCCCT GATTCTGTGG ATAACCGTAT TACCGCCTTT
3711  GAGTGAGCTG ATACCGCTCG CCGCAGCCGA ACGACCGAGC GCAGCGAGTC AGTGAGCGAG GAAGCGGAAG
3781  AGCGCCCAAT ACGCAAACCG CCTCTCCCCG CGCGTTGGCC GATTCATTAA TGCAGCTGGC ACGACAGGTT
3851  TCCCGACTGG AAAGCGGGCA GTGAGCGCAA CGCAATTAAT GTGAGTTAGC TCACTCATTA GGCACCCCAG
3921  GCTTTACACT TTATGCTTCC GGCTCGTATG TTGTGTGGAA TTGTGAGCGG ATAACAATTT CACACAGGAA
                                                                          KpnI
                                                                           ~~
3991  ACAGCTATGA CCATGATTAC GCCAAGCGCG CAATTAACCC TCACTAAAGG GAACAAAAGC TGGGTACCGG
                 XhoI
                ~~~~~~~
4061  GCCCCCCCTC GAGGTCATTC ATATGCTTGA GAAGAGAGTC GGGATAGTCC AAAATAAAAC AAAGGTAAGA
4131  TTACCTGGTC AAAAGTGAAA ACATCAGTTA AAAGGTGGTA TAAGTAAAAT ATCGGTAATA AAAGGTGGCC
4201  CAAAGTGAAA TTTACTCTTT TCTACTATTA TAAAAATTGA GGATGTTTTG TCGGTACTTT GATACGTCAT
4271  TTTTGTATGA ATTGGTTTTT AAGTTTATTC GCGATTTGGA AATGCATATC TGTATTTGAG TCGGTTTTTA
4341  AGTTCGTTGC TTTTGTAAAT ACAGAGGGAT TTGTATAAGA AATATCTTTA AAAAACCCAT ATGCTAATTT
                                          EcoRI
                                         ~~~~~~~
4411  GACATAATTT TTGAGAAAAA TATATATTCA GGCGAATTCC ACAATGAACA ATAATAAGAT TAAAATAGCT
4481  TGCCCCCGTT GCAGCGATGG GTATTTTTTC TAGTAAAATA AAAGATAAAC TTAGACTCAA AACATTTACA
4551  AAAACAACCC CTAAAGTCCT AAAGCCCAAA GTGCTATGCA CGATCCATAG CAAGCCCAGC CCAACCCAAC
4621  CCAACCCAAC CCACCCCAGT GCAGCCAACT GGCAAATAGT CTCCACCCCC GGCACTATCA CCGTGAGTTG
```

FIG._47D

```
4691  TCCGCACCAC CGCACGTCTC GCAGCCAAAA AAAAAAAAAG AAAGAAAAAA AAGAAAAAGA AAAACAGCAG
4761  GTGGGTCCGG GTCGTGGGGG CCGGAAAAGC GAGGAGGATC GCGAGCAGCG ACGAGGCCCG GCCCTCCCTC
4831  CGCTTCCAAA GAAACGCCCC CCATCGCCAC TATATACATA CCCCCCCCTC TCCTCCCATC CCCCCAACCC
4901  TACCACCACC ACCACCACCA CCTCCTCCCC CCTCGCTGCC GGACGACGAG CTCCTCCCCC CTCCCCCTCC
4971  GCCGCCGCCG GTAACCACCC CGCCCCTCTC CTCTTTCTTT CTCCGTTTTT TTTTTCGTCT CGGTCTCGAT
5041  CTTTGGCCTT GGTAGTTTGG GTGGGCGAGA GCGGCTTCGT CGCCCAGATC GGTGCGCGGG AGGGGCGGGA
                                      BamHI                             BglII
                                      ~~~~~~~~
5111  TCTCGCGGCT GGCGTCTCCG GGCGTGAGTC GGCCCGGATC CTCGCGGGGA ATGGGGCTCT CGGATGTAGA
      BglII
      ~~~
5181  TCTTCTTTCT TTCTTCTTTT TGTGGTAGAA TTTGAATCCC TCAGCATTGT TCATCGGTAG TTTTTCTTTT
5251  CATGATTTGT GACAAATGCA GCCTCGTGCG GAGCTTTTTT GTAGC
```

FIG._47E

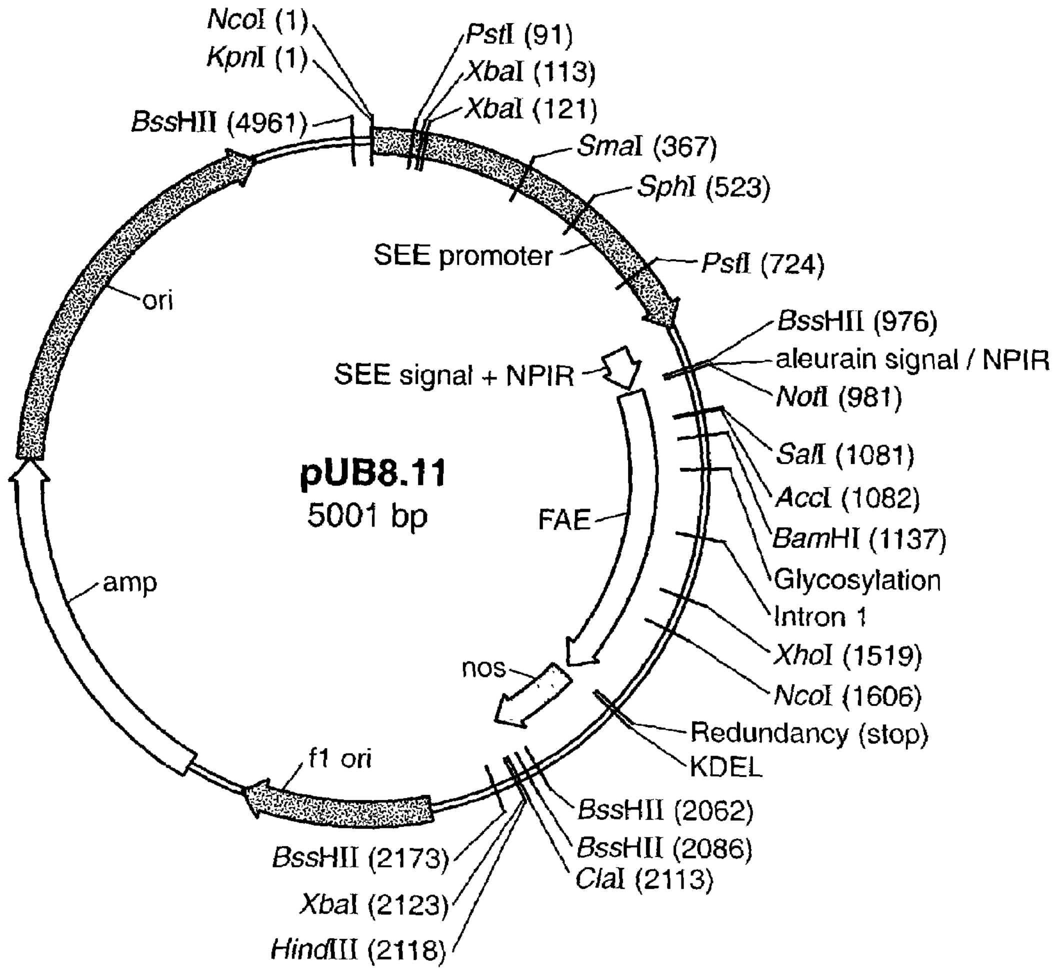
FIG._48A

```
       NcoI
       ~~~~~
       KpnI
       ~
  1    CATGGGCCAG GTATAATTAT GGGATATCTC AAGCAAATAA TCGAAATATC ACCATTGGCT ACAATATCTG
       GTACCCGGTC CATATTAATA CCCTATAGAG TTCGTTTATT AGCTTTATAG TGGTAACCGA TGTTATAGAC

                     PstI                               XbaI      XbaI
                   ~~~~~~~~                           ~~~~~~~   ~~~~~~~~
 71    AGCTCCGAGT TCTGACTGCA GTCTGGATGA CGCGTGTTGT ATCTAGAACT CTAGATAGCA CAGCCACAGC
       TCGAGGCTCA AGACTGACGT CAGACCTACT GCGCACAACA TAGATCTTGA GATCTATCGT GTCGGTGTCG

141    ACCTACAGGA GTGCGACACT TGTGGACTGT AGTAGTGTTG GAGACGGAGC TCTTTCCTAC CTCCTGACGT
       TGGATGTCCT CACGCTGTGA ACACCTGACA TCATCACAAC CTCTGCCTCG AGAAAGGATG GAGGACTGCA

211    TGCCGCCGTT GTCCATTCCA ACGGCATCAC TCTCAACCAA TCACGCGCTC CCAACAAAAT ATCGTCCCCC
       ACGGCGGCAA CAGGTAAGGT TGCCGTAGTG AGAGTTGGTT AGTGCGCGAG GGTTGTTTTA TAGCAGGGGG

281    ATGTCTTGGC GGAGAGAGAG TACATACATG CTGTCGCGCC GTTTTTGTCT GAATCTCGCT TCCACTGGCC
       TACAGAACCG CCTCTCTCTC ATGTATGTAC GACAGCGCGG CAAAAACAGA CTTAGAGCGA AGGTGACCGG

                  SmaI
                 ~~~~~~
351    AATCAGCTCA GCTCCCGGGA GCTCACTCAT TCAAGATCCC ATCGTCGTCG TCACCCCTGG CGTCATGGGA
       TTAGTCGAGT CGAGGGCCCT CGAGTGAGTA AGTTCTAGGG TAGCAGCAGC AGTGGGGACC GCAGTACCCT

421    TGGAAAAGAA CCTCCGTTGC TCGGATGAGT CAGCCATATC CCCGAACAGA GTACTGCAAG ATAACCCAAT
       ACCTTTTCTT GGAGGCAACG AGCCTACTCA GTCGGTATAG GGGCTTGTCT CATGACGTTC TATTGGGTTA

                                  SphI
                                ~~~~~~~~
491    TCAGATTCCC CCAATAGAGA AAGTATAGCA TGCTTTCGGG TTTTGTTTGG CTTAATTGAC TTTATTTTTG
       AGTCTAAGGG GGTTATCTCT TTCATATCGT ACGAAAGCCC AAAACAAACC GAATTAACTG AAATAAAAAC

561    TTGGAGTTGA ATGCTGATTT GTTGTGTAAA ATGCCCAACC ATCTGAATAT CGAGACGGAT AATAGGCTGG
       AACCTCAACT TACGACTAAA CAACACATTT TACGGGTTGG TAGACTTATA GCTCTGCCTA TTATCCGACC
```

FIG._48B

```
                                PstI
                               ~~~~~~~
 631  CTAATTAATT TATAGCAAGA TTCTGTAGTG CACATCGCAA ATATCTTTCT GGGCATTACA GCTGGAGGCT
      GATTAATTAA ATATCGTTCT AAGACATCAC GTGTAGCGTT TATAGAAAGA CCCGTAATGT CGACCTCCGA

 701  TCATCAGCCT GAAACACTCT GCAGAGCCTG AAGCAAGTGG TGAAGCGTGG CGATGAGATG GGTATAAAAC
      AGTAGTCGGA CTTTGTGAGA CGTCTCGGAC TTCGTTCACC ACTTCGCACC GCTACTCTAC CCATATTTTG

 771  CCCCGGCACC GGGACGCGAG CTCCCGCCTA CCAGTACCAT CTCGCCTCGC TCCCCCTGCC GGACGACCCA
      GGGGCCGTGG CCCTGCGCTC GAGGGCGGAT GGTCATGGTA GAGCGGAGCG AGGGGGACGG CCTGCTGGGT

 841  GTAAAATACT GTTGCCCACT CGCCGGCGAG ATGGCCCACG GCCGCATCCT CTTCTTGGCG CTCGCCGTCT
      CATTTTATGA CAACGGGTGA GCGGCCGCTC TACCGGGTGC CGGCGTAGGA GAAGAACCGC GAGCGGCAGA

                                                                          BssHII
                                                                          ~~~~~~
                                                                            NotI
                                                                              ~~
 911  TGGCCACCGC CGCGGTGGCC GCCGCATCNT TGGCGGACTC CAACCCGATC CGGCCCGTCA CCGAGCGCGC
      ACCGGTGGCG GCGCCACCGG CGGCGTAGNA ACCGCCTGAG GTTGGGCTAG GCCGGGCAGT GGCTCGCGCG

      NotI
      ~~~~~~
 981  GGCCGCCTCC ACGCAGGGCA TCTCCGAAGA CCTCTACAGC CGTTTAGTCG AAATGGCCAC TATCTCCCAA
      CCGGCGGAGG TGCGTCCCGT AGAGGCTTCT GGAGATGTCG GCAAATCAGC TTTACCGGTG ATAGAGGGTT

                                          SalI
                                        ~~~~~~~
                                          AccI
                                        ~~~~~~~
1051  GCTGCCTACG CCGACCTGTG CAACATTCCG TCGACTATTA TCAAGGGAGA GAAAATTTAC AATTCTCAAA
      CGACGGATGC GGCTGGACAC GTTGTAAGGC AGCTGATAAT AGTTCCCTCT CTTTTAAATG TTAAGAGTTT
```

FIG._48C

```
                        BamHI
                       ~~~~~~~~
1121  CTGACATTAA CGGATGGATC CTCCGCGACG ACAGCAGCAA AGAAATAATC ACCGTCTTCC GTGGCACTGG
      GACTGTAATT GCCTACCTAG GAGGCGCTGC TGTCGTCGTT TCTTTATTAG TGGCAGAAGG CACCGTGACC

1191  TAGTGATACG AATCTACAAC TCGATACTAA CTACACCCTC ACGCCTTTCG ACACCCTACC ACAATGCAAC
      ATCACTATGC TTAGATGTTG AGCTATGATT GATGTGGGAG TGCGGAAAGC TGTGGGATGG TGTTACGTTG

1261  GGTTGTGAAG TACACGGTGG ATATTATATT GGATGGGTCT CCGTCCAGGA CCAAGTCGAG TCGCTTGTCA
      CCAACACTTC ATGTGCCACC TATAATATAA CCTACCCAGA GGCAGGTCCT GGTTCAGCTC AGCGAACAGT

1331  AACAGCAGGT TAGCCAGTAT CCGGACTACG CGCTGACCGT GACCGGCCAC KCCCTCGGCG CCTCCCTGGC
      TTGTCGTCCA ATCGGTCATA GGCCTGATGC GCGACTGGCA CTGGCCGGTG MGGGAGCCGC GGAGGGACCG

1401  GGCACTCACT GCCGCCCAGC TGTCTGCGAC ATACGACAAC ATCCGCCTGT ACACCTTCGG CGAACCGCGC
      CCGTGAGTGA CGGCGGGTCG ACAGACGCTG TATGCTGTTG TAGGCGGACA TGTGGAAGCC GCTTGGCGCG

                                                          XhoI
                                                        ~~~~~~~~
1471  AGCGGCAATC AGGCCTTCGC GTCGTACATG AACGATGCCT TCCAAGCCTC GAGCCCAGAT ACGACGCAGT
      TCGCCGTTAG TCCGGAAGCG CAGCATGTAC TTGCTACGGA AGGTTCGGAG CTCGGGTCTA TGCTGCGTCA

                                                                        NcoI
                                                                       ~~~~~~
1541  ATTTCCGGGT CACTCATGCC AACGACGGCA TCCCAAACCT GCCCCCGGTG GAGCAGGGGT ACGCCCATGG
      TAAAGGCCCA GTGAGTACGG TTGCTGCCGT AGGGTTTGGA CGGGGGCCAC CTCGTCCCCA TGCGGGTACC

1611  CGGTGTAGAG TACTGGAGCG TTGATCCTTA CAGCGCCCAG AACACATTTG TCTGCACTGG GGATGAAGTG
      GCCACATCTC ATGACCTCGC AACTAGGAAT GTCGCGGGTC TTGTGTAAAC AGACGTGACC CCTACTTCAC

1681  CAGTGCTGTG AGGCCCAGGG CGGACAGGGT GTGAATAATG CGCACACGAC TTATTTTGGG ATGACGAGCG
      GTCACGACAC TCCGGGTCCC GCCTGTCCCA CACTTATTAC GCGTGTGCTG AATAAAACCC TACTGCTCGC

1751  GAGCCTGTAC ATGGTGATCA GTCATTTCAG CCTCCCCGAG TGTACCAGGA AAGATGGATG TCCTGGAGAG
      CTCGGACATG TACCACTAGT CAGTAAAGTC GGAGGGGCTC ACATGGTCCT TTCTACCTAC AGGACCTCTC
```

FIG._48D

```
1821  GGGGCCGCGT AACCACTGAA GGATGAGCTG TAAAGAAGCA GATCGTTCAA ACATTTGGCA ATAAAGTTTC
      CCCCGGCGCA TTGGTGACTT CCTACTCGAC ATTTCTTCGT CTAGCAAGTT TGTAAACCGT TATTTCAAAG

1891  TTAAGATTGA ATCCTGTTGC CGGTCTTGCG ATGATTATCA TATAATTTCT GTTGAATTAC GTTAAGCATG
      AATTCTAACT TAGGACAACG GCCAGAACGC TACTAATAGT ATATTAAAGA CAACTTAATG CAATTCGTAC

1961  TAATAATTAA CATGTAATGC ATGACGTTAT TTATGAGATG GGTTTTTATG ATTAGAGTCC CGCAATTATA
      ATTATTAATT GTACATTACG TACTGCAATA AATACTCTAC CCAAAAATAC TAATCTCAGG GCGTTAATAT

                                      BssHII                 BssHII
                                      ~~~~~~                 ~~~~~~
2031  CATTTAATAC GCGATAGAAA ACAAAATATA GCGCGCAAAC TAGGATAAAT TATCGCGCGC GGTGTCATCT
      GTAAATTATG CGCTATCTTT TGTTTTATAT CGCGCGTTTG ATCCTATTTA ATAGCGCGCG CCACAGTAGA

                                XbaI
                               ~~~~~~
                 ClaI HindIII
                 ~~~~~~~~~~~~~
2101  ATGTTACTAG ATCGATAAGC TTCTAGAGCG GCCGGTGGAG CTCCAATTCG CCCTATAGTG AGTCGTATTA
      TACAATGATC TAGCTATTCG AAGATCTCGC CGGCCACCTC GAGGTTAAGC GGGATATCAC TCAGCATAAT

       BssHII
       ~~~~~~
2171  CGCGCGCTCA CTGGCCGTCG TTTTACAACG TCGTGACTGG GAAAACCCTG GCGTTACCCA ACTTAATCGC
      GCGCGCGAGT GACCGGCAGC AAAATGTTGC AGCACTGACC CTTTTGGGAC CGCAATGGGT TGAATTAGCG

2241  CTTGCAGCAC ATCCCCCTTT CGCCAGCTGG CGTAATAGCG AAGAGGCCCG CACCGATCGC CCTTCCCAAC
      GAACGTCGTG TAGGGGGAAA GCGGTCGACC GCATTATCGC TTCTCCGGGC GTGGCTAGCG GGAAGGGTTG

2311  AGTTGCGCAG CCTGAATGGC GAATGGGACG CGCCCTGTAG CGGCGCATTA AGCGCGGCGG GTGTGGTGGT
      TCAACGCGTC GGACTTACCG CTTACCCTGC GCGGGACATC GCCGCGTAAT TCGCGCCGCC CACACCACCA

2381  TACGCGCAGC GTGACCGCTA CACTTGCCAG CGCCCTAGCG CCCGCTCCTT TCGCTTTCTT CCCTTCCTTT
      ATGCGCGTCG CACTGGCGAT GTGAACGGTC GCGGGATCGC GGGCGAGGAA AGCGAAAGAA GGGAAGGAAA
```

FIG._48E

```
2451  CTCGCCACGT TCGCCGGCTT TCCCCGTCAA GCTCTAAATC GGGGGCTCCC TTTAGGGTTC CGATTTAGTG
      GAGCGGTGCA AGCGGCCGAA AGGGGCAGTT CGAGATTTAG CCCCCGAGGG AAATCCCAAG GCTAAATCAC

2521  CTTTACGGCA CCTCGACCCC AAAAAACTTG ATTAGGGTGA TGGTTCACGT AGTGGGCCAT CGCCCTGATA
      GAAATGCCGT GGAGCTGGGG TTTTTTGAAC TAATCCCACT ACCAAGTGCA TCACCCGGTA GCGGGACTAT

2591  GACGGTTTTT CGCCCTTTGA CGTTGGAGTC CACGTTCTTT AATAGTGGAC TCTTGTTCCA AACTGGAACA
      CTGCCAAAAA GCGGGAAACT GCAACCTCAG GTGCAAGAAA TTATCACCTG AGAACAAGGT TTGACCTTGT

2661  ACACTCAACC CTATCTCGGT CTATTCTTTT GATTTATAAG GGATTTTGCC GATTTCGGCC TATTGGTTAA
      TGTGAGTTGG GATAGAGCCA GATAAGAAAA CTAAATATTC CCTAAAACGG CTAAAGCCGG ATAACCAATT

2731  AAAATGAGCT GATTTAACAA AAATTTAACG CGAATTTTAA CAAAATATTA ACGCTTACAA TTTAGGTGGC
      TTTTACTCGA CTAAATTGTT TTTAAATTGC GCTTAAAATT GTTTTATAAT TGCGAATGTT AAATCCACCG

2801  ACTTTTCGGG GAAATGTGCG CGGAACCCCT ATTTGTTTAT TTTTCTAAAT ACATTCAAAT ATGTATCCGC
      TGAAAAGCCC CTTTACACGC GCCTTGGGGA TAAACAAATA AAAAGATTTA TGTAAGTTTA TACATAGGCG

2871  TCATGAGACA ATAACCCTGA TAAATGCTTC AATAATATTG AAAAAGGAAG AGTATGAGTA TTCAACATTT
      AGTACTCTGT TATTGGGACT ATTTACGAAG TTATTATAAC TTTTTCCTTC TCATACTCAT AAGTTGTAAA

2941  CCGTGTCGCC CTTATTCCCT TTTTTGCGGC ATTTTGCCTT CCTGTTTTTG CTCACCCAGA AACGCTGGTG
      GGCACAGCGG GAATAAGGGA AAAAACGCCG TAAAACGGAA GGACAAAAAC GAGTGGGTCT TTGCGACCAC

3011  AAAGTAAAAG ATGCTGAAGA TCAGTTGGGT GCACGAGTGG GTTACATCGA ACTGGATCTC AACAGCGGTA
      TTTCATTTTC TACGACTTCT AGTCAACCCA CGTGCTCACC CAATGTAGCT TGACCTAGAG TTGTCGCCAT

3081  AGATCCTTGA GAGTTTTCGC CCCGAAGAAC GTTTTCCAAT GATGAGCACT TTTAAAGTTC TGCTATGTGG
      TCTAGGAACT CTCAAAAGCG GGGCTTCTTG CAAAAGGTTA CTACTCGTGA AAATTTCAAG ACGATACACC

3151  CGCGGTATTA TCCCGTATTG ACGCCGGGCA AGAGCAACTC GGTCGCCGCA TACACTATTC TCAGAATGAC
      GCGCCATAAT AGGGCATAAC TGCGGCCCGT TCTCGTTGAG CCAGCGGCGT ATGTGATAAG AGTCTTACTG

3221  TTGGTTGAGT ACTCACCAGT CACAGAAAAG CATCTTACGG ATGGCATGAC AGTAAGAGAA TTATGCAGTG
      AACCAACTCA TGAGTGGTCA GTGTCTTTTC GTAGAATGCC TACCGTACTG TCATTCTCTT AATACGTCAC
```

FIG._48F

```
3291  CTGCCATAAC CATGAGTGAT AACACTGCGG CCAACTTACT TCTGACAACG ATCGGAGGAC CGAAGGAGCT
      GACGGTATTG GTACTCACTA TTGTGACGCC GGTTGAATGA AGACTGTTGC TAGCCTCCTG GCTTCCTCGA

3361  AACCGCTTTT TTGCACAACA TGGGGGATCA TGTAACTCGC CTTGATCGTT GGGAACCGGA GCTGAATGAA
      TTGGCGAAAA AACGTGTTGT ACCCCCTAGT ACATTGAGCG GAACTAGCAA CCCTTGGCCT CGACTTACTT

3431  GCCATACCAA ACGACGAGCG TGACACCACG ATGCCTGTAG CAATGGCAAC AACGTTGCGC AAACTATTAA
      CGGTATGGTT TGCTGCTCGC ACTGTGGTGC TACGGACATC GTTACCGTTG TTGCAACGCG TTTGATAATT

3501  CTGGCGAACT ACTTACTCTA GCTTCCCGGC AACAATTAAT AGACTGGATG GAGGCGGATA AAGTTGCAGG
      GACCGCTTGA TGAATGAGAT CGAAGGGCCG TTGTTAATTA TCTGACCTAC CTCCGCCTAT TTCAACGTCC

3571  ACCACTTCTG CGCTCGGCCC TTCCGGCTGG CTGGTTTATT GCTGATAAAT CTGGAGCCGG TGAGCGTGGG
      TGGTGAAGAC GCGAGCCGGG AAGGCCGACC GACCAAATAA CGACTATTTA GACCTCGGCC ACTCGCACCC

3641  TCTCGCGGTA TCATTGCAGC ACTGGGGCCA GATGGTAAGC CCTCCCGTAT CGTAGTTATC TACACGACGG
      AGAGCGCCAT AGTAACGTCG TGACCCCGGT CTACCATTCG GGAGGGCATA GCATCAATAG ATGTGCTGCC

3711  GGAGTCAGGC AACTATGGAT GAACGAAATA GACAGATCGC TGAGATAGGT GCCTCACTGA TTAAGCATTG
      CCTCAGTCCG TTGATACCTA CTTGCTTTAT CTGTCTAGCG ACTCTATCCA CGGAGTGACT AATTCGTAAC

3781  GTAACTGTCA GACCAAGTTT ACTCATATAT ACTTTAGATT GATTTAAAAC TTCATTTTTA ATTTAAAAGG
      CATTGACAGT CTGGTTCAAA TGAGTATATA TGAAATCTAA CTAAATTTTG AAGTAAAAAT TAAATTTTCC

3851  ATCTAGGTGA AGATCCTTTT TGATAATCTC ATGACCAAAA TCCCTTAACG TGAGTTTTCG TTCCACTGAG
      TAGATCCACT TCTAGGAAAA ACTATTAGAG TACTGGTTTT AGGGAATTGC ACTCAAAAGC AAGGTGACTC

3921  CGTCAGACCC CGTAGAAAAG ATCAAAGGAT CTTCTTGAGA TCCTTTTTTT CTGCGCGTAA TCTGCTGCTT
      GCAGTCTGGG GCATCTTTTC TAGTTTCCTA GAAGAACTCT AGGAAAAAAA GACGCGCATT AGACGACGAA

3991  GCAAACAAAA AAACCACCGC TACCAGCGGT GGTTTGTTTG CCGGATCAAG AGCTACCAAC TCTTTTTCCG
      CGTTTGTTTT TTTGGTGGCG ATGGTCGCCA CCAAACAAAC GGCCTAGTTC TCGATGGTTG AGAAAAAGGC

4061  AAGGTAACTG GCTTCAGCAG AGCGCAGATA CCAAATACTG TCCTTCTAGT GTAGCCGTAG TTAGGCCACC
      TTCCATTGAC CGAAGTCGTC TCGCGTCTAT GGTTTATGAC AGGAAGATCA CATCGGCATC AATCCGGTGG
```

FIG._48G

```
4131  ACTTCAAGAA CTCTGTAGCA CCGCCTACAT ACCTCGCTCT GCTAATCCTG TTACCAGTGG CTGCTGCCAG
      TGAAGTTCTT GAGACATCGT GGCGGATGTA TGGAGCGAGA CGATTAGGAC AATGGTCACC GACGACGGTC

4201  TGGCGATAAG TCGTGTCTTA CCGGGTTGGA CTCAAGACGA TAGTTACCGG ATAAGGCGCA GCGGTCGGGC
      ACCGCTATTC AGCACAGAAT GGCCCAACCT GAGTTCTGCT ATCAATGGCC TATTCCGCGT CGCCAGCCCG

4271  TGAACGGGGG GTTCGTGCAC ACAGCCCAGC TTGGAGCGAA CGACCTACAC CGAACTGAGA TACCTACAGC
      ACTTGCCCCC CAAGCACGTG TGTCGGGTCG AACCTCGCTT GCTGGATGTG GCTTGACTCT ATGGATGTCG

4341  GTGAGCTATG AGAAAGCGCC ACGCTTCCCG AAGGGAGAAA GGCGGACAGG TATCCGGTAA GCGGCAGGGT
      CACTCGATAC TCTTTCGCGG TGCGAAGGGC TTCCCTCTTT CCGCCTGTCC ATAGGCCATT CGCCGTCCCA

4411  CGGAACAGGA GAGCGCACGA GGGAGCTTCC AGGGGGAAAC GCCTGGTATC TTTATAGTCC TGTCGGGTTT
      GCCTTGTCCT CTCGCGTGCT CCCTCGAAGG TCCCCCTTTG CGGACCATAG AAATATCAGG ACAGCCCAAA

4481  CGCCACCTCT GACTTGAGCG TCGATTTTTG TGATGCTCGT CAGGGGGGCG GAGCCTATGG AAAAACGCCA
      GCGGTGGAGA CTGAACTCGC AGCTAAAAAC ACTACGAGCA GTCCCCCCGC CTCGGATACC TTTTTGCGGT

4551  GCAACGCGGC CTTTTTACGG TTCCTGGCCT TTTGCTGGCC TTTTGCTCAC ATGTTCTTTC CTGCGTTATC
      CGTTGCGCCG GAAAAATGCC AAGGACCGGA AAACGACCGG AAAACGAGTG TACAAGAAAG GACGCAATAG

4621  CCCTGATTCT GTGGATAACC GTATTACCGC CTTTGAGTGA GCTGATACCG CTCGCCGCAG CCGAACGACC
      GGGACTAAGA CACCTATTGG CATAATGGCG GAAACTCACT CGACTATGGC GAGCGGCGTC GGCTTGCTGG

4691  GAGCGCAGCG AGTCAGTGAG CGAGGAAGCG GAAGAGCGCC CAATACGCAA ACCGCCTCTC CCCGCGCGTT
      CTCGCGTCGC TCAGTCACTC GCTCCTTCGC CTTCTCGCGG GTTATGCGTT TGGCGGAGAG GGGCGCGCAA

4761  GGCCGATTCA TTAATGCAGC TGGCACGACA GGTTTCCCGA CTGGAAAGCG GGCAGTGAGC GCAACGCAAT
      CCGGCTAAGT AATTACGTCG ACCGTGCTGT CCAAAGGGCT GACCTTTCGC CCGTCACTCG CGTTGCGTTA

4831  TAATGTGAGT TAGCTCACTC ATTAGGCACC CCAGGCTTTA CACTTTATGC TTCCGGCTCG TATGTTGTGT
      ATTACACTCA ATCGAGTGAG TAATCCGTGG GGTCCGAAAT GTGAAATACG AAGGCCGAGC ATACAACACA
```

FIG._48H

```
                                                                                BssHII
                                                                               ~~~~~~~~
4901  GGAATTGTGA GCGGATAACA ATTTCACACA GGAAACAGCT ATGACCATGA TTACGCCAAG CGCGCAATTA
      CCTTAACACT CGCCTATTGT TAAAGTGTGT CCTTTGTCGA TACTGGTACT AATGCGGTTC GCGCGTTAAT

                                   NcoI

                                   KpnI
                                  ~~~~~
4971  ACCCTCACTA AAGGGAACAA AAGCTGGGTA C
      TGGGAGTGAT TTCCCTTGTT TTCGACCCAT G
```

FIG._48I

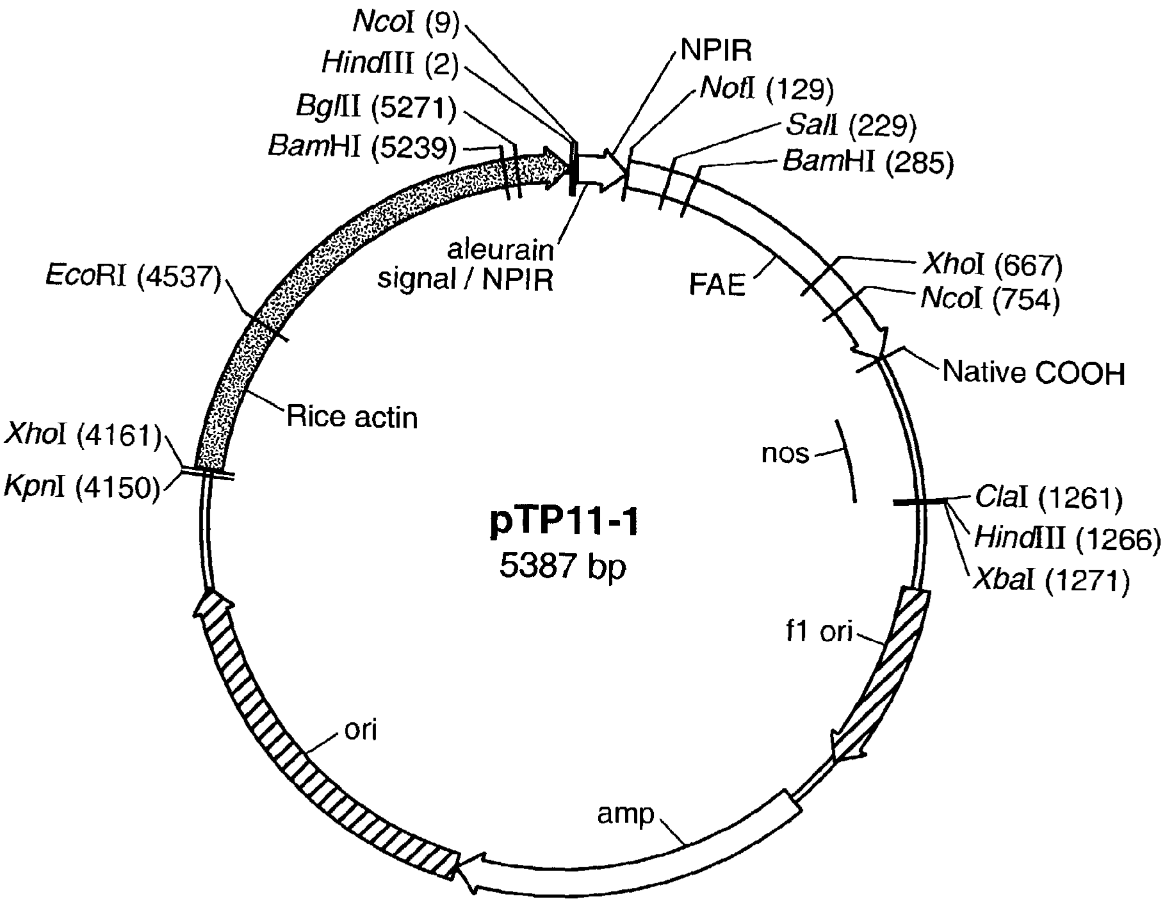
FIG._49A

```
                 NcoI
                ~~~~~~~~
         HindIII
         ~~~~~~~
                   M   A  H  A   R  V  L   L  L  A  L   A  V  L   A  T  A   A  V  A  V
   1  AAGCTTACCA TGGCCCACGC CCGCGTCCTC CTCCTGGCGC TCGCCGTGCT GGCCACGGCC GCCGTCGCCG
                                                                       NotI
                                                                     ~~~~~~~~~
      · A  S  S   S  S  F   A  D  S  N   P  I  R   P  V  T   D  R  A  A   A  S  T ·
  71  TCGCCTCCTC CTCCTCCTTC GCCGACTCCA ACCCGATCCG GCCCGTCACC GACCGCGCGG CCGCCTCCAC
      ·Q  G  I   S  E  D  L   Y  S  R   L  V  E   M  A  T  I   S  Q  A   A  Y  A
 141  GCAGGGCATC TCCGAAGACC TCTACAGCCG TTTAGTCGAA ATGGCCACTA TCTCCCAAGC TGCCTACGCC
                        SalI
                       ~~~~~~~~
                        AccI
                       ~~~~~~~~
       D  L  C  N   I  P  S   T  I  I   K  G  E  K   I  Y  N   S  Q  T   D  I  N  G
 211  GACCTGTGCA ACATTCCGTC GACTATTATC AAGGGAGAGA AAATTTACAA TTCTCAAACT GACATTAACG
        BamHI
        ~~~~~~~
      · W  I  L   R  D  D   S  S  K  E   I  I  T   V  F  R   G  T  G  S   D  T  N ·
 281  GATGGATCCT CCGCGACGAC AGCAGCAAAG AAATAATCAC CGTCTTCCGT GGCACTGGTA GTGATACGAA
      ·L  Q  L   D  T  N  Y   T  L  T   P  F  D   T  L  P  Q   C  N  G   C  E  V
 351  TCTACAACTC GATACTAACT ACACCCTCAC GCCTTTCGAC ACCCTACCAC AATGCAACGG TTGTGAAGTA
       H  G  G  Y   Y  I  G   W  V  S   V  Q  D  Q   V  E  S   L  V  K   Q  Q  V  S
 421  CACGGTGGAT ATTATATTGG ATGGGTCTCC GTCCAGGACC AAGTCGAGTC GCTTGTCAAA CAGCAGGTTA
      · Q  Y  P   D  Y  A   L  T  V  T   G  H  X   L  G  A   S  L  A  A   L  T  A ·
 491  GCCAGTATCC GGACTACGCG CTGACCGTGA CCGGCCACKC CCTCGGCGCC TCCCTGGCGG CACTCACTGC
      ·A  Q  L   S  A  T  Y   D  N  I   R  L  Y   T  F  G  E   P  R  S   G  N  Q
 561  CGCCCAGCTG TCTGCGACAT ACGACAACAT CCGCCTGTAC ACCTTCGGCG AACCGCGCAG CGGCAATCAG
                                               XhoI
                                              ~~~~~~~~
       A  F  A  S   Y  M  N   D  A  F   Q  A  S  S   P  D  T   T  Q  Y   F  R  V  T
 631  GCCTTCGCGT CGTACATGAA CGATGCCTTC CAAGCCTCGA GCCCAGATAC GACGCAGTAT TTCCGGGTCA
```

FIG._49B

```
                                                              NcoI
                                                             ~~~~~~~
      · H  A  N   D  G  I   P  N  L  P   P  V  E   Q  G  Y   A  H  G  G   V  E  Y ·
 701  CTCATGCCAA CGACGGCATC CCAAACCTGC CCCCGGTGGA GCAGGGGTAC GCCCATGGCG GTGTAGAGTA
      ·W  S  V   D  P  Y  S   A  Q  N   T  F  V   C  T  G  D   E  V  Q   C  C  E
 771  CTGGAGCGTT GATCCTTACA GCGCCCAGAA CACATTTGTC TGCACTGGGG ATGAAGTGCA GTGCTGTGAG
       A  Q  G  G   Q  G  V   N  N  A   H  T  T  Y   F  G  M   T  S  G   A  C  T  W
 841  GCCCAGGGCG GACAGGGTGT GAATAATGCG CACACGACTT ATTTTGGGAT GACGAGCGGA GCCTGTACAT
      ·  *
 911  GGTGATCAGT CATTTCAGCC TCCCCGAGTG TACCAGGAAA GATGGATGTC CTGGAGAGGG GGCCGCGTAA
 981  CCACTGAAGG ATGAGCTGTA AAGAAGCAGA TCGTTCAAAC ATTTGGCAAT AAAGTTTCTT AAGATTGAAT
1051  CCTGTTGCCG GTCTTGCGAT GATTATCATA TAATTTCTGT TGAATTACGT TAAGCATGTA ATAATTAACA
1121  TGTAATGCAT GACGTTATTT ATGAGATGGG TTTTTATGAT TAGAGTCCCG CAATTATACA TTTAATACGC
                                                                            ClaI
1191  GATAGAAAAC AAAATATAGC GCGCAAACTA GGATAAATTA TCGCGCGCGG TGTCATCTAT GTTACTAGAT
         HindIII
         ~~~~~~~
      ClaI      XbaI
      ~~~~     ~~~~~~~
1261  CGATAAGCTT CTAGAGCGGC CGGTGGAGCT CCAATTCGCC CTATAGTGAG TCGTATTACG CGCGCTCACT
1331  GGCCGTCGTT TTACAACGTC GTGACTGGGA AAACCCTGGC GTTACCCAAC TTAATCGCCT TGCAGCACAT
1401  CCCCCTTTCG CCAGCTGGCG TAATAGCGAA GAGGCCCGCA CCGATCGCCC TTCCCAACAG TTGCGCAGCC
1471  TGAATGGCGA ATGGGACGCG CCCTGTAGCG GCGCATTAAG CGCGGCGGGT GTGGTGGTTA CGCGCAGCGT
1541  GACCGCTACA CTTGCCAGCG CCCTAGCGCC CGCTCCTTTC GCTTTCTTCC CTTCCTTTCT CGCCACGTTC
1611  GCCGGCTTTC CCCGTCAAGC TCTAAATCGG GGGCTCCCTT TAGGGTTCCG ATTTAGTGCT TTACGGCACC
1681  TCGACCCCAA AAAACTTGAT TAGGGTGATG GTTCACGTAG TGGGCCATCG CCCTGATAGA CGGTTTTTCG
1751  CCCTTTGACG TTGGAGTCCA CGTTCTTTAA TAGTGGACTC TTGTTCCAAA CTGGAACAAC ACTCAACCCT
1821  ATCTCGGTCT ATTCTTTTGA TTTATAAGGG ATTTTGCCGA TTTCGGCCTA TTGGTTAAAA AATGAGCTGA
1891  TTTAACAAAA ATTTAACGCG AATTTTAACA AAATATTAAC GCTTACAATT TAGGTGGCAC TTTTCGGGGA
1961  AATGTGCGCG GAACCCCTAT TTGTTTATTT TTCTAAATAC ATTCAAATAT GTATCCGCTC ATGAGACAAT
2031  AACCCTGATA AATGCTTCAA TAATATTGAA AAAGGAAGAG TATGAGTATT CAACATTTCC GTGTCGCCCT
2101  TATTCCCTTT TTTGCGGCAT TTTGCCTTCC TGTTTTTGCT CACCCAGAAA CGCTGGTGAA AGTAAAAGAT
2171  GCTGAAGATC AGTTGGGTGC ACGAGTGGGT TACATCGAAC TGGATCTCAA CAGCGGTAAG ATCCTTGAGA
2241  GTTTTCGCCC CGAAGAACGT TTTCCAATGA TGAGCACTTT TAAAGTTCTG CTATGTGGCG CGGTATTATC
2311  CCGTATTGAC GCCGGGCAAG AGCAACTCGG TCGCCGCATA CACTATTCTC AGAATGACTT GGTTGAGTAC
2381  TCACCAGTCA CAGAAAAGCA TCTTACGGAT GGCATGACAG TAAGAGAATT ATGCAGTGCT GCCATAACCA
```

FIG._49C

```
2451  TGAGTGATAA CACTGCGGCC AACTTACTTC TGACAACGAT CGGAGGACCG AAGGAGCTAA CCGCTTTTTT
2521  GCACAACATG GGGGATCATG TAACTCGCCT TGATCGTTGG GAACCGGAGC TGAATGAAGC CATACCAAAC
2591  GACGAGCGTG ACACCACGAT GCCTGTAGCA ATGGCAACAA CGTTGCGCAA ACTATTAACT GGCGAACTAC
2661  TTACTCTAGC TTCCCGGCAA CAATTAATAG ACTGGATGGA GGCGGATAAA GTTGCAGGAC CACTTCTGCG
2731  CTCGGCCCTT CCGGCTGGCT GGTTTATTGC TGATAAATCT GGAGCCGGTG AGCGTGGGTC TCGCGGTATC
2801  ATTGCAGCAC TGGGGCCAGA TGGTAAGCCC TCCCGTATCG TAGTTATCTA CACGACGGGG AGTCAGGCAA
2871  CTATGGATGA ACGAAATAGA CAGATCGCTG AGATAGGTGC CTCACTGATT AAGCATTGGT AACTGTCAGA
2941  CCAAGTTTAC TCATATATAC TTTAGATTGA TTTAAAACTT CATTTTTAAT TTAAAAGGAT CTAGGTGAAG
3011  ATCCTTTTTG ATAATCTCAT GACCAAAATC CCTTAACGTG AGTTTTCGTT CCACTGAGCG TCAGACCCCG
3081  TAGAAAAGAT CAAAGGATCT TCTTGAGATC CTTTTTTTCT GCGCGTAATC TGCTGCTTGC AAACAAAAAA
3151  ACCACCGCTA CCAGCGGTGG TTTGTTTGCC GGATCAAGAG CTACCAACTC TTTTTCCGAA GGTAACTGGC
3221  TTCAGCAGAG CGCAGATACC AAATACTGTC CTTCTAGTGT AGCCGTAGTT AGGCCACCAC TTCAAGAACT
3291  CTGTAGCACC GCCTACATAC CTCGCTCTGC TAATCCTGTT ACCAGTGGCT GCTGCCAGTG GCGATAAGTC
3361  GTGTCTTACC GGGTTGGACT CAAGACGATA GTTACCGGAT AAGGCGCAGC GGTCGGGCTG AACGGGGGGT
3431  TCGTGCACAC AGCCCAGCTT GGAGCGAACG ACCTACACCG AACTGAGATA CCTACAGCGT GAGCTATGAG
3501  AAAGCGCCAC GCTTCCCGAA GGGAGAAAGG CGGACAGGTA TCCGGTAAGC GGCAGGGTCG GAACAGGAGA
3571  GCGCACGAGG GAGCTTCCAG GGGGAAACGC CTGGTATCTT TATAGTCCTG TCGGGTTTCG CCACCTCTGA
3641  CTTGAGCGTC GATTTTTGTG ATGCTCGTCA GGGGGGCGGA GCCTATGGAA AAACGCCAGC AACGCGGCCT
3711  TTTTACGGTT CCTGGCCTTT TGCTGGCCTT TTGCTCACAT GTTCTTTCCT GCGTTATCCC CTGATTCTGT
3781  GGATAACCGT ATTACCGCCT TTGAGTGAGC TGATACCGCT CGCCGCAGCC GAACGACCGA GCGCAGCGAG
3851  TCAGTGAGCG AGGAAGCGGA AGAGCGCCCA ATACGCAAAC CGCCTCTCCC CGCGCGTTGG CCGATTCATT
3921  AATGCAGCTG GCACGACAGG TTTCCCGACT GGAAAGCGGG CAGTGAGCGC AACGCAATTA ATGTGAGTTA
3991  GCTCACTCAT TAGGCACCCC AGGCTTTACA CTTTATGCTT CCGGCTCGTA TGTTGTGTGG AATTGTGAGC
4061  GGATAACAAT TTCACACAGG AAACAGCTAT GACCATGATT ACGCCAAGCG CGCAATTAAC CCTCACTAAA
                       KpnI          XhoI
                      ~~~~~~~       ~~~~~~
4131  GGGAACAAAA GCTGGGTACC GGGCCCCCCC TCGAGGTCAT TCATATGCTT GAGAAGAGAG TCGGGATAGT
4201  CCAAAATAAA ACAAAGGTAA GATTACCTGG TCAAAAGTGA AAACATCAGT TAAAAGGTGG TATAAGTAAA
4271  ATATCGGTAA TAAAAGGTGG CCCAAAGTGA AATTTACTCT TTTCTACTAT TATAAAAATT GAGGATGTTT
4341  TGTCGGTACT TTGATACGTC ATTTTTGTAT GAATTGGTTT TTAAGTTTAT TCGCGATTTG GAAATGCATA
4411  TCTGTATTTG AGTCGGTTTT TAAGTTCGTT GCTTTTGTAA ATACAGAGGG ATTTGTATAA GAAATATCTT
                                                                EcoRI
                                                               ~~~~~~
4481  TAAAAAACCC ATATGCTAAT TTGACATAAT TTTTGAGAAA AATATATATT CAGGCGAATT CCACAATGAA
4551  CAATAATAAG ATTAAAATAG CTTGCCCCCG TTGCAGCGAT GGGTATTTTT TCTAGTAAAA TAAAAGATAA
4621  ACTTAGACTC AAAACATTTA CAAAAACAAC CCCTAAAGTC CTAAAGCCCA AAGTGCTATG CACGATCCAT
```

FIG._49D

```
4691  AGCAAGCCCA GCCCAACCCA ACCCAACCCA ACCCACCCCA GTGCAGCCAA CTGGCAAATA GTCTCCACCC
4761  CCGGCACTAT CACCGTGAGT TGTCCGCACC ACCGCACGTC TCGCAGCCAA AAAAAAAAAA AGAAAGAAAA
4831  AAAAGAAAAA GAAAAACAGC AGGTGGGTCC GGGTCGTGGG GGCCGGAAAA GCGAGGAGGA TCGCGAGCAG
4901  CGACGAGGCC CGGCCCTCCC TCCGCTTCCA AAGAAACGCC CCCCATCGCC ACTATATACA TACCCCCCCC
4971  TCTCCTCCCA TCCCCCCAAC CCTACCACCA CCACCACCAC CACCTCCTCC CCCCTCGCTG CCGGACGACG
5041  AGCTCCTCCC CCCTCCCCCT CCGCCGCCGC CGGTAACCAC CCCGCCCCTC TCCTCTTTCT TTCTCCGTTT
5111  TTTTTTTCGT CTCGGTCTCG ATCTTTGGCC TTGGTAGTTT GGGTGGGCGA GAGCGGCTTC GTCGCCCAGA
                                                                         BamHI
                                                                        ~~~~~~
5181  TCGGTGCGCG GGAGGGGCGG GATCTCGCGG CTGGCGTCTC CGGGCGTGAG TCGGCCCGGA TCCTCGCGGG
                           BglII
                          ~~~~~~
5251  GAATGGGGCT CTCGGATGTA GATCTTCTTT CTTTCTTCTT TTTGTGGTAG AATTTGAATC CCTCAGCATT
5321  GTTCATCGGT AGTTTTTCTT TTCATGATTT GTGACAAATG CAGCCTCGTG CGGAGCTTTT TTGTAGC
```

FIG._49E

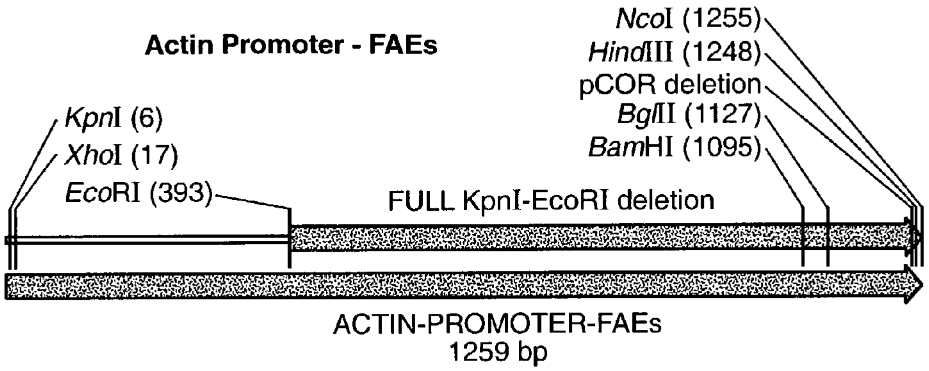

```
       KpnI           XhoI
       ~~~~~~         ~~~~~~~
  1    GGTACCGGGC CCCCCCTCGA GGTCATTCAT ATGCTTGAGA AGAGAGTCGG GATAGTCCAA AATAAAACAA
       CCATGGCCCG GGGGGGAGCT CCAGTAAGTA TACGAACTCT TCTCTCAGCC CTATCAGGTT TTATTTTGTT

 71    AGGTAAGATT ACCTGGTCAA AAGTGAAAAC ATCAGTTAAA AGGTGGTATA AGTAAAATAT CGGTAATAAA
       TCCATTCTAA TGGACCAGTT TTCACTTTTG TAGTCAATTT TCCACCATAT TCATTTTATA GCCATTATTT

141    AGGTGGCCCA AAGTGAAATT TACTCTTTTC TACTATTATA AAAATTGAGG ATGTTTTGTC GGTACTTTGA
       TCCACCGGGT TTCACTTTAA ATGAGAAAAG ATGATAATAT TTTTAACTCC TACAAAACAG CCATGAAACT

211    TACGTCATTT TTGTATGAAT TGGTTTTTAA GTTTATTCGC GATTTGGAAA TGCATATCTG TATTTGAGTC
       ATGCAGTAAA AACATACTTA ACCAAAAATT CAAATAAGCG CTAAACCTTT ACGTATAGAC ATAAACTCAG

281    GGTTTTTAAG TTCGTTGCTT TTGTAAATAC AGAGGGATTT GTATAAGAAA TATCTTTAAA AAACCCATAT
       CCAAAAATTC AAGCAACGAA AACATTTATG TCTCCCTAAA CATATTCTTT ATAGAAATTT TTTGGGTATA

                                                EcoRI
                                               ~~~~~~
351    GCTAATTTGA CATAATTTTT GAGAAAAATA TATATTCAGG CGAATTCCAC AATGAACAAT AATAAGATTA
       CGATTAAACT GTATTAAAAA CTCTTTTTAT ATATAAGTCC GCTTAAGGTG TTACTTGTTA TTATTCTAAT

421    AAATAGCTTG CCCCCGTTGC AGCGATGGGT ATTTTTTCTA GTAAAATAAA AGATAAACTT AGACTCAAAA
       TTTATCGAAC GGGGGCAACG TCGCTACCCA TAAAAAAGAT CATTTTATTT TCTATTTGAA TCTGAGTTTT

491    CATTTACAAA AACAACCCCT AAAGTCCTAA AGCCCAAAGT GCTATGCACG ATCCATAGCA AGCCCAGCCC
       GTAAATGTTT TTGTTGGGGA TTTCAGGATT TCGGGTTTCA CGATACGTGC TAGGTATCGT TCGGGTCGGG

561    AACCCAACCC AACCCAACCC ACCCCAGTGC AGCCAACTGG CAAATAGTCT CCACCCCCGG CACTATCACC
       TTGGGTTGGG TTGGGTTGGG TGGGGTCACG TCGGTTGACC GTTTATCAGA GGTGGGGGCC GTGATAGTGG

631    GTGAGTTGTC CGCACCACCG CACGTCTCGC AGCCAAAAAA AAAAAAAGAA AGAAAAAAAA GAAAAAGAAA
       CACTCAACAG GCGTGGTGGC GTGCAGAGCG TCGGTTTTTT TTTTTTTCTT TCTTTTTTTT CTTTTTCTTT

701    AACAGCAGGT GGGTCCGGGT CGTGGGGGCC GGAAAAGCGA GGAGGATCGC GAGCAGCGAC GAGGCCCGGC
       TTGTCGTCCA CCCAGGCCCA GCACCCCCGG CCTTTTCGCT CCTCCTAGCG CTCGTCGCTG CTCCGGGCCG
```

FIG._50A

```
 771  CCTCCCTCCG CTTCCAAAGA AACGCCCCCC ATCGCCACTA TATACATACC CCCCCCTCTC CTCCCATCCC
      GGAGGGAGGC GAAGGTTTCT TTGCGGGGGG TAGCGGTGAT ATATGTATGG GGGGGGAGAG GAGGGTAGGG

 841  CCCAACCCTA CCACCACCAC CACCACCACC TCCTCCCCCC TCGCTGCCGG ACGACGAGCT CCTCCCCCCT
      GGGTTGGGAT GGTGGTGGTG GTGGTGGTGG AGGAGGGGGG AGCGACGGCC TGCTGCTCGA GGAGGGGGGA

 911  CCCCCTCCGC CGCCGCCGGT AACCACCCCG CCCCTCTCCT CTTTCTTTCT CCGTTTTTTT TTTCGTCTCG
      GGGGGAGGCG GCGGCGGCCA TTGGTGGGGC GGGGAGAGGA GAAAGAAAGA GGCAAAAAAA AAAGCAGAGC

 981  GTCTCGATCT TTGGCCTTGG TAGTTTGGGT GGGCGAGAGC GGCTTCGTCG CCCAGATCGG TGCGCGGGAG
      CAGAGCTAGA AACCGGAACC ATCAAACCCA CCCGCTCTCG CCGAAGCAGC GGGTCTAGCC ACGCGCCCTC

                                                  BamHI
                                                 ~~~~~~
1051  GGGCGGGATC TCGCGGCTGG CGTCTCCGGG CGTGAGTCGG CCCGGATCCT CGCGGGGAAT GGGGCTCTCG
      CCCGCCCTAG AGCGCCGACC GCAGAGGCCC GCACTCAGCC GGGCCTAGGA GCGCCCCTTA CCCCGAGAGC

         BglII
        ~~~~~~~
1121  GATGTAGATC TTCTTTCTTT CTTCTTTTTG TGGTAGAATT TGAATCCCTC AGCATTGTTC ATCGGTAGTT
      CTACATCTAG AAGAAAGAAA GAAGAAAAAC ACCATCTTAA ACTTAGGGAG TCGTAACAAG TAGCCATCAA

                                                             HindIII  NcoI
                                                             ~~~~~~~ ~~~~~
1191  TTTCTTTTCA TGATTTGTGA CAAATGCAGC CTCGTGCGGA GCTTTTTTGT AGGTAGAAGC TTACCATGG
      AAAGAAAAGT ACTAAACACT GTTTACGTCG GAGCACGCCT CGAAAAAACA TCCATCTTCG AATGGTACC
```

KpnI-EcoRI - deletion underlined and restored NCO site in bold in vectors pJQ4.9, pJQ3.2 and pJO6.3.

*FIG._50B*

ALEURAIN_deleted NPIR (Apoplast) Structure and Sequence

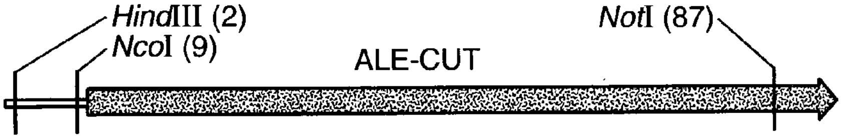

ALEURAIN-NPIR-DEL
93 bp

```
+1          M  A  H  A  R  V  L  L  L  A  L  A  V  L  A  T  A  A  V  A
  HindIII NcoI
  ~~~~~~ ~~~~~~~
1 AAGCTTACCA TGGCCCACGC CCGCGTCCTC CTCCTGGCGC TCGCCGTGCT GGCCACGGCC GCCGTCGCCG
  TTCGAATGGT ACCGGGTGCG GGCGCAGGAG GAGGACCGCG AGCGGCACGA CCGGTGCCGG CGGCAGCGGC

+1 V  A  S  S  R  A  A
                NotI
              ~~~~~~~~~
71 TCGCCTCCTC CCGCGCGGCC GCC
   AGCGGAGGAG GGCGCGCCGG CGG
```

*FIG._51*

SEE1 ( Senescence enhanced ) PROMOTER sequence

```
  1   CATGGGCCAG GTATAATTAT GGGATATCTC AAGCAAATAA TCGAAATATC ACCATTGGCT ACAATATCTG
                     PstI                                XbaI     XbaI
                    ~~~~~~~                             ~~~~~~~ ~~~~~~
 71   AGCTCCGAGT TCTGACTGCA GTCTGGATGA CGCGTGTTGT ATCTAGAACT CTAGATAGCA CAGCCACAGC
141   ACCTACAGGA GTGCGACACT TGTGGACTGT AGTAGTGTTG GAGACGGAGC TCTTTCCTAC CTCCTGACGT
211   TGCCGCCGTT GTCCATTCCA ACGGCATCAC TCTCAACCAA TCACGCGCTC CCAACAAAAT ATCGTCCCCC
281   ATGTCTTGGC GGAGAGAGAG TACATACATG CTGTCGCGCC GTTTTTGTCT GAATCTCGCT TCCACTGGCC
                  SmaI
                 ~~~~~~~
351   AATCAGCTCA GCTCCCGGGA GCTCACTCAT TCAAGATCCC ATCGTCGTCG TCACCCCTGG CGTCATGGGA
421   TGGAAAAGAA CCTCCGTTGC TCGGATGAGT CAGCCATATC CCCGAACAGA GTACTGCAAG ATAACCCAAT
                                  SphI
                                 ~~~~~~~
491   TCAGATTCCC CCAATAGAGA AAGTATAGCA TGCTTTCGGG TTTTGTTTGG CTTAATTGAC TTTATTTTTG
561   TTGGAGTTGA ATGCTGATTT GTTGTGTAAA ATGCCCAACC ATCTGAATAT CGAGACGGAT AATAGGCTGG
631   CTAATTAATT TATAGCAAGA TTCTGTAGTG CACATCGCAA ATATCTTTCT GGGCATTACA GCTGGAGGCT
                        PstI
                       ~~~~~~~
701   TCATCAGCCT GAAACACTCT GCAGAGCCTG AAGCAAGTGG TGAAGCGTGG CGATGAGATG GGTATAAAAC
771   CCCCGGCACC GGGACGCGAG CTCCCGCCTA CCAGTACCAT CTCGCCTCGC TCCCCCTGCC GGACGACCCA
841   GTAAAATACT GTTGCCCACT CGCCGGCGAG ATG
```

FIG._52

SEE1 ( Senescence enhanced ) PROMOTER plus vacuolar aleurain SIGNAL/NPIR sequence

```
  1   CATGGGCCAG GTATAATTAT GGGATATCTC AAGCAAATAA TCGAAATATC ACCATTGGCT ACAATATCTG
                     PstI                                XbaI     XbaI
                    ~~~~~~~                             ~~~~~~~ ~~~~~~
 71   AGCTCCGAGT TCTGACTGCA GTCTGGATGA CGCGTGTTGT ATCTAGAACT CTAGATAGCA CAGCCACAGC
141   ACCTACAGGA GTGCGACACT TGTGGACTGT AGTAGTGTTG GAGACGGAGC TCTTTCCTAC CTCCTGACGT
211   TGCCGCCGTT GTCCATTCCA ACGGCATCAC TCTCAACCAA TCACGCGCTC CCAACAAAAT ATCGTCCCCC
281   ATGTCTTGGC GGAGAGAGAG TACATACATG CTGTCGCGCC GTTTTTGTCT GAATCTCGCT TCCACTGGCC
                  SmaI
                 ~~~~~~~
351   AATCAGCTCA GCTCCCGGGA GCTCACTCAT TCAAGATCCC ATCGTCGTCG TCACCCCTGG CGTCATGGGA
421   TGGAAAAGAA CCTCCGTTGC TCGGATGAGT CAGCCATATC CCCGAACAGA GTACTGCAAG ATAACCCAAT
                                  SphI
                                 ~~~~~~~
491   TCAGATTCCC CCAATAGAGA AAGTATAGCA TGCTTTCGGG TTTTGTTTGG CTTAATTGAC TTTATTTTTG
561   TTGGAGTTGA ATGCTGATTT GTTGTGTAAA ATGCCCAACC ATCTGAATAT CGAGACGGAT AATAGGCTGG
631   CTAATTAATT TATAGCAAGA TTCTGTAGTG CACATCGCAA ATATCTTTCT GGGCATTACA GCTGGAGGCT
                        PstI
                       ~~~~~~~
701   TCATCAGCCT GAAACACTCT GCAGAGCCTG AAGCAAGTGG TGAAGCGTGG CGATGAGATG GGTATAAAAC
771   CCCCGGCACC GGGACGCGAG CTCCCGCCTA CCAGTACCAT CTCGCCTCGC TCCCCCTGCC GGACGACCCA
                                      M  A  H  G   R  I  L   F  L  A   L  A  V  L
841   GTAAAATACT GTTGCCCACT CGCCGGCGAG ATGGCCCACG GCCGCATCCT CTTCTTGGCG CTCGCCGTCT
                                                                           BssHII
                                                                              NotI
      · A  T  A   A  V  A   A  A  S  L   A  D  S   N  P  I   R  P  V  T   E  R  A ·
911   TGGCCACCGC CGCGGTGGCC GCCGCATCNT TGGCGGACTC CAACCCGATC CGGCCCGTCA CCGAGCGCGC
       NotI
      ~~~~~~
      · A  A
981   GGCCGCC
```

FIG._53

SEQUENCE LISTING

<160> NUMBER OF SEQ ID NOS: 97

<210> SEQ ID NO 1

-continued

<211> LENGTH: 2436
<212> TYPE: DNA
<213> ORGANISM: Aspergillus niger

<400> SEQUENCE: 1

```
ccatggtggt gtcgatatcg gcagtagtct ttgccgaaac gttgagggtt acagtgatct     60
gcgtcggaca tacttcgggg aatctacggc ggaatatcaa agtcttcgga atatccatat    120
tgggaaagga cagaagctcc ggggtagttt gatagatgag ctccggtgta ttaaatcggg    180
agctgacagg agtgagcgtc atgtagacca tctagtaatg tcagtcgcgc gcaatttcgc    240
acatgaaaca agttgatttc gggaccccat tgttacatct ctcggctaca gctcgagatg    300
tgcctgccga gtatacttag aagccatgcc agcgtgttgt tatacgacca aaagtcaggg    360
aatatgaaac gatcgtcgga tatttcttgt ttttatccta aattagtctt ccagtggttt    420
atttaagaga tagatccctt cacaaacact catccaacgg acttctcata ccactcattg    480
acataatttc aaacagctcc aggcgcattt agttcaacat gaagcaattc tccgccaaac    540
acgtcctcgc agttgtggtg actgcagggc acgccttagc agcctctacg caaggcatct    600
ccgaagacct ctacagccgt ttagtcgaaa tggccactat ctcccaagct gcctacgccg    660
acctgtgcaa cattccgtcg actattatca agggagagaa aatttacaat tctcaaactg    720
acattaacgg atggatcctc cgcgacgaca gcagcaaaga aataatcacc gtcttccgtg    780
gcactggtag tgatacgaat ctacaactcg atactaacta caccctcacg cctttcgaca    840
ccctaccaca atgcaacggt tgtgaagtac acggtggata ttatattgga tgggtctccg    900
tccaggacca agtcgagtcg cttgtcaaac agcaggttag ccagtatccg gactatgcgc    960
tgactgtgac gggccacagg tatgccctcg tgatttcttt caattaagtg tataatactc   1020
actaactcta cgatagtctc ggagcgtccc tggcagcact cactgccgcc cagctgtctg   1080
cgacatacga caacatccgc ctgtacacct tcggcgaacc gcgcagcggc aatcaggcct   1140
tcgcgtcgta catgaacgat gccttccaag cctcgagccc agatacgacg cagtatttcc   1200
gggtcactca tgccaacgac ggcatcccaa acctgccccc ggtggagcag gggtacgccc   1260
atggcggtgt agagtactgg agcgttgatc cttacagcgc ccagaacaca tttgtctgca   1320
ctggggatga agtgcagtgc tgtgaggccc agggcggaca gggtgtgaat aatgcgcaca   1380
cgacttattt tgggatgacg agcggagcct gtacatggtg atcagtcatt tcagcctccc   1440
cgagtgtacc aggaaagatg gatgtcctgg agagggcatg catgtacgta tacccgaagc   1500
acactttttc ggtaaatcag gacatgtaat aagttccttc catgaataga tatggttacc   1560
ctcaccataa gccttgaggt tgcctttctc ttttgattgt gaatatatat ttaaagtaga   1620
tgacagatat ctctaaacac cttatccgct taaacccatc atagattgtg tcacgtgata   1680
gaccccttga atgatgagcg aaatgtatca gtcccgttta aatcaaaccc tttcagccta   1740
gcacagtcag aatacaccaa ccccattcta aggtagtact aaatatgaat acagcctaaa   1800
tgcatcgcta tatgatccca taaagaagca acaacctttc agatctcgtt ttgcgctgcg   1860
aagagctagc tctaccatgg tctcaattat gagtggagcg tttagtctcg tttaagccta   1920
gctatcttat aaggacaaca catgtacatg ggcttacttg tagagaggta ggatcccggg   1980
cttcttcaca tctcgaggag ttgtctacac gtcgcgtcca tgtcataagc cggtactcga   2040
cgttgtcgtg accgtgaccc agacccctgt tgatagcgtt gagaaggccc tatatttgaa   2100
tttccaatct cagctttacg aagatatgcc catggtggag ggttagtaaa ccgatgatga   2160
tcgtgtgcag catgagatga gaccgtggcc aatcctgttc aaatgccaag acccgcctcc   2220
```

-continued

```
taccacatgt aaggcatccg tcggccgcac gttgaattgt gcaaatgccg agatcataaa   2280

agcggccaca cttccacgtc ggtactggat gggttgcgcg tggccatact gtgttttcca   2340

ttgcgtgggt cgttcgtgtt actgcgacgc agattctgta ggcaaggcgc agggctctct   2400

tctgaggtag aaaacacccc atattaatct gaattc                             2436
```

<210> SEQ ID NO 2
<211> LENGTH: 281
<212> TYPE: PRT
<213> ORGANISM: Aspergillus niger

<400> SEQUENCE: 2

```
Met Lys Gln Phe Ser Ala Lys His Val Leu Ala Val Val Val Thr Ala
 1               5                  10                  15

Gly His Ala Leu Ala Ala Ser Thr Gln Gly Ile Ser Glu Asp Leu Tyr
            20                  25                  30

Ser Arg Leu Val Glu Met Ala Thr Ile Ser Gln Ala Ala Tyr Ala Asp
        35                  40                  45

Leu Cys Asn Ile Pro Ser Thr Ile Ile Lys Gly Glu Lys Ile Tyr Asn
    50                  55                  60

Ser Gln Thr Asp Ile Asn Gly Trp Ile Leu Arg Asp Asp Ser Ser Lys
65                  70                  75                  80

Glu Ile Ile Thr Val Phe Arg Gly Thr Gly Ser Asp Thr Asn Leu Gln
                85                  90                  95

Leu Asp Thr Asn Tyr Thr Leu Thr Pro Phe Asp Thr Leu Pro Gln Cys
            100                 105                 110

Asn Gly Cys Glu Val His Gly Gly Tyr Tyr Ile Gly Trp Val Ser Val
        115                 120                 125

Gln Asp Gln Val Glu Ser Leu Val Lys Gln Gln Val Ser Gln Tyr Pro
    130                 135                 140

Asp Tyr Ala Leu Thr Val Thr Gly His Ser Leu Gly Ala Ser Leu Ala
145                 150                 155                 160

Ala Leu Thr Ala Ala Gln Leu Ser Ala Thr Tyr Asp Asn Ile Arg Leu
                165                 170                 175

Tyr Thr Phe Gly Glu Pro Arg Ser Gly Asn Gln Ala Phe Ala Ser Tyr
            180                 185                 190

Met Asn Asp Ala Phe Gln Ala Ser Ser Pro Asp Thr Thr Gln Tyr Phe
        195                 200                 205

Arg Val Thr His Ala Asn Asp Gly Ile Pro Asn Leu Pro Pro Val Glu
    210                 215                 220

Gln Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asn Ala His Thr Thr Tyr Phe
            260                 265                 270

Gly Met Thr Ser Gly Ala Cys Thr Trp
        275                 280
```

<210> SEQ ID NO 3
<211> LENGTH: 40
<212> TYPE: DNA
<213> ORGANISM: Artificial Sequence
<220> FEATURE:
<223> OTHER INFORMATION: funcional PCR product reading frame -continued

<400> SEQUENCE: 3
ggactacgcg ctgaccgtga ccggccactc cctcggcgcc 40

<210> SEQ ID NO 4
<211> LENGTH: 35
<212> TYPE: DNA
<213> ORGANISM: Artificial Sequence
<220> FEATURE:
<223> OTHER INFORMATION: inactivated PCR product reading frame

<400> SEQUENCE: 4
ccggccacgc cctcggcgcc tccctggcgg cactc 35

<210> SEQ ID NO 5
<211> LENGTH: 10
<212> TYPE: PRT
<213> ORGANISM: Artificial Sequence
<220> FEATURE:
<223> OTHER INFORMATION: retention sequence

<400> SEQUENCE: 5

Ala Ala Ala Glu Pro Leu Lys Asp Glu Leu
1 5 10

<210> SEQ ID NO 6
<211> LENGTH: 33
<212> TYPE: DNA
<213> ORGANISM: Artificial Sequence
<220> FEATURE:
<223> OTHER INFORMATION: retention sequence encoding sequence

<400> SEQUENCE: 6
gcggccgcgg aaccactgaa ggatgagctg taa 33

<210> SEQ ID NO 7
<211> LENGTH: 15
<212> TYPE: PRT
<213> ORGANISM: Artificial Sequence
<220> FEATURE:
<223> OTHER INFORMATION: FAE-linker-frameshift sequence

<400> SEQUENCE: 7

Gly Ala Cys Thr Trp Pro Val Ala Ala Ala Glu Thr Thr Glu Gly
1 5 10 15

<210> SEQ ID NO 8
<211> LENGTH: 48
<212> TYPE: DNA
<213> ORGANISM: Artificial Sequence
<220> FEATURE:
<223> OTHER INFORMATION: FAE-linker-frameshift sequence

<400> SEQUENCE: 8
ggcgcatgca cctggccggt cgcggccgcg gaaaccactg aaggatga 48

<210> SEQ ID NO 9
<211> LENGTH: 41
<212> TYPE: PRT
<213> ORGANISM: Hordeum sp.

<400> SEQUENCE: 9

Met Ala His Ala Arg Val Leu Leu Leu Ala Leu Ala Val Leu Ala Thr
1 5 10 15

Ala Ala Val Ala Val Ala Ser Ser Ser Ser Phe Ala Asp Ser Asn Pro
20 25 30

-continued

```
Ile Arg Pro Val Thr Asp Arg Ala Ala
        35                  40


<210> SEQ ID NO 10
<211> LENGTH: 134
<212> TYPE: DNA
<213> ORGANISM: Hordeum sp.

<400> SEQUENCE: 10

aagcttacca tggcccacgc ccgcgtcctc ctcctggcgc tcgccgtgct ggccacggcc     60

gccgtcgccg tcgcctcctc ctcctccttc gccgactcca acccgatccg gcccgtcacc    120

gaccgcgcgg ccgc                                                      134


<210> SEQ ID NO 11
<211> LENGTH: 46
<212> TYPE: PRT
<213> ORGANISM: Rattus sp.

<400> SEQUENCE: 11

Met Ile His Thr Asn Leu Lys Lys Lys Phe Ser Leu Phe Ile Leu Val
 1               5                  10                  15

Phe Leu Leu Phe Ala Val Ile Cys Val Trp Lys Lys Gly Ser Asp Tyr
            20                  25                  30

Glu Ala Leu Thr Leu Gln Ala Lys Glu Phe Gln Met Ala Ala
        35                  40                  45


<210> SEQ ID NO 12
<211> LENGTH: 149
<212> TYPE: DNA
<213> ORGANISM: Rattus sp.

<400> SEQUENCE: 12

aagcttacca tgatccacac caacctcaaa aagaagttct ccctcttcat cctcgtcttc     60

ctcctcttcg ccgtgatctg cgtgtggaag aagggctccg actacgaggc cctcaccctc    120

caagccaagg agttccaaat ggcggccgc                                      149


<210> SEQ ID NO 13
<211> LENGTH: 50
<212> TYPE: PRT
<213> ORGANISM: Solanum sp.
<220> FEATURE:
<221> NAME/KEY: VARIANT
<222> LOCATION: (1)...(50)
<223> OTHER INFORMATION: Xaa = Any Amino Acid

<400> SEQUENCE: 13

Met Xaa Val His Lys Glu Val Asn Phe Val Ala Tyr Leu Leu Ile Val
 1               5                  10                  15

Leu Gly Leu Leu Leu Leu Val Ser Ala Met Glu His Val Asp Ala Lys
            20                  25                  30

Ala Cys Thr Xaa Glu Cys Gly Asn Leu Gly Phe Gly Ile Cys Pro Ala
        35                  40                  45

Ala Ala
    50


<210> SEQ ID NO 14
<211> LENGTH: 159
<212> TYPE: DNA
<213> ORGANISM: Solanum sp.
```

-continued

<400> SEQUENCE: 14
aagcttacma tggmcgtgca caaggaggts aacttcgtsg cctacctcct gatcgtsctc 60
ggcctcctct tgctcgtstc cgccatggag cacgtggacg ccaaggcctg caccckcgag 120
tgcggcaacc tcggcttcgg catctgcccg gcggccgcc 159

<210> SEQ ID NO 15
<211> LENGTH: 5338
<212> TYPE: DNA
<213> ORGANISM: Artificial Sequence
<220> FEATURE:
<223> OTHER INFORMATION: pTP10-1 vector

<400> SEQUENCE: 15
aagcttacca tggcccacgc ccgcgtcctc ctcctggcgc tcgccgtgct ggccacggcc 60
gccgtcgccg tcgcctcctc ctcctccttc gccgactcca acccgatccg gcccgtcacc 120
gaccgcgcgg ccgcctccac gcagggcatc tccgaagacc tctacagccg tttagtcgaa 180
atggccacta tctcccaagc tgcctacgcc gacctgtgca acattccgtc gactattatc 240
aagggagaga aaatttacaa ttctcaaact gacattaacg gatggatcct ccgcgacgac 300
agcagcaaag aaataatcac cgtcttccgt ggcactggta gtgatacgaa tctacaactc 360
gatactgact acaccctcac gcctttcgac accctaccac aatgcaacgg ttgtgaagta 420
cacggtggat attatattgg atgggtctcc gtccaggacc aagtcgagtc gcttgtcaaa 480
cagcaggtta gccagtatcc ggactacgcg ctgaccgtga ccggccackc cctcggcgcc 540
tccctggcgg cactcactgc cgcccagctg tctgcgacat acgacaacat ccgcctgtac 600
accttcggcg aaccgcgcag cggcaatcag gccttcgcgt cgtacatgaa cgatgccttc 660
caagcctcga gcccagatac gacgcagtat ttccgggtca ctcatgccaa cgacggcatc 720
ccaaacctgc ccccggtgga gcaggggtac gcccatggcg gtgtagagta ctggagcgtt 780
gatccttaca gcgcccagaa cacatttgtc tgcactgggg atgaagtgca gtgctgtgag 840
gcccagggcg gacagggtgt gaataatgcg cacacgactt attttgggat gacgagcggc 900
gcatgcacct ggccggtcgc ggccgcggaa accactgaag gatgagctgt aaagaagcag 960
atcgttcaaa catttggcaa taaagtttct taagattgaa tcctgttgcc ggtcttgcga 1020
tgattatcat ataatttctg ttgaattacg ttaagcatgt aataattaac atgtaatgca 1080
tgacgttatt tatgagatgg gtttttatga ttagagtccc gcaattatac atttaatacg 1140
cgatagaaaa caaaatatag cgcgcaaact aggataaatt atcgcgcgcg gtgtcatcta 1200
tgttactaga tcgataagct tctagagcgg ccggtggagc tccaattcgc cctatagtga 1260
gtcgtattac gcgcgctcac tggccgtcgt tttacaacgt cgtgactggg aaaaccctgg 1320
cgttacccaa cttaatcgcc ttgcagcaca tccccctttc gccagctggc gtaatagcga 1380
agaggcccgc accgatcgcc cttcccaaca gttgcgcagc ctgaatggcg aatgggacgc 1440
gccctgtagc ggcgcattaa gcgcggcggg tgtggtggtt acgcgcagcg tgaccgctac 1500
acttgccagc gccctagcgc ccgctccttt cgctttcttc ccttcctttc tcgccacgtt 1560
cgccggcttt ccccgtcaag ctctaaatcg ggggctccct ttagggttcc gatttagtgc 1620
tttacggcac ctcgacccca aaaaacttga ttagggtgat ggttcacgta gtgggccatc 1680
gccctgatag acggtttttc gccctttgac gttggagtcc acgttcttta atagtggact 1740
cttgttccaa actggaacaa cactcaaccc tatctcggtc tattcttttg atttataagg 1800
gattttgccg atttcggcct attggttaaa aaatgagctg atttaacaaa aatttaacgc 1860

-continued

```
gaattttaac aaaatattaa cgcttacaat ttaggtggca cttttcgggg aaatgtgcgc   1920
ggaaccccta tttgtttatt tttctaaata cattcaaata tgtatccgct catgagacaa   1980
taaccctgat aaatgcttca ataatattga aaaaggaaga gtatgagtat tcaacatttc   2040
cgtgtcgccc ttattccctt ttttgcggca ttttgccttc ctgtttttgc tcacccagaa   2100
acgctggtga aagtaaaaga tgctgaagat cagttgggtg cacgagtggg ttacatcgaa   2160
ctggatctca acagcggtaa gatccttgag agttttcgcc ccgaagaacg ttttccaatg   2220
atgagcactt ttaaagttct gctatgtggc gcggtattat cccgtattga cgccgggcaa   2280
gagcaactcg gtcgccgcat acactattct cagaatgact tggttgagta ctcaccagtc   2340
acagaaaagc atcttacgga tggcatgaca gtaagagaat tatgcagtgc tgccataacc   2400
atgagtgata acactgcggc caacttactt ctgacaacga tcggaggacc gaaggagcta   2460
accgcttttt tgcacaacat gggggatcat gtaactcgcc ttgatcgttg ggaaccggag   2520
ctgaatgaag ccataccaaa cgacgagcgt gacaccacga tgcctgtagc aatggcaaca   2580
acgttgcgca aactattaac tggcgaacta cttactctag cttcccggca acaattaata   2640
gactggatgg aggcggataa agttgcagga ccacttctgc gctcggccct tccggctggc   2700
tggtttattg ctgataaatc tggagccggt gagcgtgggt ctcgcggtat cattgcagca   2760
ctggggccag atggtaagcc ctcccgtatc gtagttatct acacgacggg gagtcaggca   2820
actatggatg aacgaaatag acagatcgct gagataggtg cctcactgat taagcattgg   2880
taactgtcag accaagttta ctcatatata ctttagattg atttaaaact tcatttttaa   2940
tttaaaagga tctaggtgaa gatccttttt gataatctca tgaccaaaat cccttaacgt   3000
gagttttcgt tccactgagc gtcagacccc gtagaaaaga tcaaaggatc ttcttgagat   3060
cctttttttc tgcgcgtaat ctgctgcttg caaacaaaaa aaccaccgct accagcggtg   3120
gtttgtttgc cggatcaaga gctaccaact ctttttccga aggtaactgg cttcagcaga   3180
gcgcagatac caaatactgt ccttctagtg tagccgtagt taggccacca cttcaagaac   3240
tctgtagcac cgcctacata cctcgctctg ctaatcctgt taccagtggc tgctgccagt   3300
ggcgataagt cgtgtcttac cgggttggac tcaagacgat agttaccgga taaggcgcag   3360
cggtcgggct gaacgggggg ttcgtgcaca cagcccagct tggagcgaac gacctacacc   3420
gaactgagat acctacagcg tgagctatga gaaagcgcca cgcttcccga agggagaaag   3480
gcggacaggt atccggtaag cggcagggtc ggaacaggag agcgcacgag ggagcttcca   3540
gggggaaacg cctggtatct ttatagtcct gtcgggtttc gccacctctg acttgagcgt   3600
cgatttttgt gatgctcgtc aggggggcgg agcctatgga aaaacgccag caacgcggcc   3660
tttttacggt tcctggcctt ttgctggcct tttgctcaca tgttctttcc tgcgttatcc   3720
cctgattctg tggataaccg tattaccgcc tttgagtgag ctgataccgc tcgccgcagc   3780
cgaacgaccg agcgcagcga gtcagtgagc gaggaagcgg aagagcgccc aatacgcaaa   3840
ccgcctctcc ccgcgcgttg gccgattcat taatgcagct ggcacgacag gtttcccgac   3900
tggaaagcgg gcagtgagcg caacgcaatt aatgtgagtt agctcactca ttaggcaccc   3960
caggctttac actttatgct tccggctcgt atgttgtgtg gaattgtgag cggataacaa   4020
tttcacacag gaaacagcta tgaccatgat tacgccaagc gcgcaattaa ccctcactaa   4080
agggaacaaa agctgggtac cgggcccccc ctcgaggtca ttcatatgct tgagaagaga   4140
gtcgggatag tccaaaataa aacaaaggta agattacctg gtcaaaagtg aaaacatcag   4200
```

-continued

```
ttaaaaggtg gtataagtaa aatatcggta ataaaaggtg gcccaaagtg aaatttactc   4260

ttttctacta ttataaaaat tgaggatgtt ttgtcggtac tttgatacgt catttttgta   4320

tgaattggtt tttaagttta ttcgcgattt ggaaatgcat atctgtattt gagtcggttt   4380

ttaagttcgt tgcttttgta aatacagagg gatttgtata agaaatatct ttaaaaaacc   4440

catatgctaa tttgacataa tttttgagaa aaatatatat tcaggcgaat tccacaatga   4500

acaataataa gattaaaata gcttgccccc gttgcagcga tgggtatttt ttctagtaaa   4560

ataaaagata aacttagact caaaacattt acaaaaacaa cccctaaagt cctaaagccc   4620

aaagtgctat gcacgatcca tagcaagccc agcccaaccc aacccaaccc aacccacccc   4680

agtgcagcca actggcaaat agtctccacc cccggcacta tcaccgtgag ttgtccgcac   4740

caccgcacgt ctcgcagcca aaaaaaaaaa aagaaagaaa aaaaagaaaa agaaaaacag   4800

caggtgggtc cgggtcgtgg gggccggaaa agcgaggagg atcgcgagca gcgacgaggc   4860

ccggccctcc ctccgcttcc aaagaaacgc cccccatcgc cactatatac atacccccc   4920

ctctcctccc atccccccaa ccctaccacc accaccacca ccacctcctc ccccctcgct   4980

gccggacgac gagctcctcc cccctccccc tccgccgccg ccggtaacca ccccgcccct   5040

ctcctctttc tttctccgtt ttttttttcg tctcggtctc gatctttggc cttggtagtt   5100

tgggtgggcg agagcggctt cgtcgcccag atcggtgcgc gggaggggcg ggatctcgcg   5160

gctggcgtct ccgggcgtga gtcggcccgg atcctcgcgg ggaatggggc tctcggatgt   5220

agatcttctt tctttcttct ttttgtggta gaatttgaat ccctcagcat tgttcatcgg   5280

tagtttttct tttcatgatt tgtgacaaat gcagcctcgt gcggagcttt tttgtagc     5338
```

```
<210> SEQ ID NO 16
<211> LENGTH: 311
<212> TYPE: PRT
<213> ORGANISM: Artificial Sequence
<220> FEATURE:
<223> OTHER INFORMATION: pTP10-1 vector
<220> FEATURE:
<221> NAME/KEY: VARIANT
<222> LOCATION: (1)...(311)
<223> OTHER INFORMATION: Xaa = Any Amino Acid

<400> SEQUENCE: 16

Met Ala His Ala Arg Val Leu Leu Leu Ala Leu Ala Val Leu Ala Thr
 1               5                  10                  15

Ala Ala Val Ala Val Ala Ser Ser Ser Ser Phe Ala Asp Ser Asn Pro
            20                  25                  30

Ile Arg Pro Val Thr Asp Arg Ala Ala Ala Ser Thr Gln Gly Ile Ser
        35                  40                  45

Glu Asp Leu Tyr Ser Arg Leu Val Glu Met Ala Thr Ile Ser Gln Ala
    50                  55                  60

Ala Tyr Ala Asp Leu Cys Asn Ile Pro Ser Thr Ile Ile Lys Gly Glu
65                  70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110

Thr Asn Leu Gln Leu Asp Thr Asp Tyr Thr Leu Thr Pro Phe Asp Thr
        115                 120                 125

Leu Pro Gln Cys Asn Gly Cys Glu Val His Gly Gly Tyr Tyr Ile Gly
    130                 135                 140
```

-continued

```
Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
        275                 280                 285

Thr Thr Tyr Phe Gly Met Thr Ser Gly Ala Cys Thr Trp Pro Val Ala
    290                 295                 300

Ala Ala Glu Thr Thr Glu Gly
305                 310
```

<210> SEQ ID NO 17
<211> LENGTH: 5345
<212> TYPE: DNA
<213> ORGANISM: Artificial Sequence
<220> FEATURE:
<223> OTHER INFORMATION: pUA4-4 vector

<400> SEQUENCE: 17

```
aagcttacca tggcccacgc ccgcgtcctc ctcctggcgc tcgccgtgct ggccacggcc     60

gccgtcgccg tcgcctcctc ccgcgcggcc gcctccacgc agggcatctc cgaagacctc    120

tacagccgtt tagtcgaaat ggccactatc tcccaagctg cctacgccga cctgtgcaac    180

attccgtcga ctattatcaa gggagagaaa atttacaatt ctcaaactga cattaacgga    240

tggatcctcc gcgacgacag cagcaaagaa ataatcaccg tcttccgtgg cactggtagt    300

gatacgaatc tacaactcga tactaactac accctcacgc ctttcgacac cctaccacaa    360

tgcaacggtt gtgaagtaca cggtggatat tatattggat gggtctccgt ccaggaccaa    420

gtcgagtcgc ttgtcaaaca gcaggttagc cagtatccgg actacgcgct gaccgtgacc    480

ggccackccc tcggcgcctc cctggcggca ctcactgccg cccagctgtc tgcgacatac    540

gacaacatcc gcctgtacac cttcggcgaa ccgcgcagcg gcaatcaggc cttcgcgtcg    600

tacatgaacg atgccttcca agcctcgagc ccagatacga cgcagtattt ccgggtcact    660

catgccaacg acggcatccc aaacctgccc ccggtggagc aggggtacgc ccatggcggt    720

gtagagtact ggagcgttga tccttacagc gcccagaaca catttgtctg cactggggat    780

gaagtgcagt gctgtgaggc ccagggcgga cagggtgtga ataatgcgca cacgacttat    840

tttgggatga cgagcggagc ctgtacatgg tgatcagtca tttcagcctc cccgagtgta    900

ccaggaaaga tggatgtcct ggagaggggg ccgcgtaacc actgaaggat gagctgtaaa    960

gaagcagatc gttcaaacat ttggcaataa agtttcttaa gattgaatcc tgttgccggt   1020

cttgcgatga ttatcatata atttctgttg aattacgtta agcatgtaat aattaacatg   1080
```

-continued

```
taatgcatga cgttatttat gagatgggtt tttatgatta gagtcccgca attatacatt   1140
taatacgcga tagaaaacaa aatatagcgc gcaaactagg ataaattatc gcgcgcggtg   1200
tcatctatgt tactagatcg ataagcttct agagcggccg gtggagctcc aattcgccct   1260
atagtgagtc gtattacgcg cgctcactgg ccgtcgtttt acaacgtcgt gactgggaaa   1320
accctggcgt tacccaactt aatcgccttg cagcacatcc ccctttcgcc agctggcgta   1380
atagcgaaga ggcccgcacc gatcgccctt cccaacagtt gcgcagcctg aatggcgaat   1440
gggacgcgcc ctgtagcggc gcattaagcg cggcgggtgt ggtggttacg cgcagcgtga   1500
ccgctacact tgccagcgcc ctagcgcccg ctcctttcgc tttcttccct tcctttctcg   1560
ccacgttcgc cggctttccc cgtcaagctc taaatcgggg gctcccttta gggttccgat   1620
ttagtgcttt acggcacctc gaccccaaaa aacttgatta gggtgatggt tcacgtagtg   1680
ggccatcgcc ctgatagacg gtttttcgcc ctttgacgtt ggagtccacg ttctttaata   1740
gtggactctt gttccaaact ggaacaacac tcaaccctat ctcggtctat tcttttgatt   1800
tataagggat tttgccgatt tcggcctatt ggttaaaaaa tgagctgatt taacaaaaat   1860
ttaacgcgaa ttttaacaaa atattaacgc ttacaattta ggtggcactt ttcggggaaa   1920
tgtgcgcgga acccctattt gtttattttt ctaaatacat tcaaatatgt atccgctcat   1980
gagacaataa ccctgataaa tgcttcaata atattgaaaa aggaagagta tgagtattca   2040
acatttccgt gtcgccctta ttcccttttt tgcggcattt tgccttcctg tttttgctca   2100
cccagaaacg ctggtgaaag taaaagatgc tgaagatcag ttgggtgcac gagtgggtta   2160
catcgaactg gatctcaaca gcggtaagat ccttgagagt tttcgccccg aagaacgttt   2220
tccaatgatg agcactttta aagttctgct atgtggcgcg gtattatccc gtattgacgc   2280
cgggcaagag caactcggtc gccgcataca ctattctcag aatgacttgg ttgagtactc   2340
accagtcaca gaaaagcatc ttacggatgg catgacagta agagaattat gcagtgctgc   2400
cataaccatg agtgataaca ctgcggccaa cttacttctg acaacgatcg gaggaccgaa   2460
ggagctaacc gcttttttgc acaacatggg ggatcatgta actcgccttg atcgttggga   2520
accggagctg aatgaagcca taccaaacga cgagcgtgac accacgatgc ctgtagcaat   2580
ggcaacaacg ttgcgcaaac tattaactgg cgaactactt actctagctt cccggcaaca   2640
attaatagac tggatggagg cggataaagt tgcaggacca cttctgcgct cggcccttcc   2700
ggctggctgg tttattgctg ataaatctgg agccggtgag cgtgggtctc gcggtatcat   2760
tgcagcactg gggccagatg gtaagccctc ccgtatcgta gttatctaca cgacggggag   2820
tcaggcaact atggatgaac gaaatagaca gatcgctgag ataggtgcct cactgattaa   2880
gcattggtaa ctgtcagacc aagtttactc atatatactt tagattgatt taaaacttca   2940
tttttaattt aaaaggatct aggtgaagat cctttttgat aatctcatga ccaaaatccc   3000
ttaacgtgag ttttcgttcc actgagcgtc agaccccgta gaaaagatca aaggatcttc   3060
ttgagatcct ttttttctgc gcgtaatctg ctgcttgcaa acaaaaaaac caccgctacc   3120
agcggtggtt tgtttgccgg atcaagagct accaactctt tttccgaagg taactggctt   3180
cagcagagcg cagataccaa atactgtcct tctagtgtag ccgtagttag gccaccactt   3240
caagaactct gtagcaccgc ctacatacct cgctctgcta atcctgttac cagtggctgc   3300
tgccagtggc gataagtcgt gtcttaccgg gttggactca agacgatagt taccggataa   3360
ggcgcagcgg tcgggctgaa cggggggttc gtgcacacag cccagcttgg agcgaacgac   3420
ctacaccgaa ctgagatacc tacagcgtga gctatgagaa agcgccacgc ttcccgaagg   3480
```

-continued

```
gagaaaggcg gacaggtatc cggtaagcgg cagggtcgga acaggagagc gcacgaggga   3540
gcttccaggg ggaaacgcct ggtatcttta tagtcctgtc gggtttcgcc acctctgact   3600
tgagcgtcga tttttgtgat gctcgtcagg ggggcggagc ctatggaaaa acgccagcaa   3660
cgcggccttt ttacggttcc tggccttttg ctggcctttt gctcacatgt tctttcctgc   3720
gttatcccct gattctgtgg ataaccgtat taccgccttt gagtgagctg ataccgctcg   3780
ccgcagccga acgaccgagc gcagcgagtc agtgagcgag gaagcggaag agcgcccaat   3840
acgcaaaccg cctctccccg cgcgttggcc gattcattaa tgcagctggc acgacaggtt   3900
tcccgactgg aaagcgggca gtgagcgcaa cgcaattaat gtgagttagc tcactcatta   3960
ggcaccccag gctttacact ttatgcttcc ggctcgtatg ttgtgtggaa ttgtgagcgg   4020
ataacaattt cacacaggaa acagctatga ccatgattac gccaagcgcg caattaaccc   4080
tcactaaagg gaacaaaagc tgggtaccgg gccccccctc gaggtcattc atatgcttga   4140
gaagagagtc gggatagtcc aaaataaaac aaaggtaaga ttacctggtc aaaagtgaaa   4200
acatcagtta aaaggtggta taagtaaaat atcggtaata aaaggtggcc caaagtgaaa   4260
tttactcttt tctactatta taaaaattga ggatgttttg tcggtacttt gatacgtcat   4320
ttttgtatga attggttttt aagtttattc gcgatttgga aatgcatatc tgtatttgag   4380
tcggttttta agttcgttgc ttttgtaaat acagagggat ttgtataaga aatatcttta   4440
aaaaacccat atgctaattt gacataattt ttgagaaaaa tatatattca ggcgaattcc   4500
acaatgaaca ataataagat taaaatagct tgcccccgtt gcagcgatgg gtattttttc   4560
tagtaaaata aaagataaac ttagactcaa aacatttaca aaaacaaccc ctaaagtcct   4620
aaagcccaaa gtgctatgca cgatccatag caagcccagc ccaacccaac ccaacccaac   4680
ccaccccagt gcagccaact ggcaaatagt ctccaccccc ggcactatca ccgtgagttg   4740
tccgcaccac cgcacgtctc gcagccaaaa aaaaaaaaag aaagaaaaaa aagaaaaaga   4800
aaaacagcag gtgggtccgg gtcgtggggg ccggaaaagc gaggaggatc gcgagcagcg   4860
acgaggcccg gccctccctc cgcttccaaa gaaacgcccc ccatcgccac tatatacata   4920
ccccccccctc tcctcccatc cccccaaccc taccaccacc accaccacca cctcctcccc   4980
cctcgctgcc ggacgacgag ctcctccccc ctccccctcc gccgccgccg gtaaccaccc   5040
cgcccctctc ctctttcttt ctccgttttt tttttcgtct cggtctcgat ctttggcctt   5100
ggtagtttgg gtgggcgaga gcggcttcgt cgcccagatc ggtgcgcggg aggggcggga   5160
tctcgcggct ggcgtctccg ggcgtgagtc ggcccggatc ctcgcgggga atggggctct   5220
cggatgtaga tcttctttct ttcttctttt tgtggtagaa tttgaatccc tcagcattgt   5280
tcatcggtag tttttctttt catgatttgt gacaaatgca gcctcgtgcg gagctttttt   5340
gtagc                                                                5345
```

<210> SEQ ID NO 18
<211> LENGTH: 287
<212> TYPE: PRT
<213> ORGANISM: Artificial Sequence
<220> FEATURE:
<223> OTHER INFORMATION: pUA4-4 vector
<220> FEATURE:
<221> NAME/KEY: VARIANT
<222> LOCATION: (1)...(287)
<223> OTHER INFORMATION: Xaa = Any Amino Acid

<400> SEQUENCE: 18

-continued

```
Met Ala His Ala Arg Val Leu Leu Leu Ala Leu Ala Val Leu Ala Thr
1               5                   10                  15

Ala Ala Val Ala Val Ala Ser Ser Arg Ala Ala Ala Ser Thr Gln Gly
            20                  25                  30

Ile Ser Glu Asp Leu Tyr Ser Arg Leu Val Glu Met Ala Thr Ile Ser
        35                  40                  45

Gln Ala Ala Tyr Ala Asp Leu Cys Asn Ile Pro Ser Thr Ile Ile Lys
    50                  55                  60

Gly Glu Lys Ile Tyr Asn Ser Gln Thr Asp Ile Asn Gly Trp Ile Leu
65                  70                  75                  80

Arg Asp Asp Ser Ser Lys Glu Ile Ile Thr Val Phe Arg Gly Thr Gly
                85                  90                  95

Ser Asp Thr Asn Leu Gln Leu Asp Thr Asn Tyr Thr Leu Thr Pro Phe
            100                 105                 110

Asp Thr Leu Pro Gln Cys Asn Gly Cys Glu Val His Gly Gly Tyr Tyr
        115                 120                 125

Ile Gly Trp Val Ser Val Gln Asp Gln Val Glu Ser Leu Val Lys Gln
    130                 135                 140

Gln Val Ser Gln Tyr Pro Asp Tyr Ala Leu Thr Val Thr Gly His Xaa
145                 150                 155                 160

Leu Gly Ala Ser Leu Ala Ala Leu Thr Ala Ala Gln Leu Ser Ala Thr
                165                 170                 175

Tyr Asp Asn Ile Arg Leu Tyr Thr Phe Gly Glu Pro Arg Ser Gly Asn
            180                 185                 190

Gln Ala Phe Ala Ser Tyr Met Asn Asp Ala Phe Gln Ala Ser Ser Pro
        195                 200                 205

Asp Thr Thr Gln Tyr Phe Arg Val Thr His Ala Asn Asp Gly Ile Pro
    210                 215                 220

Asn Leu Pro Pro Val Glu Gln Gly Tyr Ala His Gly Gly Val Glu Tyr
225                 230                 235                 240

Trp Ser Val Asp Pro Tyr Ser Ala Gln Asn Thr Phe Val Cys Thr Gly
                245                 250                 255

Asp Glu Val Gln Cys Cys Glu Ala Gln Gly Gly Gln Gly Val Asn Asn
            260                 265                 270

Ala His Thr Thr Tyr Phe Gly Met Thr Ser Gly Ala Cys Thr Trp
        275                 280                 285
```

<210> SEQ ID NO 19
<211> LENGTH: 5337
<212> TYPE: DNA
<213> ORGANISM: Artificial Sequence
<220> FEATURE:
<223> OTHER INFORMATION: pTU4 vector

<400> SEQUENCE: 19

```
aagcttacca tggcccacgc ccgcgtcctc ctcctggcgc tcgccgtgct ggccacggcc     60

gccgtcgccg tcgcctcctc ctcctccttc gccgactcca acccgatccg gcccgtcacc    120

gaccgcgcgg ccgcctccac gcagggcatc tccgaagacc tctacagccg tttagtcgaa    180

atggccacta tctcccaagc tgcctacgcc gacctgtgca acattccgtc gactattatc    240

aagggagaga aaatttacaa ttctcaaact gacattaacg gatggatcct ccgcgacgac    300

agcagcaaag aaataatcac cgtcttccgt ggcactggta gtgatacgaa tctacaactc    360

gatactaact acaccctcac gcctttcgac accctaccac aatgcaacgg ttgtgaagta    420

cacggtggat attatattgg atgggtctcc gtccaggacc aagtcgagtc gcttgtcaaa    480
```

-continued

```
cagcaggtta gccagtatcc ggactacgcg ctgaccgtga ccggccackc cctcggcgcc    540
tccctggcgg cactcactgc cgcccagctg tctgcgacat acgacaacat ccgcctgtac    600
accttcggcg aaccgcgcag cggcaatcag gccttcgcgt cgtacatgaa cgatgccttc    660
caagcctcga gcccagatac gacgcagtat ttccgggtca ctcatgccaa cgacggcatc    720
ccaaacctgc ccccggtgga gcaggggtac gcccatggcg gtgtagagta ctggagcgtt    780
gatccttaca gcgcccagaa cacatttgtc tgcactgggg atgaagtgca gtgctgtgag    840
gcccagggcg gacagggtgt gaataatgcg cacacgactt attttgggat gacgagcggc    900
gcatgcacct ggccggtcgc ggccgcggaa ccactgaagg atgagctgta aagaagcaga    960
tcgttcaaac atttggcaat aaagtttctt aagattgaat cctgttgccg gtcttgcgat   1020
gattatcata taatttctgt tgaattacgt taagcatgta ataattaaca tgtaatgcat   1080
gacgttattt atgagatggg tttttatgat tagagtcccg caattataca tttaatacgc   1140
gatagaaaac aaaatatagc gcgcaaacta ggataaatta tcgcgcgcgg tgtcatctat   1200
gttactagat cgataagctt ctagagcggc cggtggagct ccaattcgcc ctatagtgag   1260
tcgtattacg cgcgctcact ggccgtcgtt ttacaacgtc gtgactggga aaaccctggc   1320
gttacccaac ttaatcgcct tgcagcacat ccccctttcg ccagctggcg taatagcgaa   1380
gaggcccgca ccgatcgccc ttcccaacag ttgcgcagcc tgaatggcga atgggacgcg   1440
ccctgtagcg gcgcattaag cgcggcgggt gtggtggtta cgcgcagcgt gaccgctaca   1500
cttgccagcg ccctagcgcc cgctcctttc gctttcttcc cttcctttct cgccacgttc   1560
gccggctttc cccgtcaagc tctaaatcgg gggctccctt tagggttccg atttagtgct   1620
ttacggcacc tcgaccccaa aaaacttgat tagggtgatg gttcacgtag tgggccatcg   1680
ccctgataga cggtttttcg ccctttgacg ttggagtcca cgttctttaa tagtggactc   1740
ttgttccaaa ctggaacaac actcaaccct atctcggtct attcttttga tttataaggg   1800
attttgccga tttcggccta ttggttaaaa aatgagctga tttaacaaaa atttaacgcg   1860
aattttaaca aaatattaac gcttacaatt taggtggcac ttttcgggga aatgtgcgcg   1920
gaacccctat ttgtttattt ttctaaatac attcaaatat gtatccgctc atgagacaat   1980
aaccctgata aatgcttcaa taatattgaa aaaggaagag tatgagtatt caacatttcc   2040
gtgtcgccct tattcccttt tttgcggcat tttgccttcc tgtttttgct cacccagaaa   2100
cgctggtgaa agtaaaagat gctgaagatc agttgggtgc acgagtgggt tacatcgaac   2160
tggatctcaa cagcggtaag atccttgaga gttttcgccc cgaagaacgt tttccaatga   2220
tgagcacttt taaagttctg ctatgtggcg cggtattatc ccgtattgac gccgggcaag   2280
agcaactcgg tcgccgcata cactattctc agaatgactt ggttgagtac tcaccagtca   2340
cagaaaagca tcttacggat ggcatgacag taagagaatt atgcagtgct gccataacca   2400
tgagtgataa cactgcggcc aacttacttc tgacaacgat cggaggaccg aaggagctaa   2460
ccgctttttt gcacaacatg ggggatcatg taactcgcct tgatcgttgg gaaccggagc   2520
tgaatgaagc cataccaaac gacgagcgtg acaccacgat gcctgtagca atggcaacaa   2580
cgttgcgcaa actattaact ggcgaactac ttactctagc ttcccggcaa caattaatag   2640
actggatgga ggcggataaa gttgcaggac cacttctgcg ctcggccctt ccggctggct   2700
ggtttattgc tgataaatct ggagccggtg agcgtgggtc tcgcggtatc attgcagcac   2760
tggggccaga tggtaagccc tcccgtatcg tagttatcta cacgacgggg agtcaggcaa   2820
```

-continued

```
ctatggatga acgaaataga cagatcgctg agataggtgc ctcactgatt aagcattggt   2880
aactgtcaga ccaagtttac tcatatatac tttagattga tttaaaactt catttttaat   2940
ttaaaaggat ctaggtgaag atcctttttg ataatctcat gaccaaaatc ccttaacgtg   3000
agttttcgtt ccactgagcg tcagaccccg tagaaaagat caaaggatct tcttgagatc   3060
cttttttttct gcgcgtaatc tgctgcttgc aaacaaaaaa accaccgcta ccagcggtgg   3120
tttgtttgcc ggatcaagag ctaccaactc tttttccgaa ggtaactggc ttcagcagag   3180
cgcagatacc aaatactgtc cttctagtgt agccgtagtt aggccaccac ttcaagaact   3240
ctgtagcacc gcctacatac ctcgctctgc taatcctgtt accagtggct gctgccagtg   3300
gcgataagtc gtgtcttacc gggttggact caagacgata gttaccggat aaggcgcagc   3360
ggtcgggctg aacggggggt tcgtgcacac agcccagctt ggagcgaacg acctacaccg   3420
aactgagata cctacagcgt gagctatgag aaagcgccac gcttcccgaa gggagaaagg   3480
cggacaggta tccggtaagc ggcagggtcg gaacaggaga gcgcacgagg gagcttccag   3540
ggggaaacgc ctggtatctt tatagtcctg tcgggtttcg ccacctctga cttgagcgtc   3600
gatttttgtg atgctcgtca ggggggcgga gcctatggaa aaacgccagc aacgcggcct   3660
ttttacggtt cctggccttt tgctggcctt ttgctcacat gttctttcct gcgttatccc   3720
ctgattctgt ggataaccgt attaccgcct ttgagtgagc tgataccgct cgccgcagcc   3780
gaacgaccga gcgcagcgag tcagtgagcg aggaagcgga agagcgccca atacgcaaac   3840
cgcctctccc cgcgcgttgg ccgattcatt aatgcagctg gcacgacagg tttcccgact   3900
ggaaagcggg cagtgagcgc aacgcaatta atgtgagtta gctcactcat taggcacccc   3960
aggctttaca ctttatgctt ccggctcgta tgttgtgtgg aattgtgagc ggataacaat   4020
ttcacacagg aaacagctat gaccatgatt acgccaagcg cgcaattaac cctcactaaa   4080
gggaacaaaa gctgggtacc gggccccccc tcgaggtcat tcatatgctt gagaagagag   4140
tcgggatagt ccaaaataaa acaaaggtaa gattacctgg tcaaaagtga aaacatcagt   4200
taaaaggtgg tataagtaaa atatcggtaa taaaaggtgg cccaaagtga aatttactct   4260
tttctactat tataaaaatt gaggatgttt tgtcggtact ttgatacgtc atttttgtat   4320
gaattggttt ttaagtttat tcgcgatttg gaaatgcata tctgtatttg agtcggtttt   4380
taagttcgtt gcttttgtaa atacagaggg atttgtataa gaaatatctt taaaaaaccc   4440
atatgctaat ttgacataat ttttgagaaa aatatatatt caggcgaatt ccacaatgaa   4500
caataataag attaaaatag cttgcccccg ttgcagcgat gggtattttt tctagtaaaa   4560
taaaagataa acttagactc aaaacattta caaaaacaac ccctaaagtc ctaaagccca   4620
aagtgctatg cacgatccat agcaagccca gcccaaccca acccaaccca acccacccca   4680
gtgcagccaa ctggcaaata gtctccaccc ccggcactat caccgtgagt tgtccgcacc   4740
accgcacgtc tcgcagccaa aaaaaaaaaa agaaagaaaa aaaagaaaaa gaaaaacagc   4800
aggtgggtcc gggtcgtggg ggccggaaaa gcgaggagga tcgcgagcag cgacgaggcc   4860
cggccctccc tccgcttcca aagaaacgcc ccccatcgcc actatataca taccccccccc   4920
tctcctccca tccccccaac cctaccacca ccaccaccac cacctcctcc cccctcgctg   4980
ccggacgacg agctcctccc ccctccccct ccgccgccgc cggtaaccac cccgcccctc   5040
tcctctttct ttctccgttt tttttttcgt ctcggtctcg atctttggcc ttggtagttt   5100
gggtgggcga gagcggcttc gtcgcccaga tcggtgcgcg ggaggggcgg gatctcgcgg   5160
ctggcgtctc cgggcgtgag tcggcccgga tcctcgcggg gaatggggct ctcggatgta   5220
```

-continued

```
gatcttcttt ctttcttctt tttgtggtag aatttgaatc cctcagcatt gttcatcggt   5280

agtttttctt ttcatgattt gtgacaaatg cagcctcgtg cggagctttt ttgtagc      5337


<210> SEQ ID NO 20
<211> LENGTH: 313
<212> TYPE: PRT
<213> ORGANISM: Artificial Sequence
<220> FEATURE:
<223> OTHER INFORMATION: pTU4 vector
<220> FEATURE:
<221> NAME/KEY: VARIANT
<222> LOCATION: (1)...(313)
<223> OTHER INFORMATION: Xaa = Any Amino Acid

<400> SEQUENCE: 20

Met Ala His Ala Arg Val Leu Leu Leu Ala Leu Ala Val Leu Ala Thr
 1               5                  10                  15

Ala Ala Val Ala Val Ala Ser Ser Ser Ser Phe Ala Asp Ser Asn Pro
            20                  25                  30

Ile Arg Pro Val Thr Asp Arg Ala Ala Ala Ser Thr Gln Gly Ile Ser
        35                  40                  45

Glu Asp Leu Tyr Ser Arg Leu Val Glu Met Ala Thr Ile Ser Gln Ala
    50                  55                  60

Ala Tyr Ala Asp Leu Cys Asn Ile Pro Ser Thr Ile Ile Lys Gly Glu
65                  70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110

Thr Asn Leu Gln Leu Asp Thr Asn Tyr Thr Leu Thr Pro Phe Asp Thr
        115                 120                 125

Leu Pro Gln Cys Asn Gly Cys Glu Val His Gly Gly Tyr Tyr Ile Gly
    130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
        275                 280                 285

Thr Thr Tyr Phe Gly Met Thr Ser Gly Ala Cys Thr Trp Pro Val Ala
    290                 295                 300

Ala Ala Glu Pro Leu Lys Asp Glu Leu
305                 310
```

-continued

<210> SEQ ID NO 21
<211> LENGTH: 5395
<212> TYPE: DNA
<213> ORGANISM: Artificial Sequence
<220> FEATURE:
<223> OTHER INFORMATION: pTT5.14 vector

<400> SEQUENCE: 21
cctgacgccg aggatccatg gcccacgccc gcgtcctcct cctggcgctc gccgtgctgg 60
ccacggccgc cgtcgccgtc gcctcctcct cctccttcgc cgactccaac ccgggccggc 120
ccgtcaccga ccgcgcggcc gcctccacgc agggcatctc cgaagacctc tacagccgtt 180
tagtcgaaat ggccactatc tcccaagctg cctacgccga cctgtgcaac attccgtcga 240
ctattatcaa gggagagaaa atttacaatt ctcaaactga cattaacgga tggatcctcc 300
gcgacgacag cagcaaagaa ataatcaccg tcttccgtgg cactggtagt gatacgaatc 360
tacaactcga tactaactac accctcacgc ctttcgacac cctaccacaa tgcaacggtt 420
gtgaagtaca cggtggatat tatattggat gggtctccgt ccaggaccaa gtcgagtcgc 480
ttgtcaaaca gcaggttagc cagtatccgg actacgcgct gaccgtgacc ggccackccc 540
tcggcgcctc cctggcggca ctcactgccg cccagctgtc tgcgacatac gacaacatcc 600
gcctgtacac cttcggcgaa ccgcgcagcg gcaatcaggc cttcgcgtcg tacatgaacg 660
atgccttcca agcctcgagc ccagatacga cgcagtattt ccgggtcact catgccaacg 720
acggcatccc aaacctgccc ccggtggagc aggggtacgc ccatggcggt gtagagtact 780
ggagcgttga tccttacagc gcccagaaca catttgtctg cactggggat gaagtgcagt 840
gctgtgaggc ccagggcgga cagggtgtga ataatgcgca cacgacttat tttgggatga 900
cgagcggagc ctgtacatgg tgatcagtca tttcagcctc cccgagtgta ccaggaaaga 960
tggatgtcct ggagaggggg ccgcgtaacc actgaaggat gagctgtaaa gaagcagatc 1020
gttcaaacat ttggcaataa agtttcttaa gattgaatcc tgttgccggt cttgcgatga 1080
ttatcatata atttctgttg aattacgtta agcatgtaat aattaacatg taatgcatga 1140
cgttatttat gagatgggtt tttatgatta gagtcccgca attatacatt taatacgcga 1200
tagaaaacaa aatatagcgc gcaaactagg ataaattatc gcgcgcggtg tcatctatgt 1260
tactagatcg ataagcttct agagcggccg gtggagctcc aattcgccct atagtgagtc 1320
gtattacgcg cgctcactgg ccgtcgtttt acaacgtcgt gactgggaaa accctggcgt 1380
tacccaactt aatcgccttg cagcacatcc ccctttcgcc agctggcgta atagcgaaga 1440
ggcccgcacc gatcgccctt cccaacagtt gcgcagcctg aatggcgaat gggacgcgcc 1500
ctgtagcggc gcattaagcg cggcgggtgt ggtggttacg cgcagcgtga ccgctacact 1560
tgccagcgcc ctagcgcccg ctcctttcgc tttcttccct tcctttctcg ccacgttcgc 1620
cggctttccc cgtcaagctc taaatcgggg gctcccttta gggttccgat ttagtgcttt 1680
acggcacctc gaccccaaaa aacttgatta gggtgatggt tcacgtagtg ggccatcgcc 1740
ctgatagacg gtttttcgcc ctttgacgtt ggagtccacg ttctttaata gtggactctt 1800
gttccaaact ggaacaacac tcaaccctat ctcggtctat tcttttgatt tataagggat 1860
tttgccgatt tcggcctatt ggttaaaaaa tgagctgatt taacaaaaat ttaacgcgaa 1920
ttttaacaaa atattaacgc ttacaattta ggtggcactt ttcggggaaa tgtgcgcgga 1980
acccctattt gtttattttt ctaaatacat tcaaatatgt atccgctcat gagacaataa 2040
ccctgataaa tgcttcaata atattgaaaa aggaagagta tgagtattca acatttccgt 2100

-continued

```
gtcgccctta ttcccttttt tgcggcattt tgccttcctg tttttgctca cccagaaacg   2160
ctggtgaaag taaaagatgc tgaagatcag ttgggtgcac gagtgggtta catcgaactg   2220
gatctcaaca gcggtaagat ccttgagagt tttcgccccg aagaacgttt tccaatgatg   2280
agcactttta aagttctgct atgtggcgcg gtattatccc gtattgacgc cgggcaagag   2340
caactcggtc gccgcataca ctattctcag aatgacttgg ttgagtactc accagtcaca   2400
gaaaagcatc ttacggatgg catgacagta agagaattat gcagtgctgc cataaccatg   2460
agtgataaca ctgcggccaa cttacttctg acaacgatcg gaggaccgaa ggagctaacc   2520
gcttttttgc acaacatggg ggatcatgta actcgccttg atcgttggga accggagctg   2580
aatgaagcca taccaaacga cgagcgtgac accacgatgc ctgtagcaat ggcaacaacg   2640
ttgcgcaaac tattaactgg cgaactactt actctagctt cccggcaaca attaatagac   2700
tggatggagg cggataaagt tgcaggacca cttctgcgct cggcccttcc ggctggctgg   2760
tttattgctg ataaatctgg agccggtgag cgtgggtctc gcggtatcat tgcagcactg   2820
gggccagatg gtaagccctc ccgtatcgta gttatctaca cgacggggag tcaggcaact   2880
atggatgaac gaaatagaca gatcgctgag ataggtgcct cactgattaa gcattggtaa   2940
ctgtcagacc aagtttactc atatatactt tagattgatt taaaacttca tttttaattt   3000
aaaaggatct aggtgaagat cctttttgat aatctcatga ccaaaatccc ttaacgtgag   3060
ttttcgttcc actgagcgtc agaccccgta gaaaagatca aaggatcttc ttgagatcct   3120
ttttttctgc gcgtaatctg ctgcttgcaa acaaaaaaac caccgctacc agcggtggtt   3180
tgtttgccgg atcaagagct accaactctt tttccgaagg taactggctt cagcagagcg   3240
cagataccaa atactgtcct tctagtgtag ccgtagttag gccaccactt caagaactct   3300
gtagcaccgc ctacatacct cgctctgcta atcctgttac cagtggctgc tgccagtggc   3360
gataagtcgt gtcttaccgg gttggactca agacgatagt taccggataa ggcgcagcgg   3420
tcgggctgaa cggggggttc gtgcacacag cccagcttgg agcgaacgac ctacaccgaa   3480
ctgagatacc tacagcgtga gctatgagaa agcgccacgc ttcccgaagg gagaaaggcg   3540
gacaggtatc cggtaagcgg cagggtcgga acaggagagc gcacgaggga gcttccaggg   3600
ggaaacgcct ggtatcttta tagtcctgtc gggtttcgcc acctctgact tgagcgtcga   3660
tttttgtgat gctcgtcagg ggggcggagc ctatggaaaa acgccagcaa cgcggccttt   3720
ttacggttcc tggccttttg ctggcctttt gctcacatgt tctttcctgc gttatcccct   3780
gattctgtgg ataaccgtat taccgccttt gagtgagctg ataccgctcg ccgcagccga   3840
acgaccgagc gcagcgagtc agtgagcgag gaagcggaag agcgcccaat acgcaaaccg   3900
cctctccccg cgcgttggcc gattcattaa tgcagctggc acgacaggtt tcccgactgg   3960
aaagcgggca gtgagcgcaa cgcaattaat gtgagttagc tcactcatta ggcaccccag   4020
gctttacact ttatgcttcc ggctcgtatg ttgtgtggaa ttgtgagcgg ataacaattt   4080
cacacaggaa acagctatga ccatgattac gccaagcgcg caattaaccc tcactaaagg   4140
gaacaaaagc tgggtaccgg gccccccctc gaggtcattc atatgcttga gaagagagtc   4200
gggatagtcc aaaataaaac aaaggtaaga ttacctggtc aaaagtgaaa acatcagtta   4260
aaaggtggta taagtaaaat atcggtaata aaaggtggcc caaagtgaaa tttactcttt   4320
tctactatta taaaaattga ggatgttttg tcggtacttt gatacgtcat ttttgtatga   4380
attggttttt aagtttattc gcgatttgga aatgcatatc tgtatttgag tcggttttta   4440
```

-continued

```
agttcgttgc ttttgtaaat acagagggat ttgtataaga aatatcttta aaaaacccat   4500

atgctaattt gacataattt ttgagaaaaa tatatattca ggcgaattcc acaatgaaca   4560

ataataagat taaaatagct tgcccccgtt gcagcgatgg gtattttttc tagtaaaata   4620

aaagataaac ttagactcaa aacatttaca aaaacaaccc ctaaagtcct aaagcccaaa   4680

gtgctatgca cgatccatag caagcccagc ccaacccaac ccaacccaac ccaccccagt   4740

gcagccaact ggcaaatagt ctccaccccc ggcactatca ccgtgagttg tccgcaccac   4800

cgcacgtctc gcagccaaaa aaaaaaaaag aaagaaaaaa aagaaaaaga aaaacagcag   4860

gtgggtccgg gtcgtggggg ccggaaaagc gaggaggatc gcgagcagcg acgaggcccg   4920

gccctccctc cgcttccaaa gaaacgcccc ccatcgccac tatatacata cccccccctc   4980

tcctcccatc cccccaaccc taccaccacc accaccacca cctcctcccc cctcgctgcc   5040

ggacgacgag ctcctccccc ctccccctcc gccgccgccg gtaaccaccc cgcccctctc   5100

ctctttcttt ctccgttttt tttttcgtct cggtctcgat ctttggcctt ggtagtttgg   5160

gtgggcgaga gcggcttcgt cgcccagatc ggtgcgcggg aggggcggga tctcgcggct   5220

ggcgtctccg ggcgtgagtc ggcccggatc ctcgcgggga atggggctct cggatgtaga   5280

tcttctttct ttcttctttt tgtggtagaa tttgaatccc tcagcattgt tcatcggtag   5340

tttttctttt catgatttgt gacaaatgca gcctcgtgcg gagctttttt gtagc        5395
```

```
<210> SEQ ID NO 22
<211> LENGTH: 301
<212> TYPE: PRT
<213> ORGANISM: Artificial Sequence
<220> FEATURE:
<223> OTHER INFORMATION: pTT5.14 vector
<220> FEATURE:
<221> NAME/KEY: VARIANT
<222> LOCATION: (1)...(301)
<223> OTHER INFORMATION: Xaa = Any Amino Acid

<400> SEQUENCE: 22

Met Ala His Ala Arg Val Leu Leu Leu Ala Leu Ala Val Leu Ala Thr
 1               5                  10                  15

Ala Ala Val Ala Val Ala Ser Ser Ser Ser Phe Ala Asp Ser Asn Pro
            20                  25                  30

Gly Arg Pro Val Thr Asp Arg Ala Ala Ala Ser Thr Gln Gly Ile Ser
        35                  40                  45

Glu Asp Leu Tyr Ser Arg Leu Val Glu Met Ala Thr Ile Ser Gln Ala
    50                  55                  60

Ala Tyr Ala Asp Leu Cys Asn Ile Pro Ser Thr Ile Ile Lys Gly Glu
65                  70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110

Thr Asn Leu Gln Leu Asp Thr Asn Tyr Thr Leu Thr Pro Phe Asp Thr
        115                 120                 125

Leu Pro Gln Cys Asn Gly Cys Glu Val His Gly Gly Tyr Tyr Ile Gly
    130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175
```

-continued

```
Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
        275                 280                 285

Thr Thr Tyr Phe Gly Met Thr Ser Gly Ala Cys Thr Trp
    290                 295                 300
```

<210> SEQ ID NO 23
<211> LENGTH: 5337
<212> TYPE: DNA
<213> ORGANISM: Artificial Sequence
<220> FEATURE:
<223> OTHER INFORMATION: pTP8-5 vector

<400> SEQUENCE: 23

```
aagcttacca tggcccacgc ccgcgtcctc ctcctggcgc tcgccgtgct ggccacggcc     60

gccgtcgccg tcgcctcctc ctcctccttc gccgactcca acccgatccg gcccgtcacc    120

gaccgcgcgg ccgcctccac gcagggcatc tccgaagacc tctacagccg tttagtcgaa    180

atggccacta tctcccaagc tgcctacgcc gacctgtgca acattccgtc gactattatc    240

aagggagaga aaatttacaa ttctcaaact gacattaacg gatggatcct ccgcgacgac    300

agcagcaaag aaataatcac cgtcttccgt ggcactggta gtgatacgaa tctacaactc    360

gatactaact acaccctcac gcctttcgac accctaccac aatgcaacgg ttgtgaagta    420

cacggtggat attatattgg atgggtctcc gtccaggacc aagtcgagtc gcttgtcaaa    480

cagcaggtta gccagtatcc ggactacgcg ctgaccgtga ccggccackc cctcggcgcc    540

tccctggcgg cactcactgc cgcccagctg tctgcgacat acgacaacat ccgcctgtac    600

accttcggcg aaccgcgcag cggcaatcag gccttcgcgt cgtacatgaa cgatgccttc    660

caagcctcga gcccagatac gacgcagtat ttccgggtca ctcatgccaa cgacggcatc    720

ccaaacctgc ccccggtgga gcaggggtac gcccatggcg gtgtagagta ctggagcgtt    780

gatccttaca gcgcccagaa cacatttgtc tgcactgggg atgaagtgca gtgctgtgag    840

gcccagggcg gacagggtgt gaataatgcg cacacgactt attttgggat gacgagcggc    900

gcatgcacct ggccggtcgc ggccgcgtaa ccactgaagg atgagctgta aagaagcaga    960

tcgttcaaac atttggcaat aaagtttctt aagattgaat cctgttgccg gtcttgcgat   1020

gattatcata taatttctgt tgaattacgt taagcatgta ataattaaca tgtaatgcat   1080

gacgttattt atgagatggg tttttatgat tagagtcccg caattataca tttaatacgc   1140

gatagaaaac aaaatatagc gcgcaaacta ggataaatta tcgcgcgcgg tgtcatctat   1200

gttactagat cgataagctt ctagagcggc cggtggagct ccaattcgcc ctatagtgag   1260

tcgtattacg cgcgctcact ggccgtcgtt ttacaacgtc gtgactggga aaaccctggc   1320

gttacccaac ttaatcgcct tgcagcacat ccccctttcg ccagctggcg taatagcgaa   1380
```

-continued

```
gaggcccgca ccgatcgccc ttcccaacag ttgcgcagcc tgaatggcga atgggacgcg   1440
ccctgtagcg gcgcattaag cgcggcgggt gtggtggtta cgcgcagcgt gaccgctaca   1500
cttgccagcg ccctagcgcc cgctcctttc gctttcttcc cttcctttct cgccacgttc   1560
gccggctttc cccgtcaagc tctaaatcgg gggctccctt tagggttccg atttagtgct   1620
ttacggcacc tcgaccccaa aaaacttgat tagggtgatg gttcacgtag tgggccatcg   1680
ccctgataga cggtttttcg ccctttgacg ttggagtcca cgttctttaa tagtggactc   1740
ttgttccaaa ctggaacaac actcaaccct atctcggtct attcttttga tttataaggg   1800
attttgccga tttcggccta ttggttaaaa aatgagctga tttaacaaaa atttaacgcg   1860
aattttaaca aaatattaac gcttacaatt taggtggcac ttttcgggga aatgtgcgcg   1920
gaacccctat ttgtttattt ttctaaatac attcaaatat gtatccgctc atgagacaat   1980
aaccctgata aatgcttcaa taatattgaa aaaggaagag tatgagtatt caacatttcc   2040
gtgtcgccct tattcccttt tttgcggcat tttgccttcc tgtttttgct cacccagaaa   2100
cgctggtgaa agtaaaagat gctgaagatc agttgggtgc acgagtgggt tacatcgaac   2160
tggatctcaa cagcggtaag atccttgaga gttttcgccc cgaagaacgt tttccaatga   2220
tgagcacttt taaagttctg ctatgtggcg cggtattatc ccgtattgac gccgggcaag   2280
agcaactcgg tcgccgcata cactattctc agaatgactt ggttgagtac tcaccagtca   2340
cagaaaagca tcttacggat ggcatgacag taagagaatt atgcagtgct gccataacca   2400
tgagtgataa cactgcggcc aacttacttc tgacaacgat cggaggaccg aaggagctaa   2460
ccgctttttt gcacaacatg ggggatcatg taactcgcct tgatcgttgg gaaccggagc   2520
tgaatgaagc cataccaaac gacgagcgtg acaccacgat gcctgtagca atggcaacaa   2580
cgttgcgcaa actattaact ggcgaactac ttactctagc ttcccggcaa caattaatag   2640
actggatgga ggcggataaa gttgcaggac cacttctgcg ctcggccctt ccggctggct   2700
ggtttattgc tgataaatct ggagccggtg agcgtgggtc tcgcggtatc attgcagcac   2760
tggggccaga tggtaagccc tcccgtatcg tagttatcta cacgacgggg agtcaggcaa   2820
ctatggatga acgaaataga cagatcgctg agataggtgc ctcactgatt aagcattggt   2880
aactgtcaga ccaagtttac tcatatatac tttagattga tttaaaactt catttttaat   2940
ttaaaaggat ctaggtgaag atcctttttg ataatctcat gaccaaaatc ccttaacgtg   3000
agttttcgtt ccactgagcg tcagaccccg tagaaaagat caaaggatct tcttgagatc   3060
cttttttct gcgcgtaatc tgctgcttgc aaacaaaaaa accaccgcta ccagcggtgg   3120
tttgtttgcc ggatcaagag ctaccaactc tttttccgaa ggtaactggc ttcagcagag   3180
cgcagatacc aaatactgtc cttctagtgt agccgtagtt aggccaccac ttcaagaact   3240
ctgtagcacc gcctacatac ctcgctctgc taatcctgtt accagtggct gctgccagtg   3300
gcgataagtc gtgtcttacc gggttggact caagacgata gttaccggat aaggcgcagc   3360
ggtcgggctg aacggggggt tcgtgcacac agcccagctt ggagcgaacg acctacaccg   3420
aactgagata cctacagcgt gagctatgag aaagcgccac gcttcccgaa gggagaaagg   3480
cggacaggta tccggtaagc ggcagggtcg gaacaggaga gcgcacgagg gagcttccag   3540
ggggaaacgc ctggtatctt tatagtcctg tcgggtttcg ccacctctga cttgagcgtc   3600
gatttttgtg atgctcgtca ggggggcgga gcctatggaa aaacgccagc aacgcggcct   3660
ttttacggtt cctggccttt tgctggcctt ttgctcacat gttctttcct gcgttatccc   3720
```

-continued

```
ctgattctgt ggataaccgt attaccgcct ttgagtgagc tgataccgct cgccgcagcc   3780

gaacgaccga gcgcagcgag tcagtgagcg aggaagcgga agagcgccca atacgcaaac   3840

cgcctctccc cgcgcgttgg ccgattcatt aatgcagctg gcacgacagg tttcccgact   3900

ggaaagcggg cagtgagcgc aacgcaatta atgtgagtta gctcactcat taggcacccc   3960

aggctttaca ctttatgctt ccggctcgta tgttgtgtgg aattgtgagc ggataacaat   4020

ttcacacagg aaacagctat gaccatgatt acgccaagcg cgcaattaac cctcactaaa   4080

gggaacaaaa gctgggtacc gggccccccc tcgaggtcat tcatatgctt gagaagagag   4140

tcgggatagt ccaaaataaa acaaaggtaa gattacctgg tcaaaagtga aaacatcagt   4200

taaaaggtgg tataagtaaa atatcggtaa taaaaggtgg cccaaagtga aatttactct   4260

tttctactat tataaaaatt gaggatgttt tgtcggtact ttgatacgtc atttttgtat   4320

gaattggttt ttaagtttat tcgcgatttg gaaatgcata tctgtatttg agtcggtttt   4380

taagttcgtt gcttttgtaa atacagaggg atttgtataa gaaatatctt taaaaaaccc   4440

atatgctaat ttgacataat tttgagaaa aatatatatt caggcgaatt ccacaatgaa   4500

caataataag attaaaatag cttgcccccg ttgcagcgat gggtattttt tctagtaaaa   4560

taaaagataa acttagactc aaaacattta caaaaacaac ccctaaagtc ctaaagccca   4620

aagtgctatg cacgatccat agcaagccca gcccaaccca acccaaccca acccacccca   4680

gtgcagccaa ctggcaaata gtctccaccc ccggcactat caccgtgagt tgtccgcacc   4740

accgcacgtc tcgcagccaa aaaaaaaaaa agaaagaaaa aaaagaaaaa gaaaaacagc   4800

aggtgggtcc gggtcgtggg ggccggaaaa gcgaggagga tcgcgagcag cgacgaggcc   4860

cggccctccc tccgcttcca aagaaacgcc ccccatcgcc actatataca taccccccc   4920

tctcctccca tccccccaac cctaccacca ccaccaccac cacctcctcc cccctcgctg   4980

ccggacgacg agctcctccc ccctccccct ccgccgccgc cggtaaccac cccgcccctc   5040

tcctctttct ttctccgttt tttttttcgt ctcggtctcg atctttggcc ttggtagttt   5100

gggtgggcga gagcggcttc gtcgcccaga tcggtgcgcg ggagggggcgg gatctcgcgg   5160

ctggcgtctc cgggcgtgag tcggcccgga tcctcgcggg gaatggggct ctcggatgta   5220

gatcttcttt ctttcttctt tttgtggtag aatttgaatc cctcagcatt gttcatcggt   5280

agtttttctt ttcatgattt gtgacaaatg cagcctcgtg cggagctttt ttgtagc      5337
```

<210> SEQ ID NO 24
<211> LENGTH: 306
<212> TYPE: PRT
<213> ORGANISM: Artificial Sequence
<220> FEATURE:
<223> OTHER INFORMATION: pTP8-5 vector
<220> FEATURE:
<221> NAME/KEY: VARIANT
<222> LOCATION: (1)...(306)
<223> OTHER INFORMATION: Xaa = Any Amino Acid

<400> SEQUENCE: 24

```
Met Ala His Ala Arg Val Leu Leu Leu Ala Leu Ala Val Leu Ala Thr
 1               5                  10                  15

Ala Ala Val Ala Val Ala Ser Ser Ser Ser Phe Ala Asp Ser Asn Pro
            20                  25                  30

Ile Arg Pro Val Thr Asp Arg Ala Ala Ala Ser Thr Gln Gly Ile Ser
        35                  40                  45

Glu Asp Leu Tyr Ser Arg Leu Val Glu Met Ala Thr Ile Ser Gln Ala
    50                  55                  60
```

-continued

```
Ala Tyr Ala Asp Leu Cys Asn Ile Pro Ser Thr Ile Ile Lys Gly Glu
65                  70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110

Thr Asn Leu Gln Leu Asp Thr Asn Tyr Thr Leu Thr Pro Phe Asp Thr
        115                 120                 125

Leu Pro Gln Cys Asn Gly Cys Glu Val His Gly Gly Tyr Tyr Ile Gly
    130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
        275                 280                 285

Thr Thr Tyr Phe Gly Met Thr Ser Gly Ala Cys Thr Trp Pro Val Ala
    290                 295                 300

Ala Ala
305
```

<210> SEQ ID NO 25
<211> LENGTH: 5277
<212> TYPE: DNA
<213> ORGANISM: Artificial Sequence
<220> FEATURE:
<223> OTHER INFORMATION: pTP5-1 vector

<400> SEQUENCE: 25

```
aagcttaaca tgaagcagtt ctccgccaaa cacgtcctcg cagttgtggt gactgcaggg     60

cacgccttag cagcctctac gcaaggcatc tccgaagacc tctacagccg tttagtcgaa    120

atggccacta tctcccaagc tgcctacgcc gacctgtgca acattccgtc gactattatc    180

aagggagaga aaatttacaa ttctcaaact gacattaacg gatggatcct ccgcgacgac    240

agcagcaaag aaataatcac cgtcttccgt ggcactggta gtgatacgaa tctacaactc    300

gatactaact acaccctcac gcctttcgac accctaccac aatgcaacgg ttgtgaagta    360

cacggtggat attatattgg atgggtctcc gtccaggacc aagtcgagtc gcttgtcaaa    420

cagcaggtta gccagtatcc ggactacgcg ctgaccgtga ccggccackc cctcggcgcc    480

tccctggcgg cactcactgc cgcccagctg tctgcgacat acgacaacat ccgcctgtac    540

accttcggcg aaccgcgcag cggcaatcag gccttcgcgt cgtacatgaa cgatgccttc    600
```

-continued

```
caagcctcga gcccagatac gacgcagtat ttccgggtca ctcatgccaa cgacggcatc    660
ccaaacctgc ccccggtgga gcaggggtac gcccatggcg gtgtagagta ctggagcgtt    720
gatccttaca gcgcccagaa cacatttgtc tgcactgggg atgaagtgca gtgctgtgag    780
gcccagggcg gacagggtgt gaataatgcg cacacgactt attttgggat gacgagcggc    840
gcatgcacct ggccggtcgc ggccgcggaa ccactgaagg atgagctgta aagaagcaga    900
tcgttcaaac atttggcaat aaagtttctt aagattgaat cctgttgccg gtcttgcgat    960
gattatcata taatttctgt tgaattacgt taagcatgta ataattaaca tgtaatgcat   1020
gacgttattt atgagatggg tttttatgat tagagtcccg caattataca tttaatacgc   1080
gatagaaaac aaaatatagc gcgcaaacta ggataaatta tcgcgcgcgg tgtcatctat   1140
gttactagat cgataagctt ctagagcggc cggtggagct ccaattcgcc ctatagtgag   1200
tcgtattacg cgcgctcact ggccgtcgtt ttacaacgtc gtgactggga aaaccctggc   1260
gttacccaac ttaatcgcct tgcagcacat ccccctttcg ccagctggcg taatagcgaa   1320
gaggcccgca ccgatcgccc ttcccaacag ttgcgcagcc tgaatggcga atgggacgcg   1380
ccctgtagcg gcgcattaag cgcggcgggt gtggtggtta cgcgcagcgt gaccgctaca   1440
cttgccagcg ccctagcgcc cgctcctttc gctttcttcc cttcctttct cgccacgttc   1500
gccggctttc cccgtcaagc tctaaatcgg gggctccctt tagggttccg atttagtgct   1560
ttacggcacc tcgaccccaa aaaacttgat tagggtgatg gttcacgtag tgggccatcg   1620
ccctgataga cggtttttcg ccctttgacg ttggagtcca cgttctttaa tagtggactc   1680
ttgttccaaa ctggaacaac actcaaccct atctcggtct attcttttga tttataaggg   1740
attttgccga tttcggccta ttggttaaaa aatgagctga tttaacaaaa atttaacgcg   1800
aattttaaca aaatattaac gcttacaatt taggtggcac ttttcgggga aatgtgcgcg   1860
gaacccctat ttgtttattt ttctaaatac attcaaatat gtatccgctc atgagacaat   1920
aaccctgata aatgcttcaa taatattgaa aaaggaagag tatgagtatt caacatttcc   1980
gtgtcgccct tattcccttt tttgcggcat tttgccttcc tgtttttgct cacccagaaa   2040
cgctggtgaa agtaaaagat gctgaagatc agttgggtgc acgagtgggt tacatcgaac   2100
tggatctcaa cagcggtaag atccttgaga gttttcgccc cgaagaacgt tttccaatga   2160
tgagcacttt taaagttctg ctatgtggcg cggtattatc ccgtattgac gccgggcaag   2220
agcaactcgg tcgccgcata cactattctc agaatgactt ggttgagtac tcaccagtca   2280
cagaaaagca tcttacggat ggcatgacag taagagaatt atgcagtgct gccataacca   2340
tgagtgataa cactgcggcc aacttacttc tgacaacgat cggaggaccg aaggagctaa   2400
ccgctttttt gcacaacatg ggggatcatg taactcgcct tgatcgttgg gaaccggagc   2460
tgaatgaagc cataccaaac gacgagcgtg acaccacgat gcctgtagca atggcaacaa   2520
cgttgcgcaa actattaact ggcgaactac ttactctagc ttcccggcaa caattaatag   2580
actggatgga ggcggataaa gttgcaggac cacttctgcg ctcggccctt ccggctggct   2640
ggtttattgc tgataaatct ggagccggtg agcgtgggtc tcgcggtatc attgcagcac   2700
tggggccaga tggtaagccc tcccgtatcg tagttatcta cacgacgggg agtcaggcaa   2760
ctatggatga acgaaataga cagatcgctg agataggtgc ctcactgatt aagcattggt   2820
aactgtcaga ccaagtttac tcatatatac tttagattga tttaaaactt catttttaat   2880
ttaaaaggat ctaggtgaag atcctttttg ataatctcat gaccaaaatc ccttaacgtg   2940
agttttcgtt ccactgagcg tcagaccccg tagaaaagat caaaggatct tcttgagatc   3000
```

-continued

```
cttttttttct gcgcgtaatc tgctgcttgc aaacaaaaaa accaccgcta ccagcggtgg   3060
tttgtttgcc ggatcaagag ctaccaactc tttttccgaa ggtaactggc ttcagcagag   3120
cgcagatacc aaatactgtc cttctagtgt agccgtagtt aggccaccac ttcaagaact   3180
ctgtagcacc gcctacatac ctcgctctgc taatcctgtt accagtggct gctgccagtg   3240
gcgataagtc gtgtcttacc gggttggact caagacgata gttaccggat aaggcgcagc   3300
ggtcgggctg aacggggggt tcgtgcacac agcccagctt ggagcgaacg acctacaccg   3360
aactgagata cctacagcgt gagctatgag aaagcgccac gcttcccgaa gggagaaagg   3420
cggacaggta tccggtaagc ggcagggtcg gaacaggaga gcgcacgagg gagcttccag   3480
ggggaaacgc ctggtatctt tatagtcctg tcgggtttcg ccacctctga cttgagcgtc   3540
gatttttgtg atgctcgtca ggggggcgga gcctatggaa aaacgccagc aacgcggcct   3600
ttttacggtt cctggccttt tgctggcctt ttgctcacat gttctttcct gcgttatccc   3660
ctgattctgt ggataaccgt attaccgcct ttgagtgagc tgataccgct cgccgcagcc   3720
gaacgaccga gcgcagcgag tcagtgagcg aggaagcgga agagcgccca atacgcaaac   3780
cgcctctccc cgcgcgttgg ccgattcatt aatgcagctg gcacgacagg tttcccgact   3840
ggaaagcggg cagtgagcgc aacgcaatta atgtgagtta gctcactcat taggcacccc   3900
aggctttaca ctttatgctt ccggctcgta tgttgtgtgg aattgtgagc ggataacaat   3960
ttcacacagg aaacagctat gaccatgatt acgccaagcg cgcaattaac cctcactaaa   4020
gggaacaaaa gctgggtacc gggccccccc tcgaggtcat tcatatgctt gagaagagag   4080
tcgggatagt ccaaaataaa acaaaggtaa gattacctgg tcaaaagtga aaacatcagt   4140
taaaaggtgg tataagtaaa atatcggtaa taaaaggtgg cccaaagtga aatttactct   4200
tttctactat tataaaaatt gaggatgttt tgtcggtact ttgatacgtc atttttgtat   4260
gaattggttt ttaagtttat tcgcgatttg gaaatgcata tctgtatttg agtcggtttt   4320
taagttcgtt gcttttgtaa atacagaggg atttgtataa gaaatatctt taaaaaaccc   4380
atatgctaat ttgacataat ttttgagaaa aatatatatt caggcgaatt ccacaatgaa   4440
caataataag attaaaatag cttgccccg ttgcagcgat gggtattttt tctagtaaaa   4500
taaaagataa acttagactc aaaacattta caaaaacaac ccctaaagtc ctaaagccca   4560
aagtgctatg cacgatccat agcaagccca gcccaaccca acccaaccca acccacccca   4620
gtgcagccaa ctggcaaata gtctccaccc ccggcactat caccgtgagt tgtccgcacc   4680
accgcacgtc tcgcagccaa aaaaaaaaaa agaaagaaaa aaaagaaaaa gaaaaacagc   4740
aggtgggtcc gggtcgtggg ggccggaaaa gcgaggagga tcgcgagcag cgacgaggcc   4800
cggccctccc tccgcttcca aagaaacgcc ccccatcgcc actatataca taccccccc   4860
tctcctccca tccccccaac cctaccacca ccaccaccac cacctcctcc cccctcgctg   4920
ccggacgacg agctcctccc ccctccccct ccgccgccgc cggtaaccac cccgcccctc   4980
tcctctttct ttctccgttt tttttttcgt ctcggtctcg atctttggcc ttggtagttt   5040
gggtgggcga gagcggcttc gtcgcccaga tcggtgcgcg ggaggggcgg gatctcgcgg   5100
ctggcgtctc cgggcgtgag tcggcccgga tcctcgcggg gaatggggct ctcggatgta   5160
gatcttcttt ctttcttctt tttgtggtag aatttgaatc cctcagcatt gttcatcggt   5220
agtttttctt ttcatgattt gtgacaaatg cagcctcgtg cggagctttt ttgtagc      5277
```

<210> SEQ ID NO 26

-continued

```
<211> LENGTH: 293
<212> TYPE: PRT
<213> ORGANISM: Artificial Sequence
<220> FEATURE:
<223> OTHER INFORMATION: pTP5-1 vector
<220> FEATURE:
<221> NAME/KEY: VARIANT
<222> LOCATION: (1)...(293)
<223> OTHER INFORMATION: Xaa = Any Amino Acid

<400> SEQUENCE: 26

Met Lys Gln Phe Ser Ala Lys His Val Leu Ala Val Val Val Thr Ala
 1               5                  10                  15

Gly His Ala Leu Ala Ala Ser Thr Gln Gly Ile Ser Glu Asp Leu Tyr
            20                  25                  30

Ser Arg Leu Val Glu Met Ala Thr Ile Ser Gln Ala Ala Tyr Ala Asp
        35                  40                  45

Leu Cys Asn Ile Pro Ser Thr Ile Ile Lys Gly Glu Lys Ile Tyr Asn
    50                  55                  60

Ser Gln Thr Asp Ile Asn Gly Trp Ile Leu Arg Asp Asp Ser Ser Lys
65                  70                  75                  80

Glu Ile Ile Thr Val Phe Arg Gly Thr Gly Ser Asp Thr Asn Leu Gln
                85                  90                  95

Leu Asp Thr Asn Tyr Thr Leu Thr Pro Phe Asp Thr Leu Pro Gln Cys
            100                 105                 110

Asn Gly Cys Glu Val His Gly Gly Tyr Tyr Ile Gly Trp Val Ser Val
        115                 120                 125

Gln Asp Gln Val Glu Ser Leu Val Lys Gln Gln Val Ser Gln Tyr Pro
    130                 135                 140

Asp Tyr Ala Leu Thr Val Thr Gly His Xaa Leu Gly Ala Ser Leu Ala
145                 150                 155                 160

Ala Leu Thr Ala Ala Gln Leu Ser Ala Thr Tyr Asp Asn Ile Arg Leu
                165                 170                 175

Tyr Thr Phe Gly Glu Pro Arg Ser Gly Asn Gln Ala Phe Ala Ser Tyr
            180                 185                 190

Met Asn Asp Ala Phe Gln Ala Ser Ser Pro Asp Thr Thr Gln Tyr Phe
        195                 200                 205

Arg Val Thr His Ala Asn Asp Gly Ile Pro Asn Leu Pro Pro Val Glu
    210                 215                 220

Gln Gly Tyr Ala His Gly Gly Val Glu Tyr Trp Ser Val Asp Pro Tyr
225                 230                 235                 240

Ser Ala Gln Asn Thr Phe Val Cys Thr Gly Asp Glu Val Gln Cys Cys
                245                 250                 255

Glu Ala Gln Gly Gly Gln Gly Val Asn Asn Ala His Thr Thr Tyr Phe
            260                 265                 270

Gly Met Thr Ser Gly Ala Cys Thr Trp Pro Val Ala Ala Ala Glu Pro
        275                 280                 285

Leu Lys Asp Glu Leu
    290


<210> SEQ ID NO 27
<211> LENGTH: 5327
<212> TYPE: DNA
<213> ORGANISM: Artificial Sequence
<220> FEATURE:
<223> OTHER INFORMATION: pTP4a2 vector

<400> SEQUENCE: 27
```

-continued

```
gatcctccgc gacgacagca gcaaagaaat aatcaccgtc ttccgtggca ctggtagtga     60
tacgaatcta caactcgata ctaactacac cctcacgcct ttcgacaccc taccacaatg    120
caacggttgt gaagtacacg gtggatatta tattggatgg gtctccgtcc aggaccaagt    180
cgagtcgctt gtcaaacagc aggttagcca gtatccggac tacgcgctga ccgtgaccgg    240
ccackccctc ggcgcctccc tggcggcact cactgccgcc cagctgtctg cgacatacga    300
caacatccgc ctgtacacct tcggcgaacc gcgcagcggc aatcaggcct tcgcgtcgta    360
catgaacgat gccttccaag cctcgagccc agatacgacg cagtatttcc gggtcactca    420
tgccaacgac ggcatcccaa acctgccccc ggtggagcag gggtacgccc atggcggtgt    480
agagtactgg agcgttgatc cttacagcgc ccagaacaca tttgtctgca ctggggatga    540
agtgcagtgc tgtgaggccc agggcggaca gggtgtgaat aatgcgcaca cgacttattt    600
tgggatgacg agcggagcct gtacatggtg atcagtcatt tcagcctccc cgagtgtacc    660
aggaaagatg gatgtcctgg agagggggcc gcgtaaccac tgaaggatga gctgtaaaga    720
agcagatcgt tcaaacattt ggcaataaag tttcttaaga ttgaatcctg ttgccggtct    780
tgcgatgatt atcatataat ttctgttgaa ttacgttaag catgtaataa ttaacatgta    840
atgcatgacg ttatttatga gatgggtttt tatgattaga gtcccgcaat tatacattta    900
atacgcgata gaaaacaaaa tatagcgcgc aaactaggat aaattatcgc gcgcggtgtc    960
atctatgtta ctagatcgat aagcttctag agcggccggt ggagctccaa ttcgccctat   1020
agtgagtcgt attacgcgcg ctcactggcc gtcgttttac aacgtcgtga ctgggaaaac   1080
cctggcgtta cccaacttaa tcgccttgca gcacatcccc ctttcgccag ctggcgtaat   1140
agcgaagagg cccgcaccga tcgcccttcc caacagttgc gcagcctgaa tggcgaatgg   1200
gacgcgccct gtagcggcgc attaagcgcg gcgggtgtgg tggttacgcg cagcgtgacc   1260
gctacacttg ccagcgccct agcgcccgct cctttcgctt tcttcccttc ctttctcgcc   1320
acgttcgccg gctttccccg tcaagctcta aatcgggggc tccctttagg gttccgattt   1380
agtgctttac ggcacctcga ccccaaaaaa cttgattagg gtgatggttc acgtagtggg   1440
ccatcgccct gatagacggt ttttcgccct ttgacgttgg agtccacgtt ctttaatagt   1500
ggactcttgt tccaaactgg aacaacactc aaccctatct cggtctattc ttttgattta   1560
taagggattt tgccgatttc ggcctattgg ttaaaaaatg agctgattta acaaaaattt   1620
aacgcgaatt ttaacaaaat attaacgctt acaatttagg tggcactttt cggggaaatg   1680
tgcgcggaac ccctatttgt ttatttttct aaatacattc aaatatgtat ccgctcatga   1740
gacaataacc ctgataaatg cttcaataat attgaaaaag gaagagtatg agtattcaac   1800
atttccgtgt cgcccttatt cccttttttg cggcattttg ccttcctgtt tttgctcacc   1860
cagaaacgct ggtgaaagta aaagatgctg aagatcagtt gggtgcacga gtgggttaca   1920
tcgaactgga tctcaacagc ggtaagatcc ttgagagttt tcgccccgaa gaacgttttc   1980
caatgatgag cacttttaaa gttctgctat gtggcgcggt attatcccgt attgacgccg   2040
ggcaagagca actcggtcgc cgcatacact attctcagaa tgacttggtt gagtactcac   2100
cagtcacaga aaagcatctt acggatggca tgacagtaag agaattatgc agtgctgcca   2160
taaccatgag tgataacact gcggccaact tacttctgac aacgatcgga ggaccgaagg   2220
agctaaccgc ttttttgcac aacatggggg atcatgtaac tcgccttgat cgttgggaac   2280
cggagctgaa tgaagccata ccaaacgacg agcgtgacac cacgatgcct gtagcaatgg   2340
caacaacgtt gcgcaaacta ttaactggcg aactacttac tctagcttcc cggcaacaat   2400
```

-continued

```
taatagactg gatggaggcg gataaagttg caggaccact tctgcgctcg gcccttccgg   2460
ctggctggtt tattgctgat aaatctggag ccggtgagcg tgggtctcgc ggtatcattg   2520
cagcactggg gccagatggt aagccctccc gtatcgtagt tatctacacg acggggagtc   2580
aggcaactat ggatgaacga aatagacaga tcgctgagat aggtgcctca ctgattaagc   2640
attggtaact gtcagaccaa gtttactcat atatacttta gattgattta aaacttcatt   2700
tttaatttaa aaggatctag gtgaagatcc tttttgataa tctcatgacc aaaatccctt   2760
aacgtgagtt ttcgttccac tgagcgtcag accccgtaga aaagatcaaa ggatcttctt   2820
gagatccttt ttttctgcgc gtaatctgct gcttgcaaac aaaaaaacca ccgctaccag   2880
cggtggtttg tttgccggat caagagctac caactctttt tccgaaggta actggcttca   2940
gcagagcgca gataccaaat actgtccttc tagtgtagcc gtagttaggc caccacttca   3000
agaactctgt agcaccgcct acatacctcg ctctgctaat cctgttacca gtggctgctg   3060
ccagtggcga taagtcgtgt cttaccgggt tggactcaag acgatagtta ccggataagg   3120
cgcagcggtc gggctgaacg gggggttcgt gcacacagcc cagcttggag cgaacgacct   3180
acaccgaact gagataccta cagcgtgagc tatgagaaag cgccacgctt cccgaaggga   3240
gaaaggcgga caggtatccg gtaagcggca gggtcggaac aggagagcgc acgagggagc   3300
ttccaggggg aaacgcctgg tatctttata gtcctgtcgg gtttcgccac ctctgacttg   3360
agcgtcgatt tttgtgatgc tcgtcagggg ggcggagcct atggaaaaac gccagcaacg   3420
cggccttttt acggttcctg gccttttgct ggccttttgc tcacatgttc tttcctgcgt   3480
tatcccctga ttctgtggat aaccgtatta ccgcctttga gtgagctgat accgctcgcc   3540
gcagccgaac gaccgagcgc agcgagtcag tgagcgagga agcggaagag cgcccaatac   3600
gcaaaccgcc tctccccgcg cgttggccga ttcattaatg cagctggcac gacaggtttc   3660
ccgactggaa agcgggcagt gagcgcaacg caattaatgt gagttagctc actcattagg   3720
caccccaggc tttacacttt atgcttccgg ctcgtatgtt gtgtggaatt gtgagcggat   3780
aacaatttca cacaggaaac agctatgacc atgattacgc caagcgcgca attaaccctc   3840
actaaaggga acaaaagctg ggtaccgggc ccccctcga ggtcattcat atgcttgaga   3900
agagagtcgg gatagtccaa aataaaacaa aggtaagatt acctggtcaa aagtgaaaac   3960
atcagttaaa aggtggtata agtaaaatat cggtaataaa aggtggccca aagtgaaatt   4020
tactcttttc tactattata aaaattgagg atgttttgtc ggtactttga tacgtcattt   4080
ttgtatgaat tggtttttaa gtttattcgc gatttggaaa tgcatatctg tatttgagtc   4140
ggtttttaag ttcgttgctt ttgtaaatac agagggattt gtataagaaa tatctttaaa   4200
aaacccatat gctaatttga cataattttt gagaaaaata tatattcagg cgaattccac   4260
aatgaacaat aataagatta aaatagcttg cccccgttgc agcgatgggt attttttcta   4320
gtaaaataaa agataaactt agactcaaaa catttacaaa aacaacccct aaagtcctaa   4380
agcccaaagt gctatgcacg atccatagca agcccagccc aacccaaccc aacccaaccc   4440
accccagtgc agccaactgg caaatagtct ccacccccgg cactatcacc gtgagttgtc   4500
cgcaccaccg cacgtctcgc agccaaaaaa aaaaaaagaa agaaaaaaaa gaaaaagaaa   4560
aacagcaggt gggtccgggt cgtgggggcc ggaaaagcga ggaggatcgc gagcagcgac   4620
gaggcccggc cctccctccg cttccaaaga aacgcccccc atcgccacta tatacatacc   4680
ccccctctc ctcccatccc cccaacccta ccaccaccac caccaccacc tcctcccccc   4740
```

-continued

```
tcgctgccgg acgacgagct cctccccct cccctccgc cgccgccggt aaccaccccg   4800

cccctctcct ctttctttct ccgttttttt tttcgtctcg gtctcgatct ttggccttgg   4860

tagtttgggt gggcgagagc ggcttcgtcg cccagatcgg tgcgcgggag gggcgggatc   4920

tcgcggctgg cgtctccggg cgtgagtcgg cccggatcct cgcggggaat ggggctctcg   4980

gatgtagatc ttctttcttt cttcttttttg tggtagaatt tgaatccctc agcattgttc   5040

atcggtagtt tttcttttca tgatttgtga caaatgcagc ctcgtgcgga gcttttttgt   5100

agcaagctta acatgaagca gttctccgcc aaacacgtcc tcgcagttgt ggtgactgca   5160

gggcacgcct tagcagcctc tacgcaaggc atctccgaag acctctacag ccgtttagtc   5220

gaaatggcca ctatctccca agctgcctac gccgacctgt gcaacattcc gtcgactatt   5280

atcaagggag agaaaattta caattctcaa actgacatta acggatg               5327
```

<210> SEQ ID NO 28
<211> LENGTH: 209
<212> TYPE: PRT
<213> ORGANISM: Artificial Sequence
<220> FEATURE:
<223> OTHER INFORMATION: pTP4a2 vector
<220> FEATURE:
<221> NAME/KEY: VARIANT
<222> LOCATION: (1)...(209)
<223> OTHER INFORMATION: Xaa = Any Amino Acid

<400> SEQUENCE: 28

```
Ile Leu Arg Asp Asp Ser Ser Lys Glu Ile Ile Thr Val Phe Arg Gly
 1               5                  10                  15

Thr Gly Ser Asp Thr Asn Leu Gln Leu Asp Thr Asn Tyr Thr Leu Thr
            20                  25                  30

Pro Phe Asp Thr Leu Pro Gln Cys Asn Gly Cys Glu Val His Gly Gly
        35                  40                  45

Tyr Tyr Ile Gly Trp Val Ser Val Gln Asp Gln Val Glu Ser Leu Val
    50                  55                  60

Lys Gln Gln Val Ser Gln Tyr Pro Asp Tyr Ala Leu Thr Val Thr Gly
65                  70                  75                  80

His Xaa Leu Gly Ala Ser Leu Ala Ala Leu Thr Ala Ala Gln Leu Ser
                85                  90                  95

Ala Thr Tyr Asp Asn Ile Arg Leu Tyr Thr Phe Gly Glu Pro Arg Ser
            100                 105                 110

Gly Asn Gln Ala Phe Ala Ser Tyr Met Asn Asp Ala Phe Gln Ala Ser
        115                 120                 125

Ser Pro Asp Thr Thr Gln Tyr Phe Arg Val Thr His Ala Asn Asp Gly
    130                 135                 140

Ile Pro Asn Leu Pro Pro Val Glu Gln Gly Tyr Ala His Gly Gly Val
145                 150                 155                 160

Glu Tyr Trp Ser Val Asp Pro Tyr Ser Ala Gln Asn Thr Phe Val Cys
                165                 170                 175

Thr Gly Asp Glu Val Gln Cys Cys Glu Ala Gln Gly Gly Gln Gly Val
            180                 185                 190

Asn Asn Ala His Thr Thr Tyr Phe Gly Met Thr Ser Gly Ala Cys Thr
        195                 200                 205

Trp
```

<210> SEQ ID NO 29
<211> LENGTH: 5338
<212> TYPE: DNA

-continued

<213> ORGANISM: Artificial Sequence
<220> FEATURE:
<223> OTHER INFORMATION: pTP3-1 vector

<400> SEQUENCE: 29
aagcttacca tggcccacgc ccgcgtcctc ctcctggcgc tcgccgtgct ggccacggcc 60
gccgtcgccg tcgcctcctc ctcctccttc gccgactcca acccgatccg gcccgtcacc 120
gaccgcgcgg ccgcctccac gcagggcatc tccgaagacc tctacagccg tttagtcgaa 180
atggccacta tctcccaagc tgcctacgcc gacctgtgca acattccgtc gactattatc 240
aagggagaga aaatttacaa ttctcaaact gacattaacg gatggatcct ccgcgacgac 300
agcagcaaag aaataatcac cgtcttccgt ggcactggta gtgatacgaa tctacaactc 360
gatactaact acaccctcac gcctttcgac accctaccac aatgcaacgg ttgtgaagta 420
cacggtggat attatattgg atgggtctcc gtccaggacc aagtcgagtc gcttgtcaaa 480
cagcaggtta gccagtatcc ggactacgcg ctgaccgtga ccggccackc cctcggcgcc 540
tccctggcgg cactcactgc cgcccagctg tctgcgacat acgacaacat ccgcctgtac 600
accttcggcg aaccgcgcag cggcaatcag gccttcgcgt cgtacatgaa cgatgccttc 660
caagcctcga gcccagatac gacgcagtat ttccgggtca ctcatgccaa cgacggcatc 720
ccaaacctgc ccccggtgga gcaggggtac gcccatggcg gtgtagagta ctggagcgtt 780
gatccttaca gcgcccagaa cacatttgtc tgcactgggg atgaagtgca gtgctgtgag 840
gcccagggcg gacagggtgt gaataatgcg cacacgactt attttgggat gacgagcggc 900
gcatgcacct ggccggtcgc ggccgcggaa accactgaag gatgagctgt aaagaagcag 960
atcgttcaaa catttggcaa taaagtttct taagattgaa tcctgttgcc ggtcttgcga 1020
tgattatcat ataatttctg ttgaattacg ttaagcatgt aataattaac atgtaatgca 1080
tgacgttatt tatgagatgg gtttttatga ttagagtccc gcaattatac atttaatacg 1140
cgatagaaaa caaaatatag cgcgcaaact aggataaatt atcgcgcgcg gtgtcatcta 1200
tgttactaga tcgataagct tctagagcgg ccggtggagc tccaattcgc cctatagtga 1260
gtcgtattac gcgcgctcac tggccgtcgt tttacaacgt cgtgactggg aaaaccctgg 1320
cgttacccaa cttaatcgcc ttgcagcaca tccccctttc gccagctggc gtaatagcga 1380
agaggcccgc accgatcgcc cttcccaaca gttgcgcagc ctgaatggcg aatgggacgc 1440
gccctgtagc ggcgcattaa gcgcggcggg tgtggtggtt acgcgcagcg tgaccgctac 1500
acttgccagc gccctagcgc ccgctccttt cgctttcttc ccttcctttc tcgccacgtt 1560
cgccggcttt ccccgtcaag ctctaaatcg ggggctccct ttagggttcc gatttagtgc 1620
tttacggcac ctcgacccca aaaaacttga ttagggtgat ggttcacgta gtgggccatc 1680
gccctgatag acggtttttc gccctttgac gttggagtcc acgttcttta atagtggact 1740
cttgttccaa actggaacaa cactcaaccc tatctcggtc tattcttttg atttataagg 1800
gattttgccg atttcggcct attggttaaa aaatgagctg atttaacaaa aatttaacgc 1860
gaattttaac aaaatattaa cgcttacaat ttaggtggca cttttcgggg aaatgtgcgc 1920
ggaaccccta tttgtttatt tttctaaata cattcaaata tgtatccgct catgagacaa 1980
taaccctgat aaatgcttca ataatattga aaaaggaaga gtatgagtat tcaacatttc 2040
cgtgtcgccc ttattccctt ttttgcggca ttttgccttc ctgtttttgc tcacccagaa 2100
acgctggtga aagtaaaaga tgctgaagat cagttgggtg cacgagtggg ttacatcgaa 2160
ctggatctca acagcggtaa gatccttgag agttttcgcc ccgaagaacg ttttccaatg 2220

-continued

```
atgagcactt ttaaagttct gctatgtggc gcggtattat cccgtattga cgccgggcaa   2280
gagcaactcg gtcgccgcat acactattct cagaatgact tggttgagta ctcaccagtc   2340
acagaaaagc atcttacgga tggcatgaca gtaagagaat tatgcagtgc tgccataacc   2400
atgagtgata acactgcggc caacttactt ctgacaacga tcggaggacc gaaggagcta   2460
accgcttttt tgcacaacat gggggatcat gtaactcgcc ttgatcgttg ggaaccggag   2520
ctgaatgaag ccataccaaa cgacgagcgt gacaccacga tgcctgtagc aatggcaaca   2580
acgttgcgca aactattaac tggcgaacta cttactctag cttcccggca acaattaata   2640
gactggatgg aggcggataa agttgcagga ccacttctgc gctcggccct tccggctggc   2700
tggtttattg ctgataaatc tggagccggt gagcgtgggt ctcgcggtat cattgcagca   2760
ctggggccag atggtaagcc ctcccgtatc gtagttatct acacgacggg gagtcaggca   2820
actatggatg aacgaaatag acagatcgct gagataggtg cctcactgat taagcattgg   2880
taactgtcag accaagttta ctcatatata ctttagattg atttaaaact tcatttttaa   2940
tttaaaagga tctaggtgaa gatccttttt gataatctca tgaccaaaat cccttaacgt   3000
gagttttcgt tccactgagc gtcagacccc gtagaaaaga tcaaaggatc ttcttgagat   3060
cctttttttc tgcgcgtaat ctgctgcttg caaacaaaaa aaccaccgct accagcggtg   3120
gtttgtttgc cggatcaaga gctaccaact ctttttccga aggtaactgg cttcagcaga   3180
gcgcagatac caaatactgt ccttctagtg tagccgtagt taggccacca cttcaagaac   3240
tctgtagcac cgcctacata cctcgctctg ctaatcctgt taccagtggc tgctgccagt   3300
ggcgataagt cgtgtcttac cgggttggac tcaagacgat agttaccgga taaggcgcag   3360
cggtcgggct gaacgggggg ttcgtgcaca cagcccagct tggagcgaac gacctacacc   3420
gaactgagat acctacagcg tgagctatga gaaagcgcca cgcttcccga agggagaaag   3480
gcggacaggt atccggtaag cggcagggtc ggaacaggag agcgcacgag ggagcttcca   3540
gggggaaacg cctggtatct ttatagtcct gtcgggtttc gccacctctg acttgagcgt   3600
cgatttttgt gatgctcgtc aggggggcgg agcctatgga aaaacgccag caacgcggcc   3660
tttttacggt tcctggcctt ttgctggcct tttgctcaca tgttctttcc tgcgttatcc   3720
cctgattctg tggataaccg tattaccgcc tttgagtgag ctgataccgc tcgccgcagc   3780
cgaacgaccg agcgcagcga gtcagtgagc gaggaagcgg aagagcgccc aatacgcaaa   3840
ccgcctctcc ccgcgcgttg gccgattcat taatgcagct ggcacgacag gtttcccgac   3900
tggaaagcgg gcagtgagcg caacgcaatt aatgtgagtt agctcactca ttaggcaccc   3960
caggctttac actttatgct tccggctcgt atgttgtgtg gaattgtgag cggataacaa   4020
tttcacacag gaaacagcta tgaccatgat tacgccaagc gcgcaattaa ccctcactaa   4080
agggaacaaa agctgggtac cgggcccccc ctcgaggtca ttcatatgct tgagaagaga   4140
gtcgggatag tccaaaataa aacaaaggta agattacctg gtcaaaagtg aaaacatcag   4200
ttaaaaggtg gtataagtaa aatatcggta ataaaaggtg gcccaaagtg aaatttactc   4260
ttttctacta ttataaaaat tgaggatgtt ttgtcggtac tttgatacgt catttttgta   4320
tgaattggtt tttaagttta ttcgcgattt ggaaatgcat atctgtattt gagtcggttt   4380
ttaagttcgt tgcttttgta aatacagagg gatttgtata agaaatatct ttaaaaaacc   4440
catatgctaa tttgacataa tttttgagaa aaatatatat tcaggcgaat tccacaatga   4500
acaataataa gattaaaata gcttgccccc gttgcagcga tgggtatttt ttctagtaaa   4560
```

-continued

```
ataaaagata aacttagact caaaacattt acaaaaacaa cccctaaagt cctaaagccc   4620

aaagtgctat gcacgatcca tagcaagccc agcccaaccc aacccaaccc aacccacccc   4680

agtgcagcca actggcaaat agtctccacc cccggcacta tcaccgtgag ttgtccgcac   4740

caccgcacgt ctcgcagcca aaaaaaaaaa aagaaagaaa aaaaagaaaa agaaaaacag   4800

caggtgggtc cgggtcgtgg gggccggaaa agcgaggagg atcgcgagca gcgacgaggc   4860

ccggccctcc ctccgcttcc aaagaaacgc cccccatcgc cactatatac atacccccccc   4920

ctctcctccc atccccccaa ccctaccacc accaccacca ccacctcctc ccccctcgct   4980

gccggacgac gagctcctcc cccctccccc tccgccgccg ccggtaacca ccccgcccct   5040

ctcctctttc tttctccgtt tttttttcg tctcggtctc gatctttggc cttggtagtt   5100

tgggtgggcg agagcggctt cgtcgcccag atcggtgcgc gggaggggcg ggatctcgcg   5160

gctggcgtct ccgggcgtga gtcggcccgg atcctcgcgg ggaatggggc tctcggatgt   5220

agatcttctt tctttcttct ttttgtggta gaatttgaat ccctcagcat tgttcatcgg   5280

tagtttttct tttcatgatt tgtgacaaat gcagcctcgt gcggagcttt tttgtagc      5338


<210> SEQ ID NO 30
<211> LENGTH: 311
<212> TYPE: PRT
<213> ORGANISM: Artificial Sequence
<220> FEATURE:
<223> OTHER INFORMATION: pTP3-1 vector
<220> FEATURE:
<221> NAME/KEY: VARIANT
<222> LOCATION: (1)...(311)
<223> OTHER INFORMATION: Xaa = Any Amino Acid

<400> SEQUENCE: 30

Met Ala His Ala Arg Val Leu Leu Leu Ala Leu Ala Val Leu Ala Thr
 1               5                  10                  15

Ala Ala Val Ala Val Ala Ser Ser Ser Ser Phe Ala Asp Ser Asn Pro
            20                  25                  30

Ile Arg Pro Val Thr Asp Arg Ala Ala Ala Ser Thr Gln Gly Ile Ser
        35                  40                  45

Glu Asp Leu Tyr Ser Arg Leu Val Glu Met Ala Thr Ile Ser Gln Ala
    50                  55                  60

Ala Tyr Ala Asp Leu Cys Asn Ile Pro Ser Thr Ile Ile Lys Gly Glu
65                  70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110

Thr Asn Leu Gln Leu Asp Thr Asn Tyr Thr Leu Thr Pro Phe Asp Thr
        115                 120                 125

Leu Pro Gln Cys Asn Gly Cys Glu Val His Gly Gly Tyr Tyr Ile Gly
    130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205
```

-continued

```
Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
        275                 280                 285

Thr Thr Tyr Phe Gly Met Thr Ser Gly Ala Cys Thr Trp Pro Val Ala
    290                 295                 300

Ala Ala Glu Thr Thr Glu Gly
305                 310


<210> SEQ ID NO 31
<211> LENGTH: 5337
<212> TYPE: DNA
<213> ORGANISM: Artificial Sequence
<220> FEATURE:
<223> OTHER INFORMATION: pTU5 vector

<400> SEQUENCE: 31

aagcttacca tggcccacgc ccgcgtcctc ctcctggcgc tcgccgtgct ggccacggcc     60

gccgtcgccg tcgcctcctc ctcctccttc gccgactcca acccgggccg gcccgtcacc    120

gaccgcgcgg ccgcctccac gcagggcatc tccgaagacc tctacagccg tttagtcgaa    180

atggccacta tctcccaagc tgcctacgcc gacctgtgca acattccgtc gactattatc    240

aagggagaga aaatttacaa ttctcaaact gacattaacg gatggatcct ccgcgacgac    300

agcagcaaag aaataatcac cgtcttccgt ggcactggta gtgatacgaa tctacaactc    360

gatactaact acaccctcac gcctttcgac accctaccac aatgcaacgg ttgtgaagta    420

cacggtggat attatattgg atgggtctcc gtccaggacc aagtcgagtc gcttgtcaaa    480

cagcaggtta gccagtatcc ggactacgcg ctgaccgtga ccggccactc cctcggcgcc    540

tccctggcgg cactcactgc cgcccagctg tctgcgacat acgacaacat ccgcctgtac    600

accttcggcg aaccgcgcag cggcaatcag gccttcgcgt cgtacatgaa cgatgccttc    660

caagcctcga gcccagatac gacgcagtat ttccgggtca ctcatgccaa cgacggcatc    720

ccaaacctgc ccccggtgga gcaggggtac gcccatggcg gtgtagagta ctggagcgtt    780

gatccttaca gcgcccagaa cacatttgtc tgcactgggg atgaagtgca gtgctgtgag    840

gcccagggcg gacagggtgt gaataatgcg cacacgactt attttgggat gacgagcggc    900

gcatgcacct ggccggtcgc ggccgcggaa ccactgaagg atgagctgta aagaagcaga    960

tcgttcaaac atttggcaat aaagtttctt aagattgaat cctgttgccg gtcttgcgat   1020

gattatcata taatttctgt tgaattacgt taagcatgta ataattaaca tgtaatgcat   1080

gacgttattt atgagatggg tttttatgat tagagtcccg caattataca tttaatacgc   1140

gatagaaaac aaaatatagc gcgcaaacta ggataaatta tcgcgcgcgg tgtcatctat   1200

gttactagat cgataagctt ctagagcggc cggtggagct ccaattcgcc ctatagtgag   1260

tcgtattacg cgcgctcact ggccgtcgtt ttacaacgtc gtgactggga aaaccctggc   1320

gttacccaac ttaatcgcct tgcagcacat ccccctttcg ccagctggcg taatagcgaa   1380

gaggcccgca ccgatcgccc ttcccaacag ttgcgcagcc tgaatggcga atgggacgcg   1440
```

-continued ccctgtagcg gcgcattaag cgcggcgggt gtggtggtta cgcgcagcgt gaccgctaca 1500
cttgccagcg ccctagcgcc cgctcctttc gctttcttcc cttcctttct cgccacgttc 1560
gccggctttc cccgtcaagc tctaaatcgg gggctccctt tagggttccg atttagtgct 1620
ttacggcacc tcgaccccaa aaaacttgat tagggtgatg gttcacgtag tgggccatcg 1680
ccctgataga cggtttttcg ccctttgacg ttggagtcca cgttctttaa tagtggactc 1740
ttgttccaaa ctggaacaac actcaaccct atctcggtct attcttttga tttataaggg 1800
attttgccga tttcggccta ttggttaaaa aatgagctga tttaacaaaa atttaacgcg 1860
aattttaaca aaatattaac gcttacaatt taggtggcac ttttcgggga aatgtgcgcg 1920
gaacccctat ttgtttattt ttctaaatac attcaaatat gtatccgctc atgagacaat 1980
aaccctgata aatgcttcaa taatattgaa aaaggaagag tatgagtatt caacatttcc 2040
gtgtcgccct tattcccttt tttgcggcat tttgccttcc tgtttttgct cacccagaaa 2100
cgctggtgaa agtaaaagat gctgaagatc agttgggtgc acgagtgggt tacatcgaac 2160
tggatctcaa cagcggtaag atccttgaga gttttcgccc cgaagaacgt tttccaatga 2220
tgagcacttt taaagttctg ctatgtggcg cggtattatc ccgtattgac gccgggcaag 2280
agcaactcgg tcgccgcata cactattctc agaatgactt ggttgagtac tcaccagtca 2340
cagaaaagca tcttacggat ggcatgacag taagagaatt atgcagtgct gccataacca 2400
tgagtgataa cactgcggcc aacttacttc tgacaacgat cggaggaccg aaggagctaa 2460
ccgctttttt gcacaacatg ggggatcatg taactcgcct tgatcgttgg gaaccggagc 2520
tgaatgaagc cataccaaac gacgagcgtg acaccacgat gcctgtagca atggcaacaa 2580
cgttgcgcaa actattaact ggcgaactac ttactctagc ttcccggcaa caattaatag 2640
actggatgga ggcggataaa gttgcaggac cacttctgcg ctcggccctt ccggctggct 2700
ggtttattgc tgataaatct ggagccggtg agcgtgggtc tcgcggtatc attgcagcac 2760
tggggccaga tggtaagccc tcccgtatcg tagttatcta cacgacgggg agtcaggcaa 2820
ctatggatga acgaaataga cagatcgctg agataggtgc ctcactgatt aagcattggt 2880
aactgtcaga ccaagtttac tcatatatac tttagattga tttaaaactt catttttaat 2940
ttaaaaggat ctaggtgaag atcctttttg ataatctcat gaccaaaatc ccttaacgtg 3000
agttttcgtt ccactgagcg tcagaccccg tagaaaagat caaaggatct tcttgagatc 3060 cttttttct gcgcgtaatc tgctgcttgc aaacaaaaaa accaccgcta ccagcggtgg 3120
tttgtttgcc ggatcaagag ctaccaactc tttttccgaa ggtaactggc ttcagcagag 3180
cgcagatacc aaatactgtc cttctagtgt agccgtagtt aggccaccac ttcaagaact 3240
ctgtagcacc gcctacatac ctcgctctgc taatcctgtt accagtggct gctgccagtg 3300
gcgataagtc gtgtcttacc gggttggact caagacgata gttaccggat aaggcgcagc 3360
ggtcgggctg aacggggggt tcgtgcacac agcccagctt ggagcgaacg acctacaccg 3420
aactgagata cctacagcgt gagctatgag aaagcgccac gcttcccgaa gggagaaagg 3480
cggacaggta tccggtaagc ggcagggtcg gaacaggaga gcgcacgagg gagcttccag 3540
ggggaaacgc ctggtatctt tatagtcctg tcgggtttcg ccacctctga cttgagcgtc 3600
gatttttgtg atgctcgtca ggggggcgga gcctatggaa aaacgccagc aacgcggcct 3660
ttttacggtt cctggccttt tgctggcctt ttgctcacat gttctttcct gcgttatccc 3720
ctgattctgt ggataaccgt attaccgcct ttgagtgagc tgataccgct cgccgcagcc 3780
gaacgaccga gcgcagcgag tcagtgagcg aggaagcgga agagcgccca atacgcaaac 3840

-continued

```
cgcctctccc cgcgcgttgg ccgattcatt aatgcagctg gcacgacagg tttcccgact   3900
ggaaagcggg cagtgagcgc aacgcaatta atgtgagtta gctcactcat taggcacccc   3960
aggctttaca ctttatgctt ccggctcgta tgttgtgtgg aattgtgagc ggataacaat   4020
ttcacacagg aaacagctat gaccatgatt acgccaagcg cgcaattaac cctcactaaa   4080
gggaacaaaa gctgggtacc gggccccccc tcgaggtcat tcatatgctt gagaagagag   4140
tcgggatagt ccaaaataaa acaaaggtaa gattacctgg tcaaaagtga aaacatcagt   4200
taaaaggtgg tataagtaaa atatcggtaa taaaaggtgg cccaaagtga aatttactct   4260
tttctactat tataaaaatt gaggatgttt tgtcggtact ttgatacgtc atttttgtat   4320
gaattggttt ttaagtttat tcgcgatttg gaaatgcata tctgtatttg agtcggtttt   4380
taagttcgtt gcttttgtaa atacagaggg atttgtataa gaaatatctt taaaaaaccc   4440
atatgctaat ttgacataat ttttgagaaa aatatatatt caggcgaatt ccacaatgaa   4500
caataataag attaaaatag cttgcccccg ttgcagcgat gggtattttt tctagtaaaa   4560
taaaagataa acttagactc aaaacattta caaaaacaac ccctaaagtc ctaaagccca   4620
aagtgctatg cacgatccat agcaagccca gcccaaccca acccaaccca acccacccca   4680
gtgcagccaa ctggcaaata gtctccaccc ccggcactat caccgtgagt tgtccgcacc   4740
accgcacgtc tcgcagccaa aaaaaaaaaa agaaagaaaa aaaagaaaaa gaaaaacagc   4800
aggtgggtcc gggtcgtggg ggccggaaaa gcgaggagga tcgcgagcag cgacgaggcc   4860
cggccctccc tccgcttcca aagaaacgcc ccccatcgcc actatataca tacccccccc   4920
tctcctccca tccccccaac cctaccacca ccaccaccac cacctcctcc cccctcgctg   4980
ccggacgacg agctcctccc ccctccccct ccgccgccgc cggtaaccac cccgcccctc   5040
tcctctttct ttctccgttt tttttttcgt ctcggtctcg atctttggcc ttggtagttt   5100
gggtgggcga gagcggcttc gtcgcccaga tcggtgcgcg ggaggggcgg gatctcgcgg   5160
ctggcgtctc cgggcgtgag tcggcccgga tcctcgcggg gaatggggct ctcggatgta   5220
gatcttcttt ctttcttctt tttgtggtag aatttgaatc cctcagcatt gttcatcggt   5280
agtttttctt ttcatgattt gtgacaaatg cagcctcgtg cggagctttt ttgtagc      5337
```

```
<210> SEQ ID NO 32
<211> LENGTH: 4773
<212> TYPE: DNA
<213> ORGANISM: Artificial Sequence
<220> FEATURE:
<223> OTHER INFORMATION: pGT6 vector

<400> SEQUENCE: 32

aagcttacca tggtgagcaa gggcgaggag ctgttcaccg gggtggtgcc catcctggtc     60
gagctggacg gcgacgtgaa cggccacaag ttcagcgtgt ccggcgaggg cgagggcgat    120
gccacctacg gcaagctgac cctgaagttc atctgcacca ccggcaagct gcccgtgccc    180
tggcccaccc tcgtgaccac cttcacctac ggcgtgcagt gcttcagccg ctaccccgac    240
cacatgaagc agcacgactt cttcaagtcc gccatgcccg aaggctacgt ccaggagcgc    300
accatcttct tcaaggacga cggcaactac aagacccgcg ccgaggtgaa gttcgagggc    360
gacaccctgg tgaaccgcat cgagctgaag ggcatcgact tcaaggagga cggcaacatc    420
ctggggcaca agctggagta caactacaac agccacaacg tctatatcat ggccgacaag    480
cagaagaacg gcatcaaggt gaacttcaag atccgccaca acatcgagga cggcagcgtg    540
```

-continued

```
cagctcgccg accactacca gcagaacacc cccatcggcg acggccccgt gctgctgccc    600
gacaaccact acctgagcac ccagtccgcc ctgagcaaag accccaacga gaagcgcgat    660
cacatggtcc tgctggagtt cgtgaccgcc gccgggatca ctcacggcat ggacgagctg    720
tacaagtaaa gcggccgccc gggctgcagg gaaaccactg aaggatgagc tgtaaagaag    780
cagatcgttc aaacatttgg caataaagtt tcttaagatt gaatcctgtt gccggtcttg    840
cgatgattat catataattt ctgttgaatt acgttaagca tgtaataatt aacatgtaat    900
gcatgacgtt atttatgaga tgggttttta tgattagagt cccgcaatta tacatttaat    960
acgcgataga aaacaaaata tagcgcgcaa actaggataa attatcgcgc gcggtgtcat   1020
ctatgttact agatcgataa gcttctagag cggccggtgg agctccaatt cgccctatag   1080
tgagtcgtat tacgcgcgct cactggccgt cgttttacaa cgtcgtgact gggaaaaccc   1140
tggcgttacc caacttaatc gccttgcagc acatccccct ttcgccagct ggcgtaatag   1200
cgaagaggcc cgcaccgatc gcccttccca acagttgcgc agcctgaatg gcgaatggga   1260
cgcgccctgt agcggcgcat taagcgcggc gggtgtggtg gttacgcgca gcgtgaccgc   1320
tacacttgcc agcgccctag cgcccgctcc tttcgctttc ttcccttcct ttctcgccac   1380
gttcgccggc tttccccgtc aagctctaaa tcgggggctc cctttagggt tccgatttag   1440
tgctttacgg cacctcgacc ccaaaaaact tgattagggt gatggttcac gtagtgggcc   1500
atcgccctga tagacggttt ttcgcccttt gacgttggag tccacgttct ttaatagtgg   1560
actcttgttc caaactggaa caacactcaa ccctatctcg gtctattctt ttgatttata   1620
agggattttg ccgatttcgg cctattggtt aaaaaatgag ctgatttaac aaaaatttaa   1680
cgcgaatttt aacaaaatat taacgcttac aatttaggtg gcacttttcg gggaaatgtg   1740
cgcggaaccc ctatttgttt atttttctaa atacattcaa atatgtatcc gctcatgaga   1800
caataaccct gataaatgct tcaataatat tgaaaaagga agagtatgag tattcaacat   1860
ttccgtgtcg cccttattcc cttttttgcg gcattttgcc ttcctgtttt tgctcaccca   1920
gaaacgctgg tgaaagtaaa agatgctgaa gatcagttgg gtgcacgagt gggttacatc   1980
gaactggatc tcaacagcgg taagatcctt gagagttttc gccccgaaga acgttttcca   2040
atgatgagca cttttaaagt tctgctatgt ggcgcggtat tatcccgtat tgacgccggg   2100
caagagcaac tcggtcgccg catacactat tctcagaatg acttggttga gtactcacca   2160
gtcacagaaa agcatcttac ggatggcatg acagtaagag aattatgcag tgctgccata   2220
accatgagtg ataacactgc ggccaactta cttctgacaa cgatcggagg accgaaggag   2280
ctaaccgctt ttttgcacaa catgggggat catgtaactc gccttgatcg ttgggaaccg   2340
gagctgaatg aagccatacc aaacgacgag cgtgacacca cgatgcctgt agcaatggca   2400
acaacgttgc gcaaactatt aactggcgaa ctacttactc tagcttcccg gcaacaatta   2460
atagactgga tggaggcgga taaagttgca ggaccacttc tgcgctcggc ccttccggct   2520
ggctggttta ttgctgataa atctggagcc ggtgagcgtg ggtctcgcgg tatcattgca   2580
gcactggggc cagatggtaa gccctcccgt atcgtagtta tctacacgac ggggagtcag   2640
gcaactatgg atgaacgaaa tagacagatc gctgagatag gtgcctcact gattaagcat   2700
tggtaactgt cagaccaagt ttactcatat atactttaga ttgatttaaa acttcatttt   2760
taatttaaaa ggatctaggt gaagatcctt tttgataatc tcatgaccaa aatcccttaa   2820
cgtgagtttt cgttccactg agcgtcagac cccgtagaaa agatcaaagg atcttcttga   2880
gatccttttt ttctgcgcgt aatctgctgc ttgcaaacaa aaaaaccacc gctaccagcg   2940
```

-continued gtggtttgtt tgccggatca agagctacca actctttttc cgaaggtaac tggcttcagc 3000
agagcgcaga taccaaatac tgtccttcta gtgtagccgt agttaggcca ccacttcaag 3060
aactctgtag caccgcctac atacctcgct ctgctaatcc tgttaccagt ggctgctgcc 3120
agtggcgata agtcgtgtct taccgggttg gactcaagac gatagttacc ggataaggcg 3180
cagcggtcgg gctgaacggg gggttcgtgc acacagccca gcttggagcg aacgacctac 3240
accgaactga gatacctaca gcgtgagcta tgagaaagcg ccacgcttcc cgaagggaga 3300
aaggcggaca ggtatccggt aagcggcagg gtcggaacag gagagcgcac gagggagctt 3360
ccagggggaa acgcctggta tctttatagt cctgtcgggt ttcgccacct ctgacttgag 3420
cgtcgatttt tgtgatgctc gtcagggggg cggagcctat ggaaaaacgc cagcaacgcg 3480
gcctttttac ggttcctggc cttttgctgg ccttttgctc acatgttctt tcctgcgtta 3540
tcccctgatt ctgtggataa ccgtattacc gcctttgagt gagctgatac cgctcgccgc 3600
agccgaacga ccgagcgcag cgagtcagtg agcgaggaag cggaagagcg cccaatacgc 3660
aaaccgcctc tccccgcgcg ttggccgatt cattaatgca gctggcacga caggtttccc 3720
gactggaaag cgggcagtga gcgcaacgca attaatgtga gttagctcac tcattaggca 3780
ccccaggctt tacactttat gcttccggct cgtatgttgt gtggaattgt gagcggataa 3840
caatttcaca caggaaacag ctatgaccat gattacgcca agcgcgcaat taaccctcac 3900
taaagggaac aaaagctgga attccacaat gaacaataat aagattaaaa tagcttgccc 3960
ccgttgcagc gatgggtatt ttttctagta aaataaaaga taaacttaga ctcaaaacat 4020
ttacaaaaac aaccccctaaa gtcctaaagc ccaaagtgct atgcacgatc catagcaagc 4080
ccagcccaac ccaacccaac ccaacccacc ccagtgcagc caactggcaa atagtctcca 4140
cccccggcac tatcaccgtg agttgtccgc accaccgcac gtctcgcagc caaaaaaaaa 4200
aaaagaaaga aaaaaaagaa aaagaaaaac agcaggtggg tccgggtcgt gggggccgga 4260
aaagcgagga ggatcgcgag cagcgacgag gcccggccct ccctccgctt ccaaagaaac 4320
gccccccatc gccactatat acataccccc ccctctcctc ccatcccccc aaccctacca 4380
ccaccaccac caccacctcc tccccctcg ctgccggacg acgagctcct ccccccctccc 4440 cctccgccgc cgccggtaac caccccgccc ctctcctctt tctttctccg ttttttttt 4500 cgtctcggtc tcgatctttg gccttggtag tttgggtggg cgagagcggc ttcgtcgccc 4560
agatcggtgc gcgggagggg cgggatctcg cggctggcgt ctccgggcgt gagtcggccc 4620
ggatcctcgc ggggaatggg gctctcggat gtagatcttc tttctttctt ctttttgtgg 4680
tagaatttga atccctcagc attgttcatc ggtagttttt cttttcatga tttgtgacaa 4740
atgcagcctc gtgcggagct tttttgtagg tag 4773

<210> SEQ ID NO 33
<211> LENGTH: 5034
<212> TYPE: DNA
<213> ORGANISM: Artificial Sequence
<220> FEATURE:
<223> OTHER INFORMATION: pJQ5 vector

<400> SEQUENCE: 33
catgggccag gtataattat gggatatctc aagcaaataa tcgaaatatc accattggct 60
acaatatctg agctccgagt tctgactgca gtctggatga cgcgtgttgt atctagaact 120
ctagatagca cagccacagc acctacagga gtgcgacact tgtggactgt agtagtgttg 180

-continued

```
gagacggagc tctttcctac ctcctgacgt tgccgccgtt gtccattcca acggcatcac    240
tctcaaccaa tcacgcgctc ccaacaaaat atcgtccccc atgtcttggc ggagagagag    300
tacatacatg ctgtcgcgcc gtttttgtct gaatctcgct tccactggcc aatcagctca    360
gctcccggga gctcactcat tcaagatccc atcgtcgtcg tcacccctgg cgtcatggga    420
tggaaaagaa cctccgttgc tcggatgagt cagccatatc cccgaacaga gtactgcaag    480
ataacccaat tcagattccc ccaatagaga aagtatagca tgctttcggg ttttgtttgg    540
cttaattgac tttatttttg ttggagttga atgctgattt gttgtgtaaa atgcccaacc    600
atctgaatat cgagacggat aataggctgg ctaattaatt tatagcaaga ttctgtagtg    660
cacatcgcaa atatctttct gggcattaca gctggaggct tcatcagcct gaaacactct    720
gcagagcctg aagcaagtgg tgaagcgtgg cgatgagatg ggtataaaac ccccggcacc    780
gggacgcgag ctcccgccta ccagtaccat ctcgcctcgc tccccctgcc ggacgaccca    840
gtaaaatact gttgcccact cgccggcgag atggmcgtgc acaaggaggt saacttcgts    900
gcctacctcc tgatcgtsct cggcctcctc ttgctcgtst ccgccatgga gcacgtggac    960
gccaaggcct gcacccckcga gtgcggcaac ctcggcttcg gcatctgccc ggcggccgcc   1020
tccacgcagg gcatctccga agacctctac agccgtttag tcgaaatggc cactatctcc   1080
caagctgcct acgccgacct gtgcaacatt ccgtcgacta ttatcaaggg agagaaaatt   1140
tacaattctc aaactgacat taacggatgg atcctccgcg acgacagcag caaagaaata   1200
atcaccgtct tccgtggcac tggtagtgat acgaatctac aactcgatac taactacacc   1260
ctcacgcctt tcgacaccct accacaatgc aacggttgtg aagtacacgg tggatattat   1320
attggatggg tctccgtcca ggaccaagtc gagtcgcttg tcaaacagca ggttagccag   1380
tatccggact acgcgctgac cgtgaccggc cackccctcg gcgcctccct ggcggcactc   1440
actgccgccc agctgtctgc gacatacgac aacatccgcc tgtacacctt cggcgaaccg   1500
cgcagcggca atcaggcctt cgcgtcgtac atgaacgatg ccttccaagc ctcgagccca   1560
gatacgacgc agtatttccg ggtcactcat gccaacgacg gcatcccaaa cctgcccccg   1620
gtggagcagg ggtacgccca tggcggtgta gagtactgga gcgttgatcc ttacagcgcc   1680
cagaacacat ttgtctgcac tggggatgaa gtgcagtgct gtgaggccca gggcggacag   1740
ggtgtgaata atgcgcacac gacttatttt gggatgacga gcggagcctg tacatggtga   1800
tcagtcattt cagcctcccc gagtgtacca ggaaagatgg atgtcctgga gaggggggccg   1860
cgtaaccact gaaggatgag ctgtaaagaa gcagatcgtt caaacatttg gcaataaagt   1920
ttcttaagat tgaatcctgt tgccggtctt gcgatgatta tcatataatt tctgttgaat   1980
tacgttaagc atgtaataat taacatgtaa tgcatgacgt tatttatgag atgggttttt   2040
atgattagag tcccgcaatt atacatttaa tacgcgatag aaaacaaaat atagcgcgca   2100
aactaggata aattatcgcg cgcggtgtca tctatgttac tagatcgata agcttctaga   2160
gcggccggtg gagctccaat tcgccctata gtgagtcgta ttacgcgcgc tcactggccg   2220
tcgttttaca acgtcgtgac tgggaaaacc ctggcgttac ccaacttaat cgccttgcag   2280
cacatccccc tttcgccagc tggcgtaata gcgaagaggc ccgcaccgat cgcccttccc   2340
aacagttgcg cagcctgaat ggcgaatggg acgcgccctg tagcggcgca ttaagcgcgg   2400
cgggtgtggt ggttacgcgc agcgtgaccg ctacacttgc cagcgcccta gcgcccgctc   2460
ctttcgcttt cttcccttcc tttctcgcca cgttcgccgg ctttccccgt caagctctaa   2520
atcgggggct ccctttaggg ttccgattta gtgctttacg gcacctcgac cccaaaaaac   2580
```

-continued

```
ttgattaggg tgatggttca cgtagtgggc catcgccctg atagacggtt tttcgccctt   2640

tgacgttgga gtccacgttc tttaatagtg gactcttgtt ccaaactgga acaacactca   2700

accctatctc ggtctattct tttgatttat aagggatttt gccgatttcg gcctattggt   2760

taaaaaatga gctgatttaa caaaaattta acgcgaattt taacaaaata ttaacgctta   2820

caatttaggt ggcacttttc ggggaaatgt gcgcggaacc cctatttgtt tatttttcta   2880

aatacattca aatatgtatc cgctcatgag acaataaccc tgataaatgc ttcaataata   2940

ttgaaaaagg aagagtatga gtattcaaca tttccgtgtc gcccttattc cctttttttgc   3000

ggcattttgc cttcctgttt ttgctcaccc agaaacgctg gtgaaagtaa aagatgctga   3060

agatcagttg ggtgcacgag tgggttacat cgaactggat ctcaacagcg gtaagatcct   3120

tgagagtttt cgccccgaag aacgttttcc aatgatgagc acttttaaag ttctgctatg   3180

tggcgcggta ttatcccgta ttgacgccgg gcaagagcaa ctcggtcgcc gcatacacta   3240

ttctcagaat gacttggttg agtactcacc agtcacagaa aagcatctta cggatggcat   3300

gacagtaaga gaattatgca gtgctgccat aaccatgagt gataacactg cggccaactt   3360

acttctgaca acgatcggag gaccgaagga gctaaccgct tttttgcaca acatggggga   3420

tcatgtaact cgccttgatc gttgggaacc ggagctgaat gaagccatac caaacgacga   3480

gcgtgacacc acgatgcctg tagcaatggc aacaacgttg cgcaaactat taactggcga   3540

actacttact ctagcttccc ggcaacaatt aatagactgg atggaggcgg ataaagttgc   3600

aggaccactt ctgcgctcgg cccttccggc tggctggttt attgctgata aatctggagc   3660

cggtgagcgt gggtctcgcg gtatcattgc agcactgggg ccagatggta agccctcccg   3720

tatcgtagtt atctacacga cggggagtca ggcaactatg gatgaacgaa atagacagat   3780

cgctgagata ggtgcctcac tgattaagca ttggtaactg tcagaccaag tttactcata   3840

tatactttag attgatttaa aacttcattt ttaatttaaa aggatctagg tgaagatcct   3900

ttttgataat ctcatgacca aaatccctta acgtgagttt tcgttccact gagcgtcaga   3960

ccccgtagaa aagatcaaag gatcttcttg agatcctttt tttctgcgcg taatctgctg   4020

cttgcaaaca aaaaaaccac cgctaccagc ggtggtttgt ttgccggatc aagagctacc   4080

aactcttttt ccgaaggtaa ctggcttcag cagagcgcag ataccaaata ctgtccttct   4140

agtgtagccg tagttaggcc accacttcaa gaactctgta gcaccgccta catacctcgc   4200

tctgctaatc ctgttaccag tggctgctgc cagtggcgat aagtcgtgtc ttaccgggtt   4260

ggactcaaga cgatagttac cggataaggc gcagcggtcg ggctgaacgg ggggttcgtg   4320

cacacagccc agcttggagc gaacgaccta caccgaactg agatacctac agcgtgagct   4380

atgagaaagc gccacgcttc ccgaagggag aaaggcggac aggtatccgg taagcggcag   4440

ggtcggaaca ggagagcgca cgagggagct tccaggggga aacgcctggt atctttatag   4500

tcctgtcggg tttcgccacc tctgacttga gcgtcgattt ttgtgatgct cgtcaggggg   4560

gcggagccta tggaaaaacg ccagcaacgc ggccttttta cggttcctgg ccttttgctg   4620

gccttttgct cacatgttct ttcctgcgtt atcccctgat tctgtggata accgtattac   4680

cgcctttgag tgagctgata ccgctcgccg cagccgaacg accgagcgca gcgagtcagt   4740

gagcgaggaa gcggaagagc gcccaatacg caaaccgcct ctccccgcgc gttggccgat   4800

tcattaatgc agctggcacg acaggtttcc cgactggaaa gcgggcagtg agcgcaacgc   4860

aattaatgtg agttagctca ctcattaggc accccaggct ttacacttta tgcttccggc   4920
```

-continued

```
tcgtatgttg tgtggaattg tgagcggata acaatttcac acaggaaaca gctatgacca   4980

tgattacgcc aagcgcgcaa ttaaccctca ctaaagggaa caaaagctgg gtac         5034
```

<210> SEQ ID NO 34
<211> LENGTH: 4950
<212> TYPE: DNA
<213> ORGANISM: Artificial Sequence
<220> FEATURE:
<223> OTHER INFORMATION: pJO6.1 vector

<400> SEQUENCE: 34

```
aagcttacca tggcccacgc ccgcgtcctc ctcctggcgc tcgccgtgct ggccacggcc     60

gccgtcgccg tcgcctcctc ctcctccttc gccgactcca acccgatccg gcccgtcacc    120

gaccgcgcgg ccgcctccac gcagggcatc tccgaagacc tctacagccg tttagtcgaa    180

atggccacta tctcccaagc tgcctacgcc gacctgtgca acattccgtc gactattatc    240

aagggagaga aaatttacaa ttctcaaact gacattaacg gatggatcct ccgcgacgac    300

agcagcaaag aaataatcac cgtcttccgt ggcactggta gtgatacgaa tctacaactc    360

gatactaact acaccctcac gcctttcgac accctaccac aatgcaacgg ttgtgaagta    420

cacggtggat attatattgg atgggtctcc gtccaggacc aagtcgagtc gcttgtcaaa    480

cagcaggtta gccagtatcc ggactacgcg ctgaccgtga ccggccackc cctcggcgcc    540

tccctggcgg cactcactgc cgcccagctg tctgcgacat acgacaacat ccgcctgtac    600

accttcggcg aaccgcgcag cggcaatcag gccttcgcgt cgtacatgaa cgatgccttc    660

caagcctcga gcccagatac gacgcagtat ttccgggtca ctcatgccaa cgacggcatc    720

ccaaacctgc ccccggtgga gcaggggtac gcccatggcg gtgtagagta ctggagcgtt    780

gatccttaca gcgcccagaa cacatttgtc tgcactgggg atgaagtgca gtgctgtgag    840

gcccagggcg gacagggtgt gaataatgcg cacacgactt attttgggat gacgagcggc    900

gcatgcacct ggccggtcgc ggccgcggaa accactgaag gatgagctgt aaagaagcag    960

atcgttcaaa catttggcaa taaagtttct taagattgaa tcctgttgcc ggtcttgcga   1020

tgattatcat ataatttctg ttgaattacg ttaagcatgt aataattaac atgtaatgca   1080

tgacgttatt tatgagatgg gtttttatga ttagagtccc gcaattatac atttaatacg   1140

cgatagaaaa caaaatatag cgcgcaaact aggataaatt atcgcgcgcg gtgtcatcta   1200

tgttactaga tcgataagct tctagagcgg ccggtggagc tccaattcgc cctatagtga   1260

gtcgtattac gcgcgctcac tggccgtcgt tttacaacgt cgtgactggg aaaaccctgg   1320

cgttacccaa cttaatcgcc ttgcagcaca tccccctttc gccagctggc gtaatagcga   1380

agaggcccgc accgatcgcc cttcccaaca gttgcgcagc ctgaatggcg aatgggacgc   1440

gccctgtagc ggcgcattaa gcgcggcggg tgtggtggtt acgcgcagcg tgaccgctac   1500

acttgccagc gccctagcgc ccgctccttt cgctttcttc ccttcctttc tcgccacgtt   1560

cgccggcttt ccccgtcaag ctctaaatcg ggggctccct ttagggttcc gatttagtgc   1620

tttacggcac ctcgacccca aaaaacttga ttagggtgat ggttcacgta gtgggccatc   1680

gccctgatag acggtttttc gccctttgac gttggagtcc acgttcttta atagtggact   1740

cttgttccaa actggaacaa cactcaaccc tatctcggtc tattcttttg atttataagg   1800

gattttgccg atttcggcct attggttaaa aaatgagctg atttaacaaa aatttaacgc   1860

gaattttaac aaaatattaa cgcttacaat ttaggtggca cttttcgggg aaatgtgcgc   1920

ggaaccccta tttgtttatt tttctaaata cattcaaata tgtatccgct catgagacaa   1980
```

-continued

```
taaccctgat aaatgcttca ataatattga aaaaggaaga gtatgagtat tcaacatttc   2040
cgtgtcgccc ttattccctt ttttgcggca ttttgccttc ctgtttttgc tcacccagaa   2100
acgctggtga aagtaaaaga tgctgaagat cagttgggtg cacgagtggg ttacatcgaa   2160
ctggatctca acagcggtaa gatccttgag agttttcgcc ccgaagaacg ttttccaatg   2220
atgagcactt ttaaagttct gctatgtggc gcggtattat cccgtattga cgccgggcaa   2280
gagcaactcg gtcgccgcat acactattct cagaatgact tggttgagta ctcaccagtc   2340
acagaaaagc atcttacgga tggcatgaca gtaagagaat tatgcagtgc tgccataacc   2400
atgagtgata acactgcggc caacttactt ctgacaacga tcggaggacc gaaggagcta   2460
accgcttttt tgcacaacat gggggatcat gtaactcgcc ttgatcgttg ggaaccggag   2520
ctgaatgaag ccataccaaa cgacgagcgt gacaccacga tgcctgtagc aatggcaaca   2580
acgttgcgca aactattaac tggcgaacta cttactctag cttcccggca acaattaata   2640
gactggatgg aggcggataa agttgcagga ccacttctgc gctcggccct tccggctggc   2700
tggtttattg ctgataaatc tggagccggt gagcgtgggt ctcgcggtat cattgcagca   2760
ctggggccag atggtaagcc ctcccgtatc gtagttatct acacgacggg gagtcaggca   2820
actatggatg aacgaaatag acagatcgct gagataggtg cctcactgat taagcattgg   2880
taactgtcag accaagttta ctcatatata ctttagattg atttaaaact tcatttttaa   2940
tttaaaagga tctaggtgaa gatccttttt gataatctca tgaccaaaat cccttaacgt   3000
gagttttcgt tccactgagc gtcagacccc gtagaaaaga tcaaaggatc ttcttgagat   3060
cctttttttc tgcgcgtaat ctgctgcttg caaacaaaaa aaccaccgct accagcggtg   3120
gtttgtttgc cggatcaaga gctaccaact ctttttccga aggtaactgg cttcagcaga   3180
gcgcagatac caaatactgt ccttctagtg tagccgtagt taggccacca cttcaagaac   3240
tctgtagcac cgcctacata cctcgctctg ctaatcctgt taccagtggc tgctgccagt   3300
ggcgataagt cgtgtcttac cgggttggac tcaagacgat agttaccgga taaggcgcag   3360
cggtcgggct gaacgggggg ttcgtgcaca cagcccagct tggagcgaac gacctacacc   3420
gaactgagat acctacagcg tgagctatga gaaagcgcca cgcttcccga agggagaaag   3480
gcggacaggt atccggtaag cggcagggtc ggaacaggag agcgcacgag ggagcttcca   3540
gggggaaacg cctggtatct ttatagtcct gtcgggtttc gccacctctg acttgagcgt   3600
cgatttttgt gatgctcgtc aggggggcgg agcctatgga aaaacgccag caacgcggcc   3660
tttttacggt tcctggcctt ttgctggcct tttgctcaca tgttctttcc tgcgttatcc   3720
cctgattctg tggataaccg tattaccgcc tttgagtgag ctgataccgc tcgccgcagc   3780
cgaacgaccg agcgcagcga gtcagtgagc gaggaagcgg aagagcgccc aatacgcaaa   3840
ccgcctctcc ccgcgcgttg gccgattcat taatgcagct ggcacgacag gtttcccgac   3900
tggaaagcgg gcagtgagcg caacgcaatt aatgtgagtt agctcactca ttaggcaccc   3960
caggctttac actttatgct tccggctcgt atgttgtgtg gaattgtgag cggataacaa   4020
tttcacacag gaaacagcta tgaccatgat tacgccaagc gcgcaattaa ccctcactaa   4080
agggaacaaa agctggaatt ccacaatgaa caataataag attaaaatag cttgccccgc   4140
ttgcagcgat gggtattttt tctagtaaaa taaaagataa acttagactc aaaacattta   4200
caaaaacaac ccctaaagtc ctaaagccca aagtgctatg cacgatccat agcaagccca   4260
gcccaaccca acccaaccca acccacccca gtgcagccaa ctggcaaata gtctccaccc   4320
```

-continued

```
ccggcactat caccgtgagt tgtccgcacc accgcacgtc tcgcagccaa aaaaaaaaa   4380

agaaagaaaa aaaagaaaaa gaaaaacagc aggtgggtcc gggtcgtggg ggccggaaaa   4440

gcgaggagga tcgcgagcag cgacgaggcc cggccctccc tccgcttcca aagaaacgcc   4500

ccccatcgcc actatataca taccccccc tctcctccca tccccccaac cctaccacca   4560

ccaccaccac cacctcctcc cccctcgctg ccggacgacg agctcctccc ccctccccct   4620

ccgccgccgc cggtaaccac cccgcccctc tcctctttct ttctccgttt tttttttcgt   4680

ctcggtctcg atctttggcc ttggtagttt gggtgggcga gagcggcttc gtcgcccaga   4740

tcggtgcgcg ggaggggcgg gatctcgcgg ctggcgtctc cgggcgtgag tcggcccgga   4800

tcctcgcggg gaatggggct ctcggatgta gatcttcttt ctttcttctt tttgtggtag   4860

aatttgaatc cctcagcatt gttcatcggt agtttttctt ttcatgattt gtgacaaatg   4920

cagcctcgtg cggagctttt ttgtaggtag                                    4950
```

<210> SEQ ID NO 35
<211> LENGTH: 4974
<212> TYPE: DNA
<213> ORGANISM: Artificial Sequence
<220> FEATURE:
<223> OTHER INFORMATION: pJQ4 vector

<400> SEQUENCE: 35

```
aattccacaa tgaacaataa taagattaaa atagcttgcc cccgttgcag cgatgggtat     60

tttttctagt aaaataaaag ataaacttag actcaaaaca tttacaaaaa caacccctaa    120

agtcctaaag cccaaagtgc tatgcacgat ccatagcaag cccagcccaa cccaacccaa    180

cccaacccac cccagtgcag ccaactggca aatagtctcc acccccggca ctatcaccgt    240

gagttgtccg caccaccgca cgtctcgcag ccaaaaaaaa aaaaagaaag aaaaaaaaga    300

aaaagaaaaa cagcaggtgg gtccgggtcg tgggggccgg aaaagcgagg aggatcgcga    360

gcagcgacga ggcccggccc tccctccgct tccaaagaaa cgccccccat cgccactata    420

tacatacccc cccctctcct cccatccccc caaccctacc accaccacca ccaccacctc    480

ctcccccctc gctgccggac gacgagctcc tccccccctcc ccctccgccg ccgccggtaa    540

ccaccccgcc cctctcctct ttctttctcc gttttttttt tcgtctcggt ctcgatcttt    600

ggccttggta gtttgggtgg gcgagagcgg cttcgtcgcc cagatcggtg cgcgggaggg    660

gcgggatctc gcggctggcg tctccgggcg tgagtcggcc cggatcctcg cggggaatgg    720

ggctctcgga tgtagatctt ctttctttct tctttttgtg gtagaatttg aatccctcag    780

cattgttcat cggtagtttt tcttttcatg atttgtgaca aatgcagcct cgtgcggagc    840

ttttttgtag gtagaagctt acmatggmcg tgcacaagga ggtsaacttc gtsgcctacc    900

tcctgatcgt sctcggcctc ctcttgctcg tstccgccat ggagcacgtg gacgccaagg    960

cctgcacccck cgagtgcggc aacctcggct tcggcatctg cccggcggcc gcctccacgc   1020

agggcatctc cgaagacctc tacagccgtt tagtcgaaat ggccactatc tcccaagctg   1080

cctacgccga cctgtgcaac attccgtcga ctattatcaa gggagagaaa atttacaatt   1140

ctcaaactga cattaacgga tggatcctcc gcgacgacag cagcaaagaa ataatcaccg   1200

tcttccgtgg cactggtagt gatacgaatc tacaactcga tactaactac accctcacgc   1260

ctttcgacac cctaccacaa tgcaacggtt gtgaagtaca cggtggatat tatattggat   1320

gggtctccgt ccaggaccaa gtcgagtcgc ttgtcaaaca gcaggttagc cagtatccgg   1380

actacgcgct gaccgtgacc ggccackccc tcggcgcctc cctggcggca ctcactgccg   1440
```

-continued

```
cccagctgtc tgcgacatac gacaacatcc gcctgtacac cttcggcgaa ccgcgcagcg   1500
gcaatcaggc cttcgcgtcg tacatgaacg atgccttcca agcctcgagc ccagatacga   1560
cgcagtattt ccgggtcact catgccaacg acggcatccc aaacctgccc ccggtggagc   1620
aggggtacgc ccatggcggt gtagagtact ggagcgttga tccttacagc gcccagaaca   1680
catttgtctg cactggggat gaagtgcagt gctgtgaggc ccagggcgga cagggtgtga   1740
ataatgcgca cacgacttat tttgggatga cgagcggcgc atgcacctgg ccggtcgcgg   1800
ccgcggaaac cactgaagga tgagctgtaa agaagcagat cgttcaaaca tttggcaata   1860
aagtttctta agattgaatc ctgttgccgg tcttgcgatg attatcatat aatttctgtt   1920
gaattacgtt aagcatgtaa taattaacat gtaatgcatg acgttattta tgagatgggt   1980
ttttatgatt agagtcccgc aattatacat ttaatacgcg atagaaaaca aaatatagcg   2040
cgcaaactag gataaattat cgcgcgcggt gtcatctatg ttactagatc gataagcttc   2100
tagagcggcc ggtggagctc caattcgccc tatagtgagt cgtattacgc gcgctcactg   2160
gccgtcgttt tacaacgtcg tgactgggaa aaccctggcg ttacccaact taatcgcctt   2220
gcagcacatc ccccttcgc cagctggcgt aatagcgaag aggcccgcac cgatcgccct   2280
tcccaacagt tgcgcagcct gaatggcgaa tgggacgcgc cctgtagcgg cgcattaagc   2340
gcggcgggtg tggtggttac gcgcagcgtg accgctacac ttgccagcgc cctagcgccc   2400
gctcctttcg ctttcttccc ttcctttctc gccacgttcg ccggctttcc ccgtcaagct   2460
ctaaatcggg ggctcccttt agggttccga tttagtgctt tacggcacct cgaccccaaa   2520
aaacttgatt agggtgatgg ttcacgtagt gggccatcgc cctgatagac ggtttttcgc   2580
cctttgacgt tggagtccac gttctttaat agtggactct tgttccaaac tggaacaaca   2640
ctcaacccta tctcggtcta ttcttttgat ttataaggga ttttgccgat ttcggcctat   2700
tggttaaaaa atgagctgat ttaacaaaaa tttaacgcga attttaacaa aatattaacg   2760
cttacaattt aggtggcact tttcggggaa atgtgcgcgg aacccctatt tgtttatttt   2820
tctaaataca ttcaaatatg tatccgctca tgagacaata accctgataa atgcttcaat   2880
aatattgaaa aaggaagagt atgagtattc aacatttccg tgtcgccctt attccctttt   2940
ttgcggcatt ttgccttcct gtttttgctc acccagaaac gctggtgaaa gtaaaagatg   3000
ctgaagatca gttgggtgca cgagtgggtt acatcgaact ggatctcaac agcggtaaga   3060
tccttgagag ttttcgcccc gaagaacgtt ttccaatgat gagcactttt aaagttctgc   3120
tatgtggcgc ggtattatcc cgtattgacg ccgggcaaga gcaactcggt cgccgcatac   3180
actattctca gaatgacttg gttgagtact caccagtcac agaaaagcat cttacggatg   3240
gcatgacagt aagagaatta tgcagtgctg ccataaccat gagtgataac actgcggcca   3300
acttacttct gacaacgatc ggaggaccga aggagctaac cgcttttttg cacaacatgg   3360
gggatcatgt aactcgcctt gatcgttggg aaccggagct gaatgaagcc ataccaaacg   3420
acgagcgtga caccacgatg cctgtagcaa tggcaacaac gttgcgcaaa ctattaactg   3480
gcgaactact tactctagct tcccggcaac aattaataga ctggatggag gcggataaag   3540
ttgcaggacc acttctgcgc tcggcccttc cggctggctg gtttattgct gataaatctg   3600
gagccggtga gcgtgggtct cgcggtatca ttgcagcact ggggccagat ggtaagccct   3660
cccgtatcgt agttatctac acgacgggga gtcaggcaac tatggatgaa cgaaatagac   3720
agatcgctga gataggtgcc tcactgatta agcattggta actgtcagac caagtttact   3780
```

-continued catatatact ttagattgat ttaaaacttc atttttaatt taaaaggatc taggtgaaga 3840
tcctttttga taatctcatg accaaaatcc cttaacgtga gttttcgttc cactgagcgt 3900
cagaccccgt agaaaagatc aaaggatctt cttgagatcc tttttttctg cgcgtaatct 3960
gctgcttgca aacaaaaaaa ccaccgctac cagcggtggt ttgtttgccg gatcaagagc 4020
taccaactct ttttccgaag gtaactggct tcagcagagc gcagatacca aatactgtcc 4080
ttctagtgta gccgtagtta ggccaccact tcaagaactc tgtagcaccg cctacatacc 4140
tcgctctgct aatcctgtta ccagtggctg ctgccagtgg cgataagtcg tgtcttaccg 4200
ggttggactc aagacgatag ttaccggata aggcgcagcg gtcgggctga acggggggtt 4260
cgtgcacaca gcccagcttg gagcgaacga cctacaccga actgagatac ctacagcgtg 4320
agctatgaga aagcgccacg cttcccgaag ggagaaaggc ggacaggtat ccggtaagcg 4380
gcagggtcgg aacaggagag cgcacgaggg agcttccagg gggaaacgcc tggtatcttt 4440
atagtcctgt cgggtttcgc cacctctgac ttgagcgtcg atttttgtga tgctcgtcag 4500
gggggcggag cctatggaaa aacgccagca acgcggcctt tttacggttc ctggcctttt 4560
gctggccttt tgctcacatg ttctttcctg cgttatcccc tgattctgtg gataaccgta 4620
ttaccgcctt tgagtgagct gataccgctc gccgcagccg aacgaccgag cgcagcgagt 4680
cagtgagcga ggaagcggaa gagcgcccaa tacgcaaacc gcctctcccc gcgcgttggc 4740
cgattcatta atgcagctgg cacgacaggt ttcccgactg gaaagcgggc agtgagcgca 4800
acgcaattaa tgtgagttag ctcactcatt aggcacccca ggctttacac tttatgcttc 4860
cggctcgtat gttgtgtgga attgtgagcg gataacaatt tcacacagga aacagctatg 4920
accatgatta cgccaagcgc gcaattaacc ctcactaaag ggaacaaaag ctgg 4974

<210> SEQ ID NO 36
<211> LENGTH: 5164
<212> TYPE: DNA
<213> ORGANISM: Artificial Sequence
<220> FEATURE:
<223> OTHER INFORMATION: pPQ10.1 vector

<400> SEQUENCE: 36
aagcttacca tggtgagcaa gggcgaggag ctgttcaccg gggtggtgcc catcctggtc 60
gagctggacg gcgacgtgaa cggccacaag ttcagcgtgt ccggcgaggg cgagggcgat 120
gccacctacg gcaagctgac cctgaagttc atctgcacca ccggcaagct gcccgtgccc 180
tggcccaccc tcgtgaccac cttcacctac ggcgtgcagt gcttcagccg ctaccccgac 240
cacatgaagc agcacgactt cttcaagtcc gccatgcccg aaggctacgt ccaggagcgc 300
accatcttct tcaaggacga cggcaactac aagacccgcg ccgaggtgaa gttcgagggc 360
gacaccctgg tgaaccgcat cgagctgaag ggcatcgact tcaaggagga cggcaacatc 420
ctggggcaca agctggagta caactacaac agccacaacg tctatatcat ggccgacaag 480
cagaagaacg gcatcaaggt gaacttcaag atccgccaca acatcgagga cggcagcgtg 540
cagctcgccg accactacca gcagaacacc cccatcggcg acggccccgt gctgctgccc 600
gacaaccact acctgagcac ccagtccgcc ctgagcaaag accccaacga gaagcgcgat 660
cacatggtcc tgctggagtt cgtgaccgcc gccgggatca ctcacggcat ggacgagctg 720
tacaagtaaa gcggccgccc gggctgcagg gaaaccactg aaggatgagc tgtaaagaag 780
cagatcgttc aaacatttgg caataaagtt tcttaagatt gaatcctgtt gccggtcttg 840
cgatgattat catataattt ctgttgaatt acgttaagca tgtaataatt aacatgtaat 900

-continued

```
gcatgacgtt atttatgaga tgggttttta tgattagagt cccgcaatta tacatttaat    960
acgcgataga aaacaaaata tagcgcgcaa actaggataa attatcgcgc gcggtgtcat   1020
ctatgttact agatcgataa gcttctagag cggccggtgg agctccaatt cgccctatag   1080
tgagtcgtat tacgcgcgct cactggccgt cgttttacaa cgtcgtgact gggaaaaccc   1140
tggcgttacc caacttaatc gccttgcagc acatccccct ttcgccagct ggcgtaatag   1200
cgaagaggcc cgcaccgatc gcccttccca acagttgcgc agcctgaatg gcgaatggga   1260
cgcgccctgt agcggcgcat taagcgcggc gggtgtggtg gttacgcgca gcgtgaccgc   1320
tacacttgcc agcgccctag cgcccgctcc tttcgctttc ttcccttcct ttctcgccac   1380
gttcgccggc tttccccgtc aagctctaaa tcgggggctc cctttagggt tccgatttag   1440
tgctttacgg cacctcgacc ccaaaaaact tgattagggt gatggttcac gtagtgggcc   1500
atcgccctga tagacggttt ttcgcccttt gacgttggag tccacgttct ttaatagtgg   1560
actcttgttc caaactggaa caacactcaa ccctatctcg gtctattctt ttgatttata   1620
agggattttg ccgatttcgg cctattggtt aaaaaatgag ctgatttaac aaaaatttaa   1680
cgcgaatttt aacaaaatat taacgcttac aatttaggtg gcacttttcg gggaaatgtg   1740
cgcggaaccc ctatttgttt atttttctaa atacattcaa atatgtatcc gctcatgaga   1800
caataaccct gataaatgct tcaataatat tgaaaaagga agagtatgag tattcaacat   1860
ttccgtgtcg cccttattcc cttttttgcg gcattttgcc ttcctgtttt tgctcaccca   1920
gaaacgctgg tgaaagtaaa agatgctgaa gatcagttgg gtgcacgagt gggttacatc   1980
gaactggatc tcaacagcgg taagatcctt gagagttttc gccccgaaga acgttttcca   2040
atgatgagca cttttaaagt tctgctatgt ggcgcggtat tatcccgtat tgacgccggg   2100
caagagcaac tcggtcgccg catacactat tctcagaatg acttggttga gtactcacca   2160
gtcacagaaa agcatcttac ggatggcatg acagtaagag aattatgcag tgctgccata   2220
accatgagtg ataacactgc ggccaactta cttctgacaa cgatcggagg accgaaggag   2280
ctaaccgctt ttttgcacaa catgggggat catgtaactc gccttgatcg ttgggaaccg   2340
gagctgaatg aagccatacc aaacgacgag cgtgacacca cgatgcctgt agcaatggca   2400
acaacgttgc gcaaactatt aactggcgaa ctacttactc tagcttcccg gcaacaatta   2460
atagactgga tggaggcgga taaagttgca ggaccacttc tgcgctcggc ccttccggct   2520
ggctggttta ttgctgataa atctggagcc ggtgagcgtg ggtctcgcgg tatcattgca   2580
gcactggggc cagatggtaa gccctcccgt atcgtagtta tctacacgac ggggagtcag   2640
gcaactatgg atgaacgaaa tagacagatc gctgagatag gtgcctcact gattaagcat   2700
tggtaactgt cagaccaagt ttactcatat atactttaga ttgatttaaa acttcatttt   2760
taatttaaaa ggatctaggt gaagatcctt tttgataatc tcatgaccaa aatcccttaa   2820
cgtgagtttt cgttccactg agcgtcagac cccgtagaaa agatcaaagg atcttcttga   2880
gatccttttt ttctgcgcgt aatctgctgc ttgcaaacaa aaaaaccacc gctaccagcg   2940
gtggtttgtt tgccggatca agagctacca actctttttc cgaaggtaac tggcttcagc   3000
agagcgcaga taccaaatac tgtccttcta gtgtagccgt agttaggcca ccacttcaag   3060
aactctgtag caccgcctac atacctcgct ctgctaatcc tgttaccagt ggctgctgcc   3120
agtggcgata agtcgtgtct taccgggttg gactcaagac gatagttacc ggataaggcg   3180
cagcggtcgg gctgaacggg gggttcgtgc acacagccca gcttggagcg aacgacctac   3240
```

-continued

```
accgaactga gatacctaca gcgtgagcta tgagaaagcg ccacgcttcc cgaagggaga   3300

aaggcggaca ggtatccggt aagcggcagg gtcggaacag gagagcgcac gagggagctt   3360

ccagggggaa acgcctggta tctttatagt cctgtcgggt ttcgccacct ctgacttgag   3420

cgtcgatttt tgtgatgctc gtcagggggg cggagcctat ggaaaaacgc cagcaacgcg   3480

gcctttttac ggttcctggc cttttgctgg ccttttgctc acatgttctt tcctgcgtta   3540

tcccctgatt ctgtggataa ccgtattacc gcctttgagt gagctgatac cgctcgccgc   3600

agccgaacga ccgagcgcag cgagtcagtg agcgaggaag cggaagagcg cccaatacgc   3660

aaaccgcctc tccccgcgcg ttggccgatt cattaatgca gctggcacga caggtttccc   3720

gactggaaag cgggcagtga gcgcaacgca attaatgtga gttagctcac tcattaggca   3780

ccccaggctt tacactttat gcttccggct cgtatgttgt gtggaattgt gagcggataa   3840

caatttcaca caggaaacag ctatgaccat gattacgcca agcgcgcaat taaccctcac   3900

taaagggaac aaaagctggg taccgggccc cccctcgagg tcattcatat gcttgagaag   3960

agagtcggga tagtccaaaa taaaacaaag gtaagattac ctggtcaaaa gtgaaaacat   4020

cagttaaaag gtggtataag taaaatatcg gtaataaaag gtggcccaaa gtgaaattta   4080

ctcttttcta ctattataaa aattgaggat gttttgtcgg tactttgata cgtcattttt   4140

gtatgaattg gtttttaagt ttattcgcga tttggaaatg catatctgta tttgagtcgg   4200

tttttaagtt cgttgctttt gtaaatacag agggatttgt ataagaaata tctttaaaaa   4260

acccatatgc taatttgaca taatttttga gaaaaatata tattcaggcg aattccacaa   4320

tgaacaataa taagattaaa atagcttgcc cccgttgcag cgatgggtat tttttctagt   4380

aaaataaaag ataaacttag actcaaaaca tttacaaaaa caacccctaa agtcctaaag   4440

cccaaagtgc tatgcacgat ccatagcaag cccagcccaa cccaacccaa cccaacccac   4500

cccagtgcag ccaactggca aatagtctcc acccccggca ctatcaccgt gagttgtccg   4560

caccaccgca cgtctcgcag ccaaaaaaaa aaaaagaaag aaaaaaaaga aaaagaaaaa   4620

cagcaggtgg gtccgggtcg tgggggccgg aaaagcgagg aggatcgcga gcagcgacga   4680

ggcccggccc tccctccgct tccaaagaaa cgccccccat cgccactata tacatacccc   4740

cccctctcct cccatccccc caaccctacc accaccacca ccaccacctc ctcccccctc   4800

gctgccggac gacgagctcc tccccccctcc ccctccgccg ccgccggtaa ccaccccgcc   4860

cctctcctct ttctttctcc gttttttttt tcgtctcggt ctcgatcttt ggccttggta   4920

gtttgggtgg gcgagagcgg cttcgtcgcc cagatcggtg cgcgggaggg gcgggatctc   4980

gcggctggcg tctccgggcg tgagtcggcc cggatcctcg cggggaatgg ggctctcgga   5040

tgtagatctt ctttctttct tctttttgtg gtagaatttg aatccctcag cattgttcat   5100

cggtagtttt tcttttcatg atttgtgaca aatgcagcct cgtgcggagc ttttttgtag   5160

gtag                                                                5164
```

<210> SEQ ID NO 37
<211> LENGTH: 4965
<212> TYPE: DNA
<213> ORGANISM: Artificial Sequence
<220> FEATURE:
<223> OTHER INFORMATION: pJQ3 vector

<400> SEQUENCE: 37

```
aattccacaa tgaacaataa taagattaaa atagcttgcc cccgttgcag cgatgggtat     60

tttttctagt aaaataaaag ataaacttag actcaaaaca tttacaaaaa caacccctaa    120
```

-continued

```
agtcctaaag cccaaagtgc tatgcacgat ccatagcaag cccagcccaa cccaacccaa    180
cccaacccac cccagtgcag ccaactggca aatagtctcc acccccggca ctatcaccgt    240
gagttgtccg caccaccgca cgtctcgcag ccaaaaaaaa aaaaagaaag aaaaaaaaga    300
aaaagaaaaa cagcaggtgg gtccgggtcg tgggggccgg aaaagcgagg aggatcgcga    360
gcagcgacga ggcccggccc tccctccgct tccaaagaaa cgccccccat cgccactata    420
tacatacccc cccctctcct cccatccccc caaccctacc accaccacca ccaccacctc    480
ctcccccctc gctgccggac gacgagctcc tccccccctcc ccctccgccg ccgccggtaa    540
ccaccccgcc cctctcctct ttctttctcc gttttttttt tcgtctcggt ctcgatcttt    600
ggccttggta gtttgggtgg gcgagagcgg cttcgtcgcc cagatcggtg cgcgggaggg    660
gcgggatctc gcggctggcg tctccgggcg tgagtcggcc cggatcctcg cggggaatgg    720
ggctctcgga tgtagatctt ctttctttct tctttttgtg gtagaatttg aatccctcag    780
cattgttcat cggtagtttt tcttttcatg atttgtgaca aatgcagcct cgtgcggagc    840
ttttttgtag gtagaagctt accatgatcc acaccaacct caaaaagaag ttctccctct    900
tcatcctcgt cttcctcctc ttcgccgtga tctgcgtgtg gaagaagggc tccgactacg    960
aggccctcac cctccaagcc aaggagttcc aaatggcggc cgcctccacg cagggcatct   1020
ccgaagacct ctacagccgt ttagtcgaaa tggccactat ctcccaagct gcctacgccg   1080
acctgtgcaa cattccgtcg actattatca agggagagaa aatttacaat tctcaaactg   1140
acattaacgg atggatcctc cgcgacgaca gcagcaaaga aataatcacc gtcttccgtg   1200
gcactggtag tgatacgaat ctacaactcg atactaacta caccctcacg cctttcgaca   1260
ccctaccaca atgcaacggt tgtgaagtac acggtggata ttatattgga tgggtctccg   1320
tccaggacca agtcgagtcg cttgtcaaac agcaggttag ccagtatccg gactacgcgc   1380
tgaccgtgac cggccackcc ctcggcgcct ccctggcggc actcactgcc gcccagctgt   1440
ctgcgacata cgacaacatc cgcctgtaca ccttcggcga accgcgcagc ggcaatcagg   1500
ccttcgcgtc gtacatgaac gatgccttcc aagcctcgag cccagatacg acgcagtatt   1560
tccgggtcac tcatgccaac gacggcatcc caaacctgcc cccggtggag caggggtacg   1620
cccatggcgg tgtagagtac tggagcgttg atccttacag cgcccagaac acatttgtct   1680
gcactgggga tgaagtgcag tgctgtgagg cccagggcgg acagggtgtg aataatgcgc   1740
acacgactta ttttgggatg acgagcggcg catgcacctg gccggtcgcg gccgcggaaa   1800
ccactgaagg atgagctgta aagaagcaga tcgttcaaac atttggcaat aaagtttctt   1860
aagattgaat cctgttgccg gtcttgcgat gattatcata taatttctgt tgaattacgt   1920
taagcatgta ataattaaca tgtaatgcat gacgttattt atgagatggg tttttatgat   1980
tagagtcccg caattataca tttaatacgc gatagaaaac aaaatatagc gcgcaaacta   2040
ggataaatta tcgcgcgcgg tgtcatctat gttactagat cgataagctt ctagagcggc   2100
cggtggagct ccaattcgcc ctatagtgag tcgtattacg cgcgctcact ggccgtcgtt   2160
ttacaacgtc gtgactggga aaaccctggc gttacccaac ttaatcgcct tgcagcacat   2220
ccccctttcg ccagctggcg taatagcgaa gaggcccgca ccgatcgccc ttcccaacag   2280
ttgcgcagcc tgaatggcga atgggacgcg ccctgtagcg gcgcattaag cgcggcgggt   2340
gtggtggtta cgcgcagcgt gaccgctaca cttgccagcg ccctagcgcc cgctcctttc   2400
gctttcttcc cttcctttct cgccacgttc gccggctttc cccgtcaagc tctaaatcgg   2460
```

-continued

```
gggctccctt tagggttccg atttagtgct ttacggcacc tcgaccccaa aaaacttgat   2520
tagggtgatg gttcacgtag tgggccatcg ccctgataga cggtttttcg ccctttgacg   2580
ttggagtcca cgttctttaa tagtggactc ttgttccaaa ctggaacaac actcaaccct   2640
atctcggtct attcttttga tttataaggg attttgccga tttcggccta ttggttaaaa   2700
aatgagctga tttaacaaaa atttaacgcg aattttaaca aaatattaac gcttacaatt   2760
taggtggcac ttttcgggga aatgtgcgcg gaacccctat ttgtttattt ttctaaatac   2820
attcaaatat gtatccgctc atgagacaat aaccctgata aatgcttcaa taatattgaa   2880
aaaggaagag tatgagtatt caacatttcc gtgtcgccct tattcccttt tttgcggcat   2940
tttgccttcc tgtttttgct cacccagaaa cgctggtgaa agtaaaagat gctgaagatc   3000
agttgggtgc acgagtgggt tacatcgaac tggatctcaa cagcggtaag atccttgaga   3060
gttttcgccc cgaagaacgt tttccaatga tgagcacttt taaagttctg ctatgtggcg   3120
cggtattatc ccgtattgac gccgggcaag agcaactcgg tcgccgcata cactattctc   3180
agaatgactt ggttgagtac tcaccagtca cagaaaagca tcttacggat ggcatgacag   3240
taagagaatt atgcagtgct gccataacca tgagtgataa cactgcggcc aacttacttc   3300
tgacaacgat cggaggaccg aaggagctaa ccgctttttt gcacaacatg ggggatcatg   3360
taactcgcct tgatcgttgg gaaccggagc tgaatgaagc cataccaaac gacgagcgtg   3420
acaccacgat gcctgtagca atggcaacaa cgttgcgcaa actattaact ggcgaactac   3480
ttactctagc ttcccggcaa caattaatag actggatgga ggcggataaa gttgcaggac   3540
cacttctgcg ctcggccctt ccggctggct ggtttattgc tgataaatct ggagccggtg   3600
agcgtgggtc tcgcggtatc attgcagcac tggggccaga tggtaagccc tcccgtatcg   3660
tagttatcta cacgacgggg agtcaggcaa ctatggatga acgaaataga cagatcgctg   3720
agataggtgc ctcactgatt aagcattggt aactgtcaga ccaagtttac tcatatatac   3780
tttagattga tttaaaactt catttttaat ttaaaaggat ctaggtgaag atcctttttg   3840
ataatctcat gaccaaaatc ccttaacgtg agttttcgtt ccactgagcg tcagaccccg   3900
tagaaaagat caaaggatct tcttgagatc cttttttttct gcgcgtaatc tgctgcttgc  3960
aaacaaaaaa accaccgcta ccagcggtgg tttgtttgcc ggatcaagag ctaccaactc   4020
tttttccgaa ggtaactggc ttcagcagag cgcagatacc aaatactgtc cttctagtgt   4080
agccgtagtt aggccaccac ttcaagaact ctgtagcacc gcctacatac ctcgctctgc   4140
taatcctgtt accagtggct gctgccagtg gcgataagtc gtgtcttacc gggttggact   4200
caagacgata gttaccggat aaggcgcagc ggtcgggctg aacggggggt tcgtgcacac   4260
agcccagctt ggagcgaacg acctacaccg aactgagata cctacagcgt gagctatgag   4320
aaagcgccac gcttcccgaa gggagaaagg cggacaggta tccggtaagc ggcagggtcg   4380
gaacaggaga gcgcacgagg gagcttccag ggggaaacgc ctggtatctt tatagtcctg   4440
tcgggtttcg ccacctctga cttgagcgtc gatttttgtg atgctcgtca ggggggcgga   4500
gcctatggaa aaacgccagc aacgcggcct ttttacggtt cctggccttt tgctggcctt   4560
ttgctcacat gttctttcct gcgttatccc ctgattctgt ggataaccgt attaccgcct   4620
ttgagtgagc tgataccgct cgccgcagcc gaacgaccga gcgcagcgag tcagtgagcg   4680
aggaagcgga agagcgccca atacgcaaac cgcctctccc cgcgcgttgg ccgattcatt   4740
aatgcagctg gcacgacagg tttcccgact ggaaagcggg cagtgagcgc aacgcaatta   4800
atgtgagtta gctcactcat taggcacccc aggctttaca ctttatgctt ccggctcgta   4860
```

-continued

```
tgttgtgtgg aattgtgagc ggataacaat ttcacacagg aaacagctat gaccatgatt   4920

acgccaagcg cgcaattaac cctcactaaa gggaacaaaa gctgg                    4965
```

<210> SEQ ID NO 38
<211> LENGTH: 5295
<212> TYPE: DNA
<213> ORGANISM: Artificial Sequence
<220> FEATURE:
<223> OTHER INFORMATION: pUG4 vector

<400> SEQUENCE: 38

```
aagcttacca tggcccacgc ccgcgtcctc ctcctggcgc tcgccgtgct ggccacggcc     60

gccgtcgccg tcgcctcctc ccgcgcggcc gcctccacgc agggcatctc cgaagacctc    120

tacagccgtt tagtcgaaat ggccactatc tcccaagctg cctacgccga cctgtgcaac    180

attccgtcga ctattatcaa gggagagaaa atttacaatt ctcaaactga cattaacgga    240

tggatcctcc gcgacgacag cagcaaagaa ataatcaccg tcttccgtgg cactggtagt    300

gatacgaatc tacaactcga tactaactac accctcacgc ctttcgacac cctaccacaa    360

tgcaacggtt gtgaagtaca cggtggatat tatattggat gggtctccgt ccaggaccaa    420

gtcgagtcgc ttgtcaaaca gcaggttagc cagtatccgg actacgcgct gaccgtgacc    480

ggccackccc tcggcgcctc cctggcggca ctcactgccg cccagctgtc tgcgacatac    540

gacaacatcc gcctgtacac cttcggcgaa ccgcgcagcg gcaatcaggc cttcgcgtcg    600

tacatgaacg atgccttcca agcctcgagc ccagatacga cgcagtattt ccgggtcact    660

catgccaacg acggcatccc aaacctgccc ccggtggagc aggggtacgc ccatggcggt    720

gtagagtact ggagcgttga tccttacagc gcccagaaca catttgtctg cactggggat    780

gaagtgcagt gctgtgaggc ccagggcgga cagggtgtga ataatgcgca cacgacttat    840

tttgggatga cgagcggcgc atgcacctgg ccggtcgcgg ccgcggaacc actgaaggat    900

gagctgtaaa gaagcagatc gttcaaacat ttggcaataa agtttcttaa gattgaatcc    960

tgttgccggt cttgcgatga ttatcatata atttctgttg aattacgtta agcatgtaat   1020

aattaacatg taatgcatga cgttatttat gagatgggtt tttatgatta gagtcccgca   1080

attatacatt taatacgcga tagaaaacaa aatatagcgc gcaaactagg ataaattatc   1140

gcgcgcggtg tcatctatgt tactagatcg ataagcttct agagcggccg gtggagctcc   1200

aattcgccct atagtgagtc gtattacgcg cgctcactgg ccgtcgtttt acaacgtcgt   1260

gactgggaaa accctggcgt tacccaactt aatcgccttg cagcacatcc ccctttcgcc   1320

agctggcgta atagcgaaga ggcccgcacc gatcgccctt cccaacagtt gcgcagcctg   1380

aatggcgaat gggacgcgcc ctgtagcggc gcattaagcg cggcgggtgt ggtggttacg   1440

cgcagcgtga ccgctacact tgccagcgcc ctagcgcccg ctcctttcgc tttcttccct   1500

tcctttctcg ccacgttcgc cggctttccc cgtcaagctc taaatcgggg gctcccttta   1560

gggttccgat ttagtgcttt acggcacctc gaccccaaaa aacttgatta gggtgatggt   1620

tcacgtagtg ggccatcgcc ctgatagacg gtttttcgcc ctttgacgtt ggagtccacg   1680

ttctttaata gtggactctt gttccaaact ggaacaacac tcaaccctat ctcggtctat   1740

tcttttgatt tataagggat tttgccgatt tcggcctatt ggttaaaaaa tgagctgatt   1800

taacaaaaat ttaacgcgaa ttttaacaaa atattaacgc ttacaattta ggtggcactt   1860

ttcggggaaa tgtgcgcgga acccctattt gtttattttt ctaaatacat tcaaatatgt   1920
```

-continued

```
atccgctcat gagacaataa ccctgataaa tgcttcaata atattgaaaa aggaagagta   1980
tgagtattca acatttccgt gtcgccctta ttcccttttt tgcggcattt tgccttcctg   2040
tttttgctca cccagaaacg ctggtgaaag taaaagatgc tgaagatcag ttgggtgcac   2100
gagtgggtta catcgaactg gatctcaaca gcggtaagat ccttgagagt tttcgccccg   2160
aagaacgttt tccaatgatg agcactttta aagttctgct atgtggcgcg gtattatccc   2220
gtattgacgc cgggcaagag caactcggtc gccgcataca ctattctcag aatgacttgg   2280
ttgagtactc accagtcaca gaaaagcatc ttacggatgg catgacagta agagaattat   2340
gcagtgctgc cataaccatg agtgataaca ctgcggccaa cttacttctg acaacgatcg   2400
gaggaccgaa ggagctaacc gcttttttgc acaacatggg ggatcatgta actcgccttg   2460
atcgttggga accggagctg aatgaagcca taccaaacga cgagcgtgac accacgatgc   2520
ctgtagcaat ggcaacaacg ttgcgcaaac tattaactgg cgaactactt actctagctt   2580
cccggcaaca attaatagac tggatggagg cggataaagt tgcaggacca cttctgcgct   2640
cggcccttcc ggctggctgg tttattgctg ataaatctgg agccggtgag cgtgggtctc   2700
gcggtatcat tgcagcactg gggccagatg gtaagccctc ccgtatcgta gttatctaca   2760
cgacggggag tcaggcaact atggatgaac gaaatagaca gatcgctgag ataggtgcct   2820
cactgattaa gcattggtaa ctgtcagacc aagtttactc atatatactt tagattgatt   2880
taaaacttca tttttaattt aaaaggatct aggtgaagat cctttttgat aatctcatga   2940
ccaaaatccc ttaacgtgag ttttcgttcc actgagcgtc agaccccgta gaaaagatca   3000
aaggatcttc ttgagatcct ttttttctgc gcgtaatctg ctgcttgcaa acaaaaaaac   3060
caccgctacc agcggtggtt tgtttgccgg atcaagagct accaactctt tttccgaagg   3120
taactggctt cagcagagcg cagataccaa atactgtcct tctagtgtag ccgtagttag   3180
gccaccactt caagaactct gtagcaccgc ctacatacct cgctctgcta atcctgttac   3240
cagtggctgc tgccagtggc gataagtcgt gtcttaccgg gttggactca agacgatagt   3300
taccggataa ggcgcagcgg tcgggctgaa cggggggttc gtgcacacag cccagcttgg   3360
agcgaacgac ctacaccgaa ctgagatacc tacagcgtga gctatgagaa agcgccacgc   3420
ttcccgaagg gagaaaggcg gacaggtatc cggtaagcgg cagggtcgga acaggagagc   3480
gcacgaggga gcttccaggg ggaaacgcct ggtatcttta tagtcctgtc gggtttcgcc   3540
acctctgact tgagcgtcga tttttgtgat gctcgtcagg ggggcggagc ctatggaaaa   3600
acgccagcaa cgcggccttt ttacggttcc tggccttttg ctggcctttt gctcacatgt   3660
tctttcctgc gttatcccct gattctgtgg ataaccgtat taccgccttt gagtgagctg   3720
ataccgctcg ccgcagccga acgaccgagc gcagcgagtc agtgagcgag gaagcggaag   3780
agcgcccaat acgcaaaccg cctctccccg cgcgttggcc gattcattaa tgcagctggc   3840
acgacaggtt tcccgactgg aaagcgggca gtgagcgcaa cgcaattaat gtgagttagc   3900
tcactcatta ggcaccccag gctttacact ttatgcttcc ggctcgtatg ttgtgtggaa   3960
ttgtgagcgg ataacaattt cacacaggaa acagctatga ccatgattac gccaagcgcg   4020
caattaaccc tcactaaagg gaacaaaagc tgggtaccgg gccccccctc gaggtcattc   4080
atatgcttga gaagagagtc gggatagtcc aaaataaaac aaaggtaaga ttacctggtc   4140
aaaagtgaaa acatcagtta aaaggtggta taagtaaaat atcggtaata aaaggtggcc   4200
caaagtgaaa tttactcttt tctactatta taaaaattga ggatgttttg tcggtacttt   4260
gatacgtcat tttgtatga attggttttt aagtttattc gcgatttgga aatgcatatc   4320
```

-continued

```
tgtatttgag tcggttttta agttcgttgc ttttgtaaat acagagggat ttgtataaga   4380
aatatcttta aaaaacccat atgctaattt gacataattt ttgagaaaaa tatatattca   4440
ggcgaattcc acaatgaaca ataataagat taaaatagct tgcccccgtt gcagcgatgg   4500
gtatttttttc tagtaaaata aaagataaac ttagactcaa aacatttaca aaaacaaccc   4560
ctaaagtcct aaagcccaaa gtgctatgca cgatccatag caagcccagc ccaacccaac   4620
ccaacccaac ccaccccagt gcagccaact ggcaaatagt ctccaccccc ggcactatca   4680
ccgtgagttg tccgcaccac cgcacgtctc gcagccaaaa aaaaaaaaag aaagaaaaaa   4740
aagaaaaaga aaaacagcag gtgggtccgg gtcgtggggg ccggaaaagc gaggaggatc   4800
gcgagcagcg acgaggcccg gccctccctc cgcttccaaa gaaacgcccc ccatcgccac   4860
tatatacata cccccccctc tcctcccatc cccccaaccc taccaccacc accaccacca   4920
cctcctcccc cctcgctgcc ggacgacgag ctcctccccc ctccccctcc gccgccgccg   4980
gtaaccaccc cgcccctctc ctctttcttt ctccgttttt tttttcgtct cggtctcgat   5040
ctttggcctt ggtagtttgg gtgggcgaga gcggcttcgt cgcccagatc ggtgcgcggg   5100
aggggcggga tctcgcggct ggcgtctccg ggcgtgagtc ggcccggatc ctcgcgggga   5160
atggggctct cggatgtaga tcttctttct ttcttctttt tgtggtagaa tttgaatccc   5220
tcagcattgt tcatcggtag tttttctttt catgatttgt gacaaatgca gcctcgtgcg   5280
gagctttttt gtagc                                                    5295
```

<210> SEQ ID NO 39
<211> LENGTH: 299
<212> TYPE: PRT
<213> ORGANISM: Artificial Sequence
<220> FEATURE:
<223> OTHER INFORMATION: pUG4 vector
<220> FEATURE:
<221> NAME/KEY: VARIANT
<222> LOCATION: (1)...(299)
<223> OTHER INFORMATION: Xaa = Any Amino Acid

<400> SEQUENCE: 39

```
Met Ala His Ala Arg Val Leu Leu Leu Ala Leu Ala Val Leu Ala Thr
 1               5                  10                  15

Ala Ala Val Ala Val Ala Ser Ser Arg Ala Ala Ala Ser Thr Gln Gly
            20                  25                  30

Ile Ser Glu Asp Leu Tyr Ser Arg Leu Val Glu Met Ala Thr Ile Ser
        35                  40                  45

Gln Ala Ala Tyr Ala Asp Leu Cys Asn Ile Pro Ser Thr Ile Ile Lys
    50                  55                  60

Gly Glu Lys Ile Tyr Asn Ser Gln Thr Asp Ile Asn Gly Trp Ile Leu
65                  70                  75                  80

Arg Asp Asp Ser Ser Lys Glu Ile Ile Thr Val Phe Arg Gly Thr Gly
                85                  90                  95

Ser Asp Thr Asn Leu Gln Leu Asp Thr Asn Tyr Thr Leu Thr Pro Phe
            100                 105                 110

Asp Thr Leu Pro Gln Cys Asn Gly Cys Glu Val His Gly Gly Tyr Tyr
        115                 120                 125

Ile Gly Trp Val Ser Val Gln Asp Gln Val Glu Ser Leu Val Lys Gln
    130                 135                 140

Gln Val Ser Gln Tyr Pro Asp Tyr Ala Leu Thr Val Thr Gly His Xaa
145                 150                 155                 160
```

-continued

```
Leu Gly Ala Ser Leu Ala Ala Leu Thr Ala Ala Gln Leu Ser Ala Thr
                165                 170                 175

Tyr Asp Asn Ile Arg Leu Tyr Thr Phe Gly Glu Pro Arg Ser Gly Asn
            180                 185                 190

Gln Ala Phe Ala Ser Tyr Met Asn Asp Ala Phe Gln Ala Ser Ser Pro
        195                 200                 205

Asp Thr Thr Gln Tyr Phe Arg Val Thr His Ala Asn Asp Gly Ile Pro
    210                 215                 220

Asn Leu Pro Pro Val Glu Gln Gly Tyr Ala His Gly Gly Val Glu Tyr
225                 230                 235                 240

Trp Ser Val Asp Pro Tyr Ser Ala Gln Asn Thr Phe Val Cys Thr Gly
                245                 250                 255

Asp Glu Val Gln Cys Cys Glu Ala Gln Gly Gly Gln Gly Val Asn Asn
            260                 265                 270

Ala His Thr Thr Tyr Phe Gly Met Thr Ser Gly Ala Cys Thr Trp Pro
        275                 280                 285

Val Ala Ala Ala Glu Pro Leu Lys Asp Glu Leu
    290                 295
```

<210> SEQ ID NO 40
<211> LENGTH: 5001
<212> TYPE: DNA
<213> ORGANISM: Artificial Sequence
<220> FEATURE:
<223> OTHER INFORMATION: pUB8.11 vector
<220> FEATURE:
<221> NAME/KEY: misc_feature
<222> LOCATION: (1)...(5001)
<223> OTHER INFORMATION: n = A,T,C or G

<400> SEQUENCE: 40

```
catgggccag gtataattat gggatatctc aagcaaataa tcgaaatatc accattggct     60
acaatatctg agctccgagt tctgactgca gtctggatga cgcgtgttgt atctagaact    120
ctagatagca cagccacagc acctacagga gtgcgacact tgtggactgt agtagtgttg    180
gagacggagc tctttcctac ctcctgacgt tgccgccgtt gtccattcca acggcatcac    240
tctcaaccaa tcacgcgctc ccaacaaaat atcgtccccc atgtcttggc ggagagagag    300
tacatacatg ctgtcgcgcc gtttttgtct gaatctcgct tccactggcc aatcagctca    360
gctcccggga gctcactcat tcaagatccc atcgtcgtcg tcacccctgg cgtcatggga    420
tggaaaagaa cctccgttgc tcggatgagt cagccatatc cccgaacaga gtactgcaag    480
ataacccaat tcagattccc ccaatagaga aagtatagca tgctttcggg ttttgtttgg    540
cttaattgac tttattttg ttggagttga atgctgattt gttgtgtaaa atgcccaacc     600
atctgaatat cgagacggat aataggctgg ctaattaatt tatagcaaga ttctgtagtg    660
cacatcgcaa atatctttct gggcattaca gctggaggct tcatcagcct gaaacactct    720
gcagagcctg aagcaagtgg tgaagcgtgg cgatgagatg ggtataaaac cccccggcacc   780
gggacgcgag ctcccgccta ccagtaccat ctcgcctcgc tccccctgcc ggacgaccca    840
gtaaaatact gttgcccact cgccggcgag atggcccacg gccgcatcct cttcttggcg    900
ctcgccgtct tggccaccgc cgcggtggcc gccgcatcnt tggcggactc caacccgatc    960
cggcccgtca ccgagcgcgc ggccgcctcc acgcagggca tctccgaaga cctctacagc   1020
cgtttagtcg aaatggccac tatctcccaa gctgcctacg ccgacctgtg caacattccg   1080
tcgactatta tcaagggaga gaaaatttac aattctcaaa ctgacattaa cggatggatc   1140
```

-continued

```
ctccgcgacg acagcagcaa agaaataatc accgtcttcc gtggcactgg tagtgatacg   1200
aatctacaac tcgatactaa ctacaccctc acgcctttcg acaccctacc acaatgcaac   1260
ggttgtgaag tacacggtgg atattatatt ggatgggtct ccgtccagga ccaagtcgag   1320
tcgcttgtca aacagcaggt tagccagtat ccggactacg cgctgaccgt gaccggccac   1380
kccctcggcg cctccctggc ggcactcact gccgcccagc tgtctgcgac atacgacaac   1440
atccgcctgt acaccttcgg cgaaccgcgc agcggcaatc aggccttcgc gtcgtacatg   1500
aacgatgcct tccaagcctc gagcccagat acgacgcagt atttccgggt cactcatgcc   1560
aacgacggca tcccaaacct gcccccggtg gagcaggggt acgcccatgg cggtgtagag   1620
tactggagcg ttgatcctta cagcgcccag aacacatttg tctgcactgg ggatgaagtg   1680
cagtgctgtg aggcccaggg cggacagggt gtgaataatg cgcacacgac ttattttggg   1740
atgacgagcg gagcctgtac atggtgatca gtcatttcag cctccccgag tgtaccagga   1800
aagatggatg tcctggagag gggggccgcgt aaccactgaa ggatgagctg taaagaagca   1860
gatcgttcaa acatttggca ataaagtttc ttaagattga atcctgttgc cggtcttgcg   1920
atgattatca tataatttct gttgaattac gttaagcatg taataattaa catgtaatgc   1980
atgacgttat ttatgagatg ggtttttatg attagagtcc cgcaattata catttaatac   2040
gcgatagaaa acaaaatata gcgcgcaaac taggataaat tatcgcgcgc ggtgtcatct   2100
atgttactag atcgataagc ttctagagcg gccggtggag ctccaattcg ccctatagtg   2160
agtcgtatta cgcgcgctca ctggccgtcg ttttacaacg tcgtgactgg gaaaaccctg   2220
gcgttaccca acttaatcgc cttgcagcac atcccccttt cgccagctgg cgtaatagcg   2280
aagaggcccg caccgatcgc ccttcccaac agttgcgcag cctgaatggc gaatgggacg   2340
cgccctgtag cggcgcatta agcgcggcgg gtgtggtggt tacgcgcagc gtgaccgcta   2400
cacttgccag cgccctagcg cccgctcctt tcgctttctt cccttccttt ctcgccacgt   2460
tcgccggctt tccccgtcaa gctctaaatc gggggctccc tttagggttc cgatttagtg   2520
ctttacggca cctcgacccc aaaaaacttg attagggtga tggttcacgt agtgggccat   2580
cgccctgata gacggttttt cgccctttga cgttggagtc cacgttcttt aatagtggac   2640
tcttgttcca aactggaaca acactcaacc ctatctcggt ctattctttt gatttataag   2700
ggattttgcc gatttcggcc tattggttaa aaaatgagct gatttaacaa aaatttaacg   2760
cgaattttaa caaaatatta acgcttacaa tttaggtggc acttttcggg gaaatgtgcg   2820
cggaacccct atttgtttat ttttctaaat acattcaaat atgtatccgc tcatgagaca   2880
ataaccctga taaatgcttc aataatattg aaaaaggaag agtatgagta ttcaacattt   2940
ccgtgtcgcc cttattccct tttttgcggc attttgcctt cctgtttttg ctcacccaga   3000
aacgctggtg aaagtaaaag atgctgaaga tcagttgggt gcacgagtgg gttacatcga   3060
actggatctc aacagcggta agatccttga gagttttcgc cccgaagaac gttttccaat   3120
gatgagcact tttaaagttc tgctatgtgg cgcggtatta tcccgtattg acgccgggca   3180
agagcaactc ggtcgccgca tacactattc tcagaatgac ttggttgagt actcaccagt   3240
cacagaaaag catcttacgg atggcatgac agtaagagaa ttatgcagtg ctgccataac   3300
catgagtgat aacactgcgg ccaacttact tctgacaacg atcggaggac cgaaggagct   3360
aaccgctttt ttgcacaaca tgggggatca tgtaactcgc cttgatcgtt gggaaccgga   3420
gctgaatgaa gccataccaa acgacgagcg tgacaccacg atgcctgtag caatggcaac   3480
aacgttgcgc aaactattaa ctggcgaact acttactcta gcttcccggc aacaattaat   3540
```

-continued agactggatg gaggcggata aagttgcagg accacttctg cgctcggccc ttccggctgg 3600
ctggtttatt gctgataaat ctggagccgg tgagcgtggg tctcgcggta tcattgcagc 3660
actggggcca gatggtaagc cctcccgtat cgtagttatc tacacgacgg ggagtcaggc 3720
aactatggat gaacgaaata gacagatcgc tgagataggt gcctcactga ttaagcattg 3780
gtaactgtca gaccaagttt actcatatat actttagatt gatttaaaac ttcattttta 3840
atttaaaagg atctaggtga agatcctttt tgataatctc atgaccaaaa tcccttaacg 3900
tgagttttcg ttccactgag cgtcagaccc cgtagaaaag atcaaaggat cttcttgaga 3960
tccttttttt ctgcgcgtaa tctgctgctt gcaaacaaaa aaaccaccgc taccagcggt 4020
ggtttgtttg ccggatcaag agctaccaac tctttttccg aaggtaactg gcttcagcag 4080
agcgcagata ccaaatactg tccttctagt gtagccgtag ttaggccacc acttcaagaa 4140
ctctgtagca ccgcctacat acctcgctct gctaatcctg ttaccagtgg ctgctgccag 4200
tggcgataag tcgtgtctta ccgggttgga ctcaagacga tagttaccgg ataaggcgca 4260
gcggtcgggc tgaacggggg gttcgtgcac acagcccagc ttggagcgaa cgacctacac 4320
cgaactgaga tacctacagc gtgagctatg agaaagcgcc acgcttcccg aagggagaaa 4380
ggcggacagg tatccggtaa gcggcagggt cggaacagga gagcgcacga gggagcttcc 4440
agggggaaac gcctggtatc tttatagtcc tgtcgggttt cgccacctct gacttgagcg 4500
tcgatttttg tgatgctcgt caggggggcg gagcctatgg aaaaacgcca gcaacgcggc 4560
ctttttacgg ttcctggcct tttgctggcc ttttgctcac atgttctttc ctgcgttatc 4620
ccctgattct gtggataacc gtattaccgc ctttgagtga gctgataccg ctcgccgcag 4680
ccgaacgacc gagcgcagcg agtcagtgag cgaggaagcg gaagagcgcc caatacgcaa 4740
accgcctctc cccgcgcgtt ggccgattca ttaatgcagc tggcacgaca ggtttcccga 4800
ctggaaagcg ggcagtgagc gcaacgcaat taatgtgagt tagctcactc attaggcacc 4860
ccaggcttta cactttatgc ttccggctcg tatgttgtgt ggaattgtga gcggataaca 4920
atttcacaca ggaaacagct atgaccatga ttacgccaag cgcgcaatta accctcacta 4980
aagggaacaa aagctgggta c 5001

<210> SEQ ID NO 41
<211> LENGTH: 5387
<212> TYPE: DNA
<213> ORGANISM: Artificial Sequence
<220> FEATURE:
<223> OTHER INFORMATION: pTP11-1 vector

<400> SEQUENCE: 41
aagcttacca tggcccacgc ccgcgtcctc ctcctggcgc tcgccgtgct ggccacggcc 60
gccgtcgccg tcgcctcctc ctcctccttc gccgactcca acccgatccg gcccgtcacc 120
gaccgcgcgg ccgcctccac gcagggcatc tccgaagacc tctacagccg tttagtcgaa 180
atggccacta tctcccaagc tgcctacgcc gacctgtgca acattccgtc gactattatc 240
aagggagaga aaatttacaa ttctcaaact gacattaacg gatggatcct ccgcgacgac 300
agcagcaaag aaataatcac cgtcttccgt ggcactggta gtgatacgaa tctacaactc 360
gatactaact acaccctcac gcctttcgac accctaccac aatgcaacgg ttgtgaagta 420
cacggtggat attatattgg atgggtctcc gtccaggacc aagtcgagtc gcttgtcaaa 480
cagcaggtta gccagtatcc ggactacgcg ctgaccgtga ccggccackc cctcggcgcc 540

-continued

```
tccctggcgg cactcactgc cgcccagctg tctgcgacat acgacaacat ccgcctgtac    600
accttcggcg aaccgcgcag cggcaatcag gccttcgcgt cgtacatgaa cgatgccttc    660
caagcctcga gcccagatac gacgcagtat ttccgggtca ctcatgccaa cgacggcatc    720
ccaaacctgc ccccggtgga gcaggggtac gcccatggcg gtgtagagta ctggagcgtt    780
gatccttaca gcgcccagaa cacatttgtc tgcactgggg atgaagtgca gtgctgtgag    840
gcccagggcg gacagggtgt gaataatgcg cacacgactt attttgggat gacgagcgga    900
gcctgtacat ggtgatcagt catttcagcc tccccgagtg taccaggaaa gatggatgtc    960
ctggagaggg ggccgcgtaa ccactgaagg atgagctgta aagaagcaga tcgttcaaac   1020
atttggcaat aaagtttctt aagattgaat cctgttgccg gtcttgcgat gattatcata   1080
taatttctgt tgaattacgt taagcatgta ataattaaca tgtaatgcat gacgttattt   1140
atgagatggg tttttatgat tagagtcccg caattataca tttaatacgc gatagaaaac   1200
aaaatatagc gcgcaaacta ggataaatta tcgcgcgcgg tgtcatctat gttactagat   1260
cgataagctt ctagagcggc cggtggagct ccaattcgcc ctatagtgag tcgtattacg   1320
cgcgctcact ggccgtcgtt ttacaacgtc gtgactggga aaaccctggc gttacccaac   1380
ttaatcgcct tgcagcacat ccccctttcg ccagctggcg taatagcgaa gaggcccgca   1440
ccgatcgccc ttcccaacag ttgcgcagcc tgaatggcga atgggacgcg ccctgtagcg   1500
gcgcattaag cgcggcgggt gtggtggtta cgcgcagcgt gaccgctaca cttgccagcg   1560
ccctagcgcc cgctcctttc gctttcttcc cttcctttct cgccacgttc gccggctttc   1620
cccgtcaagc tctaaatcgg gggctccctt tagggttccg atttagtgct ttacggcacc   1680
tcgaccccaa aaaacttgat tagggtgatg gttcacgtag tgggccatcg ccctgataga   1740
cggtttttcg ccctttgacg ttggagtcca cgttctttaa tagtggactc ttgttccaaa   1800
ctggaacaac actcaaccct atctcggtct attcttttga tttataaggg attttgccga   1860
tttcggccta ttggttaaaa aatgagctga tttaacaaaa atttaacgcg aattttaaca   1920
aaatattaac gcttacaatt taggtggcac ttttcgggga aatgtgcgcg gaacccctat   1980
ttgtttattt ttctaaatac attcaaatat gtatccgctc atgagacaat aaccctgata   2040
aatgcttcaa taatattgaa aaaggaagag tatgagtatt caacatttcc gtgtcgccct   2100
tattcccttt tttgcggcat tttgccttcc tgtttttgct cacccagaaa cgctggtgaa   2160
agtaaaagat gctgaagatc agttgggtgc acgagtgggt tacatcgaac tggatctcaa   2220
cagcggtaag atccttgaga gttttcgccc cgaagaacgt tttccaatga tgagcacttt   2280
taaagttctg ctatgtggcg cggtattatc ccgtattgac gccgggcaag agcaactcgg   2340
tcgccgcata cactattctc agaatgactt ggttgagtac tcaccagtca cagaaaagca   2400
tcttacggat ggcatgacag taagagaatt atgcagtgct gccataacca tgagtgataa   2460
cactgcggcc aacttacttc tgacaacgat cggaggaccg aaggagctaa ccgctttttt   2520
gcacaacatg ggggatcatg taactcgcct tgatcgttgg gaaccggagc tgaatgaagc   2580
cataccaaac gacgagcgtg acaccacgat gcctgtagca atggcaacaa cgttgcgcaa   2640
actattaact ggcgaactac ttactctagc ttcccggcaa caattaatag actggatgga   2700
ggcggataaa gttgcaggac cacttctgcg ctcggccctt ccggctggct ggtttattgc   2760
tgataaatct ggagccggtg agcgtgggtc tcgcggtatc attgcagcac tggggccaga   2820
tggtaagccc tcccgtatcg tagttatcta cacgacgggg agtcaggcaa ctatggatga   2880
acgaaataga cagatcgctg agataggtgc ctcactgatt aagcattggt aactgtcaga   2940
```

-continued

```
ccaagtttac tcatatatac tttagattga tttaaaactt catttttaat ttaaaaggat   3000
ctaggtgaag atcctttttg ataatctcat gaccaaaatc ccttaacgtg agttttcgtt   3060
ccactgagcg tcagaccccg tagaaaagat caaaggatct tcttgagatc cttttttttct   3120
gcgcgtaatc tgctgcttgc aaacaaaaaa accaccgcta ccagcggtgg tttgtttgcc   3180
ggatcaagag ctaccaactc tttttccgaa ggtaactggc ttcagcagag cgcagatacc   3240
aaatactgtc cttctagtgt agccgtagtt aggccaccac ttcaagaact ctgtagcacc   3300
gcctacatac ctcgctctgc taatcctgtt accagtggct gctgccagtg gcgataagtc   3360
gtgtcttacc gggttggact caagacgata gttaccggat aaggcgcagc ggtcgggctg   3420
aacggggggt tcgtgcacac agcccagctt ggagcgaacg acctacaccg aactgagata   3480
cctacagcgt gagctatgag aaagcgccac gcttcccgaa gggagaaagg cggacaggta   3540
tccggtaagc ggcagggtcg gaacaggaga gcgcacgagg gagcttccag ggggaaacgc   3600
ctggtatctt tatagtcctg tcgggtttcg ccacctctga cttgagcgtc gatttttgtg   3660
atgctcgtca ggggggcgga gcctatggaa aaacgccagc aacgcggcct ttttacggtt   3720
cctggccttt tgctggcctt ttgctcacat gttctttcct gcgttatccc ctgattctgt   3780
ggataaccgt attaccgcct ttgagtgagc tgataccgct cgccgcagcc gaacgaccga   3840
gcgcagcgag tcagtgagcg aggaagcgga agagcgccca atacgcaaac cgcctctccc   3900
cgcgcgttgg ccgattcatt aatgcagctg gcacgacagg tttcccgact ggaaagcggg   3960
cagtgagcgc aacgcaatta atgtgagtta gctcactcat taggcacccc aggctttaca   4020
ctttatgctt ccggctcgta tgttgtgtgg aattgtgagc ggataacaat ttcacacagg   4080
aaacagctat gaccatgatt acgccaagcg cgcaattaac cctcactaaa gggaacaaaa   4140
gctgggtacc gggccccccc tcgaggtcat tcatatgctt gagaagagag tcgggatagt   4200
ccaaaataaa acaaaggtaa gattacctgg tcaaaagtga aaacatcagt taaaaggtgg   4260
tataagtaaa atatcggtaa taaaaggtgg cccaaagtga aatttactct tttctactat   4320
tataaaaatt gaggatgttt tgtcggtact ttgatacgtc atttttgtat gaattggttt   4380
ttaagtttat tcgcgatttg gaaatgcata tctgtatttg agtcggtttt taagttcgtt   4440
gcttttgtaa atacagaggg atttgtataa gaaatatctt taaaaaaccc atatgctaat   4500
ttgacataat ttttgagaaa aatatatatt caggcgaatt ccacaatgaa caataataag   4560
attaaaatag cttgcccccg ttgcagcgat gggtattttt tctagtaaaa taaaagataa   4620
acttagactc aaaacattta caaaaacaac ccctaaagtc ctaaagccca aagtgctatg   4680
cacgatccat agcaagccca gcccaaccca acccaaccca acccacccca gtgcagccaa   4740
ctggcaaata gtctccaccc ccggcactat caccgtgagt tgtccgcacc accgcacgtc   4800
tcgcagccaa aaaaaaaaaa agaaagaaaa aaaagaaaaa gaaaaacagc aggtgggtcc   4860
gggtcgtggg ggccggaaaa gcgaggagga tcgcgagcag cgacgaggcc cggccctccc   4920
tccgcttcca aagaaacgcc ccccatcgcc actatataca taccccccc tctcctccca   4980
tccccccaac cctaccacca ccaccaccac cacctcctcc cccctcgctg ccggacgacg   5040
agctcctccc ccctccccct ccgccgccgc cggtaaccac cccgcccctc tcctctttct   5100
ttctccgttt tttttttcgt ctcggtctcg atctttggcc ttggtagttt gggtgggcga   5160
gagcggcttc gtcgcccaga tcggtgcgcg ggaggggcgg gatctcgcgg ctggcgtctc   5220
cgggcgtgag tcggcccgga tcctcgcggg gaatggggct ctcggatgta gatcttcttt   5280
```

-continued

```
ctttcttctt tttgtggtag aatttgaatc cctcagcatt gttcatcggt agtttttctt   5340

ttcatgattt gtgacaaatg cagcctcgtg cggagctttt ttgtagc                 5387


<210> SEQ ID NO 42
<211> LENGTH: 301
<212> TYPE: PRT
<213> ORGANISM: Artificial Sequence
<220> FEATURE:
<223> OTHER INFORMATION: pTP11-1 vector
<220> FEATURE:
<221> NAME/KEY: VARIANT
<222> LOCATION: (1)...(301)
<223> OTHER INFORMATION: Xaa = Any Amino Acid

<400> SEQUENCE: 42

Met Ala His Ala Arg Val Leu Leu Leu Ala Leu Ala Val Leu Ala Thr
 1               5                  10                  15

Ala Ala Val Ala Val Ala Ser Ser Ser Ser Phe Ala Asp Ser Asn Pro
            20                  25                  30

Ile Arg Pro Val Thr Asp Arg Ala Ala Ala Ser Thr Gln Gly Ile Ser
        35                  40                  45

Glu Asp Leu Tyr Ser Arg Leu Val Glu Met Ala Thr Ile Ser Gln Ala
    50                  55                  60

Ala Tyr Ala Asp Leu Cys Asn Ile Pro Ser Thr Ile Ile Lys Gly Glu
65                  70                  75                  80

Lys Ile Tyr Asn Ser Gln Thr Asp Ile Asn Gly Trp Ile Leu Arg Asp
                85                  90                  95

Asp Ser Ser Lys Glu Ile Ile Thr Val Phe Arg Gly Thr Gly Ser Asp
            100                 105                 110

Thr Asn Leu Gln Leu Asp Thr Asn Tyr Thr Leu Thr Pro Phe Asp Thr
        115                 120                 125

Leu Pro Gln Cys Asn Gly Cys Glu Val His Gly Gly Tyr Tyr Ile Gly
    130                 135                 140

Trp Val Ser Val Gln Asp Gln Val Glu Ser Leu Val Lys Gln Gln Val
145                 150                 155                 160

Ser Gln Tyr Pro Asp Tyr Ala Leu Thr Val Thr Gly His Xaa Leu Gly
                165                 170                 175

Ala Ser Leu Ala Ala Leu Thr Ala Ala Gln Leu Ser Ala Thr Tyr Asp
            180                 185                 190

Asn Ile Arg Leu Tyr Thr Phe Gly Glu Pro Arg Ser Gly Asn Gln Ala
        195                 200                 205

Phe Ala Ser Tyr Met Asn Asp Ala Phe Gln Ala Ser Ser Pro Asp Thr
    210                 215                 220

Thr Gln Tyr Phe Arg Val Thr His Ala Asn Asp Gly Ile Pro Asn Leu
225                 230                 235                 240

Pro Pro Val Glu Gln Gly Tyr Ala His Gly Gly Val Glu Tyr Trp Ser
                245                 250                 255

Val Asp Pro Tyr Ser Ala Gln Asn Thr Phe Val Cys Thr Gly Asp Glu
            260                 265                 270

Val Gln Cys Cys Glu Ala Gln Gly Gly Gln Gly Val Asn Asn Ala His
        275                 280                 285

Thr Thr Tyr Phe Gly Met Thr Ser Gly Ala Cys Thr Trp
    290                 295                 300


<210> SEQ ID NO 43
<211> LENGTH: 1259
<212> TYPE: DNA
```

-continued

<213> ORGANISM: Artificial Sequence
<220> FEATURE:
<223> OTHER INFORMATION: actin promoter

<400> SEQUENCE: 43
ggtaccgggc ccccctcga ggtcattcat atgcttgaga agagagtcgg gatagtccaa 60
aataaaacaa aggtaagatt acctggtcaa aagtgaaaac atcagttaaa aggtggtata 120
agtaaaatat cggtaataaa aggtggccca aagtgaaatt tactcttttc tactattata 180
aaaattgagg atgttttgtc ggtactttga tacgtcattt ttgtatgaat tggtttttaa 240
gtttattcgc gatttggaaa tgcatatctg tatttgagtc ggtttttaag ttcgttgctt 300
ttgtaaatac agagggattt gtataagaaa tatctttaaa aaacccatat gctaatttga 360
cataattttt gagaaaaata tatattcagg cgaattccac aatgaacaat aataagatta 420
aaatagcttg cccccgttgc agcgatgggt atttttcta gtaaaataaa agataaactt 480
agactcaaaa catttacaaa aacaacccct aaagtcctaa agcccaaagt gctatgcacg 540
atccatagca agcccagccc aacccaaccc aacccaaccc accccagtgc agccaactgg 600
caaatagtct ccacccccgg cactatcacc gtgagttgtc cgcaccaccg cacgtctcgc 660
agccaaaaaa aaaaaaagaa agaaaaaaaa gaaaaagaaa aacagcaggt gggtccgggt 720
cgtgggggcc ggaaaagcga ggaggatcgc gagcagcgac gaggcccggc cctccctccg 780
cttccaaaga aacgcccccc atcgccacta tatacatacc ccccctctc ctcccatccc 840 cccaacccta ccaccaccac caccaccacc tcctcccccc tcgctgccgg acgacgagct 900
cctcccccct cccctccgc cgccgccggt aaccaccccg cccctctcct ctttctttct 960
ccgttttttt tttcgtctcg gtctcgatct ttggccttgg tagtttgggt gggcgagagc 1020
ggcttcgtcg cccagatcgg tgcgcgggag gggcgggatc tcgcggctgg cgtctccggg 1080
cgtgagtcgg cccggatcct cgcggggaat ggggctctcg gatgtagatc ttctttcttt 1140
cttctttttg tggtagaatt tgaatccctc agcattgttc atcggtagtt tttcttttca 1200
tgatttgtga caaatgcagc ctcgtgcgga gcttttttgt aggtagaagc ttaccatgg 1259

<210> SEQ ID NO 44
<211> LENGTH: 27
<212> TYPE: PRT
<213> ORGANISM: Artificial Sequence
<220> FEATURE:
<223> OTHER INFORMATION: aleurain-NPIR delete structure

<400> SEQUENCE: 44

Met Ala His Ala Arg Val Leu Leu Leu Ala Leu Ala Val Leu Ala Thr
1 5 10 15

Ala Ala Val Ala Val Ala Ser Ser Arg Ala Ala
20 25

<210> SEQ ID NO 45
<211> LENGTH: 93
<212> TYPE: DNA
<213> ORGANISM: Artificial Sequence
<220> FEATURE:
<223> OTHER INFORMATION: aleurain-NPIR delete structure encoding
sequence

<400> SEQUENCE: 45
aagcttacca tggcccacgc ccgcgtcctc ctcctggcgc tcgccgtgct ggccacggcc 60
gccgtcgccg tcgcctcctc ccgcgcggcc gcc 93

-continued

<210> SEQ ID NO 46
<211> LENGTH: 873
<212> TYPE: DNA
<213> ORGANISM: Artificial Sequence
<220> FEATURE:
<223> OTHER INFORMATION: SEE1 (senescence enhanced) promoter

<400> SEQUENCE: 46
catgggccag gtataattat gggatatctc aagcaaataa tcgaaatatc accattggct 60
acaatatctg agctccgagt tctgactgca gtctggatga cgcgtgttgt atctagaact 120
ctagatagca cagccacagc acctacagga gtgcgacact tgtggactgt agtagtgttg 180
gagacggagc tctttcctac ctcctgacgt tgccgccgtt gtccattcca acggcatcac 240
tctcaaccaa tcacgcgctc ccaacaaaat atcgtccccc atgtcttggc ggagagagag 300
tacatacatg ctgtcgcgcc gtttttgtct gaatctcgct tccactggcc aatcagctca 360
gctcccggga gctcactcat tcaagatccc atcgtcgtcg tcacccctgg cgtcatggga 420
tggaaaagaa cctccgttgc tcggatgagt cagccatatc cccgaacaga gtactgcaag 480
ataacccaat tcagattccc ccaatagaga aagtatagca tgctttcggg ttttgtttgg 540
cttaattgac tttatttttg ttggagttga atgctgattt gttgtgtaaa atgcccaacc 600
atctgaatat cgagacggat aataggctgg ctaattaatt tatagcaaga ttctgtagtg 660
cacatcgcaa atatctttct gggcattaca gctggaggct tcatcagcct gaaacactct 720
gcagagcctg aagcaagtgg tgaagcgtgg cgatgagatg ggtataaaac ccccggcacc 780
gggacgcgag ctcccgccta ccagtaccat ctcgcctcgc tccccctgcc ggacgaccca 840
gtaaaatact gttgcccact cgccggcgag atg 873

<210> SEQ ID NO 47
<211> LENGTH: 39
<212> TYPE: PRT
<213> ORGANISM: Artificial Sequence
<220> FEATURE:
<223> OTHER INFORMATION: SEE1 promoter plus vacuolar aleurain signal
/NPIR sequence

<400> SEQUENCE: 47

Met Ala His Gly Arg Ile Leu Phe Leu Ala Leu Ala Val Leu Ala Thr
1 5 10 15

Ala Ala Val Ala Ala Ala Ser Leu Ala Asp Ser Asn Pro Ile Arg Pro
20 25 30

Val Thr Glu Arg Ala Ala Ala
35

<210> SEQ ID NO 48
<211> LENGTH: 987
<212> TYPE: DNA
<213> ORGANISM: Artificial Sequence
<220> FEATURE:
<223> OTHER INFORMATION: SEE1 promoter plus vacuolar aleurain signal
/NPIR encoding sequence
<220> FEATURE:
<221> NAME/KEY: misc_feature
<222> LOCATION: (1)...(987)
<223> OTHER INFORMATION: n = A,T,C or G

<400> SEQUENCE: 48
catgggccag gtataattat gggatatctc aagcaaataa tcgaaatatc accattggct 60
acaatatctg agctccgagt tctgactgca gtctggatga cgcgtgttgt atctagaact 120

-continued

```
ctagatagca cagccacagc acctacagga gtgcgacact tgtggactgt agtagtgttg    180

gagacggagc tctttcctac ctcctgacgt tgccgccgtt gtccattcca acggcatcac    240

tctcaaccaa tcacgcgctc ccaacaaaat atcgtccccc atgtcttggc ggagagagag    300

tacatacatg ctgtcgcgcc gtttttgtct gaatctcgct tccactggcc aatcagctca    360

gctcccggga gctcactcat tcaagatccc atcgtcgtcg tcacccctgg cgtcatggga    420

tggaaaagaa cctccgttgc tcggatgagt cagccatatc cccgaacaga gtactgcaag    480

ataacccaat tcagattccc ccaatagaga aagtatagca tgctttcggg ttttgtttgg    540

cttaattgac tttatttttg ttggagttga atgctgattt gttgtgtaaa atgcccaacc    600

atctgaatat cgagacggat aataggctgg ctaattaatt tatagcaaga ttctgtagtg    660

cacatcgcaa atatctttct gggcattaca gctggaggct tcatcagcct gaaacactct    720

gcagagcctg aagcaagtgg tgaagcgtgg cgatgagatg ggtataaaac ccccggcacc    780

gggacgcgag ctcccgccta ccagtaccat ctcgcctcgc tccccctgcc ggacgaccca    840

gtaaaatact gttgcccact cgccggcgag atggcccacg gccgcatcct cttcttggcg    900

ctcgccgtct tggccaccgc cgcggtggcc gccgcatcnt tggcggactc caacccgatc    960

cggcccgtca ccgagcgcgc ggccgcc                                        987
```

<210> SEQ ID NO 49
<211> LENGTH: 40
<212> TYPE: DNA
<213> ORGANISM: Artificial Sequence
<220> FEATURE:
<223> OTHER INFORMATION: primer

<400> SEQUENCE: 49

```
ggcgccgagg gagtggccgg tcacggtcag cgcgtagtcc                           40
```

<210> SEQ ID NO 50
<211> LENGTH: 35
<212> TYPE: DNA
<213> ORGANISM: Artificial Sequence
<220> FEATURE:
<223> OTHER INFORMATION: primer

<400> SEQUENCE: 50

```
ccggccacgc cctcggcgcc tccctggcgg cactc                                35
```

<210> SEQ ID NO 51
<211> LENGTH: 44
<212> TYPE: DNA
<213> ORGANISM: Artificial Sequence
<220> FEATURE:
<223> OTHER INFORMATION: primer

<400> SEQUENCE: 51

```
ctaaagctta ccatggcggc cgcctccacg cagggcatct ccga                      44
```

<210> SEQ ID NO 52
<211> LENGTH: 50
<212> TYPE: DNA
<213> ORGANISM: Artificial Sequence
<220> FEATURE:
<223> OTHER INFORMATION: primer

<400> SEQUENCE: 52

```
tctaagcttg cggccgcgac cggccaggtg catgcgccgc tcgtcatccc                50
```

-continued

<210> SEQ ID NO 53
<211> LENGTH: 325
<212> TYPE: DNA
<213> ORGANISM: Artificial Sequence
<220> FEATURE:
<223> OTHER INFORMATION: amplified nos terminator sequence from pMA406 vector

<400> SEQUENCE: 53
agactgcaga ccatggcggc cgcgkaacca ctgaaggatg agctgtaaag aagcagatcg 60
ttcaaacatt tggcaataaa gtttcttaag attgaatcct gttgccggtc ttgcgatgat 120
tatcatataa tttctgttga attacgttaa gcatgtaata attaacatgt aatgcatgac 180
gttatttatg agatgggttt ttatgattag agtcccgcaa ttatacattt aatacgcgat 240
agaaaacaaa atatagcgcg caaactagga taaattatcg cgcgcggtgt catctatgtt 300
actagatcga taagcttcta gatct 325

<210> SEQ ID NO 54
<211> LENGTH: 72
<212> TYPE: DNA
<213> ORGANISM: Artificial Sequence
<220> FEATURE:
<223> OTHER INFORMATION: primer

<400> SEQUENCE: 54
agactgcaga ccatggcggc cgcgkaacca ctgaaggatg agctgtaaag aagcagatcg 60
ttcaaacatt tg 72

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
aagactgcag accatggcgg 20

<210> SEQ ID NO 56
<211> LENGTH: 40
<212> TYPE: DNA
<213> ORGANISM: Artificial Sequence
<220> FEATURE:
<223> OTHER INFORMATION: primer

<400> SEQUENCE: 56
agatctagaa gcttatcgat ctagtaacat agatgacacc 40

<210> SEQ ID NO 57
<211> LENGTH: 33
<212> TYPE: DNA
<213> ORGANISM: Artificial Sequence
<220> FEATURE:
<223> OTHER INFORMATION: primer

<400> SEQUENCE: 57
ctaggcggcc gcgcgggagg aggcgacggc gac 33

<210> SEQ ID NO 58
<211> LENGTH: 36
<212> TYPE: DNA
<213> ORGANISM: Artificial Sequence
<220> FEATURE:
<223> OTHER INFORMATION: primer -continued

<400> SEQUENCE: 58
gagggtgtat tcggtatcga gttgcaggtt cgtatc 36

<210> SEQ ID NO 59
<211> LENGTH: 32
<212> TYPE: DNA
<213> ORGANISM: Artificial Sequence
<220> FEATURE:
<223> OTHER INFORMATION: primer

<400> SEQUENCE: 59
ctcgataccc attacaccct cacgcctttc ga 32

<210> SEQ ID NO 60
<211> LENGTH: 10
<212> TYPE: DNA
<213> ORGANISM: Artificial Sequence
<220> FEATURE:
<223> OTHER INFORMATION: Accl site

<400> SEQUENCE: 60
gtaggtagac 10

<210> SEQ ID NO 61
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 61
ctcaccatgg taagcttcta cctacaaaaa agctccgca 39

<210> SEQ ID NO 62
<211> LENGTH: 36
<212> TYPE: DNA
<213> ORGANISM: Artificial Sequence
<220> FEATURE:
<223> OTHER INFORMATION: primer

<400> SEQUENCE: 62
aaccatggcg gccgcgcgct cggtgacggg ccggat 36

<210> SEQ ID NO 63
<211> LENGTH: 29
<212> TYPE: DNA
<213> ORGANISM: Artificial Sequence
<220> FEATURE:
<223> OTHER INFORMATION: primer

<400> SEQUENCE: 63
ttcggtacca tggccaggta taattatgg 29

<210> SEQ ID NO 64
<211> LENGTH: 31
<212> TYPE: DNA
<213> ORGANISM: Artificial Sequence
<220> FEATURE:
<223> OTHER INFORMATION: primer

<400> SEQUENCE: 64
ctgcgccggc gagatggmcg tgcacaagga g 31

<210> SEQ ID NO 65

-continued

<211> LENGTH: 42
<212> TYPE: DNA
<213> ORGANISM: Artificial Sequence
<220> FEATURE:
<223> OTHER INFORMATION: primer

<400> SEQUENCE: 65
ggaattcgta gacaagctta cmatggccca cgcccgcgtc ct 42

<210> SEQ ID NO 66
<211> LENGTH: 55
<212> TYPE: DNA
<213> ORGANISM: Artificial Sequence
<220> FEATURE:
<223> OTHER INFORMATION: primer

<400> SEQUENCE: 66
tatccatggc ggccgcgcgg tcggtgacgg gccggmycgg gttggagtcg gcgaa 55

<210> SEQ ID NO 67
<211> LENGTH: 33
<212> TYPE: DNA
<213> ORGANISM: Artificial Sequence
<220> FEATURE:
<223> OTHER INFORMATION: primer

<400> SEQUENCE: 67
ctaggcggcc gcgcgggagg aggcgacggc gac 33

<210> SEQ ID NO 68
<211> LENGTH: 54
<212> TYPE: DNA
<213> ORGANISM: Artificial Sequence
<220> FEATURE:
<223> OTHER INFORMATION: primer

<400> SEQUENCE: 68
gcgacggcga cggcggccgt ggccagcacg gcgagcgcca ggaggaggac gcgg 54

<210> SEQ ID NO 69
<211> LENGTH: 33
<212> TYPE: DNA
<213> ORGANISM: Artificial Sequence
<220> FEATURE:
<223> OTHER INFORMATION: primer

<400> SEQUENCE: 69
tcgccgtcgc ctcctcctcc tccttcgccg act 33

<210> SEQ ID NO 70
<211> LENGTH: 43
<212> TYPE: DNA
<213> ORGANISM: Artificial Sequence
<220> FEATURE:
<223> OTHER INFORMATION: primer

<400> SEQUENCE: 70
actaagctta aggagatata acaatgatcc acaccaacct caa 43

<210> SEQ ID NO 71
<211> LENGTH: 45
<212> TYPE: DNA
<213> ORGANISM: Artificial Sequence
<220> FEATURE:
<223> OTHER INFORMATION: primer

<400> SEQUENCE: 71

-continued ttccatgatc cacaccaacc tcaaaaagaa gttctccctc ttcat 45

<210> SEQ ID NO 72
<211> LENGTH: 55
<212> TYPE: DNA
<213> ORGANISM: Artificial Sequence
<220> FEATURE:
<223> OTHER INFORMATION: primer

<400> SEQUENCE: 72
agagtgatca cggcgaagag gaggaagacg aggatgaaga gggagaactt ctttt 55

<210> SEQ ID NO 73
<211> LENGTH: 61
<212> TYPE: DNA
<213> ORGANISM: Artificial Sequence
<220> FEATURE:
<223> OTHER INFORMATION: primer

<400> SEQUENCE: 73
tatagatctg cgtgtggaag aagggctccg actacgaggc cctcaccctc caagccaagg 60
a 61

<210> SEQ ID NO 74
<211> LENGTH: 28
<212> TYPE: DNA
<213> ORGANISM: Artificial Sequence
<220> FEATURE:
<223> OTHER INFORMATION: primer

<400> SEQUENCE: 74
catttggaac tccttggctt ggagggtg 28

<210> SEQ ID NO 75
<211> LENGTH: 34
<212> TYPE: DNA
<213> ORGANISM: Artificial Sequence
<220> FEATURE:
<223> OTHER INFORMATION: primer

<400> SEQUENCE: 75
aaccatggcg gccgccattt ggaactcctt ggct 34

<210> SEQ ID NO 76
<211> LENGTH: 61
<212> TYPE: DNA
<213> ORGANISM: Artificial Sequence
<220> FEATURE:
<223> OTHER INFORMATION: primer

<400> SEQUENCE: 76
tatagatctg cgtgtggaag aagggctccg actacgaggc cctcaccctc caagccaagg 60
a 61

<210> SEQ ID NO 77
<211> LENGTH: 42
<212> TYPE: DNA
<213> ORGANISM: Artificial Sequence
<220> FEATURE:
<223> OTHER INFORMATION: primer

<400> SEQUENCE: 77
ggaattcgta gacaagctta cmatggmcgt gcacaaggag gt 42

-continued

<210> SEQ ID NO 78
<211> LENGTH: 37
<212> TYPE: DNA
<213> ORGANISM: Artificial Sequence
<220> FEATURE:
<223> OTHER INFORMATION: primer

<400> SEQUENCE: 78
gatcaggagg taggcwacga agttwacctc cttgtgc 37

<210> SEQ ID NO 79
<211> LENGTH: 37
<212> TYPE: DNA
<213> ORGANISM: Artificial Sequence
<220> FEATURE:
<223> OTHER INFORMATION: primer

<400> SEQUENCE: 79
cctacctcct gatcgtsctc ggcctcctct tgctcgt 37

<210> SEQ ID NO 80
<211> LENGTH: 43
<212> TYPE: DNA
<213> ORGANISM: Artificial Sequence
<220> FEATURE:
<223> OTHER INFORMATION: primer

<400> SEQUENCE: 80
ccttggcgtc cacgtgctcc atggcggawa cgagcaagag gag 43

<210> SEQ ID NO 81
<211> LENGTH: 39
<212> TYPE: DNA
<213> ORGANISM: Artificial Sequence
<220> FEATURE:
<223> OTHER INFORMATION: primer

<400> SEQUENCE: 81
gtggacgcca aggcctgcac cckcgagtgc ggcaacctc 39

<210> SEQ ID NO 82
<211> LENGTH: 47
<212> TYPE: DNA
<213> ORGANISM: Artificial Sequence
<220> FEATURE:
<223> OTHER INFORMATION: primer

<400> SEQUENCE: 82
ggaattcgcg gccgccgggc agatgccgaa gccgaggttg ccgcact 47

<210> SEQ ID NO 83
<211> LENGTH: 32
<212> TYPE: DNA
<213> ORGANISM: Artificial Sequence
<220> FEATURE:
<223> OTHER INFORMATION: primer

<400> SEQUENCE: 83
ctaaagctta acatgaagca gttctccgcc aa 32

<210> SEQ ID NO 84
<211> LENGTH: 8
<212> TYPE: DNA
<213> ORGANISM: Oryza sp.

<400> SEQUENCE: 84

-continued gtaggtag 8

<210> SEQ ID NO 85
<211> LENGTH: 7
<212> TYPE: PRT
<213> ORGANISM: Artificial Sequence
<220> FEATURE:
<223> OTHER INFORMATION: KDEL fusion peptide

<400> SEQUENCE: 85

Lys Pro Leu Lys Asp Glu Leu
1 5

<210> SEQ ID NO 86
<211> LENGTH: 7
<212> TYPE: PRT
<213> ORGANISM: Artificial Sequence
<220> FEATURE:
<223> OTHER INFORMATION: designated KDEL fusion peptide

<400> SEQUENCE: 86

Glu Pro Leu Lys Asp Glu Leu
1 5

<210> SEQ ID NO 87
<211> LENGTH: 5
<212> TYPE: PRT
<213> ORGANISM: Artificial Sequence
<220> FEATURE:
<223> OTHER INFORMATION: frameshifted terminal peptide

<400> SEQUENCE: 87

Glu Thr Thr Glu Gly
1 5

<210> SEQ ID NO 88
<211> LENGTH: 27
<212> TYPE: PRT
<213> ORGANISM: Aspergillus niger

<400> SEQUENCE: 88

Met Lys Gln Phe Ser Ala Lys His Val Leu Ala Val Val Val Thr Ala
1 5 10 15

Gly His Ala Leu Ala Ala Ser Thr Gln Gly Ile
20 25

<210> SEQ ID NO 89
<211> LENGTH: 9
<212> TYPE: PRT
<213> ORGANISM: Aspergillus niger

<400> SEQUENCE: 89

Met Ala Ala Ala Ser Thr Gln Gly Ile
1 5

<210> SEQ ID NO 90
<211> LENGTH: 7
<212> TYPE: PRT
<213> ORGANISM: Artificial Sequence
<220> FEATURE:
<223> OTHER INFORMATION: ER retention vector

<400> SEQUENCE: 90

Lys Pro Leu Lys Asp Glu Leu
1 5

-continued

<210> SEQ ID NO 91
<211> LENGTH: 5
<212> TYPE: PRT
<213> ORGANISM: Artificial Sequence
<220> FEATURE:
<223> OTHER INFORMATION: c-terminal targeting sequence

<400> SEQUENCE: 91

```
Pro Val Ala Ala Ala
 1               5
```

<210> SEQ ID NO 92
<211> LENGTH: 55
<212> TYPE: DNA
<213> ORGANISM: Artificial Sequence
<220> FEATURE:
<223> OTHER INFORMATION: primer

<400> SEQUENCE: 92

```
tatccatggc ggccgcgcgg tcggtgacgg gccggcccgg gttggagtcg gcgaa          55
```

<210> SEQ ID NO 93
<211> LENGTH: 8
<212> TYPE: PRT
<213> ORGANISM: Artificial Sequence
<220> FEATURE:
<223> OTHER INFORMATION: ferulic esterase end

<400> SEQUENCE: 93

```
Cys Thr Trp Pro Val Ala Ala Ala
 1               5
```

<210> SEQ ID NO 94
<211> LENGTH: 72
<212> TYPE: PRT
<213> ORGANISM: Artificial Sequence
<220> FEATURE:
<223> OTHER INFORMATION: pTP4a2 vector

<400> SEQUENCE: 94

```
Met Lys Gln Phe Ser Ala Lys His Val Leu Ala Val Val Val Thr Ala
 1               5                  10                  15

Gly His Ala Leu Ala Ala Ser Thr Gln Gly Ile Ser Glu Asp Leu Tyr
            20                  25                  30

Ser Arg Leu Val Glu Met Ala Thr Ile Ser Gln Ala Ala Tyr Ala Asp
        35                  40                  45

Leu Cys Asn Ile Pro Ser Thr Ile Ile Lys Gly Glu Lys Ile Tyr Asn
    50                  55                  60

Ser Gln Thr Asp Ile Asn Gly Trp
65                  70
```

<210> SEQ ID NO 95
<211> LENGTH: 17
<212> TYPE: PRT
<213> ORGANISM: Artificial Sequence
<220> FEATURE:
<223> OTHER INFORMATION: protein encoded by functional reading frame

<400> SEQUENCE: 95

```
Tyr Ala Leu Thr Val Thr Gly His Ser Leu Gly Ala Ser Leu Ala Ala
 1               5                  10                  15

Leu
```

-continued

```
<210> SEQ ID NO 96
<211> LENGTH: 17
<212> TYPE: PRT
<213> ORGANISM: Artificial Sequence
<220> FEATURE:
<223> OTHER INFORMATION: protein encoded by inactivated reading frame

<400> SEQUENCE: 96

Tyr Ala Leu Thr Val Thr Gly His Ala Leu Gly Ala Ser Leu Ala Ala
 1               5                   10                  15

Leu


<210> SEQ ID NO 97
<211> LENGTH: 4
<212> TYPE: PRT
<213> ORGANISM: Artificial Sequence
<220> FEATURE:
<223> OTHER INFORMATION: retention sequence

<400> SEQUENCE: 97

Lys Asp Glu Leu
 1
```

MANIPULATION OF THE PHENOLIC ACID CONTENT AND DIGESTIBILITY OF PLANT CELL WALLS BY TARGETED EXPRESSION OF GENES ENCODING CELL WALL DEGRADING ENZYMES

CROSS-REFERENCE TO RELATED APPLICATIONS

Pursuant to 35 U.S.C. §119(e), the present application claims benefit of and priority to U.S. Ser. No. 60/249,608, entitled "MANIPULATION OF THE PHENOLIC ACID CONTENT AND DIGESTIBILITY OF FORAGE GRASS CELL WALLS BY TARGETED EXPRESSION OF A FERULIC ACID ESTERASE GENE", filed Nov. 17, 2000, by Morris et al.

FIELD OF THE INVENTION

This invention relates to methods to enhance to availability of fermentable carbohydrates.

BACKGROUND OF THE INVENTION

The present crisis in livestock agriculture has prompted a resurgence of interest in grass-fed animals. However, while a high-forage diet may be desirable, it does not currently satisfy the demands of modern animal production. For the animal to make efficient use of the forage it consumes, the energy demands of the microorganisms in the rumen must be met and synchronized with the availability of plant proteins. Otherwise this lack of synchrony will lead to (a) proteins and other nutrients being poorly utilized in the rumen, (b) loss of nitrogen, in urine and feces and therefore, the environment and (c) the need to feed excessive amounts of protein concentrates as supplements to the ruminant diet.

Cellulose and hemicellulose in grass and maize tissues could meet the energy requirements of the ruminant or provide new feed-stocks for industrial fermentation to ethanol. This potential is not currently realized because the cell walls are lignified and the cell wall polysaccharides highly cross-linked with phenolic residues and lignin, resulting in low rates of plant cell wall digestion in comparison to rates of protein breakdown in ruminants. This is a particular problem for the most important forages in Europe, the ryegrasses *Lolium perenne* and *L. mutiflorum* as well as one of the major impediments to the wider use of better adapted species, such as *Festuca arundinacea*, as a forage crop. Increasing the digestibility index of grasses has therefore been a major breeding objective for several decades but progress has been slow due to difficulties in fixing natural variation in the synthetic varieties derived from these outbreeding species (Hayward, et al., *TAG* 70:48 (1985)).

Removing labile phenolics by chemical treatment with alkali is known to increase the biodegradability and nutritional value of low-quality feed such as cereal straw, and is employed commercially for feed upgrading. Reducing phenolic cross-linking of cell wall carbohydrates is therefore a predictable way of improving the rate of digestion and digestibility of ryegrass. However chemical modification may have other disadvantages. Therefore, genetic modification would be a preferable method of changing the cell wall chemistry of highly digestible varieties. Many in the field are pursuing this approach. An alternative, however, is to use genetic modification to reduce the levels of phenolic acids in the cell walls available for crosslinking either by directly disrupting ester bonds linking phenolics and lignins to cell wall polysaccharides or by preventing excessive ferulation of cell wall carbohydrates prior to their incorporation into the cell wall.

This invention meets this and other needs by using targeted or inducible expression of cell wall degrading enzymes in plants.

SUMMARY OF THE INVENTION

Provided herein are methods for enhancing the availability of fermentable carbohydrates. In one aspect, there is provided an expression cassette comprising a DNA sequence encoding at least one cell wall degrading enzyme. The DNA sequence encoding at least one cell wall degrading enzyme may be operatively linked to a promoter sequence. The promoter may be constitutive or inducible. The expression cassette may further comprise a targeting sequence.

In one embodiment, the cell wall degrading enzyme is selected from the group consisting of ferulic acid esterase, xylanase, xylosidase, cellulase, endoglucanase, and cellbiohydrolase. In a preferred embodiment cell wall degrading enzyme is derived from a fungal source. In a more preferred embodiment, the fungal ferulic acid esterase is an *Aspergillus* ferulic acid esterase, preferably *A. niger*. In another embodiment the xylanase is derived from *Trichoderma*, preferably *T. reesei.*

In another aspect of the invention, there is provided a plant transformed with the expression cassette comprising a DNA sequence encoding at least one cell degrading enzyme. The plant may be selected from the group consisting of *Festuca, Lolium, Avena* and *Zea*. In a preferred embodiment the plant is a forage grass. In another embodiment, the plant is maize.

Further provided herein is a method of controlling the level of phenolic acids in plant cell walls of a transgenic plant. The method, in one embodiment, comprises introducing to a plant cell an expression cassette comprising a DNA sequence encoding at least one cell wall degrading enzyme, preferably a ferulic acid esterase.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1 illustrates a restriction map of a DNA fragment containing the gene encoding the 38 kd ferulic acid esterase.

FIGS. 2A–E illustrate the complete DNA (SEQ. ID NO:1), with highlighting to point out the signal sequence, intron and various restriction endonuclease sites, and amino acid sequence (SEQ. ID. NO:2) corresponding to the gene encoding the 38 kD ferulic acid esterase isolated from *Aspergillus niger.*

FIG. 3 illustrates the DNA sequence of the gene encoding the 38 kD esterase (SEQ. ID. NO:1).

FIG. 4 illustrates the construction of the intronless ferulic acid esterase isolated from *Aspergillus niger.*

FIG. 5 illustrates that the overlapping of PCR products made with primers FAE-15 (SEQ ID NO:49) and FAE-13 (SEQ ID NO:50) creates two possible uninterrupted reading frames—the top in the figure below is functional (SEQ ID NO:3) (highlighted serine is at active site), the bottom is inactivated (SEQ ID NO:4).

FIG. 6 illustrates the possible vector constructions useful in the present invention. Various combinations are possible. Although and FAE gene is depicted another cell wall degrading enzyme may be used alone (i.e., instead of) or in conjunction with the FAE gene. Amp=ampicillin resistance gene.

FIG. 7 illustrates pCOR105.

FIG. 8 illustrates a generic ALE-TER vector.

FIG. 9 illustrates the KDEL-COOH ER retention sequences (SEQ ID NO:6).

FIG. 10 illustrates the FAE-LINKER-FRAMESHIFT structure and sequence (SEQ ID NO:7 and 8).

FIG. 11 illustrates plant transformation cassettes.

FIG. 12 is a table of the vectors used herein.

FIG. 13 depicts the barley aleurain vacuolar and apoplast signal sequence (SEQ ID NO:9 and 10).

FIG. 14 illustrates the rat sialyl transferase structure and sequence (SEQ ID NO:11 and 12).

FIG. 15 illustrates the potato protease inhibitor II (PPI) motif structure and sequence (SEQ ID NO:13 and 14).

FIG. 16 illustrates the targeted expression of gfp to different cell compartment. Also shown are schematics of the vectors used.

FIG. 17 illustrates the FAE activity in transgenic *Festuca arundinacea* leaves of different ages under ER and APO targeting sequences.

FIG. 18 illustrates the FAE activity in transgenic *Festuca arundinacea* leaves of different ages under Vac targeting sequence.

FIG. 19 illustrates the FAE activity in transgenic *Lolium mutflorum* leaves of different ages.

FIG. 20 illustrates the FAE activity in transgenic *Lolium mutflorum* leaves under Vac, ER and APO targeting sequences.

FIG. 21 illustrates the levels of esterified monomeric and dimeric hydroxycinnamic acids in *Festuca arundinacea* plants expressing FAE under Vac targeting sequence.

FIG. 22 illustrates the levels of esterified monomeric and dimeric hydroxycinnamic acids in *Festuca arundinacea* plants expressing FAE under APO and ER targeting sequence.

FIG. 23 illustrates the in vitro dry matter digestibility of leaf tissue of mature *Festuca arundinacea* plants expressing FAE under an actin promoter.

FIG. 24 illustrates the in vitro dry matter digestibility of leaf tissue of mature *Lolium mutflorum* plants expressing FAE under an actin promoter.

FIG. 25 illustrates the rate of fermentation and cumulative gas production in *Festuca arundinacea* cells.

FIG. 26 illustrates the in vitro fermentation of *Festuca arundinacea* cell walls from cell cultures expressing recombinant FAE1.

FIG. 27 illustrates the Time to maximum rate digestion for *Festuca arundinacea* cells.

FIG. 28 illustrates the total gas production in *Festuca arundinacea* cells.

FIG. 29 illustrates the kinetics of FAE activity by ferulic acid release from cell wall under self digestion in *Festuca arundinacea* and stimulation by xylanase.

FIG. 30 illustrates the beta-glucoronidase activity under the *Lolium* See1 senescence promoter in leaves of transgenic plants of *Lolium mutflorum.*

FIG. 31 illustrates the release of monomeric and dimeric HCAs on self digestion of leaves of vacuolar targeted FAE expressing plants.

FIG. 32A is a schematic of the pTP10-1 vector. Also shown in figures 32B–32D is the 5338 bp nucleotide sequence of the vector (SEQ ID NO:15).

FIG. 33A is a schematic of the pUA4-4 vector. Also shown in FIGS. 33B–33C is the 5345 bp nucleotide sequence of the vector (SEQ ID NO:17).

FIG. 34A is a schematic of the pTU4 vector. Also shown in FIGS. 34B–34C is the 5337 bp nucleotide sequence of the vector (SEQ ID NO:19).

FIG. 35A is a schematic of the pTT5.14 vector. Also shown in FIGS. 35B–35C is the 5395 bp nucleotide sequence of the vector (SEQ ID NO:21).

FIG. 36A is a schematic of the pTP8-5 vector. Also shown in FIGS. 36B–36C is the 5337 bp nucleotide sequence of the vector (SEQ ID NO:23).

FIG. 37A is a schematic of the pTP5-1 vector. Also shown in FIGS. 37B–37C is the 5277 bp nucleotide sequence of the vector (SEQ ID NO:25).

FIG. 38A is a schematic of the pTP4a2 vector. Also shown in FIGS. 38B–38C is the 5327 bp nucleotide sequence of the vector (SEQ ID NO:27).

FIG. 39A is a schematic of the pTP3-1 vector. Also shown in FIGS. 39B–39D is the 5338 bp nucleotide sequence of the vector (SEQ ID NO:29).

FIG. 40A is a schematic of the pTU5 vector. Also shown in FIGS. 40B–40H is the 5337 bp nucleotide sequence of the vector (SEQ ID NO:31).

FIG. 41A is a schematic of the pGT6 vector. Also shown in FIGS. 41B–41H is the 4773 bp nucleotide sequence of the vector (SEQ ID NO:32).

FIG. 42A is a schematic of the pJQ5 vector. Also shown in FIGS. 42B–42I is the 5034 bp nucleotide sequence of the vector (SEQ ID NO:33).

FIG. 43A is a schematic of the pJO6.1 vector. Also shown in FIGS. 43B–43I is the 4950 bp nucleotide sequence of the vector (SEQ ID NO:34).

FIG. 44A is a schematic of the pJQ4 vector. Also shown in FIGS. 44B–44I is the 4974 bp nucleotide sequence of the vector (SEQ ID NO:35).

FIG. 45A is a schematic of the pPQ10.1 vector. Also shown in FIGS. 45B–45H is the 5164 bp nucleotide sequence of the vector (SEQ ID NO:36).

FIG. 46A is a schematic of the pJQ3 vector. Also shown in FIGS. 46B–46I is the 4965 bp nucleotide sequence of the vector (SEQ ID NO:37.

FIG. 47A is a schematic of the pUG4 vector. Also shown in FIGS. 47B–47C is the 5295 bp nucleotide sequence of the vector (SEQ ID NO:38).

FIG. 48A is a schematic of the pUB8.11 vector. Also shown in FIGS. 48B–48I is the 5001 bp nucleotide sequence of the vector (SEQ ID NO:40).

FIG. 49A is a schematic of the pTP11-1 vector. Also shown in FIGS. 49B–49C is the 5387 bp nucleotide sequence of the vector (SEQ ID NO:41).

FIGS. 50A–B illustrate[s] the actin promoter and its corresponding nucleotide sequence (SEQ ID NQ:43).

FIG. 51 illustrates the Aleurain-NPIR delete structure. The corresponding nucleotide sequences are also shown (SEQ ID NO:45).

FIG. 52 illustrates the SEE1 (senescence enhanced) promoter sequence (SEQ ID NO:46).

FIG. 53 illustrates the SEE1 (senescence enhanced) promoter sequence plus the vacuolar aleurain signal/NPIR sequence (SEQ ID NO:47 and 48).

DETAILED DESCRIPTION OF THE INVENTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., Dictionary of Microbiology and Molecular Biology, 2d Ed., John Wiley and Sons, New York (1994), and Hale & Marham, The Harper Collins Dictionary of Biology, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

Definitions

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

"Conservatively modified variants" applies to both amino acid sequences and polynucleotides. With respect to particular polynucleotides, conservatively modified variants refers to those polynucleotides that encode identical or essentially identical amino acid sequences, or where the polynucleotide does not encode an amino acid sequence, to essentially identical sequences. Because of the degeneracy of the genetic code, a large number of functionally identical polynucleotides encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every polynucleotide herein which encodes a polypeptide also describes every possible silent variation of the nucleic acid. One of skill will recognize that each codon in a polynucleotide (except AUG, which is ordinarily the only codon for methionine) can be modified to yield a functionally identical molecule. Accordingly, each silent variation of a polynucleotide which encodes a polypeptide is implicit in each described sequence. For purposes of protein expression, there are "sub-optimal codons." These are codons that are not preferred by a particular genus or species. Altering these "sub-optimal codons" to "preferred codons" is a silent mutation in that the amino acid encoded by the codons is the same but one codon is preferentially expressed by the particular genus, e.g., *Triticum* spp.

As to amino acid sequences, one of skill will recognize that individual substitutions, deletions or additions to a polynucleotide, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W). (see, e.g., Creighton, *Proteins* (1984)).

"Pyroglutamic acid" is the cyclized internal amide of L-glutamic acid.

The phrase "controlling the level of phenolic acids" refers to the manipulation of phenolic acid expression in plants, particularly plant cell walls. The manipulation can be either positive; e.g., increasing the levels of phenolic acids; negative, e.g., decreasing the level of phenolic acids; or neutral, e.g., changing the relative amounts of specific phenolic acids in the cell walls but keeping the total amount relatively the same. The timing of manipulation can be during plant growth or after plant growth, e.g., after a plant has been cut or pulled from the ground or ingested. "Plant cell walls" refers to the cell walls of any cell of the plant.

The term "derived" means that a polynucleotide or protein is related to another polynucleotide or protein. The relations can be one of homology, e.g., nucleotides and proteins from certain species are homologous to similar polynucleotides and proteins of other species; analogy, e.g., proteins perform the same function and therefore are related to each other regardless of organism of origin. The relationship can be a man-made one, e.g., a protein (and a polynucleotide) can be derived from another protein by mutation; or chemical manipulation (peptidomimetics). Furthermore, a protein or a polynucleotide can be derived from an organism if, in the natural state, the protein or polynucleotide is found in one organism but recombinantly produced in another.

The term "exogenous polynucleotide" refers to a polynucleotide which is introduced into the plant by any means other than a sexual cross or sexual reproduction. Examples of means by which this can be accomplished are described below, and include *Agrobacterium*-mediated transformation, biolistic methods, electroporation, in planta techniques, and the like. Such a plant containing the exogenous polynucleotide is referred to here as an $R_1$ generation transgenic plant. Transgenic plants which arise from sexual cross or by selfing are progeny of such a plant.

The term "isolated polynucleotide molecule" or "isolated protein" refers to a polynucleotide or protein which is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated FAE1 gene is separated from open reading frames which flank the gene and encode a protein other than FAE1.

A "FAE1 encoding polynucleotide" is a nucleic acid sequence comprising (or consisting of) a coding region of an FAE 1 gene or which encodes a FAE1 polypeptide. FAE1 polynucleotides can also be identified by their ability to hybridize under low stringency conditions (see below) to nucleic acid probes having a sequence of 8 to 300 bases, preferably a sequence of 80 to 100 bases in the sequence disclosed in WO 98/14594.

The term "nucleic acid encoding," "nucleic acid sequence encoding" or "polynucleotide encoding" refers to a polynucleotide which directs the expression of a specific protein or peptide. The polynucleotides include both the DNA strand sequence that is transcribed into RNA and the RNA sequence that is translated into protein. The polynucleotides include both full length polynucleotides as well as shorter sequences derived from the full length sequences. It is understood that a particular polynucleotide includes the degenerate codons of the native sequence or sequences which may be introduced to provide codon preference in a specific host cell. The polynucleotide includes both the sense and antisense strands as either individual single strands or in the duplex form.

The term "operably linked" refers to functional linkage between a promoter and a second sequence, wherein the promoter sequence initiates transcription of RNA corresponding to the second sequence.

The term "plasmid" refers to a circular double stranded DNA molecule which comprises the coding sequence of interest, regulatory elements, a selection marker and optionally an amplification marker. A plasmid can transform prokaryotic cells or transfect eukaryotic cells. An "expression cassette" means a portion of a plasmid (or the entire plasmid) containing the regulatory elements desired for transcription, translation and/or expression and the coding region of a polynucleotide. A plasmid may contain one or more expression cassettes. If multiple expression cassettes are introduced into a plant, they can be introduced simultaneously or at different times. If simultaneous introduction is desired, the expression cassettes can be on one plasmid or more. Typically, an expression cassette comprises a promoter, poly A+ tail, and signal sequences that target the expressed polypeptide to a specific region of a cell or to be secreted, if desired. Examples of signal sequences that "target expression" of ferulic acid esterase include sequences located upstream of the FAE coding sequence. The polynucleotide that encodes the signal sequence is found preferably within the 100 nucleotides "upstream" (in the 5' direction) from the initiation codon (AUG). More preferably, the polynucleotide that encodes the signal sequence is found within the 50 nucleotides upstream from the initiation codon. Many different cellular organelles are targeted by the signal sequences used in this invention. The organelles include, but are not limited to, vacuoles, Golgi apparati, endoplasmic reticula, and apoplasts. In addition to upstream signal sequences, the expression cassette of this invention may include a polynucleotide that encodes a signal sequence at the 3' end. These signal sequences include, but are not limted to stop codons and the KDEL sequence. In addition to KDEL, other similar sequences are contemplated by this invention, including but not limited to RDEL. In addition to a KDEL sequence, a signal sequence can include a linker to a KDEL sequence. A linker is an extension of the reading frame of the encoding polynucleotide to the signal sequence. Preferably, the polynucleotide encoding the signal sequence is directly downstream from the coding sequence, more preferably less than 100 base pairs from the stop codon, more preferably less than 20 base pairs from the stop codon.

The term "polynucleotide," "polynucleotide" or "nucleic acid sequence" refers to deoxyribonucleotides or ribonucleotides and polymers thereof in either single- or double-stranded form. Unless specifically limited, the term encompasses polynucleotides containing known analogues of natural nucleotides which have similar binding properties as the reference polynucleotide and are metabolized in a manner similar to naturally occurring nucleotides. Unless otherwise indicated, a particular FAE1 polynucleotide of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8:91–98 (1994)). The term polynucleotide is used interchangeably with gene, cDNA, and mRNA encoded by a gene.

The term "polypeptide," "peptide," and "protein" are used interchangeably and refer to amino acids connected by peptide bonds. Polypeptides can be entire proteins or portions thereof. For Example. a FAE1 polypeptide may refer to the entire FAE1 protein or fragments of the FAE1 protein. A "ferulic acid esterase with an altered glycosylation site" refers to a FAE protein wherein a mutation has changed the glycosylation pattern of the protein. Mutations that effect such changes are well known in the art and include, but are not limited to, amino acid substitutions, and mutations in the proteins of the Golgi apparatus and endoplasmic reticulum that effect glycosylation of proteins.

The term "promoter" refers to a polynucleotide that directs expression of a coding sequence. A promoter can be constitutive, i.e., relatively independent of the stage of differentiation of the cell in which it is contained or it can be inducible, i.e., induced be specific environmental factors, such as the length of the day, the temperature, etc. or a promoter can be tissue-specific, i.e., directing the expression of the coding sequence in cells of a certain tissue type. A "senescence" promoter is an inducible promoter that causes transcription to be initiated upon a certain event relating to age of the organism. A "heat shock promoter" is an inducible promoter that causes transcription to be initiated upon a change in temperature. An example of a heat shock protein promoter is the Soybean Gmhsp promoter. In addition to these inducible promoters, one of skill will realize that other inducible promoters can be used. For example, a wound induced promoter, like LAP. See, U.S. Pat. No. 5,962,670.

The term "purified" denotes that a polynucleotide or protein gives rise to essentially one band in an electrophoretic gel. Particularly, it means that the polynucleotide or protein is at least 85% pure, more preferably at least 95% pure, and most preferably at least 99% pure.

The term "specifically hybridizes" refers to a nucleic acid probe that hybridizes, duplexes or binds to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., MOLECULAR CLONING: A LABORATORY MANUAL (2ND ED.), Vols. 1–3, Cold Spring Harbor Laboratory, (1989) ("Sambrook") or CURRENT PROTOCOLS IN MOLECULAR BIOLOGY, F. Ausubel et al., ed. Greene Publishing and Wiley-Interscience, New York (1987) ("Ausubel").

The term "stringent conditions" in the context of polynucleotide hybridization experiments such as Southern and northern hybridizations refers to sequence dependent, binding and washing environments. An extensive guide to the hybridization of polynucleotides is found in Tijssen (1993) LABORATORY TECHNIQUES IN BIOCHEMISTRY AND MOLECULAR BIOLOGY—HYBRIDIZATION WITH NUCLEIC ACID PROBES part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary polynucleotides which have more than 100 complementary residues on a filter in a Southern or northern blot is 50% formalin with 1 mg of heparin at between 40 and 50° C., preferably 42° C., with the hybridization being carried out overnight. An example of highly stringent wash conditions is 0.15M NaCl at from 70 to 80° C. with 72° C. being preferable for about 15 minutes. An example of stringent wash conditions is a 0.2×SSC wash at about 60 to 70° C., preferably 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1×SSC at 40 to 50° C., preferably 45° C. for 15 minutes. An example low stringency wash for a duplex of, e.g., more than 100 nucleotides, is 4–6×SSC at 35 to 45° C., with 40° C. being preferable, for 15 minutes. In general, a signal to noise ratio of 2× (or higher) than that observed for an unrelated probe in the particular hybridization assay indicates detection of a specific hybridization. Polynucleotides which do not hybridize to each other under stringent conditions are still substantially identical if the polypeptides which they encode are substantially identical. This occurs, e.g., when a copy of a polynucleotide is created using the maximum codon degeneracy permitted by the genetic code.

The term "transgenic plant" refers to a plant into which exogenous polynucleotides have been introduced and their progeny. Typically, cells of a plant are transformed with the exogenous polynucleotide and a transgenic plant is regenerated from the transformed cells. The regenerated plant is then bred to produce a strain of transgenic plants.

"Xylanase" (EC 3.2.1.8) refers to a well described class of gylcosyl hydrolases that hydrolize xylan. Commercial applications of xylanase include the degradation and bleaching of wood pulp for paper making. Xylanase can also be added to animal feed to improve the digestibility of plant matter. Typically, commercial xylanase is derived from fungi. A preferred xylanase is derived from *Trichoderma.*

Preferred Embodiments

Plant cell walls contain a range of alkali-labile ester-linked phenolic acids. In particular, grass cell walls are characterized by the presence of large amounts of esterified ferulic and p-coumaric acids (mainly in their E configurations), linked to arabinoxylans at the C5 of arabinose. These are released as ferulated oligosaccharides (FAX and PAX) by cellulase treatment but in vivo provide a substrate for peroxidase-catalyzed cross-linking of cell wall polysaccharides and lignin. The high levels of these phenolic acids and their dimers have a dramatic influence on the mechanical properties, digestibility and rates of digestion of grasses by ruminants.

Previous work has shown that ferulic acid is the predominant p-hydroxycinnamic acid esterified to grass polysaccharide but until recently the only ferulic acid dehydrodimer to have been isolated was 5,5'-diferulic acid. Recently new dehydrodiferulate dimers and cyclobutane-type dimer mixtures have been isolated from plant cell walls (Waldron, et al., *Phytochemical Analysis* 7:305 (1996)). As can be seen in FIG. 1, these mixtures are present in large amounts in grass cells. Ether linked ferulic acid-coniferyl alcohol dimers, have also been isolated from cell walls (Jacquet, et al., *Polyphenol Comm. Bordeaux* pp451 (1996)) establishing for the first time that ferulate esters are oxidatively copolymerized with lignin precursors which may anchor lignins to cell wall polysaccharides. The yield of these dimers in grass cells indicates that phenolic dehydrodimer cross-linking of cell wall polysaccharides is much more extensive than was previously thought.

An enzyme system has been reported from parsley endomembranes that catalyses the ferulation of endogenous polysaccharide acceptors from feruloyl CoA, pointing to the ER/golgi as the site of polysaccharide esterification and the CoA ester as the physiological co-substrate (Meyer, et al., *FEBS Lett.* 290:209 (1991)). Further evidence for this has been found in water-soluble extracellular polysaccharides excreted in large amounts into the medium by grass cell cultures. This material is highly esterified with ferulic and p-coumaric acid at levels similar to the cell walls of the cultured cells.

Feruloyl esterase activity has been detected in several fungal species including, anaerobic gut fungi, yeasts, actinomycetes, and a few fiber-degrading ruminal bacteria, which enables them to de-esterify arabinoxylans and pectins.

Two ferulic acid esterases (FAE), distinguished on the basis of molecular weight and substrate specificity, have been isolated from *Aspergillus niger* and have been shown to quantitatively hydrolyze ferulic acid and release dehydrodiferulate dimers from plant cell walls. Furthermore, FAE has been observed to act synergistically with xylanase to release ferulic acid from plant cell walls at a higher rate. Recently, a ferulic acid esterase (FAE) gene has been cloned from *Aspergillus niger* (Michelson, et. al. European Patent Application No. 9510370.1). The inventors have found the recombinant enzyme releases ferulic acid and diferulate dimers from grass cell walls in a concentration dependent manner and that this enzyme is stable at 30° C. pH 5.0 in the presence of substrate and has a half life of 61 h at 30° C. in the presence of vacuolar extracts (pH 4.6) of grass cells. This gene was, therefore, a candidate for targeted and indicible expression of FAE in grasses (e.g., *Lolium multiflorum*).

The present invention provides for methods of changing the cell wall structure of transgenic plants and therefore, making them more digestible. The method comprises introducing a ferulic acid esterase coding sequence into the cells of a plant. Operably linked to the coding sequence is a promoter that can be either constitutive or inducible and signal sequences that serve to target expression of the coding sequence in the desired organelle in the desired cell of the plant. The signal sequences can be either or both N terminal or C terminal sequences.

Optionally, a second and/or third coding sequence is introduced into the plant. It is preferred that a fungal xylanase coding sequence be coexpressed with the FAE coding sequence.

This invention also provides for transgenic plants which contain FAE1 coding sequences, leading to more digestible grasses.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook, et al., MOLECULAR CLONING, A LABORATORY MANUAL, 2ND ED. (1989); Kriegler, GENE TRANSFER AND EXPRESSION: A LABORATORY MANUAL (1990); and Ausubel et al., (eds.), CURRENT PROTOCOLS IN MOLECULAR BIOLOGY (1994)).

A. Isolation of Polynucleotides

The isolation of the polynucleotides, e.g., FAE1 and xylanase of the invention may be accomplished by a number of techniques. See, for example, U.S. Pat. No. 6,368,833 which describes the isolation of a FAE from *Aspergilius niger* and U.S. Pat. No. 6,555,335 which describes the isolation of a xylanase from *T. reessi.*

For instance, oligonucleotide probes based on the sequences cited here can be used to identify the desired gene in a cDNA or genomic DNA library from a desired species. To construct genomic libraries, large segments of genomic DNA are generated by random fragmentation, e.g., using restriction endonucleases, and are ligated with vector DNA to form concatemers that can be packaged into the appropriate vector. To prepare a library of cDNA from a specific cell culture, e.g., *Aspergillus niger*, mRNA is isolated from the culture and a cDNA library containing the gene transcripts is prepared from the mRNA.

The cDNA or genomic library can then be screened using a probe based upon the sequence of a known polynucleotide such as the polynucleotides cited here. Probes may be used to hybridize with genomic DNA or cDNA sequences to isolate homologous genes in the same or different plant species. In addition to probes derived from known polynucleotides, degenerate probes may be used. Techniques for making and using degenerate probes are well known in the art and can be found in Sambrook and Ausubel.

Alternatively, the polynucleotides of interest can be amplified from polynucleotide samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone polynucleotides that code for proteins to be expressed, to make polynucleotides to use as probes for detecting the presence of the desired mRNA in samples, for polynucleotide sequencing, or for other purposes.

Appropriate primers and probes for identifying ferulic acid esterase-specific genes, as well as xylanase sequences, from fungi and plant tissues are generated from comparisons of the sequences provided herein. For a general overview of PCR see PCR PROTOCOLS: A GUIDE TO METHODS AND APPLICATIONS, (Innis, M, Gelfand, D., Sninsky, J. and White, T., eds.), Academic Press, San Diego (1990). Reaction components are typically: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per mL Taq polymerase. Program: 96° C. for 3 min., 30 cycles of 96° C. for 45 sec., 50° C. for 60 sec., 72° C. for 60 sec, followed by 72° C. for 5 min.

Polynucleotides may also be synthesized by well-known techniques as described in the technical literature. See, e.g., Carruthers, et al., *Cold Spring Harbor Symp. Quant. Biol.* 47:411–418 (1982), and Adams, et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Suitable sources for the ferulic acid esterase used in this invention include but are not limited to, *Neurospora crassa, Aspergillus* spp. and specifically, *Aspergillus niger*. The xylanase used in this invention can be derived from any suitable source including, but not limited to, *Trichoderma reesei* and *Aspergillus* spp.

B. Preparation of Recombinant Vectors

To use isolated sequences in the above techniques, recombinant DNA vectors suitable for transformation of plant cells are prepared. Techniques for transforming a wide variety of plant species are well known and described in the technical and scientific literature. See, for example, Weising, et al., *Ann. Rev. Genet.* 22:421–477 (1988). A DNA sequence coding for the desired polypeptide, for example a cDNA sequence encoding the full length FAE1 protein, will preferably be combined with transcriptional and translational initiation and targeting regulatory sequences which will direct the transcription of the sequence from the gene in the intended tissues of the transformed plant under the desired conditions.

Promoters can be identified by analyzing the 5' sequences of a desired gene. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. Messing, et al., in GENETIC ENGINEERING IN PLANTS, pp. 221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell* 1:855–866 (1989); Bustos, et al., *Plant Cell* 1:839–854 (1989); Green, et al., *EMBO J.* 7:4035–4044 (1988); Meier, et al., *Plant Cell* 3:309–316 (1991); and Zhang, et al., *Plant Physiology* 110:1069–1079 (1996)).

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, the actin and ubiquitin promoters and other transcription initiation regions from various plant genes known to those of skill. A particularly preferred constitutive promoter is the rice actin promoter (see, McElroy, *Plant Cell,* 2:163 (1990)).

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as leaves, roots or seeds.

In one aspect of the instant invention, expression of FAE occurs after the the plant has been cut, removed from the ground or ingested. Thus an appropriate promoter would be a senescence promoter. For example, BFN1 has recently been shown to be a nuclease expressed in senescing leaves, Perez-Amador, et al., *Plant Physiol.* 122:169 (2000). Similarly, SAG12, a cysteine protease is also found in senescing leaves (Noh & Amasino, *Plant Mol. Biol.* 41:181 (1999). In a preferred embodiment, the promoter from the gem gene of *Festuca pratensis* is used to direct expression of FAE in senescing leaves.

In another aspect, the FAE would be expressed upon ingestion by a foraging animal. Exemplary promoters for this aspect would include Soybean Gmhsp 17.5 promoter and the leucine aminopeptidase (LAP) promoter. The GMhsp promoter is from a heat shock protein gene and initiates expression if the temperature of the environment is increased. In the laboratory, an increase of 15° C. for 2 hours is the preferred heat shock. However, in non-laboratory conditions suitable increases in temperature will occur in silos and in the rumen of animals that have ingested the plants of this invention. The LAP promoter initiates the expression of the FAE gene upon wounding of the plant. Such wounding would occur after cutting the plant or after mastication by a foraging animal. Tissue specific promoters that could be used in this invention include promoters of genes that are differentially expressed in the leaves of grasses. An example of a leaf specific promoter is the rbcs promoter of tomato (*Proc. Nat'l Acad. Sci. USA* 84:7104 (1987)). This promoter normally regulates a gene determined to be important in photosynthesis.

For proper polypeptide expression, a polyadenylation region at the 3'-end of the coding region should be included. The polyadenylation region can be derived from the natural fungal gene, from a variety of other fungal or plant genes, or from T-DNA. These sequences are well known and readily available to those of skill in the art.

In addition to a promoter and poly A+ sequences, the preferred expression vectors of this invention also will contain signal sequences. These are polynucleotides found at the 5' and/or 3' ends of the coding region and serve to target expression of the gene to specific cellular organelles. These signal sequences can be both upstream or downstream of the coding region. Some preferred examples of upstream signal sequences include the barley aleurain sequence (Rogers, *Proc. Nat'l Acad. Sci. USA* 82:6512 (1985) which targets vacuoles and the *Aspergillusapoplast signal. This signal sequence targets expression to the apoplast.*

In addition to targeting expression to specific organelles, it may be desirable to retain the expressed FAE in the Golgi or endoplasmic reticulum. The well known ER retention signal, KDEL (SEQ ID NO:97), can be added to the 3' end of the coding polynucleotide.

The vector comprising the expression cassettes (e.g., promoters and/or coding regions) of the invention will typically comprise a marker gene which confers a selectable phenotype on plant cells. For example, the marker may encode biocide resistance, particularly antibiotic resistance, such as resistance to hygromycin, kanamycin, G418, bleomycin, or herbicide resistance, such as resistance to chlorosluforon or Basta.

C. Production of Transgenic Plants

DNA constructs of the invention may be introduced into the genome of the desired plant host by a variety of conventional techniques. For example, the DNA construct can be introduced directly to plant tissue using ballistic methods, such as DNA particle bombardment or the constructs may be introduced directly into the genomic DNA of the plant cell using techniques such as electroporation and microinjection of plant cell protoplasts. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

See Dalton et al. (Co-transformed, diploid *Lolium perenne* (Perennial Ryegrass), *Lolium multiflorum* (Italian Ryegrass) and *Lolium temulentum* (Darnel) plants produced by microprojectile bombardment. Plant Cell Reports (1999) 18(9), 721–726) for exemplary methods for culturing and transformation of grasses.

Microinjection techniques are known in the art and well described in the scientific and patent literature. The introduction of DNA constructs using polyethylene glycol precipitation is described in Paszkowski, et al., *Embo J.* 3:2717–2722 (1984). Electroporation techniques are described in Fromm, et al., *Proc. Natl. Acad. Sci. USA* 82:5824 (1985).

*Agrobacterium tumefaciens*-mediated transformation techniques, including disarming and use of binary vectors, are well described in the scientific literature. See, for example Horsch, et al., *Science* 233:496–498 (1984), and Fraley, et al., *Proc. Nat'l. Acad. Sci. USA* 80:4803 (1983). U.S. Pat. No. 5,591,616 discloses *Agrobacterium* mediated transformation techniques in monocotyledons.

Ballistic transformation techniques are described in Klein, et al., *Nature* 327:70–73 (1987). In a preferred embodiment, a particle in-flow gun (PIG) is used to transform the plant cells of this invention.

Transformed plant cells which are derived by any of the above transformation techniques can be cultured to regenerate a whole plant that possesses the transformed genotype and thus the desired phenotype such as improved digestibility. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., PROTOPLASTS ISOLATION AND CULTURE, HANDBOOK OF PLANT CELL CULTURE, pp. 124–176, Macmillian Publishing Company, New York, 1983; and Binding, *Regeneration of Plants, Plantprotoplasts*, pp. 21–73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467–486 (1987).

To determine the presence of or increase of FAE1 activity, an enzymatic assay can be used or an assay to measure increases and decreases in rates of fermentation. These assays are readily available in the literature and those of skill in the art can readily find them.

One of skill will recognize that other assays can be used to detect the presence or absence of FAE1. These assays include but are not limited to; immunoassays and electrophoretic detection assays (either with staining or western blotting).

The polynucleotides of the invention can be used to confer desired traits on essentially any plant. However, the main utility of this invention is in the improved digestibility of forage plants. Thus, it is envisioned the transgenic plants of this invention will include but not be limited to the following genera *Lolium, Festuca, Triticum, Avena*, and *Medicago*. The FAE1 genes of the invention are particularly useful in the production of transgenic plants in the genus *Lolium.*

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

As mentioned above, the transgenic plants of this invention can be used as a foraging crop for animals, such as cattle, sheep, goats and horses. In addition, the methods of this invention can be used to transform any plant into which FAE expression is desired. For example, it is advantageous to break down cell walls during biomass conversion or during processing of plants for foodstuffs. This invention would help to achieve this goal more effectively and inexpensively.

The inventive methods herein may also be used to provide additional enzymes to enhance the availability of fermentable sugars in plants. Plant carbohydrates may be subject to further modification, either exogenously or endogenously, by the action of other enzymes. Such enzymes include, but are not limited to, endoglucanases, xylosidases and/or cellbiohydrolases. These enzymes may be provided either in an expression cassette provided for herein (i.e., endogenous) or applied to the plant cell walls (i.e., exogenous) to enhance the availability of mono- and/or di-saccharides.

Plants other than grasses may find a use in the present invention. For example, corn (or maize) is specifically contemplated to be useful. The grass *Festuca* is similar to maize in cell wall structure and therefore provides a good model of the ability to enhance fermentable carbohydrates in corn. Other useful plants contemplated for use in the present invention are *Festuca, Lolium, Zea, Avena, Sorghum, Millet* (tropical cereals), *Miscanthus* (a grass with potential for use as a biomass energy crop), *Cenchrus, Dichanthium, Brachiaria* and *Paspalum* (apomictic tropical range grasses) and *Poa* (Kentucky bluegrass).

Cell walls of forage grasses makes up 30–80% of forage dray matter representing a major source of energy for ruminants, but less than 50% of this fraction is digested by the animal. Conversion of low-value biomass to sugars and ethanol is also less than optimal due to the carbohydrate unavailability of the feedstocks, including but not limited to bagasse, race straw, corn stover and corn fiber.

Ferulic and other hydroxycinnamic acids are ester linked to arabinosyl residues in arabinoxylans, and play a key role in crosslinking xylans to liginin, resulting in less degradable cell walls. Ferulic acid esterase (FAE) can release both monomeric and dimeric ferulic acid (FA) from arabinoxylans making the cell wall more susceptible to further enzymatic attack. Transgenic plants have been produced expressing an FAE gene following microprojectile bombardment of cell cultures. Measurements of the level of FAE activity from different vectors targeting FAE to the vacuole, ER and apoplast under constitutive or inducible (heat shock) promoters shows that at least for constitutive expression of vacuolar targeted FAE, the activity was highest in young leaves and increased along the leaf lamina. We also show that FAE expression results in release of monomeric and dimeric FA from cell walls on cell death and this was enhanced several fold by the addition of xylanase. An effect of FAE expression on the monomeric and dimeric cell wall ester linked ferulate content in comparison to control (non-transformed) plants is seen. Generally, the lower the levels of monomers and, in particular, dimers of hydroxycinnamic acids in leaves, the higher the digestibility and/or availability of complex carbohydrates for conversion.

Senescence is the terminal phase in leaf development and occurs without grouth or morphogenesis Therefore the metabolism/physiology of this stage of the leaf's lifespan can be targeted directly for alteration with minimal detrimental impact on early development. Senescence follows leaf maturity and is associated with the expression of specific genes. These genes and their controlling elements can be exploited to manipulate development, adaptation, productivity and quality traits in crop plants. There seems to be good conservation of senescence physiology across the range of higher plant species and thus these promoters are useful in the present invention.

The following preparations and examples are given to enable those skilled in the art to more clearly understand and practice the present invention. They should not be considered as limiting the scope and/or spirit of the invention, but merely as being illustrative and representative thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); Ci (Curies) mCi (milliCuries); μCi (microCuries); TLC (thin layer achromatography); Et (ethyl), Me (methyl).

EXAMPLE 1

Preparation of Enzyme Encoding DNA Sequences

A genomic clone for FAE1 (see FIGS. 1–3, SEQ ID NO:1 and 2) was used as the starting point for the preparation of an intronless FAE1 encoding DNA sequence. The sequence for the genomic clone is given in FIGS. 2 and 3 (SEQ ID NO:1 and 2). Separate fragments for both FAE exons were recovered by PCR from a 5.5kb EcoRI fragment of the genomic clone in pLITMUS28, and 'cDNA' created by overlapping PCR. See FIG. 4.

Two 5' primers were used. FAE-S5 which amplifies the entire reading frame (including the *Aspergillus* signal), and FAE-N5 which amplifies only the mature protein (i.e. has no signal). A number of codons are optimized (underlined in primer sequences below). The overlap product may be derived from either FAE-I5 (wild type, SEQ ID NO:49) or FAE-I3 (conserved Ser changed to Ala, SEQ ID NO:50) primers, allowing production of enzymatically inactive protein to check toxicity. As shown in FIG. 5, overlapping of PCR products made with FAE-I5 and FAE-I3 creates two possible uninterrupted reading frames (SEQ ID NO:3 and 4). If the complement to FAE-I5 serves as the template when recombined then the encoded protein retains the serine moiety and the esterase is functional (highlighted serine is at active site, SEQ ID NO:95). If the FAE-I3 primer serves as the template the serine is replaced with an alanine and the esterase is inactivated (highlighted alanine in bottom amino acid sequence given in FIG. 5, SEQ ID NO:96).

Where possible, codon usage has been optimized in constructed reading frames (codon choice based on published barley preferences).

```
FAE-15 (SEQ ID NO: 49)
GGCGCCGAGGGAGTGGCCGGTCACGGTCAGCGCGTAGTCC 40-mer

FAE-13 (SEQ ID NO: 50)
CCGGCCACGCCCTCGGCGCCTCCCTGGCGGCACTC 35-mer

FAE-N5 (SEQ ID NO: 51)
CTAAAGCTTACCATGGCGGCCGCCTCCACGCAGGGCATCTCCGA 44-mer

FAE-S5 (SEQ ID NO: 83)
CTAAAGCTTAACATGAAGCAGTTCTCCGCCAA 32-mer

FAE-3 (SEQ ID NO: 52)
TCTAAGCTTGCGGCCGCGACCGGCCAGGTGCATGCGCCGCTCGTCATCCC
```

EXAMPLE 2

Preparation of Vectors

Vectors had the general structure shown in FIG. 6.

A. Plant Transformation Vector Series

Initial expression vectors were based on pCOR105 [rice actin promoter—McElroy et al. MGG 231:150–160 (1991)] (FIG. 7). pCOR105 NotI and SstII sites were first destroyed [cut with NotI and SstI, followed by heat inactivation and T4 DNA polymerase treatment in the presence of dNTPs] using standard methods as described in Maniatis et al. or following the manufacturer's instructions for enzymes to simplify subsequent Not cassette manipulation and allow use of unique Sst site (see below).

The nos terminator from pMA406 (Ainley & Key (1990) PMB 14:949–60) was amplified by POR using primers TER5 and TER3 to generate a fragment with the following sequence (SEQ ID NO:53):

```
         (Pst1)        (Not 1)
(AGACTGCAGACCATGGCGGCCGCGKAACCACTGAAGGATGAGCTGTAAG

AAGCAGATCGTTCAAACATTTGGCAATAAAGTTTCTTAAGATTGAATCCTGTT

GCCGGTCTTGCGATGATTATCATATAATTTCTGTTGAATTACGTTAAGCATGT

AATAATTAACATGTAATGCATGACGTTATTTATGAGATGGGTTTTTATGATTA

GAGTCCCGCAATTATACATTTAATACGCGATAGAAAACAAAATATAGCGCGC

AAACTAGGATAAATTATCGCGCGCGGTGTCATCTATGTTACTAGATCGATA

AGCTT CTA GATCT (where K=G or T)
(HindIII) (XbaI)
```

A redundancy in the TER5 primer (GCGKAA) creates fragments having either a stop codon (TAA) or glutamate codon (GAA) in one reading frame. The glutamate codon is in frame with a downstream KDEL motif.

The fragment and modified pCOR105 vector were cut with PstI and XbaI, according to manufacturers instructions, relevant fragments gel-purified, ligated with T4 DNA ligase and transformed into *E. coli*. Resulting clones were then sequenced to establish which TER5 alternatives were present.

Initial FAE expression vectors were then constructed from these vectors by inserting FAE-S5/FAE-3 PCR products (T4 DNA polymerase 'polished' in the presence of dNTPs, purified and digested with NotI, cloned into EcoRV and NotI digested vector) or FAE-N5/FAE-3 PCR products (purified and NotI digested, cloned into NotI digested and calf intestinal alkaline phosphatase treated vector).

The initial pCOR105-nos terminator clones were also modified by the addition of ALE-5/ALE-3 PCR products (encoding wild-type and modified barley aleurain signal peptides, see below for details). The products were 'polished' with T4 DNA polymerase in the presence of dNTPs, purified and cut with NotI, then cloned into EcoRV and NotI digested vectors. Addition of the ALE sequences creates a series of vectors which can express a reading frame inserted at the NotI or NcoI sites as a fusion to the barley aleurain signal, with or without vacuolar targetting motif, and with or without an ER retention motif. HindIII sites flanking the translation initiation codon and transcriptional terminator allow easy movement of transcription units between expression vectors providing different promoter sequences. (See FIG. 8 depicting the generic ALE-TER vector.)

Vector sequences were confirmed by sequencing. Two artifacts were found. Firstly, the redundant codon in TER5 was found to be AAA in one clone, which was subsequently used as the source of all KDEL fusions (ie peptide sequence is KPLKDEL (SEQ ID NO:85), rather than EPLKDEL (SEQ ID NO:86) as designed). See FIG. 9. Secondly, an additional base is found at the site of the redundant codon in one clone, creating a frameshifted terminal peptide (ETTEG, FIG. 10 SEQ ID NO:87) which was used as a control in some constructs.

Exploitation of the modular arrangement of signal peptides in the above vector series allowed various combinations of FAE and targeting motifs to be created using standard molecular biology procedures (i.e., restriction digest, purification of relevant fragments and ligation as appropriate). For example, the NotI fragment containing the FAE reading frame was inserted into the NotI site of the frameshifted clone described above to create vector pTP3.1. The native *Aspergillus* COOH-terminus was inserted into a FAE-S5/FAE-3 clone as a SphI (T4 DNA polymerase polished)—NcoI fragment from the FAE genomic clone (replacing the NotI (T4 DNA polymerase polished)—NcoI fragment), creating vector pTP4a2, which then encodes the entire, unmodified, *Aspergillus* FAE. Replacement of the SalI/XbaI fragment of pTP3.1 with that of pTP4a2 then created pTP11.1, which encodes FAE with a native *Aspergillus* COOH-terminus but a barley aleurain N-terminal signal.

Briefly, other vectors made in this series were; pTP8.5, the FAE NotI fragment inserted into the NotI site of an ALE-frameshifted COOH-terminus construct, aleurain N-terminus; pTP5.1, replacement of the native *Aspergillus* COOH terminus with a KDEL peptide (NotI/XbaI fragment exchange), *Aspergillus* N-terminal signal retained; pTU4.4, BamHI fragment of pTP11.1 replaces BamHI fragment of pTP5.1, creates FAE reading frame fused to heterologous N- and C-termini (aleurain signal and KDEL).

Vectors in which the aleurain vacuolar targeting motif NPIR was replaced by NPGR (found to be inactive in some plant assays) were created by replacing an EcoRV/NotI fragment with ALE PCR product which had been cut with AccI (T4 DNA polymerase polished) and NotI (vectors pTT5.5 and pTT5.14, *Aspergillus* COOH-terminus). The BamHI fragment of pTT5.5 was used to replace that of pTP5.1 to produce pTU5, creating an FAE reading frame fused to heterologous N- and C-termini (NPGR modification of aleurain signal and KDEL). The aleurain signal was also modified by PCR mutagenesis to remove the vacuolar targeting NPIR motif in its entirety (directed by primer ALECUT, which contains a NotI site to allow exchange of BglII/NotI fragments). NPIR deletion was created in this way in pTP11.1 (creating pUA4.4), and in pTP5.1 by exchange of BamHI fragments with pUA4.4 (creating pUG4).

Finally, PCR mutagenesis, using overlap of fragments generated by primers GLY3 and GLYB, was also used to alter a potential glycosylation site (asparagine codon changed to aspartate, as carried out for example in Chen, H. M., C. Ford & P. J. Reilly (1994) Biochem J 301 275–281 Substitution of asparagine residues in *Aspergillus awamori* glucoamylase by site-directed mutagenesis to eliminate N-glycosylation and inactivation by deamidation; see sequence data for exact change, vector pTP10.1).

PCR primers
TER-5 (SEQ ID NO:54)
AGACTGCAGACCATGGCGGCCGCGKAACCACTGAAGGATGAGCTGTAAAG
AAGCAGATCGTTCAAACATTTG 72-MER (The KDEL stop codon is underlined.)

TER-NOT (SEQ ID NO:55)
AAGACTGCAGACCATGGCGG 20-MER

TER-3 (SEQ ID NO:56)
AGATCTAGAAGCTTATCGATCTAGTAACATAGATGACACC

-continued

ALECUT (SEQ ID NO:57)
CTAGGCGGCCGCGCGGGAGGAGGCGACGGCGAC

GLYB (SEQ ID NO:58)
GAGGGTGTATTCGGTATCGAGTTGCAGGTTCGTATC

GLY3 (SEQ ID NO:59)
CTCGATAC<u>CC</u>ATTACACCCTCACGCCTTTCGA

B. Construction of Different Promoter Vectors

Various promoters were used to optimize expression and to establish constitutive, heat-shock inducibility and senescence enhancement.

i. Rice actin promoter and 1st intron

Initial vectors (FIGS. 11 and 12) were constructed from pCOR105 which was subsequently found to contain a 5bp deletion relative to the published sequence which destroys the AccI site (GTAG<u>GTAGA</u>C, SEQ ID NO:60, deleted bases underlined) and may affect splicing at the adjacent 3' site. The original rice actin sequence in this region (GTAGGTAG, SEQ ID NO:84) was therefore restored using oligonucleotide NCO-ACT (CTCACCATGGTAAGCTTCTACCTACAAAAAAGCTCCGCA, SEQ ID NO:61) by replacing the BglII/HindIII fragment with a PCR product, to produce vector pPQ10.1.

A rice repetitive element is present in the upstream region of the actin promoter used in pCOR105; as this may have unpredictable effects on vector expression it was removed from pPQ10.1 by deletion of the KpnI/EcoRI fragment (end-filled with T4 polymerase and ligated following digest, restoring EcoRI but not KpnI), to produce vector pGT6. The HindIII fragment containing the FAE reading frame and nos terminator of pTP3.1 (see Example 2A) was then inserted into pGT6 to produce construct pJO6.3.

ii. Soybean Heat-Shock Promoter

A soybean heat shock promoter from a 23 kD HSP was obtained from pMA406 (Ainley & Key (1990) PMB 14:949–60). This promoter when fused to β-glucuronidase (Jefferson et al 1987 EMBO J 6:3901–3907) had previously been shown to be inducible by a 10° C. heat-shock and show stable expression for 24–48 hours (data not shown). β-glucuronidase fusions are a sensitive and versatile fusion marker in higher plants. The construction of the co-integration HS vectors is given below.

iii. Senescence Enhanced Expression (See1) Promoter from *Lolium Multiflorum*

The promoter and signal sequence (including NPIR motif) of the LSee1 gene was amplified from *Lolium multiflorum* cv Tribune with oligonucleotides SEE-NCO and SEE-VAC, and cloned as an Asp718/NotI replacement of the promoter region of vector pTP11.1. Following sequencing to screen for PCR artifacts, one of three identical clones was chosen (pUB8.11).

The See1 promoter from maize has been cloned previously and has EMBL accession number is AX050343. See WO0070061.

The *Lolium* version of See1 was also cloned previously (Qiang Li (2000) Studies on leaf senescence and its genetic manipulation in *Lolium mutiflorum* PhD Thesis University of Wales, Aberystwyth) and has been shown to be senescence inducible when used to drive both β-glucuronidase and the Agrobacterium ipt gene.

An apoplast-targeted derivative was constructed by amplifying the Potato Protease Inhibitor (PPI) motif with primers PPI-AP6 and SEE-ATG, and cloning the product as an NgoMIV/NotI fragment into pUB8.11 (NgoMIV partial digest), to produce vector pJQ5.2. This vector has both the senescence induced promoter and the apoplast target sequence with the gene to be expressed inserted downstream of the apoplast sequence.

```
PCR Primers
SEE-VAC (SEQ ID NO: 62)
AACCATGGCGGCCGCGCGCTCGGTGACGGGCCGGAT

SEE-NCO (SEQ ID NO: 63)
TTCGGTACCATGGCCAGGTATAATTATGG

SEE-ATG (SEQ ID NO: 64)
CTGCGCCGGCGAGATGGMCGTGCACAAGGAG
```

C. Construction of Targeting Sequences

In order to examine whether or not the localization of the enzyme would have an effect on the phenolic acid content of the cell wall various signal sequences were utilized. The targeting sequences were added either to the N-terminus or to the C-terminus of the gene of interest.

i. N-terminal Signal Sequences

Six N-terminal signal sequences were utilized:

(a) The native *Aspergillus* end of FAE, plus excretion signal [apoplast localisation]

This is from the original clone and has the peptide sequence: MKQFSAKHVLAVVVTAGHAL<u>AASTQGI</u> (SEQ ID NO:88).

(b) The mature *Aspergillus* end, with no excretion signal [cytoplasmic localisation]

Peptide sequence is MA<u>AASTQGI</u> (SEQ ID NO:89) (underlined motif is common to all constructs). Truncation of the signal sequence in (a) above was carried out by PCR with mutagenic primer FAE-N5.

(c) The barley aleurain signal, including intact NPIR motif [vacuole localisation]

The barley aleurain vacuolar signal sequence (See FIG. 13; Swissprot database accession number P05167, SEQ ID NO:10) was derived entirely from overlapping primers (ALE-5, ALE-3, ALE-CUT ALE-CAP-5 and ALE CAP-3). Following primer annealing at 37° C. and extension with T4 DNA polymerase in the presence of dNTPs according to manufacturers instructions, PCR with flanking primers ALE-5 and ALE-3 was carried out. The product was 'polished' with T4 DNA polymerase, purified, digested with NotI and cloned into EcoRV/NotI digested pCOR105-nos terminator vector (see above). ALE-3 contains redundancies so that clones encoding NPIR or NPGR motifs may be recovered. Two versions of the signal, with and without the vacuole targeting motif, were produced, to give putative vacuolar NPIR and apoplast (NPGR) signal sequences.

```
PCR Primers
ALE-5 (SEQ ID NO: 65)
GGAATTCGTAGACAAGCTTACMATGGCCCACGCCCGCGTCCT 41-MER

ALE-3 (SEQ ID NO: 66)
TATCCATGGCGGCCGCGCGGTCGGTGACGGGCCGGMYCGGGTTGGAGTC
GGCGAA 55-MER

ALE-CUT (SEQ ID NO: 67)
CTAGGCGGCCGCGCGGGAGGAGGCGACGGCGAC  33-mer

ALECAP-5 (SEQ ID NO: 68)
GCGACGGCGACGGCGGCCGTGGCCAGCACGGCGAGCGCCAGGAGGAGG
ACGCGG 54-MER

ALECAP-3 (SEQ ID NO: 69)
TCGCCGTCGCCTCCTCCTCCTCCTTCGCCGACT 33-MER
```

(d) The barley aleurain signal, mutated to a NPGR motif [cytoplasmic localisation]

(e) The rat sialyl transferase golgi targeting motif [golgi localisation]

A Golgi targeting vector, pJQ3.2, was made by inserting a reading frame encoding the relevant rat sialyl transferase (RST) motif (See FIG. 14, SEQ ID NO:11 and 12. RST motif shown to function in plants by Boevink P, Oparka K, Cruz S S, Martin B, Betteridge A, Hawes C, (1998) PLANT JOURNAL 15 441–447 Stacks on tracks: the plant Golgi apparatus traffics on an actin/ER network) into vector pPQ10.1, and replacing the EcoRi/NotI promoter/signal fragment of pJO6.3 with the fragment from this vector. Briefly, the RST motif was constructed by annealing oligonucleotides RST-F1A, RST-F1B, RST-F2A and RST-F2B, and amplifying the product with RST-5AD and RST-3A. This product was cloned and sequenced. Clones were found to have a deletion which was corrected by PCR with RST-RPT, followed by overlap-PCR and cloning of products.

```
PCR primers
RST-5AD (SEQ ID NO: 70)
ACTAAGCTTAAGGAGATATAACAATGATCCACACCAACCTCAA

RST-F1A (SEQ ID NO: 71)
TTCCATGATCCACACCAACCTCAAAAAGAAGTTCTCCCTCTTCAT

RST-F1B (SEQ ID NO: 72)
AGAGTGATCACGGCGAAGAGGAGGAAGACGAGGATGAAGAGGGAGAACTTCTTTT

RST-F2A (SEQ ID NO: 73)
TATAGATCTGCGTGTGGAAGAAGGGCTCCGACTACGAGGCCCTCACCCTCCAAGCCAAGGA

RST-F2B (SEQ ID NO: 74)
CATTTGGAACTCCTTGGCTTGGAGGGTG

RST-3A (SEQ ID NO: 75)
AACCATGGCGGCCGCCATTTGGAACTCCTTGGCT

RST-RPT (SEQ ID NO: 76)
TATAGATCTGCGTGTGGAAGAAGGGCTCCGACTACGAGGCCCTCACCCTCCAAGCCAAGGA
```

(f) otif [cytoplasmic localisation]

(g) The potato protease inhibitor II (II) apoplast motif [apoplast localisation]

An apoplast targeting reading frame was designed to encode the relevant potato protease inhibitor II (PPI) motif (See FIG. 15) and cloned into pJO6.3, to produce vector pJQ4.9. Briefly, the PPI motif was constructed by annealing oligonucleotides PPI-AP1, PPI-AP2, PPI-AP3, PPI-AP4, PPI-AP5 and PPI-6, and cloning this product as a HindIII/NotI fragment into vector pPQ10.1; the EcoRI/NotI promoter/signal fragment of pJO6.3 was then replaced with the equivalent fragment from the modified pPQ10.1 vector.

```
PCR primers
PPI-AP1 (SEQ ID NO: 77)
GGAATTCGTAGACAAGCTTACMATGGMCGTGCACAAGGAGGT

PPI-AP2 (SEQ ID NO: 78)
GATCAGGAGGTAGGCWACGAAGTTWACCTCCTTGTGC

PPI-AP3 (SEQ ID NO: 79)
CCTACCTCCTGATCGTSCTCGGCCTCCTCTTGCTCGT

PPI-AP4 (SEQ ID NO: 80)
CCTTGGCGTCCACGTGCTCCATGGCGGAWACGAGCAAGAGGAG

PPI-AP5 (SEQ ID NO: 81)
GTGGACGCCAAGGCCTGCACCCKCGAGTGCGGCAACCTC

PPI-AP6 (SEQ ID NO: 82)
GGAATTCGCGGCCGCCGGGCAGATGCCGAAGCCGAGGTTGCCGCACT
```

ii. C-Terminal End Signal Sequences

Four C-terminal signal sequences were utilized:

(a) Native *Aspergillus* end, [CTW] (vacuole and apoplast vectors)

This was derived directly from the genomic clone (see Example 1) as a Nco1-Sph1 fragment (Sph end filled with T4 polymerase) which replaces the Nco1-Not1 region of a standard actin -FAE vector (Not1 end filled with T4 DNA polymerase). Expression vector linker alone [CTW-PVAAA, SEQ ID NO:93] (plant optimised C-terminus for vacuole, golgi and apoplast vectors).

CTW is the peptide sequence of the *Aspergillus* FAE COOH end and is here provided by oligo FAE3. In this primer the reading frame is extended to provide the additional amino acids PVAAA (SEQ ID NO:91) which are partially encoded by the Not1 site used for cloning downstream signals see c) and d) below. Some COOH amino acids/motifs may affect compartment targeting, the PVAAA (SEQ ID NO:91) sequences are expected to be neutral in this respect while the native *Aspergillus* end may not be.

(c) Linker plus KPLKDEL (SEQ ID NO:90) [first K is primer artifact, intended to be E] (ER retention vectors)

These sequences are provided by primer TER5 introduced during PCR to generate the nos terminator fragment, and identified by sequencing within a specific clone. KDEL targeting has been demonstrated in plants by Denecke et al. ((1992) EMBO J 11:2345–2355 Plant and mammalian sorting signals for protein retention in the endoplastic reticulum contain a conserved epitope).

(d) Linker plus ETTEG [frameshift of (c)] (loss of ER retention—vacuole vectors)

These sequences are provided by primer TER5 introduced during PCR to generate the nos terminator fragment, and identified by sequencing within a specific clone (see Example 2A).

The KDEL signal is for ER retention, while others provide controls. A frameshift in the TER5 region [additional A] was used in subsequent constructs to destroy the ER KDEL retention signal.

The linker in the above C-terminal targeting sequences was PVAAA (SEQ ID NO:91).

D. Co-Integration and Co-Transformation Vectors.

Co-Transformation Vectors

A Hygromycin resistance gene driven by a CaMV345S promoter (pRob5) (35S-HYG-CMV in pUC18 (modified HYG, derived from pGL2) Bilang et al (1991) Gene 100: 247–50) was used for co-transformation experiments with pTT3 and pTP3.1, pJQ4.9, pJQ3.2, pJQ5.2, pUB8.1 1 vectors.

Co-Integration Vectors

1. Actin Promoter Constructs—pTR2.22, pTR6.1, pTR8.1, pTR9.4, pTR7.1, pTT5.5 and 5.1.

The CAMV35S-hyg region from pAJEB64TCA [a plant expression vector constructed by Andy Bettany at IGER containing CaMV-HYG from pTRA151 (Zheng et al 1991 Plant Physiol 97:832–835) (CaMV35S-HYG-tmI terminator as clonable cassette in pUC4) cloned into KpnI site of pCOR105] was added as a HindIII fragment at the KpnI site (T4 polymerase blunt) of pTP4a2, in divergent orientation to FAE to create pTR2.22. The FAE/Nos HindIII fragment of this vector was replaced as follows in co-expression vectors. From pTP5.1 for pTR6.1, from pTP10.1 to pTR8.1, from pTP11.1 to pTR9.4. Signal sequences of FAE in pTR2.22 were replaced as HindIII/BglII fragments in pTR7.1 (fragment from pT09.1). PCR products (ALE5/ALE-G) was digested with Acc1 and T4 polymerase, polished, followed by Not1 digest and cloning into EcoRV/Not1 digested pTR2.22 to give clones pTT5.5 and 5.1.

```
PCR primer
ALE-G (SEQ ID NO:92)
TATCCATGGCGGCCGCGCGGTCGGTGACGGGCCGGCCCGGGTTGGAGTC
GGCGAA
```

2. Actin Promoter Constructs—pUF1, pUA1K3, pUH4, pUH5, pUH6, pUH7, pUH8, pUH9.

The HygR gene from pAJEB64TCA, driven by the CaMV promoter, was first cloned as an end-filled HindIII fragment at the end-filled XbaI site of pTP3.1, to give pHOX3. For ease of cloning the downstream HindIII site was destroyed to create pUA1K3 and replacement of the FAE/Nos terminator HindIII fragment in this vector was carried out as follows. From pTP5.1 for pUF1, from pTP11.1 for pUH4, from pTP8.5 for UH5, from pTT5 for pUH6, from pUA4.4 for pUH7, from pTU5 for pUH8 and from pUG4 for pUH9.

3. Heat-Shock Promoter Constructs—pUH10, pUH12, pUC5.11.

A co-transformation vector in which FAE is expressed from the soybean heat shock promoter was made by first modifying pMA406 to remove the nos terminator (BglII linearised and gel purified, KpnI digested, T4 DNA polymerase polished in the presence of dNTPs and recircularised), and then inserting the FAE HindIII fragment from pTP11.1, creating pTT3.1, which encodes the full aleurain signal and the native *Aspergillus* COOH-terminus.

Following assays of various constructs, co-integration vectors were constructed with FAE and HygR genes arranged in tandem.

The HygR gene from pAJEB-64-TCA, driven by the CaMV promoter, was first cloned as an end-filled HindIII fragment at the end-filled XbaI site of pTP3.1, to give pHOX3 and subsequently excised as a HindIII/SacI fragment (partial SacI digest, relevant sites found in flanking pTP3.1 sequences) which was cloned into the HindIII/SacI sites of pMA406, in tandem orientation (vector pUH1a20). FAE sequences were then cloned into the HindIII site of pUH1a20 downstream of the heat-shock promoter (HindIII fragment from pTU5 for pUH10, HindIII fragment from pTT5 for pUH12). A pTP3.1 derivative was made by cloning the CaMV/HygR HindIII cassette from pAJEB-64-TCA in tandem orientation downstream of the FAE gene in pTP3.1, inactivating the middle HindIII site by partial digestion and end-filling, and excising the combined FAE/HygR cassette as a single HindIII fragment, which was inserted at the HindIII site in pMA406 to produce pUC5.11.

EXAMPLE 3

Transformation of Plant Cells

Eight to ten weeks old embryogenic *F. arundinacea* and *L. multiflorum* suspension cultures were bombarded either with a single co-integration plasmid DNA vector containing FAE and hyg resistance genes, or with a co-transformation vector containing FAE and with plasmid pROB5 conferring hygromycin resistance (CAMV35S-hpt-nos) using a Particle Inflow Gun (PIG) (Finer et al. (1992) Development of the particle inflow gun for DNA delivery to plant cells Plant Cell Reports 11:323–328) and 1.5–3.0 μm gold particles as in Dalton et al (Dalton et al. (1999) Co-transformed diploid *Lolium perenne* (Perennial ryegrass), *Lolium multiflorum* (Italian ryegrass) and *Lolium temulentum* (Darnel) plants produced by microprojectile bombardment. Plant Cell Reports. 18: 721–726) and Kuai et al (Regeneration of fertile transgenic tall fescue (*Festuca arundinacea*) plants with a stable highly expressed foreign gene. Plant Cell Tissue and Organ Culture (1999) 58:149–154). Transformants were selected with hygromycin (25 to 50 mg/l) over a 10–12 week selection period at 25° C. under continuous white fluorescent light (60 $\mu E\ m^2\ s^{-1}$) and plants regenerated via somatic embryogenesis as in Dalton et al 1999, supra. Regenerated plants were screened for FAE activity on transfer to soil and expressing plants grown to maturity in a containment growth room at 18° C. under 16 h fluorescent lights (350 $\mu E\ m^2\ s^{-1}$) Mature plants (6–8 weeks old) were re-assayed for FAE activity and fresh tissue harvested for Southern, Northern and Western analysis, and for self digestion analysis. The remaining tissue was freeze dried and powdered for cell wall structure analysis, in vitro-dry matter digestibility (IVDMD) determinations and for in-vitro gas production determinations of rates of tissue digestion.

EXAMPLE 4

Targeting of Expression Product

To verify that the targeting sequences are effective in delivering the gene the targeting sequences were operably linked to a green fluorescent protein GFP. The vector constructs are shown in FIG. 16. Cells were transformed by particle bombardment as in Example 3. Localization of the GFP could be visualized under a microscope 1 day after bombardment (i.e., shooting). See FIG. 16.

EXAMPLE 5

FAE1 Activity

Plants regenerated from transformed cells showed FAE activity in all plant tissues tested. Cells were transformed as above under the direction of the ER and APO targeting sequences. FAE activity in transformed *Festuca arundinacea* leaves of different ages was elevated compared to control (untransformed) plants. See FIGS. 17 and 18.

Similar results were seen with *Lolium mutiflorum* leaves at different ages transformed as above under the direction of vacuolar, ER and APO targeting sequence. See FIGS. 19 and 20.

FAE expression under a heat shock promoter can also be induced. (Data not shown.)

Thus, we have demonstrated FAE expression in *Festuca* and *Lolium* leaves under constitutive and HS promoters with effective FAE targeting to the vac, ER and apo.

FAE Assay

FAE activity was determined in soluble extracts of fresh (or frozen at −70° C.) leaves or cell cultures (0.5 g) with 0.1M NaAc, pH 5.0 extraction buffer. Extracts were incubated with 24 mM EF (ethyl 4-hydroxy-3-methoxycinnamate) or 1% FAXX as substrate, at 28° C. for 24 hrs and FAE activity calculated as the amount of ferulic acid released. FAE activity was also determined by measuring the release of monomeric and dimeric ferulic acid from self-digested leaf or cell culture samples. Fresh, or frozen, leaves or cell cultures (0.5 g) were ground in 0.1M NaAc, pH 5.0 extraction buffer in the presence and absence of xylanase (1000U GC140/sample) without added substrate and incubated at 28° C. for 72 hrs. Following incubation, and centrifugation, soluble extracts were loaded onto an activated reverse phase C18 μNova sep-pak column (Waters), eluted with 100% MeOH and the MeOH sample analysed by HPLC.

EXAMPLE 6

Chemical Analysis of Cell Wall Extracts

Ester bound compounds were extracted from freeze dried powdered leaves or cell cultures (50–100 mg) with NaOH (5 ml of 1M) followed by incubation at 25° C. for 23 hrs under N2. After centrifugation and acidification of the soluble extract with concentrated HCl, the extracted phenolics were loaded onto an activated reverse phase C18 μNova sep-pak column (Waters) and eluted with 100% MeOH. and the MeOH sample analysed by HPLC.

HPLC was carried out with methanol: 5% acetic acid either with a 35–65% MeOH gradient in 15 min (FAE assay) or with a 30–70% MeOH gradient in 25 min (monomer and dimer cell wall components) at 2 ml/min on a μNova Pak C18 8×10 RCM (Waters). Extracts were detected and quantified with a diode array detector (240–400 nm Waters 996PDA) monitored at 280 nm for aldehydes and 340 nm for hydroxycinnamic acids.

Levels of esterified monomeric and dimeric hydroxycinnamic acids in *Festuca arundinacea* plants expressing FAE under VAC, and ER and APO targeting sequences are reduced compared to control (untransformed) plants. The results can be seen in FIGS. 21 and 22, respectively. Thus, we show where this does not result in reduced cell wall phenolics in growing plants with vac targeting but does result in lower phenolics with ER and apo targeting. In addition, Levels of esterified monomeric and dimeric hydroxycinnamic acids in *Festuca arundinacea* plants expressing FAE are not significantly reduced when FAE is VAC, targeting (FIG. 21) which is as predicted for correct vacuolar targeting, but are significantly reduced, as predicted, in some plants when FAE was ER and APO targeted, compared to control (untransformed) plants. The results can be seen in FIG. 22.

EXAMPLE 7

In Vitro Dry Matter Digestibility (IVDMD)

The in vitro dry matter digestibility (IVDMD) was estimated on 1.0 g dry weight of leaf or cell culture tissue using the pepsin/cellulase method of Jones and Hayward (The effect of pepsin treatment of herbage on the prediction of dry matter digestibility from solubility in fungal cellulase solutions. Journal of the Science of Food and Agriculture (1975) 26:711–718).

We show that the presence of FAE in the plants results in higher digestibility of the leaves. This may be due to internal FAE activity acting on normal cell walls with vacuole located FAE and to both FAE activity and the lower cell wall crosslinking with ER and apo targeted FAE (as also found with cell cultures).

End point digestibility as determined by IVDMD were higher in leaf tissue of some transformed plants of *Festuca* expressing FAE, compared to control (untransformed) plants. Examples are shown where vacuolar, ER or apoplast targeted FAE under a constitutive actin promoter have been effective at increasing IVDMD. Similar results were obtained with in leaves of *Lolium*, but were less pronounced. The results can be seen in FIGS. 23 and 24.

EXAMPLE 8

In Vitro Gas Production Measurements

In each experiment, 1.0-g samples of freeze dried powdered leaf tissue or cell culture were fermented in three 165-ml capacity serum bottles according to the pressure transducer technique of Theodorou et al. (Theodorou et al. (1994) A new gas production method using a pressure transducer to determine the fermentation kinetics of ruminant feeds. Animal Feed Science and Technology 48: 185–197). Grab samples of rumen-digesta were taken at 8.00 h before the morning feeding from fistulated wethers fed grass hay, and transported to the laboratory in a pre-warmed (39° C.) vacuum flask. The microbial inoculum and culture media were prepared as described by Theodorou et al. (1994). Each serum bottle received 10 ml of microbial inoculum, 85 ml of buffer and 4 ml of reducing agent.

At the end of the incubation period, (144 h) the contents of each serum bottle were filtered through pre-weighed sintered glass funnels and freeze dried to constant weight. Dry matter loss was calculated as the difference between the dry weight of the sample pre- and post-incubation. Additionally, the concentration of volatile fatty acids (VFA) in the liquid fraction of the culture media at the end of the 144-h incubation period was determined by gas chromatography. A Chrompack CP 9000 chromatograph fitted with an automatic sampler (Chrompack 911) and a flame-ionisation detector, linked to a Dell PC with A1-450 integration software, was used for VFA quantification.

Gas production data were fitted to the model of France et al. (France, J., Dhanoa, M. S., Theodorou, M. K, Lister, S. J., Davies. D. R. and Isac, D. 1993. A model to interpret gas accumulation profiles associated with in vitro degradation of ruminant feeds. *Journal of Theoretical Biology.* 163: 99–111.) using the MLP (Ross, G. J. S. 1987. *MLP, Maximum Likelihood Program Version* 3.08. Oxford Numerical Algorithms Group) package. The equation is in the form, $Y=A\{1-e^{[-b(t-T)-c(\sqrt{t}-\sqrt{T})]}\}$ where Y is the cumulative gas production (ml), A is the asymptote (i.e. gas pool), T is lag time, and b ($h^{-1}$) and c ($h^{-0.5}$) are decay rate constants. A combined fractional rate ($h^{-1}$) of gas production (μ) was calculated as, $\mu=b+c/2\sqrt{t}$, where t is the incubation time (h).

It can be seen for *Festuca arundiancea* (denoted as BN in FIG. 25) that cell cultures have a higher rate of digestion and cumulative gas production in the presence of FAE and that the addition of an exogenous xylanase further enhance the availability of fermentable carbohydrates. Similar results are found in FAE expressing cultures without added FAE . Fermentation rates are further increased compared with controls by the addition of exogenous FAE or xylanaase as these cultures expressing FAE have a reduced cell wall phenolic composition to controls FIGS. 26–28.

EXAMPLE 9

FAE & Xylanase Transformed Plants

Addition of exogenous xylanase (GC140) greatly increased FAE mediated release of phenolics from *Festuca* and *Lolium* leaves expressing *A. niger* FAE. See FIGS. 29–31 which show that phenolic release from leaf cell walls is increased in all FAE expressing plants on cell death and this is stimulated by xylanase irrespective of the targeting. Therefore expression of a fungal xylanase in plant cells is tested.

The FAE expression cassette is modified to comprise a fungal xylanase gene (either *T. reesei* or *A. niger*) to yield a FAE-xylanase expression cassette. The FAE-xylanase expression cassette is used to transform plant cells in a manner similar to those described in Example 3. The transformed cells are allowed to grow and are selected on an appropriate medium. The enzymes so expressed increase the availability of fermentable carbohydrates to a greater extent than the FAE expression cassette.

Although the foregoing invention has been described in some detail by way of illustration and example for purposes of clarity and understanding, it will be obvious that certain changes and modifications may be practiced within the scope of the appended claims.

What is claimed:

1. A transgenic plant comprising an expression cassette comprising a promoter operably linked to a polynucleotide encoding a ferulic acid esterase having the sequence of SEQ ID NO: 2 and a signal sequence that targets expression of the ferulic add esterase to the endoplasmic reticulum, vacuole, apoplast or golgi apparatus, wherein the transgenic plant is selected from the group consisting of *Festuca, Lolium, Sorghum, Zea, Triticum, Avena* and *Poa* and said transgenic plant expresses the ferulic acid esterase having ferulic add esterase activity.

2. The plant of claim 1, wherein the polynucleotide further comprises a polynucleotide that encodes CTWPVAAA (SEQ ID NO:93) at the 3' end.

3. The plant of claim 1 wherein sub-optimal codons are modified to *Triticum* spp. preferred codons.

4. The plant of claim 1, wherein the expression cassette is introduced into the plant is by sexual reproduction.

5. The plant of claim 1, wherein the promoter is an inducible promoter.

6. The plant of claim 5, wherein the promoter is a senescence promoter.

7. The plant of claim 5, wherein the promoter is a heat shock promoter.

8. The plant of claim 1, wherein the promoter is a constitutive promoter.

9. The plant of claim 1, wherein the signal sequence is upstream of the 5' end of the ferulic acid esterase encoding polynucleotide.

10. The plant of claim 9, wherein the signal sequence is derived from the signal sequence of a vacuolar targeted gene.

11. The plant of claim 10, wherein the signal sequence is derived from the signal sequence of a vacuolar targeted senescence gene.

12. The plant of claim 11, wherein the signal sequence is a *Lolium* See1 signal sequence.

13. The plant of claim 1, wherein the signal sequence is from *Aspergillus niger* ferulic acid esterase.

14. The plant of claim 1, wherein the signal sequence is downstream of the 3' end of the ferulic acid esterase encoding polynucleotide.

15. The plant of claim 14, wherein the polynucleotide sequence further comprises a stop codon.

16. The plant of claim 14, wherein the polynucleotide sequence further comprises an extension of the ferulic acid esterase reading frame to provide a linker to KDEL (SEQ ID NO: 97).

17. The plant of claim 1 further comprising a second expression cassette comprising a promoter operably linked to a xylanase encoding polynucleotide.

18. The plant of claim 17, wherein the xylanase encoding polynucleotide is from *Trichoderma reesei.*

19. The plant of claim 17, wherein the first and second expression cassettes are present on separate plasmids.

20. The transgenic plant of claim 1, wherein the plant is selected from the group consisting of *Festuca, Lolium, Zea* and *Avena.*

21. The transgenic plant of claim 20, wherein the plant is a *Festuca* plant.

22. A transgenic plant comprising an expression cassette including an inducible or tissue specific plant promoter operably linked to a polynucleotide encoding a ferulic acid esterase having the sequence of SEQ ID NO: 2, wherein the transgenic plant expresses the ferulic add esterase having ferulic acid esterase activity and wherein said transgenic plant is selected from the genera consisting of *Festuca, Lolium, Zea,* and *Avena.*

23. The transgenic plant of claim 22, wherein said plant is a *Festuca* plant.

24. The transgenic plant of claim 22, wherein said plant is a *Lolium* plant.

25. The transgenic plant of claim 22 further comprising an exogenous xylanase gene.

26. The transgenic plant of claim 1, wherein the plant is a *Lolium* plant.

27. The transgenic plant of claim 1, wherein the plant is a *Zea* plant.

28. The transgenic plant of claim 27, wherein the *Zea* plant is *Zea mays*.

29. The transgenic plant of claim 1, wherein the plant is an *Avena* plant.

* * * * *